(12) United States Patent
Jackson et al.

(10) Patent No.: US 10,975,074 B2
(45) Date of Patent: Apr. 13, 2021

(54) ANTI-LIFERATIVE AGENTS COMPRISING SUBSTITUTED BENZO[E]PYRIDO[1,2-A][1,4]DIAZEPINES

(71) Applicant: FEMTOGENIX LIMITED, Hertfordshire (GB)

(72) Inventors: Paul Joseph Mark Jackson, London (GB); David Edwin Thurston, London (GB); Khondaker Mirazur Rahman, London (GB)

(73) Assignee: Femtogenix Limited

( * ) Notice: Subject to any disclaimer, the term of this patent is extended or adjusted under 35 U.S.C. 154(b) by 0 days.

(21) Appl. No.: 16/440,424

(22) Filed: Jun. 13, 2019

(65) Prior Publication Data
US 2019/0308970 A1 Oct. 10, 2019

Related U.S. Application Data

(63) Continuation of application No. 15/953,428, filed on Apr. 14, 2018, now abandoned, which is a continuation-in-part of application No. 15/901,714, filed on Feb. 21, 2018, which is a continuation-in-part of application No. PCT/GB2016/052565, filed on Aug. 19, 2016.

(30) Foreign Application Priority Data

Aug. 21, 2015 (GB) .................... 1514928.9

(51) Int. Cl.
| | | |
|---|---|---|
| A61K 31/55 | (2006.01) |
| C07D 487/14 | (2006.01) |
| C07D 487/22 | (2006.01) |
| C07D 471/04 | (2006.01) |
| A61K 47/68 | (2017.01) |
| A61P 35/00 | (2006.01) |

(52) U.S. Cl.
CPC ........ C07D 471/04 (2013.01); A61K 47/6803 (2017.08); A61K 47/6855 (2017.08); A61P 35/00 (2018.01)

(58) Field of Classification Search
CPC ..... A61K 31/55; C07D 487/14; C07D 487/22
USPC .......................................... 514/219; 540/555
See application file for complete search history.

(56) References Cited

U.S. PATENT DOCUMENTS

| | | |
|---|---|---|
| 5,366,972 A | 11/1994 | Hargrave et al. |
| 5,418,229 A | 5/1995 | Alker et al. |
| 5,650,409 A | 7/1997 | Rogers et al. |
| 5,712,269 A | 1/1998 | McCabe et al. |
| 6,608,193 B2 | 8/2003 | Liu et al. |
| 6,864,250 B1 | 3/2005 | Funamizu et al. |
| 7,067,511 B2 | 6/2006 | Thurston et al. |
| 7,384,934 B2 | 6/2008 | Aicher et al. |
| 7,456,469 B2 | 11/2008 | Yamazaki |
| 7,528,128 B2 | 5/2009 | Ahmed et al. |
| 7,709,470 B2 | 5/2010 | Sakaki et al. |
| 8,039,464 B2 | 10/2011 | Schrattenholz |
| 8,426,402 B2 | 4/2013 | Li et al. |
| 8,569,298 B2 | 10/2013 | Barlaam et al. |
| 8,592,576 B2 | 11/2013 | Howard et al. |
| 8,637,664 B2 | 1/2014 | Howard et al. |
| 8,637,665 B2 | 1/2014 | Ahmed et al. |
| 8,642,610 B2 | 2/2014 | Brown |
| 9,006,233 B2 | 4/2015 | Cook et al. |
| 9,315,497 B2 | 4/2016 | Verdecia Reyes et al. |
| 9,376,440 B2 | 6/2016 | Howard et al. |
| 9,518,118 B2 | 12/2016 | Chen et al. |
| 9,526,801 B2 | 12/2016 | McDonald et al. |
| 9,534,000 B2 | 1/2017 | Chari |
| 9,951,133 B2 | 4/2018 | Yu et al. |
| 9,974,864 B2 | 5/2018 | Junutula et al. |
| 2007/0191349 A1 | 8/2007 | Howard et al. |
| 2008/0064870 A1 | 3/2008 | Ahmed et al. |
| 2008/0275023 A1 | 11/2008 | Guidi et al. |
| 2009/0318412 A1 | 12/2009 | Matsumoto et al. |
| 2011/0263574 A1 | 10/2011 | Schrattenholz |

(Continued)

FOREIGN PATENT DOCUMENTS

| | | |
|---|---|---|
| EP | 0556947 | 8/1993 |
| EP | 1608650 | 6/2010 |

(Continued)

OTHER PUBLICATIONS

Jordan, V. C. Nature Reviews: Drug Discovery, 2, 2003, 205-213.*

(Continued)

Primary Examiner — Douglas M Willis
(74) Attorney, Agent, or Firm — Thomas G. Peterson; Maynard Cooper & Gale

(57) ABSTRACT

The invention relates to compounds comprising a substituted pyrrolo-, indolino- or tetrahydroisoquinoline-benzodiazepines alkylating moiety linked via the A-ring to aromatic groups of formula (Ia), and to pharmaceutically acceptable salts thereof, which are useful as medicaments, in particular as anti-proliferative agents.

(Ia)

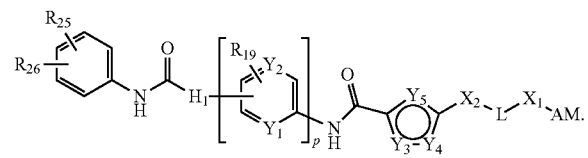

30 Claims, 34 Drawing Sheets
Specification includes a Sequence Listing.

(56) References Cited

U.S. PATENT DOCUMENTS

| | | | |
|---|---|---|---|
| 2012/0115852 | A1 | 5/2012 | Schultz et al. |
| 2013/0210804 | A1 | 8/2013 | Anthony et al. |
| 2016/0207949 | A1 | 7/2016 | Zhao |
| 2017/0253602 | A1 | 9/2017 | Schall et al. |
| 2017/0333442 | A1 | 11/2017 | Yin et al. |
| 2017/0362220 | A1 | 12/2017 | Fischer et al. |
| 2017/0369453 | A1 | 12/2017 | Thomas et al. |
| 2017/0369507 | A1 | 12/2017 | Christian et al. |
| 2018/0110873 | A1 | 4/2018 | McDonald et al. |

FOREIGN PATENT DOCUMENTS

| | | | |
|---|---|---|---|
| EP | 2421870 | | 3/2016 |
| JP | 2009263283 | | 11/2009 |
| WO | 199638422 | | 12/1996 |
| WO | 2007039752 | | 4/2007 |
| WO | 2010091150 | | 8/2010 |
| WO | 2015028850 | | 3/2015 |
| WO | 2015166289 | | 11/2015 |
| WO | 2016198869 | | 12/2016 |
| WO | WO 17/032983 | * | 3/2017 |
| WO | 2017074914 | | 5/2017 |
| WO | 2018053552 | | 3/2018 |

OTHER PUBLICATIONS

Hackam, et al. JAMA, 296(14), 2006, 1731-1732.*

Lum, Regina, "Written Opinion and Search Report, Singapore Patent App No. 11201801379S," Intellectual Property Office of Singapore, Mar. 4, 2019, pp. 1-10.

Rahman, K.M., et al., "GC-Targeted C8-Linked Pyrrolobenzodiazepine-Biaryl Conjugates with Remtomolar in Vitro Cytotoxicity and in Vivo Antitumor Activity in Mouse Models," Journal of Medicinal Chemistry, Mar. 21, 2013, vol. 56, pp. 2911-2935.

Brucoli, Federico, et al., "Novel C8-linked pyrrolobenzodiazepine (PBD)-heterocycle conjugates that recognize DNA sequences containing an inverted CCAAT box,", Bioorganic & Medicinal Chemistry Letters, Apr. 20, 2011, vol. 21, pp. 3780-3783.

Kumar, Rohtash, et al., "Design, synthesis and in vitro cytotoxic studies in novel bis-pyrrolo[2,1][1,4] benzodiazepine-pyrrole and imidazole polyamide conjugates," European Journal of Medicinal Chemistry, Apr. 2, 2005, vol. 40, No. 7. pp. 641-654.

Evans, David, "Great Britain Search Report—GB application No. GB1514928.9," Feb. 5, 2016, pp. 1-4.

Sulberg, Anna, "International Search Report and Written Opinion—International patent application No. PCT/GB2016/052565," Nov. 2, 2016; pp. 1-14.

Baraldi, et al., "Synthesis, in Vitro Antiproliferative Activity, and DNA-Binding Properties of Hybrid Molecules Containing Pyrrolo[2, 1-c] [1,4] benzodiazepine and Minor-Groove-Binding Oligopyrrole Carries," J. Med. Chem. 1999, 42, pp. 5131-5141.

Markandeya, Nagula, et al., "Asymmetric synthesis of piperidinobenzodiazepines through 'cation-pool' host/guest supramolecular approach and their DNA-binding studies," Asymmetry 21 (2010), pp. 2625-2630.

Pfau, Andrea, "Written Opinion of Int'l Searching Authority—International patent application No. PCT/GB2016/051701," Aug. 10, 2016.

Cole, Natalie, "British Search Report—application No. GB1510010. 0," Feb. 26, 2016.

Tozuka, Zenzaburo, et al., "Studies on tomaymycin, III. syntheses and antitumor activity of tomaymycin analogs," The Journal of Antibiotics, vol. 36, No. 12, Dec. 1, 1983, pp. 1699-1708.

* cited by examiner

Figure 5
TyrT
3'-AAGGCCAATGGAAATTAGGCAATGCCTACTTTTAATGCGTTGGTCAAGAAAAAA
GAGAAGGATTGTGAAATGTCGCCGCGCAGTAAACTATACTACGCGGGGCGAAGGG
CTATTCCCTCGTCCGGTCATTTTTCGTAATGGGGCACCACCCCCAAGGGCT-5'
Figure 6
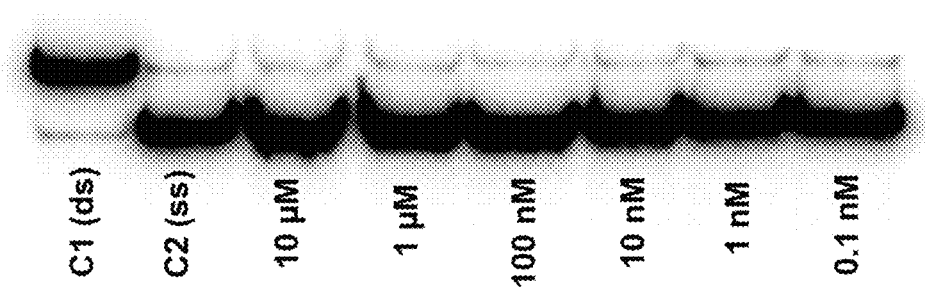
Figure 7
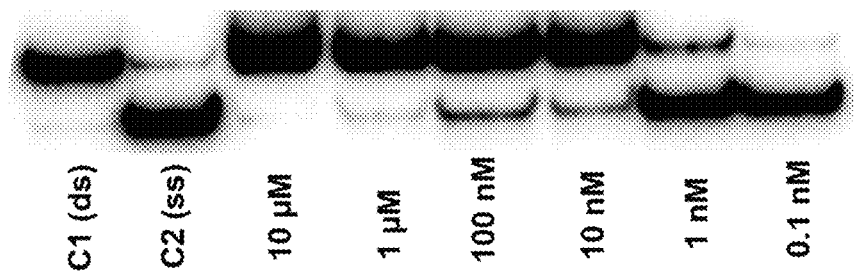

Figure 8B
Figure 8C
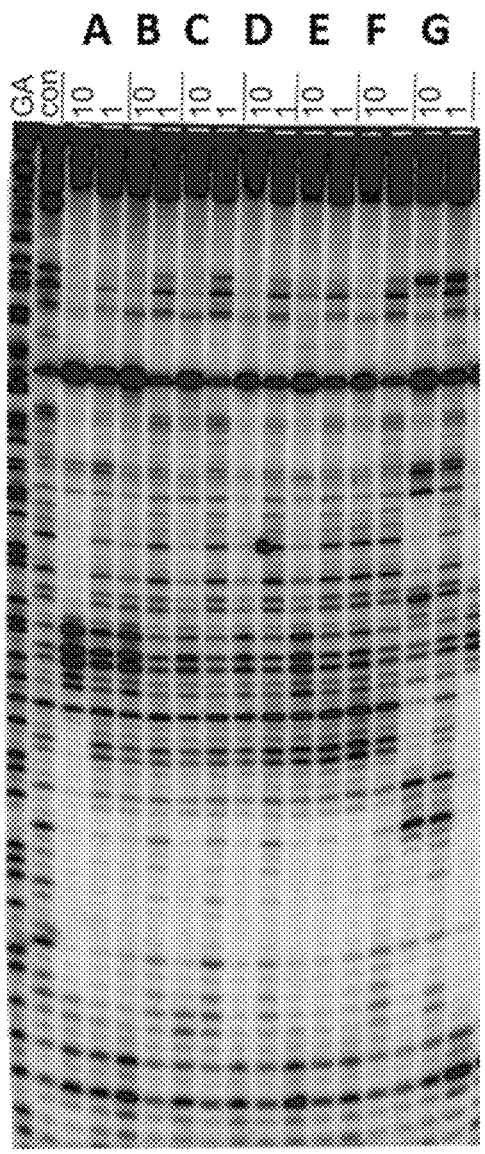
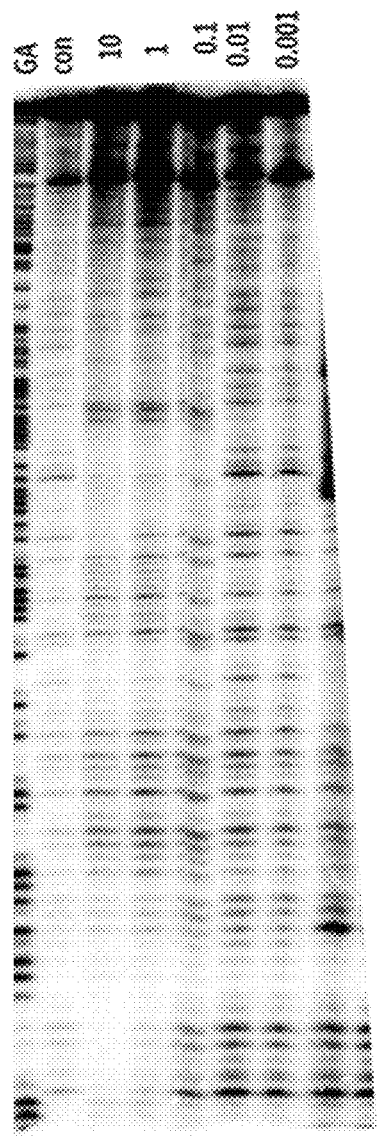

5'-GGATCCATATGCGGCAATACACATGGCAGATTTCCAACTGCACTAGTCGTAGCGC

GATCAAGGTTAAGCTCCGTTCTATCTGGTATAGCAATAGGGCGTGAAGAGTTATG

TAAAGTACGTCCGGTGGGGTCTGTTTTGTCATCTCAGCCTCGAATGCGGATCC

Figure 10

HexA

5'-GGATCCCGGGATATCGATATATGGCGCCAAATTTAGCTATAGATCTAGAA

TTCCGGACCGCGGTTTAAACGTTAACCGGTACCTAGGCCTGCAGCTGCGCATG

CTAGCGCTTAAGTACTAGTGCACGTGGCCATGGATCC-3'

Figure 11

5'-F-AAAAAAAGAAAAAATTT-3'

3'-Q-TTTTTTT CTTTTTTAAA-5'

Figure 12 B (Continued)
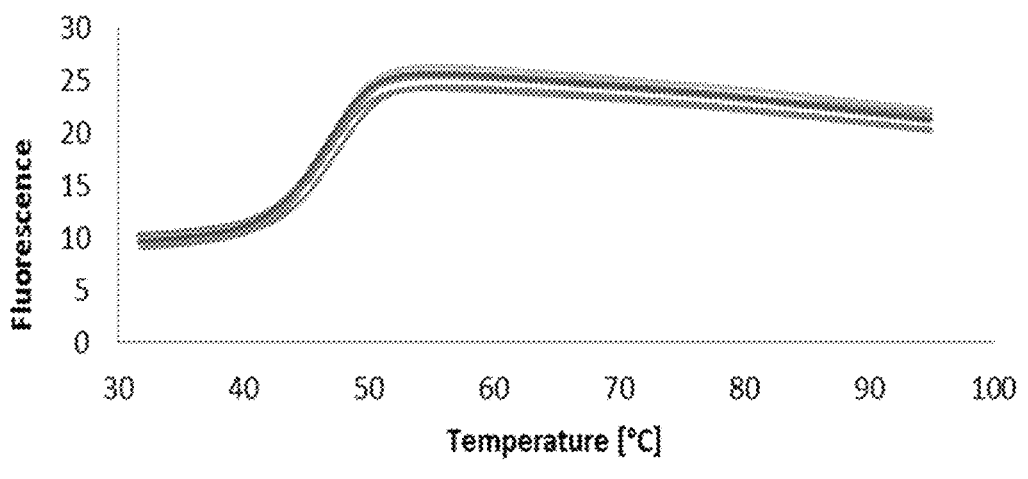
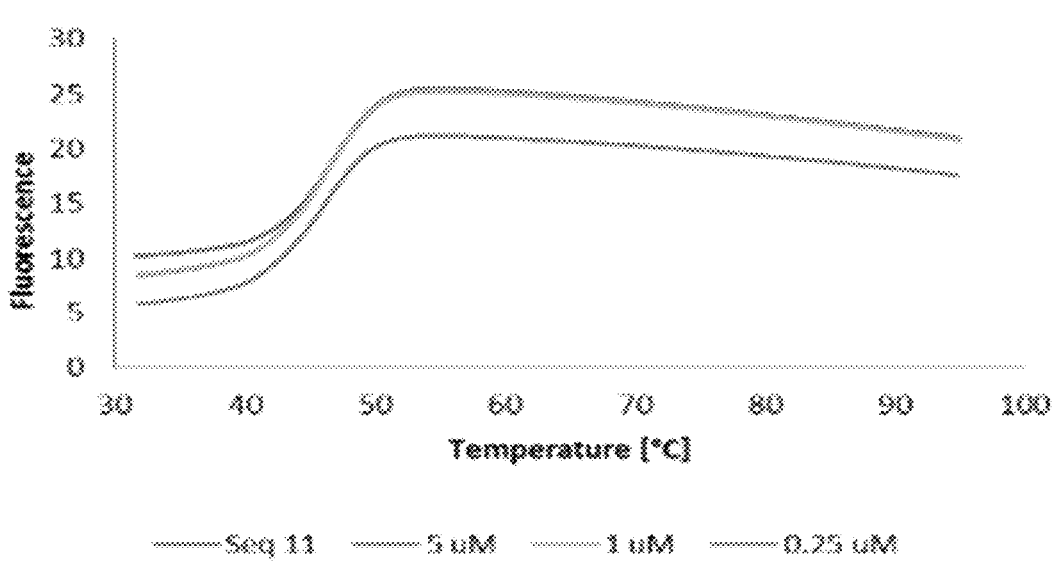

Analytical SEC trace (TOSOH TSKgel Super SW3000 4.6 mm x 300mm, 4 μm)

ANTI-LIFERATIVE AGENTS COMPRISING SUBSTITUTED BENZO[E]PYRIDO[1,2-A][1,4]DIAZEPINES

CROSS-REFERENCE TO RELATED APPLICATIONS

This application is a continuation of U.S. patent application Ser. No. 15/953,428, filed, (currently pending). U.S. patent application Ser. No. 15/953,428 is a continuation-in-part of U.S. patent application Ser. No. 15/901,714, filed Feb. 21, 2018, (currently pending). U.S. patent application Ser. No. 15/901,714 is a continuation-in-part of International patent application number PCT/GB2016/052565, filed 19 Aug. 2016, (expired). International patent application number PCT/GB2016/05265 cites the priority of Great Britain patent application number GB1514928.9, filed 21 Aug. 2015 (abandoned).

FIELD OF THE INVENTION

The invention relates to guanine alkylating moieties, such as pyrrolobenzodiazepines (PBDs, comprising three fused 6-7-5-memberedd rings), C2-substituted PBDs (including C2-endo, C1/C2-endo, and C2/C3-endo PBDs), pyrridino-benzodiazepines (PDDs, comprising three fused 6-7-6-membered rings), indolinobenzodiazapenes (IBDs, comprising four fused 6-7-5-6-membered rings), and tetrahydroisoquinolinebenzodiazapines (QBDs, comprising four fused 6-7-6-6 membered rings). In particular it relates to compounds comprising a guanine alkylating moiety linked via the A-ring to aromatic groups, and to pharmaceutically acceptable salts thereof, which are useful as medicaments, in particular as anti-proliferative agents.

BACKGROUND TO THE INVENTION

Pyrridinobenzodiazepines (PDDs) are related structures to pyrrolobenzodiazepines (PBDs). The pyrrolobenzodiazepines (PBDs) are a group of compounds some of which have been shown to be sequence-selective DNA minor-groove binding agents. The PBDs were originally discovered in *Streptomyces* species (1-5). They are tricyclic in nature, and are comprised of fused 6-7-5-membered rings that comprise an anthranilate (A ring), a diazepine (B ring) and a pyrrolidine (C ring) (3). They are characterized by an electrophilic N10=C11 imine group (as shown below) or the hydrated equivalent, a carbinolamine [NH—CH(OH)], or a carbinolamine alkyl ether ([NH—CH(OR, where R=alkyl)] which can form a covalent bond to a C2-amino group of guanine in DNA to form a DNA adduct (6).

adduct has been reported to inhibit a number of biological processes including the binding of transcription factors (7-9) and the function of enzymes such as endonucleases (10, 11) and RNA polymerase (12). PBD monomers (e.g., anthramycin) have been shown by footprinting (6), NMR (13, 14), molecular modeling (15) and X-ray crystallography (16) to span three base pairs and to have a thermodynamic preference for the sequence 5'-Pu-G-Pu-3' (where Pu=purine, and G is the reacting guanine) (17) and a kinetic preference for Py-5-Py (where Py=Pyrimidine).

PBDs are thought to interact with DNA by first locating at a low-energy binding sequence (i.e., a 5'-Pu-G-Pu-3' triplet) through Van der Waals, hydrogen bonding and electrostatic interactions (7). Then, once in place, a nucleophilic attack by the exocyclic C2-amino group of the central guanine occurs to form the covalent adduct (7). Once bound, the PBD remains anchored in the DNA minor groove, avoiding DNA repair by causing negligible distortion of the DNA helix (16). The ability of PBDs to form an adduct in the minor groove and crosslink DNA enables them to interfere with DNA processing and, hence, their potential for use as antiproliferative agents.

A number of monomeric PBD structures have been isolated from *Streptomyces* species, including anthramycin (18) the first PBD, tomamycin (19), and more recently usabamycin (20) from a marine sediment *Streptomyces* species in a marine sediment. This has led to the development of a large range of synthetic analogues which have been reviewed (1, 21). More recently, a number of monomeric PBD structures that are linked through their C8 position to pyrroles and imidazoles have been reported WO 2007/039752, WO 2013/164593 (22-27).

WO 2010/091150 discloses a dimer of a 6-7-6 ring system linked via their A-rings. WO 2015/028850 discloses 6-7-5 ring system PBD dimers that are linked via phosphine oxide containing linkers attached to their aromatic A-rings. In addition, WO 2015/028850 discloses a dimer compound containing a 6-7-6 ring system linked via the key phosphine oxide containing linkers.

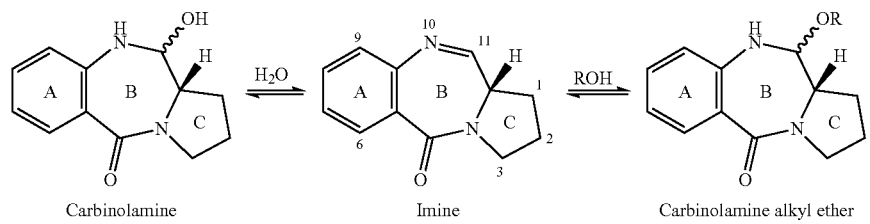

Carbinolamine      Imine      Carbinolamine alkyl ether

The natural products interact in the minor groove of the DNA helix with excellent fit (i.e., good "isohelicity") due to a right-handed longitudinal twist induced by a chiral C11a-position which has the (S)-configuration (6). The DNA Various PBDs have been shown to act as cytotoxic agents in vitro, for example, WO 00/12508, WO 2004/087711, and as anti-tumour in vivo in animal tumour models, for example, WO 2011/117882, WO 2013/164593. Furthermore, the C8/C8'-linked PBD dimer SJG-136 (28, 29) has completed Phase I clinical trials for leukaemia and ovarian cancer (30) and has shown sufficient therapeutic benefit to progress to Phase II studies.

SJG-136

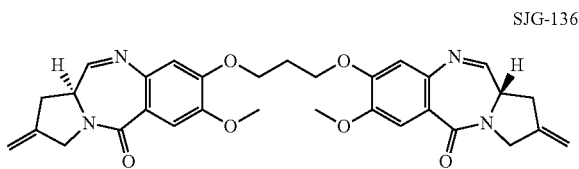

However, results from a Phase I clinical evaluation of SJG-136 revealed that the drug produced several adverse effects including lower-limb edema and fatigue (31).

Thus, there exists a need for further compounds that are therapeutically active for treating a variety of proliferative diseases. Furthermore, there exists a need for PBDs, C-2 substituted PBDs, PDDs, IBDs, and QBDs linked to additional chemical groups to provide for improved efficacy for treating a variety of proliferative diseases.

The present application reports PBDs, C2-substituted PBDs, PDDs, IBDs, and QBDs as well as compounds comprising PBDs, C2-substituted PBDs, PDDs, IBDs, and QBDs linked via the A-ring to aromatic groups. The inventors have discovered that such compounds provide properties, such as, but not limited to, cytoxicity and DNA binding, that results in effective compounds.

The present invention seeks to overcome problem(s) associated with the prior art.

SUMMARY OF THE INVENTION

The present invention provides a compound of formula (I):

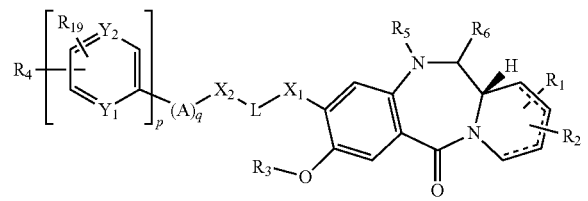

(I)

and salts and solvates thereof,
wherein;
the dotted lines indicates the optional presence of a double bond between one or more of C1 and C2, C2 and C3, and C3 and C4;

$R_1$ is selected from $R_7$, $=CH_2$, $=CH—(CH_2)_m—CH_3$, $=O$, $(CH_2)_m—OR_7$, $(CH_2)_m—CO_2R_7$, $(CH_2)_m—NR_7R_8$, $O—(CH_2)_n—NR_7R_8$, $NH—C(O)—R_7$, $O—(CH_2)_n—NH—C(O)—R_7$, $O—(CH_2)_n—C(O)—NH—R_7$, $(CH_2)_m—SO_2R_7$, $O—SO_2R_7$, $(CH_2)_m—C(O)R_7$ and $(CH_2)_m—C(O)NR_7R_8$; $R_2$ is selected from $R_9$, $=CH_2$, $=CH—(CH_2)_r—CH_3$, $=O$, $(CH_2)_r—OR_9$, $(CH_2)_r—CO_2R_9$, $(CH_2)_r—NR_9R_{10}$, $O—(CH_2)_s—NR_9R_{10}$, $NH—C(O)—R_9$, $O—(CH_2)_s—NH—C(O)—R_9$, $O—(CH_2)_s—C(O)—NH—R_9$, $(CH_2)_r—SO_2R_9$, $O—SO_2R_9$, $(CH_2)_r—COR_9$ and $(CH_2)_r—C(O)NR_9R_{10}$;

$R_3$ is selected from H, $C_{1-12}$ alkyl and $CH_2Ph$;
$R_4$ is selected from phenyl and $C_{5-9}$ heteroaryl groups optionally substituted with up to three optional substituent groups selected from OH, $C_{1-6}$ alkyl, $OC_{1-6}$ alkyl, $(CH_2)_j—CO_2R_{11}$, $O—(CH_2)_k—NR_{11}R_{12}$, $(CH_2)_j—NR_{11}R_{12}$, $C(=O)—NH—(CH_2)_k—NR_{11}R_{12}$; $C(=O)—NH—R_{24}$ and $C(=O)—NH—(CH_2)_k—C(=NH)NR_{11}R_{12}$; with the proviso that the optionally substituted $C_{5-9}$ heteroaryl is not indolyl;
$R_{19}$ is selected from H and $(CH_2)_t—NR_{20}R_{21}$;
$Y_1$ is N or CH;
$Y_2$ is N or CH; and wherein at least one of $Y_1$ and $Y_2$ is CH;
p is 0 or 1;
j, m, r and t are independently selected from an integer from 0 to 6;
k, n and s are independently selected from an integer from 1 to 6;
$X_1$ is selected from O, S, $NR_{13}$, $CR_{13}R_{14}$, $CR_{13}R_{14}O$, $C(=O)$, $C(=O)NR_{13}$, $NR_{13}C(=O)$, $O—C(O)$ and $C(O)—O$;
L is selected from an amino acid, a peptide chain having from 2 to 6 amino acids, an alkylene chain containing from 1 to 12 carbon atoms which may contain one or more carbon-carbon double or triple bonds, a paraformaldehyde chain $—(OCH_2)_{1-12}—$, a polyethylene glycol chain $—(OCH_2CH_2)_{1-6}—$, which chains may be interrupted by one or more of O, S and/or NH groups and/or $C_{3-9}$ heteroarylene and/or phenylene;
$X_2$ is selected from O, S, $NR_{15}$, $CR_{15}R_{16}$, $CR_{15}R_{16}O$, $C(=O)$, $C(=O)NR_{15}$, $NR_{15}C(=O)$, $O—C(O)$ and $C(O)—O$ or is absent;
q is selected from o, 1, 2, 3, 4, 5 and 6;
A is selected from:

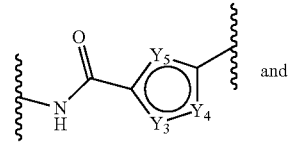 and

A1

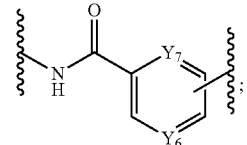

A2 for each A1 group one of $Y_3$ and $Y_4$ is independently selected from $N—R_{17}$, S and O; and the other of $Y_3$ and $Y_4$ is CH; and $Y_5$ is independently selected from CH, N, S and COH; and
for each A2 group one of $Y_6$ and $Y_7$ is independently selected from N and CH; and the other of $Y_6$ and $Y_7$ is CH;

$R_7$ and $R_9$ are independently selected from H, $C_{1-12}$ alkyl, $C_{5-9}$ heteroaryl, $C_{6-15}$ heteroarylalkyl, phenyl and $C_{7-12}$ aralkyl groups; wherein the heteroaryl, heteroarylalkyl, phenyl and aralkyl groups are optionally substituted with up to three optional substituent groups selected from $C_{1-6}$ alkyl, OH, $OC_{1-6}$ alkyl;

$R_{24}$ is a phenyl optionally substituted with up to three optional substituent groups selected from OH, $C_{1-6}$ alkyl, $OC_{1-6}$ alkyl, $(CH_2)_j—CO_2R_{11}$, $O—(CH_2)_k—NR_{11}R_{12}$, $(CH_2)_j—NR_{11}R_{12}$, $C(=O)—NH—(CH_2)_k—NR_{11}R_{12}$ and $C(=O)—NH—(CH_2)_k—C(=NH)NR_{11}R_{12}$; $R_8$, $R_{10}$, $R_{11}$, $R_{12}$, $R_{13}$, $R_{14}$, $R_{15}$, $R_{16}$, $R_{17}$, $R_{20}$ and $R_{21}$ are independently selected from H and $C_{1-6}$ alkyl;

and either:
(i) $R_5$ and $R_6$ together form a double bond;
(ii) $R_5$ is H and $R_6$ is OH; or
(iii) $R_5$ is H and $R_6$ is $OC_{1-6}$ alkyl;

with the proviso that when p is 0 and A is A1, then:
(a) for at least one A1 group one of $Y_3$ and $Y_4$ is selected from S and O; or
(b) for at least one A1 group $Y_5$ is S; or
(c) $R_4$ is not pyrrolyl, imidazolyl, optionally substituted pyrrolyl or optionally substituted imidazolyl.

The present invention provides a compound of formula (I):

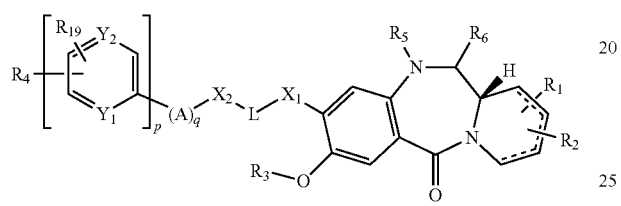

and salts and solvates thereof,
wherein;
the dotted lines indicates the optional presence of a double bond between one or more of C1 and C2, C2 and C3, and C3 and C4;

$R_1$ is selected from $R_7$, $=CH_2$, $=CH-(CH_2)_m-CH_3$, $=O$, $(CH_2)_m-OR_7$, $(CH_2)_m-CO_2R_7$, $(CH_2)_m-NR_7R_8$, $O-(CH_2)_n-NR_7R_8$, $NH-C(O)-R_7$, $O-(CH_2)_n-NH-C(O)-R_7$, $O-(CH_2)_n-C(O)-NH-R_7$, $(CH_2)_m-SO_2R_7$, $O-SO_2R_7$, $(CH_2)_m-C(O)R_7$ and $(CH_2)_m-C(O)NR_7R_8$;

$R_2$ is selected from $R_9$, $=CH_2$, $=CH-(CH_2)-CH_3$, $=O$, $(CH_2)_r-OR_9$, $(CH_2)_r-CO_2R_9$, $(CH_2)_r-NR_9R_{10}$, $O-(CH_2)_s-NR_9R_{10}$, $NH-C(O)-R_9$, $O-(CH_2)_s-NH-C(O)-R_9$, $-(CH_2)_s-C(O)-NH-R_9$, $(CH_2)_r-SO_2R_9$, $O-SO_2R_9$, $(CH_2)_r-COR_9$ and $(CH_2)_r-C(O)NR_9R_{10}$;

$R_3$ is selected from H, $C_{1-12}$ alkyl and $CH_2Ph$;

$R_4$ is selected from phenyl and $C_{5-6}$ heteroaryl groups optionally substituted with up to three optional substituent groups selected from OH, $C_{1-6}$ alkyl, $OC_{1-6}$ alkyl, $(CH_2)_j-CO_2R_{11}$, $O-(CH_2)_k-NR_{11}R_{12}$, $(CH_2)_j-NR_{11}R_{12}$, $C(=O)-NH-(CH_2)_k-NR_{11}R_{12}$; $C(=O)-NH-C_6H_4-(CH_2)_j-R_{18}$ and $C(=O)-NH-(CH_2)_k-C(=NH)NR_{11}R_{12}$; with the proviso that the optionally substituted $C_{5-9}$ heteroaryl is not indolyl;

$R_{19}$ is selected from H and $(CH_2)_t-NR_{20}R_{21}$;

$Y_1$ is N or CH;

$Y_2$ is N or CH; and wherein at least one of $Y_1$ and $Y_2$ is CH;

p is 0 or 1;

j, m, r and t are independently selected from an integer from 0 to 6;

k, n and s are independently selected from an integer from 1 to 6;

$X_1$ is selected from O, S, $NR_{13}$, $CR_{13}R_{14}$, $CR_{13}R_{14}O$, $C(=O)$, $C(=O)NR_{13}$, $NR_{13}C(=O)$, $O-C(O)$ and $C(O)-O$;

L is selected from an amino acid, a peptide chain having from 2 to 6 amino acids, an alkylene chain containing from 1 to 12 carbon atoms which may contain one or more carbon-carbon double or triple bonds, a paraformaldehyde chain $-(OCH_2)_{1-12}-$, a polyethylene glycol chain $-(OCH_2CH_2)_{1-6}-$, which chains may be interrupted by one or more of O, S and/or NH groups and/or $C_{3-9}$ heteroarylene and/or phenylene;

$X_2$ is selected from O, S, $NR_{15}$, $CR_{15}R_{16}$, $CR_{15}R_{16}O$, $C(=O)$, $C(=O)NR_{15}$, $NR_{15}C(=O)$, $O-C(O)$ and $C(O)-O$ or is absent;

q is selected from 0, 1, 2, 3, 4, 5 and 6;

A is selected from:

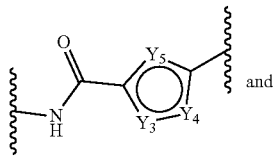

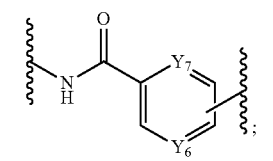

for each A1 group one of $Y_3$ and $Y_4$ is independently selected from $N-R_{17}$, S and O; and the other of $Y_3$ and $Y_4$ is CH; and $Y_5$ is independently selected from CH, N, S and COH; and for each A2 group one of $Y_6$ and $Y_7$ is independently selected from N and CH; and the other of $Y_6$ and $Y_7$ is CH;

$R_7$ and $R_9$ are independently selected from H, $C_{1-12}$ alkyl, $C_{5-9}$ heteroaryl, $C_{6-15}$ heteroarylalkyl, phenyl and $C_{7-12}$ aralkyl groups; wherein the heteroaryl, heteroarylalkyl, phenyl and aralkyl groups are optionally substituted with up to three optional substituent groups selected from $C_{1-6}$ alkyl, OH, $OC_{1-6}$ alkyl;

$R_{18}$ is selected from H, $CO_2R_{11}$ and $NR_{11}R_{12}$;

$R_8$, $R_{10}$, $R_{11}$, $R_{12}$, $R_{13}$, $R_{14}$, $R_{15}$, $R_{16}$, $R_{17}$, $R_{20}$ and $R_{21}$ are independently selected from H and $C_{1-6}$ alkyl;

and either:
(i) $R_5$ and $R_6$ together form a double bond;
(ii) $R_5$ is H and $R_6$ is OH; or
(iii) $R_5$ is H and $R_6$ is $OC_{1-6}$ alkyl;

with the proviso that when p is 0 and A is A1, then:
(a) for at least one A1 group one of $Y_3$ and $Y_4$ is selected from S and O; or
(b) for at least one A1 group $Y_5$ is S; or
(c) $R_4$ is not pyrrolyl, imidazolyl, optionally substituted pyrrolyl or optionally substituted imidazolyl.

The present invention also provides compounds comprising a guanine alkylating moiety, such as, but not limited to, a PBD, C2-substituted PBD (such as C2-endo PBD, C1/C2-endo PBD, and C2/C3-endo PBD), PDD, IBD, and QBD, and aromatic groups. Preferably the aromatic groups comprise three connected aromatic units. More preferably, the three connected aromatic units are arranged in the following order (where the heterocycle is joined to the A ring of the alkylating moiety): i) aryl-biaryl-heterocycle; or ii) aryl-benzofused-heterocycle.

The inventors have discovered that the aromatic groups as described herein provide for enhanced properties of the compounds, such as but not limited to, enhanced cytotoxicity and sequence selectivity in binding to DNA. The combination of the disclosed aromatic groups (particularly the i) aryl-biaryl-heterocycle; or ii) aryl-benzofused-heterocycle arrangement) with the alkylating moieties described herein provides compounds with improved properties as compared to the prior art.

Therefore, the present invention also provides a compound of the formula (Ia)

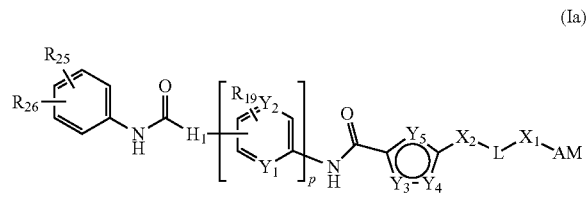

and salts and solvates thereof,
wherein
AM is an alkylating moiety;
p is 0 or 1;
when p is 1, the $H_1$ is a $C_5$ heteroaryl group optionally substituted with 1 or 2 optional substituent groups selected from OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$; C(=O)—NH—$R_{24}$ and C(=O)—NH—$(CH_2)_k$—C(=NH)$NR_{11}R_{12}$;
when p is 0, the $H_1$ is a $C_9$ heteroaryl group optionally substituted with 1 or 2 optional substituent groups selected from OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$; C(=O)—NH—$R_{24}$ and C(=O)—NH—$(CH_2)_k$—C(=NH)$NR_{11}R_{12}$;
$Y_1$ is N or CH;
$Y_2$ is N or CH; and wherein at least one of $Y_1$ and $Y_2$ is CH;
one of $Y_3$ and $Y_4$ is independently selected from N—$R_{17}$, S and O; and the other of $Y_3$ and $Y_4$ is CH;
$Y_5$ is independently selected from CH, N, S and COH;
one of $Y_8$ and $Y_9$ is independently selected from N—H, S and O; and the other of $Y_8$ and $Y_9$ is CH;
$X_1$ is selected from O, S, $NR_{13}$, $CR_{13}R_{14}$, $CR_{13}R_{14}$O, C(=O), C(=O)$NR_{13}$, $NR_{13}$C(=O), O—C(O) and C(O)—O;
L is selected from an amino acid, a peptide chain having from 2 to 6 amino acids, an alkylene chain containing from 1 to 12 carbon atoms which may contain one or more carbon-carbon double or triple bonds, a paraformaldehyde chain —(OCH$_2$)$_{1-12}$—, a polyethylene glycol chain —(OCH$_2$CH$_2$)$_{1-6}$, wherein the chain may be interrupted by one or more of O, S, NH, C, heteroarylene, phenylene, or a combination of the foregoing;
$X_2$ is selected from O, S, $NR_{15}$, $CR_{15}R_{16}$, $CR_{15}R_{16}$, C(=O), C(=O)$NR_{15}$, $NR_{15}$C(=O), O—C(O) and C(O)—O or is absent;
$R_{19}$ is selected from H and $(CH_2)_t$—$NR_{20}R_{21}$;
$R_{24}$ is a phenyl optionally substituted with up to three optional substituent groups selected from OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$ and C(=O)—NH—$(CH_2)_k$—C(=NH)$NR_{11}R_{12}$;
$R_{25}$ and $R_{26}$ are independently selected from H, OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$ and C(=O)—NH—$(CH_2)_k$—C(=NH)$NR_{11}R_{12}$; each $R_{11}$, $R_{12}$, $R_{13}$, $R_{14}$, $R_{15}$, $R_{16}$, $R_{17}$, $R_{20}$ and $R_{21}$ are independently selected from H and $C_{1-6}$ alkyl;

j and t are independently an integer from 0 to 6; and
k is an integer from 1 to 6.

The present disclosure also provides additional compound of formula (Ia).

The present disclosure provides a compound of the Formula (XXIV):

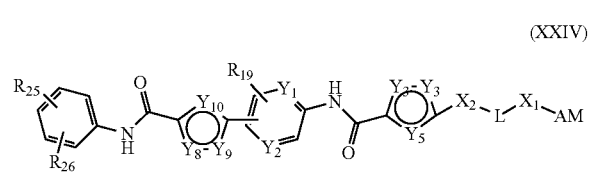

and salts and solvates thereof,
wherein
AM, $X_1$, L, $X_2$, $Y_1$, $Y_2$, $Y_3$, $Y_4$, $Y_5$, $R_{11}$, $R_{12}$, $R_{13}$, $R_{14}$, $R_{15}$, $R_{16}$, $R_{17}$, $R_{19}$, $R_{20}$, $R_{21}$, $R_{25}$, $R_{26}$, k and j are t are as defined for the compound of formula (Ia);
one of $Y_8$ and $Y_9$ is independently selected from N—H, S and O; and the other of $Y_8$ and $Y_9$ is CH; $Y_{10}$ is independently selected from CH and N, where the H of the CH and N—H are optionally substituted with optional substituent groups selected from OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$; C(=O)—NH—$C_6H_4$—$(CH_2)_j$—$R_{18}$ and C(=O)—NH—$(CH_2)_k$—C(=NH)$NR_{11}R_{12}$; and $R_{18}$ is selected from $CO_2R_{11}$ and $NR_{11}R_{12}$.

The present invention further provides a compound of the formula (X(V) and (XXVI):

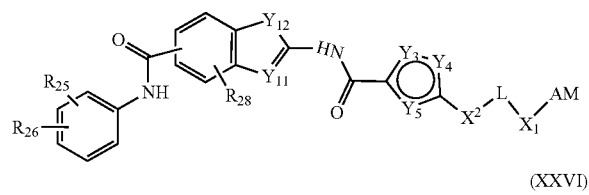

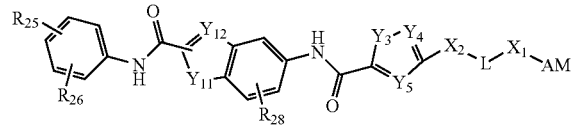

and salts and solvates thereof,
wherein
AM, $X_1$, L, $X_2$, $Y_3$, $Y_4$, $Y_5$, $R_{11}$, $R_{12}$, $R_{13}$, $R_{14}$, $R_{15}$, $R_{16}$, $R_{17}$, $R_{25}$, $R_{26}$, k and j are as defined for the compound of formula (Ia);
$Y_{11}$ is selected from N—$R_{27}$, S and O;
$Y_{12}$ is selected from CH and N;
with the proviso that the heteroaryl group containing $Y_{11}$ and $Y_{12}$ is not indolyl; and $R_{27}$ and $R_{28}$ are independently selected from H, OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$ and C(=O)—NH—$(CH_2)_k$—C(=NH)$NR_{11}R_{12}$.

In the foregoing compounds of the formula (Ia), (XXIV), (XXV), and (XXVI), the AM moiety is a compound of the formula (XXVII):

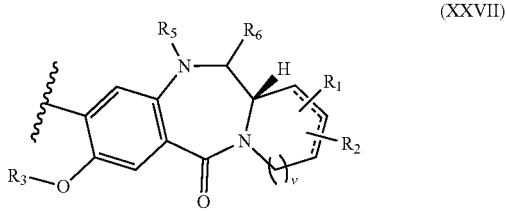

(XXVII)

wherein
v is 0 or 1;
when v is 1, the dotted lines represent single bonds; and $R_1$ and $R_2$ are attached to adjacent carbon atoms on the C-ring and together with the carbon atoms to which they are attached form an aromatic 6-membered ring substituted with groups $RD_1$, $RD_2$, $RD_3$ and $RD_4$;
when v is 0, the dotted lines represent single bonds or one double bond and one single bond wherein the double bond is between C1 and C2 or between C2 and C3;
when v is 0 and the dotted lines represent single bonds then either:
  $R_1$ and $R_2$ are attached to adjacent carbon atoms on the C-ring and together with the carbon atoms to which they are attached form an aromatic 6-membered ring substituted with groups $RD_1$, $RD_2$, $RD_3$ and $RD_4$; or
  $R_1$ is absent and $R_2$ is attached to the C2 carbon and is $=C(RD_5)(RD_6)$; or
  $R_1$ and $R_2$ are independently selected from H, OH, $C_{1-6}$ alkyl, $OC_{1-6}$ alkyl and halogen;
when v is 0 and the dotted lines represent one double bond and one single bond wherein the double bond is between C1 and C2 or between C2 and C3; then $R_1$ is absent and R2 is a $C_{1-6}$ alkyl, a phenyl ring or a $C_{5-9}$ heteroaryl group optionally substituted with groups $RD_1$, $RD_2$, $RD_3$, $RD_4$ and $RD_7$;
$RD_1$, $RD_2$, $RD_3$, $RD_4$ and $RD_7$ are independently selected from H, OH, $C_{1-6}$ alkyl, $OC_{1-6}$ alkyl and halogen;
$RD_5$ and $RD_6$ are independently selected from H and $C_{1-6}$ alkyl;
$R_3$ is selected from H, $C_{1-12}$ alkyl and $CH_2Ph$; and either:
  (i) $R_5$ and $R_6$ together form a double bond;
  (ii) $R_5$ is H and $R_6$ is selected from OH and $OC_{1-6}$ alkyl; or
  (iii) $R_5$ is $SO_3H$ and $R_6$ is H.

In a further aspect, there is provided a compound of formula (I), (XXIV), (XXV), and (XXVI) and salts and solvates thereof for use in a method of therapy.

In a further aspect, there is provided a compound of formula (I), (XXIV), (XXV), and (XXVI) and salts and solvates thereof for use as a medicament.

In a further aspect, there is provided a compound of formula (I), (XXIV), (XXV), and (XXVI) and salts and solvates thereof for use in the treatment of a proliferative disease.

In a further aspect, there is provided a pharmaceutical composition comprising at least one compound of formula (I), (XXIV), (XXV), and (XXVI) and salts and solvates thereof and a pharmaceutically acceptable excipient, carrier or diluent.

In a further aspect, the present invention provides the use of a compound of formula (I), (XXIV), (XXV), and (XXVI) and salts and solvates thereof in the manufacture of a medicament for treating a proliferative disease.

In a further aspect, the present invention provides a method of treatment of a patient suffering from a proliferative disease, comprising administering to said patient a therapeutically effective amount of at least one compound of formula (I), (XXIV), (XXV), and (XXVI) and salts and solvates thereof or a pharmaceutical composition of the present invention.

In a further aspect, the at least one compound of formula (I), (XXIV), (XXV), and (XXVI) and salts and solvates thereof may be administered alone or in combination with other treatments, either simultaneously or sequentially depending upon the condition to be treated.

The pharmaceutical composition of the present invention may further comprise one or more (e.g. two, three or four) further active agents.

In a further aspect of the compound of formula (I) and salts and solvates thereof, the following proviso applies: i) L is a peptide chain having from 2 to 6 amino acids, an alkylene chain containing from 1 to 12 carbon atoms which may contain one or more carbon-carbon double or triple bonds, a paraformaldehyde chain, a polyethylene glycol chain, which chains are interrupted by one or more of $C_{5-9}$ heteroarylene, phenylene or combinations of the foregoing; and/or ii) p is 1; and/or iii) q is 1, 2, 3, 4, 5 or 6.

In a further aspect, the compound of formula (I), (XXIV), (XXV), and (XXVI) and salts and solvates thereof, may be linked, either directly or indirectly, to a targeting agent (e.g., antibody, antibody fragment, hormone, etc.) to provide a targeted conjugate. In a further aspect, the compound of formula (I) and salts and solvates thereof, may contain a linker group, wherein the targeting agent is attached to the compound of formula (I), (XXIV), (XXV), and (XXVI) and salts and solvates thereof, through the linker group. The target conjugates of the present disclosure may contain one or multiple compounds of formula (I), (XXIV), (XXV), and (XXVI) (or salts and solvates thereof). A variety of target conjugates are known in the art and may be used with a compound of formula (I), (XXIV), (XXV), and (XXVI) and salts and solvates thereof. For example, in a particular aspect the target conjugate is an antibody-drug conjugate, wherein one or more compounds of formula (I), (XXIV), (XXV), and (XXVI) are linked, directly or indirectly, to the antibody. Therefore, the compound of formula (I), (XXIV), (XXV), and (XXVI) and salts and solvates thereof, may be used as a payload on a targeted conjugate.

Definitions

The following abbreviations are used throughout the specification: Ac acetyl; Alloc allyloxycarbonyl; BAIB bis(acetoxy)iodobenzene/(diacetoxyiodo)benzene; Boc tert-butoxycarbonyl; BPDs benzopyrridodiazecines; CBz benzyloxycarbonyl; DBU 1,8-diazabicyclo[5.4.0]undec-7-ene; DHP dihydropyran; DMAP 4-dimethylaminopyridine; DMF dimethylformamide; DMSO dimethylsulfoxide; EDCl1-Ethyl-3-(3-dimethylaminopropyl)carbodiimide; Et ethyl; $Et_2O$ diethyl ether; EtOAc ethyl acetate; EtOH ethanol; HATU (1-[Bis(dimethylamino)methylene]-1H-1,2,3-triazolo[4,5-b]pyridinium 3-oxid hexafluorophosphate); HMDST hexamethyldisilathiane; iBu iso-butyl; KOtBu potassium t-butoxide; L-Selectride Lithium tri-sec-butyl(hydride)borate; Me methyl; MeOH methanol; PBDs pyrrolo[2,1-c][1,4]benzo-diazepines; PDDs pyrridinobenzodiazepines; PIFA phenyliodine (III) bis[trifluoroacetate]; Ph phenyl; p-TSA/PTSA p-Toluenesulfonic acid; Pyr pyridine; TBAF tetrabutylammonium fluoride; TBS-Cl/TBDMSCl-tert-butyldimethylsilyl chloride; TEA triethylamine;

TEMPO (2,2,6,6-tetramethyl-piperidin-1-yl)oxyl; TFA trifluoroacetic acid; THF tetrahydrofuran; THP tetrahydropyranyl; Troc 2,2,2-Trichloroethyl carbonate and Ts (tosylate) p-toluene sulfonic acid.

"Substituted", when used in connection with a chemical substituent or moiety (e.g., an alkyl group), means that one or more hydrogen atoms of the substituent or moiety have been replaced with one or more non-hydrogen atoms or groups, provided that valence requirements are met and that a chemically stable compound results from the substitution.

"Optionally substituted" refers to a parent group which may be unsubstituted or which may be substituted with one or more substituents. Suitably, unless otherwise specified, when optional substituents are present the optional substituted parent group comprises from one to three optional substituents. Where a group may be "optionally substituted with up to three groups", this means that the group may be substituted with 0, 1, 2 or 3 of the optional substituents. Where a group may be "optionally substituted with one or two optional substituents", this means that the group may be substituted with 0, 1 or 2 of the optional substituents. Suitably groups may be optionally substituted with 0 or 1 optional substituents.

"Independently selected" is used in the context of statement that, for example, "$R_1$ and $R_2$ are independently selected from H, $C_{1-12}$ alkyl, phenyl, . . . " and means that each instance of the functional group, e.g. $R_1$, is selected from the listed options independently of any other instance of $R_1$ or $R_2$ in the compound. Hence, for example, a $C_{1-12}$ alkyl may be selected for the first instance of $R_1$ in the compound; a phenyl group may be selected for the next instance of $R_1$ in the compound; and H may be selected for the first instance of $R_2$ in the compound.

$C_{1-12}$ alkyl: refers to straight chain and branched saturated hydrocarbon groups, generally having from 1 to 12 carbon atoms; more suitably $C_{1-7}$ alkyl; more suitably $C_{1-6}$ alkyl. Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and the like.

"Alkylene" refers to a divalent radical derived from an alkane which may be a straight chain or branched, as exemplified by $CH_2CH_2CH_2CH_2$—.

"Aryl": refers to fully unsaturated monocyclic, bicyclic and polycyclic aromatic hydrocarbons having at least one aromatic ring and having a specified number of carbon atoms that comprise their ring members (e.g., $C_{6-14}$ aryl refers to an aryl group having 6 to 14 carbon atoms as ring members). The aryl group may be attached to a parent group or to a substrate at any ring atom and may include one or more non-hydrogen substituents unless such attachment or substitution would violate valence requirements. Examples of aryl groups include phenyl.

"$C_{7-12}$ aralkyl" refers to an arylalkyl group having 7 to 12 carbon atoms and comprising an alkyl group substituted with an aryl group. Suitably the alkyl group is a $C_{1-6}$ alkyl group and the aryl group is phenyl. Examples of $C_{7-12}$ aralkyl include benzyl and phenethyl. In some cases the $C_{7-12}$ aralkyl group may be optionally substituted and an example of an optionally substituted $C_{7-12}$ aralkyl group is 4-methoxybenzyl.

"$C_{5-9}$ heteroaryl": refers to unsaturated monocyclic or bicyclic aromatic groups comprising from 5 to 9 ring atoms, whether carbon or heteroatoms, of which from 1 to 5 are ring heteroatoms. Suitably, any monocyclic heteroaryl ring has from 5 to 6 ring atoms and from 1 to 3 ring heteroatoms. Suitably each ring heteroatom is independently selected from nitrogen, oxygen, and sulfur. The bicyclic rings include fused ring systems and, in particular, include bicyclic groups in which a monocyclic heterocycle comprising 5 ring atoms is fused to a benzene ring. The heteroaryl group may be attached to a parent group or to a substrate at any ring atom and may include one or more non-hydrogen substituents unless such attachment or substitution would violate valence requirements or result in a chemically unstable compound.

Examples of monocyclic heteroaryl groups include, but are not limited to, those derived from:
$N_1$: pyrrole, pyridine;
$O_1$: furan;
$S_1$: thiophene;
$N_1O_1$: oxazole, isoxazole, isoxazine;
$N_2O_1$: oxadiazole (e.g. 1-oxa-2,3-diazolyl, 1-oxa-2,4-diazolyl, 1-oxa-2,5-diazolyl, 1-oxa-3,4-diazolyl);
$N_3O_1$: oxatriazole;
$N_1S_1$: thiazole, isothiazole;
$N_2$: imidazole, pyrazole, pyridazine, pyrimidine, pyrazine;
$N_3$: triazole, triazine; and,
$N_4$: tetrazole.

Examples of heteroaryl which comprise fused rings, include, but are not limited to, those derived from:
$O_1$: benzofuran, isobenzofuran;
$N_1$: indole, isoindole, indolizine, isoindoline;
$S_1$: benzothiofuran;
$N_1O_1$: benzoxazole, benzisoxazole;
$N_1S_1$: benzothiazole;
$N_2$: benzimidazole, indazole;
$O_2$: benzodioxole;
$N_2O_1$: benzofurazan;
$N_2S_1$: benzothiadiazole;
$N_3$: benzotriazole; and
$N_4$: purine (e.g., adenine, guanine), pteridine;

"Heteroarylene" refers to a divalent radical derived from a heteroaryl group, as exemplified by pyridinylene —$C_5H_3N$)—.

"$C_{6-15}$ heteroarylalkyl" refers to an alkyl group substituted with a heteroaryl group.

Suitably the alkyl is a $C_{1-6}$ alkyl group and the heteroaryl group is $C_{5-9}$ heteroaryl as defined above. Examples of $C_{6-15}$ heteroarylalkyl groups include pyrrol-2-ylmethyl, pyrrol-3-ylmethyl, pyrrol-4-ylmethyl, pyrrol-3-ylethyl, pyrrol-4-ylethyl, imidazol-2-ylmethyl, imidazol-4-ylmethyl, imidazol-4-ylethyl, thiophen-3-ylmethyl, furan-3-ylmethyl, pyridin-2-ylmethyl, pyridin-2-ylethyl, thiazol-2-ylmethyl, thiazol-4-ylmethyl, thiazol-2-ylethyl, pyrimidin-2-ylpropyl, and the like.

Nitrogen Protecting Groups

Nitrogen protecting groups are well known in the art. Preferred nitrogen protecting groups are carbamate protecting groups that have the general formula:

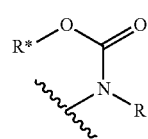

A large number of possible carbamate nitrogen protecting groups are listed on pages 706 to 771 of Wuts, P. G. M. and Greene, T. W., Protective Groups in Organic Synthesis, 4th Edition, Wiley-lnterscience, 2007, and in P. Kocienski, Protective Groups, 3rd Edition (2005) which are incorporated herein by reference.

Particularly preferred protecting groups include Alloc (allyloxycarbonyl), Troc (2,2,2-Trichloroethyl carbonate), Teoc [2-(Trimethylsilyl)ethoxycarbony], BOC (tert-butyloxycarbonyl), Doc (2,4-dimethylpent-3-yloxycarbonyl), Hoc (cyclohexyloxy-carbonyl), TcBOC (2,2,2-trichlorotert-butyloxycarbonyl), Fmoc (9-fluorenylmethyloxycarbonyl), i-Adoc (1-Adamantyloxycarbonyl) and 2-Adoc (2-adamantyloxycarbonyl).

Hydroxyl Protecting Groups

Hydroxyl protecting groups are well known in the art, a large number of suitable groups are described on pages 16 to 366 of Wuts, P. G. M. and Greene, T. W., Protective Groups in Organic Synthesis, 4th Edition, Wiley-lnterscience, 2007, and in P. Kocienski, Protective Groups, 3rd Edition (2005) which are incorporated herein by reference.

Classes of particular interest include silyl ethers, methyl ethers, alkyl ethers, benzyl ethers, esters, benzoates, carbonates, and sulfonates.

Particularly preferred protecting groups include THP (tetrahydropyranyl ether).

"Compound of formula (I) and salts and solvates thereof" refers to the compounds of formula (I); salts of compounds of formula (I); solvates of compounds of formula (I); and solvates of salts of compounds of formula (I).

"Drug", "drug substance", "active pharmaceutical ingredient", and the like, refer to a compound (e.g., compounds of formula (I) and compounds specifically named above) that may be used for treating a subject in need of treatment.

"Excipient" refers to any substance that may influence the bioavailability of a drug, but is otherwise pharmacologically inactive.

"Pharmaceutically acceptable" substances refers to those substances which are within the scope of sound medical judgment suitable for use in contact with the tissues of subjects without undue toxicity, irritation, allergic response, and the like, commensurate with a reasonable benefit-to-risk ratio, and effective for their intended use.

"Pharmaceutical composition" refers to the combination of one or more drug substances and one or more excipients.

The term "subject" as used herein refers to a human or non-human mammal. Examples of non-human mammals include livestock animals such as sheep, horses, cows, pigs, goats, rabbits and deer; and companion animals such as cats, dogs, rodents, and horses.

"Therapeutically effective amount" of a drug refers to the quantity of the drug or composition that is effective in treating a subject and thus producing the desired therapeutic, ameliorative, inhibitory or preventative effect. The therapeutically effective amount may depend on the weight and age of the subject and the route of administration, among other things.

"Treating" refers to reversing, alleviating, inhibiting the progress of, or preventing a disorder, disease or condition to which such term applies, or to reversing, alleviating, inhibiting the progress of, or preventing one or more symptoms of such disorder, disease or condition.

"Treatment" refers to the act of "treating", as defined immediately above.

As used herein the term "comprising" means "including at least in part of" and is meant to be inclusive or open ended. When interpreting each statement in this specification that includes the term "comprising", features, elements and/or steps other than that or those prefaced by the term may also be present. Related terms such as "comprise" and "comprises" are to be interpreted in the same manner.

$R_1$ $R_1$ is selected from $R_7$, $=CH_2$, $-CH-(CH_2)_m-CH_3$, $=O$, $(CH_2)_m-OR_7$, $(CH_2)_m-CO_2R_7$, $(CH_2)_m-NR_7R_8$, $O-(CH_2)_n-NR_7R_8$, $NH-C(O)-R_7$, $O-(CH_2)_n-NH-C(O)-R_7$, $O-(CH_2)_n-C(O)-NH-R_7$, $(CH_2)_m-SO_2R_7$, $O-SO_2R_7$, $(CH_2)_m-C(O)R_7$ and $(CH_2)_m-C(O)NR_7R_8$. For the options where $R_1$ is selected from $=CH_2$, $=CH-(CH_2)_m-CH_3$ and $=O$, the carbon of the C-ring to which it is attached cannot have an optional double bond in order for the valence requirements of the molecule to be met. For example, if $R_1$ is $=CH_2$, and is positioned at the C1 position of the C-ring adjacent to the fused carbon of the C-ring, and $R_2$ is H then the resulting compound of formula (I) may be represented as:

Suitably $R_1$ is selected from $R_7$, $(CH_2)_m-OR_7$, $(CH_2)_m-CO_2R_7$, $(CH_2)_m-NR_7R_8$, $O-(CH_2)_n-NR_7R_8$, $NH-C(O)-R_7$, $O-(CH_2)_n-NH-C(O)-R_7$, $O-(CH_2)_n-C(O)-NH-R_7$, $(CH_2)_m-SO_2R_7$, $O-SO_2R_7$, $(CH_2)_m-C(O)R_7$ and $(CH_2)_m-C(O)NR_7R_8$.

Suitably $R_1$ is selected from $R_7$, $(CH_2)_m-OR_7$, $(CH_2)_m-CO_2R_7$, $(CH_2)_m-NR_7R_8$, $O-(CH_2)_n-NR_7R_8$, $NH-C(O)-R_7$, $O-(CH_2)_n-NH-C(O)-R_7$, $O-(CH_2)_n-C(O)-NH-R_7$, $(CH_2)_m-C(O)R_7$ and $(CH_2)_m-C(O)NR_7R_8$.

Suitably $R_1$ is selected from $R_7$, $OR_7$, $CO_2R_7$, $NR_7R_8$, $NH-C(O)-R_7$, $O-(CH_2)_n-NH-C(O)-R_7$, $O-(CH_2)_n-C(O)-NH-R_7$, $C(O)R_7$ and $C(O)NR_7R_8$.

Suitably $R_1$ is selected from $R_7$, $OR_7$, $CO_2R_7$, $O-(CH_2)_n-NH-C(O)-R_7$, $O-(CH_2)_n-C(O)-NH-R_7$, $C(O)R_7$ and $C(O)NR_7R_8$.

Suitably $R_1$ is selected from $R_7$, $O-(CH_2)_n-NH-C(O)-R_7$ and $O-(CH_2)_n-C(O)-NH-R_7$.

In some embodiments $R_1$ is H.

$R_2$ $R_2$ is selected from $R_9$, $(CH_2)_r-OR_9$, $(CH_2)_r-CO_2R_9$, $(CH_2)_r-NR_9R_{10}$, $O-(CH_2)_s-NR_9R_{10}$, $NH-C(O)-R_9$, $O-(CH_2)_s-NH-C(O)-R_9$, $O-(CH_2)_s-C(O)-NH-R_9$, $(CH_2)_r-SO_2R_9$, $O-SO_2R_9$, $(CH_2)_r-COR_9$ and $(CH_2)_r-C(O)NR_9R_{10}$.

Suitably $R_2$ is selected from $R_9$, $(CH_2)_r-OR_9$, $(CH_2)_r-CO_2R_9$, $(CH_2)_r-NR_9R_{10}$, $O-(CH_2)_s-NR_9R_{10}$, $NH-C(O)-R_9$, $O-(CH_2)_s-NH-C(O)-R_9$, $O-(CH_2)_s-C(O)-NH-R_9$, $(CH_2)_r-COR_9$ and $(CH_2)_r-C(O)NR_9R_{10}$.

Suitably $R_2$ is selected from $R_9$, $OR_9$, $CO_2R_9$, $NR_9R_{10}$, $NH-C(O)-R_9$, $O-(CH_2)_s-NH-C(O)-R_9$, $O-(CH_2)_s-C(O)-NH-R_9$, $COR_9$ and $C(O)NR_9R_{10}$.

Suitably $R_2$ is selected from $R_9$, $OR_9$, $CO_2R_9$, $O-(CH_2)_s-NH-C(O)-R_9$, $O-(CH_2)_s-C(O)-NH-R_9$, $COR_9$ and $C(O)NR_9R_{10}$.

Suitably $R_2$ is selected from $R_9$, $O-(CH_2)_s-NH-C(O)-R_9$ and $O-(CH_2)_s-C(O)-NH-R_9$.

In some embodiments $R_2$ is H.

$R_3$

Suitably $R_3$ is selected from H, $C_{1-6}$ alkyl and $CH_2Ph$.

Suitably $R_3$ is selected from H, methyl, ethyl and $CH_2Ph$.

More suitably $R_3$ is selected from methyl and ethyl.

More suitably $R_3$ is methyl.

$R_4$ $R_4$ is selected from phenyl and $C_{5-9}$ heteroaryl groups optionally substituted with up to three optional substituent groups. Hence, any of the phenyl group or the $C_{5-9}$ heteroaryl groups selected for $R_4$ may be optionally substituted with up to three optional substituent groups.

Suitably $R_4$ is selected from phenyl, pyrrolyl, N-methylpyrrolyl, furanyl, thiophenyl, imidazolyl, N-methylimidazolyl, oxazolyl, thiazolyl, pyridyl, benzofuranyl, benzothiophenyl, benzimidazolyl, N-methylbenzoimidazolyl, benzooxazolyl and benzothiazolyl, optionally substituted with up to three optional substituent groups selected from OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$; C(=O)—NH—$R_{24}$ and C(=O)—NH—$(CH_2)_k$—C(=NH)$NR_{11}R_{12}$.

Suitably $R_4$ is selected from phenyl, pyrrolyl, N-methylpyrrolyl, furanyl, thiophenyl, imidazolyl, N-methylimidazolyl, oxazolyl, thiazolyl, benzofuranyl, benzothiophenyl, benzimidazolyl, N-methylbenzoimidazolyl, benzooxazolyl and benzothiazolyl, optionally substituted with one or two optional substituent groups selected from OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$; C(=O)—NH—$R_{24}$ and C(=O)—NH—$(CH_2)_k$—C(=NH)$NR_{11}R_{12}$.

Suitably $R_4$ is selected from phenyl, N-methylpyrrolyl, thiophenyl, N-methylimidazolyl, oxazolyl, thiazolyl, benzothiophenyl, N-methylbenzoimidazolyl and benzothiazolyl, optionally substituted with one or two optional substituent groups selected from OH, $C_{1-6}$ alkyl, $OC_{1-6}$ alkyl, $(CH_2)_j$—$CO_2R_{11}$ O—$(CH_2)_k$—$NR_{11}R_{12}$, $(CH_2)_j$—$NR_{11}R_{12}$, C(=O)—NH—$(CH_2)_k$—$NR_{11}R_{12}$; C(=O)—NH—$R_{24}$ and C(=O)—NH—$(CH_2)_k$—C(=NH)$NR_{11}R_{12}$.

Suitably $R_4$ is optionally substituted with up to three optional substituent groups selected from OH, $C_{1-6}$ alkyl, $OC_{1-6}$ alkyl, $(CH_2)_j$—$CO_2R_{11}$, O—$(CH_2)_k$—$NH_2$, $(CH_2)_j$—$NH_2$, C(=O)—NH—$(CH_2)_k$—$NH_2$; C(=O)—NH—$R_{24}$ and C(=O)—NH—$(CH_2)_k$—C(=NH)$NH_2$.

Suitably $R_4$ is an optionally substituted C(=O)—NH—$R_{24}$, wherein $R_{24}$ is —$C_6H_4$—$(CH_2)_j$—$R_{18}$, and the phenylene group —$C_6H_4$— is para substituted.

Suitably $R_4$ is optionally substituted with up to three optional substituent groups selected from OH, methyl, ethyl, $OCH_3$, $OCH_2CH_3$, $CO_2H$, $CO_2CH_3$, $CO_2CH_2CH_3$, O—$(CH_2)_k$—$NH_2$ and $(CH_2)_j$—$NH_2$.

Suitably $R_4$ is optionally substituted with one or two optional substituent groups.

More suitably $R_4$ is optionally substituted with one optional substituent group.

More suitably $R_4$ is selected from:

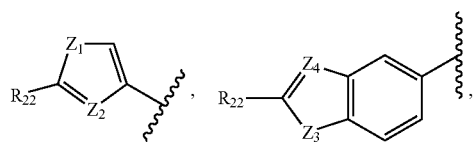

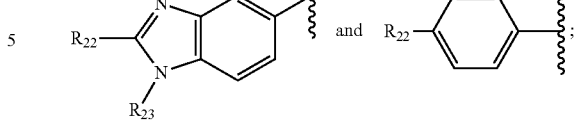

wherein $Z_1$ is selected from NH, N—$CH_3$, S and O; $Z_2$ is selected from CH and N;

$Z_3$ is selected from S and O;

$Z_4$ is selected from CH and N;

$R_{22}$ is selected from $(CH_2)_j CO_2R_{11}$, $(CH_2)_j NR_{11}R_{12}$ and C(=O)—NH—$C_6H_4(CH_2)_j$—$R_{18}$;

$R_{18}$ is selected from H, $CO_2R_{11}$ and $NR_{11}R_{12}$;

j is selected from an integer from 0 to 6;

$R_{11}$ and $R_{12}$ are independently selected from H and $C_{1-6}$ alkyl; and $R_{23}$ is selected from H and $C_{1-6}$ alkyl.

The wavy line indicates the point of attachment of the above $R_4$ group to the rest of the compound of formula (I).

More suitably $R_4$ is selected from:

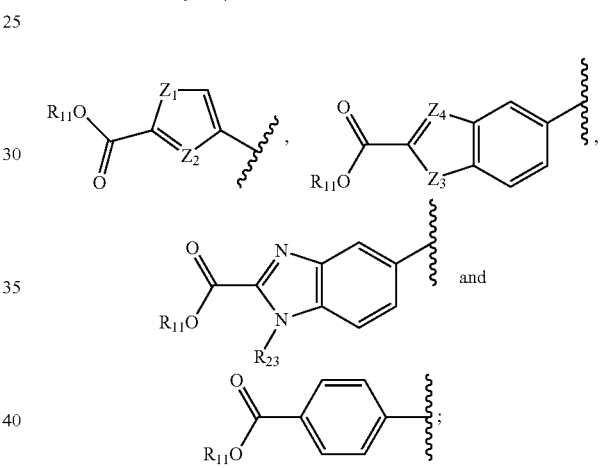

wherein $Z_1$ is selected from NH, N—$CH_3$, S and O;

$Z_2$ is selected from CH and N; and $Z_3$ is selected from S and O;

$Z_4$ is selected from CH and N;

$R_{11}$ is selected from H and $C_{1-6}$ alkyl; and $R_{23}$ is selected from H and $C_{1-6}$ alkyl.

$R_5$ and $R_6$

Suitably for (iii) $R_5$ is H and $R_6$ is an $OC_{1-6}$ alkyl selected from O—$CH_3$ and O—$CH_2CH_3$.

Most suitably, (i) $R_5$ and $R_6$ together form a double bond.

$R_7$

Suitably $R_7$ is selected from H, $C_{1-12}$ alkyl, $C_{5-9}$ heteroaryl, $C_{6-15}$ heteroarylalkyl, phenyl, benzyl and phenethyl; wherein the heteroaryl, heteroarylalkyl, phenyl and aralkyl groups are optionally substituted with up to three groups selected from $C_{1-6}$ alkyl, OH, $OC_{1-6}$ alkyl.

Suitably $R_7$ is selected from H, $C_{1-12}$ alkyl, pyrrolyl, N-methylpyrrolyl, furanyl, thiophenyl, imidazolyl, N-methylimidazolyl, oxazolyl, thiazolyl, pyridyl, indolyl, N-methylindolyl, benzofuranyl, benzothiophenyl, benzimidazolyl, N-methylbenzoimidazolyl, benzooxazolyl, benzothiazolyl, pyrrol-3-ylmethyl, pyrrol-4-ylmethyl, imidazol-2-ylmethyl, imidazol-4-ylmethyl, thiophen-3-ylmethyl, furan-3-ylmethyl, phenyl, benzyl and phenethyl; wherein the heteroaryl, heteroarylalkyl, phenyl and aralkyl groups are optionally substituted with up to three groups selected from $C_{1-6}$ alkyl, OH, $OC_{1-6}$ alkyl.

Suitably $R_7$ is selected from H, $C_{1-6}$ alkyl, pyrrolyl, N-methylpyrrolyl, furanyl, thiophenyl, imidazolyl, N-methylimidazolyl, oxazolyl, thiazolyl, pyridyl, indolyl, N-methylindolyl, benzofuranyl, benzothiophenyl, benzimidazolyl, N-methylbenzoimidazolyl, benzooxazolyl, benzothiazolyl, pyrrol-3-ylmethyl, pyrrol-4-ylmethyl, imidazol-2-ylmethyl, imidazol-4-ylmethyl, thiophen-3-ylmethyl, furan-3-ylmethyl, phenyl, benzyl and phenethyl; wherein the heteroaryl, heteroarylalkyl, phenyl and aralkyl groups are optionally substituted with up to three groups selected from $C_{1-6}$ alkyl, OH, $OC_{1-6}$ alkyl.

Suitably $R_7$ is selected from H, methyl, ethyl, n-propyl, i-propyl, n-butyl, s-butyl, i-butyl, t-butyl, pyrrolyl, N-methylpyrrolyl, furanyl, thiophenyl, imidazolyl, N-methylimidazolyl, oxazolyl, thiazolyl, pyridyl, indolyl, N-methylindolyl, benzofuranyl, benzothiophenyl, benzimidazolyl, N-methylbenzoimidazolyl, benzooxazolyl, benzothiazolyl, pyrrol-3-ylmethyl, pyrrol-4-ylmethyl, imidazol-2-ylmethyl, imidazo-4-ylmethyl, thiophen-3-ylmethyl, furan-3-ylmethyl, phenyl, benzyl and phenethyl optionally substituted with up to three groups selected from $C_{1-6}$ alkyl, OH, $OC_{1-6}$ alkyl.

Suitably $R_7$ is selected from H, methyl, ethyl, n-propyl, i-propyl, n-butyl, s-butyl, i-butyl, t-butyl, pyrrolyl, N-methylpyrrolyl, furanyl, thiophenyl, imidazolyl, N-methylimidazolyl, oxazolyl, thiazolyl, pyridyl, indolyl, N-methylindolyl, benzofuranyl, benzothiophenyl, benzimidazolyl, N-methylbenzoimidazolyl, benzooxazolyl, benzothiazolyl, phenyl, benzyl and phenethyl optionally substituted with up to three groups selected from $C_{1-6}$ alkyl, OH, $OC_{1-6}$ alkyl.

In some embodiments, $R_7$ is selected from H, methyl, ethyl, n-propyl, i-propyl, n-butyl, s-butyl, i-butyl, t-butyl.

$R_9$

Suitably $R_9$ is selected from H, $C_{1-12}$ alkyl, $C_{5-9}$ heteroaryl, $C_{6-15}$ heteroarylalkyl, phenyl, benzyl and phenethyl; wherein the heteroaryl, heteroarylalkyl, phenyl and aralkyl groups are optionally substituted with up to three groups selected from $C_{1-6}$ alkyl, OH, $OC_{1-6}$ alkyl.

Suitably $R_9$ is selected from H, $C_{1-12}$ alkyl, pyrrolyl, N-methylpyrrolyl, furanyl, thiophenyl, imidazolyl, N-methylimidazolyl, oxazolyl, thiazolyl, pyridyl, indolyl, N-methylindolyl, benzofuranyl, benzothiophenyl, benzimidazolyl, N-methylbenzoimidazolyl, benzooxazolyl, benzothiazolyl, pyrrol-3-ylmethyl, pyrrol-4-ylmethyl, imidazol-2-ylmethyl, imidazol-4-ylmethyl, thiophen-3-ylmethyl, furan-3-ylmethyl, phenyl, benzyl and phenethyl; wherein the heteroaryl, heteroarylalkyl, phenyl and aralkyl groups are optionally substituted with up to three groups selected from $C_{1-6}$ alkyl, OH, $OC_{1-6}$ alkyl.

Suitably $R_9$ is selected from H, $C_{1-6}$ alkyl, pyrrolyl, N-methylpyrrolyl, furanyl, thiophenyl, imidazolyl, N-methylimidazolyl, oxazolyl, thiazolyl, pyridyl, indolyl, N-methylindolyl, benzofuranyl, benzothiophenyl, benzimidazolyl, N-methylbenzoimidazolyl, benzooxazolyl, benzothiazolyl, pyrrol-3-ylmethyl, pyrrol-4-ylmethyl, imidazol-2-ylmethyl, imidazol-4-ylmethyl, thiophen-3-ylmethyl, furan-3-ylmethyl, phenyl, benzyl and phenethyl; wherein the heteroaryl, heteroarylalkyl, phenyl and aralkyl groups are optionally substituted with up to three groups selected from $C_{1-6}$ alkyl, OH, $OC_{1-6}$ alkyl.

Suitably $R_9$ is selected from H, methyl, ethyl, n-propyl, i-propyl, n-butyl, s-butyl, i-butyl, t-butyl, pyrrolyl, N-methylpyrrolyl, furanyl, thiophenyl, imidazolyl, N-methylimidazolyl, oxazolyl, thiazolyl, pyridyl, indolyl, N-methylindolyl, benzofuranyl, benzothiophenyl, benzimidazolyl, N-methylbenzoimidazolyl, benzooxazolyl, benzothiazolyl, pyrrol-3-ylmethyl, pyrrol-4-ylmethyl, imidazol-2-ylmethyl, imidazol-4-ylmethyl, thiophen-3-ylmethyl, furan-3-ylmethyl, phenyl, benzyl and phenethyl optionally substituted with up to three groups selected from $C_{1-6}$ alkyl, OH, $OC_{1-6}$ alkyl.

Suitably $R_9$ is selected from H, methyl, ethyl, n-propyl, i-propyl, n-butyl, s-butyl, i-butyl, t-butyl, pyrrolyl, N-methylpyrrolyl, furanyl, thiophenyl, imidazolyl, N-methylimidazolyl, oxazolyl, thiazolyl, pyridyl, indolyl, N-methylindolyl, benzofuranyl, benzothiophenyl, benzimidazolyl, N-methylbenzoimidazolyl, benzooxazolyl, benzothiazolyl, phenyl, benzyl and phenethyl optionally substituted with up to three groups selected from $C_{1-6}$ alkyl, OH, $OC_{1-6}$ alkyl.

In some embodiments, $R_9$ is selected from H, methyl, ethyl, n-propyl, i-propyl, n-butyl, s-butyl, i-butyl, t-butyl.

$R_8$, $R_{10}$, $R_{11}$, $R_{12}$, $R_{13}$, $R_{14}$, $R_{15}$, $R_{16}$, $R_{17}$, $R_{20}$ and $R_{21}$ Suitably each of $R_8$, $R_{10}$, $R_{11}$, $R_{12}$, $R_{13}$, $R_{14}$, $R_{15}$, $R_{16}$, $R_{17}$, $R_{20}$ and $R_{21}$ are independently selected from H, methyl, ethyl, n-propyl, i-propyl, n-butyl, s-butyl, i-butyl and t-butyl.

Suitably each of $R_8$, $R_{10}$, $R_{11}$, $R_{12}$, $R_{13}$, $R_{14}$, $R_{15}$, $R_{16}$, $R_{17}$, $R_{20}$ and $R_{21}$ are independently selected from H, methyl, and ethyl.

Suitably $R_8$ is H.

Suitably $R_{10}$ is H.

Suitably each $R_{11}$ is independently selected from H and methyl.

Suitably each $R_{12}$ is independently selected from H and methyl; more suitably each $R_{12}$ is H.

Suitably $R_{13}$ is H.

Suitably $R_{14}$ is H.

Suitably $R_{15}$ is H.

Suitably $R_{16}$ is H.

Suitably $R_{17}$ is methyl.

Suitably $R_{20}$ is H.

Suitably $R_{21}$ is H.

$R_{18}$

Suitably $R_{18}$ is selected from H, $CO_2H$, $CO_2CH_3$, $CO_2CH_2CH_3$, $NH(CH_3)$ and $NH_2$.

$R_{19}$

Suitably $R_{19}$ is selected from H, $(CH_2)_r$—$N(CH_2CH_3)_2$, $(CH_2)_r$—$N(CH_3)_2$, $(CH_2)_r$—$NH(CH_2CH_3)$, $(CH_2)_r$—$NH(CH_3)$ and $(CH_2)_r$—$NH_2$.

More suitably $R_{19}$ is selected from H and $(CH_2)_r$—$NH_2$.

$R_{24}$

Suitably, $R_{24}$ is a phenyl optionally substituted with up to three optional substituent groups selected from OH, methyl, ethyl, propyl, $OCH_3$, $OCH_2CH_3$, $CO_2H$, $CO_2CH_3$, $CO_2CH_2CH_3$, O—$(CH_2)_k$—$NH_2$, O—$(CH_2)_k$$NH(CH_3)$, $(CH_2)_j$—$NH_2$, $(CH_2)_j$—$NH(CH_3)$, C(=O)—NH—$(CH_2)_k$—$NH_2$, C(=O)—NH—$(CH_2)_k$$NH(CH_3)$, C(=O)—NH—$(CH_2)_k$—C(=NH)$NH(CH_3)$, and C(=O)—NH—$(CH_2)_k$—C(=NH)$NH_2$.

Suitably, $R_{24}$ is a phenyl optionally substituted with up to three optional substituent groups selected from OH, methyl, ethyl, $OCH_3$, $OCH_2CH_3$, $CO_2H$, $CO_2CH_3$, $CO_2CH_2CH_3$, O—$(CH_2)_k$—$NH_2$ and $(CH_2)_j$—$NH_2$.

Suitably, $R_{24}$ is a para substituted phenyl group.

More suitably, in some aspects $R_{24}$ is —$C_6H_4$—$(CH_2)_j$—$R_{18}$, wherein $R_{18}$ is selected from $CO_2R_{11}$ and $NR_{11}R_{12}$.

Each instance of j is independently selected from an integer from 0 to 6, hence, each j is independently selected from 0, 1, 2, 3, 4, 5 and 6.

Suitably each j is independently selected from 0, 1, 2 and 3.

More suitably each j is independently selected from 0 and 1.

More suitably each j is 0.

k

Each instance of k is independently selected from an integer from 1 to 6, hence, each k is independently selected from 1, 2, 3, 4, 5 and 6.

Suitably each k is independently selected from 1, 2 and 3.

More suitably each k is 1.

m m is selected from an integer from 0 to 6, hence, m is selected from 0, 1, 2, 3, 4, 5 and 6.

Suitably m is selected from 0, 1, 2 and 3.

More suitably m is selected from 0 and 1.

More suitably m is 0.

n n is selected from an integer from 1 to 6, hence, n is selected from 1, 2, 3, 4, 5 and 6.

Suitably n is selected from 1, 2 and 3.

More suitably n is 1.

r r is selected from an integer from 0 to 6, hence, r is selected from 0, 1, 2, 3, 4, 5 and 6.

Suitably r is selected from 0, 1, 2 and 3.

More suitably r is selected from 0 and 1.

More suitably r is 0.

s s is selected from an integer from 1 to 6, hence, s is selected from 1, 2, 3, 4, 5 and 6.

Suitably s is selected from 1, 2 and 3.

More suitably s is 1.

t t is selected from an integer from 0 to 6, hence, t is selected from 0, 1, 2, 3, 4, 5 and 6.

Suitably t is selected from 0, 1, 2 and 3.

More suitably t is selected from 0 and 1.

More suitably t is 0.

$Y_1$ $Y_1$ is N or CH; suitably $Y_1$ is CH.

$Y_2$ $Y_2$ is N or CH; suitably $Y_2$ is CH.

$X_1$

Suitably $X_1$ is selected from O, S, NH, $CH_2$, $CH_2O$, C(=O), C(=O)$NR_{13}$, $NR_{13}$C(=O, O—C(O) and C(O)—O;

Suitably, $X_1$ is selected from O, C(=O), C(=O)$NR_{13}$ and $NR_{13}$C(=O).

More suitably $X_1$ is selected from O, C(=O)NH and NHC(=O).

More suitably $X_1$ is O.

$X_2$

Suitably $X_2$ is selected from O, S, NH, $CH_2$, $CH_2O$, C(=O), C(=O)$NR_{15}$, $NR_{15}$C(=O), O—C(O) and C(O)—O or is absent.

Suitably $X_2$ is selected from O, C(=O), C(=O)$NR_{15}$ and $NR_{16}$C(=O) or is absent.

More suitably $X_2$ is selected from O, C(=O)NH and NHC(=O).

Suitably $X_2$ is the same as $X_1$.

More suitably $X_2$ is O.

L

L is a linker group. Suitably, any of the peptide chain, alkylene chain, paraformaldehyde chain or polyethylene glycol chain is interrupted by one or more hetero-atoms (e.g., N, O and S) and/or one or more $C_{5-9}$ heteroarylene groups (e.g., pyrrolylene, pyrazolylene, pyrazolylene, 1,2,3-triazolylene, pyridinylene) and/or one or more phenylene group. More suitably, the chains may be interrupted by from one to three hetero-atoms and/or from one to three $C_{5-9}$ heteroarylene groups and/or from one to three phenylene groups. Suitably, when L is any one of the chains described above, p is 1, q is 1, 2, 3, 4, 5, or 6, or p is 1 and q is 2, 3, 4, 5, or 6.

Suitably L is selected from a peptide chain having from 2 to 5 amino acids, from 2 to 4 amino acids, from 2 to 3 amino acids; an alkylene chain containing from 1 to 11 carbon atoms, from 1 to 10 carbon atoms, from 1 to 9 carbon atoms, from 1 to 8 carbon atoms, from 1 to 7 carbon atoms, from 1 to 6 carbon atoms, from 1 to 5 carbon atoms, from 1 to 4 carbon atoms, from 1 to 3 carbon atoms, which may contain one or more carbon-carbon double or triple bonds; a paraformaldehyde chain —$(OCH_2)_{1-12}$—, —$(OCH_2)_{1-11}$—, —$(OCH_2)_{1-10}$—, —$(OCH_2)_{1-9}$—, —$(OCH_2)_{1-8}$—, —$(OCH_2)_{1-7}$—, —$(OCH_2)_{1-6}$—, —$(OCH_2)_{1-5}$—, —$(OCH_2)_{1-4}$—, —$(OCH_2)_{1-3}$— a polyethylene glycol chain —$(OCH_2CH_2)_{1-5}$—, chain —$(OCH_2CH_2)_{1-4}$—, chain —$(OCH_2CH_2)_{1-3}$—; which chain may be interrupted by one or more hetero-atoms and/or $C_{5-9}$ heteroarylene groups and/or from one to three phenylene groups. Suitably, when L is any one of the chains described above, p is 1, q is 1, 2, 3, 4, 5, or 6, or p is 1 and q is 2, 3, 4, 5, or 6.

More suitably, L may be selected from an alkylene chain containing from 1 to 12 carbon atoms which may contain one or more carbon-carbon double or triple bonds.

More suitably, L may be selected from CH=CH, $CH_2$, $CH_2CH_2$, $CH_2CH_2CH_2$, $CH_2CH_2CH_2CH_2$ and $CH_2CH_2CH_2CH_2CH_2$.

A

In one embodiment A is A1:

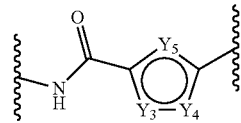

A1 wherein for each A1 group one of $Y_3$ and $Y_4$ is independently selected from N—$R_{17}$, S and O; and the other of $Y_3$ and $Y_4$ is CH; and $Y_5$ is independently selected from CH, N, S and COH.

In this embodiment, when q is selected from 2, 3, 4, 5 and 6 then A will contain multiple A1 groups connected to each other.

Hence, the 5-membered ring containing $Y_3$, $Y_4$ and $Y_5$ is a heteroaryl ring. This A1 group may be attached to the rest of the molecule in either direction. Hence, when A is A1, as in the above embodiment, the compound of formula (I) is selected from:

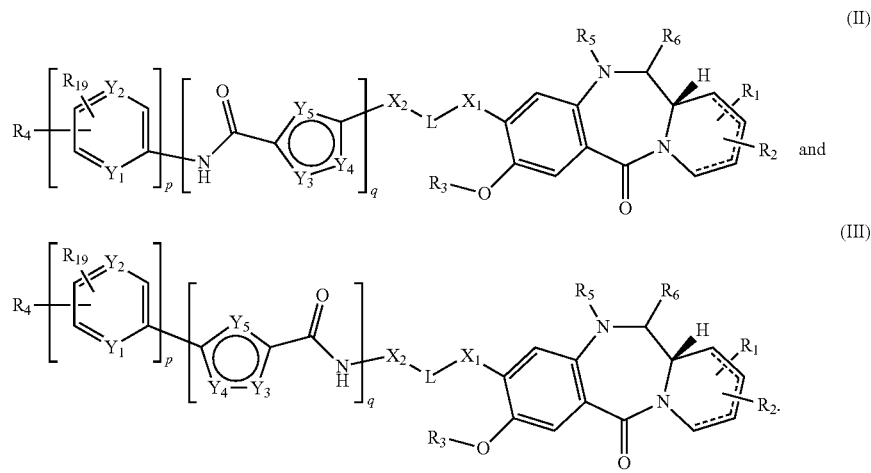
More suitably, when A is A1 the compound of formula (I) is compound (II).
Hence, the heteroaryl ring containing $Y_3$, $Y_4$ and $Y_5$, is selected from one of the following groups:
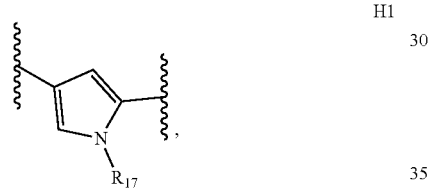 H1
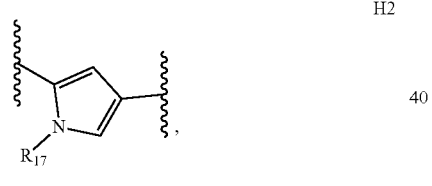 H2
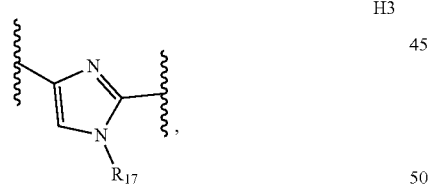 H3
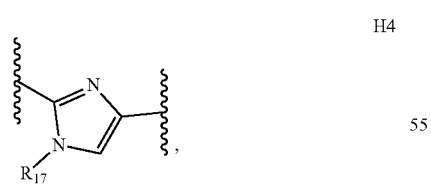 H4
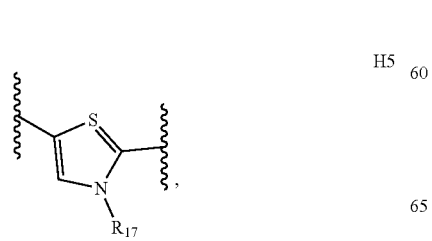 H5
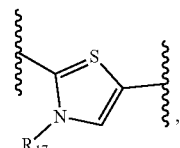 H6
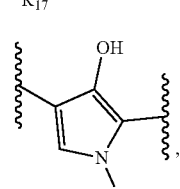 H7
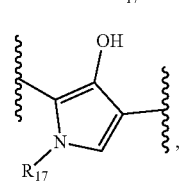 H8
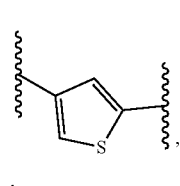 H9
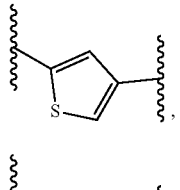 H10
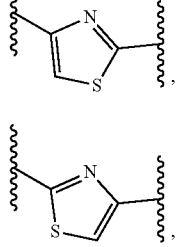 H11
H12

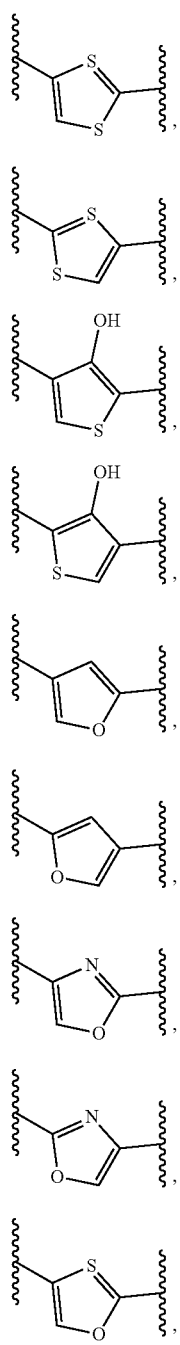

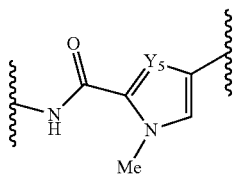

More suitably A is

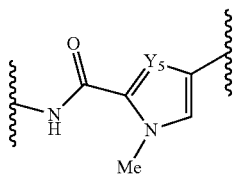

wherein $Y_5$ is selected from CH and N.

In another embodiment A is A2:

A2 wherein for each A2 group one of $Y_6$ and $Y_7$ is independently selected from N and CH; and the other of $Y_6$ and $Y_7$ is CH.

Hence, the 6-membered ring containing $Y_6$ and $Y_7$ is a phenyl or pyridinyl ring. The A2 group may be attached to the rest of the molecule in either direction. Hence, when A is A2, as in the above embodiment, the compound of formula (I) is selected from:

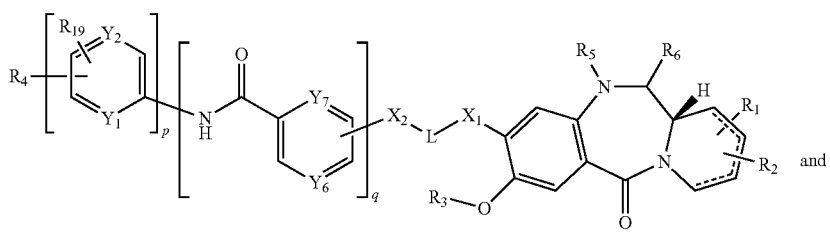

(IV)

and

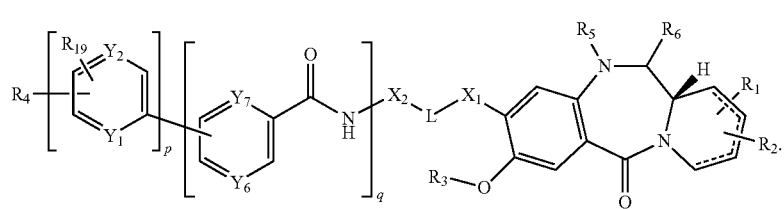

More suitably, when A is A2 the compound of formula (I) is compound (IV).

Suitably, A is A4:

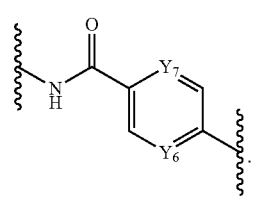

More suitably $Y_6$ is CH; and $Y_7$ is CH.

q

Suitably q is selected from 0, 1, 2 and 3.
More suitably q is 0 or 1.

6-Membered Aromatic-Ring

Suitably, the 6-membered aromatic ring of formula (I) is para-substituted:

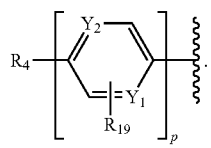

More suitably, the 6-membered aromatic ring of formula (I) is:

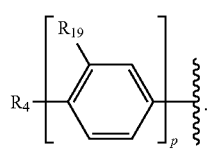

Optional Double Bonds in the C-Ring

The present invention provides a compound of formula (I):

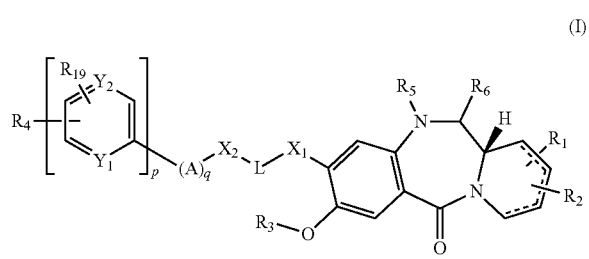

wherein the dotted lines indicates the optional presence of a double bond between one or more of C1 and C2, C2 and C3, and C3 and C4.

In one aspect, the compound of formula (I) has a double bond between C1 and C2 to give a compound of formula (VI):

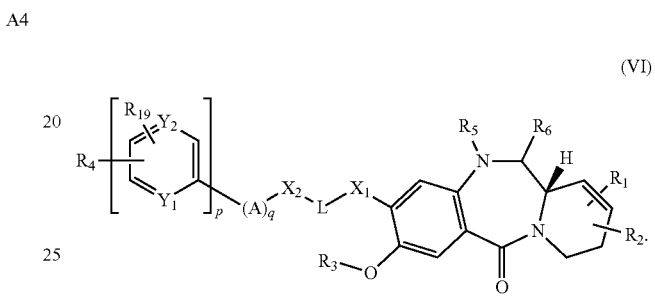

In another aspect, the compound of formula (I) has a double bond between C2 and C3 to give a compound of formula (VII):

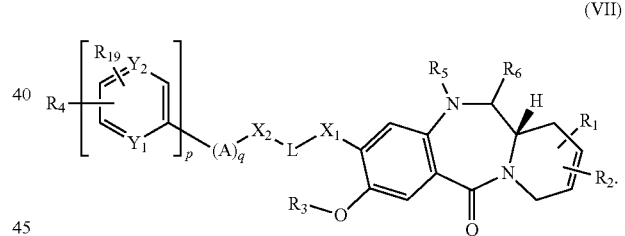

In another aspect, the compound of formula (I) has a double bond between C3 and C4 to give a compound of formula (VIII):

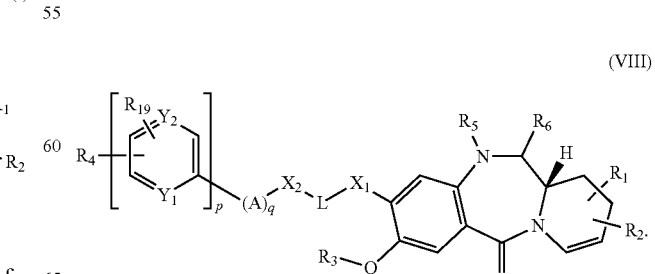

In another aspect, the compound of formula (I) has a double bond between C1 and C2 and a double bond between C3 and C4 to give a compound of formula (IX):

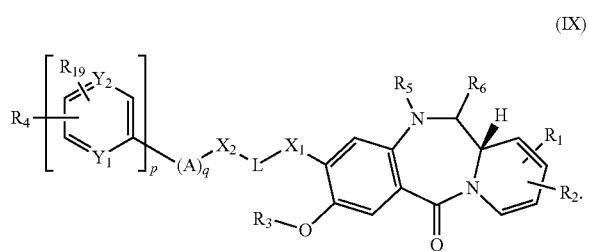

(IX)

Other Limitations

The options for compounds of formula (I) contain the proviso that when p is 0 and A is A1, then: (a) for at least one A1 group one of $Y_3$ and $Y_4$ is selected from S and O; or (b) for at least one A1 group $Y_5$ is S; or (c) $R_4$ is not an optionally substituted pyrrolyl or imidazolyl.

There will be more than one A1 group when q is selected from 2, 3, 4, 5 and 6.

Hence, when p is 0 and A is A1, the proviso requires the presence of at least one aryl group or, alternatively, the presence of a heteroaryl group (either as part of A1 or $R_4$) which does not contain a 5-membered pyrrole or imidazole ring, or optionally substituted derivatives such as N-methylpyrrole or N-methylimidazole rings. As a result, this proviso prevents the compounds of formula (I) having a purely poly-pyrrole or poly-imidazole or poly-pyrrole-imidazole long chain group attached to the PDD. Compounds having such long chain groups tend to be relatively poorly cytotoxic.

In some aspects, suitably the options for compounds of formula (I) contains the proviso that when p is 0 and A is A1, then: (a) the 5-membered ring of A1 is selected from H9, H10, H11, H12, H13, H14, H15, H16, H17, H19, H20, H21, H22, H23 and H24; or (b) the 5-membered ring of A1 is selected from H5 and H6; or (c) $R_4$ is selected from phenyl, furanyl, thiophenyl, oxazolyl, thiazolyl, pyridyl, benzofuranyl, benzothiophenyl, benzimidazolyl, N-methylbenzoimidazolyl, benzooxazolyl and benzothiazolyl, optionally substituted with up to three optional substituent groups selected from OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$; C(=O)—NH—$C_6H_4$—$(CH_2)_j$—$R_{18}$ and C(=O)—NH—$(CH_2)_k$—C(=NH)$NR_{11}R_{12}$.

In some aspects, suitably the options for compounds of formula (I) contains the proviso that when p is 0 and A is A1, then: (a) the 5-membered ring of A1 is selected from H9, H10, H11, H12, H13, H14, H15, H16, H17, H19, H20, H21, H22, H23 and H24; or (b) the 5-membered ring of A1 is selected from $H_5$ and H6; or (c) $R_4$ is selected from phenyl and $C_9$ heteroaryl groups optionally substituted with up to three optional substituent groups selected from OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$; C(=O)—NH—$C_6H_4$—$(CH_2)_j$—$R_{18}$; C(=O)—NH—$(CH_2)_k$—C(=NH)$NR_{11}R_{12}$, with the proviso that the $C_{5-9}$ heteroaryl is not indolyl.

In some aspects, suitably the options for compounds of formula (I) contains the proviso that i) L is a peptide chain having from 2 to 6 amino acids, an alkylene chain containing from 1 to 12 carbon atoms which may contain one or more carbon-carbon double or triple bonds, a paraformaldehyde chain, a polyethylene glycol chain, which chains are interrupted by one or more of $C_{5-9}$ heteroarylene, phenylene or combinations of the foregoing; and/or ii) p is 1; and/or iii) q is 1, 2, 3, 4, 5 or 6.

Suitable Structures

The compound of formula (I):

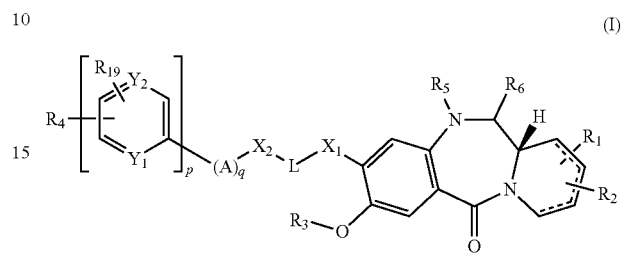

(I)

is drawn without specifying the position of $R_1$ and $R_2$ on the C-ring. Hence, $R_1$ and $R_2$ may be present on any position of the C-ring provided that the valence requirement are met. As the fused carbon and the nitrogen of the C-ring have all their substituents shown, this means that $R_1$ and $R_2$ may be present on any of the non-fused carbons of the C-ring (i.e. the C1, C2, C3 or C4 positions as designated above). Suitably $R_1$ and $R_2$ are present on two different non-fused carbons of the C-ring.

In one aspect, the compound of formula (I) is selected from:

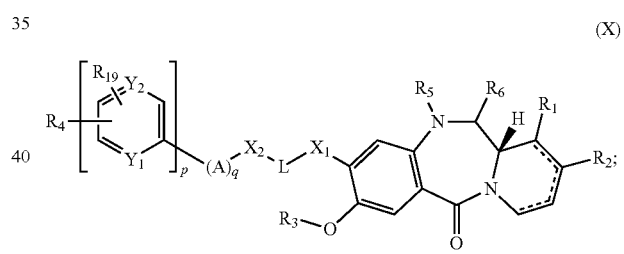

(X)

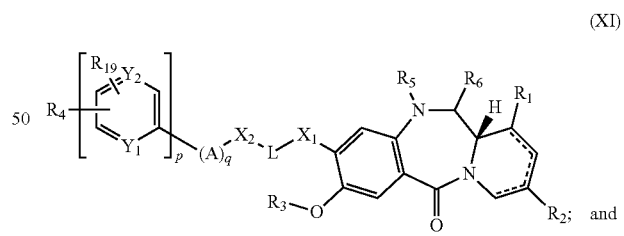

(XI)

and

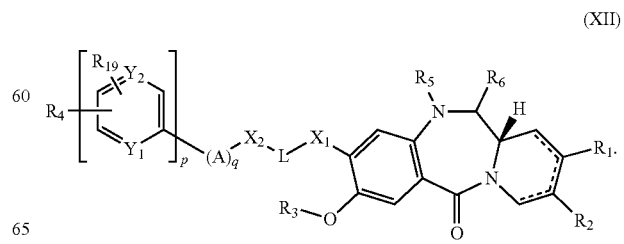

(XII)

In another aspect, the compound of formula (I) is selected from:

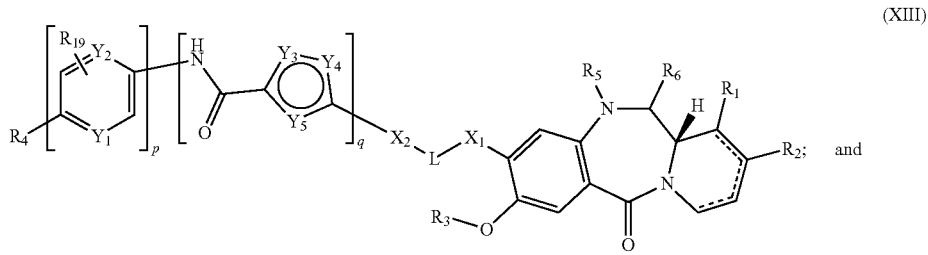
(XIII)

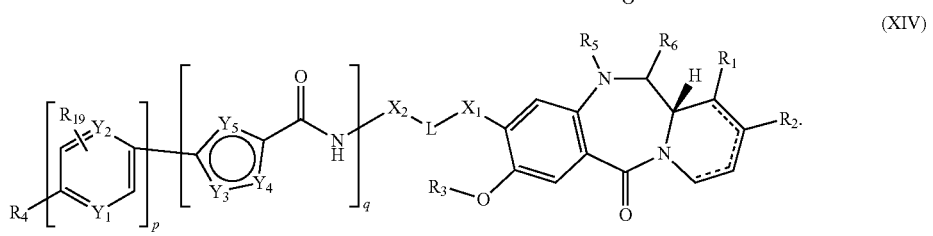
(XIV)

More suitably, the compound of formula (I) has the following structure:

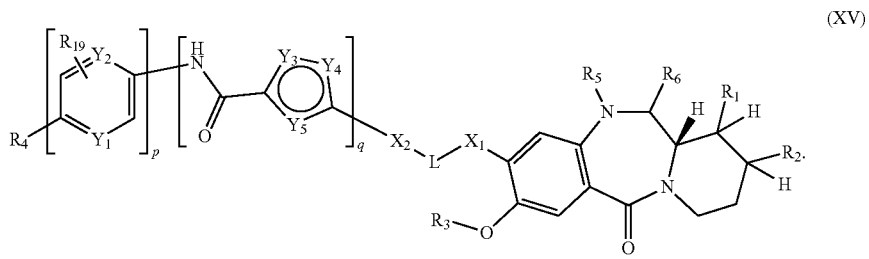
(XV)

For compounds of formula (XV) where $R_1$ and/or $R_2$ are substituents other than H, the carbons in the C-ring to which any such substituents are attached will be stereocenters. In formula (XV) $R_1$ and $R_2$ are drawn without specifying the stereochemistry of the carbons on the C-ring to which they are attached.

More suitably the compound of formula (I) is selected from:

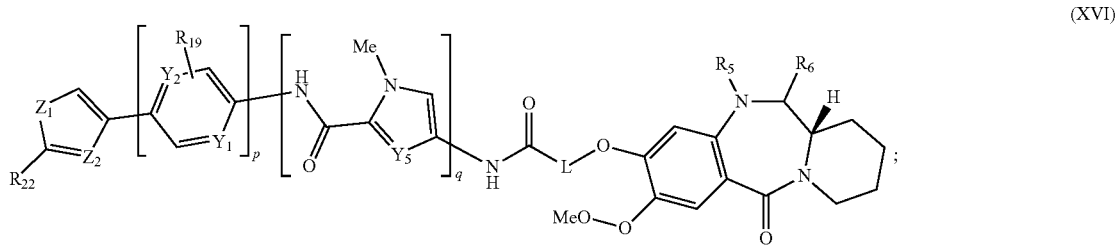
(XVI)

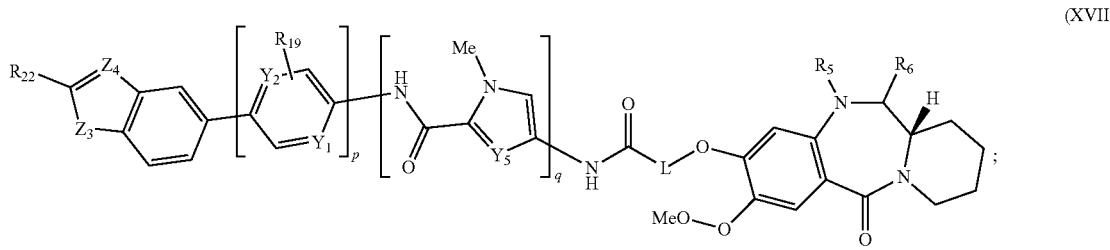
(XVII)

(XVIII)

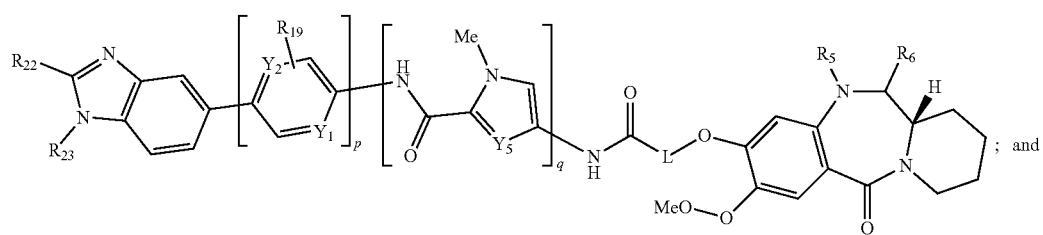

; and (XIX)

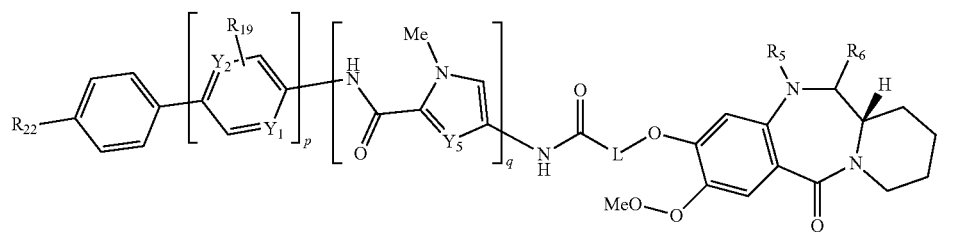

wherein q is selected from 0, 1, 2, 3, 4, 5 or 6;
p is 0 or 1;
L is an alkylene chain containing from 1 to 12 carbon atoms;
$Y_1$ is N or CH;
$Y_2$ is N or CH; and wherein at least one of $Y_1$ and $Y_2$ is CH;
$Y_5$ is selected from CH and N;
$Z_1$ is selected from O, S, NH and N—$CH_3$;
$Z_2$ is selected from CH and N;
$Z_3$ is selected from S and O;
$Z_4$ is selected from CH and N;
$R_{22}$ is selected from $(CH_2)_jCO_2H$, $(CH_2)_jCO_2C_{1-6}$ alkyl, $(CH_2)_jNR_{11}R_{12}$ and $C(=O)—NH—C_6H_4(CH_2)_j—R_{18}$;
$R_{18}$ is selected from H, $CO_2R_{11}$ and $NR_{11}R_{12}$;

$R_{19}$ is selected from H and $(CH_2)_t—NR_{20}R_{21}$;
j and t are independently selected from an integer from 0 to 6; and
$R_{11}$, $R_{12}$ and $R_{23}$ are independently selected from H and $C_{1-6}$ alkyl, and either:
(i) $R_5$ and $R_6$ together form a double bond;
(ii) $R_5$ is H and $R_6$ is OH; or
(iii) $R_5$ is H and $R_6$ is $OC_{1-6}$ alkyl;
with the proviso that when the compound is (XVI) and p is 0, that $Z_1$ is selected from O and S.

More suitably the compound of formula (I) is selected from:

(XX)

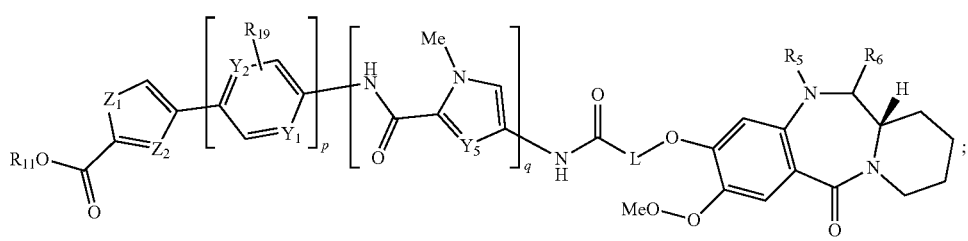

;

(XXI)

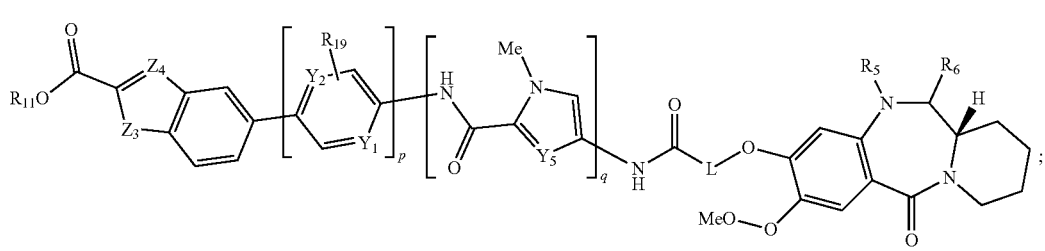

;

(XXII)

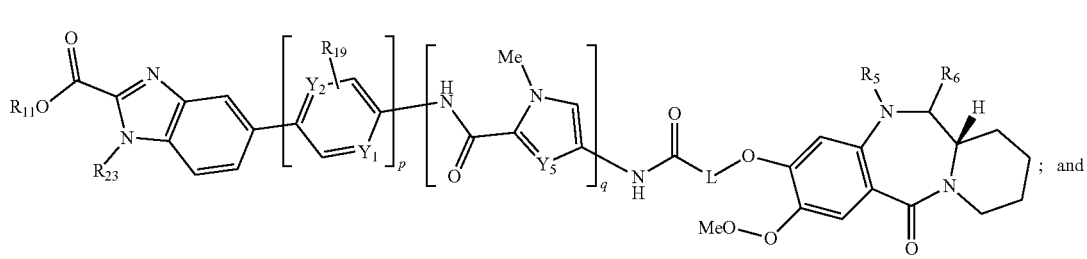

; and

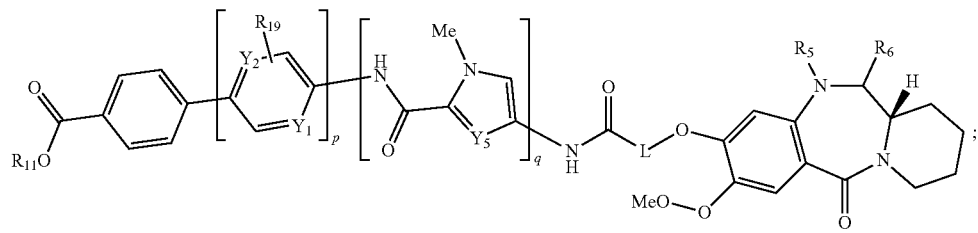

(XXIII)

wherein q is selected from 0, 1, 2, 3, 4, 5 or 6;
p is 0 or 1;
L is an alkylene chain containing from 1 to 12 carbon atoms;
$Y_1$ is N or CH;
$Y_2$ is N or CH; and wherein at least one of $Y_1$ and $Y_2$ is CH;
$Y_5$ is selected from CH and N;
$Z_1$ is selected from O, S, NH and N—$CH_3$;
$Z_2$ is selected from CH and N;
$Z_3$ is selected from S and O;
$Z_4$ is selected from CH and N;
$R_{19}$ is selected from H and $(CH_2)_t$—$NR_{20}R_{21}$;
t is selected from an integer from 0 to 6;
$R_{11}$, $R_{20}$, $R_{21}$ and $R_{23}$ are independently selected from H and $C_{1-6}$ alkyl; and either:
 (i) $R_5$ and $R_6$ together form a double bond;
 (ii) $R_5$ is H and $R_6$ is OH; or
 (iii) $R_5$ is H and $R_6$ is $OC_{1-6}$ alkyl;
with the proviso that when the compound is (XX) and p is 0, that $Z_1$ is selected from O and S.

More suitably, the compound of formula (I) is selected from:
(a) methyl (S)-5-(4-(4-((2-methoxy-12-oxo-6a,7,8,9,10,12-hexahydrobenzo[e]pyrido-[1,2-a][1,4]diazepin-3-yl)oxy) butanamido)-1-methyl-1H-pyrrole-2-carboxamido) benzo-[b]thiophene-2-carboxylate (13)

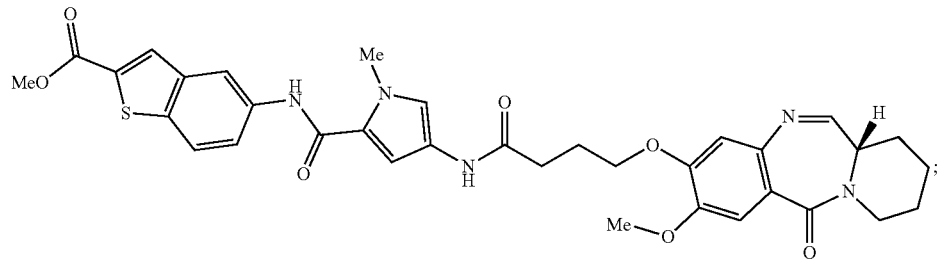

(13)

(b) methyl (S)-5-(4-(4-((2-methoxy-12-oxo-6a,7,8,9,10,12-hexahydrobenzo[e]pyrido-[1,2-a][1,4]diazepin-3-yl)oxy) butanamido)-1-methyl-1H-imidazole-2-carboxamido)-benzo[b]thiophene-2-carboxylate (17)

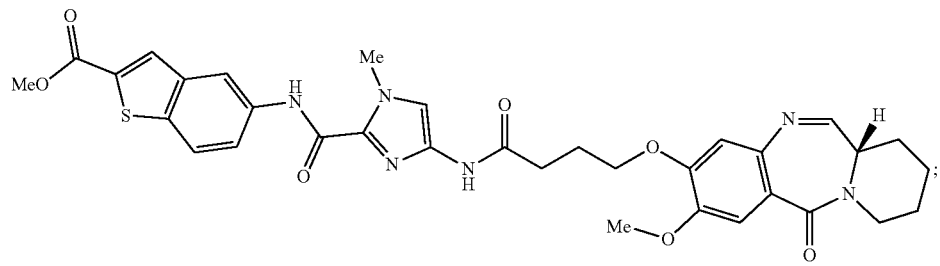

(17)

(c) methyl (S)-4-(4-(4-(4-((2-methoxy-12-oxo-6a,7,8,9,10,12-hexahydrobenzo[e]-pyrido[1,2-a][1,4]diazepin-3-yl)oxy)butanamido)-1-methyl-1H-imidazole-2-carboxamido)phenyl)-1-methyl-1H-pyrrole-2-carboxylate (20)

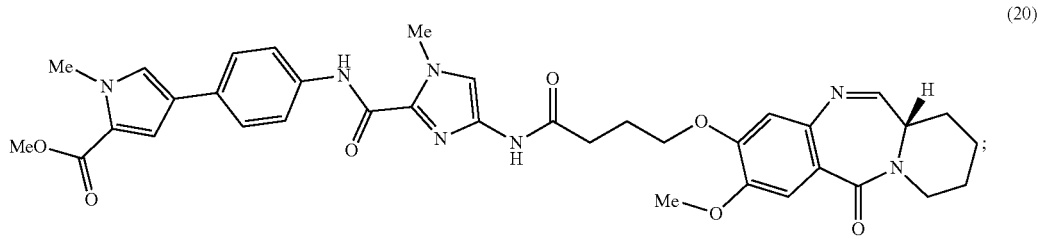 [SMILES: COC(=O)c1cc(-c2ccc(NC(=O)c3nc(NC(=O)CCCOc4cc5c(cc4OC)C(=O)N4CCCC[C@H]4C=N5)cn3C)cc2)cn1C]

(d) methyl (S)-4-(4-(4-(4-((2-methoxy-12-oxo-6a,7,8,9,10,12-hexahydrobenzo[e]-pyrido[1,2-a][1,4]diazepin-3-yl)oxy)butanamido)-1-methyl-1H-pyrrole-2-carboxamido)phenyl)-1-methyl-1H-pyrrole-2-carboxylate (24)

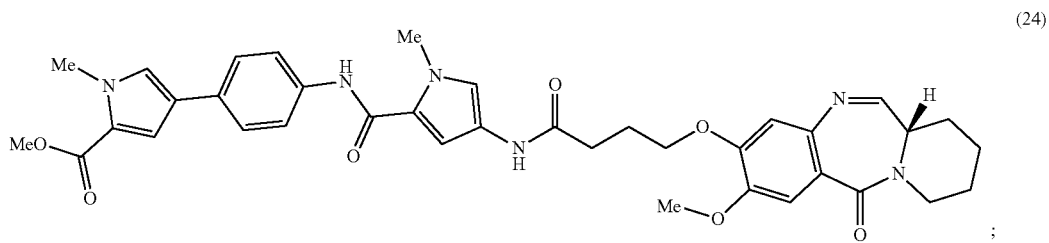 [SMILES: COC(=O)c1cc(-c2ccc(NC(=O)c3cc(NC(=O)CCCOc4cc5c(cc4OC)C(=O)N4CCCC[C@H]4C=N5)cn3C)cc2)cn1C]

(e) methyl (S)-4-(4-(4-(4-((2-methoxy-12-oxo-6a,7,8,9,10,12-hexahydrobenzo[e]-pyrido[1,2-a][1,4]diazepin-3-yl)oxy)butanamido)-benzamido)phenyl)-1-methyl-iH-pyrrole-2-carboxylate (28)

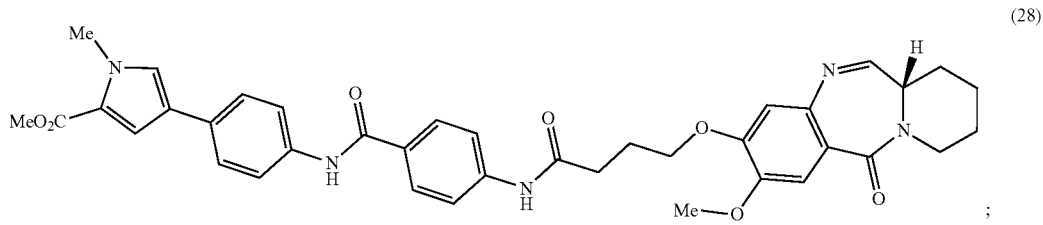 [SMILES: COC(=O)c1cc(-c2ccc(NC(=O)c3ccc(NC(=O)CCCOc4cc5c(cc4OC)C(=O)N4CCCC[C@H]4C=N5)cc3)cc2)cn1C]

(f) methyl (S)-5-(4-(4-((2-methoxy-12-oxo-6a,7,8,9,10,12-hexahydrobenzo[e]pyrido-[1,2-a][1,4]diazepin-3-yl)oxy)butanamido)-benzamido)benzo[b]thiophene-2-carboxylate (30)

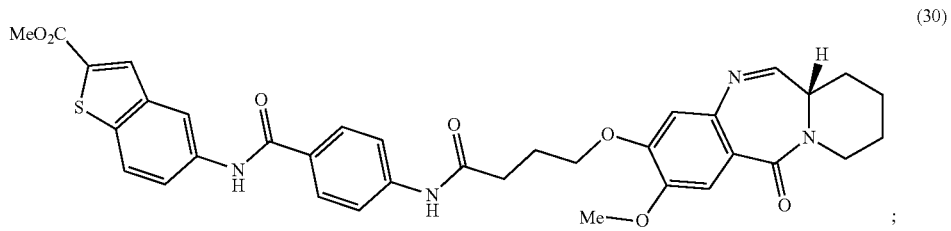 [SMILES: COC(=O)c1cc2cc(NC(=O)c3ccc(NC(=O)CCCOc4cc5c(cc4OC)C(=O)N4CCCC[C@H]4C=N5)cc3)ccc2s1]

(g) methyl (S)-4-(4-(4-((2-methoxy-12-oxo-6a,7,8,9,10,12-hexahydrobenzo[e]pyrido-[1,2-a][1,4]diazepin-3-yl)oxy)butanamido)-1-methyl-1H-imidazole-2-carboxamido)-benzoate (34)

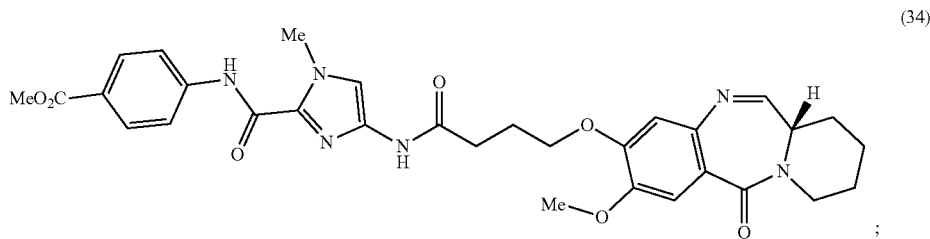

(34)

(h) methyl (S)-4-(4-(4-((2-methoxy-12-oxo-6a,7,8,9,10,12-hexahydrobenzo[e]pyrido-[1,2-a][1,4]diazepin-3-yl)oxy)butanamido)-1-methyl-1H-pyrrole-2-carboxamido)-benzoate (38)

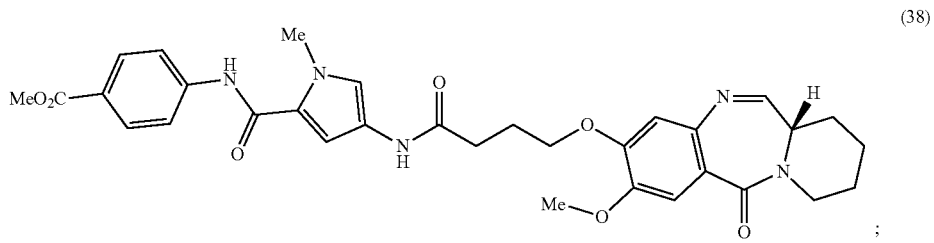 [SMILES: COC(=O)c1ccc(NC(=O)c2cc(NC(=O)CCCOc3cc4c(cc3OC)C(=O)N3CCCC[C@H]3C=N4)cn2C)cc1]

(38)

(i) (S)—N-(4-aminophenyl)-4-(4-(4-(4-((2-methoxy-12-oxo-6a,7,8,9,10,12-hexahydro-benzo[e]pyrido[1,2-a][1,4]diazepin-3-yl)oxy)butan-amido)-1-methyl-1H-pyrrole-2-carboxamido)phenyl)-1-methyl-1H-pyrrole-2-carboxamide (41)

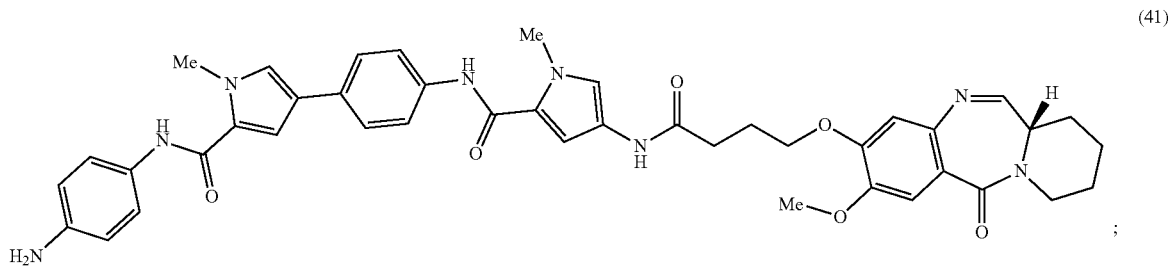 [SMILES: COc1cc2c(cc1OCCCC(=O)Nc1cc(C(=O)Nc3ccc(-c4cc(C(=O)Nc5ccc(N)cc5)n(C)c4)cc3)n(C)c1)N=C[C@@H]1CCCCN1C2=O]

(41)

(j) (S)—N-(2-((4-Aminophenyl)carbamoyl)benzo[b]thiophen-5-yl)-4-(4-((2-methoxy-12-oxo-6a,7,8,9,10,12-hexahydrobenzo[e]pyrido[1,2-a][1,4]diazepin-3-yl)oxy)-butanamido)-1-methyl-1H-pyrrole-2-carboxamide (47)
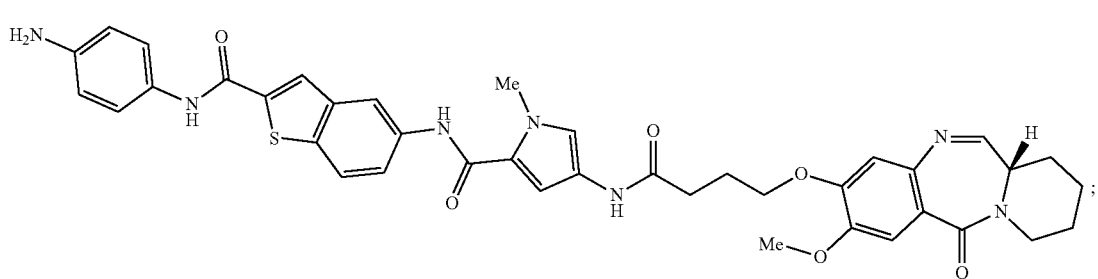
(47)
(k) Methyl 5-(4-((tert-butoxycarbonyl)amino)-1-methyl-1H-pyrrole-2-carboxamido)-benzo[b]thiophene-2-carboxylate (62)
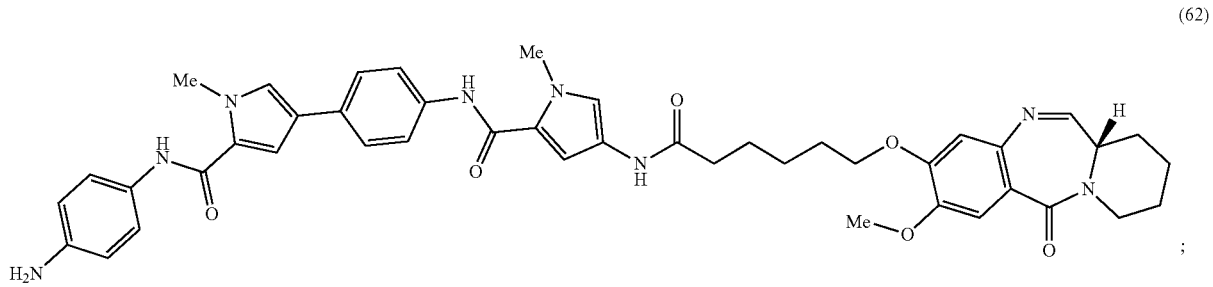 [SMILES: COc1cc2c(cc1OCCCCCC(=O)Nc1cc(C(=O)Nc3ccc(-c4cc(C(=O)Nc5ccc(N)cc5)n(C)c4)cc3)n(C)c1)N=C[C@@H]1CCCCN1C2=O]
(62)
(l) (S)—N-(4-Aminophenyl)-4-(6-((2-methoxy-12-oxo-6a,7,8,9,10,12-hexahydrobenzo[e]pyrido[1,2-a][1,4]diazepin-3-yl)oxy)hexan-amido)-1-methyl-1H-pyrrole-2-carboxamide (66)
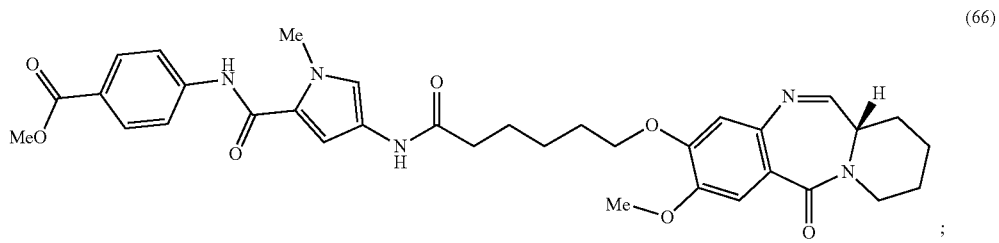 [SMILES: COC(=O)c1ccc(NC(=O)c2cc(NC(=O)CCCCCOc3cc4c(cc3OC)C(=O)N3CCCC[C@H]3C=N4)cn2C)cc1]
(66)

(m) (S)—N-(2-Aminoethyl)-4-(4-(4-(4-((2-methoxy-12-oxo-6a,7,8,9,10,12-hexahydro-benzo[e]pyrido[1,2-a][1,4]diazepin-3-yl)oxy)butanamido)-1-methyl-1H-pyrrole-2-carboxamido)phenyl)-1-methyl-1H-pyrrole-2-carboxamide (68)

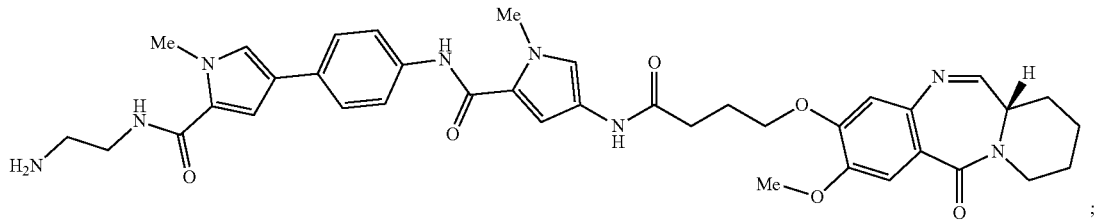

(S)-4-(4-((2-Methoxy-12-oxo-6a,7,8,9,10,12-hexahydrobenzo[e]pyrido[1,2-a][1,4]diazepin-3-yl)oxy)butanamido)-1-methyl-N-(4-(1-methyl-5-(phenylcarbamoyl)-1H-pyrrol-3-yl)phenyl)-1H-pyrrole-2-carboxamide (73)

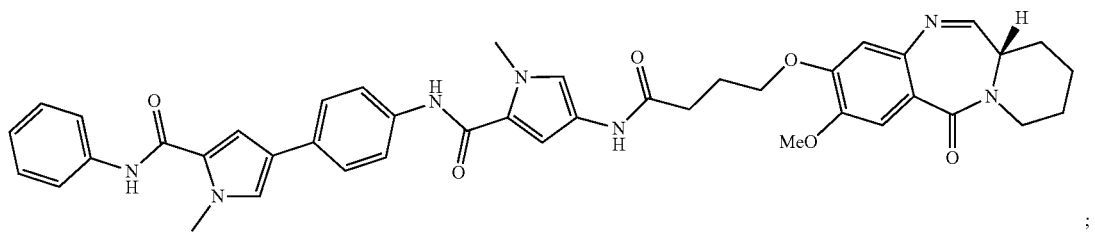

(S)-4-(4-(2-Methoxy-12-oxo-6a,7,8,9,10,12-hexahydrobenzo[e]pyrido[1,2-a][1,4]diazepin-3-yl)oxy)butanamido)-1-methyl-N-(4-(1-methyl-5-(p-tolylcarbamoyl)-1H-pyrrol-3-yl)phenyl)-1H-pyrrole-2-carboxamide (76)

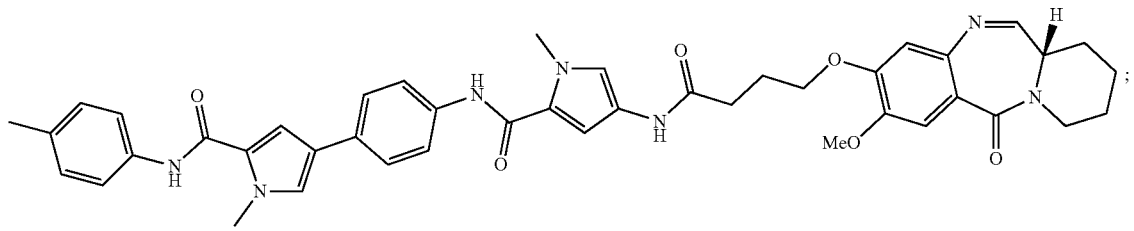

Methyl (S)-4-(4-(4-(4-(4-((2-methoxy-12-oxo-6a,7,8,9,10,12-hexahydrobenzo[e]pyrido[1,2-α][1,4]diazepin-3-yl)oxy)butanamido)-1-methyl-1H-pyrrole-2-carboxamido)phenyl)-1-methyl-ill-pyrrole-2-carboxamido)benzoate (81)

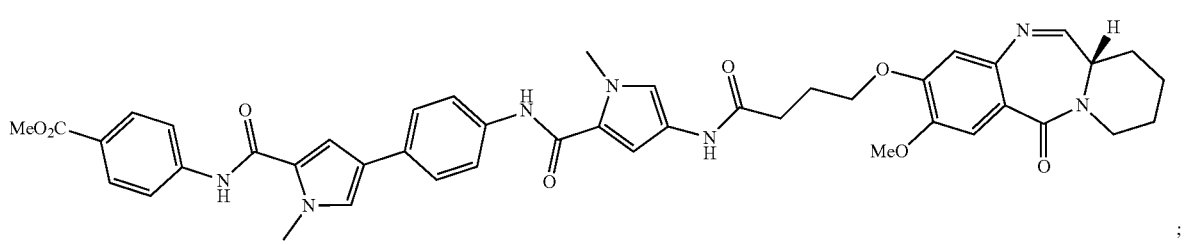

(S)-4-(4-(4-(4-((2-Methoxy-12-oxo-6a,7,8,9,10,12-hexahydrobenzo[e]pyrido[1,2-α][1,4]diazepin-3-yl)oxy)butanamido)-1-methyl-1H-pyrrole-2-carboxamido)phenyl)-1-methyl-N-phenyl-1-methyl-N-phenyl-1H-imidazole-2-carboxamide (88)

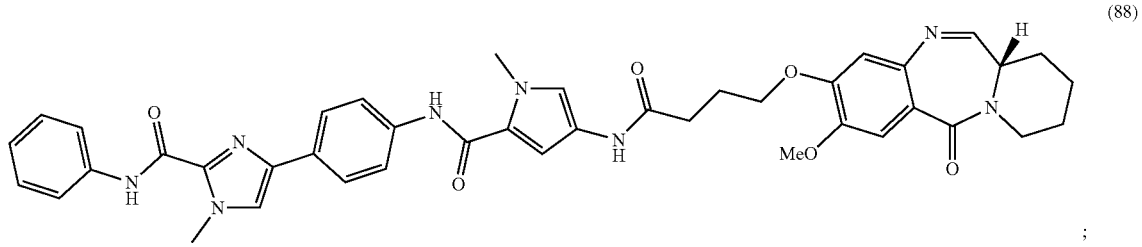 [SMILES: COc1cc2c(cc1OCCCC(=O)Nc1cc(C(=O)Nc3ccc(-c4cn(C)c(C(=O)Nc5ccccc5)n4)cc3)n(C)c1)N=C[C@@H]1CCCCN1C2=O]

(S)-4-(4-((2-Methoxy-12-oxo-6a,7,8,9,10,12-hexahydrobenzo[e]pyrido[1,2-α][1,4]diazepin-3-yl)oxy)butanamido)-1-methyl-N-(4-(1-methyl-5-(phenylcarbamoyl)-1H-pyrrol-3-yl)phenyl)-1H-imidazole-2-carboxamide (93)

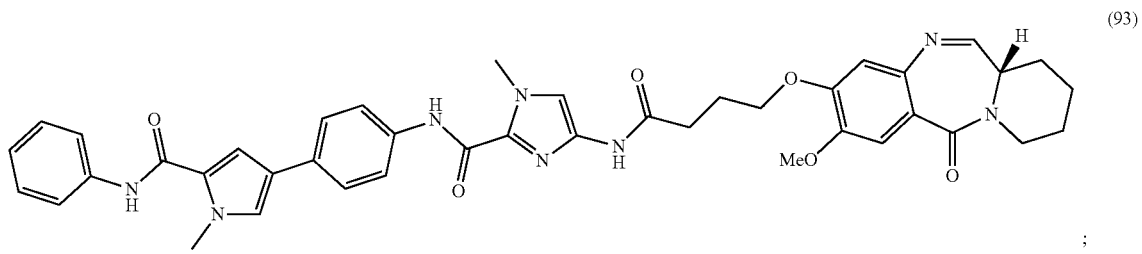 [SMILES: COc1cc2c(cc1OCCCC(=O)Nc1cn(C)c(C(=O)Nc3ccc(-c4cc(C(=O)Nc5ccccc5)n(C)c4)cc3)n1)N=C[C@@H]1CCCCN1C2=O]

Methyl (S)-4-(2-(3-(((2-methoxy-12-oxo-6a,7,8,9,10,12-hexahydrobenzo[e]pyrido[1,2-a][1,4]diazepin-3-yl)oxy)methyl)phenyl)acetamido)-1-methyl-1H-pyrrole-2-carboxylate (112)

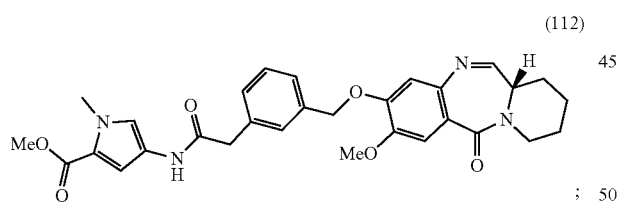

Ethyl (S)-4-(2-(3-(((2-methoxy-12-oxo-6a,7,8,9,10,12-hexahydrobenzo[e]pyrido[1,2-a][1,4]diazepin-3-yl)oxy)methyl)phenyl)acetamido)-1-methyl-1H-imidazole-2-carboxylate (114)

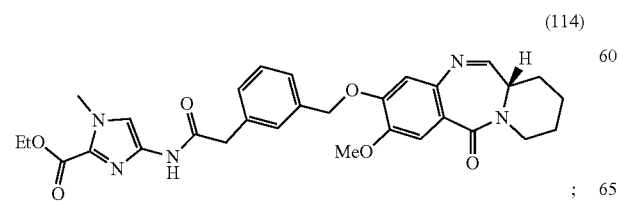

(S)-2-(4-(2-(3-(((2-Methoxy-12-oxo-6a,7,8,9,10,12-hexa-hydrobenzo[e]pyrido[1,2-a][1,4]diazepin-3-yl)oxy)methyl)phenyl)acetamido)-1-methyl-1H-imidazole-2-carboxamido)-N-phenylbenzo[d]thiazole-5-carboxamide (119)

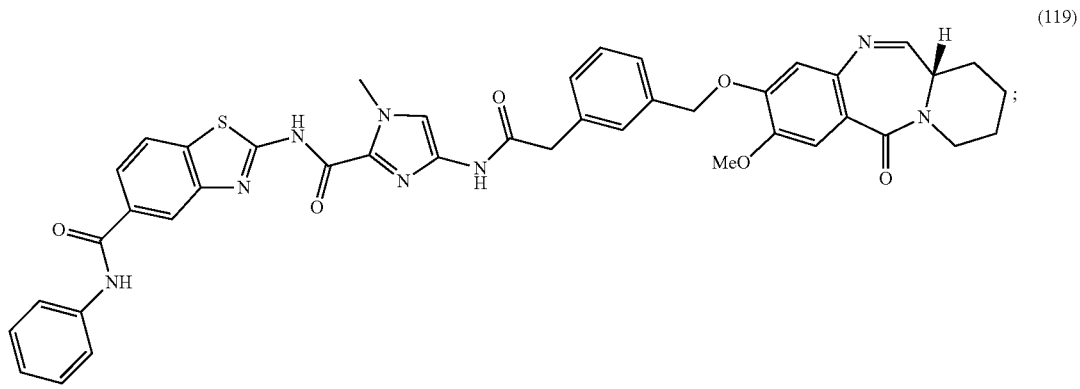 [SMILES: COc1cc2c(cc1OCc1cccc(CC(=O)Nc3cn(C)c(C(=O)Nc4nc5cc(C(=O)Nc6ccccc6)ccc5s4)n3)c1)N=C[C@@H]1CCCCN1C2=O]

(S)-2-(4-(4-((2-Methoxy-12-oxo-6a,7,8,9,10,12-hexahydrobenzo[e]pyrido[1,2-a][1,4]diazepin-3-yl)oxy)butanamido)-1-methyl-1H-imidazole-2-carboxamido)-N-phenylbenzo[d]thiazole-5-carboxamide (125)

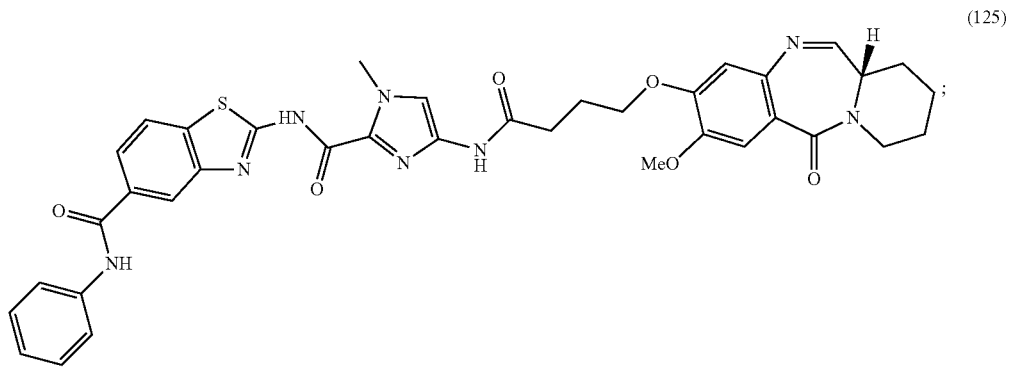 [SMILES: COc1cc2c(cc1OCCCC(=O)Nc1cn(C)c(C(=O)Nc3nc4cc(C(=O)Nc5ccccc5)ccc4s3)n1)N=C[C@@H]1CCCCN1C2=O]

(S)-4-(2-(3-(((2-Methoxy-12-oxo-6a,7,8,9,10,12-hexahydrobenzo[e]pyrido[1,2-a][1,4]diazepin-3-yl)oxy)methyl)phenyl)acetamido)-1-methyl-N-(4-(1-methyl-5-(phenylcarbamoyl)-1H-pyrrol-3-yl)phenyl)-1H-pyrrole-2-carboxamide (130)

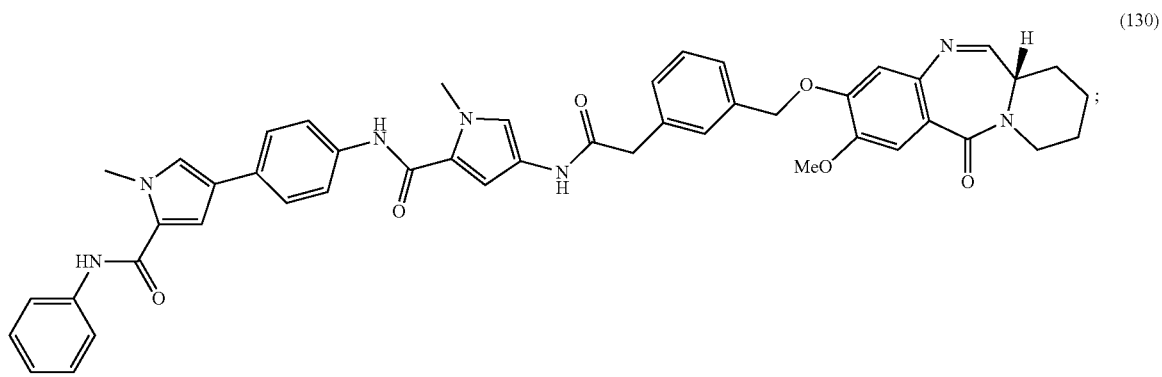 [SMILES: COc1cc2c(cc1OCc1cccc(CC(=O)Nc3cc(C(=O)Nc4ccc(-c5cc(C(=O)Nc6ccccc6)n(C)c5)cc4)n(C)c3)c1)N=C[C@@H]1CCCCN1C2=O]

In a further aspect, there is provided a compound of formula (I):

$$\text{(I)}$$

and salts and solvates thereof, wherein:

the dotted lines indicates the optional presence of a double bond between one or more of C1 and C2, C2 and C3, and C3 and C4;

$R_1$ is selected from $R_7$, =$CH_2$, =CH—$(CH_2)_m$—$CH_3$, =O, $(CH_2)_m$—$OR_7$, $(CH_2)_m$—$CO_2R_7$, $(CH_2)_m$—$NR_7R_8$, O—$(CH_2)_n$—$NR_7R_8$, NH—C(O)—$R_7$, O—$(CH_2)_n$—NH—C(O)—$R_7$, O—$(CH_2)_n$—C(O)—NH—$R_7$, $(CH_2)_m$—$SO_2R_7$, O—$SO_2R_7$, $(CH_2)_m$—C(O)$R_7$ and $(CH_2)_m$—C(O)$NR_7R_8$;

$R_2$ is selected from $R_9$, =$CH_2$, =CH—$(CH_2)$—$CH_3$, =O, $(CH_2)_r$—$OR_9$, $(CH_2)_r$—$CO_2R_9$, $(CH_2)_r$—$NR_9R_{10}$, O—$(CH_2)_s$—$NR_9R_{10}$, NH—C(O)—$R_9$, O—$(CH_2)_s$—NH—C(O)—$R_9$, O—$(CH_2)_s$—C(O)—NH—$R_9$, $(CH_2)_r$—$SO_2R_9$, O—$SO_2R_9$, $(CH_2)_r$—$COR_s$ and $(CH_2)_r$—C(O)$NR_9R_{10}$;

$R_3$ is selected from H, $C_{1-12}$ alkyl and $CH_2Ph$;

$R_4$ is selected from phenyl and $C_{5-9}$ heteroaryl groups optionally substituted with up to three optional substituent groups selected from OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$; C(=O)—NH—$C_6H_4$—$(CH_2)_j$—$R_{18}$ and C(=O)—NH—$(CH_2)_k$—C(=NH)$NR_{11}R_{12}$;

$R_{19}$ is selected from H and $(CH_2)_t$—$NR_{20}R_{21}$;

$Y_1$ is N or CH; $Y_2$ is N or CH; and wherein at least one of $Y_1$ and $Y_2$ is CH;

p is 0 or 1; j, m, r and t are independently selected from an integer from 0 to 6;

k, n and s are independently selected from an integer from 1 to 6;

$X_1$ is selected from O, S, $NR_{13}$, $CR_{13}R_{14}$, $CR_{13}R_{14}$; O, C(=O), C(=O)$NR_{13}$, $NR_{13}$C(=O), O—C(O) and C(O)—O;

L is selected from an amino acid, a peptide chain having from 2 to 6 amino acids, an alkylene chain containing from 1 to 12 carbon atoms which may contain one or more carbon-carbon double or triple bonds, a paraformaldehyde chain —$(OCH_2)_{1-2}$—, a polyethylene glycol chain —$(OCH_2CH_2)_{1-6}$—, which chains may be interrupted by one or more of O, S and/or NH groups and/or $C_{3-9}$ heteroarylene and/or phenylene;

$X_2$ is selected from O, S, $NR_{15}$, $CR_{15}R_{16}$, $CR_{15}R_{16}$O, C(=O), C(=O)$NR_{15}$, $NR_{15}$C(=O), O—C(O) and C(O)—O or is absent;

q is selected from 0, 1, 2, 3, 4, 5 and 6;

A is selected from:

$$\text{A1}$$

$$\text{A2}$$

for each A1 group one of $Y_3$ and $Y_4$ is independently selected from N—$R_{17}$, S and O; and the other of $Y_3$ and $Y_4$ is CH; and $Y_5$ is independently selected from CH, N, S and COH; and for each A2 group one of $Y_6$ and $Y_7$ is independently selected from N and CH; and the other of $Y_6$ and $Y_7$ is CH;

$R_7$ and $R_9$ are independently selected from H, $C_{1-12}$ alkyl, $C_{5-9}$ heteroaryl, $C_{6-15}$ heteroarylalkyl, phenyl and $C_{7-12}$ aralkyl groups; wherein the heteroaryl, heteroarylalkyl, phenyl and aralkyl groups are optionally substituted with up to three optional substituent groups selected from $C_{1-6}$ alkyl, OH, $OC_{1-6}$ alkyl;

$R_{18}$ is selected from H, $CO_2R_{11}$ and $NR_{11}R_{12}$;

$R_8$, $R_{10}$, $R_{11}$, $R_{12}$, $R_{13}$, $R_{14}$, $R_{15}$, $R_{16}$, $R_{17}$, $R_{20}$ and $R_{21}$ are independently selected from H and $C_{1-6}$ alkyl; and (i) $R_5$ and $R_6$ together form a double bond; or (ii) $R_5$ is H and $R_6$ is OH; or (iii) $R_5$ is H and $R_6$ is $OC_{1-6}$ alkyl.

Therefore, the present invention also provides a compound of the formula (Ia)

$$\text{(Ia)}$$

and salts and solvates thereof,
wherein
AM is an alkylating moiety;
p is 0 or 1;
when p is 1, the $H_1$ is a $C_5$ heteroaryl group optionally substituted with 1 or 2 optional substituent groups selected from OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$; C(=O)—NH—$R_{24}$ and C(=O)—NH—$(CH_2)_k$—C(=NH)$NR_{11}R_{12}$;

when p is 0, the $H_1$ is a $C_9$ heteroaryl group optionally substituted with 1 or 2 optional substituent groups selected from OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$; C(=O)—NH—$R_{24}$ and C(=O)—NH—$(CH_2)_k$—C(=NH)$NR_{11}R_{12}$;

$Y_1$ is N or CH;
$Y_2$ is N or CH; and wherein at least one of $Y_1$ and $Y_2$ is CH;

one of $Y_3$ and $Y_4$ is independently selected from N—$R_{17}$, S and O; and the other of $Y_3$ and $Y_4$ is CH;

$Y_5$ is independently selected from CH, N, S and COH;

one of $Y_8$ and $Y_9$ is independently selected from N—H, S and O; and the other of $Y_8$ and $Y_9$ is CH;

$X_1$ is selected from O, S, $NR_{13}$, $CR_{13}R_{14}$, $CR_{13}R_{14}O$, C(=O), C(=O)$NR_{13}$, $NR_{13}$C(=O), O—C(O) and C(O)—O;

L is selected from an amino acid, a peptide chain having from 2 to 6 amino acids, an alkylene chain containing from 1 to 12 carbon atoms which may contain one or more carbon-carbon double or triple bonds, a paraformaldehyde chain —(OCH$_2$)$_{1-2}$—, a polyethylene glycol chain —(OCH$_2$CH$_2$)$_{1-6}$, wherein the chain may be interrupted by one or more of O, S, NH, C, heteroarylene, phenylene, or a combination of the foregoing;

$X_2$ is selected from O, S, $NR_{15}$, $CR_{15}R_{16}$, $CR_{15}R_{16}O$, C(=O), C(=O)$NR_{15}$, $NR_{15}$C(=O), O—C(O) and C(O)—O or is absent;

$R_{19}$ is selected from H and $(CH_2)_t$—$NR_{20}R_{21}$;

$R_{24}$ is a phenyl optionally substituted with up to three optional substituent groups selected from OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$ and C(=O)—NH—$(CH_2)_k$—C(=NH)$NR_{11}R_{12}$;

$R_{25}$ and $R_{26}$ are independently selected from H, OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$ and C(=O)—NH—$(CH_2)_k$—C(=NH)$NR_{11}R_{12}$;

each $R_{11}$, $R_{12}$, $R_{13}$, $R_{14}$, $R_{15}$, $R_{16}$, $R_{17}$, $R_{20}$ and $R_{21}$ are independently selected from H and $C_{1-6}$ alkyl;

j and t are independently an integer from 0 to 6; and k is an integer from 1 to 6.

The present disclosure also provides additional compound of formula (Ia).

In certain embodiments, the present invention provides a compound of the formula (XXIV):

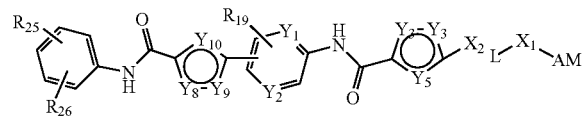

(XXIV)

and salts and solvates thereof, wherein

AM, $X_1$, L, $X_2$, $Y_1$, $Y_2$, $Y_3$, $Y_4$, $Y_5$, $R_{11}$, $R_{12}$, $R_{13}$, $R_{14}$, $R_{15}$, $R_{16}$, $R_{17}$, $R_{19}$, $R_{20}$, $R_{21}$, $R_{25}$, $R_{26}$, k and j are t are as defined for the compound of formula (Ia);

one of $Y_8$ and $Y_9$ is independently selected from N—H, S and O; and the other of $Y_8$ and $Y_9$ is CH; $Y_{10}$ is independently selected from CH and N, where the H of the CH and N—H are optionally substituted with optional substituent groups selected from OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$; C(=O)—NH—$C_6H_4$—$(CH_2)_j$—$R_{18}$ and C(=O)—NH—$(CH_2)_k$—C(=NH)$NR_{11}R_{12}$; and $R_{18}$ is selected from $CO_2R_{11}$ and $NR_{11}R_{12}$.

In one embodiment, a compound of the formula (XXIV) is selected from the structures below:

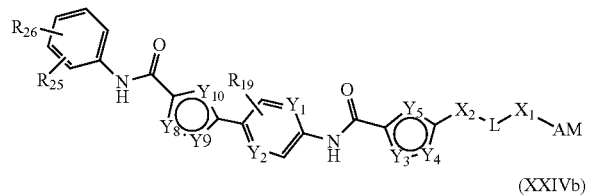

(XXIVa)

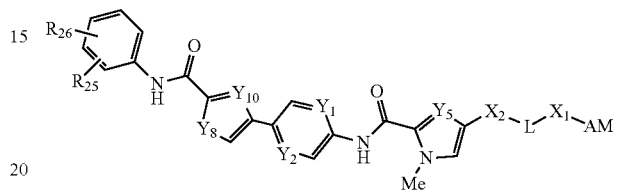

(XXIVb)

In a first aspect of the compounds of the formula XXIV, suitably $Y_3$ is N—$CH_3$—$R_{17}$ and $Y_4$ is CH and $Y_5$ is N or CH. In a second aspect of the compounds of the formula XXIV, suitably $Y_3$ is N—$CH_3$ and $Y_4$ is CH and $Y_5$ is N or CH.

In a third aspect of the compounds of the formula XXIV, suitably $Y_8$ is N—$R_{17}$ and $Y_9$ is CH and $Y_{10}$ is N. In a fourth aspect of the compounds of the formula XXIV, suitably $Y_8$ is N—$CH_3$ and $Y_9$ is CH and $Y_{10}$ is N or CH. The foregoing applies in particular when $Y_3$, $Y_5$, and $Y_4$ are as described in the first and second aspects.

In a fifth aspect of the compounds of the formula XXIV, suitably at least one of $Y_1$ and $Y_2$ are $CH_2$ or both of $Y_1$ and $Y_2$ are $CH_2$. In a sixth aspect of the compounds of the formula XXIV, suitably when at least one or both of $Y_1$ and $Y_2$ are $CH_2$, $R_{19}$ is H. The foregoing applies in particular when $Y_3$, $Y_5$, and $Y_4$ are as described in the first and second aspects and/or $Y_8$, $Y_9$, and $Y_{10}$ are as described in the third and fourth aspects.

Suitably, in the foregoing first to sixth aspects, at least one of $R_{25}$ and $R_{26}$ is H or both of $R_{25}$ and $R_{26}$ are H. Suitably, in the foregoing first to sixth aspects, at least one of $R_{25}$ and $R_{26}$ is $NH_2$, $CO_2CH_3$, or $CH_3$, and the other of $R_{25}$ and $R_{26}$ is suitably H. In certain embodiments, the invention provides a compound of the formula (XXV) and (XXVI):

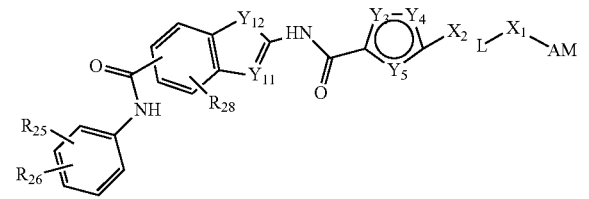

(XXV)

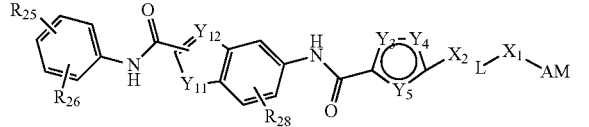

(XXVI)

and salts and solvates thereof,
wherein
AM, $X_1$, L, $X_2$, $Y_3$, $Y_4$, $Y_5$, $R_{11}$, $R_{12}$, $R_{13}$, $R_{14}$, $R_{15}$, $R_{16}$, $R_{17}$, $R_{25}$, $R_{26}$, k and j are as defined for the compound of formula (Ia);

$Y_{11}$ is selected from N—$R_{27}$, S and O;

$Y_{12}$ is selected from CH and N;

with the proviso that the heteroaryl group containing $Y_{11}$ and $Y_{12}$ is not indoylyl; and $R_{27}$ and $R_{28}$ are independently selected from H, OH, $C_{1-6}$ alkyl, $OC_{1-6}$ alkyl, $(CH_2)_j$—$CO_2R_{11}$, O—$(CH_2)_k$—$NR_{11}R_{12}$, $(CH_2)_j$—$NR_{11}R_{12}$, C(=O)—NH—$(CH_2)_k$—$NR_{11}R_{12}$ and C(=O)—NH—$(CH_2)_k$—C(=NH)$NR_{11}R_{12}$.

In one embodiment, a compound of the formula (XXV) is selected from the structures below:

(XXVa)
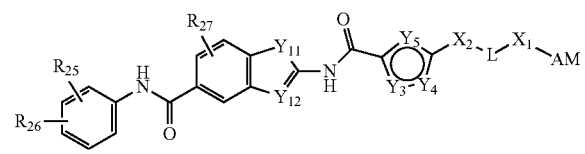

(XXVb)
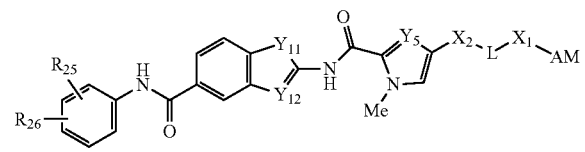

In a first aspect of the compounds of the formula XXV, suitably $Y_3$ is N—$R_{17}$ and $Y_4$ is CH and $Y_5$ is N. In a second aspect of the compounds of the formula XXV, suitably $Y_3$ is N—$CH_3$ and $Y_4$ is CH and $Y_5$ is N or CH.

In a third aspect of the compounds of the formula XXV, suitably $Y_8$ is N—$R_{17}$ and $Y_9$ is CH and $Y_{10}$ is N. In a fourth aspect of the compounds of the formula XXV, suitably $Y_8$ is N—$CH_3$ and $Y_9$ is CH and $Y_{10}$ is N or CH. The foregoing applies in particular when $Y_3$, $Y_5$, and $Y_4$ are as described in the first and second aspects.

In a fifth aspect of the compounds of the formula XXV, suitably one of $Y_{11}$ or $Y_{12}$ is S and the other of $Y_{11}$ or $Y_{12}$ is CH. In a sixth aspect of the compounds of the formula XXV, suitably one of $Y_{11}$ or $Y_{12}$ is S and the other of $Y_{11}$ or $Y_{12}$ is N. The foregoing applies in particular when $Y_3$, $Y_5$, and $Y_4$ are as described in the first and second aspects and/or when $Y_8$, $Y_9$, and $Y_{10}$ are as described in the third and fourth aspects.

In a seventh aspect of the compounds of the formula XXV, suitably at least one of $R_{25}$ and $R_{26}$ is H or both of $R_{25}$ and $R_{26}$ are H. In an eighth aspect of the compounds of the formula XXV, suitably at least one of $R_{25}$ and $R_{26}$ is $NH_2$, $CO_2CH_3$, or $CH_3$; when only one of $R_{25}$ and $R_{26}$ is $NH_2$, $CO_2CH_3$, or $CH_3$, the other of $R_{25}$ and $R_{26}$ is suitably H.

Suitably, in the foregoing first to eighth aspects of the compounds of formula XXV, $R_{27}$ is H or $CH_3$.

In one embodiment, a compound of the formula (XXVI) is selected from the structures below:

(XXVIa)
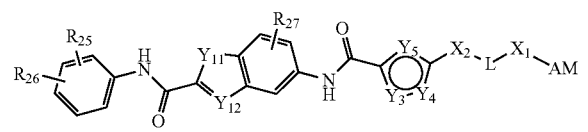

(XXVIb)
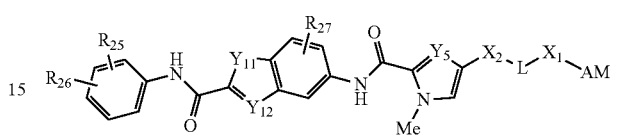

In a first aspect of the compounds of the formula XXVI, suitably $Y_3$ is N—$R_{17}$ and $Y_4$ is CH and $Y_5$ is N. In a second aspect of the compounds of the formula XXVI, suitably $Y_3$ is N—$CH_3$ and $Y_4$ is CH and $Y_5$ is N or CH.

In a third aspect of the compounds of the formula XXVI, suitably $Y_8$ is N—$R_{17}$ and $Y_9$ is CH and $Y_{10}$ is N. In a fourth aspect of the compounds of the formula XXVI, suitably $Y_8$ is N—$CH_3$ and $Y_9$ is CH and $Y_{10}$ is N or CH. The foregoing applies in particular when $Y_3$, $Y_5$, and $Y_4$ are as described in the first and second aspects.

In a fifth aspect of the compounds of the formula XXVI, suitably one of $Y_{11}$ or $Y_{12}$ is S and the other of $Y_{11}$ or $Y_{12}$ is CH. In a sixth aspect of the compounds of the formula XXVI, suitably one of $Y_{11}$ or $Y_{12}$ is S and the other of $Y_{11}$ or $Y_{12}$ is N. The foregoing applies in particular when $Y_3$, $Y_5$, and $Y_4$ are as described in the first and second aspects and/or when $Y_8$, $Y_9$, and $Y_{10}$ are as described in the third and fourth aspects.

In a seventh aspect of the compounds of the formula XXVI, suitably at least one of $R_{25}$ and $R_{26}$ is H or both of $R_{25}$ and $R_{26}$ are H. In an eighth aspect of the compounds of the formula XXVI, suitably at least one of $R_{25}$ and $R_{26}$ is $NH_2$, $CO_2CH_3$, or $CH_3$; when only one of $R_{25}$ and $R_{26}$ is $NH_2$, $CO_2CH_3$, or $CH_3$, the other of $R_{25}$ and $R_{26}$ is suitably H.

Suitably, in the foregoing first to eighth aspects of the compounds of the formula XXVI, at least one of $R_{27}$ is H or $CH_3$.

In the foregoing compounds of the formula (XXIV), (XXV), and (XXVI), the AM moiety is a compound of the formula (XXVII):

(XXVII)
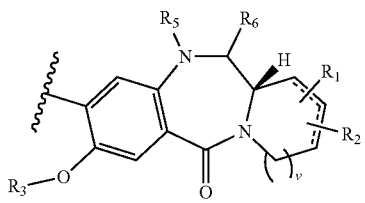

wherein
v is 0 or 1;
when v is 1, the dotted lines represent single bonds; and $R_1$ and $R_4$ are attached to adjacent carbon atoms on the C-ring and together with the carbon atoms to which they are attached form an aromatic 6-membered ring substituted with groups $RD_1$, $RD_2$, $RD_3$ and $RD_4$;

when v is 0 the dotted lines represent single bonds or one double bond and one single bond wherein the double bond is between C1 and C2 or between C2 and C3;

when v is 0 and the dotted lines represent single bonds then either:
  $R_1$ and $R_4$ are attached to adjacent carbon atoms on the C-ring and together with the carbon atoms to which they are attached form an aromatic 6-membered ring substituted with groups $RD_1$, $RD_2$, $RD_3$ and $RD_4$; or
  $R_1$ is absent and $R_2$ is attached to the C2 carbon and is =$C(RD_5)(RD_6)$; or $R_1$ and $R_2$ are independently selected from H, OH, $C_{1-6}$ alkyl, $OC_{1-6}$ alkyl and halogen;

when v is 0 and the dotted lines represent one double bond and one single bond wherein the double bond is between C1 and C2 or between C2 and C3; then $R_1$ is absent and $R_4$ is a $C_{1-6}$ alkyl, a phenyl ring or a $C_{5-9}$ heteroaryl group optionally substituted with groups $RD_1$, $RD_2$, $RD_3$, $RD_4$ and $RD_7$;

$RD_1$, $RD_2$, $RD_3$, $RD_4$ and $RD_7$ are independently selected from H, OH, $C_{1-6}$ alkyl, $OC_{1-6}$ alkyl and halogen;

$RD_5$ and $RD_6$ are independently selected from H and $C_{1-6}$ alkyl;

$R_3$ is selected from H, $C_{1-12}$ alkyl and $CH_2Ph$;

and either:
  (i) $R_5$ and $R_6$ together form a double bond;
  (ii) $R_5$ is H and $R_6$ is selected from OH and $OC_{1-6}$ alkyl; or
  (iii) $R_5$ is $SO_3H$ and $R_6$ is H.

In one aspect, the alkylating moiety is a compound of formula (XXVIII) and represents a QBD.

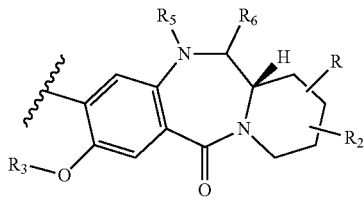

(XXVIII)

In compound (XXVIII), v is 1, the dotted lines represent single bonds, and $R_1$ and $R_2$ are attached to adjacent carbon atoms on the C-ring and together with the carbon atoms to which they are attached form an aromatic 6-membered ring substituted with groups $RD_1$, $RD_2$, $RD_3$ and $RD_4$. $R_1$ and $R_2$ may be attached to C1 and C2, C2 and C3, or C3 and C4, providing a compound of Formula (XXVIIIa), (XXVIIIb), and (XXVIIIc) as shown below.

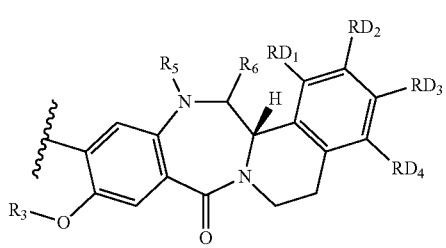

(XXVIIIa)

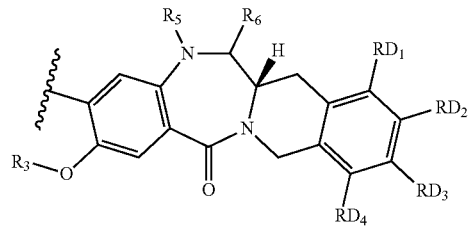

(XXVIIIb)

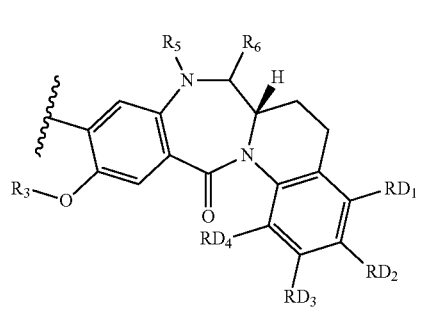

(XXVIIIc)

Suitably, at least one, at least two, at least three, or all of $RD_1$, $RD_2$, $RD_3$ and $RD_4$H. In another aspect, the alkylating moiety is a compound of formula (XXIX) and represents an IBD.

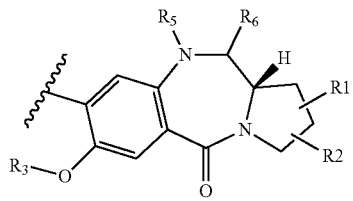

(XXIX)

In compound (XXIX), v is 0, the dotted lines represent single bonds, and $R_1$ and $R_2$ are attached to adjacent carbon atoms on the C-ring and together with the carbon atoms to which they are attached form an aromatic 6-membered ring substituted with groups $RD_1$, $RD_2$, $RD_3$ and $RD_4$.

$R_1$ and $R_2$ may be attached to C1 and C2, C2 and C3, or C3 and C4, providing a compound of Formula (XXIXa) and (XXIXb) as shown below.

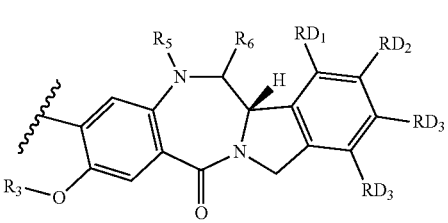

(XXIXa)

(XXIXb)

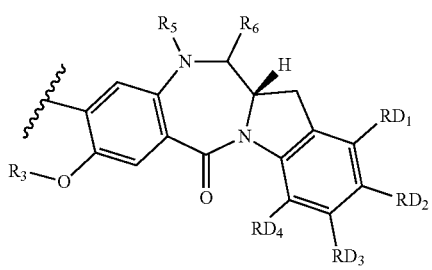

Suitably, at least one, at least two, at least three, or all of RD$_1$, RD$_2$, RD$_3$ and RD$_4$ are H.

In another aspect, the alkylating moiety is a compound of formula (XXX) and represents a PBD.

(XXX)

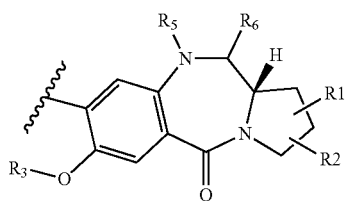

In compound (XXX), v is 0, the dotted lines represent single bonds, and R$_1$ and R$_2$ are independently selected from H, OH, C$_{1-6}$ alkyl, OC$_{1-6}$ alkyl and halogen. R$_1$ and R$_2$ may be attached to C1, C2, or C3 as shown below, providing a compound of Formula (XXXa), (XXXb) and (XXXc) as shown below.

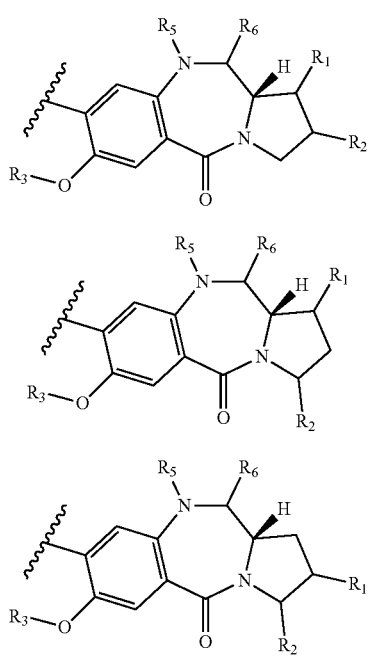

In another aspect, the alkylating moiety is a compound of formula (XSSI) and represents a C2-substuituted PBD (C2-endo PBD).

(XXXI)

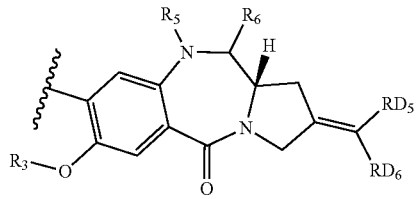

In compound (XXXI), v is 0, the dotted lines represent single bonds, R$_1$ is absent and R$_2$ is =C(RD$_5$)(RD$_6$).

In another aspect, the alkylating moiety is a compound of formula (XXXII) and represents a C1/C2-endo PBD.

(XXXII)

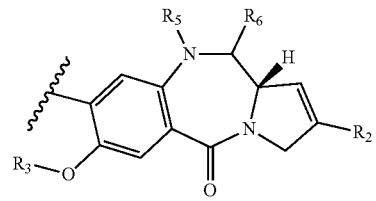

In compound (XXXII), v is 0, the dotted lines represent one double bond, wherein the double bond is between C1 and C2, R$_1$ is absent, and R$_2$ is a C$_{1-6}$ alkyl, a phenyl ring or a C$_{5-9}$ heteroaryl group optionally substituted with one or more R$_1$, RD$_2$, RD$_3$, RD$_4$ or RD$_7$ groups. Representative structures (XXXIIa) and (XXXIIb) are shown below.

(XXXIIa)

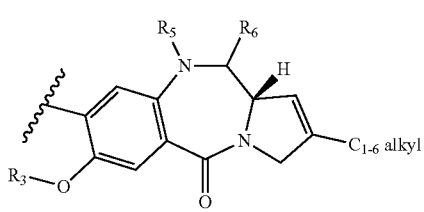

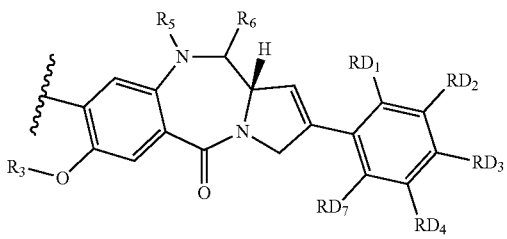

Suitably, at least one, at least two, at least three, at least four, or all of RD$_1$, RD$_2$, RD$_3$, RD$_4$ and RD$_7$ are H.

In another aspect, the alkylating moiety is a compound of formula (XXXIII) and represents a C2/C3-endo PBD.

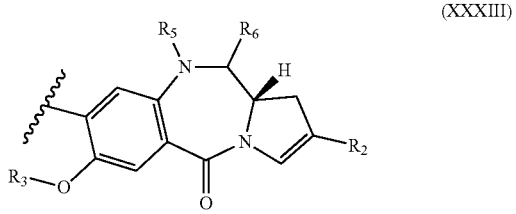

(XXXIII)

In compound (XXXIII), v is 0, the dotted lines represent one double bond, wherein the double bond is between C2 and C3, $R_1$ is absent, and $R_2$ is a $C_{1-6}$ alkyl, a phenyl ring or a $C_{5-9}$ heteroaryl group optionally substituted with one or more $RD_1$, $RD_2$, $RD_3$, $RD_4$ or $RD_7$ groups. Representative structures (XXXIIIa) and (XXXIIIb) are shown below.

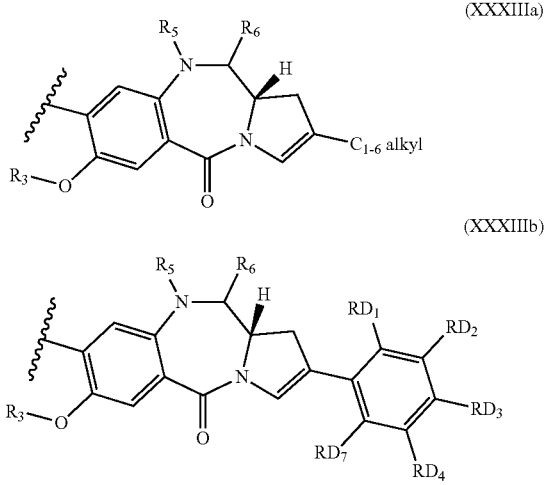

Suitably, at least one, at least two, at least three, at least four, or all of $RD_1$, $RD_2$, $RD_3$, $RD_4$ and $RD_7$ are H.

Applications

The invention finds application in the treatment of proliferative diseases.

In certain aspects a method of treating a proliferative disease is provided, the method comprising administering to a subject a therapeutically effective amount of a compound of the formula (I), (XXIV), (XXV) and/or (XXVI) and salts and solvates thereof or a composition comprising a compound of formula (I), (XXIV), (XXV) and/or (XXVI) and salts and solvates thereof.

In certain aspects a method of treating a proliferative disease is provided, the method comprising administering to a subject a therapeutically effective amount of a targeted compound comprising a compound of the formula (I), (XXIV), (XXV) and/or (XXVI) and salts and solvates thereof.

In certain aspects a method of treating a proliferative disease is provided, the method comprising administering to a subject a therapeutically effective amount of an antibody-drug conjugate comprising a compound of the formula (I), (XXIV), (XXV) and/or (XXVI) and salts and solvates thereof.

The term "proliferative disease" refers to an unwanted or uncontrolled cellular proliferation of excessive or abnormal cells which is undesired, such as, neoplastic or hyperplastic growth, whether in vitro or in vivo. Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, hepatocellular cancer, gastric or stomach cancer including gastrointestinal cancer, bowel cancer, colon cancer, hepatoma, breast cancer, glioblastoma, cervical cancer, ovarian cancer, oesophageal [or esophageal] cancer, oral cancer, prostate cancer, testicular cancer, liver cancer, rectal cancer, colorectal cancer, endometrial or uterine carcinoma, uterine cancer, salivary gland carcinoma, kidney or renal cancer, prostate cancer, vulval cancer, thyroid cancer, hepatic carcinoma, anal carcinoma, penile carcinoma, head and neck cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Suitably the proliferative disease is selected from bladder cancer, bone cancer, bowel cancer, brain cancer, breast cancer, cervical cancer, colon cancer, head and neck cancer, leukemia, liver cancer, lung cancer, lymphoma, melanoma, oesophageal cancer, oral cancer, ovarian cancer, pancreatic cancer, prostate cancer, rectal cancer, renal cancer, retinoblastoma, sarcoma, skin cancer, stomach cancer, testicular cancer, thyroid cancer and uterine cancer. Suitably the proliferative disease is selected from breast cancer and cervical cancer.

Any type of cell may be treated, including but not limited to, bone, eye, head and neck, lung, gastrointestinal (including, e.g. mouth, oesophagus, bowel, colon), breast (mammary), cervix, ovarian, uterus, prostate, liver (hepatic), kidney (renal), bladder, pancreas, brain, and skin.

A skilled person is readily able to determine whether or not a candidate compound treats a proliferative condition for any particular cell type.

Suitably subjects are human, livestock animals and companion animals.

In a further aspect, the compound of formula (I), (XXIV), (XXV) and (XXVI) and salts and solvates thereof, may be linked, either directly or indirectly, to a targeting agent (e.g., antibody, antibody fragment, hormone, etc.) to provide a targeted conjugate. The target conjugates of the present disclosure may contain one or multiple compounds of formula (I), (XXIV), (XXV) and/or (XXVI) (or salts and solvates thereof). A variety of target conjugates are known in the art and may be used with a compound of formula (I), (XXIV), (XXV) and (XXVI) and salts and solvates thereof. For example, in a particular aspect the target conjugate is an antibody-drug conjugate, wherein one or more compounds of formula (I), (XXIV), (XXV) and/or (XXVI) are linked, directly or indirectly, to the antibody. Therefore, the compound of formula (I) and salts and solvates thereof, may be used as a payload on a targeted conjugate.

Suitably, a compound of formula (I), (XXIV), (XXV) and/or (XXVI) and salts and solvates thereof, for use as a drug in targeted conjugate is prepared by attaching a compound of formula (I), (XXIV), (XXV) and/or (XXVI) and salts and solvates thereof to a targeting agent, either directly or via an optional linker group. Suitably, the compound of formula (I), (XXIV), (XXV) and/or (XXVI) and salts and solvates thereof, is attached to a targeting agent via a linker group. Suitably, the targeted conjugate is for use in the treatment of a disease, more specifically of a proliferative disease. Suitably, the drug may be attached by any suitable functional group that it contains to the targeting agent either directly or via a linker group. Typically, the drug contains, or can be modified to contain, one or more functional groups such as amine, hydroxyl or carboxylic acid groups for attaching the drug to the targeting agent either directly or via a linker group. In some aspects, one or more atoms or groups of the compound of formula (I), (XXIV), (XXV) and/or (XXVI) may be eliminated during the attachment of the drug to the antibody. In some aspects, the targeting agent binds to a cell surface receptor or a tumor-associated antigen. In some aspects, the targeting agent is an antibody. In some aspects, the targeting agent is a hormone. In some aspects, the targeting agent is a protein. In some aspects, the targeting agent is a polypeptide. In some aspects, the targeting agent is a small molecule (for example, folic acid).

The compounds of formula (I), (XXIV), (XXV) and/or (XXVI) find application as payloads for antibodies or antibody fragments. The compounds of formula (I), (XXIV), (XXV) and/or (XXVI) readily allow conjugation to antibodies or antibody fragments.

Antibody Drug Conjugates

Antibody therapy has been established for the targeted treatment of patients with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumor cells in the treatment of cancer, targets delivery of the drug moiety to tumors, and intracellular accumulation therein, whereas systemic administration of these unconjugated drug agents may result in unacceptable levels of toxicity to normal cells (Xie et al (2006) Expert. Opin. Biol. Ther. 6(3):281-291; Kovtun ef a/ (2006) Cancer Res. 66(6): 3214-3121; Law et al (2006) Cancer Res. 66(4):2328-2337; Wu et al (2005) Nature Biotech. 23(9): 1 137-1 145; Lambert J. (2005) Current Opin. in Pharmacol. 5:543-549; Hamann P. (2005) Expert Opin. Ther. Patents 15(9): 1087-1 103; Payne, G. (2003) Cancer Cell 3:207-212; Trail ef a/ (2003) Cancer Immunol. Immunother. 52:328-337; Syrigos and Epenetos (1999) Anticancer Research 19:605-614).

Maximal efficacy with minimal toxicity is sought thereby. Efforts to design and refine ADC have focused on the selectivity of monoclonal antibodies (mAbs) as well as drug mechanism of action, drug-linking, drug/antibody ratio (loading), and drug-releasing properties (Junutula, et al., 2008b Nature Biotech., 26(8):925-932; Doman et al., (2009) Blood 114(13):2721-2729; U.S. Pat. Nos. 7,521,541; 7,723, 485; WO2009/052249; McDonagh (2006) Protein Eng. Design & Sel. 19(7): 299-307; Doronina et al., (2006) Bioconj. Chem. 17:114-124; Erickson et al., (2006) Cancer Res. 66(8): 1-8; et al., (2005) Clin. CancerRes. 11: 843-852; Jeffrey et al., (2005) J. Med. Chem. 48:1344-1358; Hamblett et al., (2004) Clin. Cancer Res. 10:7063-7070).

In some aspects, the present invention relates to a compound of formula (I), (XXIV), (XXV) and/or (XXVI) and salts and solvates thereof, for use as a drug in an antibody-drug conjugate. Suitably, a compound of formula (I), (XXIV), (XXV) and/or (XXVI) and salts and solvates thereof, for use as a drug in an antibody-drug conjugate is prepared by attaching a compound of formula (I), (XXIV), (XXV) and/or (XXVI) and salts and solvates thereof to an antibody, either directly or via an optional linker group. Suitably, the compound of formula (I), (XXIV), (XXV) and/or (XXVI) and salts and solvates thereof, is attached to an antibody via a linker group. Suitably, the antibody-drug conjugate is for use in for treatment of a disease, more specifically of a proliferative disease. Suitably, the antibody-drug conjugate is for use in for treatment of a disease, more specifically of a proliferative disease. Suitably, the drug may be attached by any suitable functional group that it contains to the antibody either directly or via a linker group. Typically, the drug contains, or can be modified to contain, one or more functional groups such as amine, hydroxyl or carboxylic acid groups for attaching the drug to the antibody either directly or via a linker group. In some aspects, the antibody of the antibody drug conjugate is an antibody fragment, such as, but not limited to a single chain antibody. In some aspects, one or more atoms or groups of the compound of formula (I), (XXIV), (XXV) and/or (XXVI) may be eliminated during the attachment of the drug to the antibody. In some aspects, the antibody binds to a cell surface receptor or a tumor-associated antigen.

In some aspects, the present invention relates to a compound of formula (I), (XXIV), (XXV) and/or (XXVI) and salts and solvates thereof, for use in preparing a drug in an antibody-drug conjugate. Suitably, a compound of formula (I), (XXIV), (XXV) and/or (XXVI) and salts and solvates thereof, may be used directly to prepare an antibody-drug conjugate when a compound of formula (I), (XXIV), (XXV) and/or (XXVI) and salts and solvates thereof, contains one or more functional groups (such as amine, hydroxyl or carboxylic acid groups) for attaching the drug to the antibody either directly or via a linker group. Suitably, a compound of formula (I), (XXIV), (XXV) and/or (XXVI) and salts and solvates thereof, may be used in preparing an antibody-drug conjugate by being modified to contain one or more functional groups (such as amine, hydroxyl or carboxylic acid groups) for attaching the drug to the antibody either directly or via a linker group. Suitably, a compound of formula (I), (XXIV), (XXV) and/or (XXVI) and salts and solvates thereof, may be used in preparing an antibody-drug conjugate by being modified to contain one or more linker groups, wherein the antiobody is attached to the drugh through the one or more linker groups. Therefore, the present disclosure provides for a compounds of the formula (I), (XXIV), (XXV) and/or (XXVI) further comprising one or more linker group. Suitably, a compound of the formula (I), (XXIV), (XXV) and/or (XXVI) may contain 1, 2, or 3 linker groups.

Suitably, a compound of the formula (I), (XXIV), (XXV) and/or (XXVI) may contain 1 or 2 linker groups. Suitably, a compound of the formula (I), (XXIV), (XXV) and/or (XXVI) may contain 1 linker group. In some aspects, one or more atoms or groups of the compound of formula (I), (XXIV), (XXV) and/or (XXVI) may be eliminated during the attachment of the drug to the antibody or the attachment of the linker to the drug or the modification of the drug to contain one or more functional groups (such as amine, hydroxyl or carboxylic acid groups) for attaching the drug to the antibody either directly or via a linker group.

A variety of suitable linker groups are known in the art and may be used as described herein. For example, the maleimide methodology is routinely used as a method to attach antibodies to drug compounds by providing a linker attached to the drug with a terminal maleimide group. Examples 143, 144 and 148 provide compounds of the formula (I) attached to linker groups containing terminal maleimide groups. In addition, methodologies using diaryic, clooct) ne (such as, but not limited to, DBCO, dibenzylcyclooctyne) are also alternatives used in the art. Diarylcyclooctynes react with azides to provide attachment via the formation of stable triazoles. Diarylcyclooctynes are thermostable with very narrow and specific reactivity toward azides, resulting in almost quantitative yields of stable triazoles. Furthermore, the reaction does not require a cytotoxic Cu(I) catalyst (that is toxic to most organisms) and thus, prevents its use in many biological systems. Still further, alkoxyamine methodologies are also alternatives used in the art. For site-specific conjugation of the drug to an antibody, the antibodies may comprise a "tag" (which may be proprietary) that will react with a dairylcyclooctyne (for example, DBCO), an alkyloxyamine and/or maleimide group to attach the antibody to the drug. The tag in some instances may be a mutated amino acid. Suitable linker groups incorporating the various groups described above are available in the art. FIGS. 34A and B provides examples of compounds of the formula (I) (exemplified by compound 140 of Example 143) attached to linker group containing an exemplary terminal alkoxyamine groups (FIG. 34A) and an exemplary terminal diarylcyclooctyne group, DBCO (FIG. 34B).

In some aspects, the present invention relates to the use of a compound of formula (I), (XXIV), (XXV) and/or (XXVI) and salts and solvates thereof, as a drug in an antibody-drug conjugate. Suitably, the use of a compound of formula (I), (XXIV), (XXV) and/or (XXVI) and salts and solvates thereof, as a drug in an antibody-drug conjugate is accomplished by attaching a compound of formula (I), (XXIV), (XXV) and/or (XXVI) and salts and solvates thereof to an antibody, either directly or via an optional linker group. Suitably, the compound of formula (I), (XXIV), (XXV) and/or (XXVI) and salts and solvates thereof, is attached to an antibody via a linker group. Suitably, the antibody-drug conjugate is for use in for treatment of a disease, more specifically of a proliferative disease. Suitably, the drug may be attached by any suitable functional group that it contains to the antibody either directly or via a linker group. Typically, the drug contains, or can be modified to contain, one or more functional groups such as amine, hydroxyl or carboxylic acid groups for attaching the drug to the antibody either directly or via a linker group. In some aspects, the antibody of the antibody drug conjugate is an antibody fragment, such as, but not limited to a single chain antibody.

In some aspects, one or more atoms or groups of the compound of formula (I), (XXIV), (XXV) and/or (XXVI) may be eliminated during the attachment of the drug to the antibody. In some aspects, the antibody binds to a cell surface receptor or a tumor-associated antigen.

The substituent groups of the compounds of formula (I), (XXIV), (XXV) and/or (XXVI) may interact with DNA sequences and may be selected so as to target specific sequences. In particular, the following groups in compounds of formula (I):

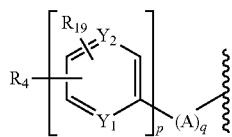

may be selected to target specific sequences.

In particular, the following groups in compounds of formula (XXIV):

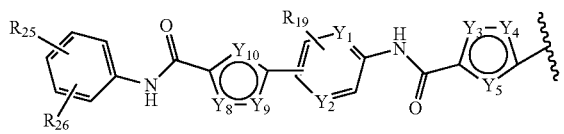

may be selected to target specific sequences.

In particular, the following groups in compounds of formula (XXV):

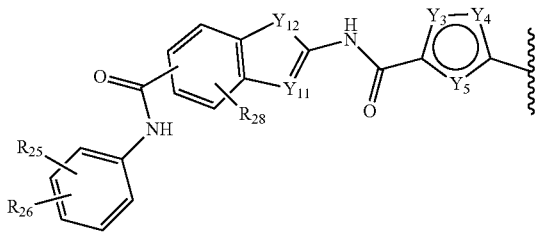

may be selected to target specific sequences.

In particular, the following groups in compounds of formula (XXVI):

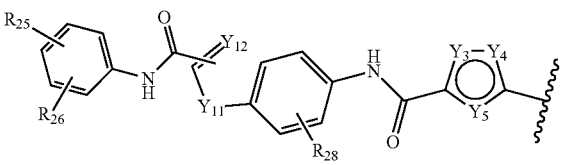

may be selected to target specific sequences.

Hence, when the substituent groups are tailored in this way, the compounds of formula (I), (XXIV), (XXV) and/or (XXVI) find application in targeted chemotherapy.

Antibody and Antibody Fragments

The term "antibody" specifically covers monoclonal antibodies, polyclonal antibodies, dimers, multimers, multispecific antibodies (e.g., bispecific antibodies), intact antibodies and antibody fragments, so long as they exhibit the desired biological activity, for example, the ability to bind a desired antigen on a target cell or tissue. Antibodies may be murine, human, humanized, chimeric, or derived from other species. An antibody is a protein generated by the immune system that is capable of recognizing and binding to a specific antigen. (Janeway, C, Travers, P., Walport, M., Shlomchik (2001) Immuno Biology, 5th Ed., Garland Publishing, New York). A target antigen generally has numerous binding sites, also called epitopes, recognized by CDRs on the antibody. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, lgA1 and lgA2) or subclass, or allotype (e.g. human G1 m1, G1 m2, G1 m3, non-G1 m1 [that, is any allotype other than G1 m1], G1 m17, G2m23, G3m21, G3m28, G3m11, G3m5, G3m13, G3m14, G3m10, G3m15, G3m16, G3m6, G3m24, G3m26, G3m27, A2M1, A2m2, Km1, Km2 and Km3) of immunoglobulin molecule. The immunoglobulins can be derived from any species, including human, murine, or rabbit origin.

As used herein, "binds an epitope" is used to mean the antibody binds an epitope with a higher affinity than a non-specific partner such as Bovine Serum Albumin (BSA, Genbank accession no. CAA$_7$6847, version no. CAA76847.1 G1:3336842, record update date: Jan. 7, 2011 02:30 PM). In some embodiments the antibody binds an epitope with an association constant (Ka) at least 2, 3, 4, 5, 10, 20, 50, 100, 200, 500, 1000, 2000, 5000, $10^4$, $10^5$ or $10^6$-fold higher than the antibody's association constant for BSA, when measured at physiological conditions.

The term "antibody fragment" refers to a portion of a full length antibody, for example, the antigen binding or variable region thereof. Examples of antibody fragments include Fab, Fab', F(ab')2, and scFv fragments; diabodies; linear antibodies; fragments produced by a Fab expression library, anti-idiotypic (anti-Id) antibodies, CDR (complementary determining region), single-chain antibody molecules; and multispecific antibodies formed from antibody fragments and epitope-binding fragments of any of the above which immunospecifically bind to target antigens, such as, for example, cancer cell antigens, viral antigens or microbial antigens. The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant or epitope on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256: 495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597 or from transgenic mice carrying a fully human immunoglobulin system (Lonberg (2008) Curr. Opinion 20(4): 450-459)

The antibodies, including monoclonal antibodies, herein specifically include "chimeric" antibodies in which a portion of the antibody structure, for example the heavy and/or light chain, is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81: 6851-6855). Chimeric antibodies include "primatized" antibodies comprising variable domain antigen-binding sequences derived from a non-human primate (e.g. Old World Monkey or Ape) and human constant region sequences. An "intact antibody" herein is one comprising VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1 q binding; complement dependent cytotoxicity; Fc receptor binding; antibody-dependent cell-mediated cytotoxicity (ADCC); phagocytosis; and down regulation of cell surface receptors such as B cell receptor and BCR.

The antibodies disclosed herein may be modified. For example, to make them less immunogenic to a human subject. This may be achieved using any of a number of techniques familiar to the person skilled in the art, such as humanisation.

Administration & Dose

Compounds of formula (I), (XXIV), (XXV) and/or (XXVI) may be administered alone or in combination with one or another or with one or more pharmacologically active compounds which are different from the compounds of formula (I), (XXIV), (XXV) and/or (XXVI).

Compounds of the invention may suitably be combined with various components to produce compositions of the invention. Suitably the compositions are combined with a pharmaceutically acceptable carrier or diluent to produce a pharmaceutical composition (which may be for human or animal use). Suitable carriers and diluents include isotonic saline solutions, for example phosphate-buffered saline. Useful pharmaceutical compositions and methods for their preparation may be found in standard pharmaceutical texts. See, for example, *Handbook for Pharmaceutical Additives*, 3rd Edition (eds. M. Ash and I. Ash), 2007 (Synapse Information Resources, Inc., Endicott, N.Y., USA) and Remington: *The Science and Practice of Pharmacy*, 21st Edition (ed. D. B. Troy) 2006 (Lippincott, Williams and Wilkins, Philadelphia, USA) which are incorporated herein by reference.

The compounds of the invention may be administered by any suitable route. Suitably the compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form.

The compounds of the invention, their pharmaceutically acceptable salts, and pharmaceutically acceptable solvates of either entity can be administered alone but will generally be administered in admixture with a suitable pharmaceutical excipient diluent or carrier selected with regard to the intended route of administration and standard pharmaceutical practice.

For example, the compounds of the invention or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, modified-, sustained-, controlled-release or pulsatile delivery applications. The compounds of the invention may also be administered via fast dispersing or fast dissolving dosages forms.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol.

The compounds of the invention can also be administered parenterally, for example, intravenously, intra-arterially, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Suitably formulation of the invention is optimised for the route of administration e.g. oral, intravenously, etc.

Administration may be in one dose, continuously or intermittently (e.g. in divided doses at appropriate intervals) during the course of treatment. Methods of determining the most effective means and dosage are well known to a skilled person and will vary with the formulation used for therapy, the purpose of the therapy, the target cell(s) being treated, and the subject being treated. Single or multiple administrations can be carried out with the dose level and the dose regimen being selected by the treating physician, veterinarian, or clinician.

Depending upon the disorder and patient to be treated, as well as the route of administration, the compositions may be administered at varying doses. For example, a typical dosage for an adult human may be 100 ng to 25 mg (suitably about 1 micro g to about 10 mg) per kg body weight of the subject per day.

Suitably guidance may be taken from studies in test animals when estimating an initial dose for human subjects. For example when a particular dose is identified for mice, suitably an initial test dose for humans may be approx. 0.5× to 2× the mg/Kg value given to mice.

Other Forms

Unless otherwise specified, included in the above are the well known ionic, salt, solvate, and protected forms of these substituents. For example, a reference to carboxylic acid (—COOH) also includes the anionic (carboxylate) form (—COO—), a salt or solvate thereof, as well as conventional protected forms. Similarly, a reference to an amino group includes the protonated form (—$N^+HR_1R_2$), a salt or solvate of the amino group, for example, a hydrochloride salt, as well as conventional protected forms of an amino group. Similarly, a reference to a hydroxyl group also includes the anionic form (—O—), a salt or solvate thereof, as well as conventional protected forms.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; alpha- and beta-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$.

A reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not apply to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof.

Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

In some embodiments, the compound of formula (I), (XXIV), (XXV) and/or (XXVI) and salts and solvates thereof, comprises pharmaceutically acceptable salts of the compounds of formula (I), (XXIV), (XXV) and/or (XXVI).

Compounds of formula (I), (XXIV), (XXV) and/or (XXVI), which include compounds specifically named above, may form pharmaceutically acceptable complexes, salts, solvates and hydrates. These salts include nontoxic acid addition salts (including di-acids) and base salts.

If the compound is cationic, or has a functional group which may be cationic (e.g. —$NH_2$ may be —$NH_3^+$), then an acid addition salt may be formed with a suitable anion. Examples of suitable inorganic anions include, but are not limited to, those derived from the following inorganic acids hydrochloric acid, nitric acid, nitrous acid, phosphoric acid, sulfuric acid, sulphurous acid, hydrobromic acid, hydroiodic acid, hydrofluoric acid, phosphoric acid and phosphorous acids. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfonate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

For example, if the compound is anionic, or has a functional group which may be anionic (e.g. —COOH may be —COO—), then a base salt may be formed with a suitable cation. Examples of suitable inorganic cations include, but are not limited to, metal cations, such as an alkali or alkaline earth metal cation, ammonium and substituted ammonium cations, as well as amines. Examples of suitable metal cations include sodium ($Na^+$) potassium ($K^+$), magnesium ($Mg^{2+}$), calcium ($Ca^{2+}$), zinc ($Zn^{2+}$), and aluminum ($Al^{3+}$). Examples of suitable organic cations include, but are not limited to, ammonium ion (i.e. $NH4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$. Examples of suitable amines include arginine, N,N'-dibenzylethylene-diamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2011)

Pharmaceutically acceptable salts may be prepared using various methods. For example, one may react a compound of Formula 1 with an appropriate acid or base to give the desired salt. One may also react a precursor of the compound of Formula 1 with an acid or base to remove an acid- or base-labile protecting group or to open a lactone or lactam group of the precursor. Additionally, one may convert a salt of the compound of Formula 1 to another salt through treatment with an appropriate acid or base or through contact with an ion exchange resin. Following reaction, one may then isolate the salt by filtration if it precipitates from solution, or by evaporation to recover the salt. The degree of ionization of the salt may vary from completely ionized to almost non-ionized.

It may be convenient or desirable to prepare, purify, and/or handle a corresponding solvate of the active compound. The term "solvate" describes a molecular complex comprising the compound and one or more pharmaceutically acceptable solvent molecules (e.g., EtOH). The term "hydrate" is a solvate in which the solvent is water.

Pharmaceutically acceptable solvates include those in which the solvent may be isotopically substituted (e.g., $D_2O$, acetone-d6, DMSO-d6).

A currently accepted classification system for solvates and hydrates of organic compounds is one that distinguishes between isolated site, channel, and metal-ion coordinated solvates and hydrates. See, e.g., K. R. Morris (H. G. Brittain ed.) Polymorphism in Pharmaceutical Solids (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions.v In such cases, non-stoichiometry will typically be observed.

Compounds of formula I include imine, carbinolamine and carbinolamine ether forms of the PDD. The carbinolamine or the carbinolamine ether is formed when a nucleophilic solvent ($H_2O$, ROH) adds across the imine bond of the PDD moiety. The balance of these equilibria between these forms depend on the conditions in which the compounds are found, as well as the nature of the moiety itself.

These compounds may be isolated in solid form, for example, by lyophilisation.

Further particular and preferred aspects are set out in the accompanying independent and dependent claims. Features of the dependent claims may be combined with features of the independent claims as appropriate, and in combinations other than those explicitly set out in the claims.

Synthetic Strategies

The compounds of formula (I), (XXIV), (XXV) and/or (XXVI) may be prepared using the techniques described herein. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations, A Guide to Functional Group Preparations,* 2nd Ed (2010), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a diacid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, Protecting Groups in Organic Chemistry, 4th Edition, (2006) and P. Kocienski, Protective Groups, 3rd Edition (2005).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

Further particular and preferred aspects are set out in the accompanying independent and dependent claims. Features of the dependent claims may be combined with features of the independent claims as appropriate, and in combinations other than those explicitly set out in the claims.

BRIEF DESCRIPTION OF THE DRAWINGS

Embodiments of the present invention will now be described further, with reference to the accompanying drawings, in which:

FIG. 5 shows the sequence of the labelled strand of the TyrT DNA fragment used in the cross-linking study.

FIG. 6 shows the autoradiograph of a denaturing polyacrylamide gel investigating the mechanism of DNA interaction of 41 with linear $^{32}$P-end-labelled TyrT DNA following overnight incubation at 37° C. at various concentrations.

FIG. 7 shows an autoradiograph of a denaturing polyacrylamide gel showing DNA interstrand cross-linking by the PBD dimer Talirine with linear $^{32}$P-end-labelled TyrT DNA following overnight incubation at 37° C. at various concentrations.

FIG. 8B shows DNA footprint illustrating the interaction of 73 (B), 76 (D), 81 (E), 88 (C) and 93 (G) with the HexA DNA fragment. Ligand concentrations are shown at the top of the gel. Tracks labelled "GA" are markers for specific purines.

FIG. 8C shows DNA footprint illustrating the interaction of the PBD dimer Talirine with the MS1 DNA fragment. Ligand concentrations are shown at the top of the gel. Tracks labelled "GA" are markers for specific purines.

FIG. 9 shows the sequence of the MS1 DNA fragment showing the possible mono-alkylated adducts produced by the compounds analysed.

FIG. 10 shows the sequence of the HexA DNA fragment showing the possible mono-alkylated adducts produced by the compounds analysed.

FIG. 11 shows fluorescently labelled DNA duplex used in the FRET melting study to study the stabilisation of DNA by 41, 106, 107 and 148. The labels were fluorescein (F) and dabcyl (Q).

EXAMPLES

General Remarks

Figure 1:
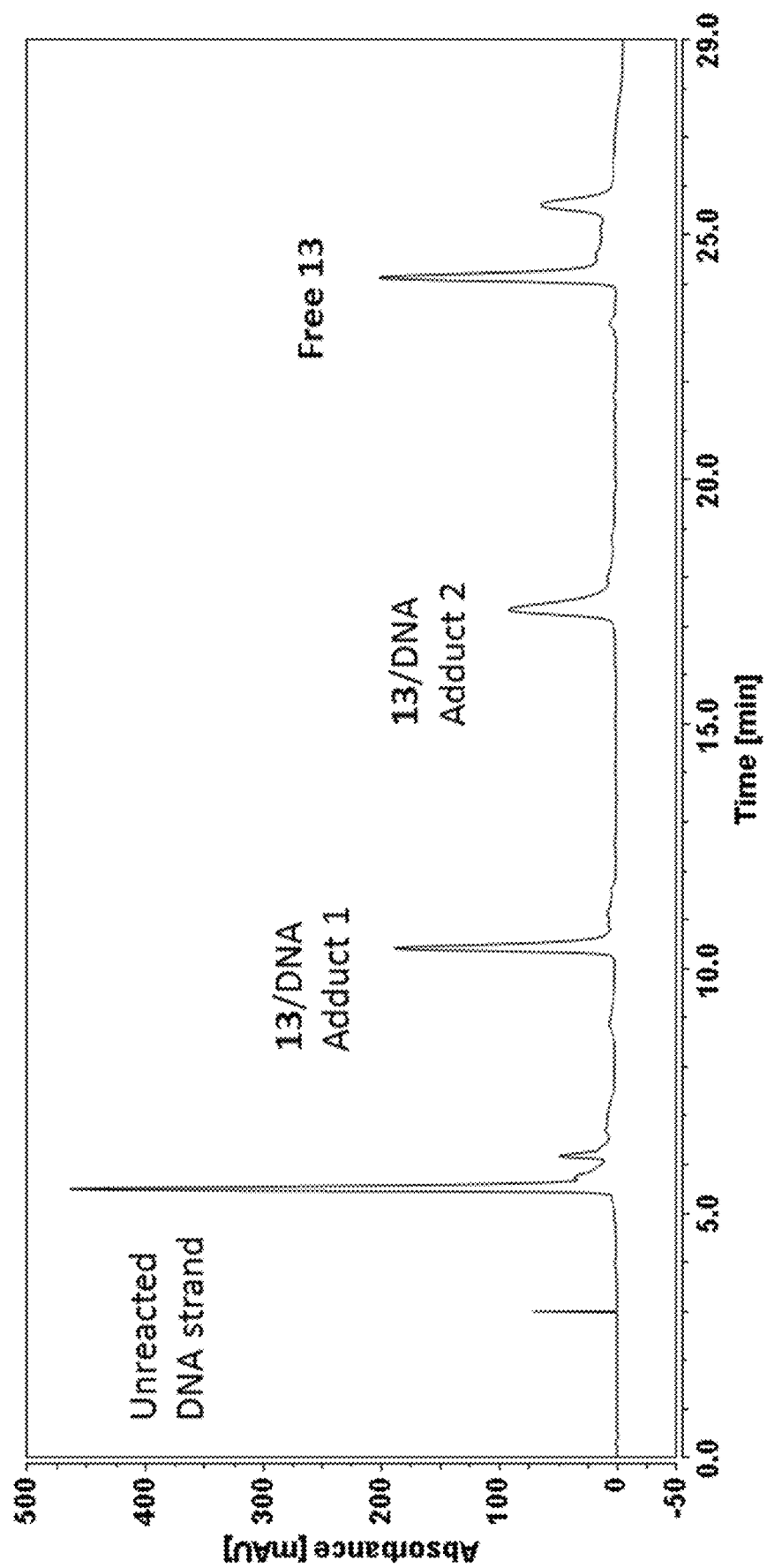
FIG. 1 shows a HPLC chromatogram that provides evidence of DNA adduct formation with NFκB transcription factor binding sequence with C8-linked PDD monomer 13.
Figure 2:
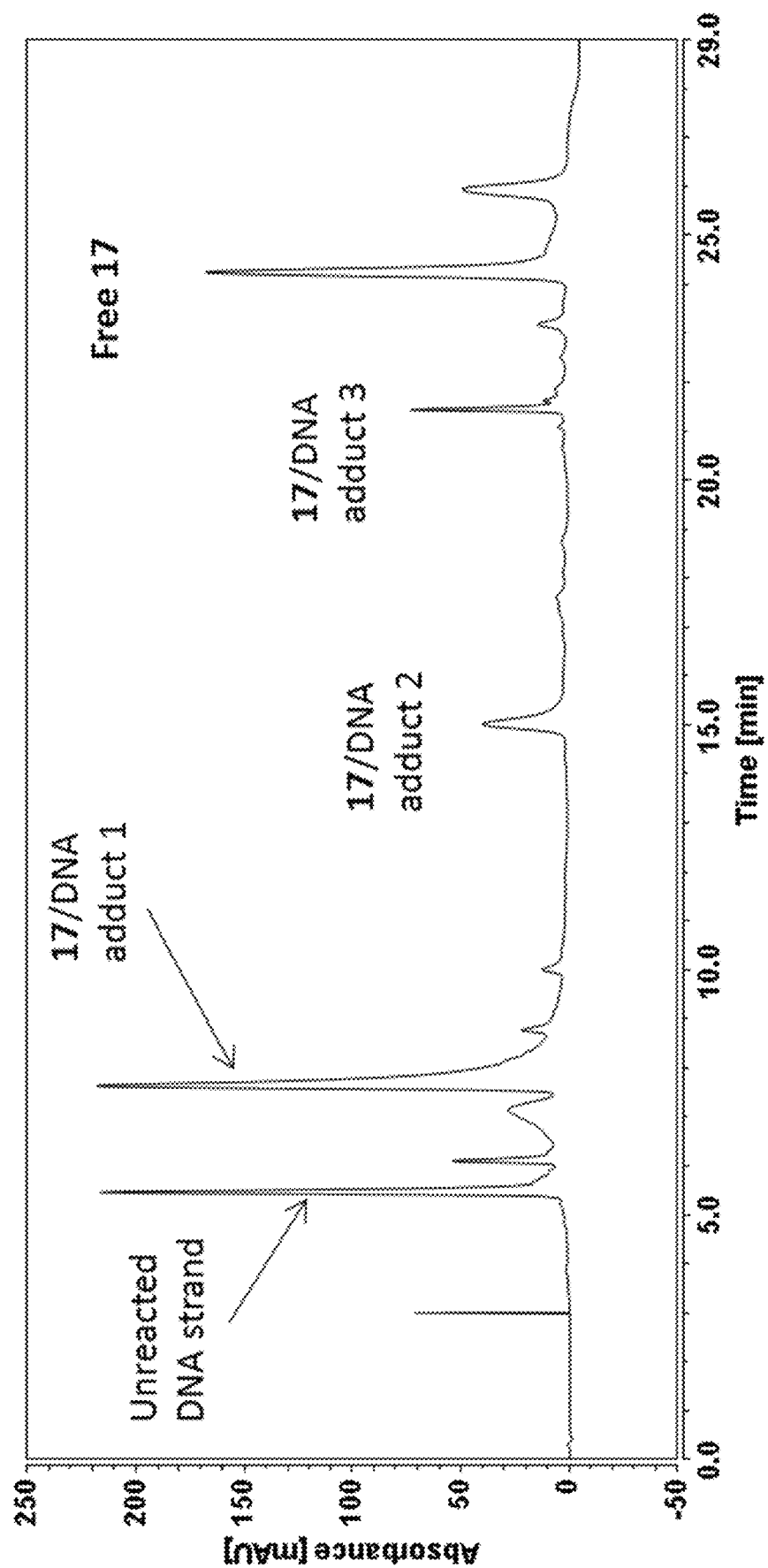
FIG. 2 shows a HPLC chromatogram that provides evidence of DNA adduct formation with NFκB transcription factor binding sequence with C8-linked PDD monomer 17.
Figure 3:
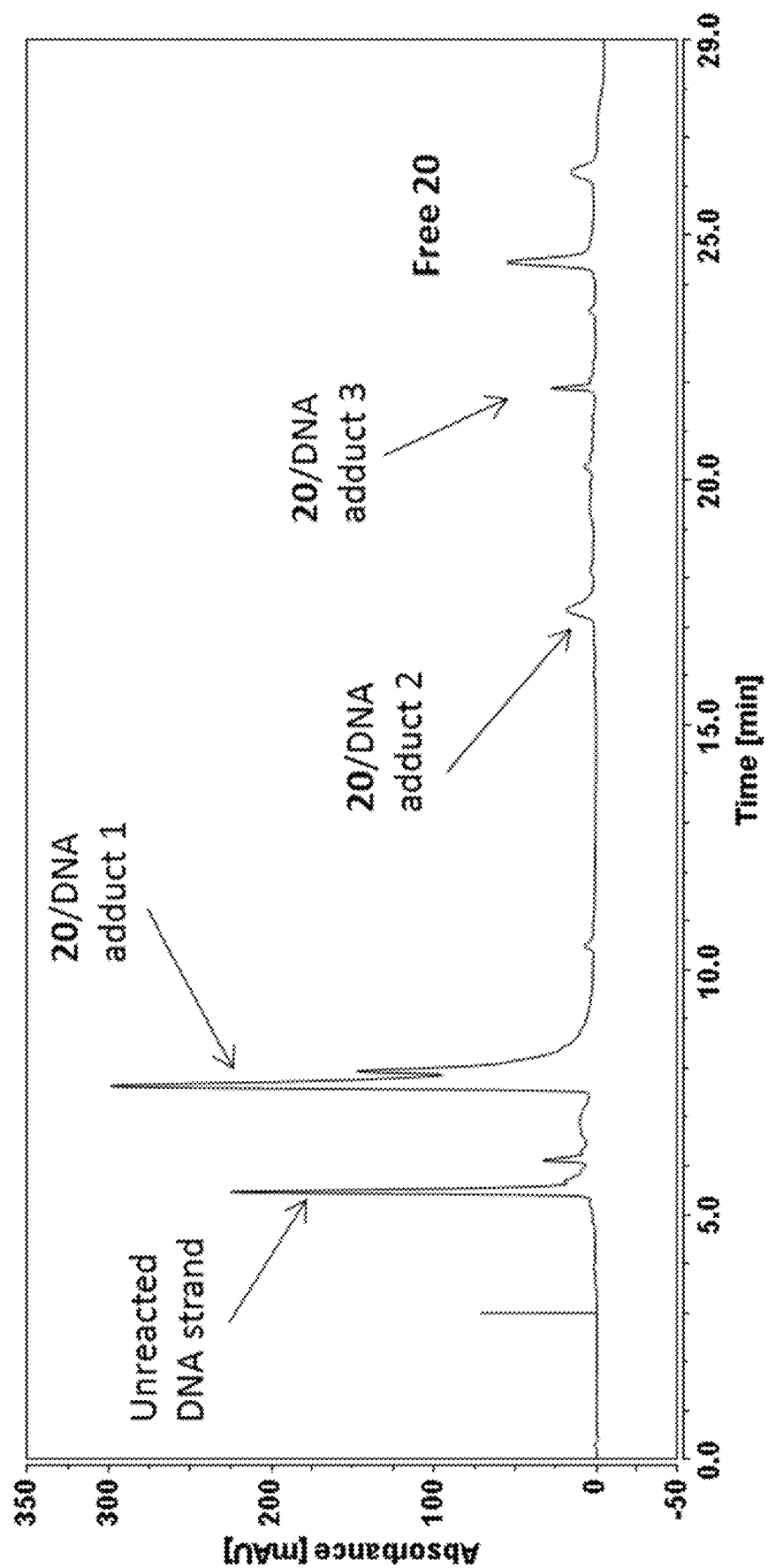
FIG. 3 shows a HPLC chromatogram that provides evidence of DNA adduct formation with NFκB transcription factor binding sequence with C8-linked PDD monomer 20.
Figure 4:
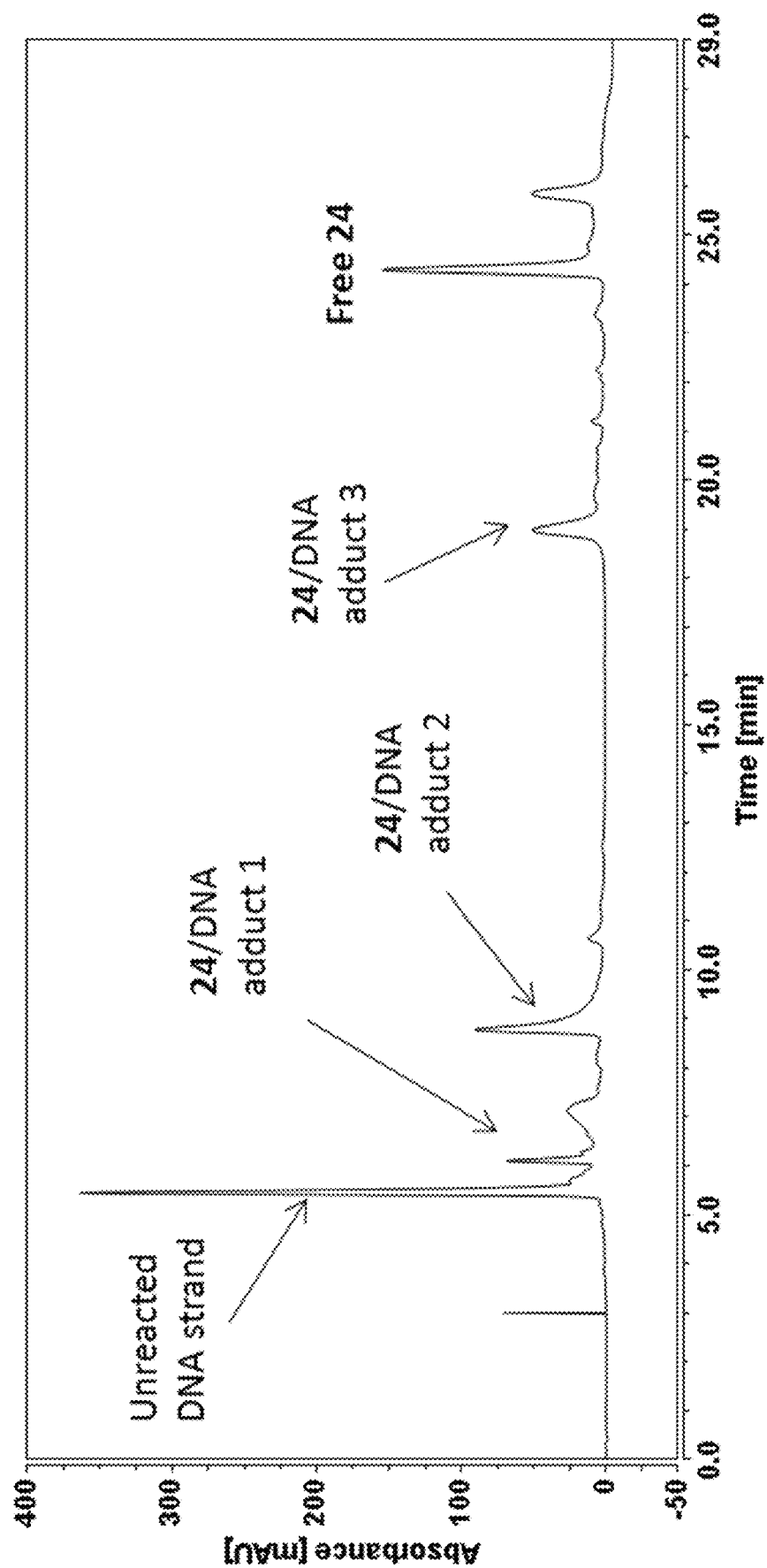
FIG. 4 shows a HPLC chromatogram that provides evidence of DNA adduct formation with NFκB transcription factor binding sequence with C8-linked PDD monomer 24.

Reagents were purchased from standard commercial suppliers. Solvents were purchased from Sigma-Aldrich (UK) and Fisher Scientific (UK). Anhydrous reactions were carried out in pre-oven-dried glassware under an inert atmosphere of nitrogen. Anhydrous solvents were used as purchased without further drying. Thin Layer Chromatography (TLC) was performed on silica gel aluminium plates (Merck 60, $F_{254}$), and column chromatography was carried out either manually using silica gel (Merck 9385, 230-400 mesh ASTM, 40-63 μM) (whilst monitoring by thin layer chromatography: UV (254 nm) and an aqueous alkaline solution of potassium permanganate as stain), or using a Biotage Isolera One. All NMR spectra were obtained at room temperature using a Bruker $DPX_{400}$ spectrometer, for which chemical shifts are expressed in ppm relative to the solvent and coupling constants are expressed in Hz. All Liquid Chromatography Mass Spectroscopy (LCMS) analysis was performed on a Waters Alliance 2695 with water (A) and acetonitrile (B) comprising the mobile phases. Formic acid (0.1%) was added to the acetonitrile to ensure acidic conditions throughout the analysis. Function type: Diode array (535 scans). Column type: Monolithic C18 50×4.60 mm. Mass spectrometry data were collected using a Waters Micromass 2,Q instrument coupled to a Waters 2695 HPLC with a Waters 2996 PDA, Waters Micromass ZQ parameters used were: Capillary (kV), 3.38; Cone (V), 35; Extractor (V), 3.0: Source temperature (° C.), 100: Desolvation Temperature (° C.), 200; Cone flow rate (L/h), 50; De-solvation flow rate (L/h), 250. Microwave reactions were carried out on a Biotage Initiator+microwave synthesis reactor. FIRMS was performed on a Thermo Scientific-Exactive HCD Orbitrap Mass Spectrometer. Yields refer to isolated material (homogeneous by TLC or NMR) unless otherwise stated and names are assigned according to IUPAC nomenclature. LCMS gradient conditions are described as follows.

Method A (10 min): from 95% A/5% B to 50% B over 3 min. Then from 50% B to 80% B over 2 min. Then from 80% B to 95% B over 1.5 min and held constant for 1.5 min. This was then reduced to 5% B over 0.2 min and maintained to 5% B for 1.8 min. The flow rate was 0.5 mL/min, 200 μL, was split via a zero dead volume T piece which passed into the mass spectrometer. The wavelength range of the UV detector was 220-400 nm.

Method B (5 min): from 95% A/5% B to 90% B over 3 min. Then from 90% B to 95% B over 0.5 min and held constant for 1 min. This was then reduced to 5% B over 0.5 min. The flow rate was 1.0 mL/min, 100 μL was split via a zero dead volume T piece which passed into the mass spectrometer. The wavelength range of the UV detector was 220-500 nm.

General synthetic scheme

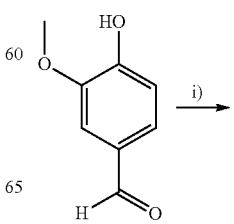

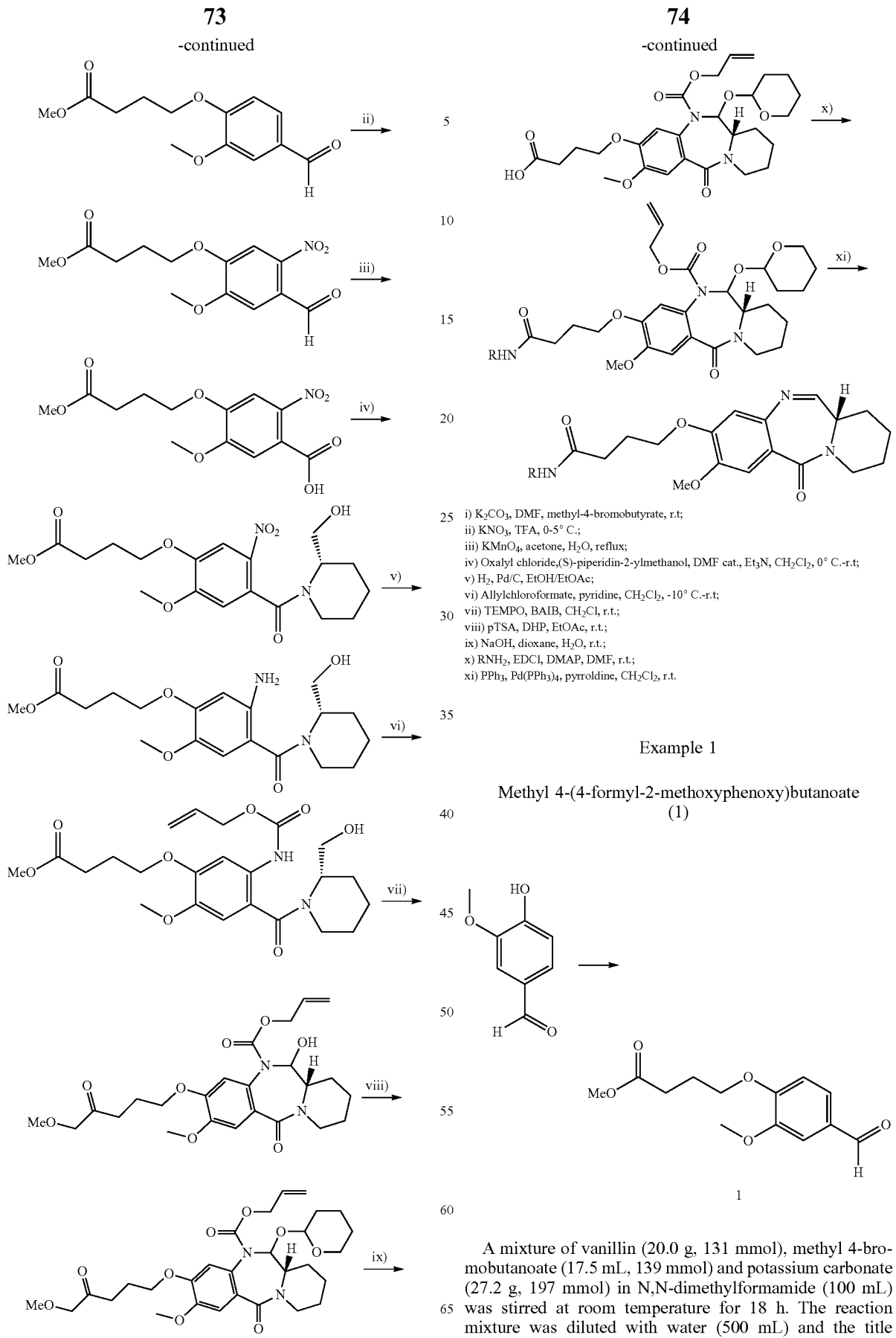

i) K$_2$CO$_3$, DMF, methyl-4-bromobutyrate, r.t;
ii) KNO$_3$, TFA, 0-5° C.;
iii) KMnO$_4$, acetone, H$_2$O, reflux;
iv) Oxalyl chloride,(S)-piperidin-2-ylmethanol, DMF cat., Et$_3$N, CH$_2$Cl$_2$, 0° C.-r.t;
v) H$_2$, Pd/C, EtOH/EtOAc;
vi) Allylchloroformate, pyridine, CH$_2$Cl$_2$, -10° C.-r.t;
vii) TEMPO, BAIB, CH$_2$Cl, r.t.;
viii) pTSA, DHP, EtOAc, r.t;
ix) NaOH, dioxane, H$_2$O, r.t.;
x) RNH$_2$, EDCl, DMAP, DMF, r.t.;
xi) PPh$_3$, Pd(PPh$_3$)$_4$, pyrroldine, CH$_2$Cl$_2$, r.t.

Example 1

Methyl 4-(4-formyl-2-methoxyphenoxy)butanoate (1)

A mixture of vanillin (20.0 g, 131 mmol), methyl 4-bromobutanoate (17.5 mL, 139 mmol) and potassium carbonate (27.2 g, 197 mmol) in N,N-dimethylformamide (100 mL) was stirred at room temperature for 18 h. The reaction mixture was diluted with water (500 mL) and the title compound (30.2 g, 91%) was obtained by filtration as a white solid. The product was carried through to the next step without any further purification.

¹H NMR (400 MHz, CDCl₃) δ 9.84 (s, 1H), 7.4-7.37 (m, 2H), 6.98 (d, J=8.2 Hz, 1H), 4.16 (t, J=6.3 Hz, 2H), 3.91 (s, 3H), 3.69 (s, 3H), 2.56 (t, J=7.2 Hz, 2H), 2.20 (quin, J=6.7 Hz, 2H); ¹³C NMR (100 MHz, CDCl₃) δ 190.9, 173.4, 153.8, 149.9, 130.1, 126.8, 111.6, 109.2, 67.8, 56.0, 51.7, 30.3, 24.2; MS m/z (EIMS)=271.9 (M+Na)⁺; LCMS (Method A): $t_R$=6.48 min.

Example 2

Methyl 4-(4-formyl-2-methoxy-5-nitrophenoxy)butanoate (2)

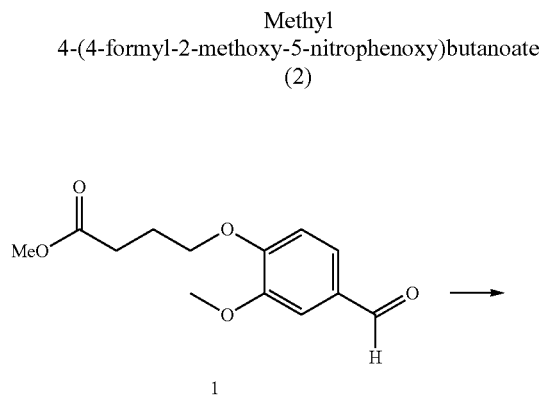

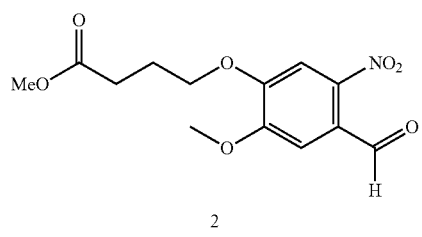

To a stirring solution of potassium nitrate (10.0 g, 98.9 mmol) in TFA (50 mL) at 0° C. was added dropwise a solution of methyl 4-(4-formyl-2-methoxyphenoxy)butanoate (1) (20.0 g, 79.2 mmol) in TFA (50 mL). The reaction mixture was stirred at room temperature for 1 h. It was then concentrated in vacua and diluted with ethyl acetate (400 mL). The organic layer was washed with brine (3×100 mL) and a saturated aqueous solution of sodium hydrogen carbonate (2×80 mL), dried over sodium sulfate, filtered and concentrated to give the title compound (23.5 g, 100%) as a yellow solid. The product was carried through to the next step without any further purification.

¹H NMR (400 MHz, CDCl₃) δ10.42 (s, 1H), 7.60 (s, 1H), 7.39 (s. 1H), 4.21 (t, J=6.3 Hz, 2H), 3.98 (s, 3H), 3.70 (s, 3H), 2.61-2.53 (m, 2H), 2.22 (quin, J=6.6 Hz, 2H); ¹³C NMR (100 MHz, CDCl₃) δ 187.8, 173.2, 153.5, 151.7, 143.8, 125.5, 109.9, 108.1, 68.6, 56.6, 51.8, 30.2, 24.1; MS m/z (EIMS)=296.1 (M−H)⁻; LCMS (Method A): $t_R$=6.97 min.

Example 3

5-Methoxy-4-(4-methoxy-4-oxobutoxy)-2-nitrobenzoic acid (3)

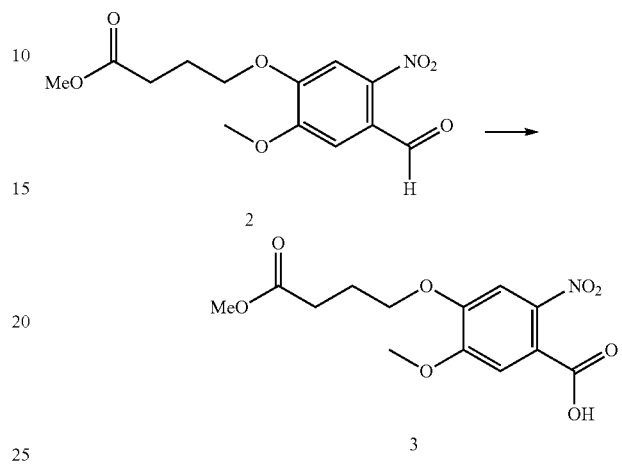

To a solution of methyl 4-(4-formyl-2-methoxy-5-nitrophenoxy)butanoate (2) (23.0 g, 77.4 mmol) in acetone (600 mL) was quickly added a hot (70° C.) solution of potassium permanganate (460 g, 291 mmol) in water (400 mL). The reaction mixture was stirred at 70° C. for 3 h. The reaction mixture was cooled to room temperature and passed through celite. The cake of celite was washed with hot water (200 mL). A solution of sodium bisulfite in hydrochloric acid (1M, 200 mL) was added to the filtrate which was extracted with dichloromethane (2×400 mL). The organic layer was dried over sodium sulfate, filtered and concentrated. The resulting residue was purified by column chromatography (silica), eluting with methanol/dichloromethane (from 0% to 50%), to give the title compound (17.0 g, 70%) as a pale yellow solid.

¹H NMR (400 MHz, MeOD) δ 7.47 (s, 1H), 7.25 (s, 1H), 4.13 (t, J=6.2 Hz, 2H), 3.94 (s, 3H), 3.68 (s, 3H), 2.54 (t, J=7.2 Hz, 2H), 2.17-2.06 (m, 2H); ¹³C NMR (100 MHz, MeOD) δ 175.3, 168.6, 153.8, 151.3, 143.1, 122.8, 112.4, 109.2, 69.6, 57.0, 52.2, 31.2, 25.5; MS m/z (EIMS)=311.9 (M−H); LCMS (Method A): $t_R$=6.22 min.

Example 4

Methyl (S)-4-(4-(2-(hydroxymethyl)piperidine-1-carbonyl)-2-methoxy-5-nitrophenoxy)butanoate (4)

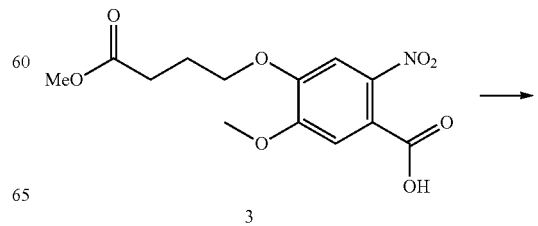

-continued

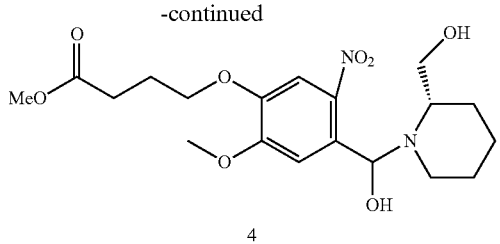

4

A mixture of 5-methoxy-4-(4-methoxy-4-oxobutoxy)-2-nitrobenzoic acid (3) (8.0 g, 25.5 mmol), oxalyl chloride (6.6 mL, 77.0 mmol) and anhydrous N,N-dimethl-formamide (2 drops) in anhydrous dichloromethane (100 mL) was stirred at room temperature for 1 h. Anhydrous toluene (20 mL) was added to the reaction mixture which was then concentrated in vacua. A solution of the resulting residue in anhydrous dichloromethane (10 mL) was added dropwise to a solution of (S)-piperidin-2-ylmethanol (3.8 g, 33.4 mmol) and tri-ethylamine (10.7 mL, 77.0 mmol) in anhydrous dichloromethane (90 mL) at −10° C. The reaction mixture was stirred at room temperature for 2 h and then washed with hydrochloric acid (1 M, 50 mL) and a saturated aqueous solution of sodium chloride (50 mL), dried over sodium sulfate, filtered and concentrated. The resulting residue was purified by column chromatography (silica), eluting with methanol/dichloromethane (from 0% to 5%), to give the title compound (9.2 g, 73%) as a yellow oil.

$^1$H NMR (400 MHz, CDCl$_3$) δ 7.68-7.64 (m, 1H), 6.77-6.70 (m, 1H), 4.16-4.07 (m, 3H), 3.93-3.89 (m, 3H), 3.83 (s, 1H), 3.67 (s, 3H), 3.15 (d, J=1.4 Hz, 1H), 3.11 (s, 1H), 2.78 (s, 1H), 2.56-2.50 (m, 3H), 2.21-2.12 (m, 4H), 1.74-1.55 (m, 4H); $^{13}$C NMR (100 MHz, CDCl$_3$) δ 173.3, 168.1, 154.6, 148.2, 137.4, 127.6, 111.4, 108.3, 68.3, 60.6, 56.7, 53.5, 51.7 43.3, 38.0, 34.9, 30.3, 24.1, 19.7; MS m/z (EIMS)=411.0 (M+H)$^+$; LCMS (Method A): t$_R$=6.28 min.

Example 5

Methyl (S)-4-(5-amino-4-(2-(hydroxymethyl)piperidine-1-carbonyl)-2-methoxyphenoxy)butanoate (5)

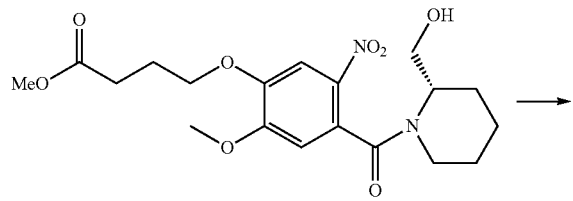

4

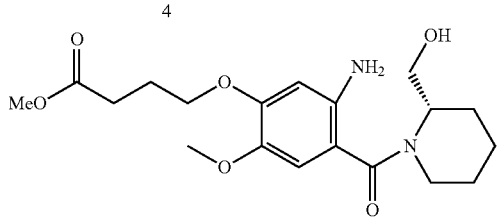

5

To a solution of methyl (S)-4-(4-(2-(hydoroxymethyl)piperdine-1-carbonyl)-2-methoxy-5-nitrophenoxy)butanoate (4) (9.2 g, 22.4 mmol) in ethanol (40 mL) and ethyl acetate (10 mL) was added palladium on activated charcoal (10% wt. basis) (920 mg). The reaction mixture was hydrogenated at 35 psi for 3 h in a Parr apparatus. The reaction mixture was filtered through celite and the resulting cake was washed with ethyl acetate. The filtrate was concentrated in vacuo to give the title compound (9.0 g, 90%) as a pink solid. The product was carried through to the next step without any further purification.

$^1$H NMR (400 MHz, CDCl$_3$) δ 6.69 (s, 1H), 6.27-6.18 (m, 1H), 4.03-3.94 (m, 3H), 3.94-3.82 (m, 3H), 3.81-3.76 (m, 1H), 3.74 (s, 3H), 3.73-3.68 (m, 1H), 3.67-3.65 (m, 3H), 3.56 (d, J=4.8 Hz, 1H), 3.03 (s, 1H), 2.51 (t, J=7.2 Hz, 2H), 2.11 (quin, J=6.7 Hz, 2H), 1.68-1.59 (m, 4H), 1.55-1.40 (m, 2H); $^{13}$C NMR (100 MHz, CDCl$_3$) δ 173.6, 171.2, 150.3, 141.8, 141.1, 113.2, 112.3, 102.4, 67.5, 60.8, 60.4, 56.8, 51.6, 30.4, 25.8, 24.3, 21.0, 19.9, 14.2; MS m/z (EMS) =381.0 (M+H)$^+$; LCMS (Method A): t$_R$=5.52 min.

Example 6

Methyl (S)-4-(S)-(5-(((allyloxy)carbonyl)amino)-4-(2-(hydroxyl-methyl)piperidine-1-carbonyl)-2-methoxyphenoxy)butanoate (6)

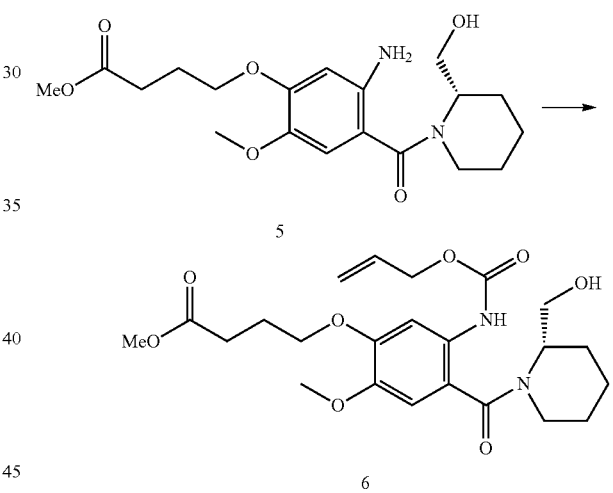

To a solution of methyl (S)-4-(5-amino-4-(2-(hydroxymethyl)piperidine-1-carbonyl)-2-methoxyphenoxy)butanoate (5) (9.0 g, 23.7 mmol) and pyridine (4.4 mL, 54.4 mmol) in anhydrous dichloromethane (100 mL) at −10° C. was added dropwise a solution of allylchloroformate (2.6 mL, 24.8 mmol) in anhydrous dichloromethane (20 mL). The reaction mixture was stirred at room temperature for 30 min. The reaction mixture was sequentially washed with a saturated aqueous solution of copper (II) sulfate (80 mL), water (80 mL) and a saturated aqueous solution of sodium hydrogen carbonate (80 mL). The organic layer was dried over sodium sulfate, filtered and concentrated. The resulting residue (2.0 g out of the 11.0 g crude) was purified by column chromatography (silica), eluting with methanol/dichloromethane (from 0% to 1%), to give the title compound (930 mg, 47% based on the amount purified) as a yellow oil.

1H NMR (400 MHz, CDCl$_3$) δ 8.30 (br s, 1H), 7.63 (br s, 1H), 6.76 (br s, 1H), 5.92 (ddt, J=17.2, 10.6, 5.4, 5.4 Hz, 1H), 5.37-5.28 (m, 1H), 5.20 (dq, J=10.4, 1.3 Hz, 1H), 4.65-4.56 (m, 2H), 4.06 (t, J=6.2 Hz, 2H), 3.94-3.82 (m, 1H), 3.79 (s, 3H), 3.66 (s, 3H), 3.62-3.54 (m, 1H), 3.40 (br s, 1H), 3.10-2.88 (m, 1H), 2.52 (t, J=7.4 Hz, 2H), 2.22-2.04 (m, 3H), 1.64 (br s, 4H), 1.56-1.31 (m, 2H); $^{13}$C NMR (100 MHz, CDCl$_3$) δ 173.5, 170.6, 153.9, 149.7, 144.8, 132.6, 130.1, 117.6, 116.9, 110.8, 107.1, 106.0, 67.7, 65.6, 60.7, 56.3, 53.5, 51.6, 43.1, 30.5, 25.7, 24.4, 19.7; MS m/z (EIMS)=465.1 (M+H)$^+$; LCMS (Method A): $t_R$=6.47 min.

Example 7

Allyl (6aS)-6-hydroxy-2-methoxy-3-(4-methoxy-4-oxobutoxy)-12-oxo-6,6a,7,8,9,10-hexahydrobenzo[e]pyrido[1,2-a][1,4]diazepine-5(12H)-carboxylate (7)

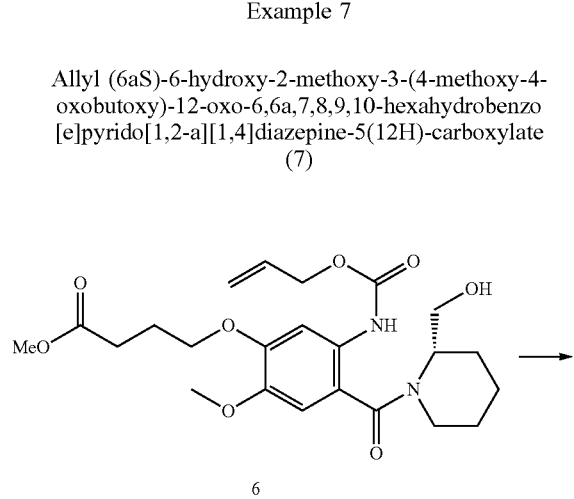

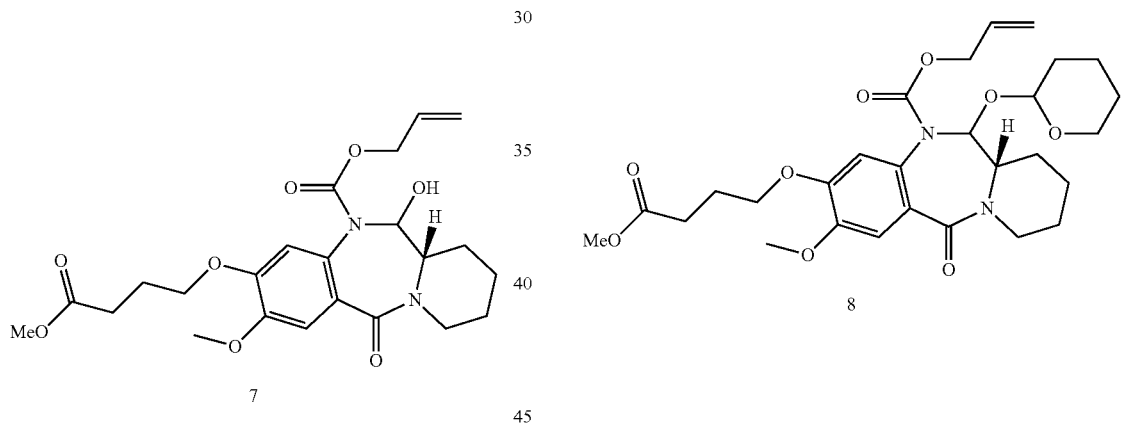

To a solution of methyl (S)-4-(5-(((allyloxy)carbonyl) amino)-4-(2-(hydroxymethyl)-piperidine-1-carbonyl)-2-methoxyphenoxy)butanoate (6) (930 mg, 2.0 mmol) in dichloromethane (45 mL) was added TEMPO (32 mg, 0.20 mmol) and (diacetoxyiodo)-benzene (773 mg, 2.4 mmol). The reaction mixture was stirred at room temperature for 16 h, and was then sequentially washed with a saturated aqueous solution of sodium metabisulfite (20 mL), a saturated aqueous solution of sodium hydrogen carbonate (20 mL), water (20 mL) and brine (20 mL). The organic layer was then dried over sodium sulfate, filtered and concentrated. The resulting residue was purified by column chromatography (silica), eluting with methanol/dichloromethane (from 0% to 5%), to give the title compound (825 mg, 89%) as a cream solid.

MS m/z (EIMS)=462.9 (M+H)$^+$: LCMS (Method A): $t_R$=6.30 min.

Example 8

Allyl (6aS)-2-methoxy-3-(4-methoxy-4-oxobutoxy)-12-oxo-6-((tetrahydro-2H-pyran-2-yl)oxy)-6,6a,7,8,9,10-hexahydrobenzo[e]pyrido-[1,2-a][1,4]diazepine-5(12H)-carboxylate (8)

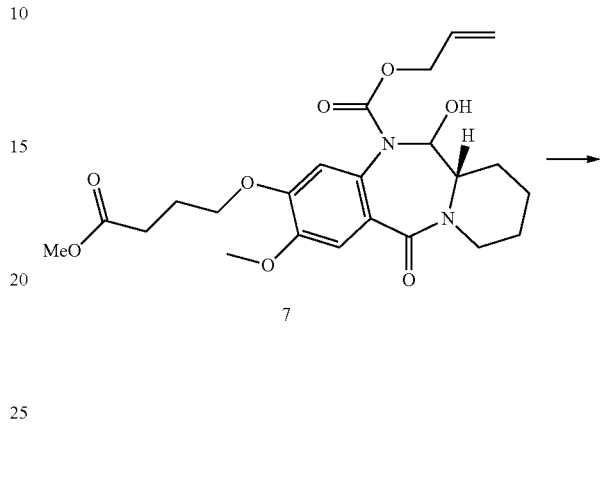

A mixture of allyl (6aS)-6-hydroxy-2-methoxy-3-(4-methoxy-4-oxobutoxy)-12-oxo-6,6a,7,8,9,10-hexahydrobenzo[e]pyrido[1,2-a][1,4]diazepine-5(12H)-carboxylate (7) (825 mg, 1.8 mmol), 3,4-dihydro-2H-pyran (1.7 mL, 18.2 mmol) and pTSA (8.5 mg, 1% w/w) in ethyl acetate (12 mL) was stirred at room temperature for 16 h. The reaction mixture was then diluted with ethyl acetate (50 mL) and washed with a saturated aqueous solution of sodium hydrogen carbonate (20 mL) and brine (30 mL). The organic layer was dried over sodium sulfate, filtered and concentrated. The resulting residue was purified by column chromatography (silica), eluting with methanol/dichloromethane (from 0% to 2%), to give the title compound (820 mg, 84%) as a cream solid.

MS m/z (EIMS)=546.7 (M+H)$^+$: LCMS (Method A): $t_R$=7.70 min.

Example 9

4-(((6aS)-5-(Allyloxy)carbonyl)-2-methoxy-12-oxo-6-((tetra-hydro-2H-pyran-2-yl)oxy)-5,6,6a,7,8,9,10,12-octahydrobenzo[e]pyrido[1,2-a][1,4]diazepin-3-yl)oxy)butanoic acid (9)

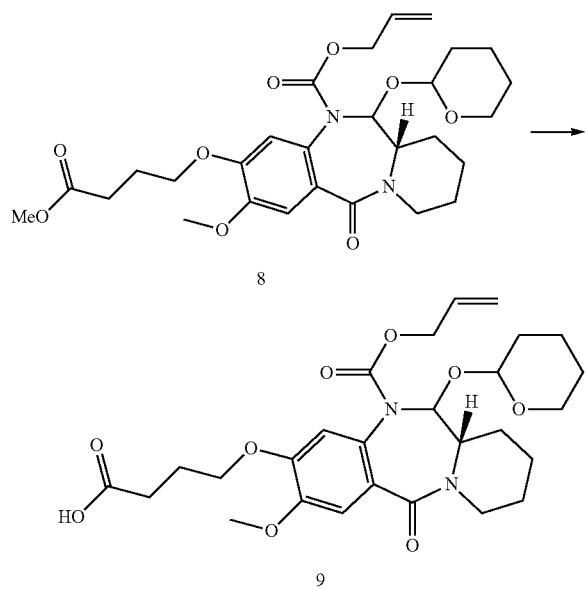

To a solution of allyl (6aS)-2-methoxy-3-(4-methoxy-4-oxobutoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (8) (770 mg, 1.4 mmol) in 1,4-dioxane (10 mL) was added a 0.5 M aqueous solution of sodium hydroxide (10 mL, 5.0 mmol). The reaction mixture was stirred at room temperature for 2 h and was then concentrated in vacua, after which water (20 mL) was added and the aqueous layer was acidified to pH=1 with a 1 M citric acid solution (5 mL). The aqueous layer was then extracted with ethyl acetate (2×50 mL). The combined organic extracts were then washed with brine (50 mL), dried over sodium sulfate, filtered and concentrated to give the title compound (700 mg, 93%) as a yellow oil. The product was carried through to the next step without any further purification.

MS m/z (EIMS)=532.9 (M+H)$^+$: LCMS (Method A): $t_R$=6.98 min.

Example 10

Methyl 5-(4-((tert-butoxycarbonyl)amino)-1-methyl-1H-pyrrole-2-carboxamido)benzo[b]thiophene-2-carboxylate (10)

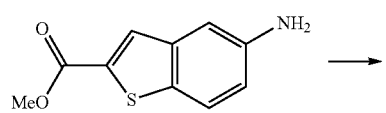

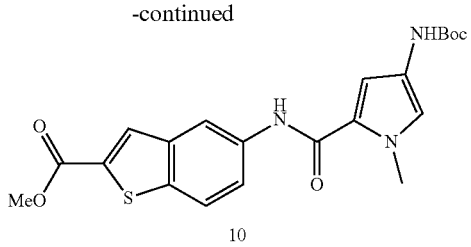

A solution of 4-((tert-butoxycarbonl)amino)-1-methyl-1H-pyrrole-2-carboxylic acid (500 mg, 2.1 mmol) in N,N-dimethylformamide (10 mL) was charged with 1-(3-dimethylaminopropyl)-3-ethylcarbodiimide hydrochloride (725 mg, 3.8 mmol) and 4-(dimethylamino)pyridine (577 mg, 4.7 mmol). The reaction mixture was stirred at room temperature for 2 h. Methyl 5-aminobenzo[b]thiophene-2-carboxylate (392 mg, 1.9 mmol) was then added and the resulting mixture was stirred at room temperature for 16 h. This was then poured into ice-water (20 mL) and extracted with ethyl acetate (3×50 mL). The combined organic extracts were sequentially washed with 1 M citric acid (30 mL), a saturated aqueous solution of sodium hydrogen carbonate (35 mL), water (35 mL) and brine (35 mL). The organic layer was then dried over sodium sulfate, filtered and concentrated. The resulting residue was purified by column chromatography (silica), eluting with ethyl acetate/hexane (from 0% to 50%), to give the title compound (610 mg, 75%) as a beige solid.

MS m/z (EIMS)=430.2 (M+H)$^+$: LCMS (Method A): $t_R$=7.90 min.

Example 11

Methyl 5-(4-amino-1-methyl-1H-pyrrole-2-carboxamido)-benzo[b]thiophene-2-carboxylate hydrochloride (11)

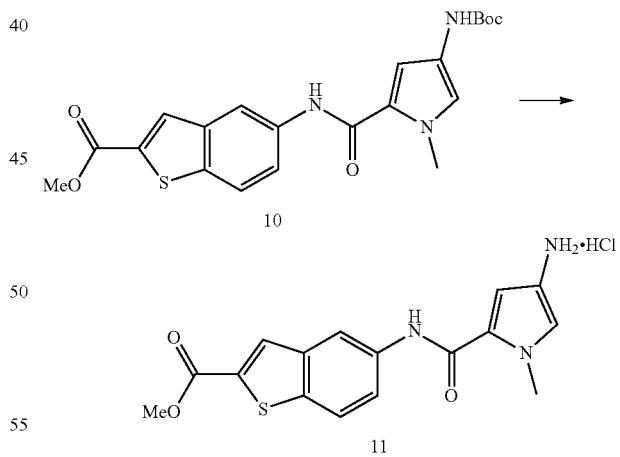

Methyl 5-(4-((tert-butoxycarbonyl)amino)-1-methyl-1H-pyrrole-2-carboxamido)benzo-[b]thiophene-2-carboxylate (10) (610 mg, 1.4 mmol) was dissolved in hydrochloric acid (4 M in dioxane) (3.6 mL) and the reaction mixture was stirred at room temperature for 2 h. The reaction mixture was concentrated in vacuo to give the title compound (600 mg, 99%) as a brown solid. The product was carried through to the next step without any further purification.

MS m/z (EIMS)=329.9 (M+H)$^+$: LCMS (Method A): $t_R$=5.52 min.

Example 12

Allyl (6aS)-2-methoxy-3-(4-((5-((2-(methoxycarbonyl)benzo-[b]thiophen-5-yl)carbamoyl)-1-methyl-1H-pyrrol-3yl)amino)-4-oxo-butoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (12)

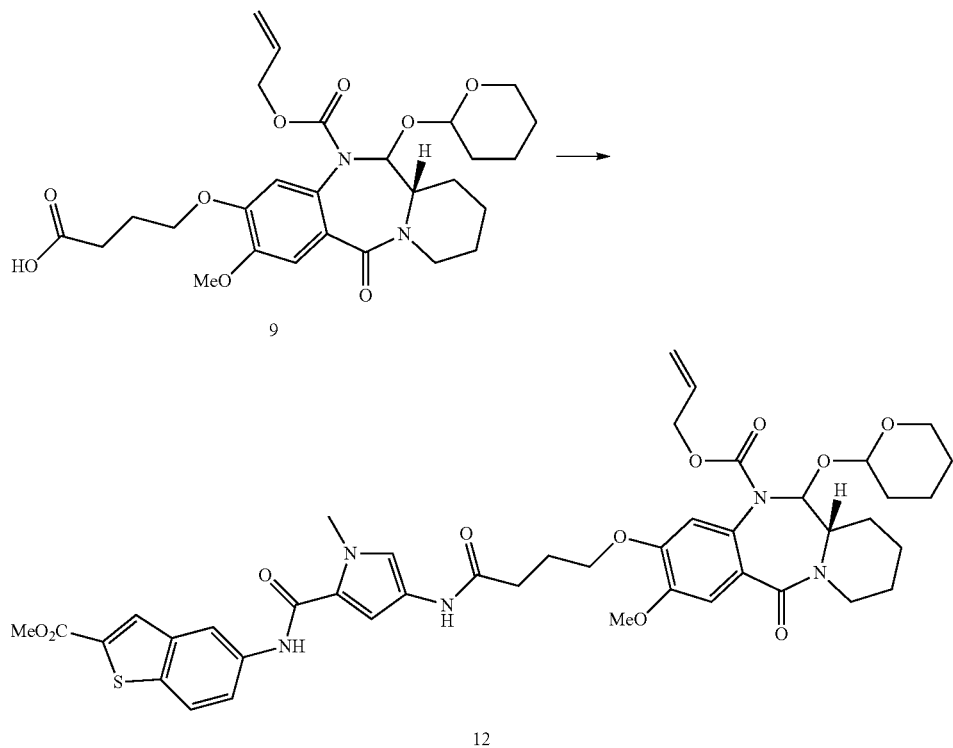 [SMILES: C=CCOC(=O)N1c2cc(OCCCC(=O)O)c(OC)cc2C(=O)N2CCCC[C@H]2C1OC1CCCCO1 ; C=CCOC(=O)N1c2cc(OCCCC(=O)Nc3cc(C(=O)Nc4ccc5sc(C(=O)OC)cc5c4)n(C)c3)c(OC)cc2C(=O)N2CCCC[C@H]2C1OC1CCCCO1]

A solution of 4-((((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanoic acid (9) (150 mg, 0.28 mmol) in N,N-dimethylformamide (4 mL) was charged with 1-(3-dimethylaminopropyl)-3-ethylcarbodiimide hydrochloride (100 mg, 0.52 mmol) and 4-(dimethylamino)pyridine (80 mg, 0.65 mmol). The reaction mixture was stirred at room temperature for 30 min. Methyl 5-(4-amino-1H-methyl-1H-pyrrole-2-carboxamido)benzo[b]thiophene-2-carboxylate hydrochloride (11) (95 mg, 0.26 mmol) was then added and the resulting mixture was stirred at room temperature for 16 h. This was then poured into ice-water (20 mL) and extracted with ethyl acetate (3×50 mL). The combined organic extracts were sequentially washed with 1 M citric acid (30 mL), a saturated aqueous solution of sodium hydrogen carbonate (35 mL), water (35 mL) and brine (35 mL). The organic layer was then dried over sodium sulfate, filtered and concentrated in vacua to give the title compound (190 mg, 87%) as a yellow oil. The product was carried through to the next step without any further purification.

MS m/z (EIMS)=844.0 (M+H)$^+$: LCMS (Method A): $t_R$=8.10 min.

Example 13

Methyl (S)-5-(4-(4-((2-methoxy-12-oxo-6a,7,8,9,10,12-hexa-hydrobenzo[e]pyrido[1,2-a][1,4]diazepin-3-yl)oxy)butanamido)-1-methyl-1H-pyrrole-2-carbox-amido)benzo[b]thiophene-2-carboxylate (13)

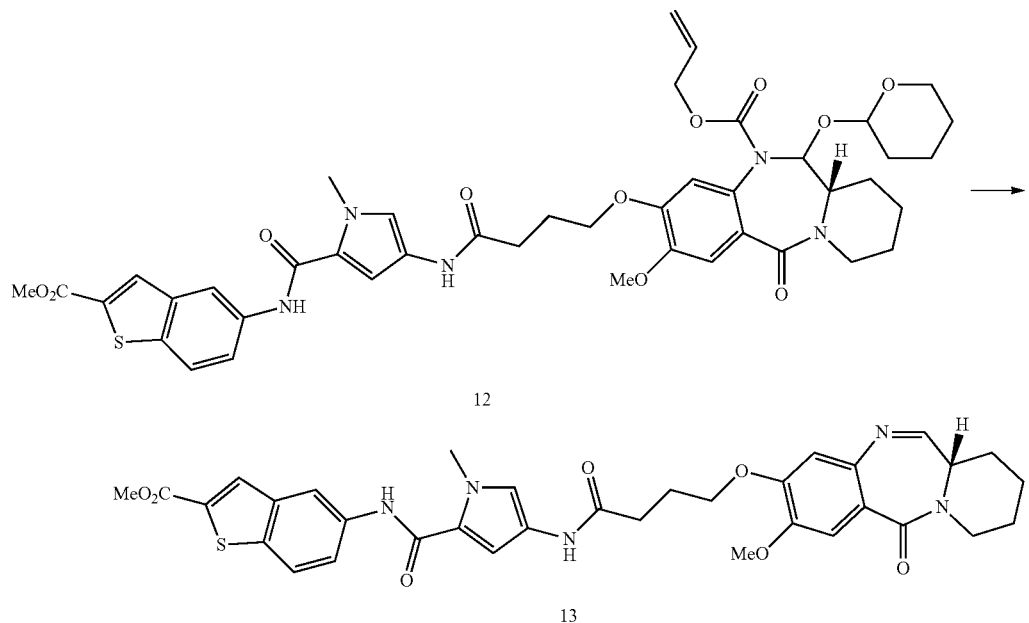

To a solution of allyl (6aS)-2-methoxy-3-(4-((5-(2-(methoxycarbonyl)benzo[b]-thiophen-5-yl)carbamoyl)-1-methyl-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-a][1,4]-diazepine-5(12H)-carboxylate (12) (190 mg, 0.22 mmol) in dichloromethane (10 mL) was added tetrakis(triphenylphosphine)palladium (0) (13 mg, 5 mol %), triphenyl-phosphine (15 mg, 25 mol %) and pyrrolidine (22 μLt, 0.27 mmol). The reaction mixture was stirred at room temperature for 30 min. The reaction mixture was subjected to high vacuum for 30 min until excess pyrrolidine was thoroughly removed. The resulting residue was then purified by column chromatography (silica), eluting with acetone/dichloromethane (from 0% to 70%), to give the title compound (60 mg, 40%) as a yellow solid.

$^1$H NMR (CDCl$_3$, 400 MHz) δ 8.35 (s, 1H), 8.28 (s, 1H), 8.02 (s, 1H), 7.94 (s, 1H), 7.90 (d, J=5.7 Hz, 1H), 7.75 (d, J=8.8 Hz, 1H), 7.58 (dd, J=8.7, 2.1 Hz, 1H), 7.42-7.41 (m, 1H), 7.13 (d, J=1.6 Hz, 1H), 6.78 (s, 1H), 6.56 (d, J=1.6 Hz, 1H), 4.25-4.18 (m, 1H), 4.08 (t, J=6.0 Hz, 2H), 3.93 (s, 3H), 3.88 (s, 3H), 3.83 (s, 3H), 3.79-3.75 (m, 1H), 3.23-3.16 (m, 1H), 2.52-2.47 (m, 2H), 2.21 (d, J=6.4 Hz, 1H), 2.18 (d, J=2.1 Hz, 1H), 1.96 (br s, 2H), 1.86-1.81 (m, 2H), 1.77-1.66 (m, 2H); 13C NMR (100 MHz, CDCl$_3$) δ 170.0, 167.6, 163.4, 163.2, 160.0, 150.7, 148.0, 140.0, 139.2, 137.6, 135.8, 134.2, 130.6, 123.0, 122.9, 121.5, 121.0, 120.1, 116.2, 111.7, 110.3, 104.3, 68.1, 56.1, 53.5, 52.5, 49.7, 40.0, 36.8, 33.0, 24.9, 24.5, 22.9, 18.3; MS m/z (EIMS)=658.0 (M+H)$^+$; LCMS (Method A): t$_R$=6.92 min.

Example 14

Allyl (6aS)-3-(4-((2-(ethoxycarbonyl)-1-methyl-1H-imidazol-4-yl)amino)-4-oxobutoxy)-2-methoxy-12-oxo-6-((tetrahydro-2H-pyran-2-yl)-oxy)-6,6a,7,8,9,10-hexahydrobenzo[e]pyrido[1,2-a][1,4]iazepine-5(12H)-carboxylate (14)

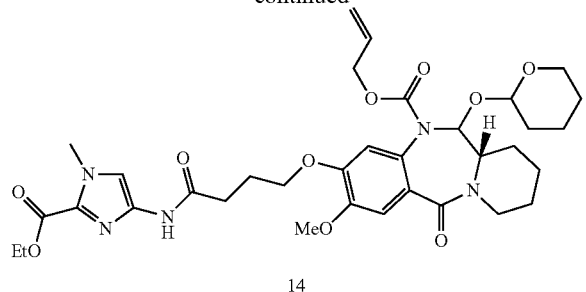

14

A solution of 4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanoic acid (9) (340 mg, 0.64 mmol) in N,N-dimethylformamide (10 mL) was charged with 1-(3-dimethylaminopropyl)-3-ethylcarbodiimide hydrochloride (222 mg, 1.2 mmol) and 4-(dimethylamino)pyridine (177 mg, 1.4 mmol). The reaction mixture was stirred at room temperature for 30 min. Ethyl 4-amino-1-methyl-1H-imidazole-2-carboxylate hydrochloride (120 mg, 0.58 mmol) was then added and the resulting mixture was stirred at room temperature for 16 h. This was then poured into ice-water (40 mL) and extracted with ethyl acetate (3×100 mL). The combined organic extracts were sequentially washed with 1 M citric acid (60 mL), a saturated aqueous solution of sodium hydrogen carbonate (70 mL), water (70 mL) and brine (70 mL). The organic layer was then dried over sodium sulfate, filtered and concentrated in vacuo to give the title compound (350 mg, 80%) as a yellow oil. The product was carried through to the next step without any further purification.

MS m/z (EIMS)=683.7 (M+H)$^+$: LCMS (Method A): $t_R$=7.35 min.

Example 15

4-(4-((((6aS)-5-((Allyloxy)carbonyl)-2-methoxy-12-oxo-6-((tetrahydro-2H-pyran-2-yl)oxy)-5,6,6a,7,8,9,10,12-octahydrobenzo[e]-pyrido[1,2-a][1,4]diazepin-3-yl)oxy)butanamido)-1-methyl-1H-imidazole-2-carboxylic acid (15)

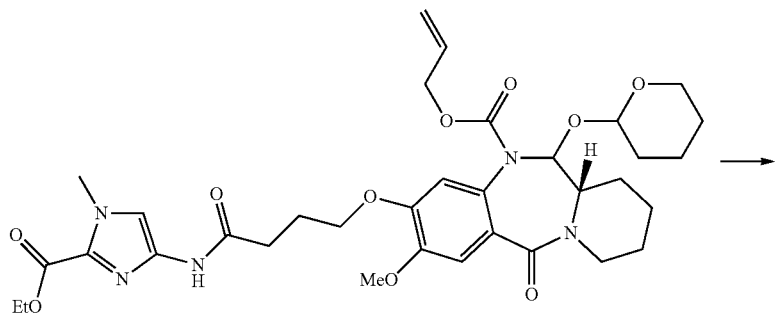

14

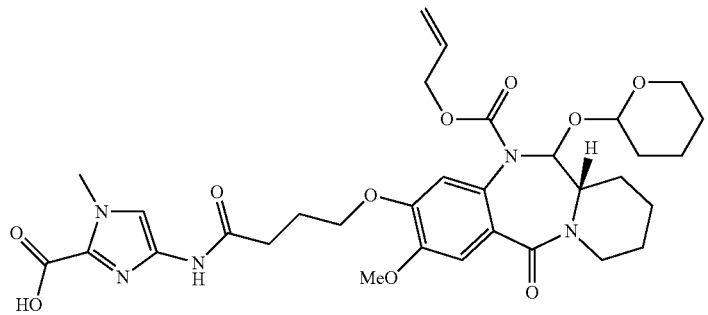

15

To a solution of allyl (6aS)-3-(4-((2-(ethoxycarbonyl)-1-methyl-1H-imidazol-4-yl)amino)-4-oxobutoxy)-2-methoxy-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (14) (350 mg, 0.46 mmol) in 1,4-dioxane (10 mL) was added a 0.5 M aqueous solution of sodium hydroxide (10 mL, 5.0 mmol). The reaction mixture was stirred at room temperature for 2 h and was then concentrated in vacua, after which water (20 mL) was added and the aqueous layer was acidified to pH=1 with a 1 M citric acid solution (10 mL). The aqueous layer was then extracted with ethyl acetate (2×50 mL). The combined organic extracts were then washed with a saturated aqueous solution of sodium chloride (50 mL), dried over sodium sulfate, filtered and concentrated. The resulting residue was triturated in hexane, filtered and dried to give the title compound (220 mg, 74%) as a beige solid. The product was carried through to the next step without any further purification.

MS m/z (EIMS)=656.2 (M+H)$^+$: LCMS (Method A): $t_R$=6.53 min.

Example 16

Allyl (6aS)-2-methoxy-3-(4-((2-((2-(methoxycarbonyl)-benzo[b]thiophen-5-yl)carbamoyl)-1-methyl-1H-1-imidazol-4-yl)amino)-4-oxobutoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (16)

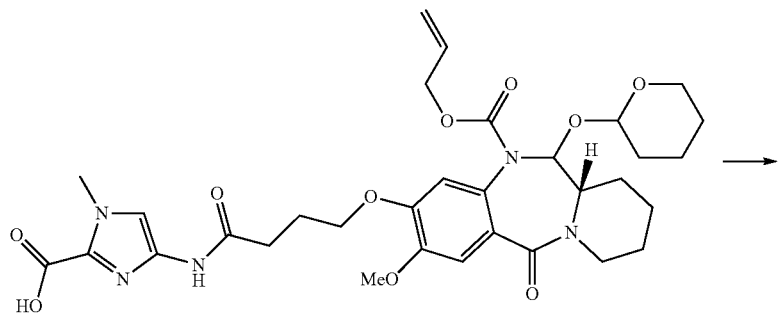

15

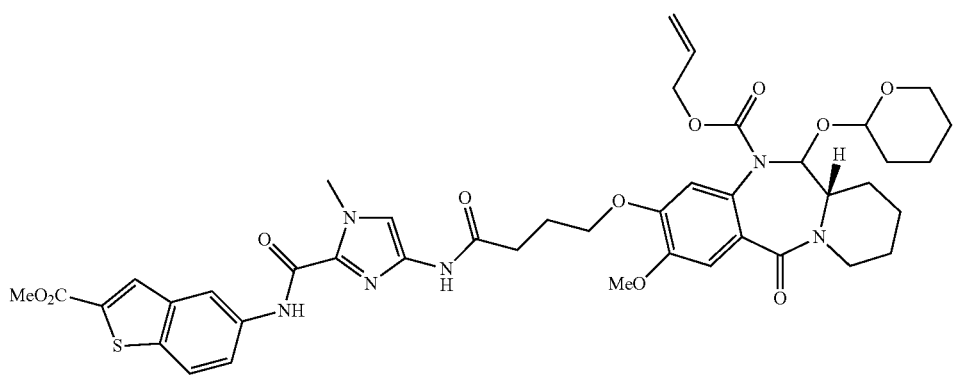

16

A solution of 4-(4-((((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanamido)-1-methyl-1H-imidazole-2-carboxylic acid (15) (110 mg, 0.17 mmol) in N,N-dimethylformamide (4 mL) was charged with 1-(3-dimethylaminopropyl)-3-ethylcarbodiimide hydrochloride (59 mg, 0.31 mmol) and 4-(dimethylamino)pyridine (47 mg, 0.38 mmol). The reaction mixture was stirred at room temperature for 30 min. Methyl 5-aminobenzo[b]thiophene-2-carboxylate (32 mg, 0.15 mmol) was then added and the resulting mixture was stirred at room temperature for 16 h. This was then poured into ice-water (40 mL) and extracted with ethyl acetate (3×100 mL). The combined organic extracts were sequentially washed with 1 M citric acid (60 mL), a saturated aqueous solution of sodium hydrogen carbonate (70 mL), water (70 mL) and brine (700 mL). The organic layer was then dried over sodium sulfate, filtered and concentrated. The resulting residue was then purified by column chromatography (silica), eluting with ethyl acetate/dichloromethane (0% to 100%), followed by methanol/dichloromethane (from 0% to 10%), to give the title compound (50 mg, 39%) as a yellow oil.

MS m/z (EIMS)=844.9 (M+H)$^+$: LCMS (Method A): $t_R$=8.22 min.

Example 17

Methyl (S)-5-(4-(4-((2-methoxy-12-oxo-6a,7,8,9,10,12-hexa-hydrobenzo[e]pyrido[1,2-a][1,4]diazepin-3-yl)oxy)butanamido)-1-methyl-1H-imidazole-2-carboxamido)benzo[b]thiophene-2-carboxylate (17)

To a solution of allyl (6aS)-2-methoxy-3-(4-((2-(2-(methoxycarbonyl)benzo[b]-thiophen-5-yl)carbamoyl)-1-methyl-1H-imidazol-4-yl)amino)-4-oxobutoxy)-12-oxo-6-((tetrahydro-2H-pyran-2-yl)oxy)-6,6a,7,8,9,10-hexahydrobenzo[e]pyrido[1,2-a][1,4]-diazepine-5(12H)-carboxylate (16) (50 mg, 0.06 mmol) in dichloromethane (3 mL) was added tetrakis(triphenylphosphine)palladium(0) (3.5 mg, 5 mol %), triphenylphosphine (3.9 mg, 25 mol %) and pyrrolidine (5.8 µL, 0.07 mmol). The reaction mixture was stirred at room temperature for 30 min. The reaction mixture was subjected to high vacuum for 30 min until excess pyrrolidine was thoroughly removed. The resulting residue was then purified by column chromatography (silica), eluting with acetone/dichloromethane (from 0% to 50%), to give the title compound (10 mg, 26%) as a yellow solid.

$^1$H NMR (CDCl$_3$, 400 MHz) δ 9.07 (s, 1H), 8.36 (d, J=2.0 Hz, 1H), 8.13 (s, 1H), 8.03 (s, 1H), 7.90 (d, J=5.7 Hz, 1H), 7.82 (d, J=8.7 Hz, 1H), 7.56 (dd, J=8.7, 2.1 Hz, 1H), 7.49-7.43 (m, 2H), 6.81 (s, 1H), 4.26-4.17 (m, 2H), 4.10-4.06 (m, 3H), 3.98-3.93 (m, 6H), 3.93-3.85 (m, 1H), 3.74 (td, J=5.8, 4.0 Hz, 1H), 3.27-3.16 (m, 1H), 2.68-2.60 (m, 2H), 2.29 (quin, J=6.4 Hz, 2H), 2.10-2.02 (m, 1H), 1.97-1.89 (m, 1H), 1.83-1.77 (m, 2H), 1.76 (s, 2H); $^{13}$C NMR (100 MHz, CDCl$_3$) δ 169.7, 167.5, 163.3, 163.2, 160.3, 156.7, 150.4, 148.0, 140.0, 139.3, 135.8, 135.0, 130.6, 123.2, 120.1, 115.4, 114.9, 110.3, 98.0, 67.8, 65.2, 56.1, 52.6, 49.6, 39.8, 35.9, 32.9, 31.0, 29.3, 24.7, 24.6, 22.9, 18.4; MS m/z (EIMS)=659.1 (M+H)$^+$: LCMS (Method A): $t_R$=7.00 min.

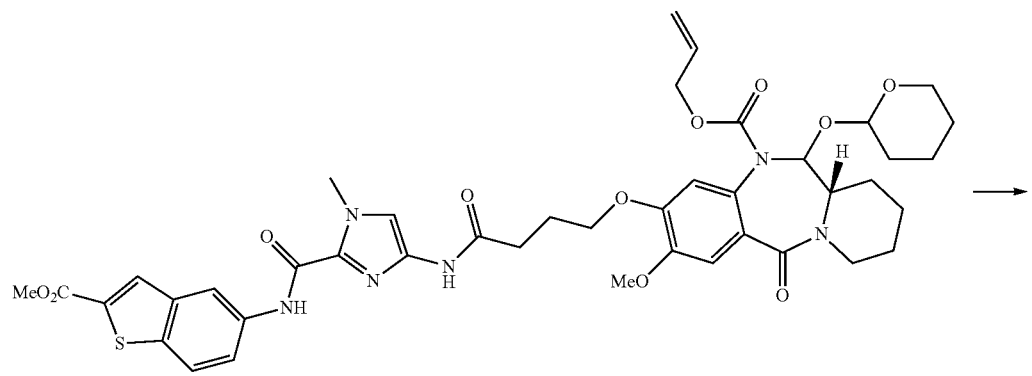

16

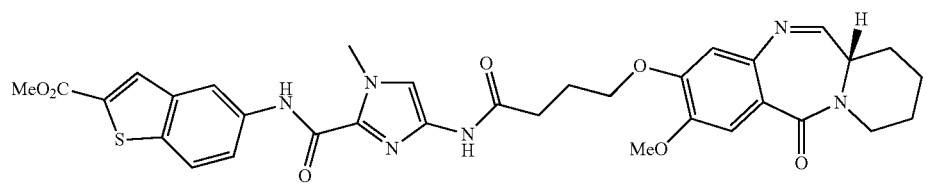

17

Example 18

Methyl 4-(4-aminophenyl)-1-methyl-1H-pyrrole-2-carboxylate (18)

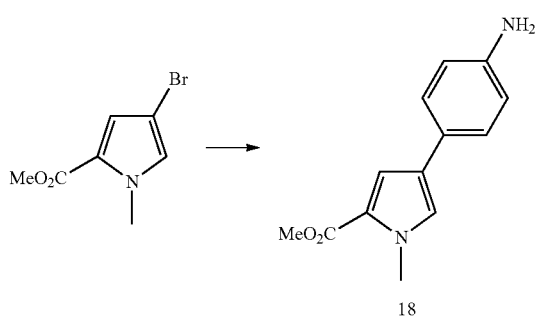 [SMILES: COC(=O)c1cc(Br)cn1C ; COC(=O)c1cc(-c2ccc(N)cc2)cn1C]

18

A mixture of methyl 4-bromo-1-methyl-1H-pyrrole-2-carboxylate (750 mg, 3.44 mmol), 4-(4,4,5,5-tetramethyl-1,3,2-dioxaborolan-2-yl)aniline (905 mg, 4.13 mmol) and potassium carbonate (1.43 g, 10.3 mmol) in toluene/ethanol/water (9:3:1) (13 mL total) was degassed with nitrogen for 5 mins. Tetrakis(triphenylphosphine)palladium(0) (230 mg, 6 mol %) was then charged and the reaction mixture was irradiated with microwaves at 100° C. for 15 mins. Water (10 mL) was then added to the reaction mixture, which was extracted with ethyl acetate (3×40 mL). The combined organic extracts were then dried over sodium sulfate, filtered and concentrated. The resulting residue was purified by column chromatography (silica), eluting with ethyl acetate/hexanes (from 0% to 50%), to give the title compound (145 mg, 18%) as a yellow solid.

MS m/z (EIMS)=230.9 (M+H)$^+$: LCMS (Method A): $t_R$=5.17 min.

Example 19

Allyl (6S,6aS)-2-methoxy-3-(4-((2-((4-(5-(methoxycarbonyl)-1-methyl-1H-pyrrol-3-yl)phenyl)carbamoyl)-1-methyl-1H-imidazol-4-yl)amino)-4-oxobutoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (19)

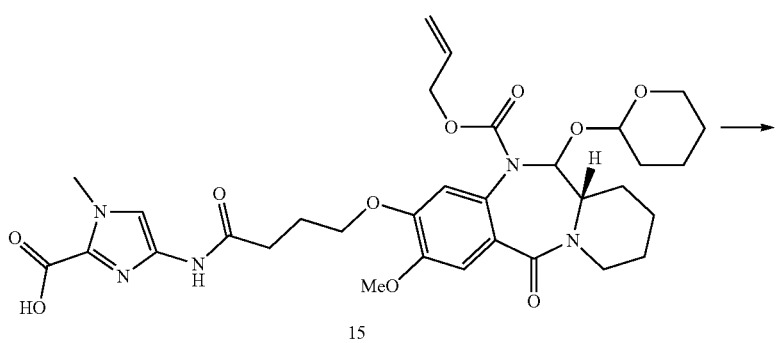

15

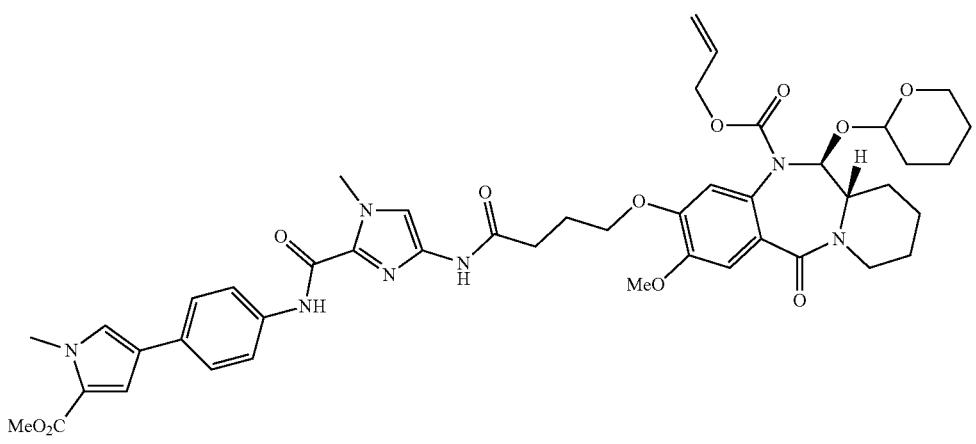

19

A solution of 4-(4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanamido)-1-methyl-1H-imidazole-2-carboxylic acid (15) (110 mg, 0.17 mmol) in N,N-dimethylformamide (4 mL) was charged with 1-(3-dimethylaminopropyl)-3-ethylcarbodiimide hydrochloride (59 mg, 0.31 mmol) and 4-(dimethylamino)pyridine (47 mg, 0.38 mmol). The reaction mixture was stirred at room temperature for 30 min. Methyl 4-(4-aminophenyl)-1-methyl-1H-pyrrole-2-carboxylate (18) (35 mg, 0.15 mmol) was then added and the resulting mixture was stirred at room temperature for 16 h. This was then poured into ice-water (40 mL) and extracted with ethyl acetate (3×100 mL). The combined organic extracts were sequentially washed with 1 M citric acid (60 mL), a saturated aqueous solution of sodium hydrogen carbonate (70 mL), water (70 mL) and brine (70 mL). The organic layer was then dried over sodium sulfate, filtered and concentrated. The resulting residue was then purified by column chromatography (silica), eluting with acetone/dichloromethane (0% to 50%), to give the title compound (54 mg, 37%) as a yellow oil.

MS m/z (EIMS)=868.1 (M+H)$^+$: LCMS (Method A): $t_R$=8.22 min.

Example 20

Methyl (S)-4-(4-(4-(4-((2-methoxy-12-oxo-6a,7,8,9,10,12-hexahydrobenzo[e]pyrido[1,2-a][1,4]diazepin-3-yl)oxy)butanamido)-1-methyl-1H-imidazole-2-carboxamido)phenyl)-1-methyl-1H-pyrrole-2-carboxylate (20)

hexahydrobenzo[e]pyrido[1,2-a][1,4]diazepine-5(12H)-carboxylate (19) (54 mg, 0.06 mmol) in dichloromethane (3 mL) was added tetrakis(triphenylphosphine)palladium(0) (3.6 mg, 5 mol %), triphenylphosphine (4.1 mg, 25 mol %) and pyrrolidine (6.2 μL, 0.07 mmol). The reaction mixture was stirred at room temperature for 30 min. The reaction mixture was subjected to high vacuum for 30 min until excess pyrrolidine was thoroughly removed. The resulting residue was then purified by column chromatography (silica), eluting with acetone/dichloromethane (from 0% to 50%), to give the title compound (22 mg, 52%) as a yellow solid.

$^1$H NMR (CDCl$_3$, 400 MHz) δ 8.95 (s, 1H), 8.27 (s, 1H), 7.89 (d, J=5.7 Hz, 1H), 7.59 (d, J=8.6 Hz, 2H), 7.47-7.41 (m, 4H), 7.19 (d, J=2.0 Hz, 1H), 7.05 (d, J=1.9 Hz, 1H), 6.79 (s, 1H), 4.25-4.18 (m, 1H), 4.17-4.12 (m, 1H), 4.12-4.06 (m, 1H), 4.04 (s, 3H), 3.95 (s, 3H), 3.93 (s, 3H), 3.84 (s, 3H), 3.76-3.71 (m, 1H), 3.26-3.16 (m, 1H), 2.65-2.57 (m, 2H), 2.26 (t, J=6.4 Hz, 2H), 2.09-2.01 (m, 2H), 1.96-1.89 (m, 1H), 1.85-1.77 (m, 2H), 1.67 (dd, J=10.9, 5.5 Hz, 1H); $^{13}$C NMR (100 MHz, CDCl$_3$) δ 169.7, 167.5, 163.3, 161.7, 156.5, 150.4, 148.0, 140.0, 135.8, 135.6, 133.7, 130.6,

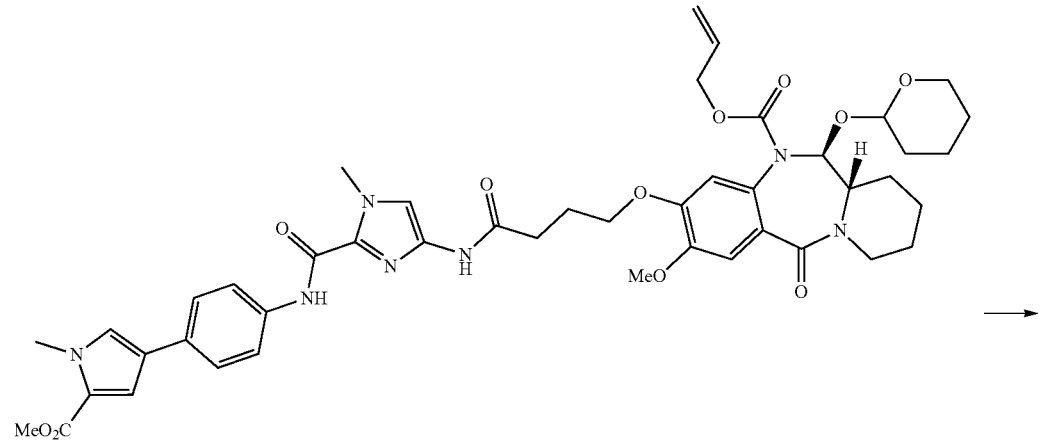

19

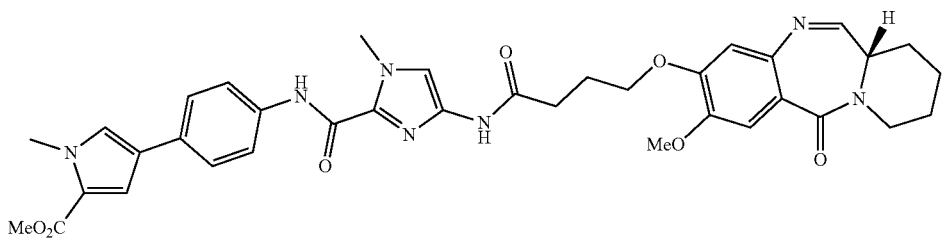

20

To a solution of allyl (6S,6aS)-2-methoxy-3-(4-((2-((4-(5-(methoxycarbonyl)-1-methyl-1H-pyrrol-3-yl)phenyl)carbamoyl)-1-methyl-1H-imidazol-4-yl)amino)-4-oxobutoxy)-12-oxo-6-((tetrahydro-2H-pyran-2-yl)oxy)-6,6a,7,8,9,10-

126.1, 125.5, 123.1, 122.8, 120.0, 114.6, 111.6, 110.2, 67.8, 56.1, 51.2, 49.6, 39.8, 37.0, 35.8, 32.8, 31.0, 29.7, 24.7, 24.5, 22.9, 18.4; MS (EIMS)=682.1 (M+H)$^+$: LCMS (Method A): $t_R$=7.03 min.

Example 21

Allyl (6aS)-2-methoxy-3-(4-((5-(methoxycarbonyl)-1-methyl-1H-1-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (21)

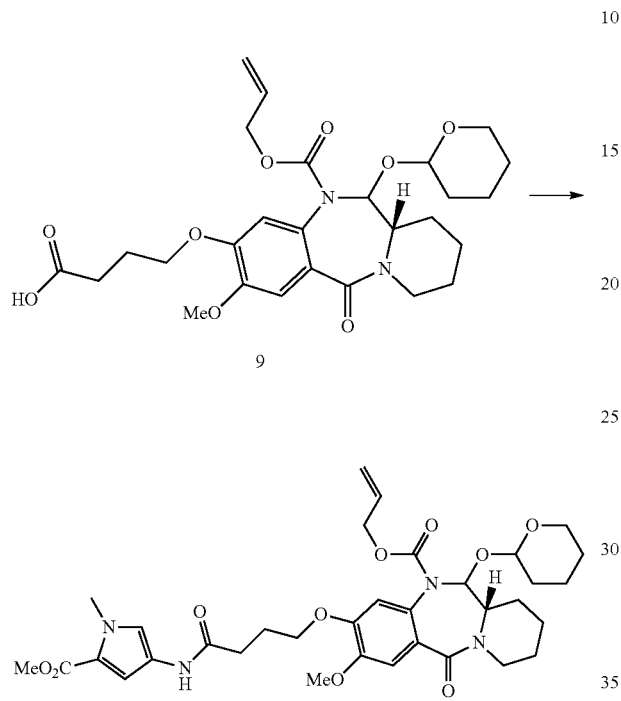

Chemical Formula: C$_{34}$H$_{44}$N$_4$O$_{10}$
Molecular Weight: 668.74
21

A solution of 4-((((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanoic acid (9) (150 mg, 0.64 mmol) in N,N-dimethylformamide (4 mL) was charged with 1-(3-dimethylaminopropyl)-3-ethylcarbodiimide hydrochloride (98 mg, 0.51 mmol) and 4-(dimethylamino)pyridine (79 mg, 0.64 mmol). The reaction mixture was stirred at room temperature for 30 min. Methyl 4-amino-1-methyl-1H-pyrrole-2-carboxylate hydrochloride (49 mg, 0.26 mmol) was then added and the resulting mixture was stirred at room temperature for 16 h. This was then poured into ice-water (40 mL) and extracted with ethyl acetate (3×100 mL). The combined organic extracts were sequentially washed with 1 M citric acid (60 mL), a saturated aqueous solution of sodium hydrogen carbonate (70 mL), water (70 mL) and brine (70 mL). The organic layer was then dried over sodium sulfate, filtered and concentrated in vacuo to give the title compound (150 mg, 88%) as a yellow oil. The product was carried through to the next step without any further purification.

MS m/z (EIMS)=668.8 (M+H)$^+$: LCMS (Method A): t$_R$=7.42 min.

Example 22

4-(4-(((6aS)-5-((Allyloxy)carbonyl)-2-methoxy-12-oxo-6-((tetrahydro-2H-pyran-2-yl)oxy)-5,6,6a,7,8,9,10,12-octahydrobenzo[e]-pyirido[1,2-a][1,4]diazepin-3-yl)oxy)butanamido)-1-methyl-1H-pyrrole-2-carboxylic acid (22)

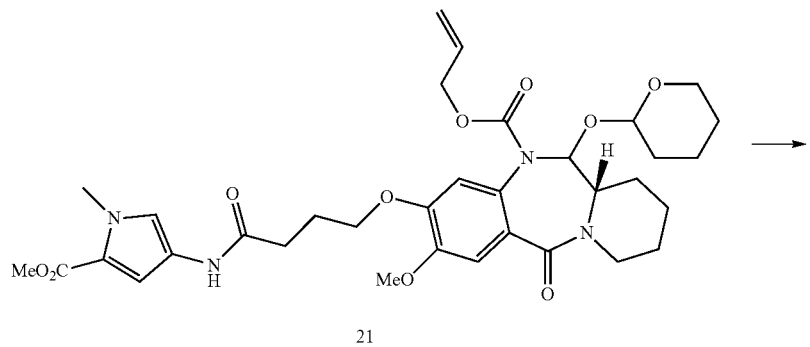

21

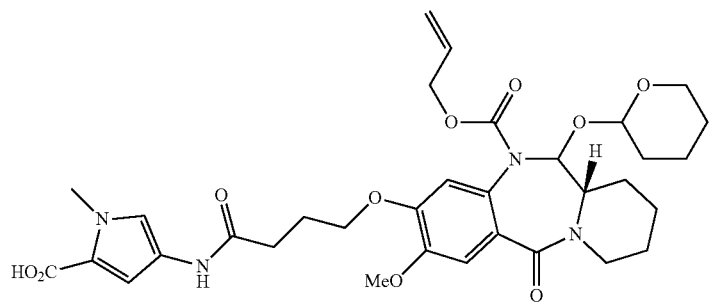

Chemical Formula: $C_{33}H_{42}N_4O_{10}$
Molecular Weight: 654.72

22

To a solution of allyl (6aS)-2-methoxy-3-(4-((5-(methoxycarbonyl)-1-methyl-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (21) (150 mg, 0.22 mmol) in 1,4-dioxane (5 mL) was added a 0.5 M aqueous solution of sodium hydroxide (5 mL, 5.0 mmol). The reaction mixture was stirred at room temperature for 2 h and was then concentrated in vacua, after which water (20 mL) was added and the aqueous layer was acidified to pH=1 with a 1 M citric acid solution (10 mL). The aqueous layer was then extracted with ethyl acetate (2×50 mL). The combined organic extracts were then washed with brine (50 mL), dried over sodium sulfate, filtered and concentrated in vacua to give the title compound (140 mg, 90%) as a beige solid. The product was carried through to the next step without any further purification.

MS m/z (EIMS)=677.0 (M+Na)$^+$; LCMS (Method A): $t_R$=6.92 min.

Example 23

Allyl (6S,6aS)-2-methoxy-3-(4-((5-((4-(5-(methoxy-carbonyl)-1-methyl-1H-pyrrol-3-yl)phenyl)carbamoyl)-1-methyl-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (23)

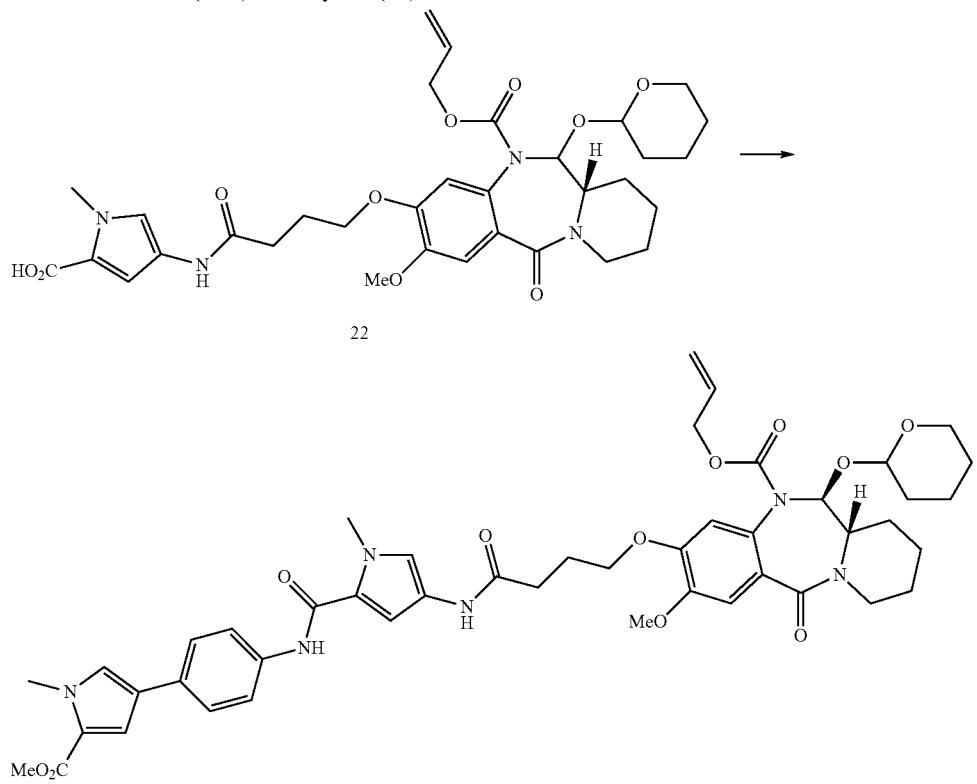

Chemical Formula: C₄₆H₅₄N₆O₁₁
Molecular Weight: 866.97

23

A solution of 4-(4-((((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanamido)-1-methyl-1H-pyrrole-2-carboxylic acid (22) (140 mg, 0.21 mmol) in N,N-dimethylformamide (4 mL) was charged with 1-(3-dimethylaminopropyl)-3-ethylcarbodiimide hydrochloride (74 mg, 0.39 mmol) and 4-(dimethylamino)pyridine (59 mg, 0.48 mmol). The reaction mixture was stirred at room temperature for 30 min. Methyl 4-(4-aminophenyl)-1-methyl-1H-pyrrole-2-carboxylate (18) (45 mg, 0.19 mmol) was then added and the resulting mixture was stirred at room temperature for 16 h. This was then poured into ice-water (40 mL) and extracted with ethyl acetate (3×100 mL). The combined organic extracts were sequentially washed with 1 M citric acid (60 mL), a saturated aqueous solution of sodium hydrogen carbonate (70 mL), water (70 mL) and brine (70 mL). The organic layer was then dried over sodium sulfate, filtered and concentrated. The resulting residue was then purified by column chromatography (silica), eluting with acetone/dichloromethane (0% to 50%), to give the title compound (160 mg, 95%) as a yellow solid.

MS m/z (EIMS)=867.0 (M+H)⁺: LCMS (Method A): $t_R$=8.10 min.

Example 24

Methyl (S)-4-(4-(4-(4-((2-methoxy-12-oxo-6a,7,8,9,10,12-hexahydrobenzo[e]pyrido[1,2-a][1,4]diazepin-3-yl)oxy)butanamido)-1-methyl-1H-pyrrole-2-carboxamido)phenyl)-1-methyl-1H-pyrrole-2-carboxylate (24)

1H), 3.25-3.15 (m, 1H), 2.49 (t, J=7.0 Hz, 2H), 2.24-2.18 (m, 2H), 2.10-2.03 (m, 1H), 2.01-1.93 (m, 2H), 1.86-1.80 (m, 2H), 1.73-1.66 (m, 1H); $^{13}$C NMR (100 MHz, CDCl$_3$) δ 169.9, 167.6, 163.5, 161.7, 159.7, 150.7, 147.9, 139.9, 136.4, 130.2, 126.1, 125.4, 123.3, 123.0, 120.6, 119.8, 114.6, 111.7 110.2, 103.9, 68.1, 56.1, 53.8, 51.2, 49.7, 39.9, 37.0, 36.7, 33.0, 31.0, 29.3, 24.9, 24.5, 22.9, 18.4; MS m/z (EIMS)=681.0 (M+H)$^+$: LCMS (Method A): t$_R$=6.98 min.

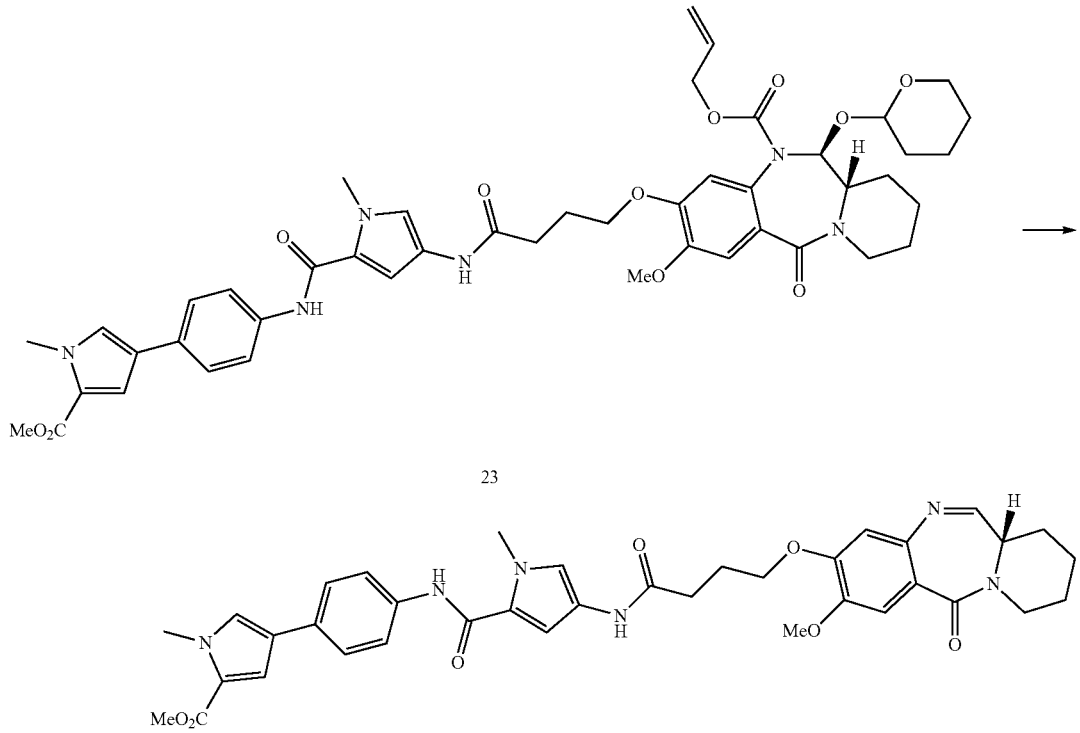

Chemical Formula: C$_{37}$H$_{40}$N$_6$O$_7$
Molecular Weight: 680.76

24

To a solution of allyl (6S,6aS)-2-methoxy-3-(4-((5-((4-(5-(methoxycarbonyl)-1-methyl-1H-pyrro-3-yl)phenyl)carbamoyl)-1-methyl-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (23) (80 mg, 0.09 mmol) in dichloromethane (3 mL) was added tetrakis(triphenylphosphine)palladium(0) (5.3 mg, 5 mol %), triphenyl-phosphine (6.1 mg, 25 mol %) and pyrrolidine (9.1 µL, 0.11 mmol). The reaction mixture was stirred at room temperature for 30 min. The reaction mixture was subjected to high vacuum for 30 min until excess pyrrolidine was thoroughly removed. The resulting residue was then purified by column chromatography (silica), eluting with acetone/dichloromethane (from 0% to 50%), to give the title compound (23 mg, 37%) as a yellow solid.

$^1$H NMR (CDCl$_3$, 400 MHz) δ 8.09 (s, 1H), 8.04-8.01 (m, 1H), 7.90 (d, J=5.8 Hz, 1H), 7.58 (s, 1H), 7.56 (s, 1H), 7.44-7.40 (m, 3H), 7.18 (d, J=2.0 Hz, 1H), 7.12 (d, J=1.8 Hz, 1H), 7.04 (d, J=2.0 Hz, 1H), 6.78 (s, 1H), 6.50 (d, J=1.9 Hz, 1H), 4.26-4.18 (m, 1H), 4.07 (t, J=6.0 Hz, 2H), 3.94 (s, 3H), 3.87 (s, 3H), 3.84 (d, J=2.9 Hz, 6H), 3.76 (td, J=5.7, 3.9 Hz,

Example 25

Allyl (6aS)-2-methoxy-3-(4-((4-(methoxycarbonyl)phenyl)-amino)-4-oxobutoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (25)

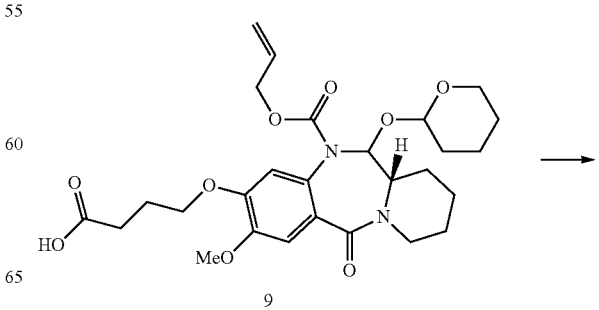

9

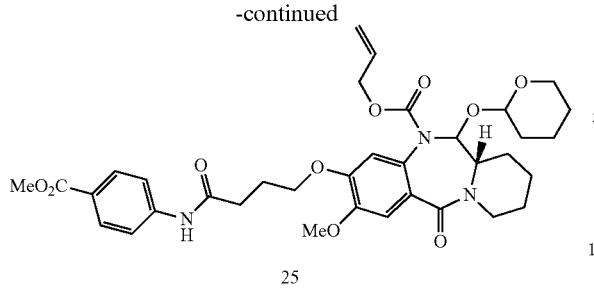

A solution of 4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanoic acid (9) (200 mg, 0.376 mmol) in anhydrous dichloromethane (5 mL) was charged with N-[(dimethylamino)-1H-1,2,3-triazolo-[4,5-b]pyridin-1-yl-methylene]-N-methylmethanaminium hexafluorophosphate N-oxide (150 mg, 0.394 mmol) and anhydrous triethylamine (220 μL, 1.58 mmol). The reaction mixture was stirred at room temperature for 30 min. Methyl 4-aminobenzoate (57.0 mg, 0.376 mmol) was then added and the resulting mixture was stirred at room temperature for 16 h. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacua. The resulting residue was then purified by column chromatography (silica), eluting with methanol/dichloromethane (from 0% to 10%), to give the title compound (110 mg, 44%) as a yellow solid.

MS (ES+): m/z=666 (M+H)$^+$: LCMS (Method A): $t_R$=7.88 min.

Example 26

4-(4-((((6aS)-5-((Allyloxy)carbonyl)-2-methoxy-12-oxo-6-((tetrahydro-2H-pyran-2-yl)oxy)-5,6,6a,7,8,9,10,12-octahydrobenzo[e]-pyrido[1,2-a][1,4]diazepin-3-yl)oxy)butanamido)benzoic acid (26)

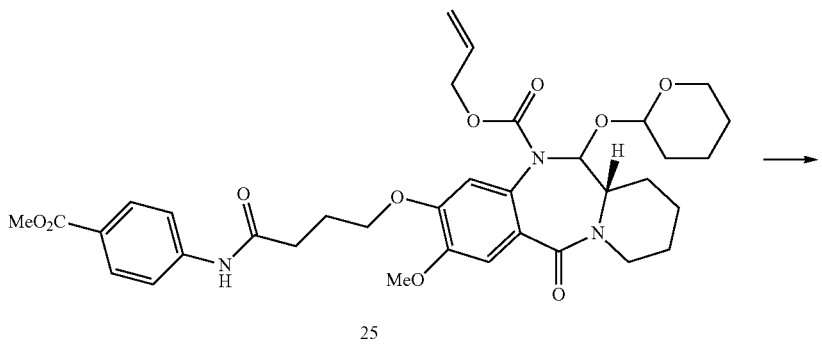

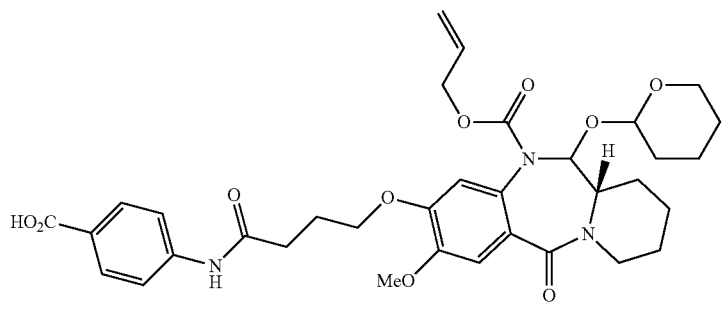

To a solution of allyl (6a5)-2-methoxy-3-(4-((4-(methoxycarbonyl)phenyl)amino)-4-oxobutoxy)-12-oxo-6-((tetrahydro-2H-pyran-2-yl)oxy)-6,6a,7,8,9,10-hexahydrobenzo-[e]pyrido[1,2-a][1,4]diazepine-5(12H)-carboxylate (25) (90 mg, 0.14 mmol) in 1,4-dioxane (2.5 mL) was added an aqueous solution of sodium hydroxide (0.5 M, 2.5 mL, 1.3 mmol). The reaction mixture was stirred at room temperature for 16 h and was then concentrated in vacua, after which water (20 mL) was added and the aqueous layer was acidified to pH=1 with an aqueous solution of citric acid (1 M, 10 mL). The aqueous layer was then extracted with ethyl acetate (2×50 mL). The combined organic extracts were then washed with brine (50 mL), dried over sodium sulfate, filtered and concentrated in vacua to give the title compound (86 mg, 98%) as a cream solid. The product was carried through to the next step without any further purification.

MS (ES+): m/z=652 (M+H)$^+$: LCMS (Method A): $t_R$=7.13 min.

Example 27

Allyl (6aS)-2-methoxy-3-(4-((4-((4-(5-(methoxycarbonyl)-1-methyl-1H-1-pyrrol-3-yl)phenyl)carbamoyl)phenyl)amino)-4-oxobutoxy)-12-oxo-6-((tetrahydro-2H-pyran-2-yl)oxy)-6,6a,7,8,940-hexahydrobenzo[e]-pyrido[1,2-a][1,4]diazepine-5(12H)-carboxylate (27)

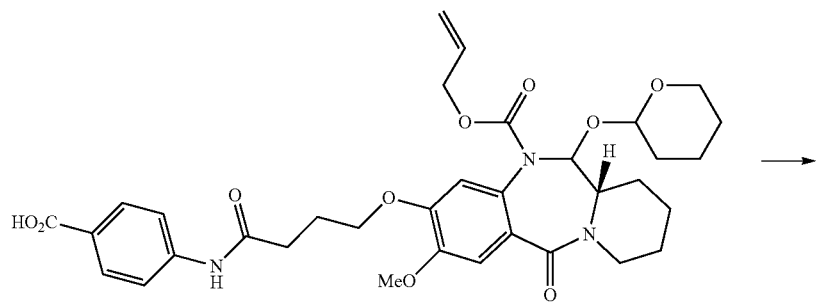

26

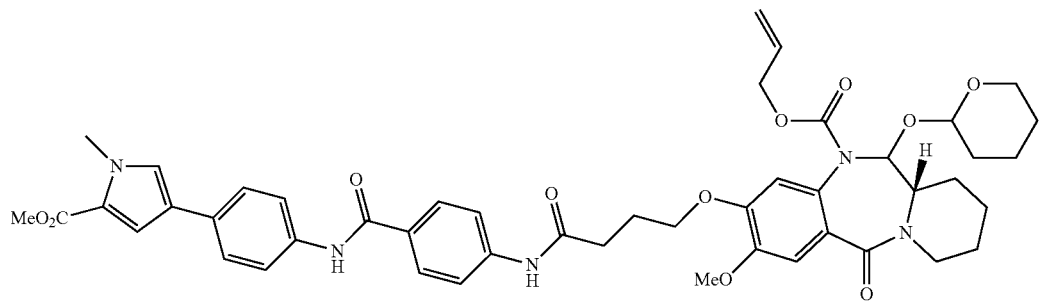

27

A solution of 4-(4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanamido)benzoic acid (26) (40 mg, 0.01 mmol) in anhydrous dichloro-methane (1 mL) was charged with N-[(dimethylamino)-1H-1,2,3-triazolo-[4,5-b]-pyridin-1-yl-methylene]-N-methylmethanaminium hexafluorophosphate N-oxide (25 mg, 0.064 mmol) and anhydrous triethylamine (36 μL, 0.26 mmol). The reaction mixture was stirred at room temperature for 30 min. Methyl 4-(4-aminophenyl)-1-methyl-1H-pyrrole-2-carboxylate (18) (14 mg, 0.061 mmol) was then added and the resulting mixture was stirred at room temperature for 16 h. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacua. The resulting residue was then purified by column chromatography (silica), eluting with methanol/dichloromethane (from 0% to 10%), to give the title compound (43 mg, 63%) as a yellow oil.

MS (ES+): m/z=864 (M+H)$^+$: LCMS (Method A): $t_R$=8.10 min.

Example 28

Methyl (S)-4-(4-(4-(4-((2-methoxy-12-oxo-6a,7,8,940,12-hexahydrobenzo[e]pyrido[1,2-a][1,4]diazepin-3-yl)oxy)butanamido)-benzamido)phenyl)-1-methyl-1H-pyrrole-2-carboxylate (28)

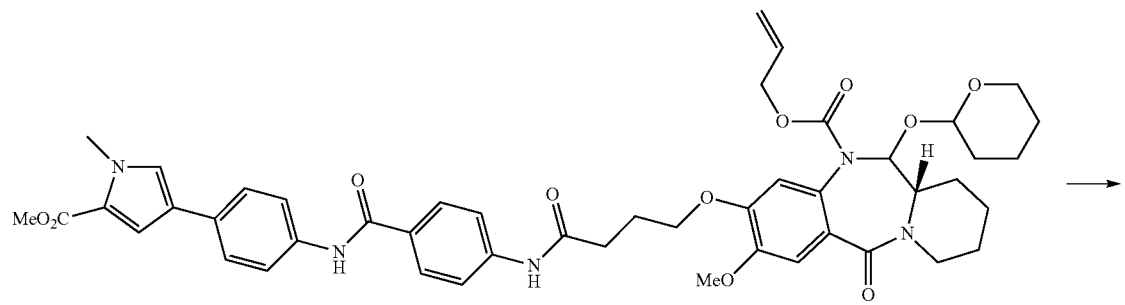

27

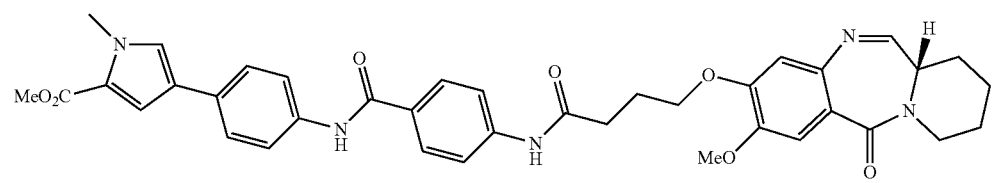

28

To a solution of allyl (6aS)-2-methoxy-3-(4-((4-(4-(5-(methoxycarbonyl)-1-methyl-1H-pyrrol-3-yl)phenyl)carbamoyl)phenyl)amino)-4-oxobutoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (27) (33 mg, 0.038 mmol) in dichloromethane (3 mL) was added tetrakis-(triphenylphosphine)palladium(0) (2.2 mg, 5 mol %), triphenylphosphine (2.5 mg, 25 mol %) and pyrrolidine (4 µL, 0.11 mmol). The reaction mixture was stirred at room temperature for 30 min. The reaction mixture was subjected to high vacuum for 30 min until excess pyrrolidine was thoroughly removed. The resulting residue was then purified by column chromatography (silica), eluting with acetone/dichloromethane (from 0% to 100%), to give the title compound (5.8 mg, 21%) as a yellow solid.

$^1$H NMR (CDCl$_3$, 400 MHz) δ 8.14 (br s, 1H), 8.06 (br s, 1H), 7.91 (d, J=5.7 Hz, 1H), 7.81 (d, J=8.7 Hz, 2H), 7.65 (d, J=8.6 Hz, 2H), 7.60 (d, J=8.4 Hz, 2H), 7.46-7.50 (m, 2H), 7.41 (s, 1H), 7.21 (d, J=2.1 Hz, 1H), 7.08 (d, J=1.9 Hz, 1H), 6.78-6.82 (m, 1H), 4.24 (d, J=14.0 Hz, 1H), 4.11-4.18 (m, 2H), 3.95-3.98 (m, 3H), 3.83-3.86 (m, 6H), 3.74-3.79 (m, 2H), 3.18-3.30 (m, 2H), 2.60-2.66 (m, 2H), 2.28 (t, J=6.3 Hz, 2H), 1.97 (d, J=6.3 Hz, 2H), 1.82-1.88 (m, 2H); $^{13}$C NMR (100 MHz, CDCl$_3$) δ 215.5, 171.1, 167.5, 165.0, 163.4, 161.7, 150.3, 147.8, 141.3, 140.0, 136.2, 130.8, 128.1, 125.6, 123.5, 123.1, 121.5, 120.6, 119.3, 114.7, 111.7, 110.2, 67.9, 56.1, 51.2, 49.7, 39.8, 37.0, 34.3, 30.9, 25.6, 24.5, 23.0, 18.4; MS (ES+): m/z=678 (M+H)$^+$: LCMS (Method A): $t_R$=7.05 min.

Example 29

Allyl (6aS)-2-methoxy-3-(4-((4-((2-(methoxycarbonyl)benzo-[b]thiophen-5-yl)carbamoyl)phenyl)amino)-4-oxobutoxy)-12-oxo-6-((tetra-hydro-2H-pyran-2-yl)oxy)-6,6a,7,8,9,10-hexahydrobenzo[e]pyrido[1,2-a]-[1,4]diazepine-5(12H)-carboxylate (29)

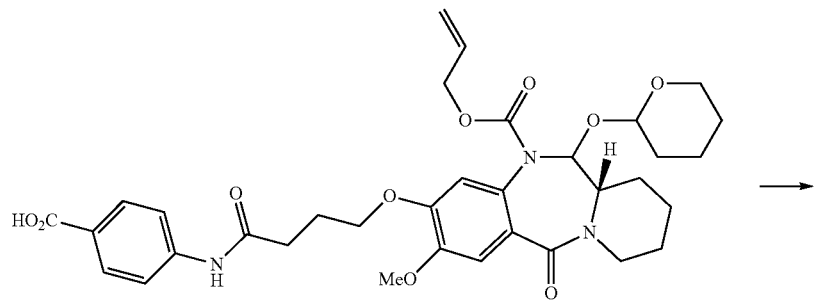

26

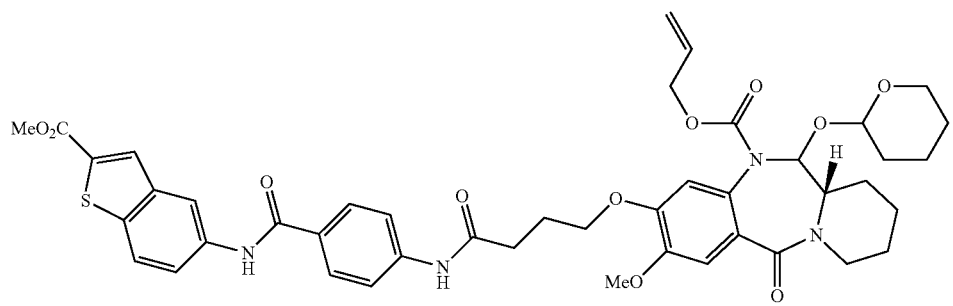

29

A solution of 4-(4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanamido)benzoic acid (26) (40 mg, 0.061 mmol) in anhydrous dichloro-methane (1 mL) was charged with N-[(dimethylamino)-1H-1,2,3-triazolo-[4,5-b]-pyridin-1-ylmethylene]-N-methylmethanaminium hexafluorophosphate N-oxide (25 mg, 0.064 mmol) and anhydrous triethylamine (36 μL, 0.26 mmol). The reaction mixture was stirred at room temperature for 30 min. Methyl 5-amino-benzo[b]-thiophene-2-carboxylate (13 mg, 0.063 mmol) was then added and the resulting mixture was stirred at room temperature for 16 h. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacua. The resulting residue was then purified by column chromatography (silica), eluting with methanol/dichloromethane (from 0% to 10%), to give the title compound (34 mg, 45%) as a brown oil.

MS (ES+): m/z=841 (M+H)$^+$: LCMS (Method A): $t_R$=8.15 min.

Example 30

Methyl (S)-5-(4-(4-((2-methoxy-12-oxo-6a,7,8,9,10,12-hexa-hydrobenzo[e]pyrido[1,2-a][1,4]diazepin-3-yl)oxy)butanamido)-benzamido)benzo[b]thiophene-2-carboxylate (30)

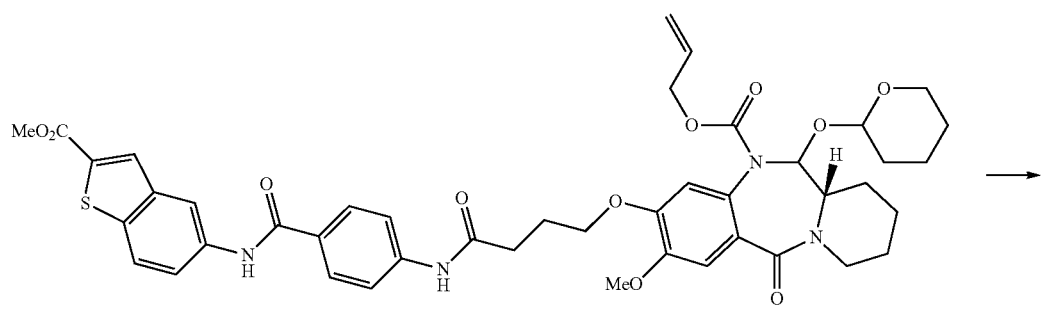

29

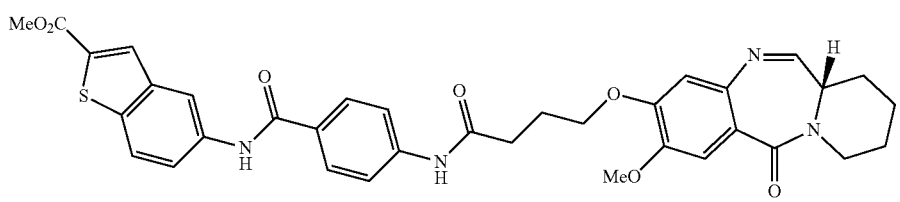

30

To a solution of allyl (6a5)-2-methoxy-3-(4-((4-(2-(methoxycarbonyl)benzo[b]-thiophen-5-yl)carbamoyl)phenyl)amino)-4-oxobutoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (29) (23 mg, 0.028 mmol) in dichloromethane (1.5 mL) was added tetrakis(triphenylphosphine)palladium(0) (1.6 mg, 5 mol %), triphenylphosphine (1.8 mg, 25 mol %) and pyrrolidine (3.0 µL, 0.11 mmol). The reaction mixture was stirred at room temperature for 30 min. The reaction mixture was subjected to high vacuum for 30 min until excess pyrrolidine was thoroughly removed. The resulting residue was then purified by column chromatography (silica), eluting with acetone/dichloro-methane (from 0% to 100%) followed by methanol/dichloromethane (from 0% to 100%), to give the title compound (5.4 mg, 30%) as a pink solid.

$^1$H NMR (CDCl$_3$, 400 MHz) δ 8.48 (br s, 1H), 8.39 (d, J=1.9 Hz, 1H), 8.31 (s, 1H), 7.97 (s, 1H), 7.91 (d, J=5.8 Hz, 1H), 7.77-7.84 (m, 3H), 7.65 (dd, J=8.8, 2.0 Hz, 1H), 7.57 (d, J=8.6 Hz, 2H), 7.38 (s, 1H), 6.79 (s, 1H), 4.24 (dt, J=13.7, 4.1 Hz, 1H), 4.09-4.17 (m, 2H), 3.95 (s, 3H), 3.79-3.82 (m, 3H), 3.74-3.79 (m, 1H), 3.49 (d, J=3.9 Hz, 1H), 3.29-3.41 (m, 1H), 3.17-3.28 (m, 1H), 2.58-2.64 (m, 2H), 2.26 (quin, J=6.2 Hz, 2H), 2.05-2.13 (m, 1H), 1.92-2.01 (m, 1H), 1.83-1.87 (m, 1H), 1.07-1.19 (m, 1H); $^{13}$C NMR (CDCl$_3$, 100 MHz) δ 171.2, 167.5, 165.5, 163.4, 163.2, 150.4, 147.8, 141.5, 140.0, 139.3, 138.0, 135.1, 134.4, 130.6, 128.2, 123.0, 121.4, 120.9, 119.2, 116.4, 111.7, 110.1, 67.9, 56.0, 52.6, 49.7, 39.8, 34.2, 30.9, 24.7, 24.5, 22.9, 18.3; MS (ES+): m/z=655 (M+H)$^+$: LCMS (Method A): t$_R$=7.00 min.

Example 31

Methyl 4-(4-((tert-butoxycarbonyl)amino)-1-methyl-1H-imidazole-2-carboxamido)benzoate (31)

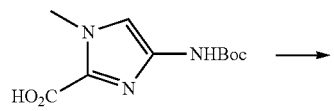

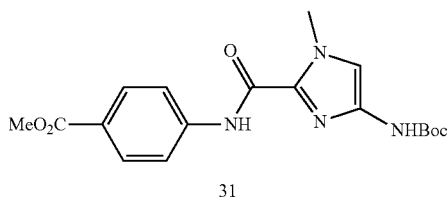

A solution of 4-((tert-butoxycarbonyl)amino)-1-methyl-1H-imidazole-2-carboxylic acid (100 mg, 0.415 mmol) in anhydrous dichloromethane (3 mL) was charged with N-[(dimethylamino)-1H-1,2,3-triazolo-[4,5-b]pyridin-1-yl-methylene]-N-methyl-methanaminium hexafluorophosphateN-oxide (165 mg, 0.435 mmol) and anhydrous triethylamine (242 µL, 1.74 mmol). The reaction mixture was stirred at room temperature for 30 min. Methyl 4-aminobenzoate (63 mg, 0.42 mmol) was then added and the resulting mixture was stirred at room temperature for 16 h. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacua. The resulting residue was then purified by column chromatography (silica), eluting with methanol/dichloromethane (from 0% to 10%), to give the title compound (40 mg, 26%) as a cream solid.

$^1$H NMR (CDCl$_3$, 400 MHz) δ 9.16 (s, 1H), 8.01-8.07 (m, 2H), 7.69-7.75 (m, 2H), 7.21 (br s, 1H), 6.84 (s, 1H), 4.07 (s, 3H), 3.92 (s, 3H), 1.53 (s, 9H); MS (ES-): m/z=373 (M-H)$^-$; LCMS (Method A): t$_R$=7.68 min.

Example 32

Methyl 4-(4-amino-1-methyl-1H-1-imidazole-2-carboxamido)-benzoate hydrochloride (32)

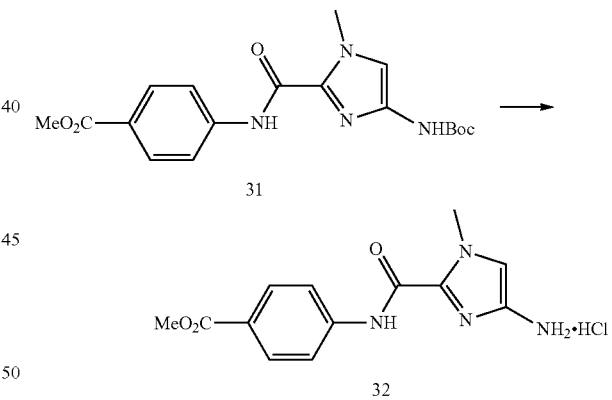

Methyl 4-(4-((tert-butoxycarbonyl)amino)-1-methyl-1H-imidazole-2-carboxamido)-benzoate (31) (40 mg, 0.11 mmol) was dissolved in hydrochloric acid (4 M in 1,4-dioxane) (2 mL) and the reaction mixture was stirred at room temperature for 2 h. The reaction mixture was concentrated in vacua to give the title compound (33 mg, 99%) as a brown solid. The product was carried through to the next step without any further purification.

$^1$H NMR (MeOD, 400 MHz) δ 7.89-7.95 (m, 2H), 7.72-7.78 (m, 2H), 7.31 (s, 1H), 4.01 (s, 3H), 3.80 (s, 3H); $^{13}$C NMR (MeOD, 100 MHz) δ 168.0, 143.6, 132.5, 131.6, 126.9, 123.3, 120.6, 92.6, 68.1, 52.3, 36.7; MS (ES+): m/z=275 (M+H)$^+$: LCMS (Method A): t$_R$=5.43 min.

Example 33

Allyl (6aS)-2-methoxy-3-(4-((2-((4-(methoxycarbonyl)phenyl)-carbamoyl)-1-methyl-1H-imidazol-4-yl)amino)-4-oxobutoxy)-12-oxo-6-((tetrahydro-2H-pyran-2-yl)oxy)-6,6a,7,8,9,10-hexahydrobenzo[e]pyrido-[1,2-a][1,4]diazepine-5(12H)-carboxylate (33)

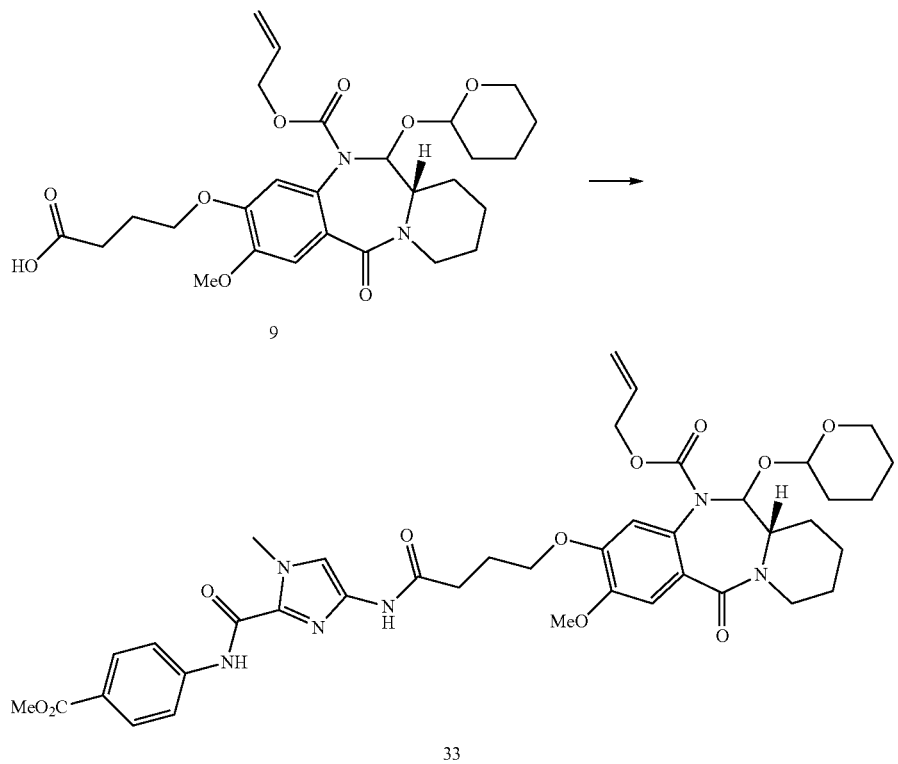

A solution of 4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanoic acid (9) (50 mg, 0.094 mmol) in anhydrous dichloromethane (0.5 mL) was charged with N-[(dimethylamino)-1H-1,2,3-triazolo-[4,5-b]pyridin-1-yl-methylene]-N-methylmethanaminium hexafluorophosphate N-oxide (38 mg, 0.099 mmol) and anhydrous triethylamine (55 μL, 0.40 mmol). The reaction mixture was stirred at room temperature for 30 min. Methyl 4-(4-amino-1-methyl-1H-imidazole-2-carboxamido)-benzoate hydrochloride (32) (30 mg, 0.094 mmol) was then added and the resulting mixture was stirred at room temperature for 16 h. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacua. The resulting residue was then purified by column chromatography (silica), eluting with methanol/dichloromethane (from 0% to 10%), to give the title compound (72 mg, 97%) as a brown oil.

MS (ES+): m/z=789 (M+H)$^+$: LCMS (Method A): $t_R$=7.87 min.

Example 34

Methyl (S)-4-(4-(4-((2-methoxy-12-oxo-6a,7,8,9,10,12-hexa-hydrobenzo[e]pyrido[1,2-α][1,4]diazepin-3-yl)oxy)butanamido)-1-methyl-1H-imidazole-2-carboxamido)benzoate (34)

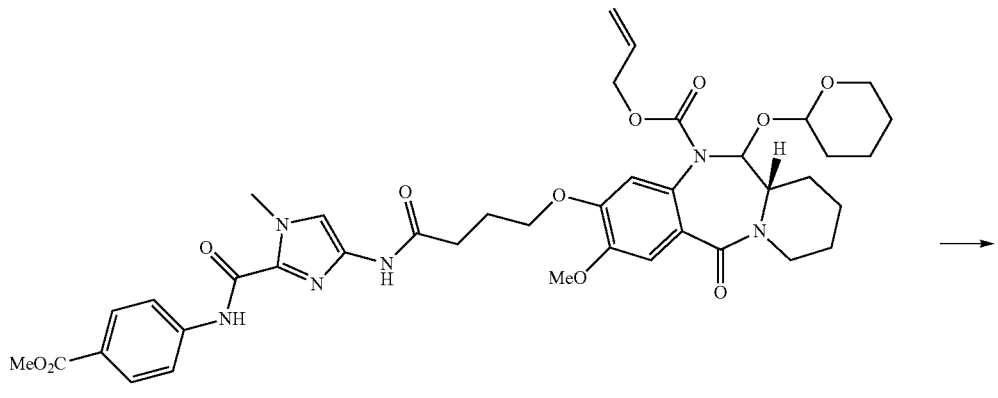

33

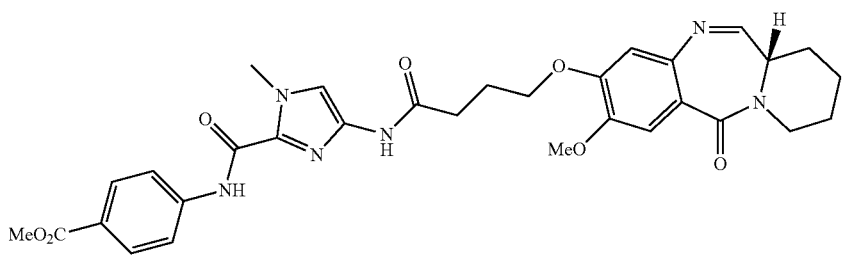

34

To a solution of allyl (6as)-2-methoxy-3-(4-((2-((4-(methoxycarbonyephenyl)-carbamoyl)-1-methyl-1H-imidazol-4-yl)amino)-4-oxobutoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (33) (72 mg, 0.091 mmol) in dichloromethane (2 mL) was added tetrakis(triphenylphosphine)palladium(0) (5.3 mg, 5 mol %), triphenylphosphine (6.0 mg, 25 mol %) and pyrrolidine (9.0 μL, 0.11 mmol). The reaction mixture was stirred at room temperature for 30 min. The reaction mixture was subjected to high vacuum for 30 min until excess pyrrolidine was thoroughly removed. The resulting residue was then purified by column chromatography (silica), eluting with acetone/dichloro-methane (from 0% to 100%), to give the title compound (15 mg, 27%) as a yellow solid.

$^1$H NMR (CDCl$_3$, 400 MHz) δ 9.13 (s, 1H), 8.24 (s, 1H), 8.03 (d, J=8.7 Hz, 2H), 7.90 (d, J=5.7 Hz, 1H), 7.65-7.75 (m, 2H), 7.43-7.50 (m, 2H), 6.77-6.83 (m, 1H), 4.12-4.23 (m, 2H), 4.07 (s, 3H), 3.93 (s, 3H), 3.91 (s, 3H), 3.18-3.27 (m, 1H), 2.80 (s, 3H), 2.56-2.68 (m, 3H), 2.23-2.31 (m, 2H), 1.85 (d, J=10.1 Hz, 4H); $^{13}$C NMR (CDCl$_3$, 100 MHz) δ 169.3, 167.1, 166.2, 162.9, 156.2, 150.1, 147.6, 147.4, 141.4, 139.6, 135.6, 132.8, 130.5, 130.3, 125.2, 121.1, 118.2, 114.8, 111.2, 109.9, 94.1, 67.4, 63.5, 55.7, 53.4, 51.6, 49.2, 39.4, 38.2, 35.5, 32.5, 31.6, 30.9, 28.9, 24.9, 24.3, 24.1, 22.5, 19.9, 18.0; MS (ES+): m/z=603 (M+H)$^+$: LCMS (Method A): t$_R$=6.57 min.

Example 35

Methyl 4-(4-((tert-butoxycarbonyl)amino)-1-methyl-1H-pyrrole-2-carboxamido)benzoate (35)

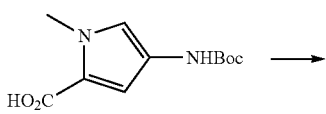

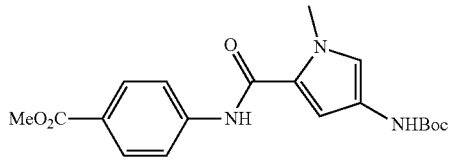

35

A solution of 4-((tert-butoxycarbonyl)amino)-1-methyl-1H-pyrrole-2-carboxylic acid (100 mg, 0.416 mmol) in N,N-dimethylformamide (3 mL) was charged with 1-(3-dimethylaminopropyl)-3-ethylcarbodiimide hydrochloride (145 mg, 0.756 mmol) and 4-(dimethylamino)pyridine (115 mg, 0.941 mmol). The reaction mixture was stirred at room temperature for 3 h. Methyl 4-aminobenzoate (57 mg, 0.38 mmol) was then added and the resulting mixture was stirred at room temperature for 16 h. This was then poured onto ice-water (40 mL) and extracted with ethyl acetate (3×100 mL). The combined organic extracts were sequentially washed with an aqueous solution of citric acid (1 M, 60 mL), a saturated aqueous solution of sodium hydrogen carbonate (70 mL), water (70 mL) and brine (70 mL). The organic layer was then dried over sodium sulfate, filtered and concentrated. The resulting residue was then purified by column chromatography (silica), eluting with methanol/dichloromethane (from 0% to 10%), to give the title compound (90 mg, 58%) as a white solid.

$^1$H NMR (CDCl$_3$, 400 MHz) δ 7.99-8.07 (m, 2H), 7.69 (s, 1H), 7.61-7.67 (m, 2H), 6.88 (s, 1H), 6.69 (br S, 1H), 6.25 (br s, 1H), 3.93 (s, 3H), 3.91 (s, 3H), 1.52 (s, 9H); $^{13}$C NMR (CDCl$_3$, 100 MHz) δ 166.6, 159.4, 153.4, 142.3, 130.9, 125.5, 123.1, 122.5, 119.2, 118.7, 140.1, 80.5, 52.0, 36.8, 28.4; MS (ES+): m/z=374 (M+H)$^+$: LCMS (Method A): t$_R$=7.52 min.

Example 36

Methyl 4-(4-amino-1-methyl-1H-pyrrole-2-carboxamido)-benzoate hydrochloride (36)

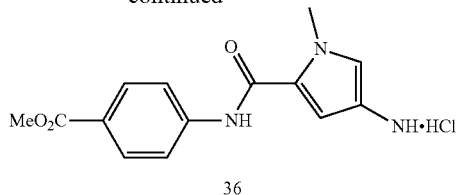

Methyl 4-(4-(tert-butoxycarbonyl)amino)-1-methyl-1H-pyrrole-2-carboxamido)-benzoate (35) (90 mg, 0.24 mmol) was dissolved in hydrochloric acid (4 M in 1,4-dioxane) (3 mL) and the reaction mixture was stirred at room temperature for 16 h. The reaction mixture was concentrated in vacua to give the title compound (79 mg, 99%) as a cream solid. The product was carried through to the next step without any further purification.

$^1$H NMR (MeOD, 400 MHz) δ 7.99 (d, J=8.7 Hz, 2H), 7.80 (d, J=8.7 Hz, 2H), 7.13 (d, J=1.9 Hz, 1H), 7.09 (d, J=1.9 Hz, 1H), 3.96 (s, 3H), 3.89 (s, 3H); $^{13}$C NMR (MeOD, 100 MHz) δ 168.2, 161.2, 144.5, 131.5, 126.9, 126.4, 123.7, 120.8, 114.2, 109.0, 52.5, 37.5; MS (ES+): m/z=274 (M+H)$^+$: LCMS (Method A): t$_R$=4.98 min.

Example 37

Allyl (6aS)-2-methoxy-3-(4-((5-((4-methoxycarbonyl)phenyl)-carbamoyl)-1-methyl-1H-pyrrol-3-yl)amino)-4-oxobutoxy)-12-oxo-6-((tetrahydro-2H-pyran-2-yl)oxy-6,6a,7,8,9,10-hexahydrobenzo[e]pyrido-[1,2-a][1,4]diazepine-5(12H)-carboxylate (37)

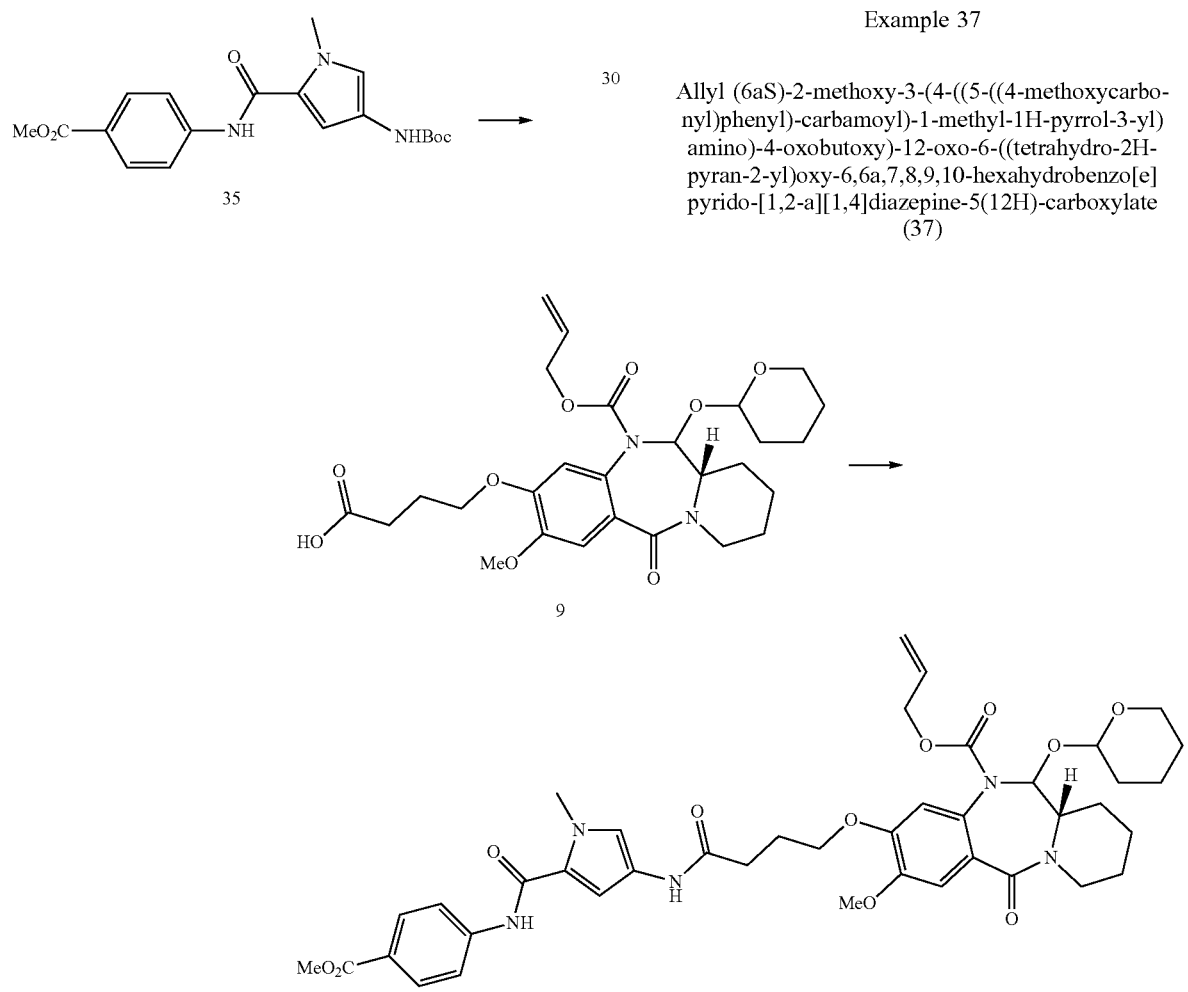

A solution of 4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)-oxy)butanoic acid (9) (50 mg, 0.094 mmol) in anhydrous dichloromethane (0.5 mL) was charged with N—Rdimethylamino)-1H-1,2,3-triazolo-[4,5-b]pyridin-1-ylmethylene]-N-methylmethanaminium hexafluorophosphate N-oxide (38 mg, 0.099 mmol) and anhydrous triethylamine (55 μL, 0.40 mmol). The reaction mixture was stirred at room temperature for 30 min. Methyl 4-(4-amino-1-methyl-1H-pyrrole-2-carboxamido)benzoate hydrochloride (36) (30 mg, 0.094 mmol) was then added and the resulting mixture was stirred at room temperature for 16 h. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacuo. The resulting residue was then purified by column chromatography (silica), eluting with methanol/dichloromethane (from 0% to 10%), to give the title compound (72 mg, 97%) as a brown oil.

MS (ES+): m/z=788 (M+H)⁺: LCMS (Method A): $t_R$=7.77 min.

Example 38

Methyl (S)-4-(4-(4-((2-methoxy-12-oxo-6a,7,8,9,10,12-hexa-hydrobenzo[e]pyrido[1,2-a][1,4]diazepin-3-yl)oxy)butanamido)-1-methyl-1H-pyrrole-2-carboxamido)benzoate (38)

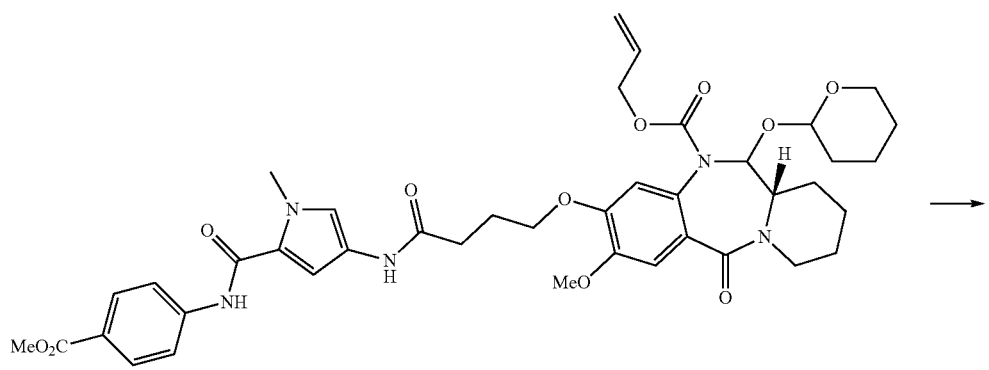

37

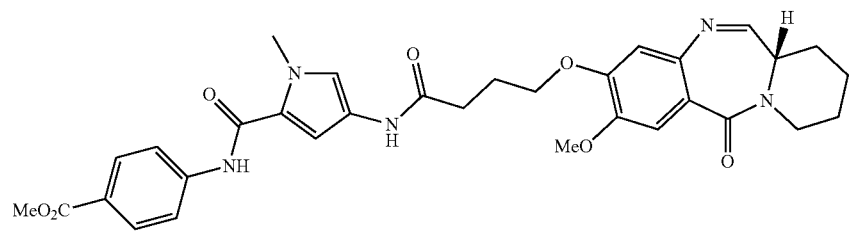

38

To a solution of allyl (6aS)-2-methoxy-3-(4-((5-((4-(methoxycarbonyephenyl)-carbamoyl)-1-methyl-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (37) (72 mg, 0.091 mmol) in dichloromethane (2 mL) was added tetrakis-(triphenylphosphine)palladium(0) (5.3 mg, 5 mol %), triphenylphosphine (6.0 mg, 25 mol %) and pyrrolidine (9.0 µL, 0.11 mmol). The reaction mixture was stirred at room temperature for 30 min. The reaction mixture was subjected to high vacuum for 30 min until excess pyrrolidine was thoroughly removed. The resulting residue was then purified by column chromatography (silica), eluting with acetone/dichloromethane (from 0% to 100%), to give the title compound (15.0 mg, 27%) as a yellow solid.

$^1$H NMR (CDCl$_3$, 400 MHz) δ 8.41 (s, 1H), 8.00 (s, 2H), 7.98 (s, 1H), 7.90 (d, J=5.8 Hz, 1H), 7.72-7.74 (m, 1H), 7.70-7.72 (m, 1H), 7.41 (s, 1H), 7.14 (d, J=1.8 Hz, 1H), 6.79 (s, 1H), 6.57 (d, J=1.8 Hz, 1H), 4.22 (d, J=14.1 Hz, 1H), 4.09 (t, J=6.0 Hz, 2H), 3.89 (s, 3H), 3.88 (s, 3H), 3.83 (s, 3H), 3.74-3.79 (m, 2H), 3.21 (d, J=3.3 Hz, 1H), 2.47-2.52 (m, 2H), 2.17-2.23 (m, 2H), 1.93 (br S, 3H), 1.79-1.85 (m, 2H); $^{13}$C NMR (CDCl$_3$, 100 MHz) δ 170.0, 167.6, 166.8, 163.6, 159.8, 150.7, 147.9, 142.9, 139.9, 130.7, 124.9, 122.8, 121.6, 121.5, 120.8, 119.1, 111.8, 110.4, 104.6, 68.1, 56.1, 52.0, 49.7, 39.9, 36.9, 33.0, 31.0, 25.0, 24.5, 22.9, 18.3; MS (ES+): m/z=602 (M+H)$^+$: LCMS (Method A): t$_R$=6.52 min.

Example 39

4-(4-(4-(4-(((6aS)-5-((Allyloxy)carbonyl)-2-methoxy-12-oxo-6-((tetrahydro-2H-pyran-2-yl)oxy)-5,6,6a,7,8,9,10,12-octahydrobenzo[e]-pyirido[1,2-α][1,4]diazepin-3-yl)oxy)butanamido)-1-methyl-1H-pyrrole-2-carboxamido)phenyl)-1-methyl-1H-1-pyrrole-2-carboxylic acid (39)

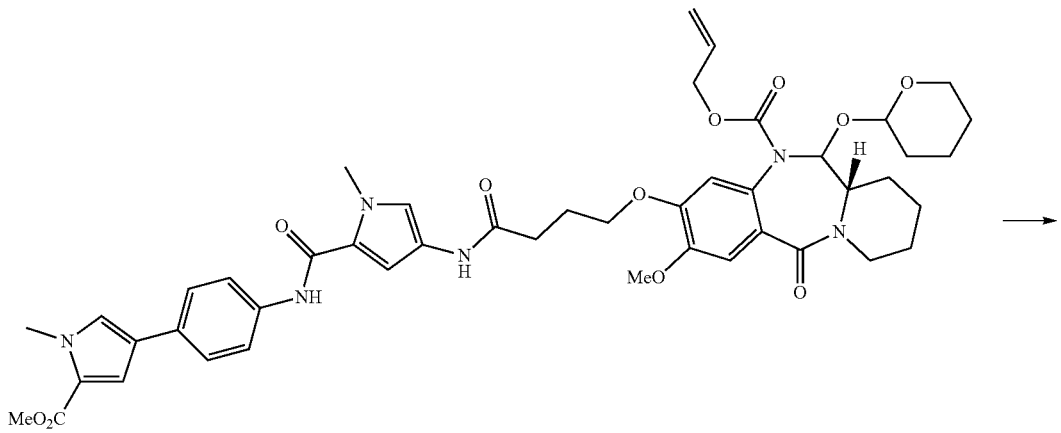

23

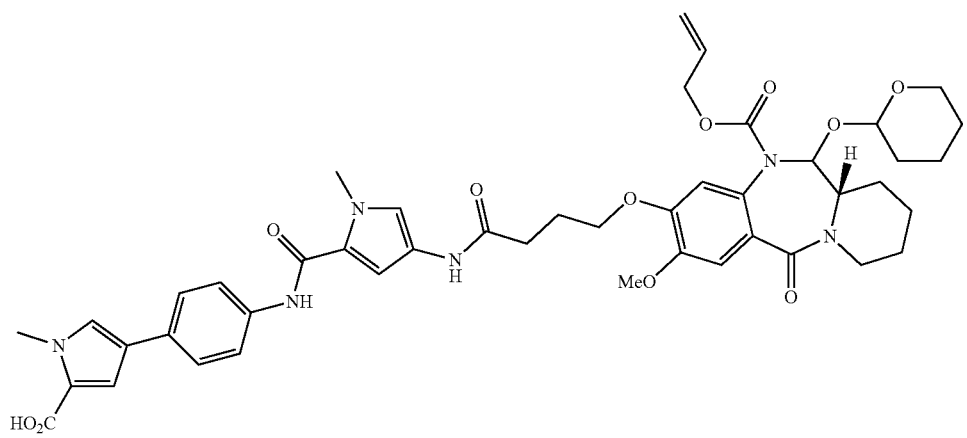

39

To a solution of allyl (6aS)-2-methoxy-3-(4-((5-((4-(5-(methoxycarbonye-1-methyl-1H-pyrrol-3-yl)phenyl)carbamoyl)-1-methyl-1-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (23) (195 mg, 0.225 mmol) in 1,4-dioxane (5 mL) was added an aqueous solution of sodium hydroxide (0.5 M, 5 mL, 2.5 mmol). The reaction mixture was stirred at room temperature for 16 h and was then concentrated in vacuo, after which water (20 mL) was added and the aqueous layer was acidified to pH=1 with an aqueous solution of citric acid (1 M, 5 mL). The aqueous layer was then extracted with ethyl acetate (2×50 mL). The combined organic extracts were then washed with brine (50 mL), dried over sodium sulfate, filtered and concentrated to give the title compound (190 mg, 99%) as a cream solid. The product was carried through to the next step without any further purification.

MS (ES+): m/z=853 (M+H)$^+$: LCMS (Method B): $t_R$=3.83 min.

Example 40

Allyl (6aS)-3-(44(54(4-(54(4-aminophenyl)carbamoyl)-1-methyl-1H-pyrrol-3-yl)phenyl)carbamoyl)-1-methyl-1H-pyrrol-3-yl)amino)-4-oxobutoxy)-2-methoxy-12-oxo-6-((tetrahydro-2H-pyran-2-yl)oxy)-6,6a,7,8,9,10-hexahydrobenzo[e]pyrido[2-α][1,4]diazepine-5(12H)-carboxylate (40)

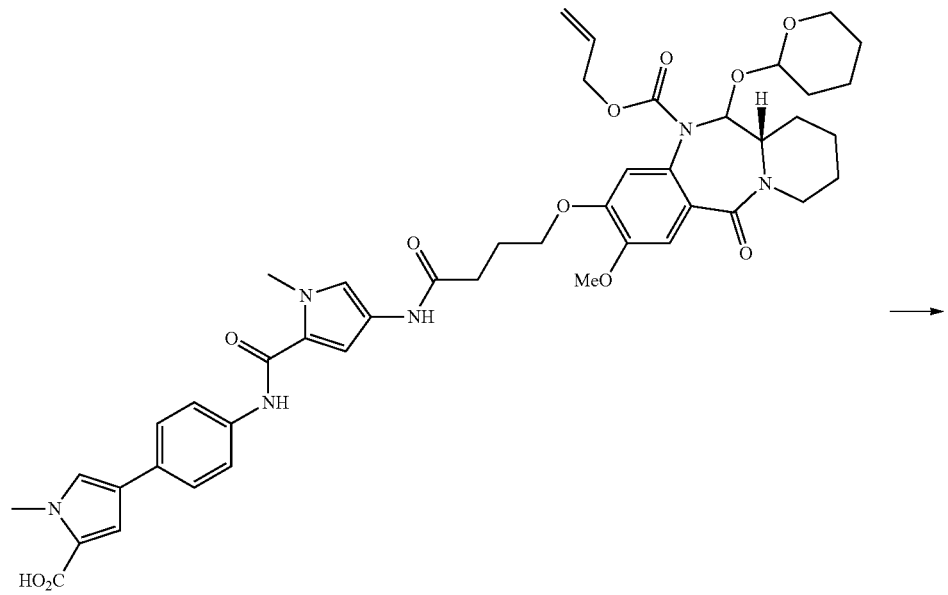

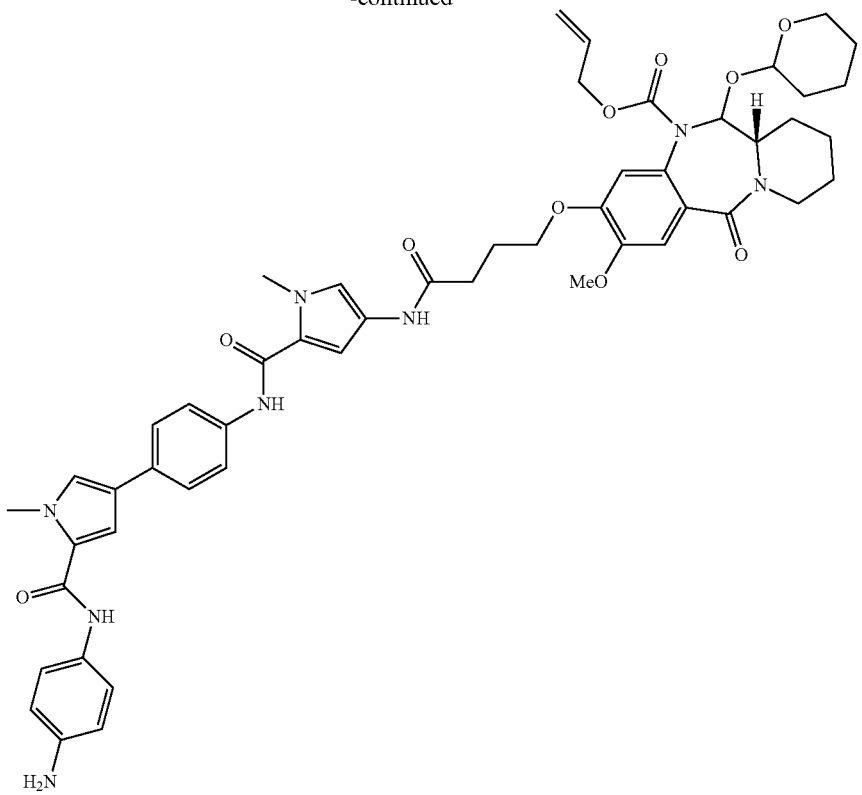

40

A solution of 4 4-(4-(4-(4-(4-((((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)butanamido)-1-methyl-1H-pyrrole-2-carboxamido)phenyl)-1-methyl-1H-pyrrole-2-carboxylic acid (39) (320 mg, 0.375 mmol) in anhydrous dichloromethane (1.5 mL) was charged with N-[(dimethylamino)-1H-1,2,3-triazolo-[4,5-b]pyridin-1-ylmethylene]-N-methylmethanaminium hexafluorophosphateN-oxide (150 mg, 0.395 mmol) and anhydrous triethylamine (220 µL, 1.58 mmol). The reaction mixture was stirred at room temperature for 30 min. Benzene-1,4-diamine (41 mg, 0.38 mmol) was then added and the resulting mixture was stirred at room temperature for 16 h. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacua. The resulting residue was then purified by column chromatography (silica), eluting with methanol/dichloromethane (from 0% to 10%), to give the title compound (250 mg, 71%) as a cream solid.

MS (ES+): m/z=944 (M+H)$^+$: LCMS (Method B): $t_R$=3.45 min.

Example 41

(S)—N-(4-aminophenyl)-4-(4-(4-(4-((2-methoxy-12-oxo-6a,7,8,9,10,12-hexahydrobenzo[e]pyrido[1,2-α][1,4]diazepin-3-yl)oxy)butan-amido)-1-methyl-1H-pyrrole-2-carboxamido)phenyl)-1-methyl-1H-1-pyrrole-2-carboxamide (41)

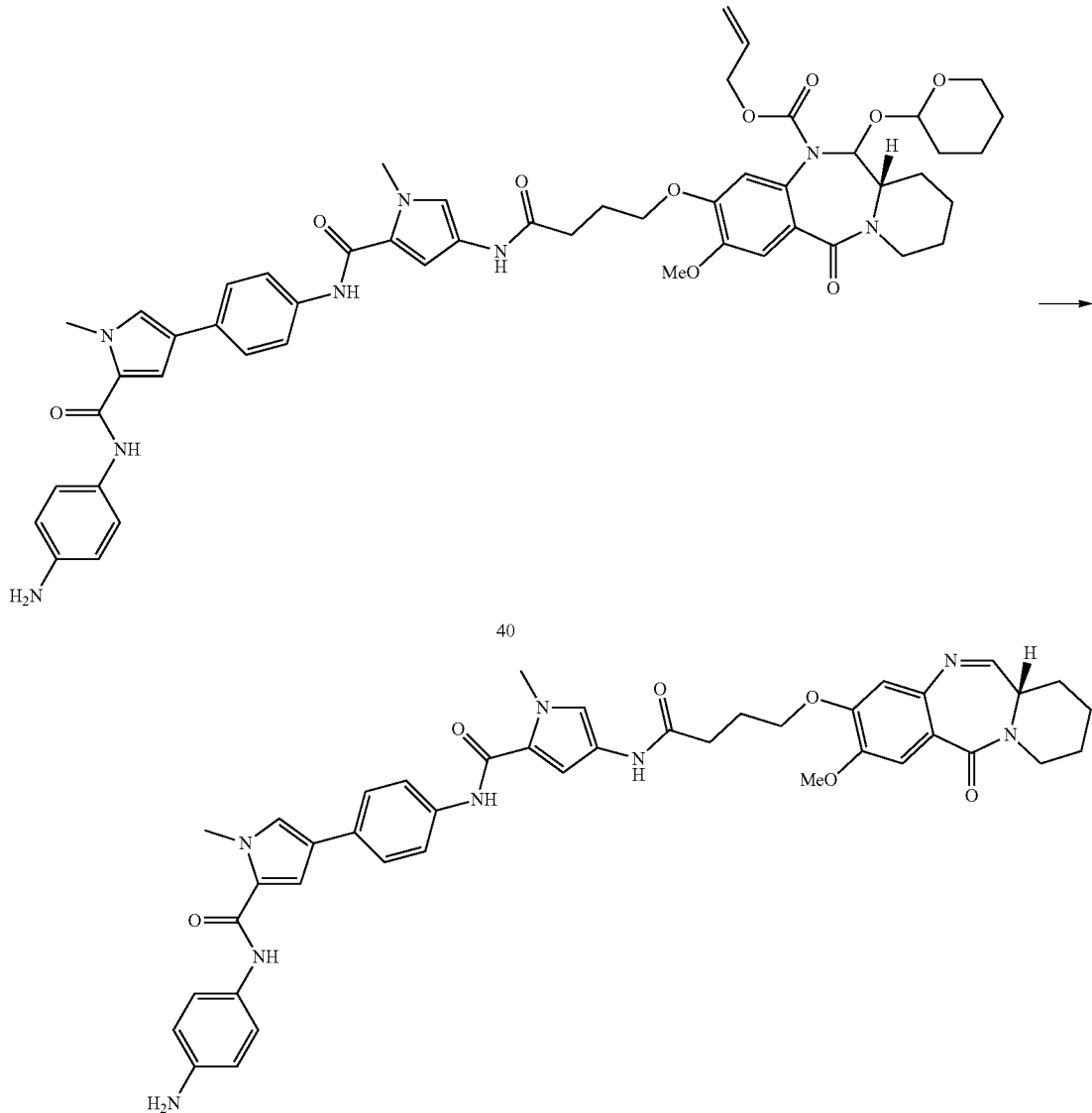

min until excess pyrrolidine was thoroughly removed. The resulting residue was then purified by column chromatography (silica), eluting with acetone/dichloromethane (from 0% to 100%) followed by methanol/acetone (from 0% to 100%), to give the title compound (118 mg, 59%) as a yellow solid.

$^1$H NMR (DMSO-hd 6, 400 MHz) δ 9.88-9.96 (m, 1H), 9.81 (s, 2H), 9.50 (s, 1H), 8.32 (br s, 2H), 8.00 (d, J=5.7 Hz, 1H), 7.67-7.73 (m, 2H), 7.48 (d, J=8.6 Hz, 2H), 7.39 (d, J=1.8 Hz, 1H), 7.31-7.35 (m, 2H), 7.30 (d, J=1.6 Hz, 1H), 7.27 (s, 1H), 7.22 (d, J=1.5 Hz, 1H), 6.96 (d, J=1.6 Hz, 1H), 6.80 (s, 1H), 6.51-6.55 (m, 2H), 4.09-4.17 (m, 1H), 3.99-4.05 (m, 1H), 3.90-3.97 (m, 1H), 3.88 (s, 3H), 3.83 (s, 3H), 3.82 (s, 3H), 3.68-3.72 (m, 1H), 3.05-3.16 (m, 2H), 2.44 (t, J=7.3 Hz, 2H), 2.02-2.07 (m, 2H), 1.81-1.91 (m, 1H), 1.68-1.78 (m, 2H), 1.56 (d, J=4.9 Hz, 2H); $^{13}$C NMR (DMSO-d$_6$, 100 MHz) δ 168.8, 166.3, 164.7, 159.5, 159.2, 150.2, 147.1, 144.7, 139.8, 137.0, 129.6, 128.2, 126.1, 124.6, 124.3, 122.0, 121.8, 120.4, 120.2, 118.8, 113.7, 111.3,

To a solution of allyl (6aS)-3-(4-((5-((4-(5-((4-aminophenyl)carbamoyl)-1-methyl-1H-pyrrol-3-yl)phenyl)carbamoyl)-1-methyl-1H-pyrrol-3-yl)amino)-4-oxobutoxy)-2-methoxy-12-oxo-6-((tetrahydro-2H-pyran-2-yl)oxy)-6,6a,7,8,9,10-hexahydrobenzo[e]-pyrido[1,2-α][1,4]diazepine-5(12H)-carboxylate (40) (250 mg, 0.265 mmol) in dichloromethane (3 mL) was added tetrakis(triphenylphosphine)palladium(0) (15 mg, 5 mol %), triphenylphosphine (17 mg, 25 mol %) and pyrrolidine (26 μL, 0.32 mmol). The reaction mixture was stirred at room temperature for 16 h. The reaction mixture was subjected to high vacuum for 30

109.6, 104.7, 67.7, 67.2, 55.6, 51.1, 49.2, 38.5, 36.2, 36.1, 35.4, 31.8, 30.2, 24.7, 23.7, 22.5, 17.7; MS (ES+): m/z=757 (M+H)⁺: LCMS (Method A): $t_R$=5.80 min. HRMS (EI m/z): calculated for $C_{42}H_{44}N_8O_6$ (M+1)⁺ 757.3457, observed 757.3457.

Example 42

Methyl 5-(4-((tert-butoxycarbonyl)amino)-1-methyl-1H-pyrrole-2-carboxamido)benzo[b]thiophene-2-carboxylate (42)

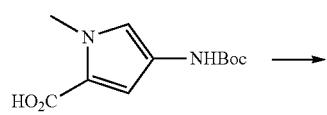

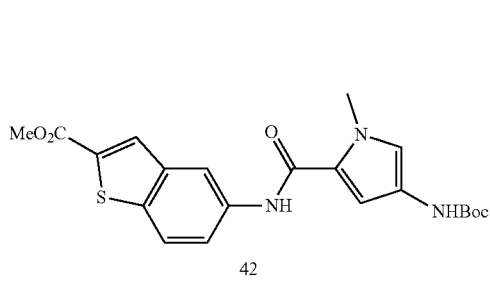

A solution of 4-((tert-butoxycarbonyeamino)-1-methyl-1H-pyrrole-2-carboxylic acid (127 mg, 0.530 mmol) in N,N-dimethylformamide (1 mL) was charged with 1-(3-dimethylaminopropyl)-3-ethylcarbodiimide hydrochloride (185 mg, 0.960 mmol) and 4-(dimethylamino)pyridine (147 mg, 1.20 mmol). The reaction mixture was stirred at room temperature for 4 h. Methyl 5-aminobenzo[b]thiophene-2-carboxylate (100 mg, 0.480 mmol) was then added and the resulting mixture was stirred at room temperature for 16 h. This was then poured onto ice-water (40 mL) and extracted with ethyl acetate (3×100 mL). The combined organic extracts were sequentially washed with an aqueous solution of citric acid (1 M, 60 mL), a saturated aqueous solution of sodium hydrogen carbonate (70 mL), water (70 mL) and brine (70 mL). The organic layer was then dried over sodium sulfate, filtered and concentrated to give the title compound (185 mg, 90%) as a cream solid. The product was carried through to the next step without any further purification.

MS (ES+): m/z=430 (M+H)⁺: LCMS (Method B): $t_R$=4.07 min.

Example 43

Methyl 5-(4-amino-1-methyl-1H-1-pyrrole-2-carboxamido)-benzo[b]thionhene-2-carboxylate hydrochloride (43)

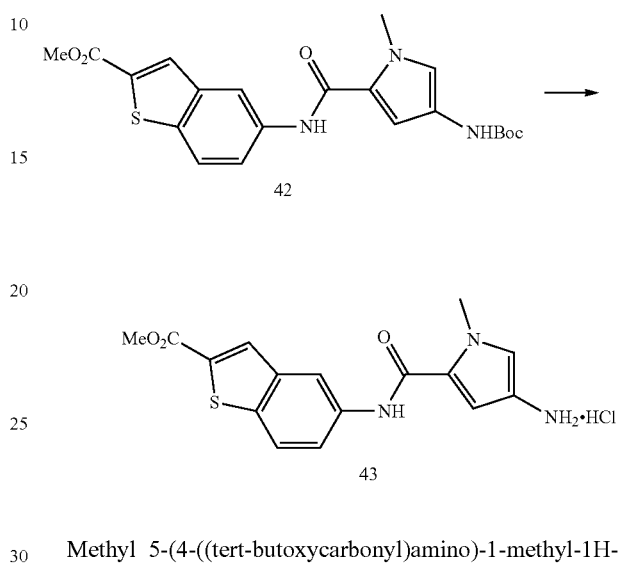

Methyl 5-(4-((tert-butoxycarbonyl)amino)-1-methyl-1H-pyrrole-2-carboxamido)benzo-[b]thiophene-2-carboxylate (42) (150 mg, 0.340 mmol) was dissolved in hydrochloric acid (4 M in 1,4-dioxane) (1 mL) and the reaction mixture was stirred at room temperature for 16 h. The reaction mixture was concentrated in vacua to give the title compound (118 mg, 95%) as a pale brown solid. The product was carried through to the next step without any further purification.

MS (ES+): m/z=364 (M+H)⁺: LCMS (Method B): $t_R$=2.78 min.

Example 44

Allyl (6aS)-2-methoxy-3-(4-((5-((2-(methoxycarbonyl)benzo-[b]thiophen-5-yl)carbamoyl)-1-methyl-1H-pyrrol-3-yl)amino)-4-oxo-butoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (44)

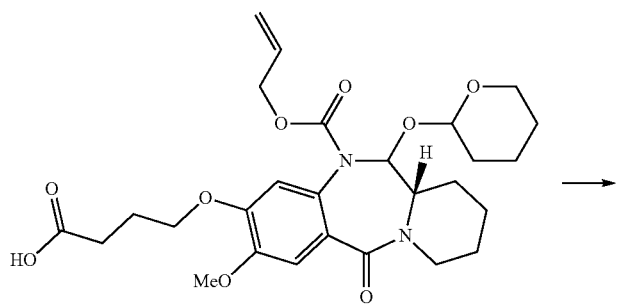

-continued

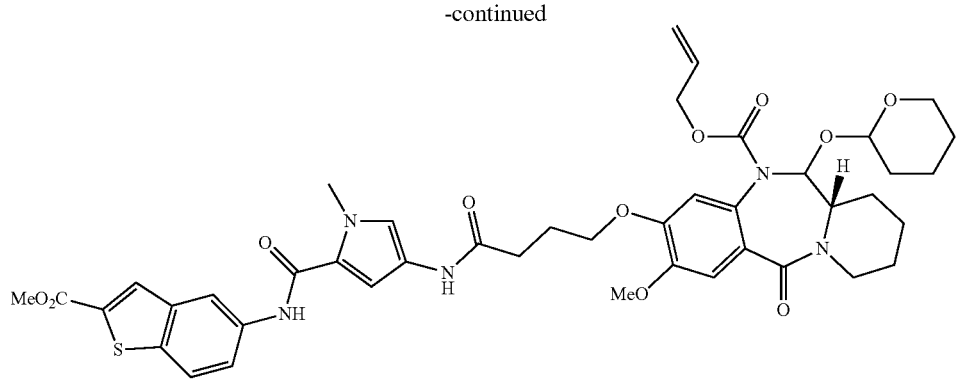

44

A solution 4-((((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy) butanoic acid (9) (300 mg, 0.560 mmol) in N,N-dimethylformamide (3 mL) was charged with 1-(3-dimethylaminopropyl)-3-ethylcarbodiimide hydrochloride (238 mg, 1.23 mmol) and 4-(dimethylamino)pyridine (189 mg, 1.55 mmol). The reaction mixture was stirred at room temperature for 4 h. Methyl 5-(4-amino-1-methyl-1H-pyrrole-2-carboxamido)benzo[b]thiophene-2-carboxylate hydrochloride (43) (225 mg, 0.620 mmol) was then added and the resulting mixture was stirred at room temperature for 16 h. This was then poured onto ice-water (40 mL) and extracted with ethyl acetate (3×100 mL). The combined organic extracts were sequentially washed with an aqueous solution of citric acid (1 M, 60 mL), a saturated aqueous solution of sodium hydrogen carbonate (70 mL), water (70 mL) and brine (70 mL). The organic layer was then dried over sodium sulfate, filtered and concentrated in vacuo. The resulting residue was then purified by column chromatography (silica), eluting with acetone/dichloromethane (from 0% to 30%), to give the title compound (348 mg, 66%) as a brown solid.

MS (ES+): m/z=844 (M+H)$^+$: LCMS (Method B): $t_R$ 4.23 min.

Example 45

5-(4-(4-((((6aS)-5-((Allyloxy)carbonyl)-2-methoxy-12-oxo-6-((tetrahydro-2H-pyran-2-yl)oxy)-5, 6,6a,7,8,9,10,12-octahydrobenzo[e]-pyrido[1,2-a][1,4]diazepin-3-yl)oxy)butanamido)-1-methyl-1H-pyrrole-2-carboxamido)benzo[b]thiophene-2-carboxylic acid (45)

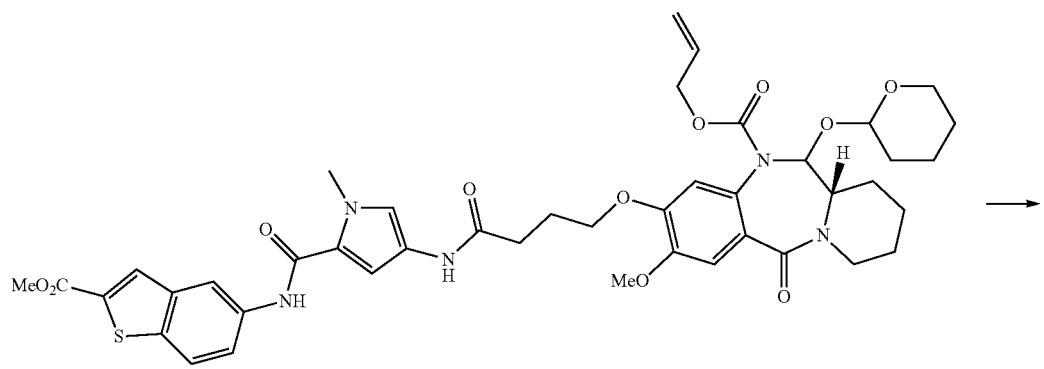

44

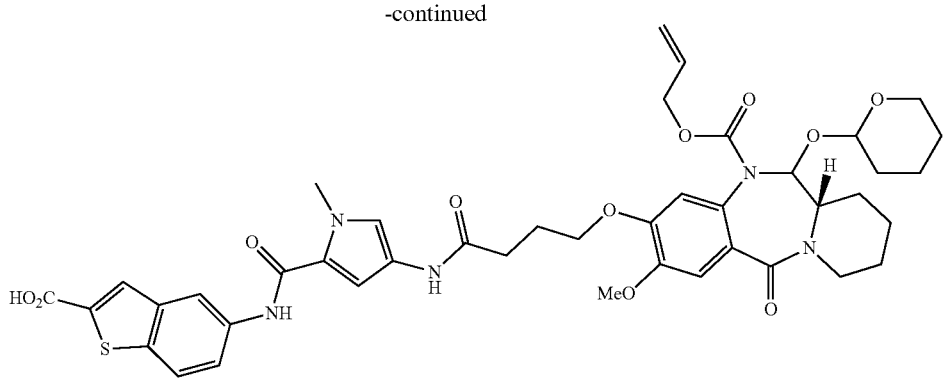

45

To a solution of 4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanoic acid (44) (327 mg, 0.387 mmol) in 1,4-dioxane (5 mL) was added an aqueous solution of sodium hydroxide (0.5 M, 5 mL, 2.5 mmol). The reaction mixture was stirred at room temperature for 3 h and was then concentrated in vacuo, after which water (20 mL) was added and the aqueous layer was acidified to pH=1 with an aqueous solution of citric acid (1 M, 5 mL). The aqueous layer was then extracted with ethyl acetate (2×50 mL). The combined organic extracts were then washed with brine (50 mL), dried over sodium sulfate, filtered and concentrated to give the title compound (315 mg, 99%) as a brown solid. The product was carried through to the next step without any further purification.

MS (ES+): m/z=831 (M+H)$^+$: LCMS (Method B): $t_R$=3.82 min.

Example 46

Allyl (6a9)-3-(4-((5-2-((4-aminophenyl)carbamoyl)benzo-[b]thiophen-5-yl)carbamoyl)-1-methyl-1H-pyrrol-3-yl)amino)-4-oxo-butoxy)-2-methoxy-12-oxo-6-((tetrahydro-2H-pyran-2-yl)oxy)-6,6a,7,8,9,10-hexahydrobenzo[e]pyrido[1,2-al][1,4]diazepine-5(12H)-carboxylate (46)

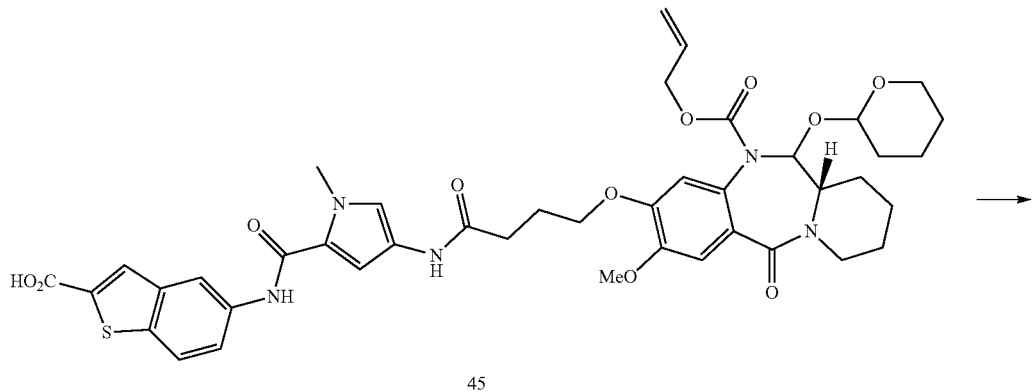

45

46

A solution of 5-(4-(4-((((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]thazepin-3-yl)oxy)butanamido)-1-methyl-1H-pyrrole-2-carboxamido)benzo[b]thiophene-2-carboxylic acid (45) (50 mg, 0.060 mmol) in anhydrous dichloromethane (1 mL) was charged with N-[(dimethylamino)-1H-1,2,3-triazolo-[4,5-b]pyridin-1-ylmethylene]-N-methylmethanaminium hexafluorophosphateN-oxide (28 mg, 0.072 mmol) and anhydrous triethylamine (35 μL, 0.25 mmol). The reaction mixture was stirred at room temperature for 30 min. Benzene-1,4-diamine (7.0 mg, 0.066 mmol) was then added and the resulting mixture was stirred at room temperature for 16 h. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacuo. The resulting residue was then purified by column chromatography (silica), eluting with acetone/dichloromethane (from 0% to 50%), to give the title compound (6.8 mg, 12%) as a yellow solid.

MS (ES+): m/z=921 (M+H)$^+$: LCMS (Method B): $t_R$=3.48 mi n

Example 47

(S)—N-(2-((4-Aminophenyl)carbamoyl)benzo[b]thiophen-5-yl)-4-(4-((2-methoxy-12-oxo-6a,7,8,9,10,12-hexahydrobenzo[e]pyrido[1,2-α][1,4]diazepin-3-yl)oxy)butanamido)-1-methyl-1H-pyrrole-2-carboxamide (47)

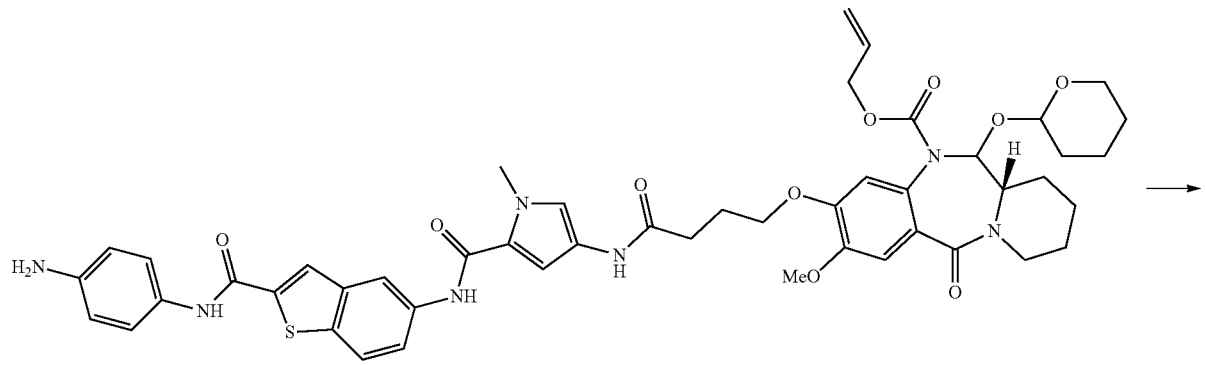

46

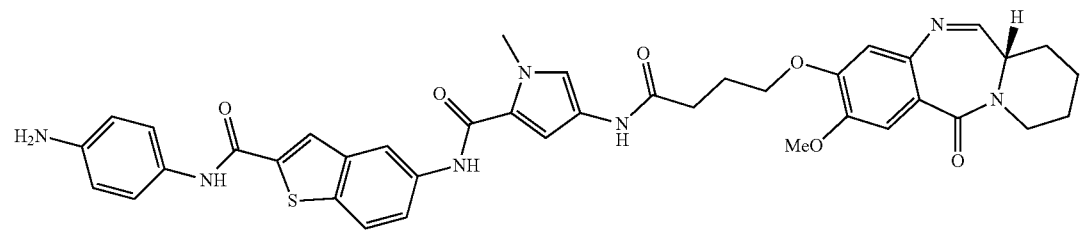

47

To a solution of allyl (6aS)-3-(4-((5-((2-((4-aminophenyl)carbamoyl)benzo[b]thiophen-5yl)carbamoyl)-1-methyl-1H-pyrrol-3-yl)amino)-4-oxobutoxy)-2-methoxy-12-oxo-6-((tetrahydro-2H-pyran-2-yl)oxy)-6,6a,7,8,9,10-hexahydrobenzo[e]pyrido[1,2-a][1,4]-diazepine-5(12H)-carboxylate (46) (6.8 mg, 0.0074 mmol) in dichloromethane (1 mL) was added tetrakis(triphenylphosphine)palladium(0) (0.4 mg, 5 mol %), triphenyl-phosphine (0.5 mg, 25 mol %) and pyrrolidine (1 µL, 0.012 mmol). The reaction mixture was stirred at room temperature for 16 h. The reaction mixture was subjected to high vacuum for 30 min until excess pyrrolidine was thoroughly removed. The resulting residue was then purified by column chromatography (silica), eluting with acetone/dichloromethane (from 0% to 100%) followed by methanol/dichloromethane (from 0% to 5%), to give the title compound (1.7 mg, 31%) as a pale yellow solid.

$^1$H NMR (DMSO-$d_6$, 400 MHz) δ 10.13 (s, 1H), 9.98-10.03 (m, 1H), 9.95 (s, 1H), 8.35 8.42 (m, 1H), 8.19 (s, 1H), 8.01 (d, J=5.7 Hz, 1H), 7.95 (d, J=8.9 Hz, 1H), 7.33-7.40 (m, 2H), 7.23-7.28 (m, 2H), 7.02 (s, 1H), 6.81 (s, 1H), 6.57 (d, J=8.7 Hz, 2H), 5.00 (br. s., 2H), 4.10-4.14 (m, 1H), 3.86 (s, 3H), 3.83 (s, 3H), 3.65-3.74 (m, 2H), 3.15-3.19 (m, 1H), 3.06-3.14 (m, 1H), 2.45 (t, J=7.5 Hz, 3H), 2.11-2.13 (m, 1H), 2.00-2.08 (m, 4H) 1.74 (dd, J=9.0, 5.3 Hz, 3H); MS (ES+): m/z=734 (M+H)$^+$: LCMS (Method A): $t_R$=5.63 min.

General synthetic scheme

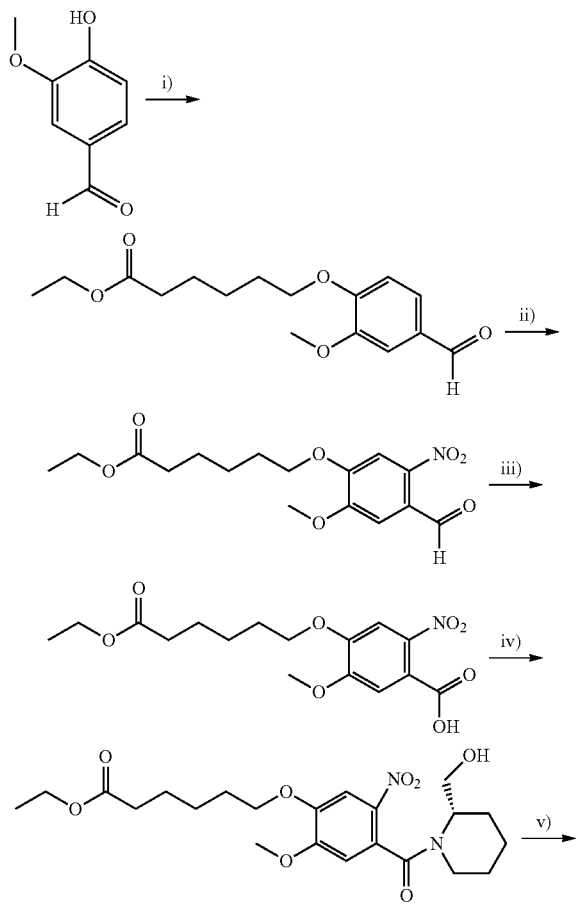

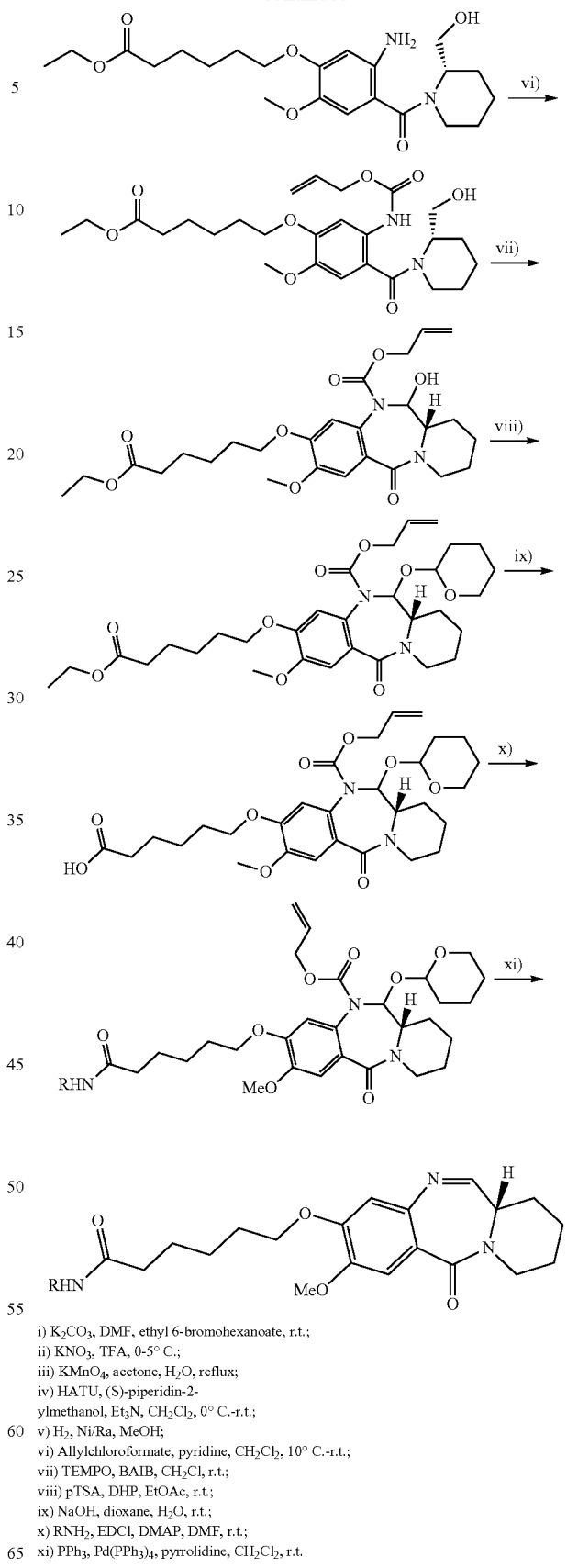

i) $K_2CO_3$, DMF, ethyl 6-bromohexanoate, r.t.;
ii) $KNO_3$, TFA, 0-5° C.;
iii) $KMnO_4$, acetone, $H_2O$, reflux;
iv) HATU, (S)-piperidin-2-ylmethanol, $Et_3N$, $CH_2Cl_2$, 0° C.-r.t.;
v) $H_2$, Ni/Ra, MeOH;
vi) Allylchloroformate, pyridine, $CH_2Cl_2$, 10° C.-r.t.;
vii) TEMPO, BAIB, $CH_2Cl$, r.t.;
viii) pTSA, DHP, EtOAc, r.t.;
ix) NaOH, dioxane, $H_2O$, r.t.;
x) $RNH_2$, EDCl, DMAP, DMF, r.t.;
xi) $PPh_3$, $Pd(PPh_3)_4$, pyrrolidine, $CH_2Cl_2$, r.t.

Example 48

Ethyl 6-(4-formyl-2-methoxyphenoxy)hexanoate (48)

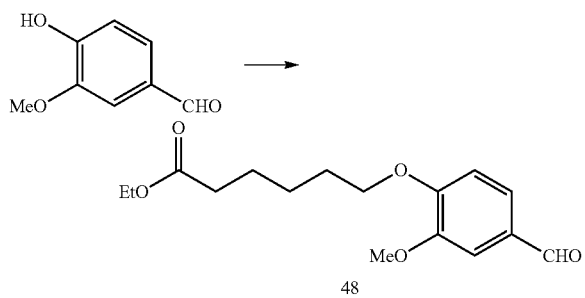

A mixture of vanillin (6.5 g, 42.7 mmol), ethyl 6-bromohexanoate (8.0 mL, 45.0 mmol) and potassium carbonate (8.70 g, 63.0 mmol) in N,N-dimethylformaldehyde (50 mL) was stirred at room temperature for 18 h. The reaction mixture was diluted with water (100 mL), separated and extracted with ethyl acetate (120 mL). The combined organic extracts were sequentially washed with water (100 mL), brine (100 mL), dried over magnesium sulfate, filtered and concentrated to give the title compound as a pale yellow oil (12.5 g, 99%). The product was carried through to the next step without any further purification.

$^1$H NMR (400 MHz, CDCl$_3$) δ 9.84 (s, 1H), 7.42-7.44 (dd, J=8.2, 1.9 Hz, 1H), 7.40 (d, J=1.9 Hz, 1H), 6.96 (d, J=8.1 Hz, 1H), 4.08-4.15 (m, 4H), 3.92 (s, 3H), 2.34 (t, J=7.5 Hz, 2H), 1.87-1.94 (m, 2H), 1.68-1.75 (m, 2H), 1.49-1.56 (m, 2H), 1.25 (t, J=7.2 Hz, 3H); MS (ES+): m/z=317 (M+Na)$^+$; LCMS (Method B): t$_R$=3.82 min.

Example 49

Ethyl 6-(4-formyl-2-methoxy-5-nitrophenoxy)hexanoate (49)

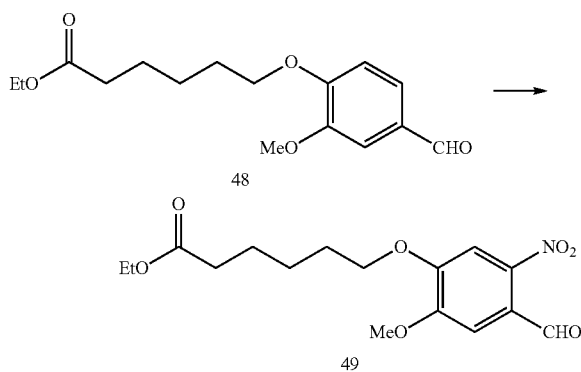

To a stirred solution of potassium nitrate (5.4 g, 53 mmol) in trifluoroacetic acid (25 mL) at room temperature was added dropwise a solution of ethyl 6-(4-formyl-2-methoxyphenoxy)hexanoate (48) (12.5 g, 42 mmol) in trifluoroacetic acid (25 mL). The reaction mixture was stirred for 1 h. It was then concentrated in vacua and the residue was dissolved in ethyl acetate (200 mL). This was washed with brine (3×50 mL) followed by a saturated aqueous solution of sodium hydrogen carbonate (2×40 mL), dried over magnesium sulfate, filtered and concentrated in vacua to give the title compound as a yellow solid (14.4 g, 100%). The product was carried through to the next step without any further purification.

$^1$H NMR (400 MHz, CDCl$_3$) δ 10.43 (s, 1H) 7.58 (s, 1H), 7.40 (s, 1H), 4.10-4.16 (m, 4H), 4.00 (s, 3H), 2.35 (t, J=7.4 Hz, 2H), 1.84-1.96 (m, 2H), 1.69-1.76 (m, 2H), 1.50-1.58 (m, 2H), 1.25 (t, J=7.2 Hz, 3H); MS (ES+): m/z=340 (M+H)$^+$; LCMS (Method B): t$_R$=4.02 min.

Example 50

4-((6-Ethoxy-6-oxohexyl)oxy)-5-methoxy-2-nitrobenzoic acid (50)

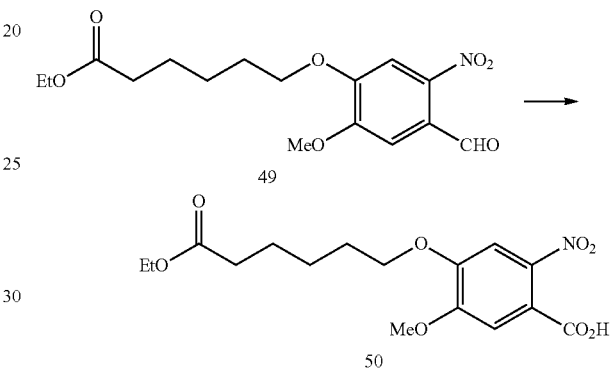

To a solution of ethyl 6-(4-formyl-2-methoxy-5-nitrophenoxy)hexanoate (49) (7.8 g, 23.0 mmol) in acetone (200 mL) was added a hot (70° C.) solution of potassium permanganate (13.6 g, 86.0 mmol) in water (100 ml). The mixture was then stirred at 70° C. for 4 h. The reaction mixture was cooled to room temperature and passed through celite. The cake was then washed with hot water (100 mL). A solution of sodium bisulfite in hydrochloric acid (100 mL) was added to the filtrate and extracted with dichloromethane (2×200 mL). The combined organic extracts were dried over sodium sulfate, filtrated and concentrated in vacuo to give the title compound as a yellow solid (5.0 g, 61%) which was used in the subsequent step without further purification.

$^1$H NMR (400 MHz, CDCl$_3$) δ 7.34 (s, 1H), 7.14 (s, 1H), 3.96-4.03 (m, 4H), 3.84 (s, 3H), 2.24 (t, J=7.4 Hz, 2H), 1.70-1.77 (m, 2H) 1.55-1.62 (m, 2H) 1.39-1.45 (m, 2H), 1.13 (t, J=7.1 Hz, 3H); MS (ES+): m/z=354 (M−H)$^+$; LCMS (Method B): t$_R$=3.63 min.

Example 51

Ethyl (S)-6-(4-(2-(hydroxymethyl)piperidine-1-carbonyl)-2-methoxy-5-nitrophenoxy)hexanoate (51)

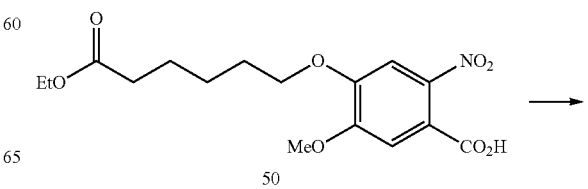

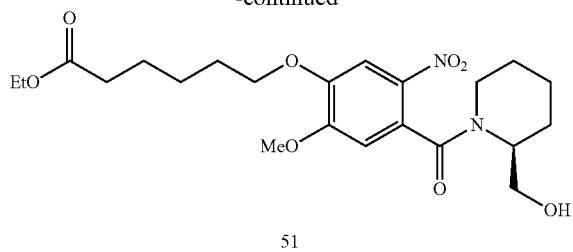

51

To a stirred solution of 4-((6-ethoxy-6-oxohexyl)oxy)-5-methoxy-2-nitrobenzoic acid (50) (2.0 g, 5.6 mmol) and trimethylamine (4.70 mL, 33.8 mmol) in dichloromethane (40 mL) was added O-(7-azabenzotriazole-1-yl)-N,N,N,N'-tetramethyluronium hexa-fluorophosphate (2.2 g, 5.9 mmol) in one portion and the resulting mixture was stirred for 2 h at room temperature. A solution of (S)-piperidin-2-ylmethanol (647 mg, 5.63 mmol) in dichloromethane (10 mL) was then added dropwise and the resulting mixture was stirred for 16 h at room temperature. The reaction was quenched with a saturated aqueous solution of sodium hydrogen carbonate (40 mL), the phases were separated and the aqueous layer was further extracted with dichloromethane (20 mL). The combined organic extracts were washed with brine (40 mL), dried over magnesium sulfate, filtered and concentrated to give an amber oil. Purification was carried out by column chromatography (silica), eluting with ethyl acetate/hexane (from 0% to 100%), to give the title compound (1.2 g, 48%) as a colourless oil.

$^1$H NMR (400 MHz, CDCl$_3$) δ 7.60-7.63 (m, 1H), 6.75-6.77 (m, 1H), 4.02-4.13 (m, 4H), 3.93 (s, 3H), 3.70-3.78 (m, 1H), 3.39-3.68 (m, 1H), 3.11-3.18 (m, 1H), 2.32 (t, J=7.6 Hz, 2H), 1.83-1.91 (m, 2H), 1.39-1.72 (m, 11H), 1.26 (t, J=7.1 Hz, 3H); MS (ES+): m/z=453 (M+H)$^+$: LCMS (Method B): t$_R$=3.63 min.

Example 52

Ethyl (S)-6-(5-amino-4-(2-(hydroxymethyl)piperidine-1-carbonyl)-2-methoxyphenoxy)hexanoate (52)

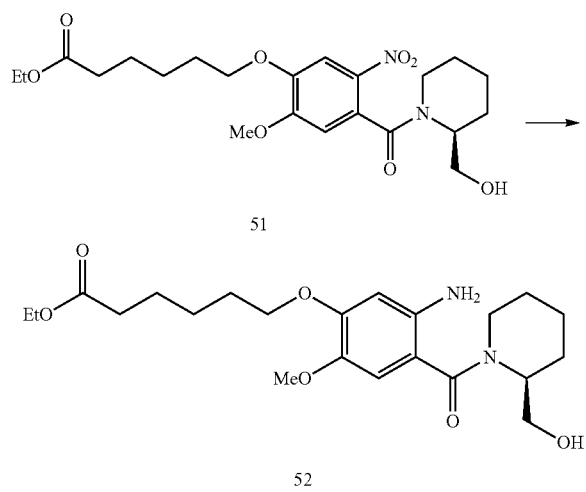

To a solution of ethyl (S)-6-(4-(2-(hydroxymethyppiperidine-1-carbonyl)-2-methoxy-5-nitrophenoxy)hexanoate (51) (1.2 g, 2.7 mmol) in methanol (20 mL) was added Raney®-Nickel (slurry in H$_2$O) (120 mg). The resulting mixture was hydrogenated at 50 psi for 1.5 h in a Parr apparatus, then filtered through a celite pad and concentrated in vacuo to give the title compound (991 mg, 87%) as a grey oil that solidifies upon standing. The resulting material was carried through to the next step without further purification.

$^1$H NMR (400 MHz, CDCl$_3$) δ 6.69 (s, 1H), 6.32 (s, 1H), 4.13 (m, 4H), 3.98 (t, J=6.5 Hz, 2H), 3.79 (s, 3H), 3.67-3.57 (m, 1H), 3.19-3.22 (m, 4H), 2.87 (s, 2H), 2.32-2.36 (m, 2H), 1.82-1.89 (m, 2H), 1.65-1.73 (m, 6H), 1.47-1.55 (m, 3H), 1.27 (t, J=7.1 Hz, 3H); MS (ES+): m/z=423 (M+H)$^+$: LCMS (Method B): t$_R$=3.23 min.

Example 53

Ethyl (S)-6-(5-(((allyloxy)carbonyl)amino)-4-(2-(hydroxy-methyl)piperidine-1-carbonyl)-2-methoxyphenoxy)hexanoate (53)

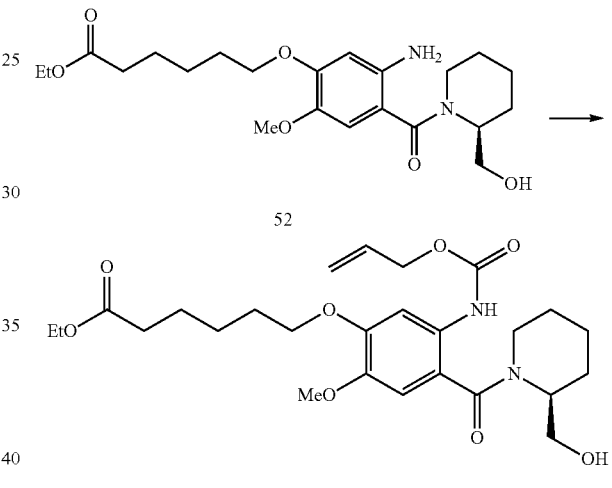

To a solution of ethyl (S)-6-(5-amino-4-(2-(hydroxymethyppiperidine-1-carbonyl)-2-methoxyphenoxy)hexanoate (52) (1.23 g, 2.91 mmol) and pyridine (542 µL, 6.69 mmol) in anhydrous dichloromethane (20 mL) at −10° C., a solution of allyl chloroformate (278 µL, 2.62 mmol) in dichloromethane (12 mL) was added dropwise. The resulting reaction mixture was stirred at room temperature for 0.5 h, quenched with a saturated aqueous solution of copper (II) sulfate (25 mL), diluted with dichloromethane (10 mL), separated, and successively washed with water (20 mL), a saturated aqueous solution of sodium hydrogen carbonate (20 mL) and brine (20 mL). The organic layer was then dried over magnesium sulfate, filtered and concentrated in vacuo to give the title compound (588 mg, 40%) as an orange oil. The resulting material was carried through to the next step without further purification.

$^1$H NMR (400 MHz, CDCl$_3$) δ 8.23 (br s, 1H), 7.70 (br s, 1H), 6.78 (s, 1H), 5.90-6.00 (m, 1H), 5.33-5.38 (m, 1H), 5.24 (dd, J=10.4, 1.3 Hz, 1H), 4.63 (m, 2H), 4.12 (q, J=7.1 Hz, 2H) 4.05 (t, J=6.6 Hz, 2H), 3.83 (s, 3H), 3.64-3.72 (m, 1H), 3.02-3.12 (m, 1H), 2.33 (t, J=7.6 Hz, 2H), 1.84-1.91 (m, 2H), 1.67-1.74 (m, 10H), 1.66-1.54 (m, 4H), 1.26 (t, J=7.1 Hz, 3H); MS (ES+): m/z=507 (M+H)$^+$: LCMS (Method B): t$_R$=3.70 min.

Example 54

Allyl (6aS)-3-((6-ethoxy-6-oxohexyl)oxy)-6-hydroxy-2-methoxy-12-oxo-6,6a,7,8,9,10-hexahydrobenzo[e]pyrido[1,2-α][1,4]-diazepine-5(12H)-carboxylate (54)

Example 55

Allyl (6aS)-3-((6-ethoxy-6-oxohexyl)oxy)-2-methoxy-12-oxo-6-((tetrahydro-2H-pyran-2-yl)oxy)-6,6a,7,8,9,10-hexahydrobenzo[e]pyrido-[1,2-α][1,4]diazepine-5(12H)-carboxylate (55)

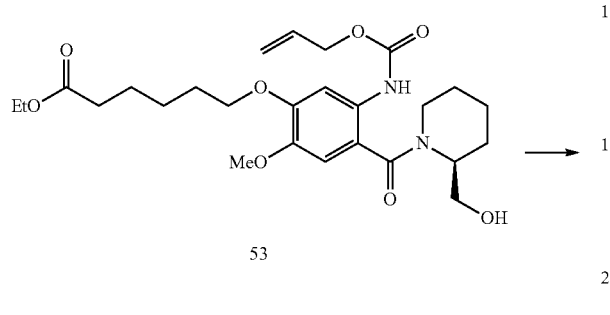

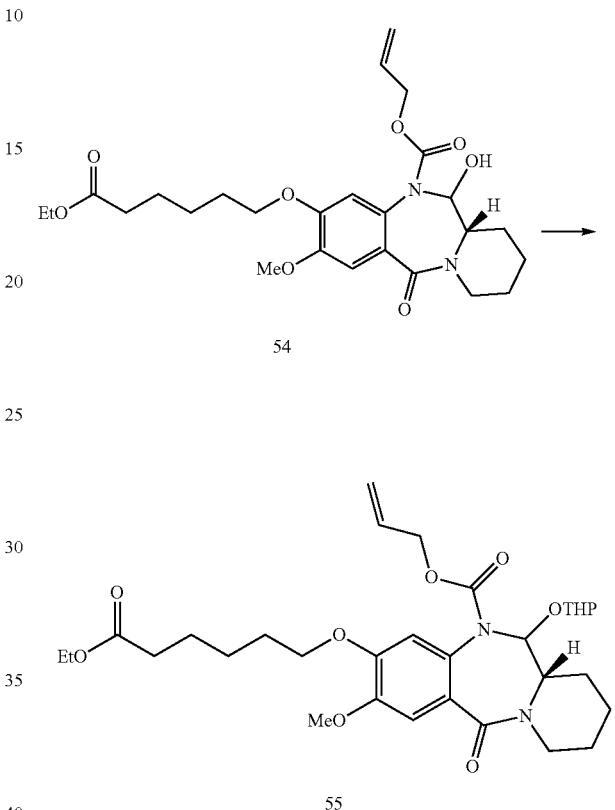

To a solution of ethyl (S)-6-(5-(((allyloxy)carbonyl)amino)-4-(2-(hydroxymethyl)-piperidine-1-carbonyl)-2-methoxyphenoxy)hexanoate (53) (1.7 g, 3.4 mmol) in dichloromethane (80 mL) was added 2,2,6,6-tetramethyl-1-piperidinyloxy (53 mg, 0.30 mmol) and (diacetoxyiodo)benzene (1.3 g, 4.0 mmol). The reaction mixture was stirred at room temperature for 16 h, and was then placed in an ice bath and quenched with a saturated aqueous solution of sodium metabisulfite (35 mL). The mixture was diluted with dichloromethane (30 mL), separated, and sequentially washed with a saturated aqueous solution of sodium hydrogen carbonate (30 mL), water (30 mL) and brine (30 mL). The organic layer was then dried over magnesium sulfate, filtered and concentrated in vacuo. Purification was carried out by column chromatography (silica), eluting with ethyl acetate/hexane (from 0% to 80%) to give the desired compound (1.1 g, 66%) as a colourless oil.

1H NMR (400 MHz, CDCl$_3$) δ 7.70-7.72 (m, 1H), 7.09-7.13 (m, 1H), 5.80-5.98 (m, 1H), 5.25-5.38 (m, 1H), 5.14-5.19 (m, 2H), 4.63-4.72 (m, 2H), 4.35-4.50 (m, 1H), 4.13 (q, J=7.1 Hz, 2H), 4.03-4.08 (m, 1H), 3.96-4.01 (m, 2H), 3.91 (s, 3H), 3.81-3.83 (m, 1H), 3.45-3.53 (m, 1H), 3.03-3.10 (m, 1H), 2.33 (t, J=7.6 Hz, 2H), 1.83-1.90 (m, 2H), 1.62-1.74 (m, 10H), 1.48-1.53 (m, 2H); MS (ES+): m/z=505 (M+H)$^+$: LCMS (Method B): t$_R$=3.57 min.

To containing solution of allyl (6aS)-3-((6-ethoxy-6-oxohexyl)oxy)-6-hydroxy-2-methoxy-12-oxo-6,6a,7,8,9,10-hexahydrobenzo[e]pyrido[1,2-α][1,4]diazepine-5(12H)-carboxylate (54) (1.1 g, 2.2 mmol) in dichloromethane (50 mL) were added 3,4-dihydro-2H-pyran (2.00 mL, 22.4 mmol) and p-toluenesulfonic acid monohydrate (113 mg, 1% w/w), and the resulting mixture was stirred at room temperature for 4 h. The reaction mixture was then diluted with dichloromethane (50 mL) and washed with a saturated aqueous solution of sodium hydrogen carbonate (50 mL) and brine (50 mL). The organic layer was dried over magnesium sulfate, filtered and concentrated to give the title compound as a yellow oil (863 mg, 66%) after purification by column chromatography (silica) eluting with ethyl acetate/hexane (from 0% to 70%).

$^1$H NMR (400 MHz, CDCl$_3$) δ 7.16 (m, 1H), 6.50 (s, 1H), 6.10 (m, 1H), 5.76-5.81 (m, 1H), 5.03-5.14 (m, 2H), 4.57-4.69 (m, 2H), 4.37-4.49 (m, 1H), 4.26-4.34 (m, 1H), 4.12 (q, J=7.1 Hz, 2H), 3.94-4.01 (m, 3H), 3.90 (s, 3H), 3.62-3.68 (m, 1H), 3.46-3.68 (m, 2H), 3.03-3.12 (m, 1H), 2.33 (t, J=7.4 Hz, 2H), 1.66-1.89 (m, 11H), 1.47-1.57 (m, 6H), 1.25 (t, J=7.1 Hz, 3H); MS (ES+): m/z=589 (M+H)$^+$: LCMS (Method B): t$_R$=4.32 min.

Example 56

6-((((6aS)-5-(Allyloxy)carbonyl)-2-methoxy-12-oxo-6-((tetra-hydro-2H-pyran-2-yl)oxy)-5,6,6a,7,8,9,10,12-octahydrobenzo[e]pyrido[1,2-α][1,4]diazepin-3-yl)oxy)hexanoic acid (56)

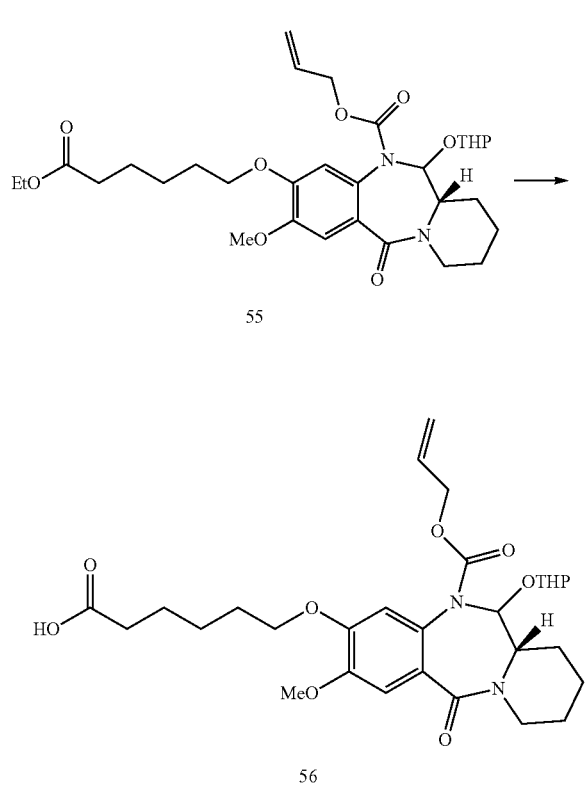

To a solution of allyl (6aS)-3-((6-ethoxy-6-oxohexyl)oxy)-2-methoxy-12-oxo-6-((tetrahydro-2H-pyran-2-yl)oxy)-6,6a,7,8,9,10-hexahydrobenzo[e]pyrido[1,2-α][1,4]-diazepine-5(12H)-carboxylate (55) (200 mg, 0.34 mmol) in 1,4-dioxane (3 ml) was added an aqueous solution of sodium hydroxide (0.5 M, 1.2 mL). The reaction mixture was stirred at room temperature for 2 h and was then concentrated in vacuo, after which water (6 ml) was added and the aqueous layer was then acidified to pH=1 with acetic acid. The aqueous layer was then extracted with ethyl acetate (2×40 mL). The combined organic extracts were then washed with brine (40 ml), dried over sodium sulfate, filtered and concentrated to give the title compound as a yellow oil (181 mg, 95%) which was used in the next step without further purification.

$^1$H NMR (400 MHz, CDCl$_3$) δ 7.18 (s, 1H), 6.19 (s, 1H), 5.99-6.19 (m, 1H), 5.71-5.81 (m, 1H), 5.02-5.12 (m, 2H), 4.51-4.67 (m, 1H), 4.36-4.48 (m, 1H), 4.23-4.31 (m, 1H), 3.88-4.00 (m, 7H), 3.46-3.66 (m, 2H), 3.02-3.12 (m, 1H), 2.36 (t, J=7.4 Hz, 2H), 1.79-1.81 (m, 2H), 1.65-1.75 (m, 10H), 1.49-1.55 (m, 7H); MS (ES+): m/z=561 (M+H)$^+$: LCMS (Method B): t$_R$=3.78 min.

Example 57

Methyl 4-(4-(4-((tert-butoxycarbonyl)amino)-1-methyl-1H-pyrrole-2 carboxamido)phenyl)-1-methyl-1H-pyrrole-2 carboxylate (57)

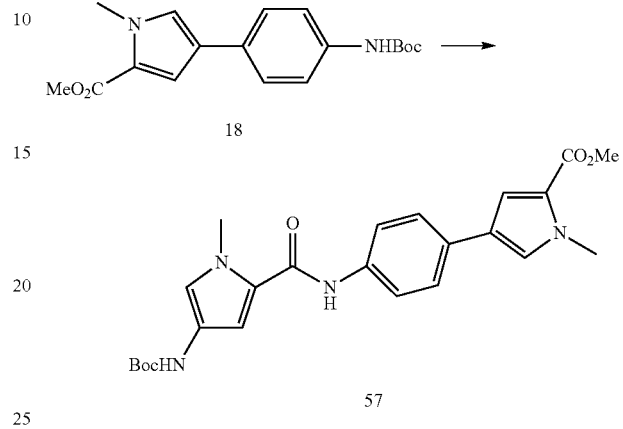

To a solution of 4-((tert-butoxycarbonyl)amino)-1-methyl-1H-pyrrole-2-carboxylic acid (18) (59 mg, 0.23 mmol) in N,N-dimethylformamide (4 mL) was added 1-(3-dimethylaminopropyl)-3-ethylcarbodiimide hydrochloride (67 mg, 0.36 mmol) and 4-(dimethylamino)pyridine (65 mg, 0.53 mmol). The reaction mixture was stirred at room temperature for 2 h. Methyl 4-(4-aminophenyl)-1-methyl-1H-pyrrole-2-carboxylate (41 mg, 0.18 mmol) was added to the reaction mixture which was then stirred at room temperature for 16 h. The reaction mixture was poured into ice-water (40 mL) and extracted with ethyl acetate (3×100 mL). The combined organic layer was sequentially washed with 1 M citric acid (60 mL), a saturated aqueous solution of sodium hydrogen carbonate (70 mL), water (70 mL) and brine (70 mL). The organic layer was dried over sodium sulfate, filtered and concentrated. The resulting residue was purified by column chromatography (silica), eluting with ethyl acetate/dichloromethane (from 0% to 50%), to give the title compound (36 mg, 45%) as a cream solid.

MS (ES+): m/z=453 (M+H)$^+$: LCMS (Method B): t$_R$=4.07 min.

Example 58

Methyl 4-(4-(4-amino-1-methyl-1H-pyrrole-2-carboxamido)-phenyl)-1-methyl-1H-pyrrole-2-carboxylate (58)

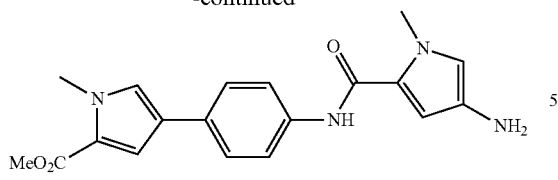

58

Methyl 4-(4-(4-((tert-butoxycarbonyl)amino)-1-methyl-1H-pyrrole-2-carboxamido)-phenyl)-1-methyl-1H-pyrrole-2-carboxylate (57) (150 mg, 0.330 mmol) was dissolved in hydrochloric acid (4 M in 1,4-dioxane) (1 mL) and the reaction mixture was stirred at room temperature for 2 h. The reaction mixture was concentrated in vacua to give the title compound (114 mg, 99%) as a brown solid. The product was carried through to the next step without further purification.

MS (ES+): m/z=353 (M+H)$^+$: LCMS (Method B): $t_R$=2.88 min.

Example 59

Allyl (6aS)-2-methoxy-3-((6-((5-((4-(5-(methoxycarbonyl)-1-methyl-1H-pyrrol-3-yl)phenyl)carbamoyl)-1-methyl-1H-pyrrol-3-yl)amino)-6-oxohexyfloxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (59)

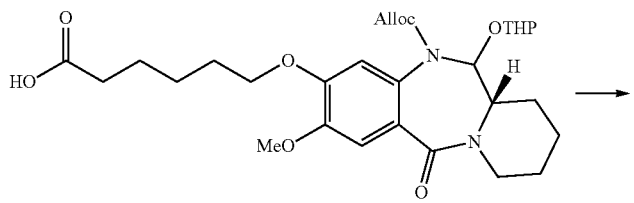

56

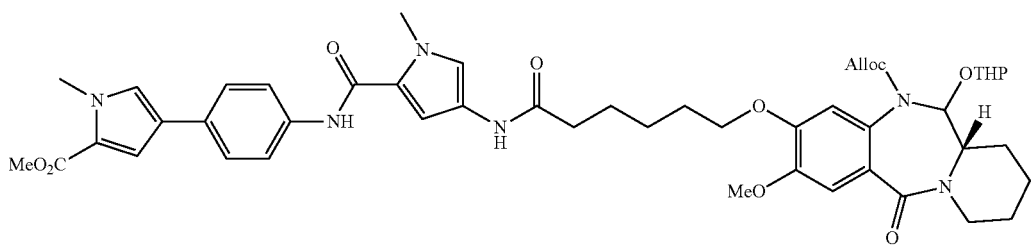

59

A solution of 6-((((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)hexanoic acid (56) (194 mg, 0.360 mmol) in N,N-dimethylformamide (5 mL) was charged with 1-(3-dimethylaminopropyl)-3-ethylcarbodiimide hydrochloride (126 mg, 0.660 mmol) and 4-(dimethylamino)pyridine (121 mg, 0.990 mmol). The reaction mixture was stirred at room temperature for 3 h. Methyl 4-(4-(4-amino-1-methyl-1H-pyrrole-2-carboxamido)phenyl)-1-methyl-1H-pyrrole-2-carboxylate (58) (150 mg, 0.330 mmol) was then added and the resulting mixture was stirred at room temperature for 16 h. This was then poured onto ice-water (20 mL) and extracted with ethyl acetate (3×75 mL). The combined organic extracts were sequentially washed with an aqueous solution of citric acid (1 M, 50 mL), a saturated aqueous solution of sodium hydrogen carbonate (50 mL), water (50 mL) and brine (50 mL). The organic layer was then dried over sodium sulfate, filtered and concentrated in vacua to give the title compound (133 mg, 45%) as a yellow oil. The product was carried through to the next step without further purification.

MS (ES+): m/z=896 (M+H)$^+$: LCMS (Method B): $t_R$=4.25 min.

Example 60

4-(4-(4-(6-((((6aS)-5-((Allyloxy)carbonyl)-2-methoxy-12-oxo-6-((tetrahydro-2H-pyran-2-yl)oxy)-5,6,6a,7,8,9,10,12-octahydrobenzo[e]-pyrido[1,2-α][1,4]diazepin-3-yl)oxy)hexanamido)-1-methyl-1H-pyrrole-2-carboxamido)phenyl)-1-methyl-1H-pyrrole-2-carboxylic acid (60)

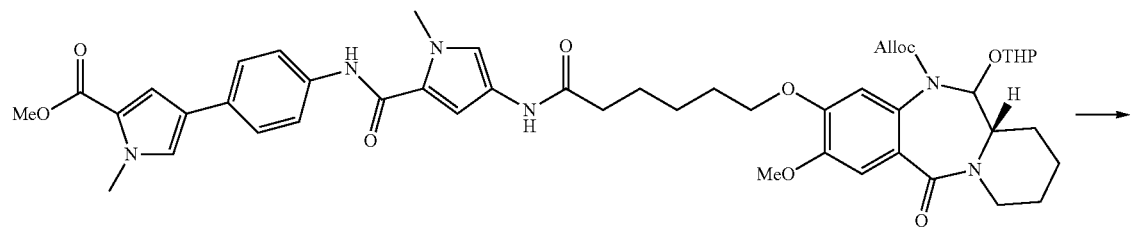

59

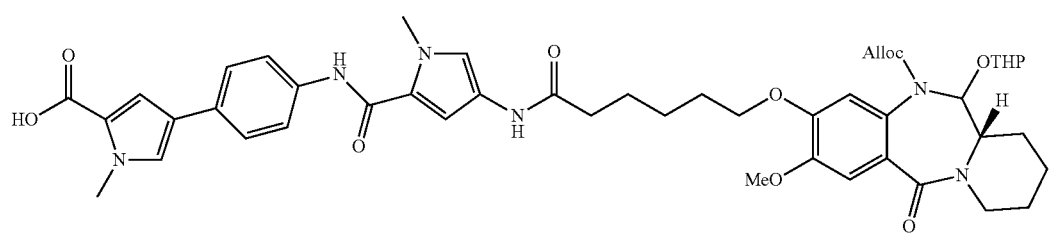

60

To a solution of allyl (6aS)-2-methoxy-3-((6-((5-((4-(5-(methoxycarbonyl)-1-methyl-1H-pyrrol-3-yl)phenyl)carbamoyl)-1-methyl-1H-pyrrol-3-yl)amino)-6-oxohexyl)oxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (59) (200 mg, 0.340 mmol) in 1,4-dioxane (3 ml) was added an aqueous solution of sodium hydroxide (1 M, 1.2 mL). The reaction mixture was stirred at room temperature for 2 h and was then concentrated in vacua, after which water (6 ml) was added and the aqueous layer was acidified to pH=1 with acetic acid. The aqueous layer was then extracted with ethyl acetate (2×40 mL). The combined organic extracts were then washed with brine (40 ml), dried over sodium sulfate, filtered and concentrated to give the title compound as a yellow oil (181 mg, 95%) which was used in the next step without further purification.

MS (ES+): m/z=882 (M+H)$^+$: LCMS (Method B): $t_R$=3.92 min.

Example 61

Allyl (6aS)-3-((6-((5-((4-(5-((4-aminophenyl)carbamoyl)-1-methyl-1H-pyrrol-3-yl)phenyl)carbamoyl)-1-methyl-1H-pyrrol-3-yl)amino)-6-oxohexyl)oxy)-2-methoxy-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (61)

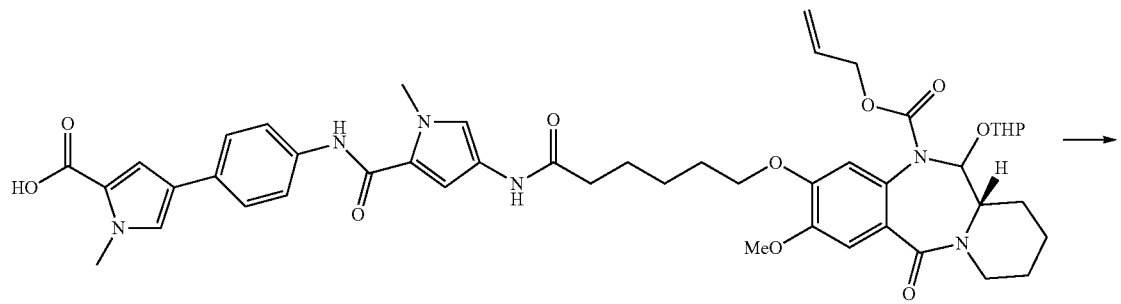

60

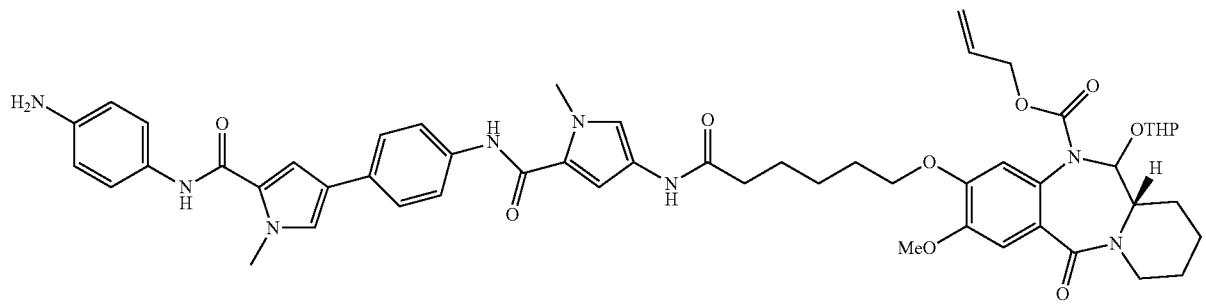

61

A solution of 4-(4-(4-(6-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)hexanamido)-1-methyl-1H-pyrrole-2-carboxamido)phenyl)-1-methyl-1H-pyrrole-2-carboxylic acid (60) (123 mg, 0.14 mmol) in anhydrous dichloromethane (2 mL) was charged with N-[(dimethylamino)-1H-1,2,3-triazolo-[4,5-b]pyridin-1-ylmethylene]-N-methylmethanaminium hexafluorophosphate N-oxide (54 mg, 0.14 mmol) and anhydrous triethylamine (117 μL, 0.84 mmol). The reaction mixture was stirred at room temperature for 30 min. Benzene-1,4-diamine (15.1 mg, 0.14 mmol) was then added and the resulting mixture was stirred at room temperature for 16 h. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacua. The resulting residue was then purified by column chromatography (silica), eluting with acetone/dichloromethane (from 0% to 50%), to give the title compound (63 mg, 46%) as a yellow solid.

MS (ES+): m/z=972 (M+H)$^+$: LCMS (Method B): $t_R$=3.55 min

Example 62

Methyl 5-(4-((tert-butoxycarbonyl)amino)-1-methyl-1H-pyrrole-2-carboxamido)benzo[b]thiophene-2-carboxyiate (62)

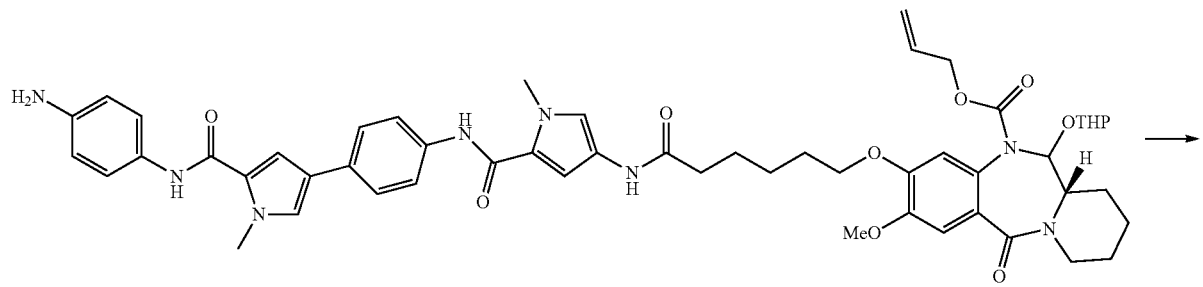

61

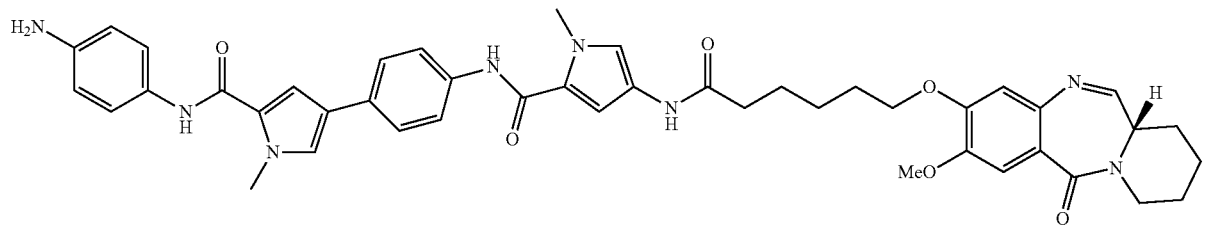

62

To a solution of Allyl (6aS)-3-((6-((5-((4-(5-((4-aminophenyl)carbamoyl)-1-methyl-1H-pyrrol-3-yl)phenyl)carbamoyl)-1-methyl-1H-pyrrol-3-yl)amino)-6-oxohexyl)oxy)-2-methoxy-12-oxo-6-((tetrahydro-2H-pyran-2-yl)oxy)-6,6a,7,8,9,10-hexahydrobenzo[e]-pyrido[1,2-α][1,4]diazepine-5(12H)-carboxylate (61) (25 mg, 0.026 mmol) in dichloromethane (1 mL) was added tetrakis(triphenylphosphine)palladium(0) (2.5 mg, 5 mol %), triphenylphosphine (1.7 mg, 25 mol %) and pyrrolidine (21 µL, 0.260 mmol). The reaction mixture was stirred at room temperature for 16 h. The reaction mixture was subjected to high vacuum for 30 min until excess pyrrolidine was thoroughly removed. The resulting residue was then purified by column chromatography (silica), eluting with acetate/hexane (from 0% to 100%) to give the title compound (6.8 mg, 33%) as a pale yellow solid.

$^1$H NMR (DMSO-d$_6$, 400 MHz) δ 9.81-9.85 (m, 1H), 9.58 (s, 1H), 9.51 (s, 2H), 8.00 (d, J=5.7 Hz, 1H), 7.69-7.72 (m, 2H), 7.47-7.49 (m, 2H), 7.38-7.43 (m, 1H), 7.30-7.35 (m, 2H), 7.18-7.24 (m, 1H), 7.11-7.13 (m, 1H), 7.07 (s, 1H), 6.94-6.98 (m, 1H), 6.80 (br s, 1H), 6.63-6.72 (m, 2H), 6.52-6.54 (m, 1H), 3.95-4.14 (m, 3H), 3.89 (s, 3H), 3.83 (s, 3H), 3.70 (s, 3H), 3.65-3.69 (m, 1H), 3.17 (d, J=5.2 Hz, 2H), 2.28 (t, J=6.5 Hz, 2H), 1.72-1.78 (m, 4H), 1.62-1.68 (m, 4H), 1.42-1.48 (m, 3H) $^{13}$C NMR (DMSO-d$_6$, 100 MHz) δ 169.5, 166.3, 164.6, 159.5, 159.2, 150.3, 147.1, 144.8, 139.8, 137.0, 129.6, 128.2, 126.6, 124.6, 124.3, 122.7, 122.1, 121.8, 121.7, 120.5, 120.4, 118.7, 113.7, 111.3, 109.6, 109.3, 104.7, 68.1, 55.6, 36.3, 36.1, 35.5, 28.3, 25.2, 25.1, 23.7, 22.5, 17.7; MS (ES+): m/z=785 (M+H)$^+$: LCMS (Method A): t$_R$=3.08 min.

Example 63

Allyl (6S,6aS)-2-methoxy-3-((6-((5-(methoxycarbonyl)-1-methyl-1H-pyrrol-3-yl)amino)-6-oxohexyl)oxy)-12-oxo-6-((tetrahydro-2H-pyran-2-yl)oxy)-6,6a,7,8,9,10-hexahydrobenzo[e]pyrido[1,2-α][1,4]-diazepine-5(12H)-carboxylate (63)

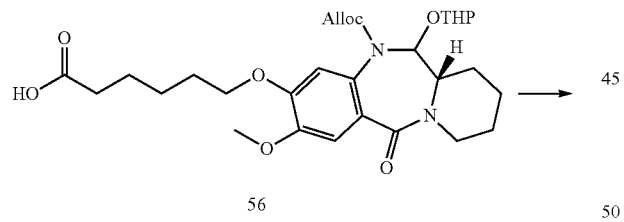

56

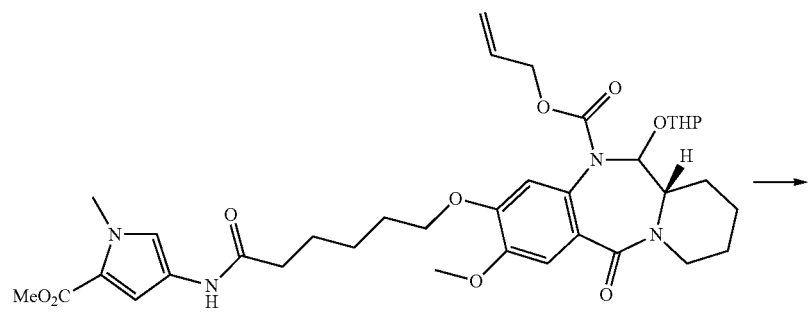

63

A solution of 6-(((6S,6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)hexanoic acid (56) (109 mg, 0.190 mmol) in anhydrous dichloromethane (3 mL) was charged with N-[(dimethylamino)-1H-1,2,3-triazolo-[4,5-b]pyridin-1-ylmethylene]-N-methylmethanaminium hexafluorophosphate N-oxide (76 mg, 0.20 mmol) and anhydrous triethylamine (115 µL, 1.14 mmol). The reaction mixture was stirred at room temperature for 30 min. Methyl 4-amino-1-methyl-1H-pyrrole-2-carboxylate (37 mg, 0.24 mmol) was then added and the resulting mixture was stirred at room temperature for 16 h. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacuo. The resulting residue was then purified by column chromatography (silica), eluting with acetone/dichloromethane (from 0% to 30%), to give the title compound (82 mg, 62%) as a white solid.

MS (ES+): m/z=697 (M+H)$^+$: LCMS (Method B): t$_R$=3.98 min.

Example 64

4-(6-((((6S,6aS)-5-((Allyloxy)carbonyl)-2-methoxy-12-oxo-6-((tetrahydro-2H-pyran-2-yl)oxy)-5,6, 6a,7, 8,9,10,12-octahydrobenzo[e]-pyrido[1,2-α][1,4]diazepin-3-yl)oxy)hexanamido)-1-methyl-1H-pyrrole-2-carboxylic acid (64)

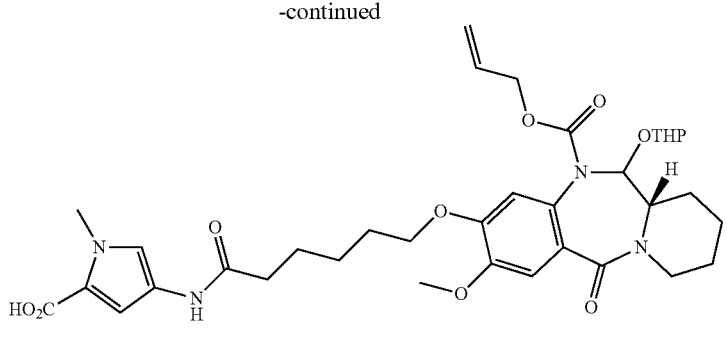

64

To a solution of allyl (6S,6aS)-2-methoxy-3-((6-((5-(methoxycarbonyl)-1-methyl-1H-pyrrol-3-yl)amino)-6-oxohexyl)oxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (63) (76 mg, 0.11 mmol) in 1,4-dioxane (1 mL) was added an aqueous solution of sodium hydroxide (0.5 M, 1.0 mL, 0.50 mmol). The reaction mixture was stirred at room temperature for 16 h and was then concentrated in vacua, after which water (20 mL) was added and the aqueous layer was acidified to pH=1 with an aqueous solution of citric acid (1 M, 10 mL). The aqueous layer was then extracted with ethyl acetate (2×50 mL). The combined organic extracts were then washed with brine (50 mL), dried over sodium sulfate, filtered and concentrated in vacuo to give the title compound (74 mg, 98%) as a cream solid. The product was carried through to the next step without any further purification.

MS (ES+): m/z=683 (M+H)⁺: LCMS (Method B): $t_R$=3.68 min.

Example 65

Allyl (6S,6aS)-3-((6-((5-((4-aminophenyl)carbamoyl)-1-methyl-1H-pyrrol-3-yl)amino)-6-oxohexyl)oxy)-2-methoxy-12-oxo-6-((tetrahydro-2H-pyran-2-yl)oxy)-6,6a,7,8,9,10-hexahydrobenzo[e]-pyrido[1,2-α][1.4]diazepine-5(12H)-carboxylate (65)

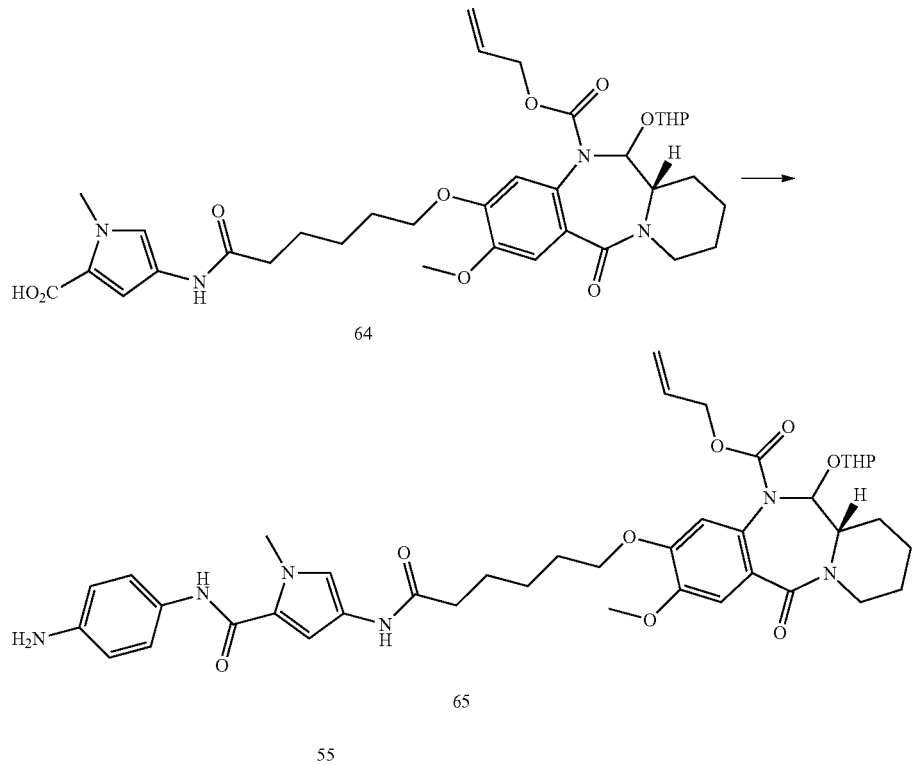

A solution of 4-(6-(((6S,6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy) hexanamido)-1-methyl-1H-pyrrole-2-carboxylic acid (64) (60 mg, 0.090 mmol) in anhydrous dichloromethane (1 mL) was charged with N-[(dimethylamino)-1H-1,2,3-triazolo-[4,5-b]pyridin-1-ylmethylene]-N-methylmethanaminium hexafluorophosphate N-oxide (67.0 mg, 0.175 mmol) and anhydrous triethylamine (73 μL, 0.52 mmol). The reaction mixture was stirred at room temperature for 30 min. Benzene-1,4-diamine (10 mg, 0.10 mmol) was then added and the resulting mixture was stirred at room temperature for 16 h. The reaction mixture was quenched with a saturated aqueous solution of sodium hydrogen carbonate (20 mL) and extracted with dichloromethane (2×50 mL). The combined organic extracts were then washed with water containing a few drops of acetic acid (30 mL). The organic layer was then dried over sodium sulfate, filtered and concentrated in vacua. The resulting residue was then purified by column chromatography (silica), eluting with acetone/dichloromethane (from 30% to 50%+5% MeOH), to give the title compound (18 mg, 26%) as a brown solid.

MS (ES+): m/z=773 (M+H)⁺: LCMS (Method B): $t_R$=3.27 min.

Example 66

(S)—N-(4-Aminophenyl)-4-(6-((2-methoxy-12-oxo-6a,7,8,9,10,12-hexahydrobenzo[e]pyrido[1,2-α][1,4]diazepin-3-yl)oxy)hexan-amido)-1-methyl-1H-pyrrole-2-carboxamide (66)

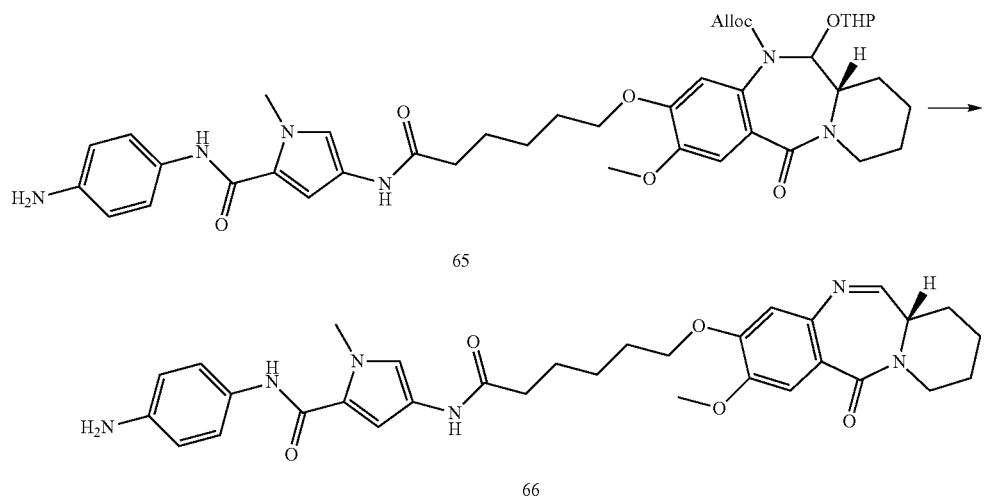

To a solution of allyl (6S,6aS)-3-((6-((5-((4-aminophenyl)carbamoyl)-1-methyl-1H-pyrrol-3-yl)amino)-6-oxohexyl)oxy)-2-methoxy-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (65) (18 mg, 0.020 mmol) in dichloromethane (1 mL) was added tetrakis(triphenylphosphine)palladium(0) (1.3 mg, 5 mol %) and pyrrolidine (2.3 µL, 0.030 mmol). The reaction mixture was stirred at room temperature for 30 min and then subjected to high vacuum for 30 min until excess pyrrolidine was thoroughly removed. The resulting residue was then purified by column chromatography (silica), eluting with methanol/dichloromethane (from 0% to 100%), to give the title compound (11.6 mg, 86%) as an off-white solid.

¹H NMR (DMSO-d₆, 400 MHz) δ 9.78 (s, 1H), 9.48 (s, 1H), 8.00 (d, J=5.7 Hz, 1H), 7.32 (d, J=8.8 Hz, 2H), 7.25 (s, 1H), 7.17 (d, J=1.8 Hz, 1H), 6.82 (d, J=1.9 Hz, 1H), 6.79 (s, 1H), 6.56 (d, J=8.6 Hz, 2H), 4.13 (dd, J=5.7, 3.4 Hz, 5H), 3.80 (s, 3H), 3.79 (s, 3H), 3.17 (s, 1H), 3.07-3.11 (m, 1H), 2.26 (t, J=7.2 Hz, 3H), 1.75 (dd, J=13.8, 7.0 Hz, 6H), 1.60-1.65 (m, 5H); MS (ES+): m/z=587 (M+H)⁺: LCMS (Method B): $t_R$=2.72 min, MS (ES+): m/z=587 (M+H)⁺: LCMS (Method A): $t_R$=5.23 min.

Example 67

Allyl (6aS)-3-(4-((5-((4-(5-((2-aminoethyl)carbamoyl)-1-methyl-1H-1-pyrrol-3-yl)phenyl)carbamoyl)-1-methyl-1H-pyrrol-3-yl)amino)-4-oxobutoxy)-2-methoxy-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (67)

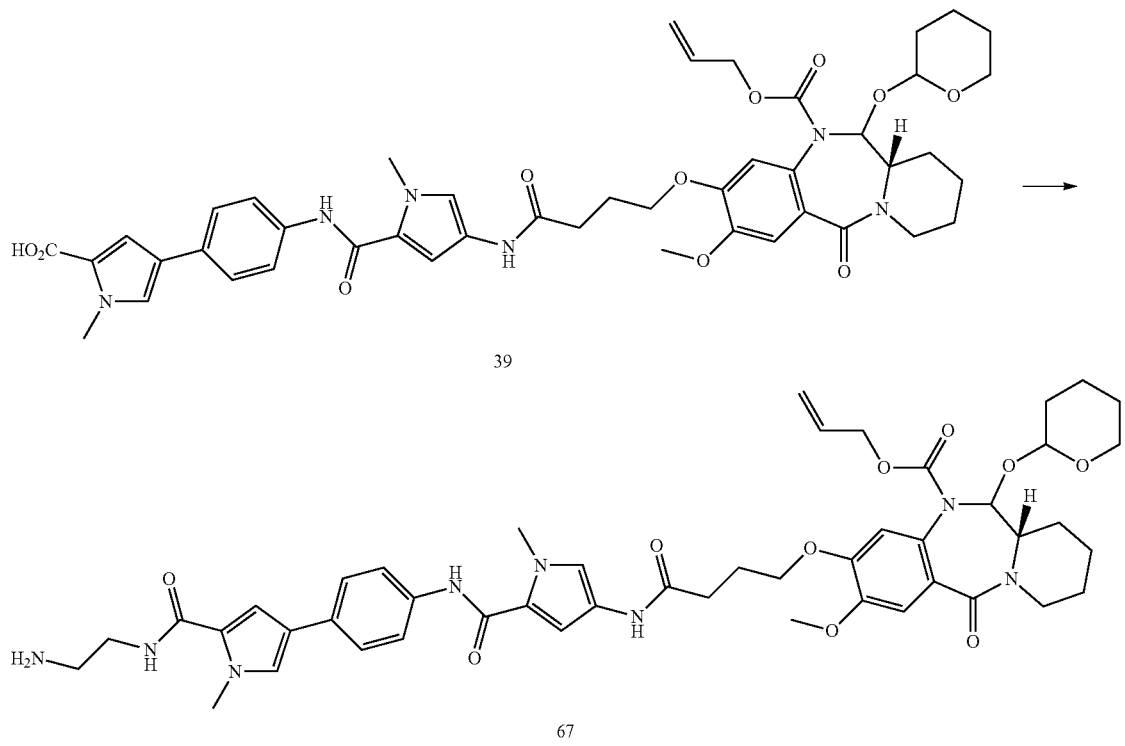

A solution of 4-(4-(4-(4-(((6aS)-5-((allyloxy)carbonyl)-2-methoxy-12-oxo-6-((tetra-hydro-2H-pyran-2-yl)oxy)-5,6,6a,7,8,9,10,12-octahydrobenzo[e]pyrido[1,2-α][1,4]-diazepin-3-yl)oxy)butanamido)-1-methyl-1H-pyrrole-2-carboxamido)phenyl)-1-methyl-1H-pyrrole-2-carboxylic acid (39) (270 mg, 0.317 mmol) in anhydrous dichloromethane (6 mL) was charged with N-[(dimethylamino)-1H-1,2,3-triazolo-[4,5-b]pyridin-1-ylmethylene]-N-methylmethanaminium hexafluorophosphate-N-oxide (126 mg, 0.333 mmol) and anhydrous triethylamine (185 μL, 1.33 mmol). The reaction mixture was stirred at room temperature for 30 min. Ethane-1,2-diamine (379 mg, 6.33 mmol) was then added and the resulting mixture was stirred at room temperature for 16 h. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacua. The resulting residue was then purified by column chromatography (silica), eluting with ammonia in methanol (2 M)/dichloromethane (from 0% to 10%), to give the title compound (180 mg, 63%) as a white solid.

MS (ES+): m/z=896 (M+H)$^+$: LCMS (Method B): $t_R$=3.12 min.

Example 68

(S)—N-(2-Aminoethyl)-4-(4-(4-(4-((2-methoxy-12-oxo-6a,7,8,9,10,12-hexahydrobenzo[e]pyrido[1,2-a][1,4]diazepin-3-yl)oxy)butanamido)-1-methyl-1H-pyrrole-2-carboxamido)phenyl)-1-methyl-1H-pyrrole-2-carboxamide (68)

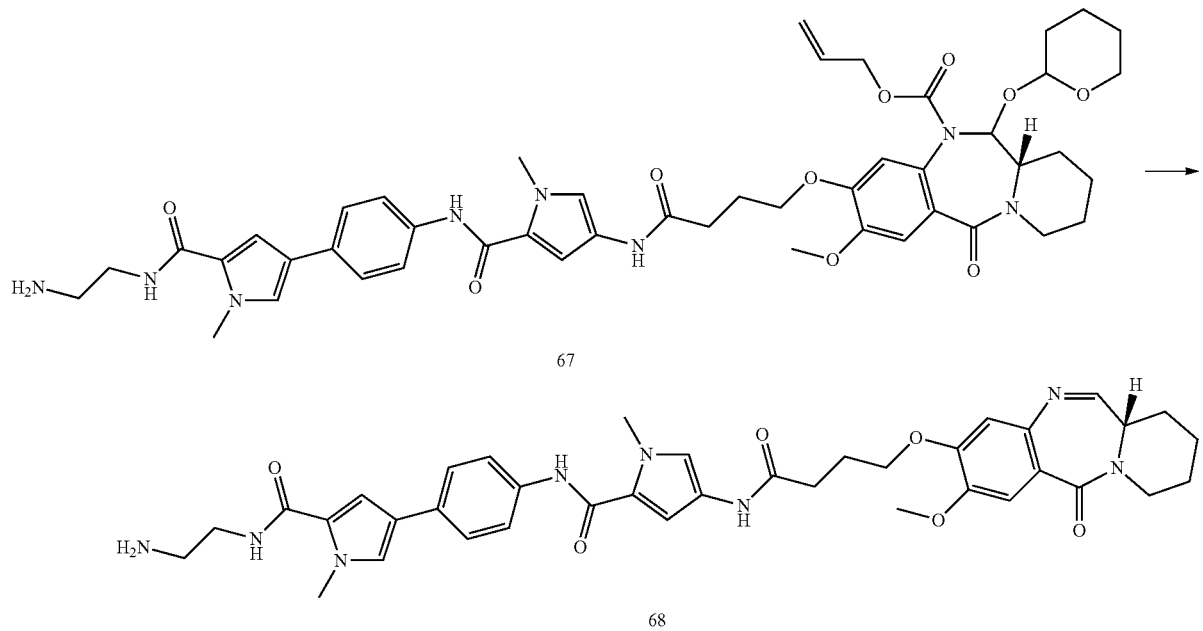

To a solution of allyl (6aS)-3-(4-((5-((4-(5-((2-aminoethyl)carbamoyl)-1-methyl-1H-pyrrol-3-yl)phenyl)carbamoyl)-1-methyl-1H-pyrrol-3-yl)amino)-4-oxobutoxy)-2-methoxy-12-oxo-6-((tetrahydro-2H-pyran-2-yl)oxy)-6,6a,7,8,9,10-hexahydrobenzo[e]-pyrido[1,2-a][1,4]diazepine-5(12H)-carboxylate (67) (22 mg, 0.025 mmol) in dichloromethane (4 mL) was added tetrakis(triphenylphosphine)palladium(0) (1.4 mg, 5 mol %) and pyrrolidine (3.0 μL, 0.037 mmol). The reaction mixture was stirred at room temperature for 2 h and then subjected to high vacuum for 30 min until excess pyrrolidine was thoroughly removed. The resulting residue was then purified by column chromatography (silica), eluting with methanol/dichloromethane (from 0% to 20%), to give the title compound (11 mg, 62%) as a white solid.

$^1$H NMR (DMSO-$d_6$, 400 MHz) δ 10.01 (s, 1H), 9.84 (s, 1H), 9.21 (br s, 2H), 8.41 (s, 1H), 8.01 (d, J=5.7 Hz, 1H), 7.70 (d, J=8.8 Hz, 2H), 7.44 (d, J=8.7 Hz, 2H), 7.38 (d, J=1.8 Hz, 1H), 7.31 (d, J=1.9 Hz, 1H), 7.27 (s, 1H), 7.22 (d, J=1.8 Hz, 1H), 6.98 (d, J=1.8 Hz, 1H), 6.80 (s, 1H), 4.09-4.19 (m, 2H), 3.99-4.05 (m, 2H), 3.87 (s, 3H), 3.82 (m, 6H), 3.65-3.72 (m, 2H), 3.45-3.50 (m, 2H), 3.16 (d, J=5.3 Hz, 3H), 2.96 (t, J=5.8 Hz, 2H), 2.45 (t, J=7.4 Hz, 2H), 2.00-2.09 (m, 4H); (DMSO-$d_6$, 100 MHz) δ 203.1, 168.8, 166.3, 164.7, 161.6, 159.6, 150.2, 147.1, 139.8, 137.0, 129.5, 125.9, 124.2, 122.0, 120.6, 120.4, 111.2, 109.8, 109.3, 98.8, 95.4, 85.9, 78.8, 71.0, 67.7, 55.6, 49.2, 48.5, 36.3, 31.8, 30.2, 24.7, 22.5, 17.7; MS (ES+): m/z=709 (M+H)$^+$: LCMS (Method B): $t_R$=2.80 min, MS (ES+): m/z=709 (M+H)$^+$: LCMS (Method A): $t_R$=5.38 min.

Example 69

Allyl (6aS)-6-hydroxy-2-methoxy-3-(4-methoxy-4-oxobutoxy)-12-oxo-6,6a,7,8,9,10-hexahydrobenzo[e]pyrido[1,2-α][1,4]diazepine-5(12H)-carboxylate (7)

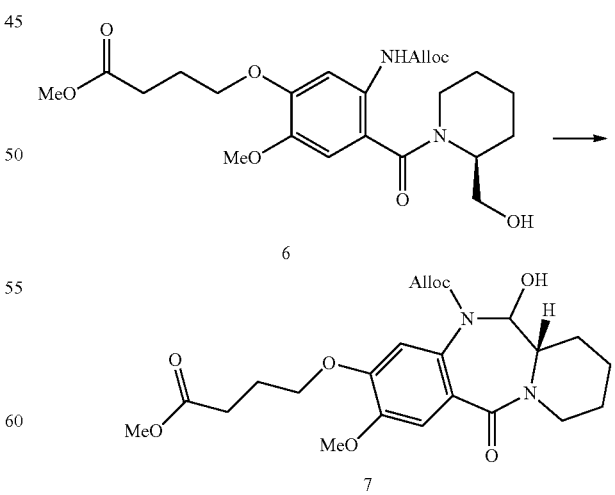

To a solution of methyl (S)-4-(5-(((allyloxy)carbonyl)amino)-4-(2-(hydroxymethyl)piperidine-1-carbonyl)-2-methoxyphenoxy)butanoate (6) (930 mg, 2.00 mmol) in dichloromethane (45 mL) was added 2,2,6,6-tetramethyl-1-piperidinyloxy (32 mg, 0.20 mmol) and (diacetoxyiodo)benzene (773 mg, 2.40 mmol). The reaction mixture was stirred at room temperature for 16 h, and was then sequentially washed with a saturated aqueous solution of sodium metabisulfite (20 mL), a saturated aqueous solution of sodium hydrogen carbonate (20 mL), water (20 mL) and brine (20 mL). The organic layer was then dried over sodium sulfate, filtered and concentrated. The resulting residue was purified by column chromatography (silica), eluting with methanol/dichloromethane (from 0% to 5%), to give the title compound (825 mg, 89%) as a cream solid, mixture of diastereomers.

$^{1}$H NMR (400 MHz, CDCl$_{3}$) δ 7.12, (s, 1H), 6.63 (s, 1H), 5.87 (d, J=10.1 Hz, 1H), 5.81-5.65 (m, 1H), 5.08 (d, J=12.1 Hz, 2H), 4.62 (dd, J=13.3 Hz, 5.3 Hz, 1H), 4.41 (br. s., 1H), 4.31-4.21 (m, 1H), 4.08-3.95 (m, 3H), 3.84 (s, 3H), 3.62 (s, 3H), 3.45-3.38 (m, 1H), 3.01 (ddd, J=3.9, 10.3, 14.0 Hz, 1H), 2.48 (t, J=7.2 Hz, 3H), 2.13-2.05 (m, 3H), 1.77-1.57 (m, 6H); $^{13}$C NMR (100 MHz, CDCl$_{3}$) δ 173.4, 169.0, 150.0, 148.9, 131.8, 125.2, 117.9, 113.5, 117.9, 113.5, 110.6, 82.3, 67.9, 66.7, 56.0, 55.4, 51.6, 38.6, 30.6, 30.3, 30.3, 24.2, 23.1, 22.9, 18.1; MS (ES+): m/z=463 (M+H)$^{+}$: LCMS (Method A): t$_{R}$=6.30 min.

Example 70

Allyl (6αS)-2-methoxy-3-(4-methoxy-4-oxobutoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (8)

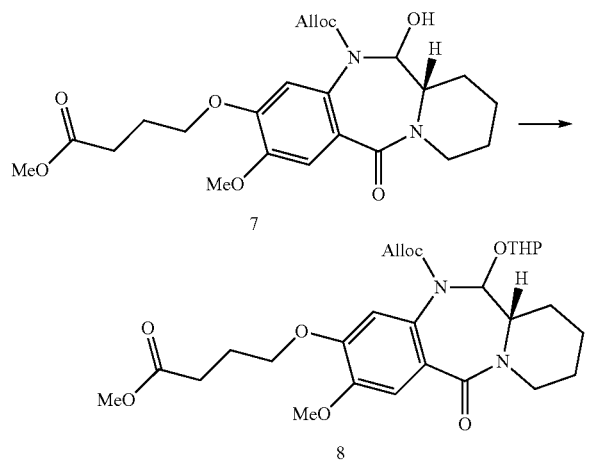

A mixture of allyl (6aS)-6-hydroxy-2-methoxy-3-(4-methoxy-4-oxobutoxy)-12-oxo-6,6a,7,8,9,10-hexahydrobenzo[e]pyrido[1,2-a][1,4]diazepine-5(12H)-carboxylate (7) (825 mg, 1.80 mmol), 3,4-dihydro-2H-pyran (1.70 mL, 18.2 mmol) and p-toluenesulfonic acid monohydrate (8.5 mg, 1% w/w) in ethyl acetate (12 mL) was stirred at room temperature for 16 h. The reaction mixture was then diluted with ethyl acetate (50 mL) and washed with a saturated aqueous solution of sodium hydrogen carbonate (20 mL) and brine (30 mL). The organic layer was dried over sodium sulfate, filtered and concentrated. The resulting residue was purified by column chromatography (silica), eluting with methanol/dichloromethane (from 0% to 2%), to give the title compound (820 mg, 84%) as a cream solid, mixture of diastereomers.

$^{1}$H NMR (400 MHz, CDCl$_{3}$) δ 7.50 (s, 0.6H), 7.02 (s, 0.4H), 6.74 (s, 0.4H), 6.48 (s, 0.6H), 6.07 (d, J=9.8 Hz, 0.6H), 5.9 (d, J=10.2 Hz, 0.4H), 5.70-5.62 (m, 1H), 5.01-4.92 (m, 3H), 4.55-4.20 (m, 2H), 4.18-4.13 (m, 1H), 3.96-3.91 (m, 3H), 3.78 (s, 3H), 3.55 (s, 3H), 3.40-3.34 (m, 2H), 3.00-2.91 (m, 1H), 2.24 (t, J=7.0 Hz, 2H), 2.05-2.02 (m, 2H), 1.67-1.43 (m, 12H); $^{13}$C NMR (100 MHz, CDCl$_{3}$) δ 173.2, 170.8, 169.2, 169.0, 149.3, 132.1, 131.9, 126.4, 126.0, 116.8, 114.4, 114.0, 110.6, 110.2, 100.0, 952.2, 87.9, 84.0, 67.8, 67.6, 66.3, 66.1, 63.8, 60.2, 55.9, 55.3, 51.4, 38.7, 30.9, 30.6, 30.2, 30.1, 25.2, 24.1, 23.1, 20.9, 20.8, 19.9, 19.6, 18.3, 18.1, 14.1 MS (ES+): m/z=547 (M+H)$^{+}$: LCMS (Method A): t$_{R}$=7.70 min.

Example 71

4-(((6αS)-5-(Allyloxy)carbonyl)-2-methoxy-12-oxo-6-((tetrahydro-2H-pyran-2-yl)oxy)-5,6,6a,7,8,9,10,12-octahydrobenzo[e]pyrido[1.2-α][1,4]diazepin-3-yl)oxy)butanoic acid (9)

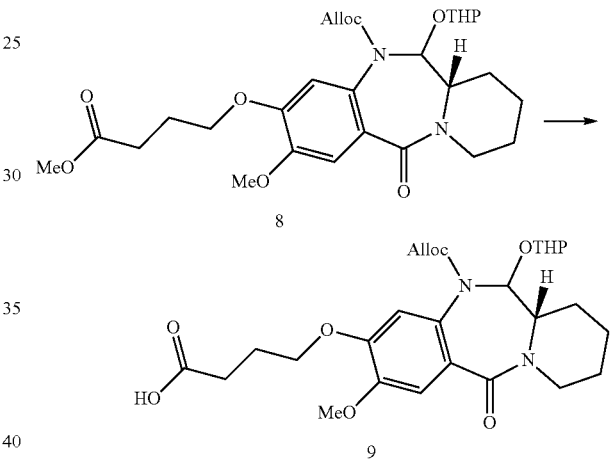

To a solution of allyl (6aS)-2-methoxy-3-(4-methoxy-4-oxobutoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (8) (770 mg, 1.40 mmol) in 1,4-dioxane (10 mL) was added a 0.5 M aqueous solution of sodium hydroxide (10.0 mL, 5.00 mmol). The reaction mixture was stirred at room temperature for 2 h and was then concentrated in vacuo, after which water (20 mL) was added and the aqueous layer was acidified to pH=4 with an aqueous solution of acetic acid (5 M, 10 mL). The aqueous layer was extracted with ethyl acetate (2×50 mL). The combined organic extracts were washed with brine (50 mL), dried over sodium sulfate, filtered and concentrated to give the title compound (700 mg, 93%) as a yellow oil, mixture of diastereomers. The product was carried through to the next step without any further purification (mixture of diastereomers).

$^{1}$H NMR (400 MHz, (CD$_{3}$)$_{2}$SO) δ 12.15 (br. s., 1H), 7.03 (s, 0.6H), 7.01 (s, 0.4H), 6.86 (s, 0.6H), 6.78 (s, 0.4H), 6.01 (d, J=10.1, 0.6H), 5.92 (d, J=9.8, 0.4H), 5.83-5.69 (m, 1H), 5.11-4.96 (m, 3H), 4.64-4.36 (m, 2H), 4.16-4.02 (m, 1H), 400-3.92 (m, 2H), 3.80 (s, 3H), 3.79-3.70 (m, 2H), 3.54-3.46 (m, 1H), 2.89-2.83 (m, 1H), 2.36 (t, J=7.2 Hz, 2H), 1.96-1.89 (m, 2H), 1.71-1.41 (m, 12H); $^{13}$C NMR (100 MHz, (CD$_{3}$)$_{2}$SO) δ 174.5, 174.4, 168.5, 168.5, 150.1, 149.1, 133.1, 127.6, 126.3, 114.5, 110.7, 109.1, 99.7, 84.4, 68.0, 67.9, 56.2, 52.9, 38.5, 30.6, 30.3, 30.02, 25.4, 25.3, 23.1, 23.0, 18.3; MS (ES+): m/z=533 (M+H)⁺: LCMS (Method A): $t_R$=6.98 min.

Example 72

Methyl 4-(4-((tert-butoxycarbonyl)amino)phenyl)-1-methyl-1H-pyrrole-2-carboxylate (70)

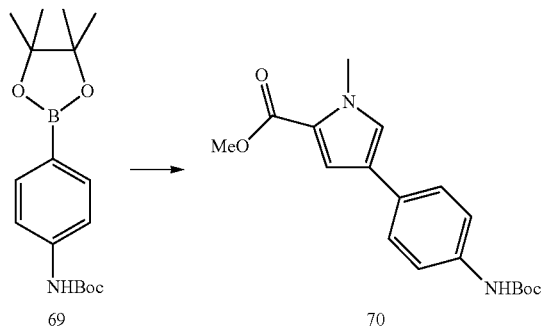

To a solution of methyl 4-bromo-1-methyl-1H-pyrrole-2-carboxylate (1.0 g, 4.60 mmol) in acetonitrile (40 mL) and water (36 mL) tert-butyl (4-(4,4,5,5-tetramethyl-1,3,2-dioxaborolan-2-yl)phenyl)carbamate (1.8 mg, 5.06 mmol), potassium carbonate (69) (1.7 g, 13.36 mmol), and tetrakis (triphenylphosphine)palladium (280 mg, mol 5%) were added. The reaction mixture was purged with nitrogen for 5 min and the reaction was carried out in a microwave reactor at 100° C. for 6 min. The mixture was filtered through a celite pad. The pad was washed with ethyl acetate (500 mL) and the resulting organic solution was concentrated in vacua. The residue was purified by column chromatography (silica), eluting with ethyl acetate/hexane (from 0% to 40%), to give the title compound (958 mg, 63%) as a white solid.

¹H NMR (400 MHz, CDCl₃) δ 7.37-7.42 (m, 2H), 7.32-7.36 (m, 2H), 7.16 (d, J=2.0 Hz, 1H), 7.02 (d, J=2.0 Hz, 1H), 6.56 (s, 1H), 3.94 (s, 3H), 3.83 (s, 3H), 1.52 (s, 9H); ¹³C NMR (100 MHz, CDCl₃) δ 161.7, 136.5, 129.4, 127.1, 125.9, 125.5, 123.6, 119.0, 115.6, 114.6, 60.4, 51.1, 36.9, 28.3; MS (ES+): m/z=330.9 (M+H)⁺: LCMS (Method B): $t_R$=4.22 min.

Example 73

Methyl 4-(4-(4-((tert-butoxycarbonyl)amino)-1-methyl-1H-pyrrole-2-carboxamido)phenyl)-1-methyl-1H-rpyrrole-2-carboxylate (57)

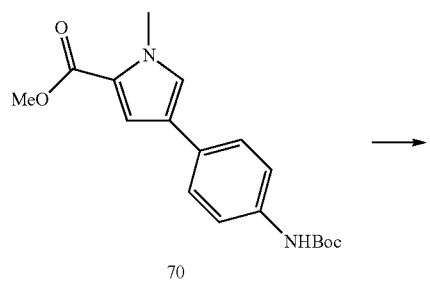

-continued

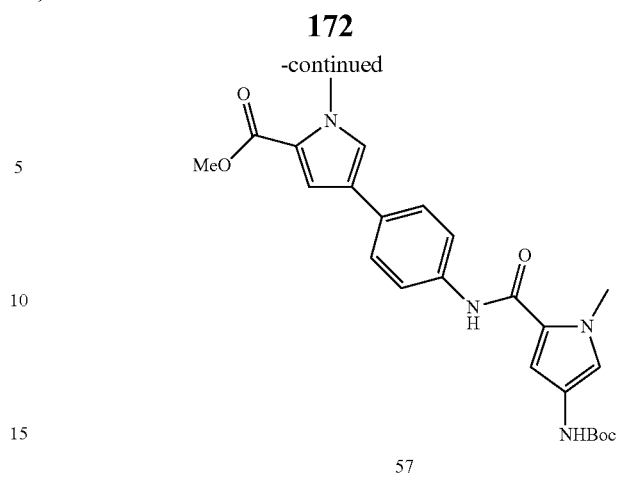

To a solution of methyl 4-(4-((tert-butoxycarbonyl) amino)phenyl)-1-methyl-1H-pyrrole-2-carboxylate (70) (950 mg, 2.88 mmol) in dioxane and methanol (1:1) (8 mL) hydrochloric acid (4 M in 1,4-dioxane) (8 mL) was added drop wise. The reaction mixture was stirred for 3 h and then concentrated in vacuo. The residue was added to a mixture of 4-((tert-butoxycarbonyl)amino)-1-methyl-1H-pyrrole-2-carboxylic acid (830 mg, 3.45 mmol), N,N-dimethylpyridin-4-amine (1.05 g, 8.64 mmol) and N-(3-Dimethylaminopropyl)-N'-ethylcarbodiimide hydrochloride (1.38 g, 7.20 mmol) in N,N-dimethylformamide (15 mL) which was previously stirred for 30 min. The resulting solution was allowed to react at room temperature for 18 h. The reaction mixture was quenched with a saturated aqueous solution of sodium hydrogen carbonate (20 mL) and loaded with brine (150 mL). The aqueous phase was extracted with ethyl acetate (2×60 mL). The combined organic extracts were concentrated in vacua. The resulting residue was purified by column chromatography (silica), eluting to with acetone/dichloromethane (from 0% to 30%), to give the title compound (860 mg, 66%) as a cream solid.

¹H NMR (400 MHz, CDCl₃) δ 8.01 (2, 1H), 7.71 (s, 1H), 7.49-7.54 (m, 2H), 7.40-7.44 (m, 2H), 7.17 (d, J=2.0, 1H), 7.03 (d, J=1.8, 1H), 6.85 (s, 1H), 6.63 (s, 1H), 3.94 (s, 3H), 3.88 (s, 3H), 3.83 (s, 3H) 1.50 (s, 9H); ¹³C NMR (100 MHz, CDCl₃) δ 161.7, 159.5, 136.0, 130.4, 126.0, 125.5, 123.5, 123.5, 121.8, 120.3, 118.6, 114.6, 110.0, 103.7, 51.1, 36.9, 36.7, 28.4; MS (ES+): m/z=453.1 (M+H)⁺: LCMS (Method B): $t_R$=4.07 min.

Example 74

Allyl (6αS)-2-methoxy-3-(4-((5-((4-(5-(methoxycarbonyl)-1-methyl-1H-pyrrol-3-yl)phenyl)carbamoyl)-1-methyl-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (23)

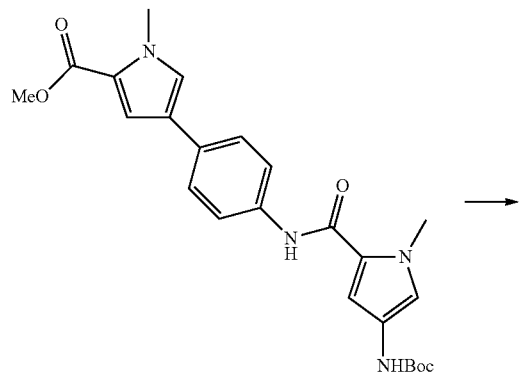

57

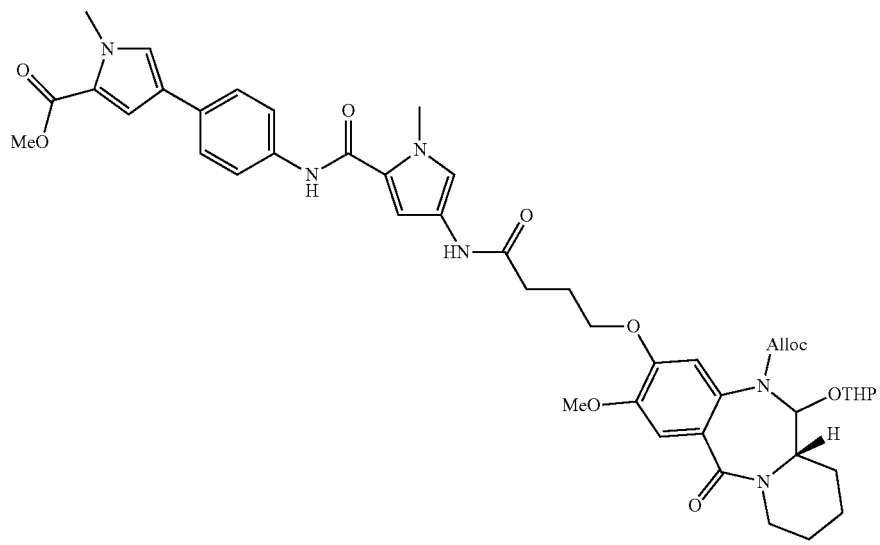

23

To a solution of methyl 4-(4-(4-((tert-butoxycarbonyl)amino)-1-methyl-1H-pyrrole-2-carboxamido)phenyl)-1-methyl-1H-pyrrole-2-carboxylate (57) (440.0 mg, 0.97 mmol) in dioxane and methanol (1:1) (4 mL) hydrochloric acid (4 M in 1,4-dioxane) (4 mL) was added drop wise. The reaction mixture was stirred for 4 h and then concentrated in vacua. The residue was added to a mixture of 4-(((6a5)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)butanoic acid (9) (470.0 mg, 0.88 mmol), N,N-dimethylpyridin-4-amine (322.0 mg, 2.64 mmol) and N-(3-Dimethylaminopropyl)-N'-ethylcarbodiimide hydrochloride (421.7 mg, 2.20 mmol) in N,N-dimethylformamide (7 mL) which was previously stirred for 30 min. The resulting solution was allowed to react at room temperature for 18 h. The reaction mixture was quenched with a saturated aqueous solution of sodium hydrogen carbonate (10 mL) and loaded with brine (90 mL). The aqueous phase was extracted with ethyl acetate (2×50 mL). The combined organic extracts were concentrated in vacuo. The resulting residue was purified by column chromatography (silica), eluting with acetone/dichloromethane (from 0% to 30%), to give the title compound (600 mg, 78%) as an orange solid (mixture of diastereomers).

$^1$H NMR (400 MHz, CDCl$_3$) δ 7.42 (d, J=8.3 Hz, 2H), 7.22-7.10 (m, 4H), 7.04 (s, 2H), 6.76 (br. s., 1H), 6.02-5.87 (m, 1H), 5.74-5.68 (m, 1H), 5.38-5.25 (m, 1H), 5.11-5.05 (m, 1H), 4.38-4.26 (m, 1H), 4.11 (br. s., 2H), 3.93 (s, 3H), 3.88 (br. s., 5H), 3.82 (s, 6H), 3.78 (br. s., 2H), 3.62 (br. s., 3H), 2.48-2.39 (m, 2H), 2.12-2.03 (m, 2H), 1.75-1.50 (m, 12H); $^{13}$C NMR (100 MHz, CDCl$_3$) δ 184.1, 169.7, 169.7, 169.6, 169.2, 168.0, 161.6, 159.9, 136.5, 130.0, 127.8, 127.6, 126.0, 125.2, 123.5, 122.9, 122.8, 121.8, 121.6, 121.6, 120.7, 120.6, 117.6, 114.6, 104.0, 56.0, 55.9, 51.1, 51.1, 36.9, 36.7, 30.9, 30.7, 25.1, 23.2; MS (ES+): m/z=867.4 (M+H)$^+$; LCMS (Method B): t$_R$=4.17 min.

Example 75

4-(4-(4-(4-((((6αS)-5-((Allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)butanamido)-1-methyl-1H-pyrrole-2-carboxamido)phenyl)-1-methyl-1H-pyrrole-2-carboxylic acid (71)

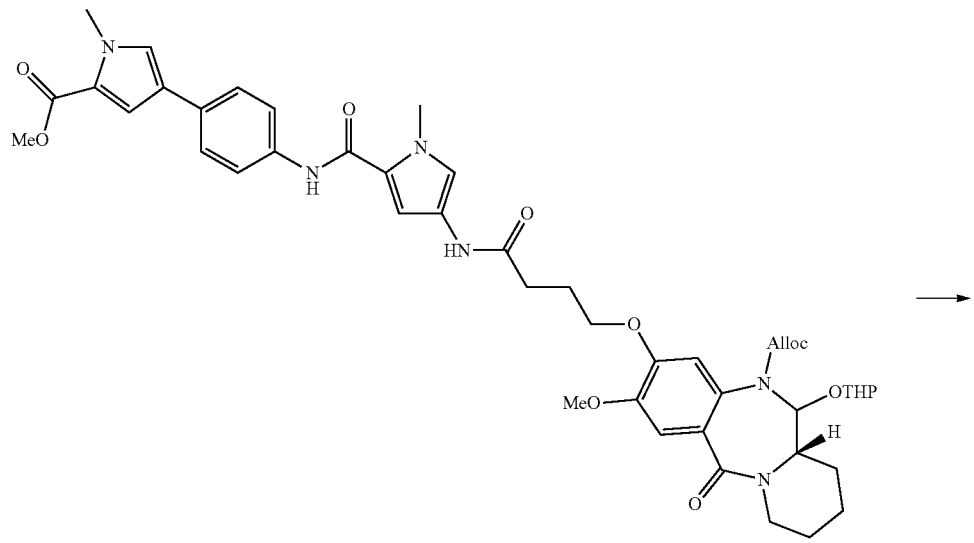

23

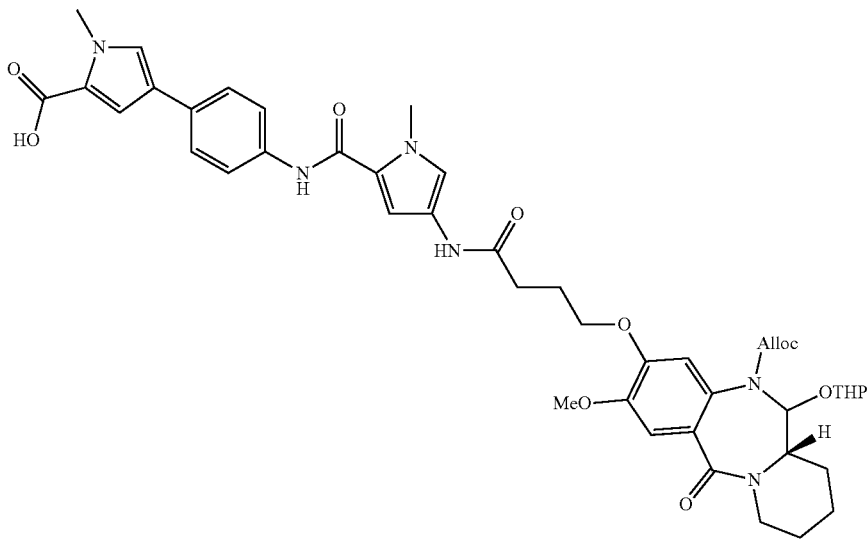

71

To a solution of allyl (6αS)-2-methoxy-3-(4-((5-((4-(5-(methoxycarbonyl)-1-methyl-1H-pyrrol-3-yl)phenyl)carbamoyl)-1-methyl-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (23) (600 mg, 0.69 mmol) in 1,4-dioxane (10 mL) was added an aqueous solution of sodium hydroxide (1 M, 10 mL, 10 mmol). The reaction mixture was stirred at room temperature for 18 h and was then concentrated in vacuo, after which water (100 mL) was added and the aqueous layer was acidified to pH=4 with an aqueous solution of acetic acid (5 M, 20 mL). The aqueous layer was then extracted with ethyl acetate (2×100 mL). The combined organic extracts were dried over sodium sulfate, filtered and concentrated to give the title compound (558 mg, 97%) as a cream solid. The product was carried through to the next step without any further purification (mixture of diastereomers).

$^1$H NMR (400 MHz, CD$_3$OD) δ 7.58-7.54 (m, 2H), 7.46 (d, J=8.3 Hz, 2H), 7.24 (s, 1H), 7.18 (s, 2H), 7.13 (s, 1H), 6.88 (br. s., 2H), 6.17 (d, J=9.8 Hz, 1H), 5.78-5.74 (m, 1H), 4.66-4.38 (m, 3H), 4.26-4.12 (m, 1H), 4.06 (m, 3H), 3.91 (s, 3H), 3.87 (s, 3H), 3.84 (br. s., 4H), 3.67-3.49 (m, 2H), 3.44 (br. s., 1H), 3.11-2.96 (m, 1H), 2.51 (t, J=7.30 Hz, 2H), 2.15-2.12 (m, 2H), 1.72-1.48 (m, 12H); $^{13}$C NMR (100 MHz, CD$_3$OD) δ 175.6, 172.2, 171.4, 164.6, 162.2, 152.1, 150.9, 137.8, 133.5, 132.1, 129.2, 127.6, 126.1, 125.0, 124.7, 124.6, 123.4, 122.4, 117.6, 115.8, 115.6, 106.4, 85.5, 69.5, 67.7, 56.6, 40.2, 37.3, 37.0, 31.8, 26.5, 26.4, 24.0, 21.0, 20.6, 19.1; MS (ES+): m/z=853 (M+H)$^+$: LCMS (Method B): t$_R$=3.83 min.

Example 76

Allyl (6αS)-2-methoxy-3-(4-((1-methyl-5-((4-(1-methyl-5-(phenylcarbamoyl)-1H-pyrrol-3-yl)phenyl)carbamoyl)-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (72)

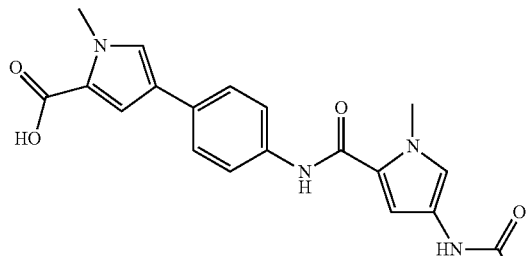

71

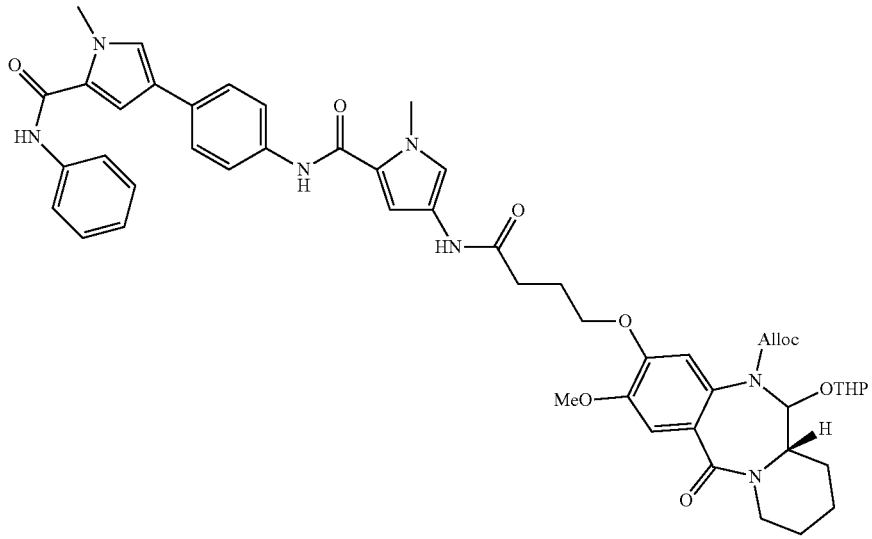

72

A solution of 4-(4-(4-(4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)butanamido)-1-methyl-1H-pyrrole-2-carboxamido)phenyl)-1-methyl-1H-pyrrole-2-carboxylic acid (71) (50.0 mg, 0.06 mmol) in N,N-dimethylformamide (4 mL) was charged with N,N-dimethylpyridin-4-amine (34.5 mg, 0.18 mmol) and N-(3-Dimethylaminopropyl)-N'-ethylcarbodiimide hydrochloride (28.7 mg, 0.15 mmol) and it was stirred for 30 min at room temperature. To the reaction mixture, aniline (6.9 g, 0.07 mmol) was then added and the solution was stirred for further 18 h. The reaction mixture was quenched with a saturated aqueous solution of sodium hydrogen carbonate (10 mL) and loaded with brine (40 mL). The aqueous phase was extracted with ethyl acetate (2×30 mL). The combined organic extracts were concentrated in vacuo. The resulting residue was purified by column chromatography (silica), eluting with acetone/dichloromethane (from 0% to 40%), to give the title compound (43.0 mg, 77%) as a cream solid, (mixture of diastereomers).

$^1$H NMR (400 MHz, CD$_3$OD) δ 7.66 (dd, J=8.7, 1.1 Hz, 2H), 7.61-7.57 (m, 2H), 7.55-7.52 (m, 2H), 7.37-7.32 (m, 3H), 7.27 (d, J=1.5 Hz, 1H), 7.19 (d, J=1.8 Hz, 1H), 7.16 (s, 1H), 7.14-7.09 (m, 1H), 6.93-6.84 (m, 2H), 6.21 (d, J=10.1 Hz, 1H), 6.01-5.71 (m, 1H), 5.17-4.97 (m, 2H), 4.64-4.45 (m, 2H), 4.24-4.04 (m, 3H), 3.97 (s, 3H), 3.90 (s, 3H), 3.87 (br. s., 5H), 3.64-3.41 (m, 3H), 3.13-3.01 (m, 1H), 2.54 (t, J=6.9 Hz, 2H), 2.19-2.15 (m, 2H), 1.83-1.48 (m, 12H); $^{13}$C NMR (100 MHz, CD$_3$OD) δ 162.5, 162.2, 151.0, 140.0, 137.7, 133.5, 132.2, 129.8, 127.7, 126.8, 126.1, 125.0, 124.7, 124.6, 123.3, 122.4, 122.1, 115.7, 111.9, 106.4, 101.3, 85.6, 69.6, 69.5, 64.2, 63.2, 56.7, 40.2, 37.2, 37.0, 36.9, 31.8, 31.7, 30.7, 29.6, 26.6, 26.5, 24.2, 24.0, 20.6, 20.5, 19.1; MS (ES+): m/z=928 (M+H)$^+$; LCMS (Method B): t$_R$=4.33 min.

Example 77

(S)-4-(4-((2-Methoxy-12-oxo-6a,7,8,9,10,12-hexa-hydrobenzo[e]pyrido[1.2-α][1,4]diazepin-3-yl)oxy)butanamido)-1-methyl-N-(4-(1-methyl-5-(phenylcarbamoyl)-1H-pyrrol-3-yl)phenyl)-1H-pyrrole-2-carboxamide (73)

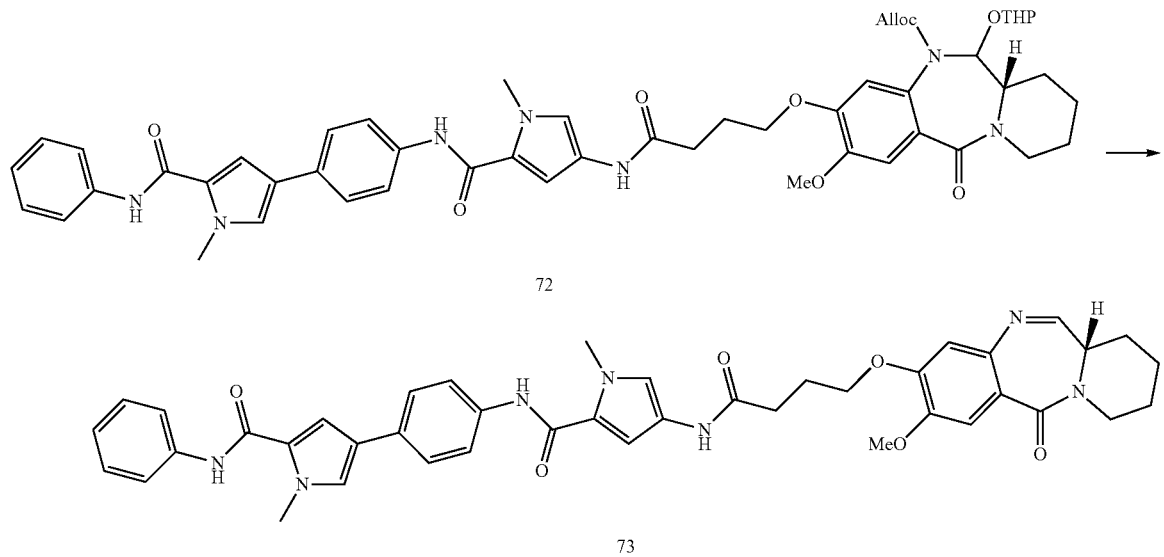

To a solution of allyl (6aS)-2-methoxy-3-(4-((1-methyl-5-((4-(1-methyl-5-(phenylcarbamoyl)-1H-pyrrol-3-yl)phenyl)carbamoyl)-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (72) (43 mg, 0.05 mmol) in dichloromethane (2 mL) was sequentially added tetrakis(triphenylphosphine)palladium(0) (3 mg, 5 mol %), and pyrrolidine (5 μL, 0.06 mmol). The reaction mixture was stirred at room temperature for 30 min. The reaction mixture concentrated in vacua and subjected to high vacuum for 40 min until excess pyrrolidine was removed. The resulting residue was then purified by column chromatography (silica), eluting with methanol/dichloromethane (from 0% to 10%) to give the title compound (11.0 mg, 30%) as a cream solid.

$^1$H NMR (400 MHz, (CD$_3$)$_2$CO) δ 9.20 (s, 1H), 9.12 (s, 1H), 9.10 (s, 1H), 7.98 (d, J=5.5 Hz, 1H), 7.80 (d, J=7.8 Hz, 2H), 7.75 (d, J=8.6 Hz, 2H), 7.49 (d, J=8.6 Hz, 2H), 7.36-7.30 (m, 5H), 7.22 (s, 1H), 7.10-7.04 (m, 1H), 6.92 (d, J=1.6 Hz, 1H), 6.78 (s, 1H), 4.20-4.04 (m, 2H), 4.00 (s, 3H), 3.91 (s, 3H), 3.86 (s, 3H), 3.81-3.70 (m, 2H), 3.23-3.10 (1H), 2.52 (t, J=7.2 Hz, 2H), 2.20-2.12 (m, 3H), 2.02-1.90 (m, 1H), 1.88-1.56 (m, 4H); $^{13}$C NMR (100 MHz, (CD$_3$)$_2$CO) δ 159.8, 159.7, 139.6, 131.8, 137.5, 130.0, 128.5, 126.6, 125.1, 124.7, 123.2, 123.1, 122.7, 120.2, 119.7, 118.8, 111.8, 109.9, 104.2, 68.0, 56.8, 55.4, 49.6, 39.1, 36.1, 35.8, 32.2, 28.4, 25.0, 24.1, 22.9, 18.2, 18.0; MS (ES+): m/z=742 (M+H)$^+$: LCMS (Method B): t$_R$=3.78 min. HRMS (EI, m/z): calculated for C$_{42}$H$_{43}$N$_7$O$_6$ (M+1)$^+$742.3348, observed 742.3328.

Example 78

Allyl (6aα)-3-(4-((5-((4-(5-((4-aminophenyl)carbamoyl)-1-methyl-1H-pyrrol-3-yl)phenyl)carbamoyl)-1-methyl-1H-pyrrol-3-yl)amino)-4-oxobutoxy)-2-methoxy-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (74)

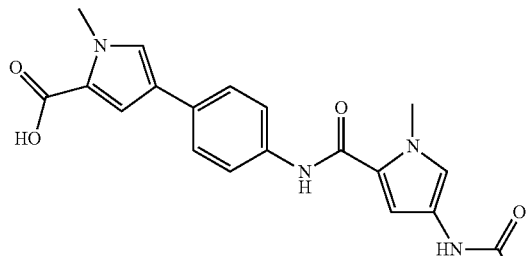
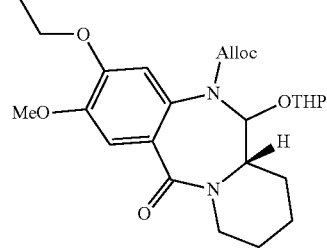
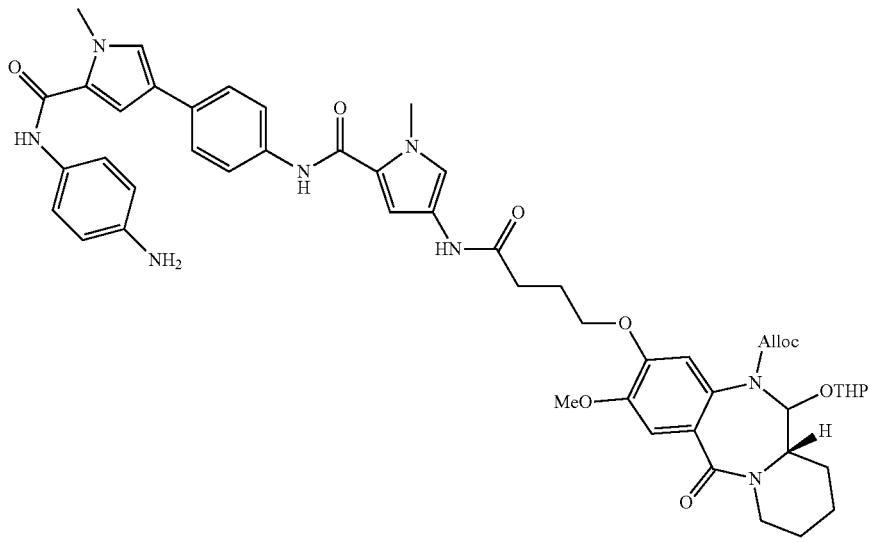

A solution of 4-(4-(4-(4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)butanamido)-1-methyl-1H-pyrrole-2-carboxamido)phenyl)-1-methyl-1H-pyrrole-2-carboxylic acid (71) (340.0 mg, 0.40 mmol) in N,N-dimethylformamide (6 mL) was charged with N,N-dimethylpyridin-4-amine (146.0 mg, 1.19 mmol) and N-(3-Dimethylaminopropyl)-N'-ethylcarbodiimide hydrochloride (190.7 mg, 0.99 mmol) and it was stirred for 30 min at room temperature. To the reaction mixture, p-phenylenediamine (52 mg, 0.48 mmol) was then added and the solution was stirred for further 18 h. The reaction mixture was quenched with a saturated aqueous solution of sodium hydrogen carbonate (20 mL) and loaded with brine (70 mL). The aqueous phase was extracted with ethyl acetate (2×50 mL). The combined organic extracts were concentrated in vacuo. The resulting residue was purified by column chromatography (silica), eluting with methanol/dichloromethane (from 0% to 10%), to give the title compound (320 mg, 85%) as a cream solid, (mixture of diastereomers).

$^1$H NMR (400 MHz, (CD$_3$)$_2$SO) δ 9.93 (s, 1H), 9.80 (s, 1H), 9.50 (s, 1H), 7.70 (d, J=8.6 Hz, 2H), 7.48 (d, J=8.6 Hz, 2H), 7.40 (d, J=1.2 Hz, 1H), 7.36-7.28 (m, 3H), 7.23 (s, 1H), 7.06 (d, J=2.2 Hz, 1H), 6.95 (br. s., 1H), 6.92 (br. s., 0.4H), 6.80 (s, 0.6H), 6.53 (d, J=8.6 Hz, 2H), 6.03 (d, J=9.8 Hz, 0.6H), 5.94 (d, J=10.0 Hz, 0.4H), 5.84-5.67 (m, 1H), 5.05 (br. s., 2H), 4.67-4.37 (m, 2H), 4.16-3.93 (m, 3H), 3.89 (s, 3H), 3.85-3.80 (m, 6H), 3.79-3.73 (m, 1H), 3.57-3.45 (m, 1H), 2.98-2.83 (m, 1H), 2.44 (t, J=6.7 Hz, 2H), 2.10-1.98 (m, 2H), 1.78-1.32 (m, 12H); $^{13}$C NMR (100 MHz, $(CD_3)_2SO$) δ 169.3, 169.2, 168.6, 168.5, 160.0 159.7, 149.1, 145.3, 137.5, 133.2, 130.1, 128.7, 127.6, 127.1, 125.1, 124.8, 123.2, 122.5, 122.3, 122.2, 120.9, 119.2, 116.9, 114.5, 114.2, 110.1, 105.1, 68.5, 66.0, 63.2, 56.2, 55.3, 38.7, 38.6, 36.8, 32.2, 32.1, 30.6, 25.4, 23.1, 18.3; MS (ES+): m/z=943 (M+H)$^+$, 941 (M−H)$^−$; LCMS (Method B): $t_R$=3.43 min.

Example 79

(S)—N-(4-aminophenyl)-4-(4-(4-(4-((2-methoxy-12-oxo-6a,7,8,9,10,12-hexahydrobenzo[e]pyrido[1,2-α][1,4]diazepin-3-yl)oxy)butanamido)-1-methyl-1H-pyrrole-2-carboxamido)phenyl)-1-methyl-1H-pyrrole-2-carboxamide (41)

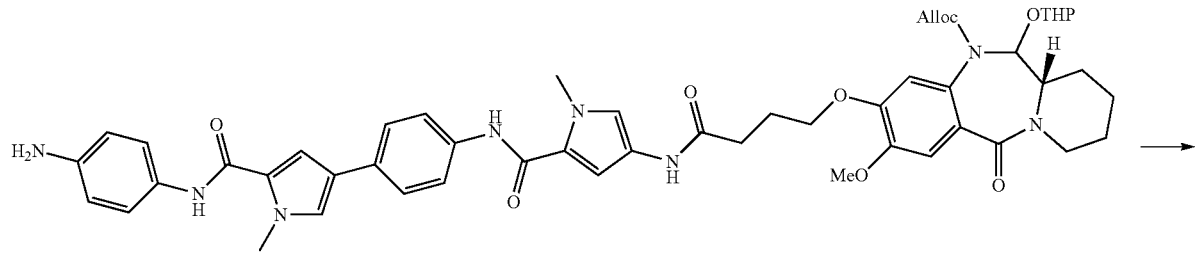

74

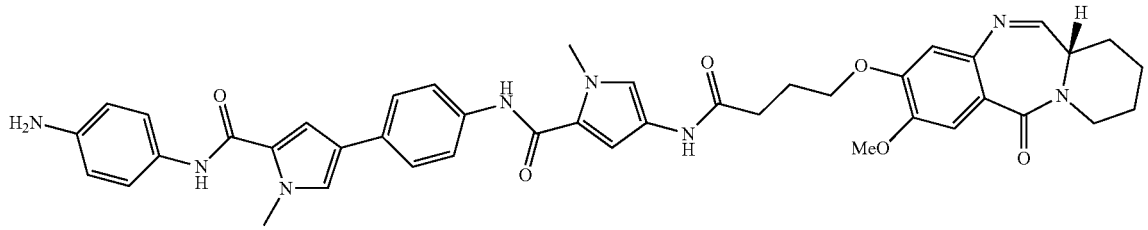

41

To a solution of allyl (6aS)-3-(4-((5-((4-(5-((4-aminophenyl)carbamoyl)-1-methyl-1H-pyrrol-3-yl)phenyl)carbamoyl)-1-methyl-1H-pyrrol-3-yl)amino)-4-oxobutoxy)-2-methoxy-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (74) (250 mg, 0.265 mmol) in dichloromethane (3 mL) was sequentially added tetrakis(triphenylphosphine)palladium(0) (15 mg, 5 mol %), and pyrrolidine (26 mL, 0.32 mmol). The reaction mixture was stirred at room temperature for 30 min. The reaction mixture concentrated in vacua and subjected to high vacuum for 40 min until excess pyrrolidine was removed. The resulting residue was then purified by column chromatography (silica), eluting with methanol/dichloromethane (from 0% to 10%) to give the title compound (118 mg, 59%) as a cream solid.

¹H NMR (400 MHz, (CD₃)₂SO) δ 9.88-9.96 (m, 1H), 9.81 (s, 2H), 9.50 (s, 1H), 8.32 (br s, 2H), 8.00 (d, J=5.7 Hz, 1H), 7.67-7.73 (m, 2H), 7.48 (d, J=8.6 Hz, 2H), 7.39 (d, J=1.8 Hz, 1H), 7.31-7.35 (m, 2H), 7.30 (d, J=1.6 Hz, 1H), 7.27 (s, 1H), 7.22 (d, J=1.5 Hz, 1H), 6.96 (d, J=1.6 Hz, 1H), 6.80 (s, 1H), 6.51-6.55 (m, 2H), 4.09-4.17 (m, 1H), 3.99-4.05 (m, 1H), 3.90-3.97 (m, 1H), 3.88 (s, 3H), 3.83 (s, 3H), 3.82 (s, 3H), 3.68-3.72 (m, 1H), 3.05-3.16 (m, 2H), 2.44 (t, J=7.3 Hz, 2H), 2.02-2.07 (m, 2H), 1.81-1.91 (m, 1H), 1.68-1.78 (m, 2H), 1.56 (d, J=4.9 Hz, 2H); ¹³C NMR (100 MHz, (CD₃)₂SO) δ 168.8, 166.3, 164.7, 159.5, 159.2, 150.2, 147.1, 144.7, 139.8, 137.0, 129.6, 128.2, 126.1, 124.6, 124.3, 122.0, 121.8, 120.4, 120.2, 118.8, 113.7, 111.3, 109.6, 104.7, 67.7, 67.2, 55.6, 51.1, 49.2, 38.5, 36.2, 36.1, 35.4, 31.8, 30.2, 24.7, 23.7, 22.5, 17.7; MS (ES+): m/z=757 (M+H)⁺; LCMS (Method A): t$_R$=5.80 min.

Example 80

Allyl (6aS)-2-methoxy-3-(4-((1-methyl-5-((4-(1-methyl-5-(p-tolylcarbamoyl)-1H-pyrrol-3-yl)phenyl)carbamoyl)-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (75)

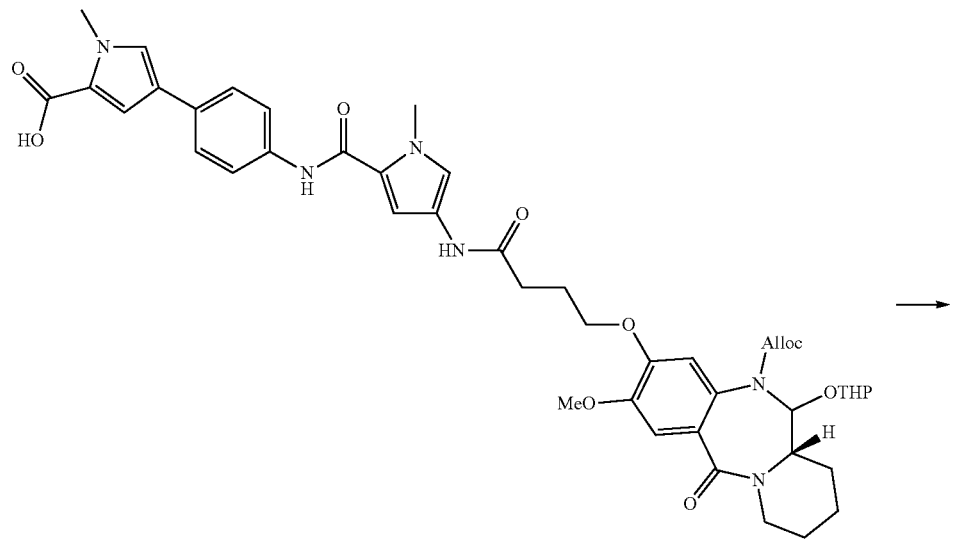

71

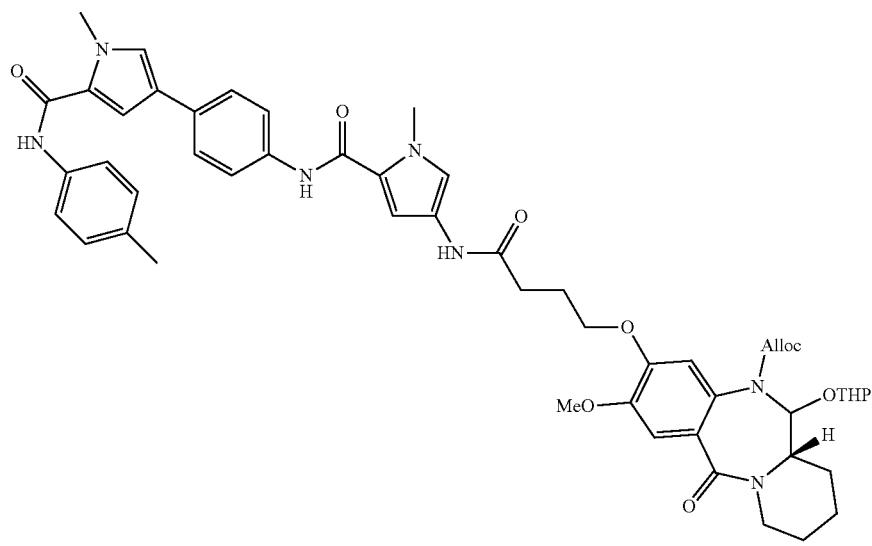

75

A solution of 4-(4-(4-(4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)butanamido)-1-methyl-1H-pyrrole-2-carboxamido)phenyl)-1-methyl-1H-pyrrole-2-carboxylic acid (71) (50.0 mg, 0.06 mmol) in N,N-dimethylformamide (4 mL) was charged with N,N-dimethylpyridin-4-amine (34.5 mg, 0.18 mmol) and N-(3-Dimethylaminopropyl)-N'-ethylcarbodiimide hydrochloride (28.7 mg, 0.15 mmol) and it was stirred for 30 min at room temperature. To the reaction mixture, p-toluidine (7.7 mg, 0.07 mmol) was then added and the solution was stirred for further 18 h. The reaction mixture was quenched with a saturated aqueous solution of sodium hydrogen carbonate (10 mL) and washed with a saturated aqueous solution of sodium chloride (40 mL). The aqueous phase was extracted with ethyl acetate (2×30 mL). The combined organic extracts were concentrated in vacua. The resulting residue was purified by column chromatography (silica), eluting with acetone/dichloromethane (from 0% to 40%), to give the title compound (40 mg, 71%) as a cream solid, (mixture of diastereomers).

$^1$H NMR (400 MHz, CD$_3$OD) δ 7.62-7.57 (m, 2H), 7.56-7.52 (m, 3H), 7.52-7.50 (m, 1H), 7.30 (d, J=2.0 Hz, 1H), 7.27 (d, J=1.8 Hz, 1H), 7.21-7.19 (m, 1H), 7.18-7.15 (m, 3H), 6.93-6.85 (m, 2H), 6.21 (d, J=10.1 Hz, 0.7H), 5.99 (d, J=10.6 Hz, 0.3H), 5.75 (br. s., 1H), 5.09 (br. s., 2H), 4.64-4.48 (m, 2H), 4.23-4.03 (m, 3H), 3.97 (s, 3H), 3.91 (s, 3H), 3.89-3.79 (m, 5H), 3.63-3.44 (m, 2H), 3.14-3.03 (m, 1H), 2.54 (t, J=6.9 Hz, 2H), 2.33 (s, 3H), 2.14-2.02 (m, 2H); $^{13}$C NMR (100 MHz, CD$_3$OD) δ 1.84-1.48 (m, 12H); 162.4, 151.0, 137.7, 137.3, 134.8, 133.5, 132.3, 130.2, 127.8, 126.7, 126.1, 124.7, 124.6, 122.4, 122.2, 115.7, 111.7, 106.4, 69.6, 56.7, 54.8, 40.2, 37.1, 36.9, 31.8, 31,66, 30.7, 29.6, 26.5, 24.2, 24.0, 21.0, 20.6, 20.5, 19.1; MS (ES+): m/z=943 (M+H)$^+$: LCMS (Method A): t$_R$=4.32 min.

Example 81

(S)-4-(4-((2-Methoxy-12-oxo-6a,7,8,9,10,12-hexahydrobenzo[e]pyrido[1,2-α][1,4]diazepin-3-yl)oxy)butanamido)-1-methyl-N-(4-(1-methyl-5-(p-tolylcarbamoyl)-1H-pyrrol-3-yl)phenyl)-1H-pyrrole-2-carboxamide (76)

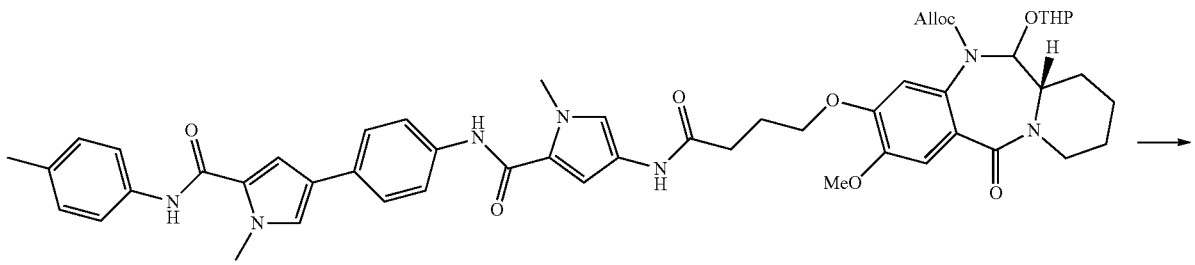

75

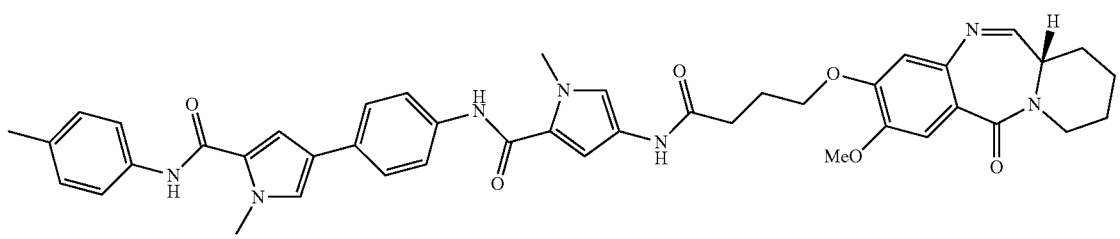

76

To a solution of allyl (6aS)-2-methoxy-3-(4-((1-methyl-5-((4-(1-methyl-5-(p-tolylcarbamoyl)-1H-pyrrol-3-yl)phenyl)carbamoyl)-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (75) (60 mg, 0.07 mmol) in dichloromethane (2 mL) was sequentially added tetrakis(triphenylphosphine)palladium(0) (4 mg, 5 mol %), and pyrrolidine (6.8 mL, 0.08 mmol). The reaction mixture was stirred at room temperature for 30 min. The reaction mixture concentrated in vacua and subjected to high vacuum for 40 min until excess pyrrolidine was removed. The resulting residue was then purified by column chromatography (silica), eluting with acetone/dichloromethane (from 0% to 40%) to give the title compound (30 mg, 57%) as a cream solid.

$^1$H NMR (400 MHz, CDCl$_3$) δ 8.29 (s, 2H), 8.12 (s, 1H), 7.86 (d, J=5.5 Hz, 1H), 7.50 (d, J=8.2 Hz, 2H), 7.44 (d, J=8.6 Hz, 2H), 7.39 (s, 1H), 7.28 (d, J=8.6 Hz, 2H), 7.13-7.07 (m, 3H), 6.96 (d, J=2.3 Hz, 2H), 6.74 (s, 1H), 6.48 (s, 1H), 3.98 (t, J=5.9 Hz, 2H), 3.92 (s, 3H), 3.80 (d, J=4.7 Hz, 6H), 3.76-3.66 (m, 2H), 3.23-3.10 (m, 1H), 2.47-2.38 (m, 2H), 2.29 (s, 3H), 2.18-2.10 (m, 2H), 2.09-197 (m, 2H), 1.95-1.58 (m, 4H); $^{13}$C NMR (100 MHz, CDCl$_3$) δ 170.1, 167.6, 163.5, 160.0, 159.9, 150.7, 147.9, 140.3, 139.9, 136.1, 135.6, 133.5, 130.3, 129.4, 126.6, 125.2, 125.0, 123.1, 121.6, 121.2, 120.8, 120.3, 119.9, 110.1, 109.5, 68.1, 61.1, 56.0, 50.7, 49.7, 39.8, 36.9, 36.6, 24.9, 24.4, 22.9, 20.9, 18.3; MS (ES+): m/z=756 (M+H)$^+$: LCMS (Method A): t$_R$=3.83 min. HRMS (EI, m/z): calculated for C$_{43}$H$_{45}$N$_7$O$_6$ (M+1)$^+$756.3504, observed 756.3489.

Example 82

4-(4-((tert-Butoxycarbonyl)amino)phenyl)-1-methyl-1H-pyrrole-2-carboxylic acid (77)

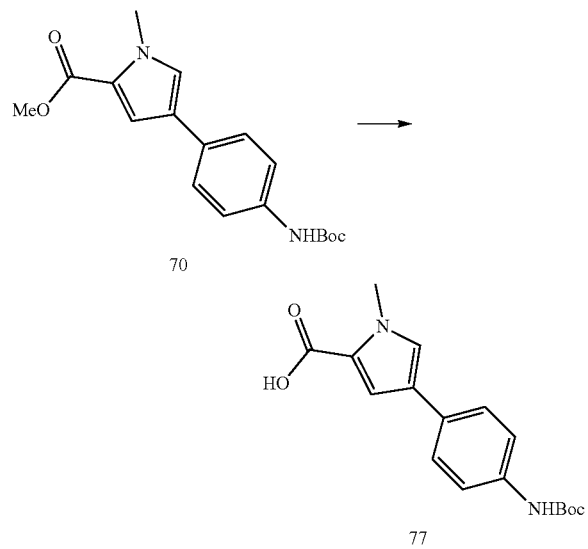

To a solution of methyl 4-(4-((tert-butoxycarbonyl)amino)phenyl)-1-methyl-1H-pyrrole-2-carboxylate (70) (800 mg, 2.42 mmol) in 1,4-dioxane (15 mL) was added an aqueous solution of sodium hydroxide (1 M, 15 mL, 10 mmol). The reaction mixture was stirred at room temperature for 18 h and was then concentrated in vacua, after which water (100 mL) was added and the aqueous layer was acidified to pH=4 with an aqueous solution of acetic acid (5 M, 25 mL). The aqueous layer was then extracted with ethyl acetate (2×100 mL). The combined organic extracts were dried over sodium sulfate, filtered and concentrated to give the title compound (700 mg, 91%) as a white solid. The product was carried through to the next step without any further purification.

$^1$H NMR (400 MHz, CD$_3$OD) δ 7.45-7.42 (m, 2H), 7.38-7.34 (m, 2H), 7.25 (d, J=2.0 Hz, 1H), 7.19 (d, J=2.0 Hz, 1H), 3.92 (s, 3H), 1.52 (s, 9H); $^{13}$C NMR (100 MHz, CD$_3$OD) δ 172.1, 164.5, 155.5, 138.3, 136.6, 130.8, 129.8, 127.8, 126.3, 124.9, 124.4, 120.4, 116.3, 116.1, 81.1, 61.8, 37.4, 28.8; MS (ES+): m/z=315 (M−H)$^-$; LCMS (Method A): t$_R$=3.68 min.

Example 83

Methyl 4-(4-(4-((tert-butoxycarbonyl)amino)phenyl)-1-methyl-1H-pyrrole-2-carboxamido)benzoate (78)

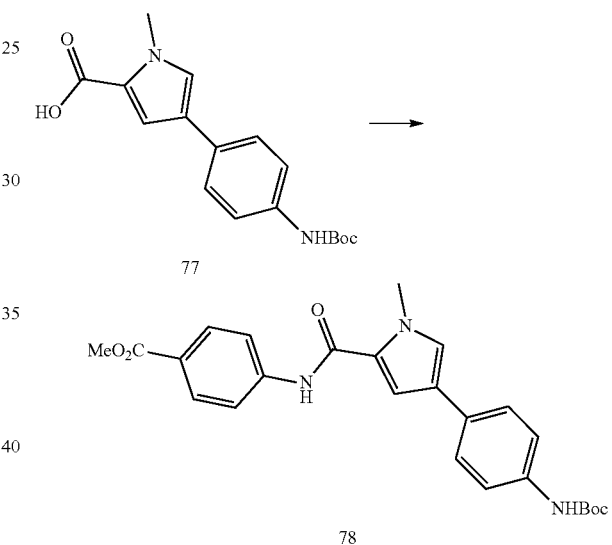

A solution of 4-(4-((tert-butoxycarbonyl)amino)phenyl)-1-methyl-1H-pyrrole-2-carboxylic acid (77) (250.0 mg, 0.79 mmol) in N,N-dimethylformamide (6 mL) was charged with N,N-dimethylpyridin-4-amine (291.0 mg, 2.38 mmol) and N-(3-Dimethylaminopropyl)-N'-ethylcarbodiimide hydrochloride (380.5 mg, 1.98 mmol) and it was stirred for 30 min at room temperature. To the reaction mixture, methyl 4-aminobenzoate (132.0 mg, 0.87 mmol) was then added and the solution was stirred for further 18 h. The reaction mixture was quenched with a saturated aqueous solution of sodium hydrogen carbonate (20 mL) and loaded with brine (80 mL). The aqueous phase was extracted with ethyl acetate (2×60 mL). The combined organic extracts were concentrated in vacuo. The resulting residue was purified by column chromatography (silica), eluting with ethyl acetate/dichloromethane (from 0% to 40%), to give the title compound (61 mg, 17%) as a brown solid.

$^1$H NMR (400 MHz, CDCl$_3$) δ 7.96 (d, J=8.8 Hz, 2H), 7.81 (s, 1H), 7.61 (d, J=8.8 Hz, 2H), 7.35-7.31 (m, 2H), 7.30-7.26 (m, 2H), 6.97 (d, J=1.8 Hz, 1H), 6.88 (d, J=1.8 Hz, 1H), 6.46 (s, 1H), 3.92 (s, 3H), 3.84 (s, 3H), 1.46 (s, 9H); $^{13}$C NMR (100 MHz, CDCl$_3$) δ 166.7, 159.6, 142.4, 136.6, 130.9, 129.2, 126.0, 125.8, 125.6, 123.6, 119.0, 118.8, 109.7, 52.0, 37.1, 29.7, 28.4; MS (ES+): m/z=450 (M+H)⁺: LCMS (Method A): $t_R$=4.32 min.

Example 84

Methyl 4-(4-(4-(4-((tert-butoxycarbonyl)amino)-1-methyl-1H-pyrrole-2-carboxamido)phenyl)-1-methyl-1H-pyrrole-2-carboxamido)benzoate (79)

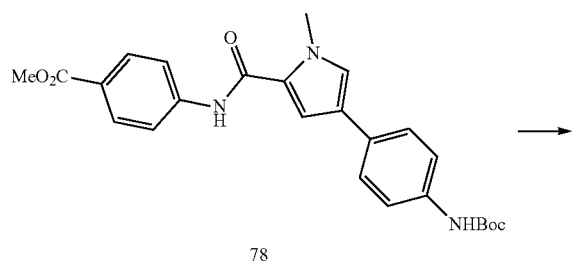

78

To a solution of methyl 4-(4(4-(4-((tert-butoxycarbonyl)amino)-1-methyl-1H-pyrrole-2-carboxamido)phenyl)-1-methyl-1H-pyrrole-2-carboxamido)benzoate (78) (77.0 mg, 0.17 mmol) in dioxane and methanol (1:1) (6 mL) hydrochloric acid (4 M in 1,4-dioxane) (6 mL) was added drop wise. The reaction mixture was stirred for 3 h and then concentrated in vacua. The residue was added to a mixture of 4-((tert-butoxycarbonyl)amino)-1-methyl-1H-pyrrole-2-carboxylic acid (45.0 mg, 0.19 mmol), N,N-dimethylpyridin-4-amine (63.0 mg, 0.52 mmol) and N-(3-dimethylaminopropyl)-N'-ethylcarbodiimide hydrochloride (82.4 mg, 0.43 mmol) in N,N-dimethylformamide (4 mL) which was previously stirred for 30 min. The resulting solution was allowed to react at room temperature for 18 h. The reaction mixture was quenched with a saturated aqueous solution of sodium hydrogen carbonate (5 mL) and washed with a saturated aqueous solution of sodium chloride (80 mL). The aqueous phase was extracted with ethyl acetate (2×30 mL). The combined organic extracts were concentrated in vacua. The resulting residue was purified by column chromatography (silica), eluting with acetone/dichloromethane (from 0% to 30%), to give the title compound (89.0 mg, %) as a brown solid.

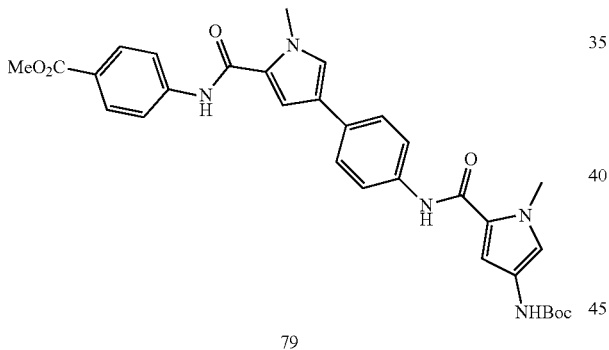

79

¹H NMR (400 MHz, CDCl₃) δ 8.38 (s, 1H), 7.94-7.91 (m, 3H), 7.71 (s, 1H), 7.66 (d, J=8.6 Hz, 2H), 7.40 (d, J=8.6 Hz, 2H), 7.27 (d, J=8.3 Hz, 2H), 6.96 (s, 1H), 6.94 (s, 1H), 6.77 (br. s., 1H), 3.89 (s, 3H), 3.82 (s, 3H), 3.79 (s, 3H), 1.43 (s, 9H); ¹³C NMR (100 MHz, CDCl₃) δ 166.8, 162.6, 160.1, 159.9, 159.7, 142.8, 136.1, 130.8, 130.2, 126.1, 125.7, 125.4, 125.0, 123.4, 123.3, 121.9, 120.6, 119.0, 110.3, 104.2, 61.7, 52.0, 37.1, 36.7, 36.5, 31.5, 28.4; MS (ES+): m/z=572 (M+H)⁺: LCMS (Method A): $t_R$=4.17 min.

Example 85

Allyl (6αS)-2-methoxy-3-(4-((5-((4-(5-((4-(methoxycarbonyl)phenyl)carbamoyl)-1-methyl-1H-pyrrol-3-yl)phenyl)carbamoyl)-1-methyl-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (80)

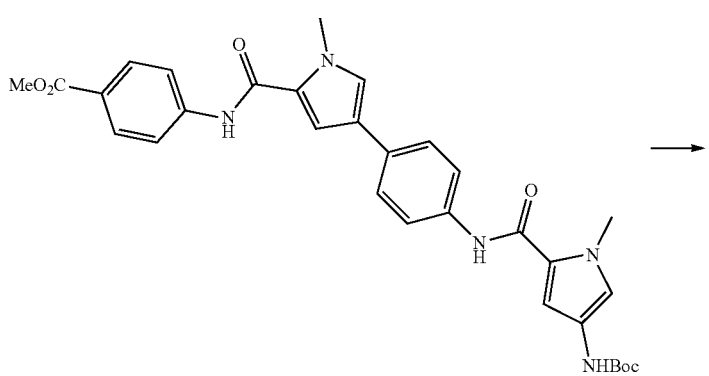

79

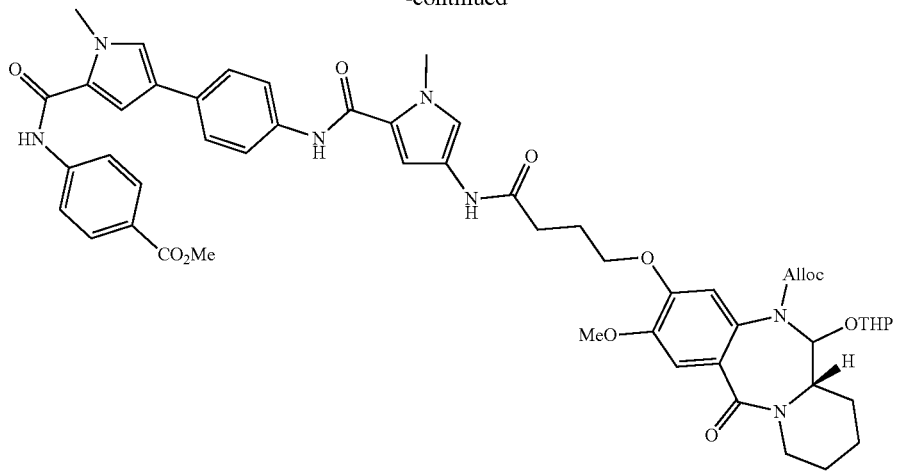

80

To a solution of methyl 4-(4-(4-(4-((tert-butoxycarbonyl)amino)-1-methyl-1H-pyrrole-2-carboxamido)phenyl)-1-methyl-1H-pyrrole-2-carboxamido)benzoate (79) (93.0 mg, 0.16 mmol) in dioxane and methanol (1:1) (3 mL) hydrochloric acid (4 M in 1,4-dioxane) (3 mL) was added drop wise. The reaction mixture was stirred for 4 h and then concentrated in vacua. The residue was added to a mixture of 4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)butanoic acid (9) (71.0 mg, 0.13 mmol), N,N-dimethylpyridin-4-amine (47.6 mg, 0.39 mmol) and N-(3-Dimethylaminopropyl)-N'-ethylcarbodiimide hydrochloride (61.3 mg, 0.32 mmol) in N,N-dimethylformamide (4 mL) which was previously stirred for 30 min. The resulting solution was allowed to react at room temperature for 18 h. The reaction mixture was quenched with a saturated aqueous solution of sodium hydrogen carbonate (5 mL) and washed with a saturated aqueous solution of sodium chloride (70 mL). The aqueous phase was extracted with ethyl acetate (2×60 mL). The combined organic extracts were concentrated in vacua. The resulting residue was purified by column chromatography (silica), eluting with acetone/dichloromethane (from 0% to 30%), to give the title compound (80.0 mg, 62%) as an orange solid (mixture of diastereomers).

$^1$H NMR (400 MHz, CD$_3$OD) δ 7.91-7.86 (m, 4H), 7.75-7.69 (m, 2H), 7.53-7.47 (m, 2H), 7.46-7.41 (m, 2H), 7.27 (d, J=2.0 Hz, 1H), 7.21 (d, J=1.5 Hz, 1H), 7.05 (s, 1H), 6.84-6.73 (m, 2H), 6.09 (d, J=10.3 Hz, 1H), 5.79-5.59 (m, 1H), 4.96 (br. s., 2H), 4.43-4.36 (m, 2H), 4.08-4.03 (m, 1H), 4.03-3.03 (m, 3H), 3.88 (s, 3H), 3.81-3.70 (m, ii H), 3.66-3.58 (m, 1H), 3.02-2.94 (m, 1H), 2.48-2.41 (m, 2H) 2.10-2.04 (m, 2H), 1.69-1.42 (m, 12H); $^{13}$C NMR (100 MHz, CD$_3$OD) δ 177.5, 168.3, 145.1, 141.6, 137.8, 132.1, 131.5, 127.4, 127.3, 126.1, 125.9, 124.7, 124.6, 123.2, 122.4, 120.6, 112.4, 112.2, 111.3, 70.6, 69.5, 67.0, 63.1, 56.6, 56.1, 54.8, 52.5, 43.7, 37.3, 37.0, 36.9, 34.6, 31.7, 29.5, 26.6, 24.1, 20.5, 19.2; MS (ES+): m/z=986 (M+H)$^+$: LCMS (Method A): t$_R$=4.28 min.

Example 86

Methyl (S)-4-(4-(4-(4-(4-((2-methoxy-12-oxo-6a,7,8,9,10,12-hexahydrobenzo[e]pyrido[1,2-α][1,4]diazepin-3-yl)oxy)butanamido)-1-methyl-1H-pyrrole-2-carboxamido)phenyl)-1-methyl-1H-pyrrole-2-carboxamido)benzoate (81)

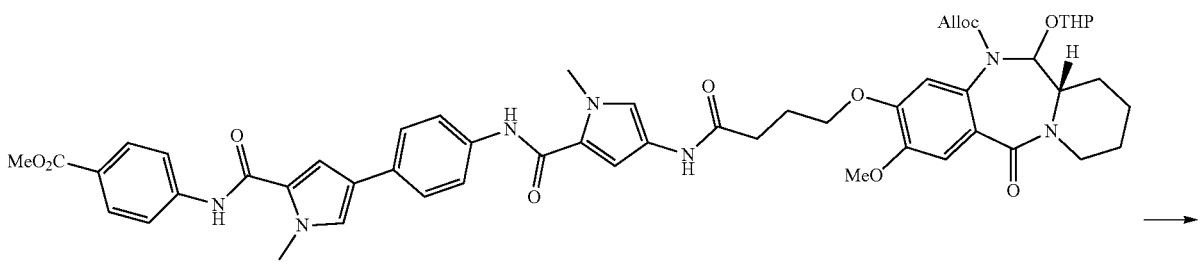

80

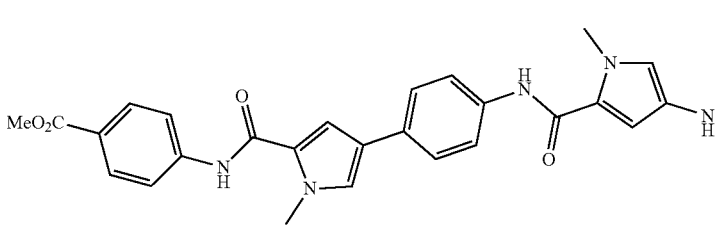

-continued

81

To a solution of allyl (6αS)-2-methoxy-3-(4-((5-((4-(5-((4-(methoxycarbonyl)phenyl)carbamoyl)-1-methyl-1H-pyrrol-3-yl)phenyecarbamoyl)-1-methyl-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (80) (80 mg, 0.08 mmol) in dichloromethane (3 mL) was sequentially added tetrakis(triphenylphosphine)palladium(0) (4.7 mg, 5 mol %), and pyrrolidine (5.6 mL, 0.07 mmol). The reaction mixture was stirred at room temperature for 30 min. The reaction mixture concentrated in vacua and subjected to high vacuum for 40 min until excess pyrrolidine was removed. The resulting residue was then purified by column chromatography (silica), eluting with acetone/dichloromethane (from 0% to 40%) to give the title compound (14 mg, 22%) as a cream solid.

$^1$H NMR (400 MHz, CDCl$_3$) δ 8.71 (s, 1H), 8.21 (s, 1H), 8.11 (s, 1H), 7.98 (d, J=8.6 Hz, 2H), 7.86 (d, J=5.9 Hz, 1H), 7.76 (d, J=8.6 Hz, 2H), 7.43 (d, J=8.6 Hz, 2H), 7.39 (s, 1H), 7.24 (d, J=8.6 Hz, 2H), 7.09 (s, 1H), 7.02 (s, 1H), 6.98 (s, 1H), 6.73 (s, 1H), 6.48 (s, 1H), 3.99 (t, J=5.5 Hz, 2H), 3.94 (s, 3H), 3.88 (s, 3H), 3.79 (d, J=5.1 Hz, 6H), 3.77-3.66 (m, 2H), 3.23-3.11 (m, 1H), 2.45 (t, J=6.8 Hz, 2H), 2.19-2.10 (m, 2H), 2.06-1.70 (m, 6H); $^{13}$C NMR (100 MHz, CDCl$_3$) δ 174.7, 170.2, 1668, 161.6, 160.0, 157.5, 154.2, 147.9, 146.1, 142.9, 139.9, 136.1, 132.2, 130.7, 126.1, 125.6, 125.6, 125.2, 124.9, 123.2, 120.9, 120.1, 119.1, 87.6, 81.4, 62.6, 56.0, 52.0, 39.8, 37.1, 36.6, 31.2, 24.4, 23.0, 18.3; MS (ES+): m/z=800 (M+H)$^+$: LCMS (Method A): t$_R$=3.78 min. HRMS (EI m/z): calculated for C$_{44}$H$_{45}$N$_7$O$_8$ (M+1)$^+$ 800.3402, observed 800.3387.

Example 87

4-Bromo-1-methyl-1H-imidazole-2-carboxylic acid (83)

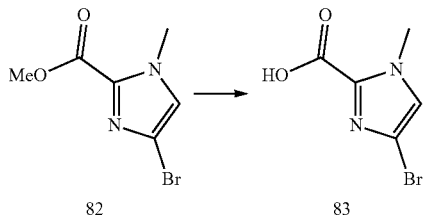

To a solution of methyl 4-bromo-1-methyl-1H-imidazole-2-carboxylate (200 mg, 0.91 mmol) in 1,4-dioxane (8 mL) was added an aqueous solution of sodium hydroxide (1 M, 8 mL, 10 mmol). The reaction mixture was stirred at room temperature for 2 h and was then concentrated in vacua, after which water (80 mL) was added and the aqueous layer was acidified to pH=4 with an aqueous solution of acetic acid (5 M, 15 mL). The aqueous layer was then extracted with ethyl acetate (2×60 mL). The combined organic extracts were dried over sodium sulfate, filtered and concentrated to give the title compound (190 mg, 93%) as a yellow solid. The product was carried through to the next step without any further purification.

$^1$H NMR (400 MHz, CDCl$_3$) δ 10.90 (br. S., 1H), 7.44 (s, 1H), 3.66 (s, 3H); $^{13}$C NMR (100 MHz, CDCl$_3$) δ 175.7, 154.4, 137.6, 125.3, 34.1; MS (ES+): m/z=207 (M+H)$^+$, 205 (M−H); LCMS (Method B): t$_R$=1.80 min.

Example 88

4-Bromo-1-methyl-N-phenyl-1H-imidazole-2-carboxamide (84)

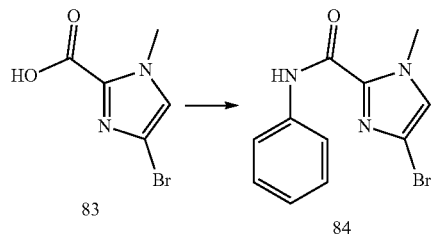

To a solution of 4-bromo-1-methyl-1H-imidazole-2-carboxylic acid (83) (190.0 mg, 0.92 mmol) in N,N-dimethylformamide (3 mL) was charged with N,N-dimethylpyridin-4-amine (338.0 mg, 2.77 mmol) and N-(3-Dimethylaminopropyl)-N'-ethylcarbodiimide hydrochloride (442.0 mg, 2.30 mmol) and it was stirred for 30 min at room temperature. To the reaction mixture, aniline (90.2 mg, 1.01 mmol) was then added and the solution was stirred for further 20 h. The reaction mixture was quenched with a saturated aqueous solution of sodium hydrogen carbonate (10 mL) and washed with a saturated aqueous solution of sodium chloride (40 mL). The aqueous phase was extracted with ethyl acetate (2×30 mL). The combined organic extracts were concentrated in vacua. The resulting residue was purified by column chromatography (silica), eluting with ethyl acetate/petroleum ether (from 0% to 40%), to give the title compound (60 mg, 23%) as a cream solid.

$^1$H NMR (400 MHz, CDCl$_3$) δ 9.05 (br. s., 1H), 7.63 (d, J=7.8 Hz, 2H), 7.35 (t, J=7.6 Hz, 2H), 7.13 (t, J=8.0 Hz, 1H), 6.98 (s, 1H), 4.08 (s, 3H); $^{13}$C NMR (100 MHz, CDCl$_3$) δ 155.8, 138.6, 137.2, 129.1, 125.3, 124.5, 119.8, 36.1; MS (ES+): m/z=280 (M+H)$^+$, 205 (M−H)$^−$; LCMS (Method B): t$_R$=3.97 min.

Example 89 tert-Butyl (4-(1-methyl-2-(phenylcarbamoyl)-1H-imidazol-4-yl)phenyl)carbamate (85)

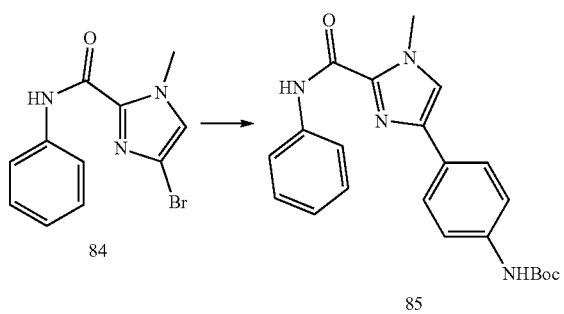 [SMILES: Cn1cc(Br)nc1C(=O)Nc1ccccc1 ; Cn1cc(-c2ccc(NC(=O)OC(C)(C)C)cc2)nc1C(=O)Nc1ccccc1]

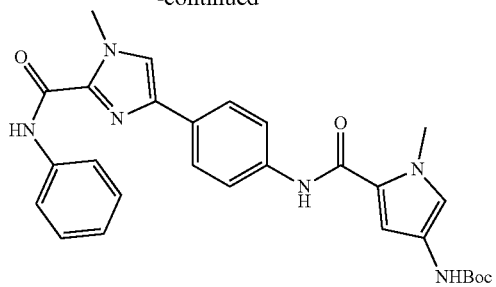

To a solution of 4-bromo-1-methyl-N-phenyl-1H-imidazole-2-carboxamide (84) (60.0 mg, 0.21 mmol) in N,N-dimethylformamide (3 mL) and water (2 mL) tert-butyl (4-(dihydroxyamino)phenyl)carbamate (96.0 mg, 0.30 mmol), caesium carbonate (209 mg, 0.64 mmol), and tetrakis(triphenylphosphine)palladium (13 mg, mol 5%) were added. The reaction mixture was purged with nitrogen for 5 min and the reaction was carried out in a microwave reactor at 100° C. for 2 h. The mixture was filtered through a celite pad. The pad was washed with ethyl acetate (100 mL) and the resulting organic solution was concentrated in vacua. The residue was purified by column chromatography (silica), eluting with ethyl acetate/hexane (from 0% to 50%), to give the title compound (40 mg, 47%) as a cream solid.

$^1$H NMR (400 MHz, CDCl$_3$) δ 9.33 (br. s., 1H), 7.74-7.66 (m, 4H), 7.44-7.33 (m, 4H), 7.22 (d, J=1.6 Hz, 1H), 7.16-7.11 (m, 1H), 6.61 (s, 1H), 4.10 (s, 3H), 1.53 (s, 9H); $^{13}$C NMR (100 MHz, CDCl$_3$) δ 157.2, 140.1, 138.6, 137.7, 137.6, 129.0, 125.7, 124.2, 121.4, 119.7, 119.6, 118.6, 80.6, 35.9, 28.3; MS (ES+): m/z=393 (M+H)$^+$; LCMS (Method B): $t_R$=4.40 min

Example 90 tert-Butyl (1-methyl-5-((4-(1-methyl-2-(phenylcarbamoyl)-1H-imidazol-4-yl)phenyl)carbamoyl)-1H-pyrrol-3-yl)carbamate (86)

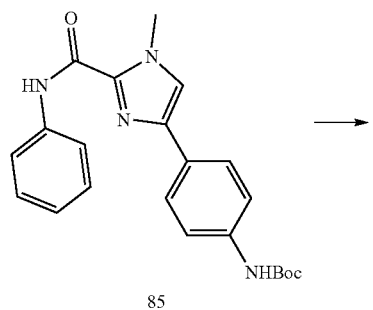

To a solution of tert-butyl (4-(1-methyl-2-(phenylcarbamoyl)-1H-imidazol-4-yl)phenyl)carbamate (85) (40.0 mg, 0.10 mmol) in dioxane and methanol (1:1) (2 mL) hydrochloric acid (4 M in 1,4-dioxane) (2 mL) was added drop wise. The reaction mixture was stirred for 3 h and then concentrated in vacuo. The residue was added to a mixture of 4-((tert-butoxycarbonyl)amino)-1-methyl-1H-pyrrole-2-carboxylic acid (30.0 mg, 0.12 mmol), N,N-dimethylpyridin-4-amine (38.0 mg, 0.31 mmol) and N-(3-Dimethylaminopropyl)-N'-ethylcarbodiimide hydrochloride (49.0 mg, 0.25 mmol) in N,N-dimethylformamide (3 mL) which was previously stirred for 30 min. The resulting solution was allowed to react at room temperature over 20 h. The reaction mixture was quenched with a saturated aqueous solution of sodium hydrogen carbonate (10 mL) and washed with a saturated aqueous solution of sodium chloride (50 mL). The aqueous phase was extracted with ethyl acetate (2×40 mL). The combined organic extracts were concentrated in vacua. The resulting residue was purified by column chromatography (silica), eluting with acetone/dichloromethane (from 0% to 30%), to give the title compound (43 mg, 82%) as a cream solid.

$^1$H NMR (400 MHz, CDCl$_3$) δ 9.34 (s, 1H), 7.75-7.67 (m, 4H), 7.58 (d, J=8.2 HZ, 2H), 7.38-7.33 (m, 2H), 7.21 (s, 1H), 7.13 (t, J=8.0 Hz, 1H), 7.06 (br. s., 11-1), 6.85 (br. s., 1H), 6.64 (br. s., 1H), 6.45 (br. s., 1H), 4.09 (s, 3H), 3.89 (s, 3H), 1.50 (s, 9H); $^{13}$C NMR (100 MHz, CDCl$_3$) δ 159.5, 157.0, 140.0, 137.6, 137.4, 129.0, 125.6, 124.3, 123.4, 121.9, 121.6, 120.1, 119.9, 119.8, 118.8, 110.4, 104.0, 36.7, 35.9, 28.4, 28.3; MS (ES+): m/z=515 (M+H)$^+$: LCMS (Method B): $t_R$=4.33 min.

Example 91

Allyl (6αS)-2-methoxy-3-(4-((1-methyl-5-((4-(1-methyl-2-(phenylcarbamoyl)-1H-imidazol-4-yl)phenyl)carbamoyl)-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrid[1,2-α][1,4]diazepine-5(12H)-carboxylate (87)

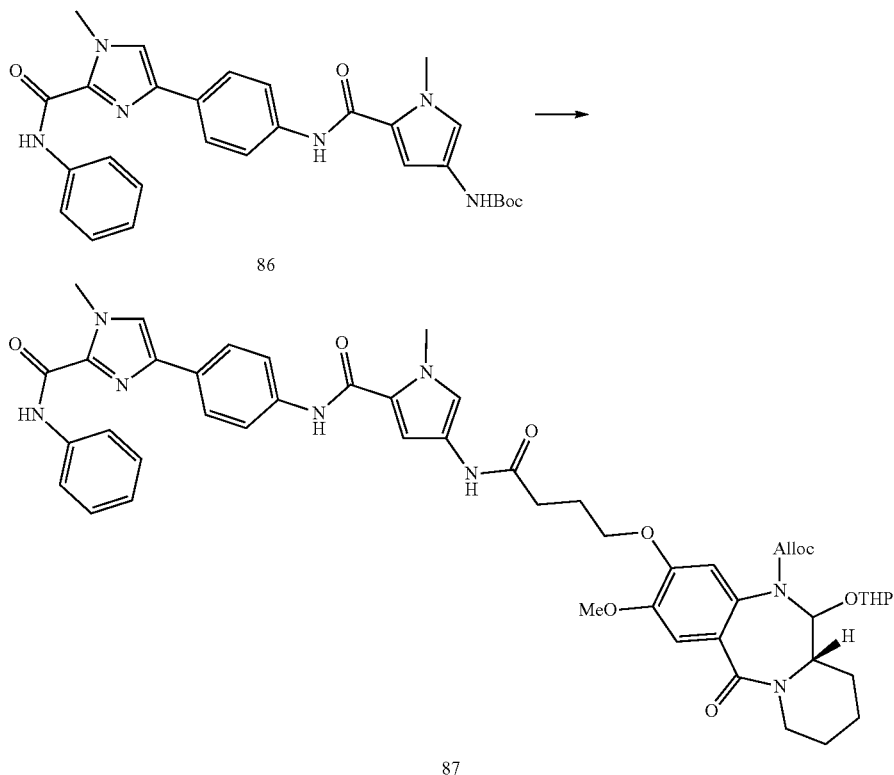

To a solution of tert-butyl (1-methyl-5-((4-(1-methyl-2-(phenylcarbamoyl)-1H-imidazol-4-yl)phenyl)carbamoyl)-1H-pyrrol-3-yl)carbamate (86) (41.5 mg, 0.10 mmol) in dioxane and methanol (1:1) (2 mL) hydrochloric acid (4 M in 1,4-dioxane) (2 mL) was added drop wise. The reaction mixture was stirred for 4 h and then concentrated in vacua. The residue was added to a mixture of 4-(((6αS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)butanoic acid (9) (64.0 mg, 0.12 mmol), N,N-dimethylpyridin-4-amine (37.0 mg, 0.3 mmol) and N-(3-dimethylaminopropyl)-N'-ethylcarbodiimide hydrochloride (48.0 mg, 0.25 mmol) in N,N-dimethylformamide (3 mL) which was previously stirred for 30 min. The resulting solution was left to react at room temperature for 18 h. The reaction mixture was quenched with a saturated aqueous solution of sodium hydrogen carbonate (3 mL) and washed with a saturated aqueous solution of sodium chloride (40 mL). The aqueous phase was extracted with ethyl acetate (2×30 mL). The combined organic extracts were concentrated in vacuo. The resulting residue was purified by column chromatography (silica), eluting with acetone/dichloromethane (from 0% to 40%), to give the title compound (33 mg, 78%) as a brown viscous oil.

¹H NMR (400 MHz, CDCl₃) δ 9.34 (s, 1H), 7.73 (d, J=6.2 Hz, 3H), 7.68 (d, J=7.8 Hz, 2H), 7.36 (t, J=7.8 Hz, 2H), 7.25 (d, J=8.2 Hz, 2H), 7.19-7.08 (m, 3H), 6.78 (br. s., 1H), 6.18 (br. s., 1H), 6.02-5.75 (m, 1H), 5.11-5.01 (m, 2H), 4.67-4.29 (m, 2H), 4.11 (s, 4H), 3.89-3.77 (m, 9H), 3.6.2 (br. s., 3H), 3.12-3.05 (m, 1H), 2.52-2.37 (m, 2H), 2.19-2.14 (m, 2H), 1.76-1.46 (m, 12H); ¹³C NMR (100 MHz, CDCl₃) δ 188.2, 157.0, 148.3, 147.2, 138.8, 138.7, 138.6, 137.6, 135.1, 134.4, 132.0, 131.8, 129.2, 129.0, 127.6, 125.4, 124.2, 122.3, 121.6, 121.4, 120.4, 119.8, 118.3, 115.2, 110.9, 107.9, 99.9, 89.8 84.2, 68.8, 56.1, 54.2, 53.8, 53.4, 50.4, 42.6, 39.0, 36.8, 35.9, 31.0, 30.6, 29.2, 25.2, 22.9, 19.6, 18.1; MS (ES+): m/z=930 (M+H)⁺; LCMS (Method B): t$_R$=4.42 min Example 92

(S)-4-(4-(4-(4-((2-Methoxy-12-oxo-6a,7,8,9,10,12-hexahydrobenzo[e]pyrido[1,2-α][1,4]diazepin-3-yl)oxy)butanamido)-1-methyl-01H-pyrrole-2-carboxamido)phenyl)-1-methyl-N-phenyl-1H-imidazole-2-carboxamide (88)

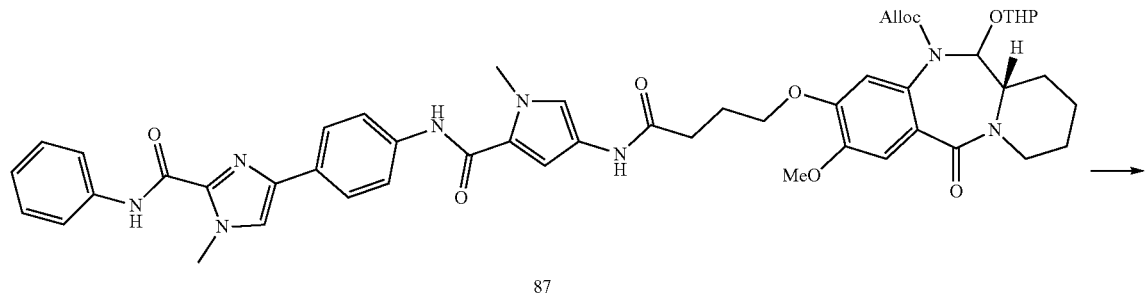

87

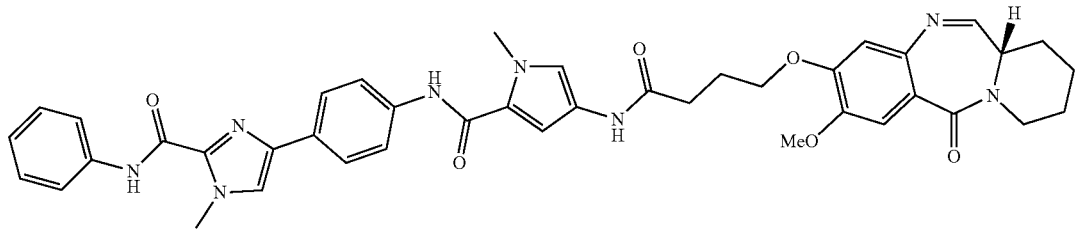

88

To a solution of allyl (6αS)-2-methoxy-3-(4-((1-methyl-5-((4-(1-methyl-2-(phenlylcarbamoyl)-1H-imidazol-4-yl)phenyl)carbamoyl)-1H-pyrrol-3-yl)amino)-4-oxobutoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (87) (30.0 mg, 0.03 mmol) in dichloromethane (2 mL) was sequentially added tetrakis(triphenylphosphine) palladium(0) (1.9 mg, 5 mol %), and pyrrolidine (3.5 mL, 0.04 mmol). The reaction mixture was stirred at room temperature for 30 min. The reaction mixture concentrated in vacua and subjected to high vacuum for 40 min until excess pyrrolidine was removed. The resulting residue was then purified by column chromatography (silica), eluting with methanol/dichloromethane (from 0% to 10%) to give the title compound (12 mg, 50%) as a cream solid.

$^1$H NMR (400 MHz, CDCl$_3$) δ 9.34 (s, 1H), 8.04 (s, 1H), 7.91 (s, 1H), 7.89 (d, J=5.9 Hz, 1H), 7.76-7.71 (m, 2H), 7.68 (d, J=8.2 Hz, 2H), 7.66-7.61 (m, 2H), 7.43 (s, 1H), 7.36 (t, J=7.8 Hz, 2H), 7.22 (s, 1H), 7.16-7.09 (m, 2H), 6.79 (s, 1H), 6.52 (s, 1H), 4.13-4.07 (m, 5H), 3.88 (s, 3H), 3.85 (s, 3H), 3.80-3.69 (m, 2H), 3.26-3.15 (m, 1H), 2.50 (t, J=6.83 Hz, 2H), 2.21 (t, J=6.2 Hz, 2H), 2.10-2.02 (m, 6H); $^{13}$C NMR (100 MHz, CDCl$_3$) δ 169.9, 167.6, 163.5, 159.7, 157.0, 150.7, 148.0, 140.0, 139.9, 138.6, 137.6, 137.6, 129.0, 128.8, 125.5, 124.3, 123.2, 121.6, 121.5, 121.4, 120.3, 119.9, 119.8, 111.8, 110.4, 104.1, 68.1, 56.1, 49.7, 39.8, 36.7, 35.9, 33.0, 29.3, 24.5, 22.9, 18.3; MS (ES+): m/z=743 (M+H)$^+$; LCMS (Method B): t$_R$=3.75 min.

Example 93

Methyl 4-(4-(4-((tert-butoxycarbonyl)amino)-1-methyl-1H-imidazole-2-carboxamido)phenyl)-1-methyl-1H-pyrrole-2-carboxylate (89)

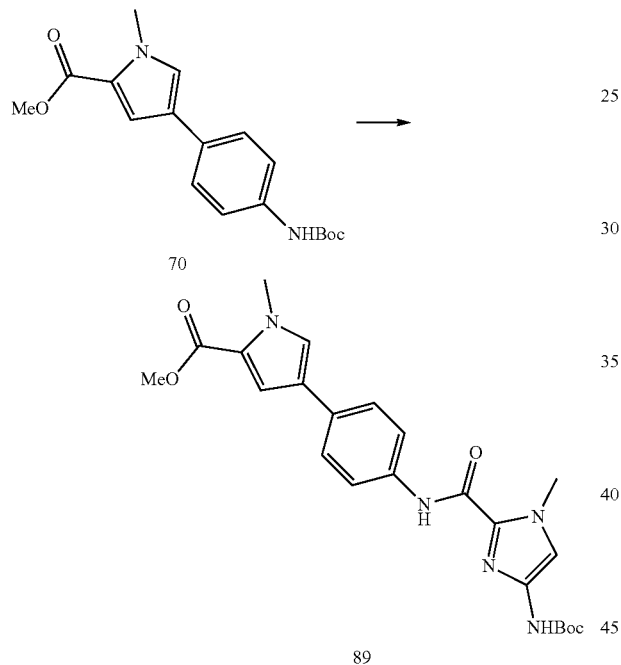

To a solution of methyl 4-(4-((tert-butoxycarbonyl)amino)phenyl)-1-methyl-1H-pyrrole-2-carboxylate (70) (700 mg, 2.12 mmol) in 1,4-dioxane and methanol (1:1) (8 mL) hydrochloric acid (4 M in 1,4-dioxane) (8 mL) was added drop wise. The reaction mixture was stirred for 3 h and then concentrated in vacuo. The residue was added to a mixture of 4-((tert-butoxycarbonyl)amino)-1-methyl-1H-imidazole-2-carboxylic acid (613.1 mg, 2.54 mmol), N,N-dimethylpyridin-4-amine (777.0 mg, 6.36 mmol) and N-(3-Dimethylaminopropyl)-N'-ethylcarbodiimide hydrochloride (1.02 g, 5.30 mmol) in N,N-dimethylformamide (8 mL) which was previously stirred for 30 min. The resulting solution was allowed to react at room temperature for 18 h. The reaction mixture was quenched with a saturated aqueous solution of sodium hydrogen carbonate (20 mL) and washed with a saturated aqueous solution of sodium chloride (130 mL). The aqueous phase was extracted with ethyl acetate (2×60 mL). The combined organic extracts were concentrated in vacua. The resulting residue was purified by column chromatography (silica), eluting with acetone/dichloromethane (from 0% to 30%), to give the title compound (580 mg, 60%) as a brown solid.

$^1$H NMR (400 MHz, CDCl$_3$) δ 8.99 (br. s., 1H), 7.90 (br. s., 1H), 7.55 (d, J=8.6 Hz, 2H), 7.38 (d, J=8.6 Hz, 2H), 7.17 (br. s., 1H), 7.14 (d, J=2.3 Hz, 1H), 6.99 (d, J=1.9 Hz, 1H), 4.01 (s, 3H), 3.90 (s, 3H), 3.80 (s, 3H), 1.44 (br. s., 9H); $^{13}$C NMR (100 MHz, CDC$_3$) δ 171.1, 161.6, 156.4, 136.8, 135.6, 130.5, 126.0, 125.4, 123.5, 123.0, 120.0, 114.6, 112.7, 80.8, 51.1, 36.9, 35.8, 28.2; MS (ES+): m/z=454 (M+H)$^+$; LCMS (Method B): t$_R$=4.28 min.

Example 94

Allyl (6αS)-2-methoxy-3-(4-((2-((4-(5-(methoxycarbonyl)-1-methyl-1H-pyrrol-3-yl)phenyl)carbamoyl)-1-methyl-1H-imidazol-4-yl)amino)-4-oxobutoxy)-12-oxo-6-((tetrahydro-2H-pyran-2-yl)oxy)-6,6a,7,8,940-hexahydrobenzo[e]pyrid[1.2-α][1,4]diazepine-5(12H)-carboxylate (90)

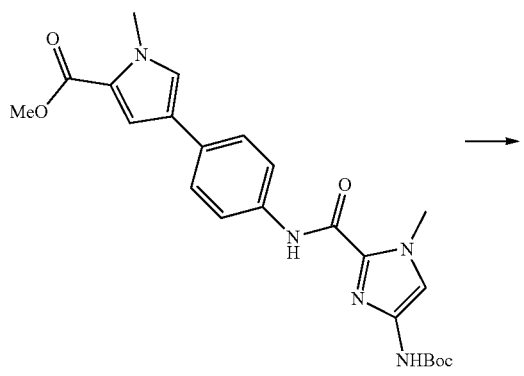

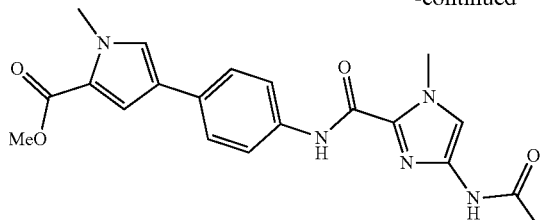

90

To a solution of methyl 4-(4-(4-((tert-butoxycarbonyl)amino)-1-methyl-1H-imidazole-2-carboxamido)phenyl)-1-methyl-1H-pyrrole-2-carboxylate (89) (77.0 mg, 0.17 mmol) in dioxane and methanol (1:1) (2 mL) hydrochloric acid (4 M in 1,4-dioxane) (2 mL) was added drop wise. The reaction mixture was stirred for 4 h and then concentrated in vacua. The residue was added to a mixture of 4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)butanoic acid (9) (75.5 mg, 0.14 mmol), N,N-dimethylpyridin-4-amine (52.0 mg, 0.42 mmol) and N-(3-Dimethylaminopropyl)-N'-ethylcarbodiimide hydrochloride (67.6 mg, 0.35 mmol) in N,N-dimethylformamide (4 mL) which was previously stirred for 30 min. The resulting solution was allowed to react at room temperature for 18 h. The reaction mixture was quenched with a saturated aqueous solution of sodium hydrogen carbonate (5 mL) and loaded with brine (50 mL). The aqueous phase was extracted with ethyl acetate (2×30 mL). The combined organic extracts were concentrated in vacua. The resulting residue was purified by column chromatography (silica), eluting with acetone/dichloromethane (from 0% to 30%), to give the title compound (97.4 mg, 66%) as a yellow oil (mixture of diastereomers).

$^1$H NMR (400 MHz, CDCl$_3$) δ 9.01-8.93 (m, 1H), 8.11-7.99 (m, 1H), 7.62-7.58 (m, 2H), 7.45 (d, J=8.6 Hz, 2H), 7.42 (s, 1H), 7.20-7.16 (m, 2H), 7.06 (d, J=1.9 Hz, 1H), 6.60 (s, 1H), 6.18 (d, J=10.5 Hz, 0.7H), 6.00 (d, J=9.8 Hz, 0.3H), 5.82-5.63 (m, 1H), 5.12-4.98 (m, 2H), 4.68-4.43 (m, 2H), 4.33-4.09 (m, 4H), 4.06 (s, 3H), 3.95 (s, 3H), 3.90 (s, 3H), 3.85-3.82 (m, 4H), 3.66-3.54 (m, 1H), 3.51-3.42 (m, 1H), 3.14-3.00 (m, 1H), 2.59 (t, J=7.0 Hz, 2H), 2.28-2.19 (m, 2H), 1.78-1.5-(m, 12H); $^{13}$C NMR (100 MHz, CDCl$_3$) δ 180.4, 162.9, 161.6, 156.5, 149.4, 135.6, 132.0, 130.7, 126.0, 125.6, 123.5, 123.1, 120.0, 114.6, 112.5, 101.6, 97.4, 84.2, 76.7, 68.0, 64.2, 56.1, 55.5, 51.1, 38.8, 36.9, 35.8, 30.7, 25.2, 23.2, 22.9, 19.6, 18.1, 14.2; MS (ES+): m/z=868 (M+H)$^+$; LCMS (Method B): t$_R$=4.05 min.

Example 95

4-(4-(4-(4-(((6αS)-5-((Allyloxy)carbonyl)-2-methoxy-12-oxo-6-((tetrahydro-2H-pyran-2-yl)oxy)-5,6,6a,7,8,9,10,12-octahydrobenzo[e]pyrido[1,2α][1,4]diazepin-3-yl)oxy)butanamido)-1-methyl-1H-imidazole-2-carboxamido)phenyl)-1-methyl-1H-pyrrole-2-carboxylic acid (91)

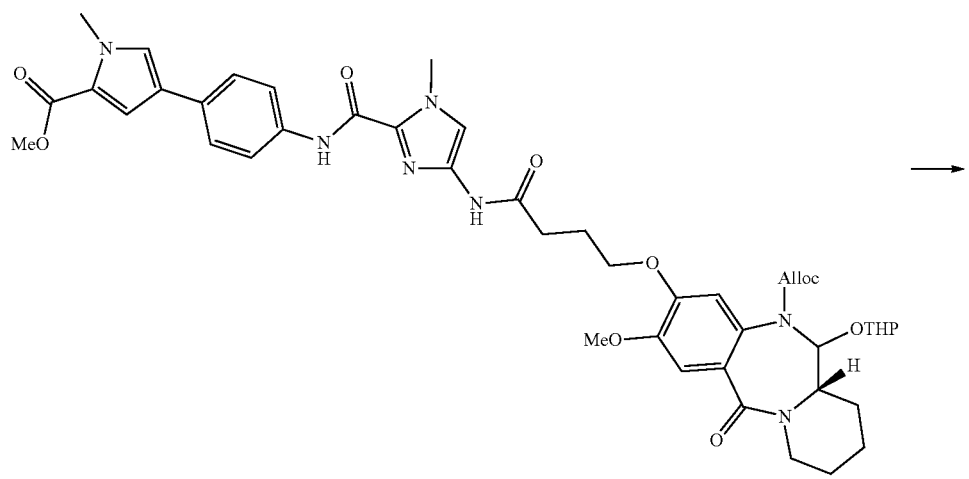

90

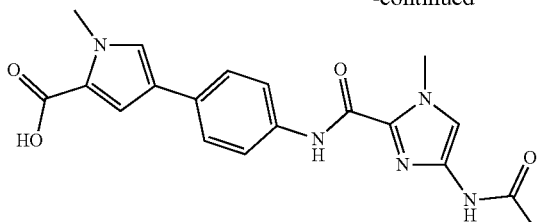

To a solution of allyl (6αS)-2-methoxy-3-(4-((2-((4-(5-(methoxycarbonyl)-1-methyl-1H-pyrrol-3-yl)phenyl)carbamoyl)-1-methyl-1H-imidazol-4-yl)amino)-4-oxobutoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (90) (158.0 mg, 0.18 mmol) in 1,4-dioxane (6 mL) was added an aqueous solution of sodium hydroxide (1 M, 6 mL, 6 mmol). The reaction mixture was stirred at room temperature for 18 h and was then concentrated in vacua, after which water (60 mL) was added and the aqueous layer was acidified to pH=4 with an aqueous solution of acetic acid (5 M, 5 mL). The aqueous layer was then extracted with ethyl acetate (2×40 mL). The combined organic extracts were dried over sodium sulfate, filtered and concentrated to give the title compound (100.0 mg, 64%) as a cream solid. The product was carried through to the next step without any further purification (mixture of diastereomers).

1H NMR (400 MHz, (CD$_3$)$_2$CO) δ 7.66 (d, J=7.8 Hz, 2H), 7.58 (br. s., 1H), 7.53-7.48 (m, 2H), 7.37 (s, 1H), 7.21 (s, 1H), 7.11 (s, 1H), 6.95 (s, 1H), 6.19 (d, J=10.1 Hz, 0.7H), 6.03 (d, J=9.8 Hz, 0.3H), 5.80 (br. s., 1H), 5.15-5.03 (m, 2H), 4.65-4.43 (m, 2H), 4.26-4.08 (m, 4H), 4.02-3.90 (m, 6H), 3.86 (s, 3H), 3.62-3.51 (m, 2H), 3.42 (br. s., 1H), 3.02-2.95 (m, 1H), 2.66-2.53 (m, 2H), 2,22 (m, 2H), 1.74-1.45 (m, 12H); $^{13}$C NMR (100 MHz, (CD$_3$)$_2$CO) δ 161.5, 154.9, 149.4, 132.7, 126.5, 126.3, 125.8, 125.1, 124.9, 119.8, 119.5, 116.3, 114.5, 114.2, 110.6, 104.2, 68.2, 65.8, 64.9, 55.4, 55.2, 38.4, 36.1, 34.9, 30.6, 26.9, 25.3, 24.5, 23.0, 19.4, 18.2; MS (ES+): m/z=854 (M+H)$^+$; LCMS (Method B): t$_R$=3.97 min.

Example 96

Allyl (6αS)-2-methoxy-3-(4-((1-methyl-2-((4-(1-methyl-5-(phenylcarbamoyl)-1H-pyrrol-3-yl)phenyl)carbamoyl)-1H-imidazol-4-yl)amino)-4-oxobutoxy)-12-oxo-6-((tetrahydro-2H-pyran-2-yl)oxy)-6,6a,7,8,9,10-hexahydrobenzo[e]pyrido[1.2-α][1,4]diazepine-5(12H)-carboxylate (92)

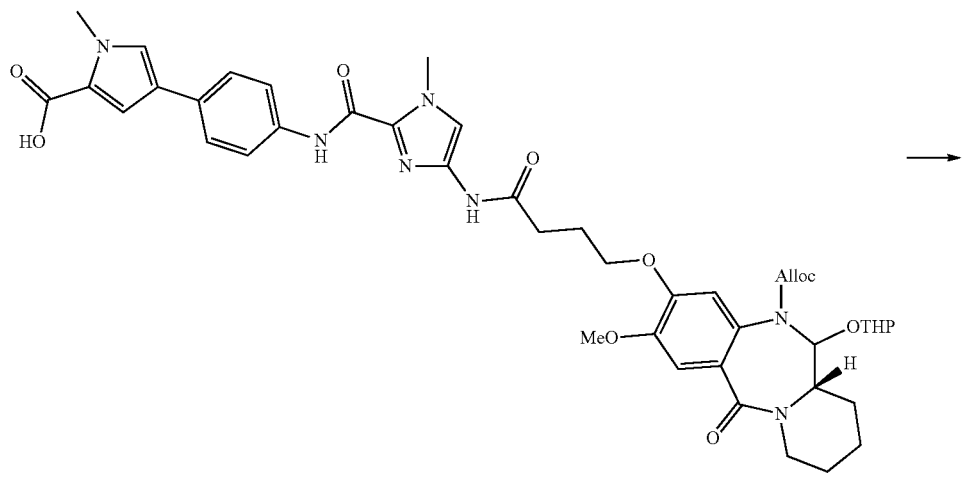

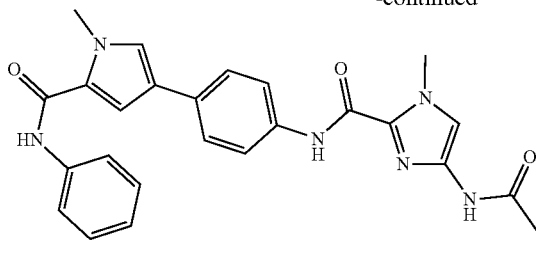

92

A solution of 4-(4-(4-(4-((((6αS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)butanamido)-1-methyl-1H-imidazole-2-carboxamido)phenyl)-1-methyl-1H-pyrrole-2-carboxylic acid (91) (70.0 mg, 0.08 mmol) in N,N-dimethylformamide (4 mL) was charged with N,N-dimethylpyridin-4-amine (30.0 mg, 0.25 mmol) and N-(3-Dimethylaminopropyl)-N'-ethylcarbodiimide hydrochloride (39.0 mg, 0.20 mmol) and it was stirred for 30 min at room temperature. To the reaction mixture, aniline (8.8 mg, 0.10 mmol) was then added and the solution was stirred for further 18 h. The reaction mixture was quenched with a saturated aqueous solution of sodium hydrogen carbonate (10 mL) and loaded with brine (40 mL). The aqueous phase was extracted with ethyl acetate (2×30 mL). The combined organic extracts were concentrated in vacua. The resulting residue was purified by column chromatography (silica), eluting with acetone/dichloromethane (from 0% to 40%), to give the title compound (52 mg, 69%) as a yellow oil (mixture of diastereomers).

$^1$H NMR (400 MHz, CDCl$_3$) δ 7.63-7.60 (m, 2H), 7.43-7.37 (m, 2H), 7.33 (t, J=7.8 Hz, 2H), 7.25-7.22 (m, 2H), 7.18-7.14 (m, 3H), 7.13-7.07 (m, 1H), 7.01 (d, J=6.2 Hz, 1H), 6.61 (br. S., 1H), 6.19 (d, J=8.6 Hz, 0.7H), 6.07-5.96 (m, 0.3H), 5.74 (br. S., 1H), 5.12-5.01 (m, 2H), 4.66-4.47 (m, 2H), 4.31-4.22 (m, 1H), 4.15-4.05 (m, 2H), 4.02 (s, 3H), 3.99 (s, 3H), 3.88 (s, 3H), 3.82 (br. S., 1H), 3.68-3.58 (m, 1H), 3.50-3.44 (m, 2H), 3.15-3.02 (m, 1H), 2.65-2.50 (m, 2H), 2.28-2.13 (m, 2H), 1.75-1.49 (m, 12H); $^{13}$C NMR (100 MHz, CDCl$_3$) δ 183.0, 181.8, 169.6, 162.5, 159.9, 148.3, 138.2, 137.8, 135.8, 132.8, 132.0, 129.7, 129.0, 128.9, 128.0, 126.6, 125.4, 125.3, 125.2, 124.0, 123.5, 120.2, 120.0, 114.5, 111.8, 111.7, 110.7, 109.5, 103.9, 97.1, 81.7, 69.8, 56.0, 52.0, 38.9, 37.0, 36.5, 31.4, 30.7, 27.5, 25.2, 22.9, 21.4, 19.7, 18.1; MS (ES+): m/z=929 (M+H)$^+$; LCMS (Method B): t$_R$=4.33 min.

Eample 97

(S)-4-(4-((2-Methoxy-12-oxo-6a,7,8,9,103,12-hexahydrobenzo[e]pyrido[1,2-α][1,4]diazepin-3-yl)oxy)butanamido)-1-methyl-N-(4-(1-methyl-5-(phenylcarbamoyl)-1H-pyrrol-3-yl)phenyl)-1H-imidazole-2-carboxamide (93)

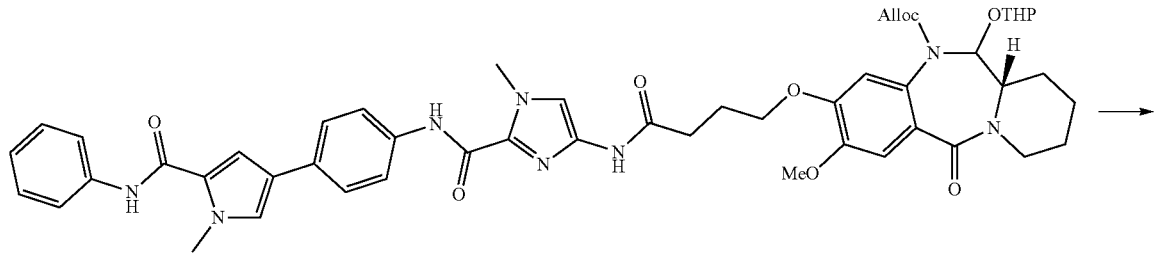

92

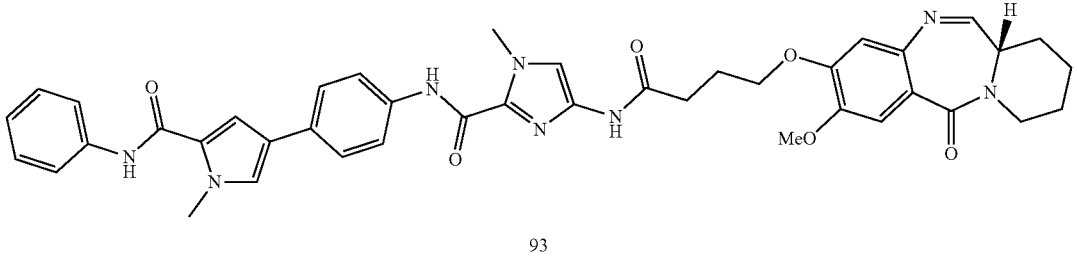

93

To a solution of allyl (6αS)-2-methoxy-3-(44(1-methyl-2-((4-(1-methyl-5-(phenylcarbamoyl)-1H-pyrrol-3-yl)phenyl)carbamoyl)-1H-imidazol-4-yl)amino)-4-oxobutoxy)-12-oxo-6-((tetrahydro-2H-pyran-2-yl)oxy)-6,6a,7,8,9,10-hexahydrobenzo[e]pyrido[1,2-α][1,4]diazepine-5(12H)-carboxylate (92) (50.0 mg, 0.05 mmol) in dichloromethane (3 mL) was sequentially added tetrakis(triphenylphosphine)palladium(0) (3.1 mg, 5 mol %), and pyrrolidine (4.5 □L, 0.06 mmol). The reaction mixture was stirred at room temperature for 30 min. The reaction mixture concentrated in vacua and subjected to high vacuum for 40 min until excess pyrrolidine was removed. The resulting residue was then purified by column chromatography (silica), eluting with methanol/dichloromethane (from 0% to 10%) to give the title compound (25 mg, 62%) as a cream solid.

$^1$H NMR (400 MHz, (CD$_3$)$_2$SO) δ 10.40 (s, 1H), 9.82 (s, 2H), 7.89 (d, J=5.5 Hz, 1H), 7.73 (d, J=3.9 Hz, 2H), 7.71 (d, J=2.7 Hz, 2H), 7.54-7.48 (m, 3H), 7.46 (s, 1H), 7.39 (s, 1H), 7.31 (t, J=7.8 Hz, 2H), 7.25 (s, 1H), 7.07-7.00 (m, 1H), 6.78 (s, 1H), 4.13-3.99 (m, 2H), 3.95 (s, 3H), 3.88 (s, 3H), 3.80 (s, 3H), 3.68-3.65 (m, 2H), 3.10-3.06 (m, 1H), 2.51 (br. s., 2H), 2.08-1.97 (m, 3H), 1.88-1.50 (m, 5H); $^{13}$C NMR (100 MHz, (CD$_3$)$_2$SO) δ 167.3, 165.1, 157.2, 153.9, 151.6, 147.6, 140.1, 139.8, 136.6, 136.5, 134.7, 134.2, 130.7, 129.0, 126.7, 126.0, 125.1, 123.5, 122.2, 120.7, 120.4, 115.0, 111.0, 90.7, 86.9, 79.2, 72.6, 56.3, 49.0, 40.6, 40.4, 40.2, 40.0, 39.8, 39.5, 39.3, 36.9, 36.7, 35.7, 35.5, 31.9, 25.0; MS (ES+): m/z=743 (M+H)$^+$; LCMS (Method B): t$_R$=3.78 min. HRMS (EI, m/z): calculated for C$_{41}$H$_{42}$N$_8$O$_6$(M+1)$^+$743.3300, observed 743.3291.

Example 98

4-(Benzyloxy)-3-methoxybenzaldehyde (95)

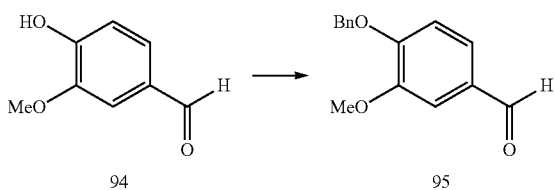 [SMILES: COc1cc(C=O)ccc1O ; COc1cc(C=O)ccc1OCc1ccccc1]

A mixture of 4-hydroxy-3-methoxybenzaldehyde (94) (200.00 g, 1.31 mol), benzyl bromide (236.07 g, 1.38 mol) and K$_2$CO$_3$ (545.02 g, 3.94 mol) in methanol (1.2 L) was refluxed for 5 h. The reaction mixture was filtered and the filtrate was evaporated under reduced pressure to give the title compound (271.00 g, 85%) as a light yellow solid. The product was carried through to the next step without any further purification.

$^1$H NMR (400 MHz, CDCl$_3$) δ 9.83 (s, 1H), 7.29-7.46 (m, 7H), 6.98 (d, J=8.1 Hz, 1H), 5.25 (s, 2H), 3.94 (s, 3H); $^{13}$C NMR (100 MHz, CDCl$_3$) δ 191.0, 153.6, 150.1, 136.0, 130.3, 128.7, 128.2, 127.2, 126.6, 112.3, 109.3, 70.9, 56.1; MS (ES+): m/z=243 (M+H)$^+$; LCMS (Method A): t$_R$=7.53 min.

Example 99

4-(Benzyloxy)-5-methoxy-2-nitrobenzaldehyde (96)

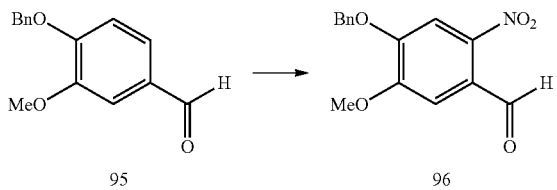 [SMILES: COc1cc(C=O)ccc1OCc1ccccc1 ; COc1cc(C=O)c([N+](=O)[O-])cc1OCc1ccccc1]

To a stirred solution of 4-(benzyloxy)-3-methoxybenzaldehyde (95) (130.00 g, 536.6 mmol) in TFA (600 mL) was added KNO$_3$ (65.10 g, 643.9 mmol, in 600 mL of TFA) dropwise at 0° C. The reaction mixture was stirred for another hour. The reaction mixture was diluted with water (2.4 L). The precipitate was filtered and washed with cold water (2×500 mL) to give the title compound (125.00 g, 81%) as a yellow solid. The product was carried through to the next step without any further purification.

$^1$H NMR (400 MHz, CDCl$_3$) δ 10.42 (s, 1H), 7.66 (s, 1H), 7.34-7.46 (m, 6H), 5.26 (s, 2H), 4.0 (s, 3H); $^{13}$C NMR (100 MHz, CDCl$_3$) δ 187.8, 153.7, 151.4, 134.85, 129.0, 128.9, 128.7, 127.6, 125.7, 110.0, 108.9, 71.6, 56.73; MS (ES+): m/z=286 (M−H)$^-$; LCMS (Method A): t$_R$=7.87 min.

Example 100

4-Hydroxy-5-methoxy-2-nitrobenzaldehyde (97)

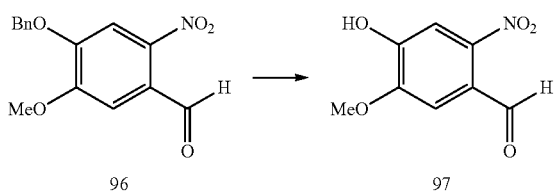 [SMILES: COc1cc(C=O)c([N+](=O)[O-])cc1OCc1ccccc1 ; COc1cc(C=O)c([N+](=O)[O-])cc1O]

To a stirred solution of 4-(benzyloxy)-5-methoxy-2-nitrobenzaldehyde (96) (100.00 g, 348.1 mmol) in AcOH (800 mL) was added HBr (48%, 88.02 mL, 522.16 mmol). The reaction mixture was stirred at 85° C. for 1 h. The reaction mixture was diluted with H₂O (1.6 L), the precipitate was filtered and washed with cold water (3×100 mL) to give the title compound (50.00 g, 73%) as a yellow solid. The product was carried through to the next step without any further purification.

¹H NMR (400 MHz, d6-DMSO) δ 11.11 (br s, 1H), 10.15 (br s, 1H), 7.50 (s, 1H), 7.35 (s, 1H), 3.94 (s, 3H); MS (ES+): m/z=196.1 (M−H)⁻; LCMS (Method B): $t_R$=2.55 min.

Example 101

5-Methoxy-2-nitro-4-((triisopropylsilyl)oxy)benzaldehyde (98)

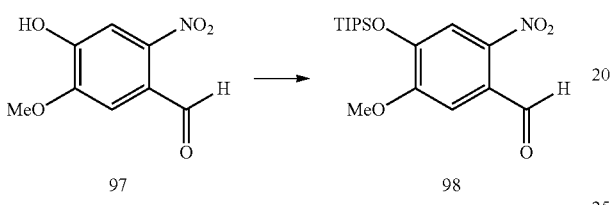

A mixture of 4-hydroxy-5-methoxy-2-nitrobenzaldehyde (97) (50.00 g, 253.6 mmol), TIPS-Cl (59.70 mL, 279.0 mmol) and imidazole (51.80 g, 760.9 mmol) was heated at 100° C. for 30 min. The reaction mixture was poured into ice-cold water and extracted with ethyl acetate (3×500 mL). The organic layer was dried over Na₂SO₄, filtered and concentrated under reduced pressure. The resulting residue was purified by column chromatography (silica), eluting with ethyl acetate/hexane (isocratic 5%), to give the title compound (57.50 g, 64%) as a yellow solid.

¹H NMR (400 MHz, CDCl₃) δ 10.42 (s, 1H), 7.59 (s, 1H), 7.40 (s, 1H), 3.95 (s, 3H), 1.33-1.24 (m, 3H), 1.07 (s, 18H).

Example 102

5-Methoxy-2-nitro-4-((triisopropylsilyl)oxy)benzoic acid (99)

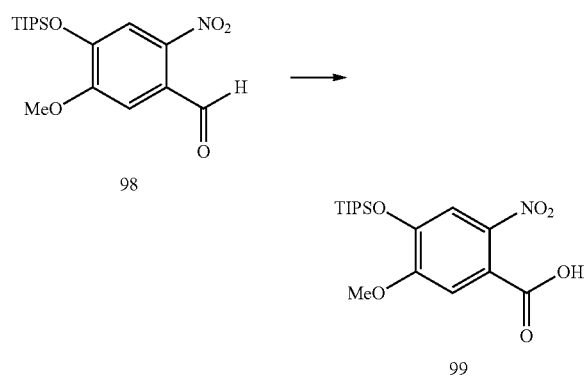

A solution of sodium chlorite (45.97 g, 406.7 mmol, 80% technical grade) and NaH₂PO₄·2H₂O (35.53 g, 227.7 mmol) in water (200 mL) was added to a solution of 5-methoxy-2-nitro-4-((triisopropylsilyl)oxy)benzaldehyde (98) (57.50 g, 162.7 mmol) in THF (800 mL) at room temperature. H₂O₂ (30% w/w, 235 mL, 2.28 mol) was immediately added to the vigorously stirred biphasic mixture. The starting material dissolved and the temperature of the reaction mixture rose to 45° C. After 30 min, the reaction was judged to have completed by TLC. The mixture was acidified to pH=3-4 with citric acid. The mixture was extracted with ethyl acetate (3×500 mL). The combined extracts were washed with water (150 mL) and brine (150 mL), dried over anhydrous Na₂SO₄, filtered and concentrated under vacuum. The resulting residue was purified by column chromatography (silica), eluting with ethyl acetate/hexane (isocratic 10%) followed by methanol/dichloromethane (from 0% to 10%), to give the title compound (38.00 g, 63%) as a yellow oil.

¹H NMR (400 MHz, CDCl₃) δ 9.81 (s, 1H), 7.35 (s, 1H), 7.25 (s, 1H), 3.91 (s, 3H), 1.26 (q, J=7.4 Hz, 3H), 1.09 (d, J=7.4 Hz, 18H); MS (ES+): m/z=368.1 (M−H)⁻; LCMS (Method B): $t_R$=4.75 min.

Example 103

(S)-(2-(Hydroxymethy)piperidin-1-yl)(5-methoxy-2-nitro-4 ((triisopropylsilyl)oxy)phenyl)methanone (100)

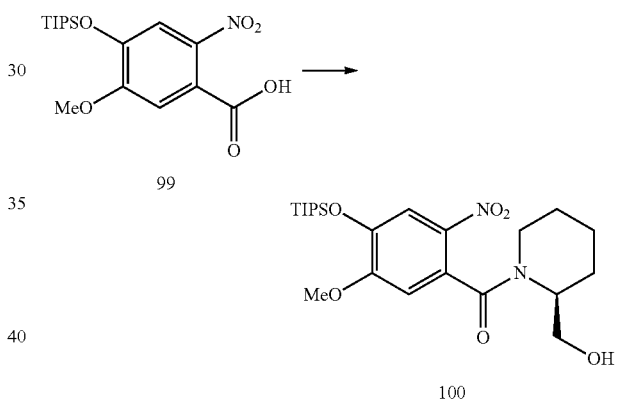

A solution of 5-methoxy-2-nitro-4-((triisopropylsilyl)oxy)benzoic acid (99) (28.00 g, 75.8 mmol), HATU (31.70 g, 83.4 mmol) and dry Et₃N (44 mL) in dry DCM (300 mL) was stirred at room temperature for 30 min. (S)-Piperidin-2-ylmethanol (11.35 g, 98.5 mmol) was added and the reaction mixture was stirred at room temperature for 2 h. The reaction mixture was partitioned between DCM (500 mL×2) and water (100 mL).

Organic layer was dried over Na₂SO₄, filtered and concentrated under reduced pressure. The resulting residue was purified by column chromatography (silica), eluting with ethyl acetate/hexane (from 50% to 75%), to give the title compound (20.00 g, 57%) as a yellow solid.

¹H NMR (400 MHz, CDCl₃) δ 7.68-7.65 (m, 1H), 7.03-6.65 (m, 1H), 5.04-4.69 (m, 1H), 4.12-4.05 (m, 0.41H), 4.01-3.95 (m, 0.46H), 3.92-3.89 (m, 2.57H), 3.83-3.74 (m, 1.47H), 3.64-3.59 (m, 0.351H), 3.45-3.40 (m, 0.28H), 3.21-3.01 (m, 1.39H), 2.87-2.79 (m, 0.38H), 1.97-1.94 (m, 0.55H), 1.88-1.77 (m, 0.58H), 1.73-1.62 (m, 3H), 1.56-1.44 (m, 2H), 1.29-1.24 (m, 3H), 1.09 (d, J=7.3 Hz, 18H); MS (ES+): m/z=467.3 (M+H)⁺; LCMS (Method A): $t_R$=4.75 min.

Example 104

(S)-(2-Amino-5-methoxy-4-((triisopropylsilyl)oxy)
phenyl)(2-(hydroxymethyl)piperidin-1-yl)methanone
(101)

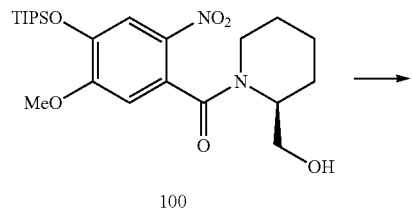

100

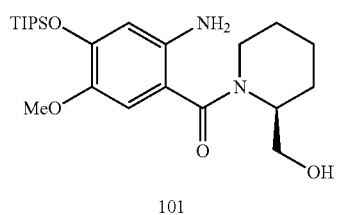

101

A mixture of (S)-(2-(hydroxymethyl)piperidin-1-yl)(5-methoxy-2-nitro-4 ((triisopropylsilyl)oxy)phenyl)methanone (100) (10.0 g, 21.4 mmol), palladium on activated charcoal (10% wt. basis) (1.00 g) in methanol (100 mL) was stirred at room-temperature under H$_2$ for 18 h. The reaction mixture was filtered through Celite® and the cake was washed with ethyl acetate (150 mL). The filtrate was concentrated under reduced pressure. The resulting residue was purified by column chromatography (silica), eluting with ethyl acetate/hexane (from 50% to 67%), to give the title compound (8.00 g, 85%) as a yellow oil.

$^1$H NMR (400 MHz, CDCl$_3$) δ 6.67 (s, 1H), 6.30 (s, 1H), 4.00-3.81 (m, 4H), 3.72 (s, 3H), 3.57 (s, 1H), 3.08 (s, 1H), 1.68-1.64 (m, 4H), 1.57-1.43 (m, 2H), 1.28-1.17 (m, 3H), 1.08 (d, J=7.4 Hz, 18H); MS (ES+): m/z=437.3 (M+H)$^+$: LCMS (Method B): t$_R$=1.94 min.

Example 105

Allvy (S)-(2-(2-(hydroxymethyl)piperidine-1-carbonyl)-4-methoxy-5 ((triisopropylsilyl)oxy)phenyl)
carbamate (102)

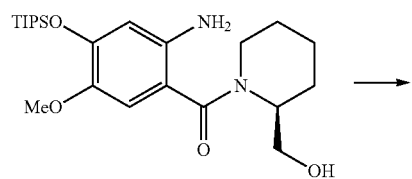

101

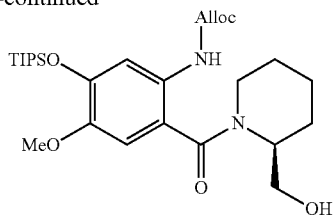

102

To a stirred solution of (S)-(2-amino-5-methoxy-4-((triisopropylsilyl)oxy)phenyl)(2-(hydroxymethyppiperidin-1-yl)methanone (101) (22.00 g, 50.4 mmol) and pyridine (7.97 g, 100.8 mmol) in dichloromethane (300 mL) was added allyl chloroformate (6.38 g, 52.9 mmol) dropwise at −10° C. After 30 min, the reaction was judged to have completed by TLC. Reaction mixture was diluted with dichloromethane (500 mL) and washed with a saturated aqueous solution of copper (II) sulfate (150 mL), water (100 mL) and a saturated aqueous solution of sodium hydrogen carbonate (100 mL). The organic layer was dried over Na$_2$SO$_4$, filtered and concentrated under reduced pressure.

The resulting residue was purified by column chromatography (silica), eluting with ethyl acetate/hexane (from 50% to 75%), to give the title compound (17.00 g, 65%) as a yellow oil.

$^1$H NMR (400 MHz, CDCl$_3$) δ 8.08 (s, 1H), 7.62 (s, 1H), 6.75 (s, 1H), 5.92 (ddt, J=17.2, 10.7, 5.5 Hz, 1H), 5.32 (dt, J=17.3, 1.7 Hz, 1H), 5.20 (dt, J=10.6, 1.4 Hz, 1H), 4.61 (dt, J=5.5, 1.5 Hz, 2H), 3.88 (t, J=10.7 Hz, 1H), 3.76 (s, 3H), 3.61-3.57 (m, 1H), 3.20-3.02 (m, 2H), 2.03 (s, 1H), 1.65-1.62 (m, 3H), 1.53-1.40 (m, 2H), 1.29-1.24 (m, 4H), 1.11-1.08 (m, 18H); MS (ES+): m/z=522.3 (M+H)$^+$: LCMS (Method A): t$_R$=5.23 min.

Example 106

Allyl (6αS)-6-hydroxy-2-methoxy-12-oxo-3-((triisopropylsilyl)oxy)-6,6a,7,8,9,10-hexahydrobenzo[e]
pyrido[1,2-a][1,4]diazepine-5(12H)-carboxylate
(103)

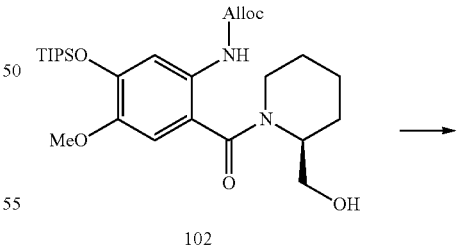

102

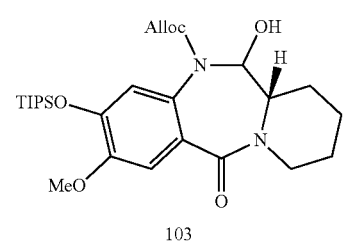

103

A mixture of allyl (S)-(2-(2-(hydroxymethyl)piperidine-1-carbonyl)-4-methoxy-5 ((triisopropylsilyl)oxy)phenyl)carbamate (102) (17.00 g, 32.7 mmol), TEMPO (510 mg, 3.3 mmol) and PIDA (12.62 g, 39.2 mmol) in DCM (150 mL) was stirred at room-temperature for 16 h. The reaction mixture was diluted with DCM (350 mL), washed with aq. Na$_2$SO$_3$ (100 mL), aq. NaHCO$_3$ (100 mL) and brine (100 mL). The organic phase was dried over anhydrous Na$_2$SO$_4$, filtered and concentrated under reduced pressure. The resulting residue was purified by column chromatography (silica), eluting with ethyl acetate/hexane (from 50% to 75%), to give the title compound (13.00 g, 77%) as a yellow oil.

$^1$H NMR (400 MHz, CDCl$_3$) δ 7.13 (s, 1H), 6.65 (s, 1H), 5.90 (d, J=10.3 Hz, 1H), 5.78 (td, J=10.6, 5.3 Hz, 1H), 5.19-5.13 (m, 2H), 4.60 (dd, J=13.1, 5.8 Hz, 1H), 4.52-4.40 (m, 1H), 4.35 (dt, J=13.6, 4.5 Hz, 1H), 3.84 (s, 3H), 3.57-3.39 (m, 2H), 3.14-2.99 (m, 1H), 2.08-1.99 (m, 1H), 1.76-1.61 (m, 5H), 1.25-1.18 (m, 3H), 1.09-1.05 (m, 18H); MS (ES+): m/z=519.3 (M+H)$^+$: LCMS (Method A): t$_R$=2.41 min.

Example 107

Allyl (6αS)-2-methoxy-12-oxo-6-((tetrahydro-2H-pyran-2-yl)oxy)-3-((triisopropylsilyl)oxy)-6,6a,7,8,9,10-hexahydrobenzo[e]pyrido[1,2-a][1,4]diazepine-5(12H)-carboxylate (104)

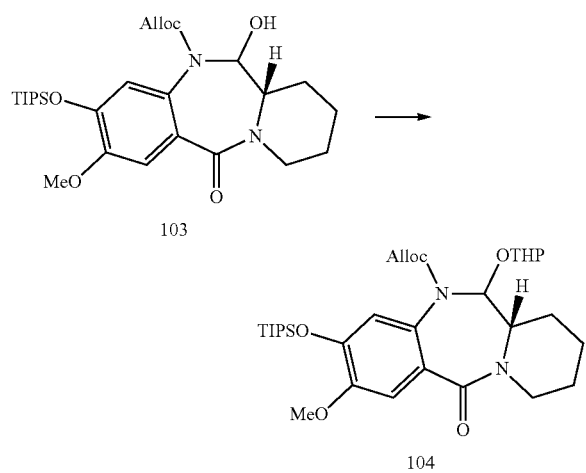

A mixture of allyl (6aS)-2-methoxy-12-oxo-6-((tetrahydro-2H-pyran-2-yl)oxy)-3-((triisopropylsilyl)oxy)-6,6a,7,8,9,10-hexahydrobenzo[e]pyrido[1,2-α][1,4]diazepine-5(12H)-carboxylate (103) (14.00 g, 27.0 mmol), DHP (22.70 g, 269.9 mmol) and pTSA·H$_2$O (140 mg, 0.76 mmol) in THF (130 mL) was stirred at room-temperature for 18 h. The reaction mixture was diluted with ethyl acetate (360 mL), washed with aq. NaHCO$_3$ (200 mL) and brine (100 mL). The organic phase was dried over anhydrous Na$_2$SO$_4$, filtered and concentrated under reduced pressure. The resulting residue was purified by column chromatography (silica), eluting with ethyl acetate/hexane (isocratic 17%), to give the title compound (12.50 g, 77%) as a yellow oil.

$^1$H NMR (400 MHz, CDCl$_3$) δ 7.13 (s, 0.38H), 7.10 (s, 0.53H), 6.90 (s, 0.50H), 6.52 (s, 0.35H), 6.15 (d, J=10.0 Hz, 0.37H), 5.98 (d, J=10.0 Hz, 0.51H), 5.80-5.68 (m, 0.88H), 5.17-4.94 (m, 2.73H), 4.64-4.21 (m, 3H), 3.91-3.85 (m, 0.85H), 3.83 (d, J=1.8 Hz, 3H), 3.66-3.39 (m, 2H), 3.14-3.00 (m, 1H), 2.08-1.87 (m, 1H), 1.83-1.33 (m, 12H), 1.26-1.19 (m, 3H), 1.08-1.05 (m, 18H); MS (ES+): m/z=603.4 (M+H)$^+$: LCMS (Method A): t$_R$=6.41 min.

Example 108

Allyl (6αS)-3,6-dihydroxy-2-methoxy-12-oxo-6,6a,7,8,9,10-hexahydrobenzo[e]pyrido[1,2-a][1,4]diazepine-5(12H)-carboxylate (105)

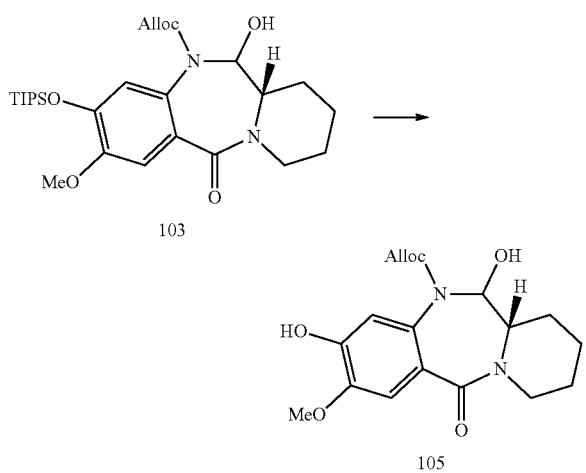

A 1 M solution of tetrabutylammonium fluoride in tetrahydrofuran (0.3 mL) was added to a mixture of allyl (6aS)-2-methoxy-12-oxo-6-((tetrahydro-2H-pyran-2-yl)oxy)-3-((triisopropylsilyl)oxy)-6,6a,7,8,9,10-hexahydrobenzo[e]pyrido[1,2-α][1,4]diazepine-5(12H)-carboxylate (103) (50 mg, 0.10 mmol) in 1,4-dioxane (2 mL). the reaction mixture was stirred for 30 min and it was then washed with a saturated aqueous solution of sodium chloride (30 mL). The aqueous solution was washed with ethyl acetate (2×30 mL) and the organic solvent was concentrated under vacuum. The resulting residue was purified by column chromatography (silica), eluting with acetone/dichloromethane to give the title compound (36 mg, 99%) as a yellow oil.

MS (ES+): m/z=363 (M+H)$^+$: LCMS (Method B): t$_R$=2.60 min.

Example 109

(S)-3-1-hydroxy-2-methoxy-7,8,9,10-tetrahydrobenzo[e]pyrido[1,2-α][1,4]diazepin-12(6aH)-one (106)

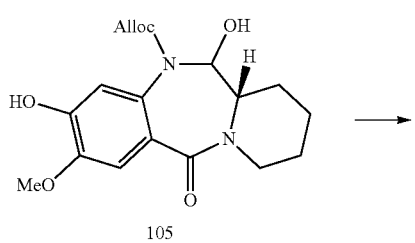

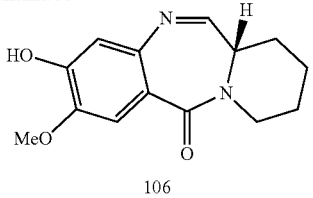

106

To a solution of allyl (6a5)-3,6-dihydroxy-2-methoxy-12-oxo-6,6a,7,8,9,10-hexahydrobenzo[e]pyrido[1,2-a][1,4]diazepine-5(12H)-carboxylate (105) (36.0 mg, 0.10 mmol) in dichloromethane (3 mL) was sequentially added tetrakis(triphenylphosphine)palladium(0) (5.7 mg, 5 mol %), and pyrrolidine (9.7 mL, 0.12 mmol). The reaction mixture was stirred at room temperature for 30 min. The reaction mixture concentrated in vacua and subjected to high vacuum for 40 min until excess pyrrolidine was removed. The resulting residue was then purified by column chromatography (silica), eluting with methanol/dichloromethane (from 0% to 10%) to give the title compound (20 mg, 76%) as a cream solid.

$^1$H NMR (400 MHz, CDCl$_3$) δ 7.89 (d, J=5.9 Hz, 1H), 7.41 (s, 1H), 6.84 (s, 1H), 3.92 (s, 3H), 3.80-3.69 (m, 2H), 3.28-3.16 (m, 1H), 2.18-2.01 (m, 2H), 1.99-1.81 (m, 4H); $^{13}$C NMR (100 MHz, CDCl$_3$) δ 163.2, 148.4, 145.9, 145.6, 120.8, 112.0, 111.2, 56.2, 49.6, 39.7, 24.4, 22.9, 18.3; MS (ES+): m/z=279 (M+H+H$_2$O)$^+$; LCMS (Method A): t$_R$=4.68 min.

Example 110

(S)-4-((2-Methoxy-12-oxo-6a,7,8,9,10,12-hexahydrobenzo[e]pyrido[1,2-α][1,4]diazepin-3-yl)oxy)butanoic acid (107)

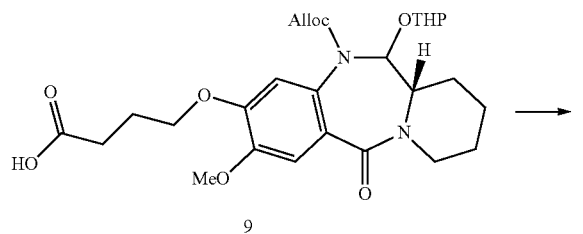

9

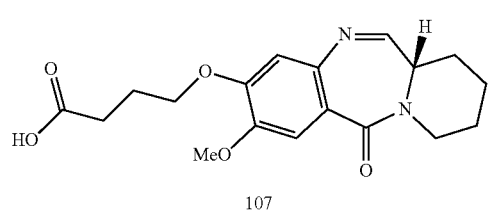

107

To a solution 4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)butanoic acid (9) (50.0 mg, 0.09 mmol) in dichloromethane (3 mL) was sequentially added tetrakis(triphenylphosphine)palladium(0) (5.4 mg, 5 mol %), and pyrrolidine (90 µL, 0.11 mmol). The reaction mixture was stirred at room temperature for 30 min. The reaction mixture concentrated in vacuo and subjected to high vacuum for 40 min until excess pyrrolidine was removed. The resulting residue was then purified by column chromatography (silica), eluting with methanol/dichloromethane (from 0% to 10%) to give the title compound (25 mg, 80%) as a cream solid.

$^1$H NMR (400 MHz, CDCl$_3$) δ 7.87 (br. s., 1H), 7.39 (s, 1H), 6.81 (s, 1H), 4.16-4.00 (m, 3H), 3.88 (s, 3H), 3.83-3.72 (m, 2H), 3.29-3.15 (m, 1H), 2.52 (br. s., 2H), 2.20-1.77 (m, 8H); $^{13}$C NMR (100 MHz, CDCl$_3$) δ 176.5, 167.7, 150.7, 139.2, 128.5, 121.1, 111.7, 109.7, 67.8, 56.1, 49.7, 39.8, 30.3, 24.4, 22.9, 18.2; MS (ES+): m/z=347 (M+H)$^+$: LCMS (Method B): t$_R$=2.73 min.

Example 111

Allyl (6αS)-3-hydroxy-2-methoxy-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (108)

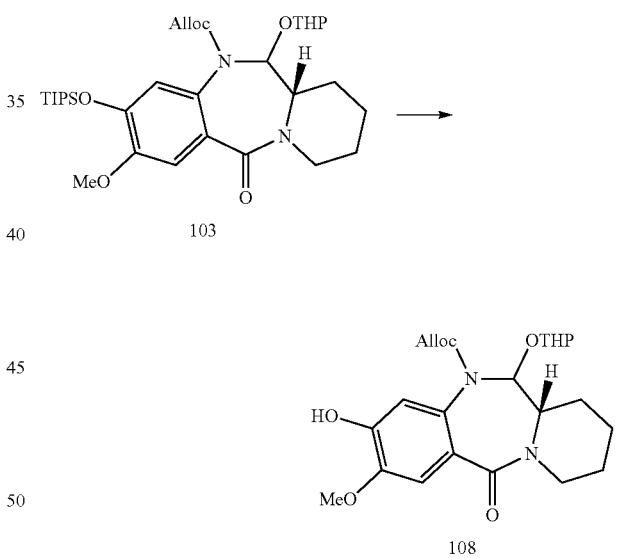

To a solution of allyl (6αS)-2-methoxy-12-oxo-6-((tetrahydro-2H-pyran-2-yl)oxy)-3-((triisopropylsilyl)oxy)-6,6a,7,8,9,10-hexahydrobenzo[e]pyrido[1,2-a][1,4]diazepine-5(12H)-carboxylate (103) (2.0 g, 3.32 mmol) in THF (10 mL) was added TBAF (1 M, 5 mL). The reaction mixture was stirred at room temperature for 5 min and concentrated under reduced pressure. The resulting residue was purified by column chromatography (silica), eluting with ethyl acetate/hexane (from 0% to 100%), to give the title compound (1.2 g, 83%) as a white solid.

MS (ES+): m/z=446.7 (M+H)$^+$: LCMS (Method A): t$_R$=3.22 min.

Example 112

Allyl (6αS)-2-methoxy-3-((3-(2-methoxy-2-oxo-ethyl)benzyl)oxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (109)

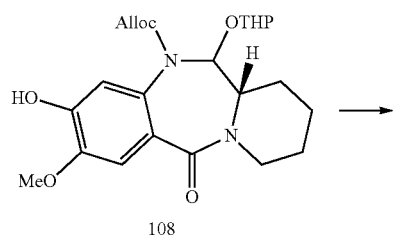

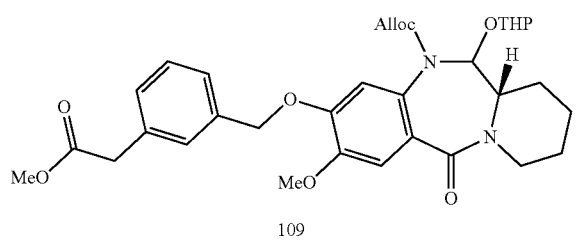

A mixture of allyl (6αS)-3-hydroxy-2-methoxy-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (108) (1.2 g, 2.69 mmol), methyl 2-(3-(bromomethyl)phenyl)acetate (686 mg, 2.82 mmol) and $K_2CO_3$ (560 mg, 4.05 mmol), in DMF (15 mL) was stirred at room temperature for 18 h. The reaction mixture was poured into ice-cold water (50 mL) and extracted with ethyl acetate (2×80 mL). The combined organic extracts were concentrated in vacua. The resulting residue was purified by column chromatography (silica), eluting with ethyl acetate/hexane (from 0% to 100%), to give the title compound (1.08 g, 66%) as a colourless oil.

MS (ES+): m/z=608.8 (M+H)$^+$: LCMS (Method B): $t_R$=3.73 min.

Example 113

2-(3-(((((6αS)-5-((Allyloxy)carbonyl)-2-methoxy-12-oxo-6-((tetrahydro-2H-pyran-2-yl)oxy)-5,6,6a,7,8,9,10,12-octahydrobenzo[e]pyrid[1,2-a][1,4]diazepin-3-yl)oxy)methyl)phenyl)acetic acid (110)

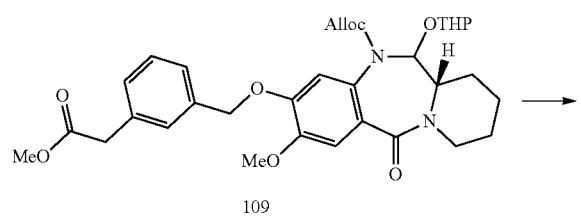

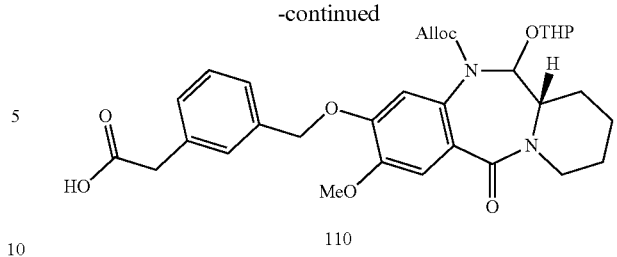

To a solution of (6αS)-2-methoxy-3-((3-(2-methoxy-2-oxoethyl)benzypoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (109) (1.08 g, 1.77 mmol) in 1,4-dioxane (9 mL) was added an aqueous solution of sodium hydroxide (1 M, 9 mL, 9 mmol). The reaction mixture was stirred at room temperature for 1 h and was then concentrated in vacua, after which water (15 mL) was added and the aqueous layer was acidified to pH=4 with an aqueous solution of citric acid (1 M, 10 mL). The aqueous layer was then extracted with ethyl acetate (2×50 mL). The organic layer was washed with brine (50 mL). The combined organic extracts were dried over sodium sulfate, filtered and concentrated to give the title compound (900 mg, 86%) as a white solid. The product was carried through to the next step without any further purification.

MS (ES+): m/z=594.7 (M+H)$^+$: LCMS (Method B): $t_R$=3.43 min.

Example 114

Allyl (6αS)-2-methoxy-3-((3-(2-((5-(methoxycarbonyl)-1-methyl-1H-pyrrol-3-yl)amino)-2-oxoethyl)benzyl)oxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (111)

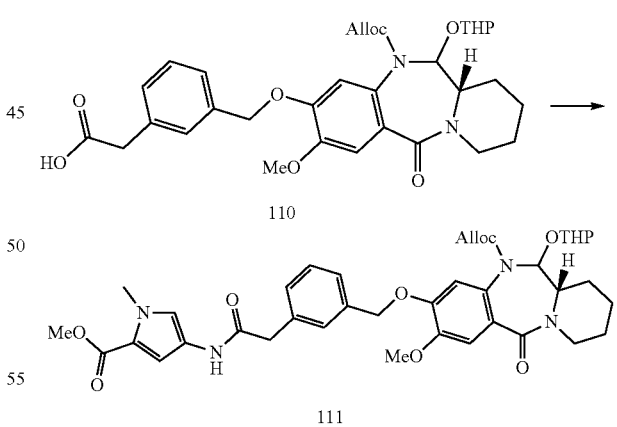

A solution of 2-(3-(((((6αS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)methyl)phenyl)acetic acid (110) (450 mg, 0.757 mmol) in N,N-dimethylformamide (4 mL) was charged with N,N-dimethylpyridin-4-amine (232 mg, 1.90 mmol) and N-(3-dimethylaminopropyl)-N'-ethylcarbodiimide hydrochloride (291 mg, 1.52 mmol) and it was stirred for 30 min at room temperature. Methyl 4-amino-1-methyl-1H-pyrrole- 2-carboxylate hydrochloride (145 mg, 0.761 mmol) was added and the solution was stirred for further 18 h. The reaction mixture was poured into ice-cold water (50 mL) and extracted with ethyl acetate (2×80 mL). The combined organic extracts were concentrated in vacua. The resulting residue was purified by column chromatography (silica), eluting with ethyl acetate/hexane (from 0% to 100%), to give the title compound (245 mg, 44%) as a brown oil.

MS (ES+): m/z=730.8 (M+H)$^+$: LCMS (Method B): $t_R$=3.58 min.

Example 115

Methyl (S)-4-(2-(3-(((2-methoxy-12-oxo-6a,7,8,9,10,12-hexahydrobenzo[e]pyrido[1,2-a][1,4]diazepin-3-yl)oxy)methyl)phenyl)acetamido)-1-methyl-1H-pyrrole-2-carboxylate (112)

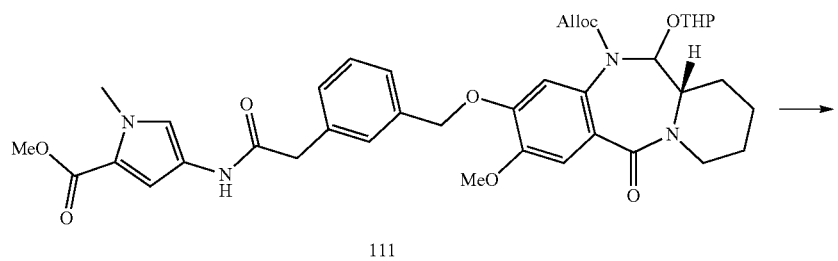

111

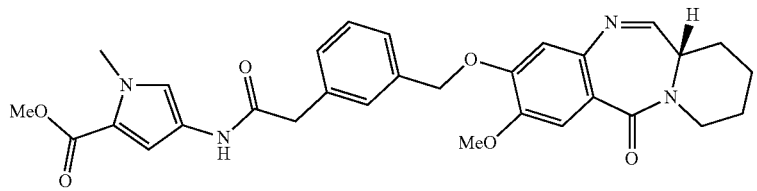

112

To a solution of allyl (6αS)-2-methoxy-3-((3-(2-((5-(methoxycarbonye-1-methyl-1H-pyrrol-3-yl)amino)-2-oxo-ethyl)benzyl)oxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (111) (20 mg, 0.0274 mmol) in dichloromethane (1 mL) was sequentially added tetrakis(triphenylphosphine)palladium(0) (1.6 mg, 5 mol %), and pyrrolidine (2.7 µL, 0.0329 mmol). The reaction mixture was stirred at room temperature for 30 min. The reaction mixture concentrated in vacua and subjected to high vacuum for 40 min until excess pyrrolidine was removed. The resulting residue was then purified by column chromatography (silica), eluting with methanol/dichloromethane (from 0% to 10%) to give the title compound (11.0 mg, 74%) as a yellow oil.

$^1$H NMR (400 MHz, CDCl$_3$) δ 7.90 (d, J=5.9 Hz, 1H), 7.46 (s, 1H), 7.34-7.40 (m, 5H), 6.86 (s, 1H), 6.62 (d, J=1.9 Hz, 1H), 5.18 (q, J=12.5 Hz, 2H), 4.24 (d, J=13.7 Hz, 1H), 3.94 (s, 3H), 3.88 (s, 1H), 3.86 (s, 3H), 3.78 (s, 3H), 3.73 (s, 1H), 3.71 (s, 1H), 3.69 (s, 2H), 3.18-3.27 (m, 1H), 1.80-1.91 (m, 3H), 1.70-1.77 (m, 2H); MS (ES+): m/z=544.7 (M+H)$^+$: LCMS (Method B): $t_R$=3.03 min; LCMS (Method A): $t_R$=6.35 min.

Example 116

Allyl (6αS)-3-((3-(2-((2-(ethoxycarbonyl)-1-methyl-1H-imidazol-4-yl)amino)-2-oxoethyl)benzyl)oxy)-2-methoxy-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (113)

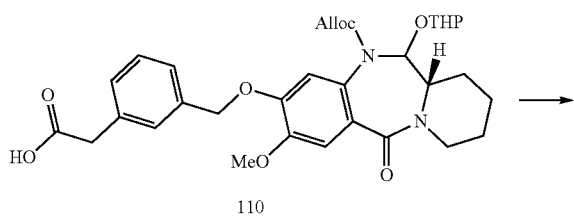

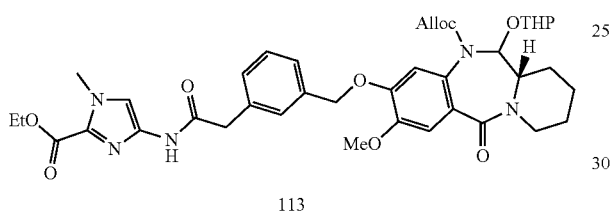

A solution of 2-(3-(((((6αS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)methyl)phenyl)acetic acid (110) (450 mg, 0.757 mmol) in N,N-dimethylformamide (4 mL) was charged with N,N-dimethylpyridin-4-amine (232 mg, 1.90 mmol) and N-(3-dimethylaminopropyl)-N'-ethylcarbodiimide hydrochloride (291 mg, 1.52 mmol) and it was stirred for 30 min at room temperature. Ethyl 4-amino-1-methyl-1H-imidazole-2-carboxylate hydrochloride (156 mg, 0.759 mmol) was added and the solution was stirred for further 18 h. The reaction mixture was poured into ice-cold water (50 mL) and extracted with ethyl acetate (2×80 mL). The combined organic extracts were concentrated in vacuo. The resulting residue was purified by column chromatography (silica), eluting with ethyl acetate/hexane (from 0% to 100%), followed by methanol/dichloromethane (from 0% to 100%), to give the title compound (407 mg, 72%) as a colourless oil.

MS (ES+): m/z=745.9 (M+H)+: LCMS (Method B): $t_R$=3.55 min.

Example 117

Ethyl (S)-4-(2-(3-(((2-methoxy-12-oxo-6a,7,8,9,10,12-hexahydrobenzo[e]pyrido[1,2-a][1,4]diazepin-3-yl)oxy)methyl)phenyl)acetamido)-1-methyl-1H-imidazole-2-carboxylate (114)

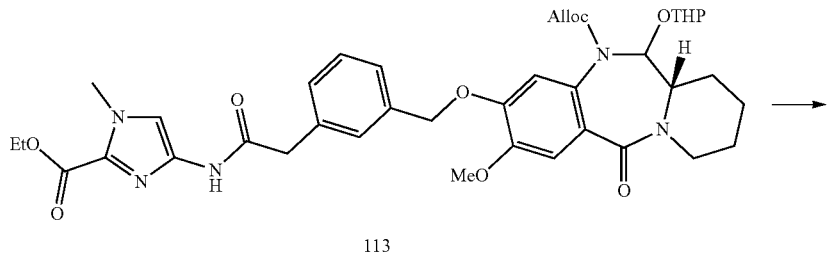

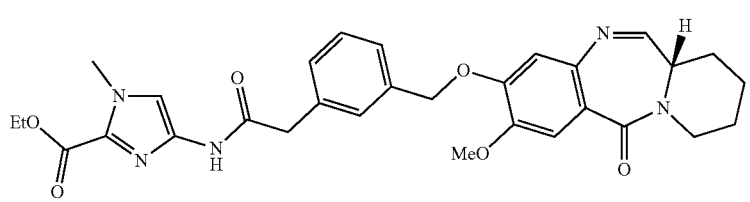

To a solution of allyl (6αS)-3-((3-(2-((2-(ethoxycarbonyl)-1-methyl-1H-imidazol-4-yl)amino)-2-oxoethyl)benzyl)oxy)-2-methoxy-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (113) (20 mg, 0.0268 mmol) in dichloromethane (1 mL) was sequentially added tetrakis(triphenylphosphine)palladium(0) (1.6 mg, 5 mol %), and pyrrolidine (2.6 mL, 0.0268 mmol). The reaction mixture was stirred at room temperature for 30 min. The reaction mixture concentrated in vacua and subjected to high vacuum for 40 min until excess pyrrolidine was removed. The resulting residue was then purified by column chromatography (silica), eluting with methanol/dichloromethane (from 0% to 5%) to give the title compound (4.05 mg, 29%) as a yellow oil.

$^1$H NMR (400 MHz, CDCl$_3$) δ 7.89 (br. s., 1H), 7.54-7.51 (m, 1H), 7.46 (br. s., 1H), 7.43-7.32 (m, 3H), 7.26-7.21 (m, 1H), 6.83 (br. s., 1H), 5.25-5.08 (m, 2H), 4.42-4.35 (m, 2H), 4.24 (d, J=14.1 Hz, 1H), 4.00-3.97 (m, 2H), 3.97-3.94 (m, 3H), 3.77-3.71 (m, 3H), 3.32-3.12 (m, 1H), 2.16-2.01 (M, 2H), 1.96 (br. S., 1H), 1.89-1.64 (m, 5H), 1.42-1.36 (m, 3H); MS (ES+): m/z=559.9 (M+H)$^+$: LCMS (Method B): t$_R$=2.95 min; LCMS (Method A): t$_R$=6.15 min.

Example 118

4-(2-(3-(((((6αS)-5-((Allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)methyl)phenyl)acetamido)-1-methyl-1H-imidazole-2-carboxylic acid (115)

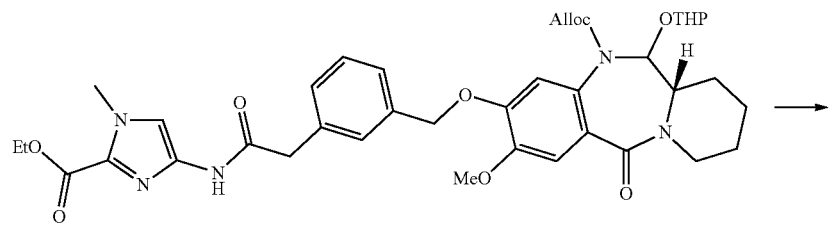

114

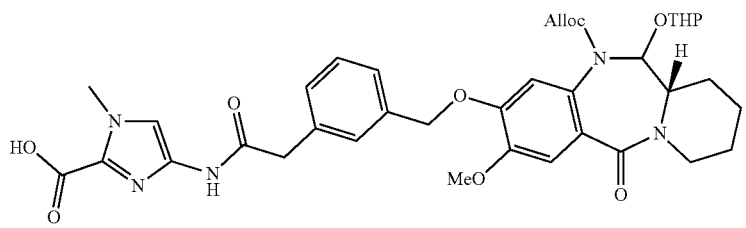

115

To a solution of allyl (6αS)-3-((3-(2-((2-(ethoxycarbonyl)-1-methyl-1H-imidazol-4-yl)amino)-2-oxoethyl)benzyl)oxy)-2-methoxy-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (114) (330 mg, 0.442 mmol) in 1,4-dioxane (2.5 mL) was added an aqueous solution of sodium hydroxide (1 M, 2.5 mL, 2.5 mmol). The reaction mixture was stirred at room temperature for 1.5 h and was then concentrated in vacua, after which water (15 mL) was added and the aqueous layer was acidified to pH=4 with an aqueous solution of citric acid (1 M, 10 mL). The aqueous layer was then extracted with ethyl acetate (2×50 mL). The organic layer was washed with brine (50 mL). The combined organic extracts were dried over sodium sulfate, filtered and concentrated in vacua The resulting residue was then purified by column chromatography (silica), eluting with methanol/dichloromethane (from 0% to 10%) to give the title compound (133 mg, 42%) as a cream solid.

MS (ES+): m/z=717.8 (M+H)$^+$: LCMS (Method B): $t_R$=3.23 min.

Example 119

Methyl 2-(4-(2-(3-(((((6αS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)methyl)phenyl)acetamido)-1-methyl-1H-imidazole-2-carboxamido)benzo[d]thiazole-5-carboxylate (116)

A solution of 4-(2-(3-(((((6αS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)methyl)phenyl)acetamido)-1-methyl-1H-imidazole-2-carboxylic acid (115) (65 mg, 0.0906 mmol) in anhydrous dichloromethane (1 mL) was charged with N-[(dimethylamino)-1H-1,2,3-triazolo-[4,5-b]pyridin-1-yl-methylene]-N-methylmethanaminium hexafluorophosphate N-oxide (37 mg, 0.0973 mmol) and anhydrous triethylamine (54 μL, 0.387 mmol). The reaction mixture was stirred at room temperature for 20 min. Methyl 2-aminobenzo[d]thiazole-5-carboxylate (19 mg, 0.0912 mmol) was then added and the resulting mixture was stirred at room temperature for 16 h. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacua. The resulting residue was then purified by column chromatography (silica), eluting with ethyl acetate/hexane (from 0% to 100%), followed by methanol/dichloromethane (from 0% to 100%), to give the title compound (23 mg, 28%) as a yellow oil.

MS (ES+): m/z=907.8 (M+H)$^+$: LCMS (Method B): $t_R$=3.98 min.

Example 120

2-(4-(2-(3-(((((6αS)-5-((Allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)methyl)phenyl)acetamido)-1-methyl-1H-imidazole-2-carboxamido)benzo[d]thiazole-5-carboxylic acid (117)

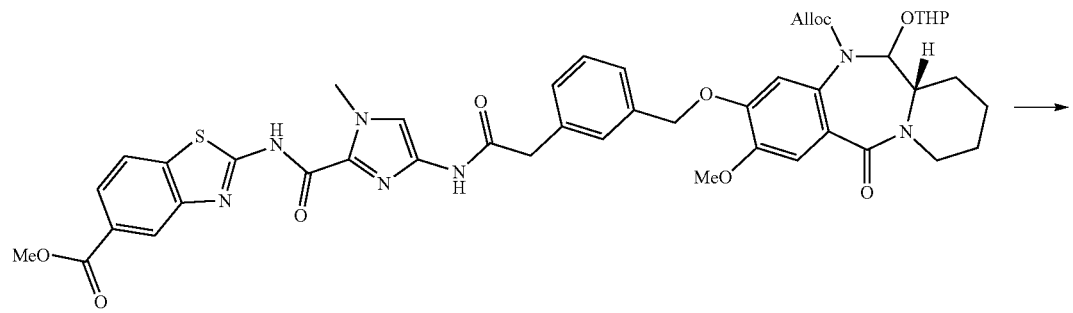

116

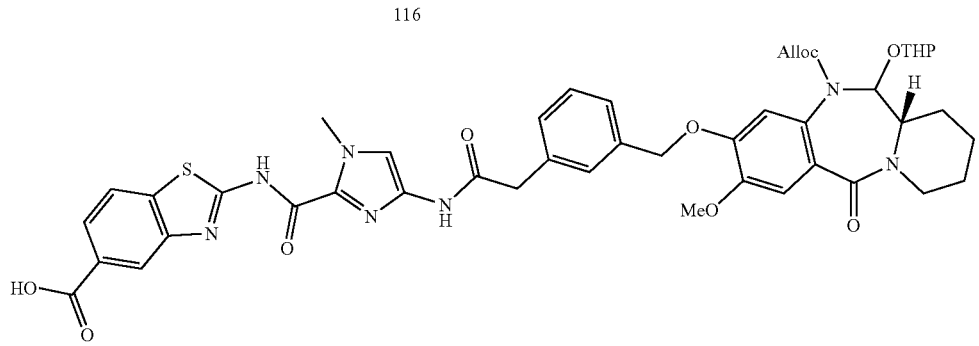

117

To a solution of methyl 2-(4-(2-(3-(((((6αS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)methyl)phenyl)acetamido)-1-methyl-1H-imidazole-2-carboxamido)benzo[d]thiazole-5-carboxylate (116) (10 mg, 0.011 mmol) in 1,4-dioxane (0.5 mL) was added an aqueous solution of sodium hydroxide (1 M, 0.5 mL, 0.5 mmol). The reaction mixture was stirred at room temperature for 1 h and was then concentrated in vacua, after which water (15 mL) was added and the aqueous layer was acidified to pH=4 with an aqueous solution of citric acid (1 M, 10 mL). The aqueous layer was then extracted with ethyl acetate (×50 mL). The organic layer was washed with brine (50 mL). The combined organic extracts were dried over sodium sulfate, filtered and concentrated in vacua to give the title compound (9.7 mg, 98%) as a white solid. The product was carried through to the next step without any further purification MS (ES+): m/z=893.8 (M+H)$^+$: LCMS (Method B): $t_R$=3.58 min.

Example 121

Allyl (6αS)-2-methoxy-3-((3-(2-((1-methyl-2-((5-(phenylcarbamoyl)benzo[d]thiazol-2-yl)carbamoyl)-1H-imidazol-4-yl)amino)-2-oxoethyl)benzyl)oxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (118)

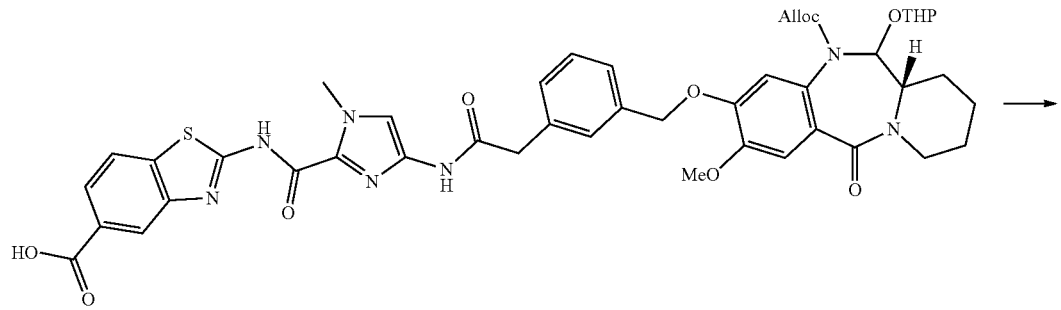

117

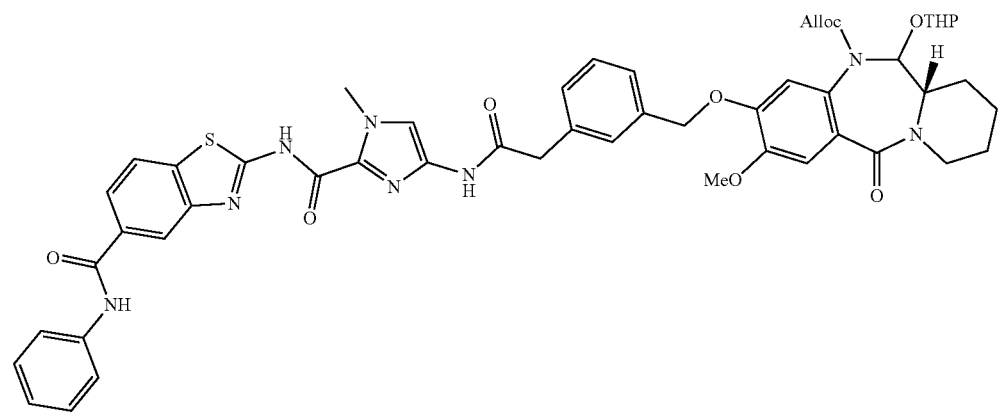

118

A solution of 2-(4-(2-(3-(((((6αS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)methyl)phenyl)acetamido)-1-methyl-1H-imidazole-2-carboxamido)benzo[d]thiazole-5-carboxylic acid (117) (9.7 mg, 0.0109 mmol) in anhydrous dichloromethane (0.5 mL) was charged with N-[(dimethylamino)-1H-1,2,3-triazolo-[4,5-b]pyridin-1-ylmethylene]-N-methyl-methanaminium hexafluorophosphate N-oxide (4.3 mg, 0.0113 mmol) and anhydrous triethylamine (6.5 µL, 0.0466 mmol). The reaction mixture was stirred at room temperature for 20 min. Aniline (1.0 µL, 0.0109 mmol) was then added and the resulting mixture was stirred at room temperature for 2 h. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacua. The resulting residue was then purified by column chromatography (silica), eluting with ethyl acetate/hexane (from 0% to 100%), followed by methanol/dichloromethane (from 0% to 100%), to give the title compound (3.4 mg, 32%) as a cream film.

MS (ES+): m/z=968.9 (M+H)$^+$: LCMS (Method B): $t_R$=3.88 min.

Example 122

(S)-2-(4-(2-(3-(((2-Methoxy-12-oxo-6a,7,8,9,10,12-hexahydrobenzo[e]pyrido[1,2-a][1,4]diazepin-3-yl)oxy)methyl)phenyl)acetamido)-1-methyl-1H-imidazole-2-carboxamido)-N-phenylbenzo[d]thiazole-5-carboxamide (119)

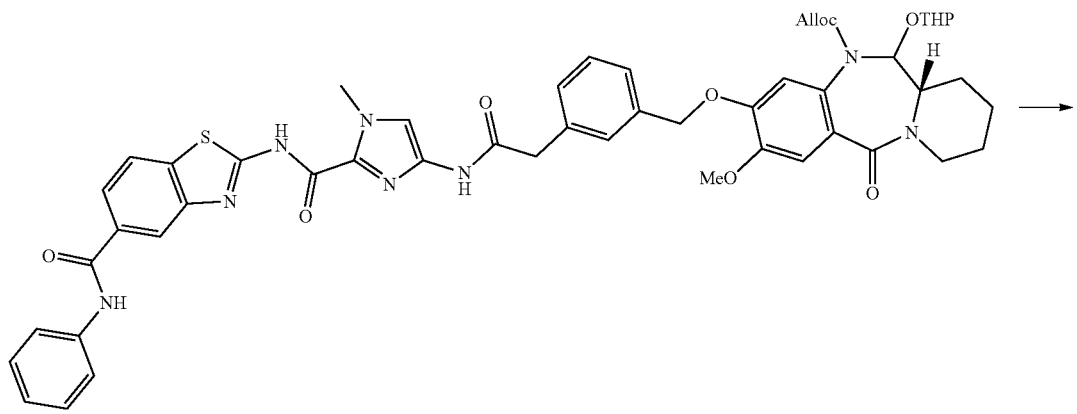

118

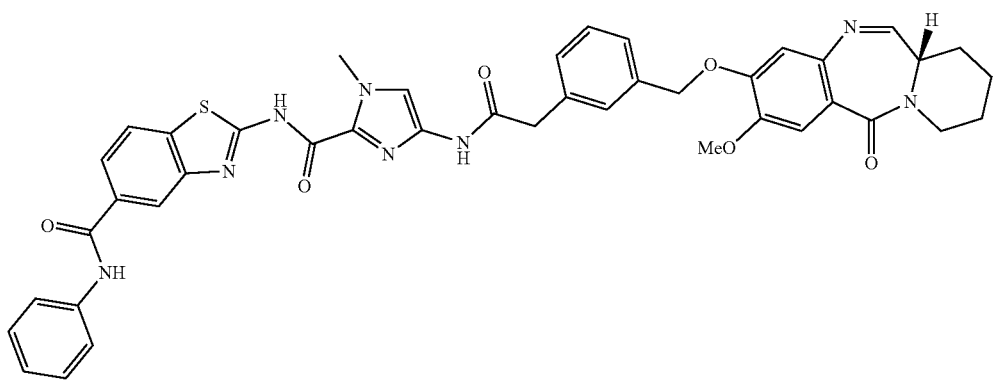

119

To a solution of allyl (6αS)-2-methoxy-3-((3-(2-((1-methyl-2-((5-(phenylcarbamoyebenzo[d]thiazol-2-yl)carbamoyl)-1H-imidazol-4-yl)amino)-2-oxoethyl)benzyl)oxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (118) (3.4 mg, 0.00351 mmol) in dichloromethane (0.5 mL) was sequentially added tetrakis(triphenylphosphine)palladium(0) (0.2 mg, 5 mol %), and pyrrolidine (0.4 μL, 0.00487 mmol). The reaction mixture was stirred at room temperature for 1 h. The reaction mixture concentrated in vacua and subjected to high vacuum for 40 min until excess pyrrolidine was removed. The resulting residue was then purified by column chromatography (silica), eluting with methanol/dichloromethane (from 0% to 100%) to give the title compound (1.5 mg, 55%) as a cream film.

$^1$H NMR (400 MHz, DMSO-d6) δ 10.73 (s, 1H), 10.33 (s, 1H), 8.36 (br. s., 1H), 8.10 (br. s., 1H), 7.88 (d, J. 7.0 Hz, 1H), 7.83 (d, J=8.2 Hz, 1H), 7.58 (br. s., 1H), 7.45-7.27 (m, 6H), 7.15-7.07 (m, 1H), 5.22-4.97 (m, 2H), 4.01 (s, 2H), 3.83-3.79 (m, 1H), 3.71 (br. s., 1H), 3.70 (s, 2H), 3.66-3.64 (m, 2H), 3.63-3.56 (m, 1H), 3.46-3.37 (m, 1H), 2.11-1.95 (m, 1H), 1.90-1.82 (m, 1H), 1.80-1.64 (m, 2H), 1.62-1.45 (m, 2H), 1.18-1.09 (m, 2H); MS (ES+): m/z=782.7 (M+H)$^+$: LCMS (Method B): $t_R$=3.38 min; LCMS (Method A): $t_R$=7.28 min.

Example 123

Allyl (6αS)-3-(4-((2-(ethoxycarbonyl)-1-methyl-1H-imidazol-4-yl)amino)-4-oxobutoxy)-2-methoxy-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (120)

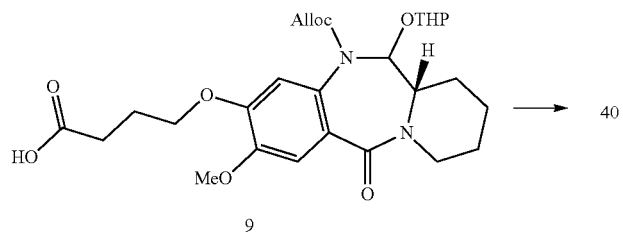

9

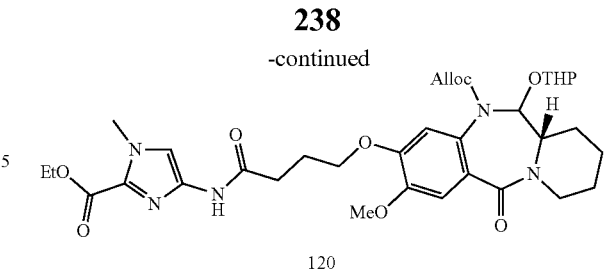

120

A solution of 4-(((6aS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-α][1,4]diazepin-3-yl)oxy)butanoic acid (9) (500 mg, 0.939 mmol) in N,N-dimethylformamide (5 mL) was charged with N,N-dimethylpyridin-4-amine (287 mg, 2.35 mmol) and N-(3-dimethylaminopropyl)-N'-ethylcarbodiimide hydrochloride (360 mg, 1.88 mmol) and it was stirred for 15 min at room temperature. Ethyl 4-amino-1-methyl-1H-imidazole-2-carboxylate hydrochloride (195 mg, 0.948 mmol) was added and the solution was stirred for further 18 h. The reaction mixture was poured into ice-cold water (50 mL) and extracted with ethyl acetate (2×80 mL). The combined organic extracts were concentrated in vacua to give the title compound (642 mg, 99%) as a brown oil. The product was carried through to the next step without any further purification.

MS (ES+): m/z=683.9 (M+H)$^+$: LCMS (Method B): $t_R$=3.35 min.

Example 124

4-(4-(((6aS)-5-((Allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanamido)-1-methyl-1H-imidazole-2-carboxylic acid (121)

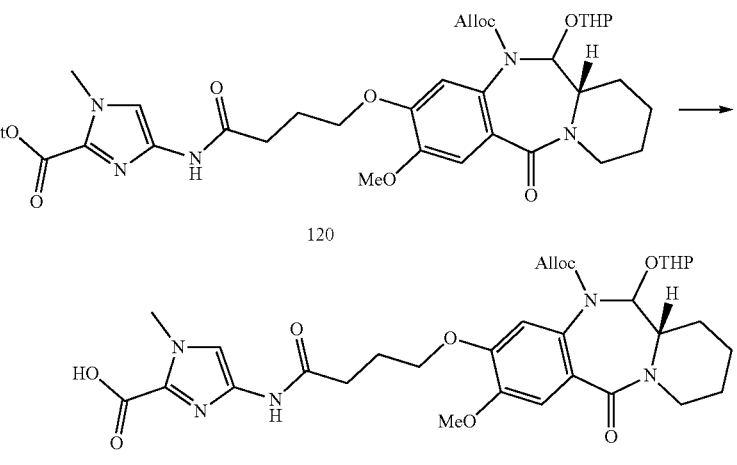

120

121

To a solution of allyl (6αS)-3-(4-((2-(ethoxycarbonyl)-1-methyl-1H-imidazol-4-yl)amino)-4-oxobutoxy)-2-methoxy-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (120) (642 mg, 0.939 mmol) in 1,4-dioxane (5 mL) was added an aqueous solution of sodium hydroxide (1 M, 5 mL, 5 mmol). The reaction mixture was stirred at room temperature for 1.5 h and was then concentrated in vacua, after which water (15 mL) was added and the aqueous layer was acidified to pH=4 with an aqueous solution of citric acid (1 M, 10 mL). The aqueous layer was then extracted with ethyl acetate (2×50 mL). The organic layer was washed with brine (50 mL). The combined organic extracts were dried over sodium sulfate, filtered and concentrated in vacuo to give the title compound (615 mg, 99%) as a cream solid. The product was carried through to the next step without any further purification MS (ES+): m/z=655.8 (M+H)$^+$: LCMS (Method B): $t_R$=3.00 min.

Example 125

Methyl 2-(4-(4-(((6αS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanamido)-1-methyl-1H-imidazole-2-carboxamido)benzo[d]thiazole-5-carboxylate (122)

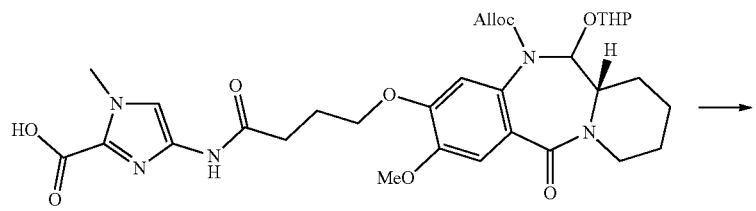

121

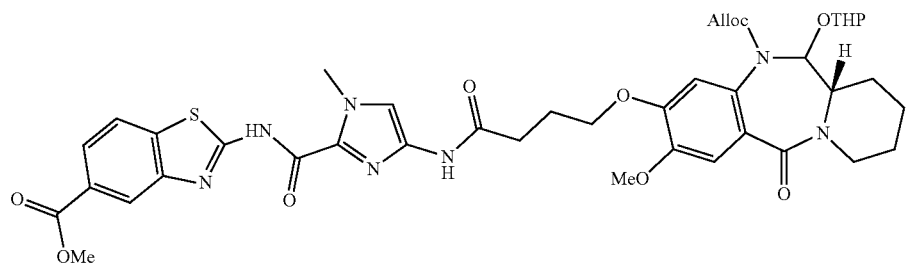

122

A solution of 4-(4-((((6αS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanamido)-1-methyl-1H-imidazole-2-carboxylic acid (121) (100 mg, 0.153 mmol) in N,N-dimethylformamide (1 mL) was charged with N,N-dimethylpyridin-4-amine (47 mg, 0.385 mmol) and N-(3-dimethylaminopropyl)-N'-ethylcarbodiimide hydrochloride (59 mg, 0.308 mmol) and it was stirred for 30 min at room temperature. Methyl 2-aminobenzo[d]thiazole-5-carboxylate (32 mg, 0.154 mmol) was added and the solution was stirred for further 18 h. The reaction mixture was poured into ice-cold water (50 mL) and extracted with ethyl acetate (2×80 mL). The combined organic extracts were concentrated in vacua. The resulting residue was purified by column chromatography (silica), eluting with ethyl acetate/hexane (from 0% to 100%), followed by methanol/dichloromethane (from 0% to 100%), to give the title compound (7.0 mg, 5%) as a yellow solid.

MS (ES+): m/z=845.8 (M+H)$^+$: LCMS (Method B): $t_R$=3.80 min.

Example 126

2-(4-(4-(((6αS)-5-((Allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanamido)-1-methyl-1H-imidazole-2-carboxamido)benzo[d]thiazole-5-carboxylic acid (124)

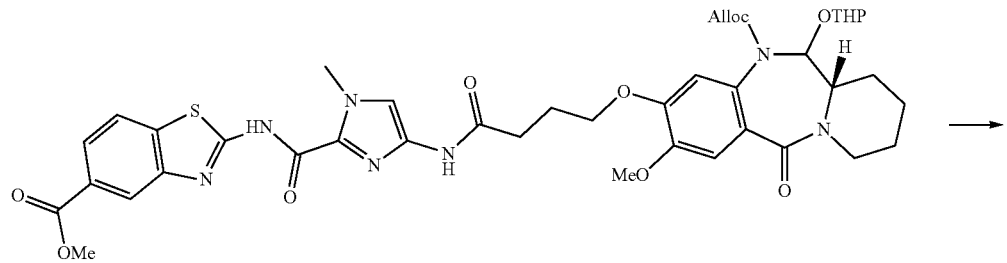

122

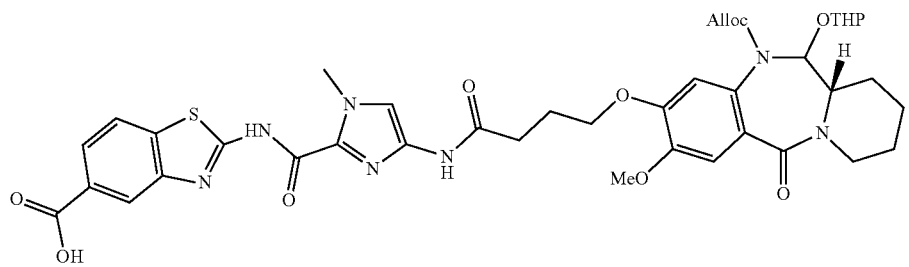

123

To a solution of methyl 2-(4-(4-(((6αS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanamido)-1-methyl-1H-imidazole-2-carboxamido)benzo[d]thiazole-5-carboxylate (122) (7 mg, 0.00828 mmol) in 1,4-dioxane (0.5 mL) was added an aqueous solution of sodium hydroxide (1 M, 0.5 mL, 0.5 mmol). The reaction mixture was stirred at room temperature for 1 h and was then concentrated in vacua, after which water (15 mL) was added and the aqueous layer was acidified to pH=4 with an aqueous solution of citric acid (1 M, 10 mL). The aqueous layer was then extracted with ethyl acetate (2×50 mL). The organic layer was washed with brine (50 mL). The combined organic extracts were dried over sodium sulfate, filtered and concentrated in vacua to give the title compound (6.4 mg, 93%) as a white solid. The product was carried through to the next step without any further purification MS (ES+): m/z=829.8 (M–H)⁻; LCMS (Method B): $t_R$=3.47 min.

Example 127

Allyl (6αS)-2-methoxy-3-(4-((1-methyl-2-((5-(phenylcarbamoyl)benzo[d]thiazol-2-yl)carbamoyl)-1H-imidazol-4-yl)amino)-4-oxobutoxy)-12-oxo-6-((tetrahydro-2H-pyran-2-yl)oxy)-6,6a,7,8,9,10-hexahydrobenzo[e]pyrido[1,2-a][1,4]diazepine-5 (12H)-carboxylate (124)

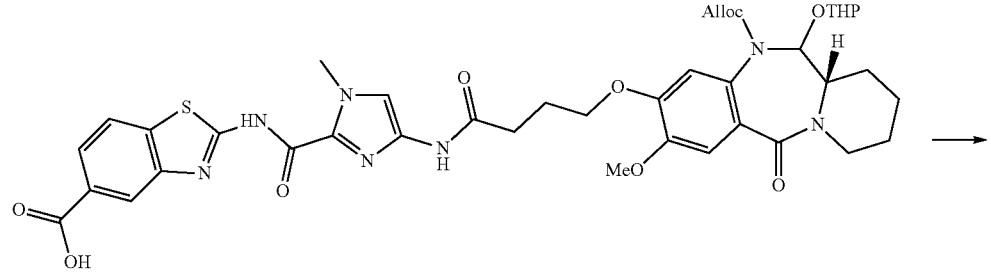

123

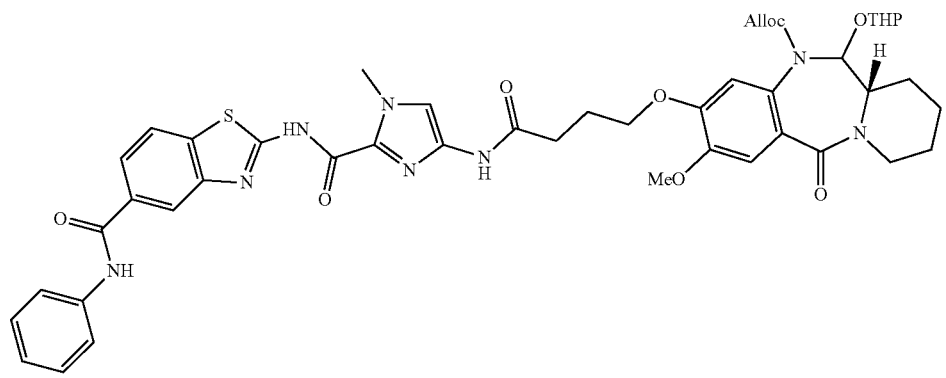

124

A solution of 2-(4-(4-((((6αS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)butanamido)-1-methyl-1H-imidazole-2-carboxamido)benzo[d]thiazole-5-carboxylic acid (123) (6.4 mg, 0.00769 mmol) in anhydrous dichloromethane (0.5 mL) was charged with N-[(dimethylamino)-1H-1,2,3-triazolo-[4,5-b]pyridin-1-ylmethylene]-N-methylmethanaminium hexafluorophosphate N-oxide (3.0 mg, 0.00789 mmol) and anhydrous triethylamine (5.0 μL, 0.0359 mmol). The reaction mixture was stirred at room temperature for 20 min. Aniline (1.0 μL, 0.0109 mmol) was then added and the resulting mixture was stirred at room temperature for 2 h. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacuo. The resulting residue was then purified by column chromatography (silica), eluting with ethyl acetate/hexane (from 0% to 100%), followed by methanol/ethyl acetate (from 0% to 100%), to give the title compound (2.2 mg, 32%) as a cream film.

MS (ES+): m/z=906.8 (M+H)$^+$: LCMS (Method B): $t_R$=3.77 min.

Example 128

(S)-2-(4-(4-((2-Methoxy-12-oxo-6a,7,8,9,10,12-hexahydrobenzo[e]pyrido[1,2-a][1,4]diazepin-3-yl)oxy)butanamido)-1-methyl-1H-imidazole-2-carboxamido)-N-phenylbenzo[d]thiazole-5-carboxamide (125)

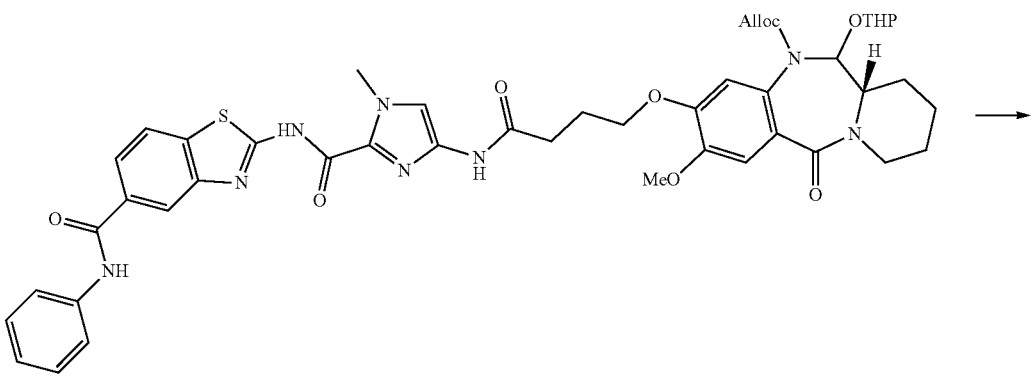

124

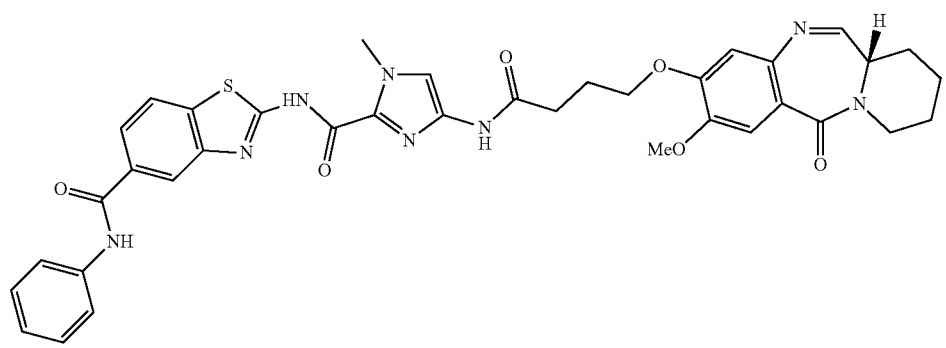

125

To a solution allyl (6αS)-2-methoxy-3-(4-((1-methyl-2-((5-(phenylcarbamoyl)benzo[d]thiazol-2-yl)carbamoyl)-1H-imidazol-4-yl)amino)-4-oxobutoxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (124) (2.2 mg, 0.00243 mmol) in dichloromethane (0.5 mL) was sequentially added tetrakis(triphenylphosphine)palladium (0) (0.2 mg, 7 mol %), and pyrrolidine (0.3 µL, 0.00365 mmol). The reaction mixture was stirred at room temperature for 1 h. The reaction mixture concentrated in vacua and subjected to high vacuum for 40 min until excess pyrrolidine was removed. The resulting residue was then purified by column chromatography (silica), eluting with methanol/dichloromethane (from 0% to 100%) to give the title compound (1.7 mg, 97%) as a cream film.

¹H NMR (400 MHz, DMSO-d6) δ 10.51 (s, 1H), 10.32 (br. s., 2H), 8.35 (br. s., 1H), 8.00 (d, J=5.9 Hz, 1H), 7.85-7.80 (m, 2H), 7.73 (br. s., 1H), 7.68-7.66 (m, 2H), 7.59 (br. s., 1H), 7.36 (t, J=7.8 Hz, 2H), 7.23 (s, 1H), 7.12 (d, J=7.0 Hz, 1H), 4.12 (s, 3H), 4.04-3.99 (m, 3H), 3.85-3.78 (m, 2H), 3.71 (s, 1H), 3.61-3.56 (m, 1H), 3.08 (s, 1H), 2.68-2.65 (m, 2H), 2.08-1.96 (m, 4H), 1.65-1.60 (m, 4H); MS (ES+): m/z=720.9 (M+H)⁺: LCMS (Method B): $t_R$=3.25 min; LCMS (Method A): $t_R$=6.98 min.

Example 129

4-(4-(4-((tert-Butoxycarbonyl)amino)-1-methyl-1H-pyrrole-2-carboxamido)phenyl)-1-methyl-1H-pyrrole-2-carboxylic acid (126)

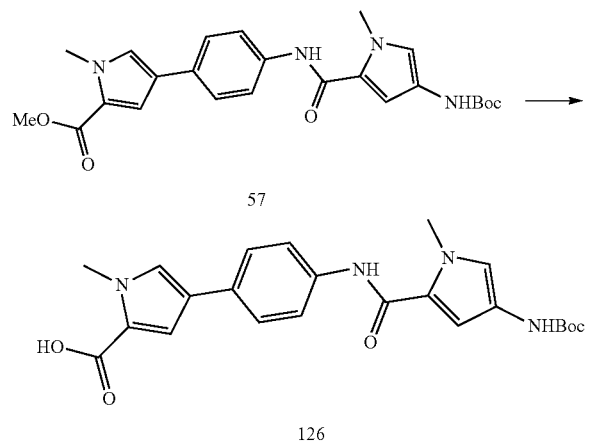

To a solution of methyl 4-(4-(4-((tert-butoxycarbonyl)amino)-1-methyl-1H-pyrrole-2-carboxamido)phenyl)-1-methyl-1H-pyrrole-2-carboxylate (57) (3.1 g, 6.85 mmol) in 1,4-dioxane (120 mL) was added an aqueous solution of sodium hydroxide (1 M, 120 mL, 120 mmol). The reaction mixture was stirred at room temperature for 18 h and was then concentrated in vacua, after which water (80 mL) was added and the aqueous layer was acidified to pH=4 with an aqueous solution of citric acid (1 M, 80 mL). The aqueous layer was then extracted with ethyl acetate (2×150 mL). The organic layer was washed with brine (150 mL). The combined organic extracts were dried over sodium sulfate, filtered and concentrated in vacua to give the title compound (2.5 g, 83%) as a cream solid. The product was carried through to the next step without any further purification.

MS (ES+): m/z=438.8 (M+H)⁺: LCMS (Method B): $t_R$=3.27 min.

Example 130 tert-Butyl (1-methyl-5-((4-(1-methyl-5-(phenylcarbamoyl)-1H-pyrrol-3-yl)phenyl)carbamoyl)-1H-pyrrol-3-yl)carbamate (127)

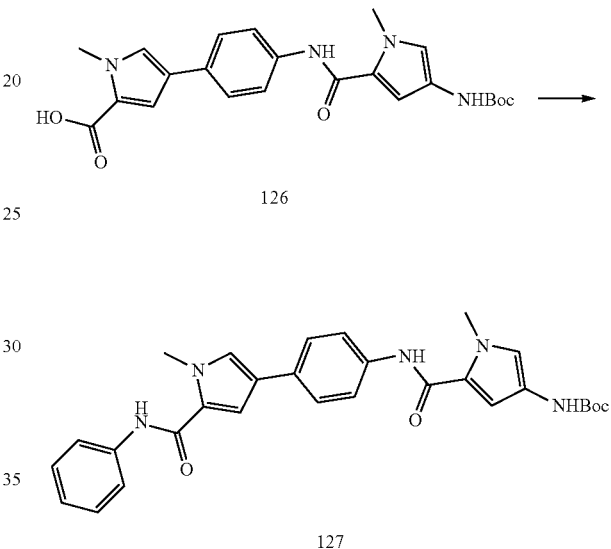

A solution of 4-(4-(4-((tert-butoxycarbonyl)amino)-1-methyl-1H-pyrrole-2-carboxamido)phenyl)-1-methyl-1H-pyrrole-2-carboxylic acid (126) (2.0 g, 4.56 mmol) in anhydrous dichloromethane (14 mL) was charged with N-[(dimethylamino)-1H-1,2,3-triazolo-[4,5-b]pyridin-1-ylmethylene]-N-methylmethanaminium hexafluorophosphate N-oxide (1.85 g, 4.87 mmol) and anhydrous triethylamine (2.7 mL, 19.4 mmol). The reaction mixture was stirred at room temperature for 30 min. Aniline (440 mL, 4.82 mmol) was added and the resulting mixture was stirred at room temperature for 16 h. The reaction mixture was quenched with a saturated aqueous solution of sodium hydrogen carbonate (50 mL) and extracted with dichloromethane (2×150 mL). The combined organic extracts were washed with water containing a few drops of acetic acid (75 mL). The organic layer was then dried over sodium sulfate, filtered and concentrated in vacua, to give the title compound (2.0 g, 85%) as a cream film.

¹H NMR (400 MHz, DMSO-d6) δ 9.83 (br. s., 1H), 9.77 (br. s., 1H), 9.12 (br. s., 1H), 7.73 (br. s., 4H), 7.50 (d, J=7.4 Hz, 2H), 7.46 (br. s., 1H), 7.41 (br. s., 1H), 7.33 (br. s., 2H), 7.06 (br. s., 1H), 6.94 (br. s., 2H), 3.91 (br. s., 3H), 3.81 (br. s., 3H), 1.46 (br. s., 9H) MS (ES+): m/z=513.8 (M+H)⁺: LCMS (Method B): $t_R$=3.70 min.

Example 131

4-Amino-1-methyl-N-(4-(1-methyl-5-(phenylcarbamoyl)-1H-pyrrol-3-yl)phenyl)-1H-pyrrole-2-carboxamide hydrochloride (128)

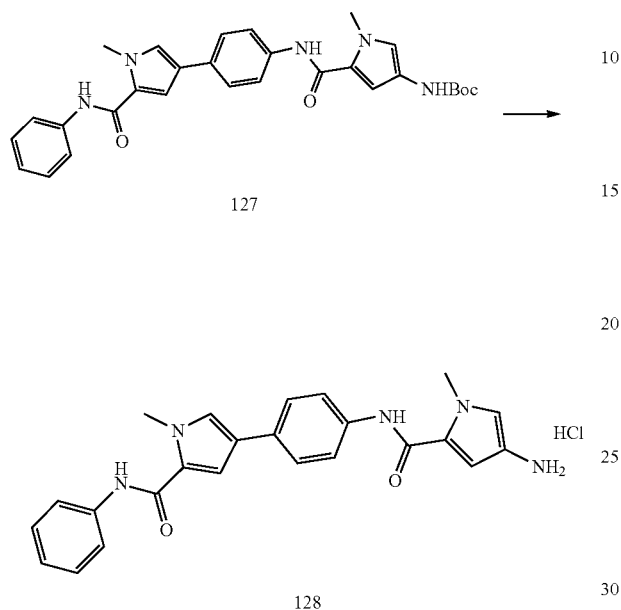

127

128 tert-Butyl (1-methyl-5-((4-(1-methyl-5-(phenylcarbamoyl)-1H-pyrrol-3-yl)phenyl)carbamoyl)-1H-pyrrol-3-yl)carbamate (127) (1.0 g, 1.95 mmol) was dissolved in hydrochloric acid (4 M in 1,4-dioxane) (5 mL) and the reaction mixture was stirred at room temperature for 1 h. The reaction mixture was concentrated in vacuo to give the title compound (975 mg, 99%) as a brown solid. The product was carried through to the next step without any further purification.

MS (ES+): m/z=413.8 (M+H)$^+$: LCMS (Method B): $t_R$=3.07 min.

Example 132

Allyl (6αS)-2-methoxy-3-((3-(2-((1-methyl-5-((4-(1-methyl-5-(phenylcarbamoyl)-1H-pyrrol-3-yl)phenyl)carbamoyl)-1H-pyrrol-3-yl)amino)-2-oxoethyl)benzyl)oxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (129)

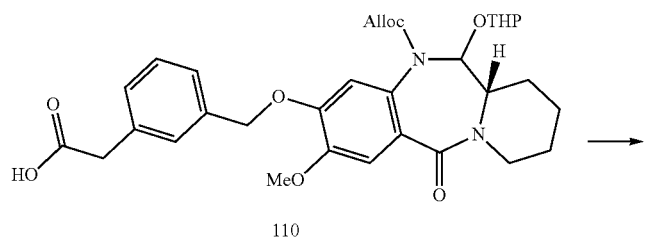

110

-continued

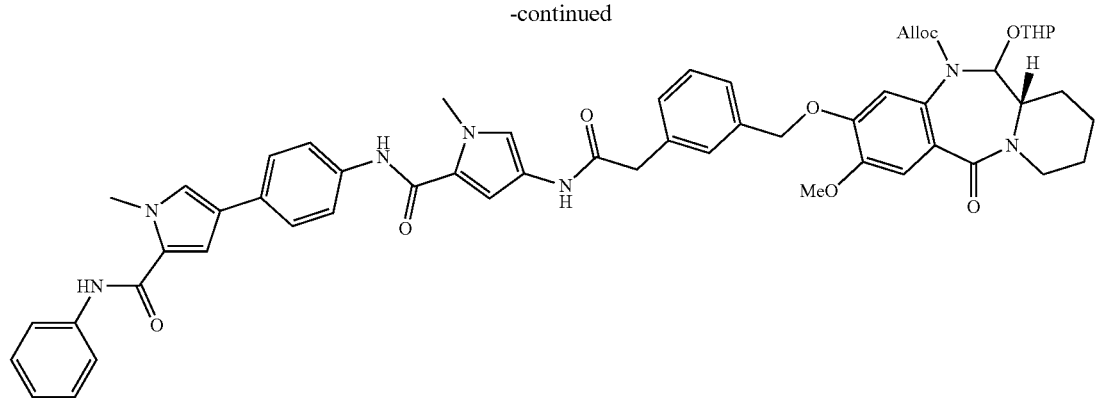

129

A solution of 2-(3-(((((6αS)-5-((allyloxy)carbonyl)-2-methoxy-12-oxo-6-((tetrahydro-2H-pyran-2-yl)oxy)-5,6,6a,7,8,9,10,12-octahydrobenzo[e]pyrido[1,2-a][1,4]diazepin-3-yl)oxy)methyl)phenyl)acetic acid (110) (50 mg, 0.084 mmol) in N,N-dimethylformamide (1 mL) was charged with N,N-dimethylpyridin-4-amine (30 mg, 0.245 mmol) and N-(3-dimethylaminopropyl)-N'-ethylcarbodiimide hydrochloride (32 g, 0.168 mmol) and it was stirred for 30 min at room temperature. 4-Amino-1-methyl-N-(4-(1-methyl-5-(phenylcarbamoyl)-1H-pyrrol-3-yl)phenyl)-1H-pyrrole-2-carboxamide hydrochloride (128) (41.6 mg, 0.092 mmol) was added and the solution was stirred for further 18 h. The reaction mixture was poured into ice-cold water (50 mL) and extracted with ethyl acetate (2×80 mL). The combined organic extracts were concentrated in vacuo. The resulting residue was purified by column chromatography (silica), eluting with ethyl acetate/hexane (from 0% to 100%), to give the title compound (21 mg, 25%) as a white solid.

MS (ES+): m/z=989.8 (M+H)$^+$: LCMS (Method B): $t_R$=4.35 min.

Example 133

(S)-4-(2-(3-(((2-Methoxy-12-oxo-6a,7,8,9,10,12-hexahydrobenzo[e]pyrido[1,2-a][1,4]diazepin-3-yl)oxy)methyl)phenyl)acetamido)-1-methyl-N-(4-(1-methyl-5-(phenylcarbamoyl)-1H-pyrrol-3-yl)phenyl)-1H-pyrrole-2-carboxamide (130)

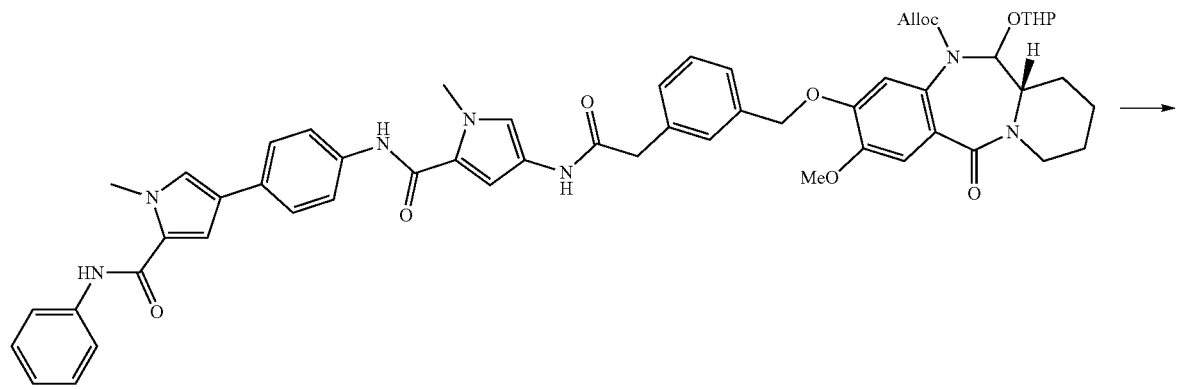

129

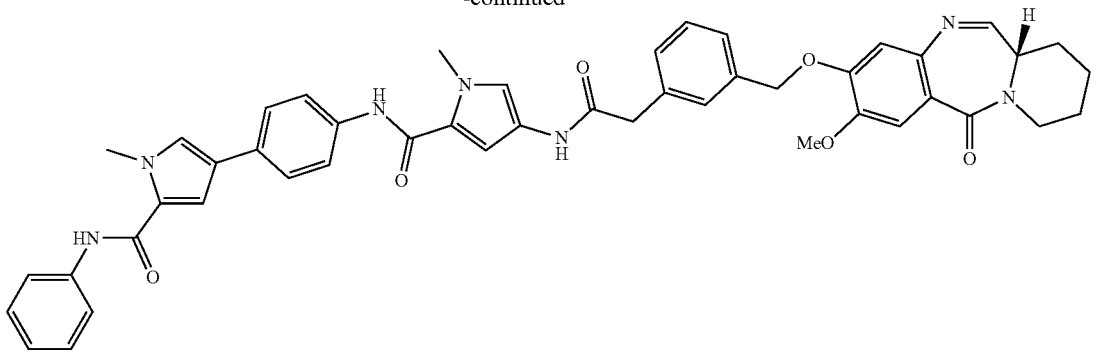

130

To a solution allyl (6αS)-2-methoxy-3-((3-(2-((1-methyl-5-((4-(1-methyl-5-(phenylcarbamoyl)-1H-pyrrol-3-yl)phenyl)carbamoyl)-1H-pyrrol-3-yl)amino)-2-oxoethyl)benzyl)oxy)-12-oxo-6-((tetrahydro-2H-pyran-2-yl)oxy)-6,6a,7,8,9,10-hexahydrobenzo[e]pyrido[1,2-a][1,4]diazepine-5(12H)-carboxylate (129) (21 mg, 0.0212 mmol) in dichloromethane (0.5 mL) was sequentially added tetrakis(triphenylphosphine)palladium(0) (1.2 mg, 5 mol %), and pyrrolidine (2.1 µL, 0.0256 mmol). The reaction mixture was stirred at room temperature for 1 h. The reaction mixture concentrated in vacua and subjected to high vacuum for 40 min until excess pyrrolidine was removed. The resulting residue was then purified by column chromatography (silica), eluting with methanol/dichloromethane (from 0% to 100%) to give the title compound (8.0 mg, 47%) as a cream solid.

$^1$H NMR (400 MHz, DMSO-d6) δ 10.13 (s, 1H), 9.83 (s, 1H), 9.80 (s, 1H), 7.75 (s, 1H), 7.72 (d, J=2.3 Hz, 2H), 7.70 (s, 1H), 7.50 (d, J=8.6 Hz, 2H), 7.46 (s, 1H), 7.44-7.39 (m, 2H), 7.35 (s, 2H), 7.33 (s, 2H), 7.31 (br. s., 1H), 7.21 (s, 1H), 7.11-7.07 (m, 1H), 7.07-7.03 (m, 1H), 6.99 (s, 1H), 6.66 (s, 1H), 6.12 (s, 1H), 5.15-4.95 (m, 2H), 3.91 (s, 3H), 3.83 (s, 3H), 3.72-3.66 (m, 3H), 3.61 (s, 2H), 3.48-3.39 (m, 1H), 1.93-1.71 (m, 2H), 1.69-1.47 (m, 5H), 1.25-1.22 (m, 1H); MS (ES+): m/z=804.0 (M+H)$^+$: LCMS (Method B): $t_R$=3.45 min; LCMS (Method A): $t_R$=7.52 min.

Example 134

(S)-(2-(((tert-Butyldimethylsilyl)oxy)methyl)piperidin-1-yl)(5-methoxy-2-nitro-4 ((triisopropylsilyl)oxy)phenyl)methanone (131)

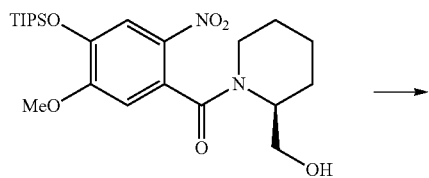

100

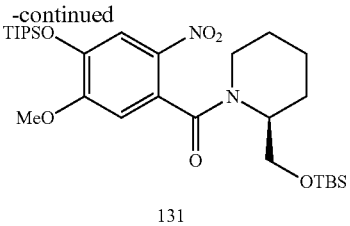

131

TBS-OTf (3.12 g, 11.8 mmol) was added to a solution of (S)-(2-(hydroxymethyppiperidin-1-yl)(5-methoxy-2-nitro-4 ((triisopropylsilyl)oxy)phenyl)methanone (100) (5.50 g, 11.8 mmol) and 2,6-lutidine (5.05 g, 47.2 mmol) in dry DCM (50 mL) at 0° C. for 4 h. The reaction mixture was diluted with DCM (300 mL) and sequentially washed with water (50 mL), sat. aq. NaHCO₃ (50 mL) and brine (50 mL). Organic layer was dried over Na₂SO₄, filtered and concentrated under reduced pressure. The resulting residue was then purified by column chromatography (silica), eluting with ethyl acetate/hexane (from 9% to 50%) to give the title compound (4.1 g, 60%) as a yellow oil.

$^1$H NMR (400 MHz, CDCl₃) δ 7.68 (s, 1H), 6.74-6.64 (m, 1H), 4.99-4.65 (m, 1H), 3.91-3.86 (m, 3H), 3.81-3.61 (m, 1H), 3.57-3.39 (m, 0.62H), 3.16-3.03 (m, 1H), 2.77 (d, J=12.4 Hz, 0.34H), 2.14 (d, J=13.4 Hz, 0.31H), 1.86-1.44 (m, 5H), 1.31-1.25 (m, 3.75H), 1.10-1.04 (m, 18H), 0.92-0.82 (m, 9H), 0.12-0.04 (m, 6H); MS (ES+): m/z=580.9 (M+H)$^+$: LCMS (Method A): $t_R$=9.21 min.

Example 135

(S)-(4-Hydroxy-5-methoxy-2-nitrophenyl) (2-(hydroxymethyl)piperidin-1-yl)methanone (132)

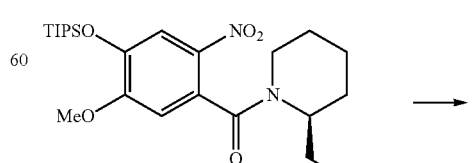

131

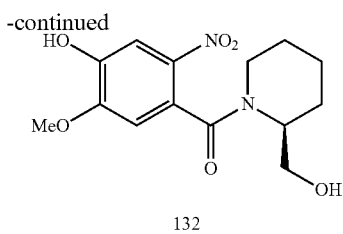

132

To a solution of (S)-(2-(((tert-butyldimethylsilyl)oxy)methyl)piperidin-1-yl)(5-methoxy-2-nitro-4 ((triisopropylsilyl)oxy)phenyl)methanone (131) (3.9 g, 6.72 mmol) in THF (40 mL) was added TBAF (1 M, 15 mL). The reaction mixture was stirred at room temperature for 20 h and concentrated under reduced pressure to give the title compound (2.1 g, 99%) as a yellow oil. The product was carried through to the next step without any further purification.

MS (ES+): m/z=310.8 (M+H)⁺: LCMS (Method B): $t_R$=2.57 min.

Example 136

Methyl (S)-4-(4-(2-(hydroxymethyl)piperidine-1-carbonyl)-2-methoxy-5-nitrophenoxy)butanoate (133)

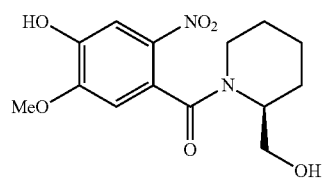

132

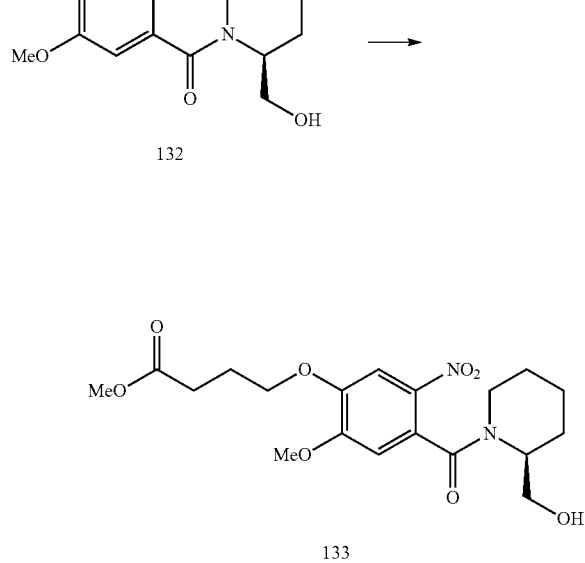

133

A mixture of (S)-(4-hydroxy-5-methoxy-2-nitrophenyl)(2-(hydroxymethyl)piperidin-1-yl)methanone (132) (2.1 g, 6.77 mmol), methyl 4-bromobutanoate (900 μL, 7.13 mmol) and potassium carbonate (1.4 g, 10.13 mmol) in N,N-dimethylformamide (30 mL) was stirred at room temperature for 18 h. The reaction mixture was diluted with water (60 mL) and extracted with ethyl acetate (2×100 mL). The combined organic extracts were concentrated in vacuo. The resulting residue was purified by column chromatography (silica), eluting with methanol/dichloromethane (from 0% to 100%), to give the title compound (2.3 g, 83%) as a yellow oil.

MS (ES+): m/z=410.8 (M+H)⁺: LCMS (Method B): $t_R$=2.93 min.

Example 137

Methyl (S)-4-(5-amino-4-(2-(hydroxymethyl)piperidine-1-carbonyl)-2-methoxyphenoxy)butanoate (134)

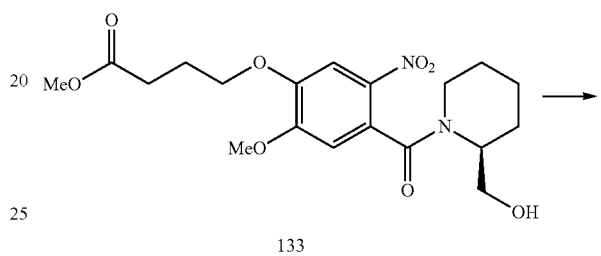

133

134

Ammonium formate (2.95 g, 46.78 mmol) and palladium on activated charcoal (10% wt. basis) (5.0 g) were added to a solution of methyl (S)-4-(4-(2-(hydroxymethyl)piperidine-1-carbonyl)-2-methoxy-5-nitrophenoxy)butanoate (133) in THF (90 mL) and water (10 mL). The reaction mixture was stirred at 35° C. for 2 h. The reaction mixture was filtered through celite® and washed with ethyl acetate (200 mL). The filtrate was concentrated in vacuo to give the title compound (1.75 g, 79%) as an amber oil. The product was carried through to the next step without any further purification.

¹H NMR (400 MHz, CDCl₃) δ 6.68 (s, 1H), 6.24 (s, 1H), 4.53 (br. s., 1H), 3.96 (t, J=6.2 Hz, 2H), 3.93-3.82 (n, 4H), 3.73 (s, 3H), 3.65 (d, J=0.8 Hz, 3H), 3.55 (d, J=5.1 Hz, 1H), 3.06 (br. s., 1H), 2.49 (t, J=7.2 Hz, 2H), 2.14-2.05 (m, 2H), 1.68-1.58 (m, 4H), 1.56-1.41 (m, 2H), 1.04-0.98 (m, 1H); MS (ES+): m/z=380.8 (M+H)⁺; LCMS (Method B): $t_R$=2.58 min.

Example 138

Methyl 4-(5-((((4-((S)-2-((S)-2-(((allyloxy)carbonyl)amino)-3-methylbutanamido)propanamido(benzyl)oxy)carbonyl)amino)-4-((S)-2-(hydroxymethyl)piperidine-1-carbonyl)-2-methoxyphenoxy)butanoate (135)

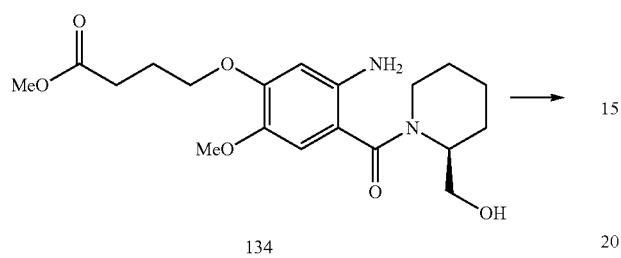

134

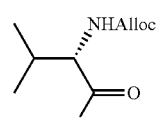
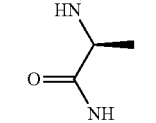
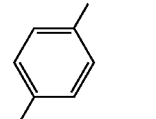
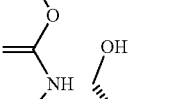
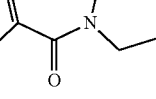
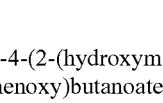

135

A solution of methyl (S)-4-(5-amino-4-(2-(hydroxymethyl)piperidine-1-carbonyl)-2-methoxyphenoxy)butanoate (134) (1.75 g, 4.60 mmol) and allyl ((S)-3-methyl-1-(((S)-1-((4-((((4-nitrophenoxy)carbonyl)oxy)methyl)phenyl)amino)-1-oxopropan-2-yl)amino)-1-oxobutan-2-yl)carbamate (2.5 g, 4.61 mmol) in DMF (9 mL) was stirred at room temperature for 5 min. 1H-Benzo[d][1,2,3]triazol-1-ol (622 mg, 4.60 mmol) was added to the reaction mixture which was heated to 60° C. for 22 h. The reaction mixture was partitioned between ethyl acetate (2×50 mL) and water (30 mL). The combined organic extracts were concentrated in vacua. The resulting residue was purified by column chromatography (silica), eluting with methanol/dichloromethane (from 0% to 100%), to give the title compound (2.5 g, 62%) as a beige solid.

MS (ES+): m/z=783.9 (M+H)$^+$: LCMS (Method B): $t_R$=3.15 min.

Example 139

4-(5-((((4-((S)-2-((S) 2-(((Allyloxy)carbonyl)amino)-3-methylbutanamido)propanamido)benzyl)oxy)carbonyl)amino)-4-((S)-2-(hydroxymethyflpiperidine-1-carbonyl)-2-methoxyphenoxy)butanoic acid (136)

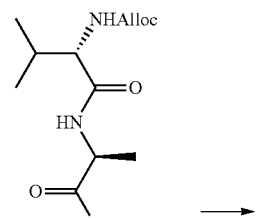

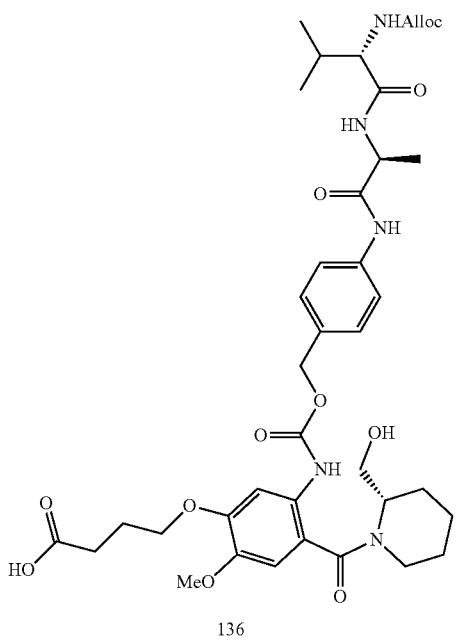

135

136

To a solution of methyl 4-(5-((((4-((S)-2-((S)-2-(((allyloxy)carbonyeamino)-3-methylbutanamido)propanamido)benzyl)oxy)carbonyl)amino)-4-((S)-2-(hydroxymethyppiperidine-1-carbonyl)-2-methoxyphenoxy)butanoate (135) (2.5 g, 2.87 mmol) in 1,4-dioxane (12 mL) was added an aqueous solution of sodium hydroxide (0.5 M, 18 mL, 9.00 mmol) dropwise. The reaction mixture was stirred at room temperature for 4 h. The reaction mixture was acidified to pH=1 with 1 M HCl (10 mL) before being diluted with water (30 mL) and extracted with ethyl acetate (2×100 mL). The combined organic extracts were concentrated in vacuo. The resulting residue was purified by column chromatography (silica), eluting with methanol/dichloromethane (from 0% to 100%), to give the title compound (1.2 g, 54%) as a cream solid.

MS (ES+): m/z=769.8 (M+H)$^+$: LCMS (Method B): $t_R$=2.95 min.

Example 140

4-(((6S,6αS)-5-(((4-((S)-2-((S)-2-(((Allyloxy)carbonyl)amino)-3-methylbutanamido)propanamido)benzyl)oxy)carbonyl)-6-hydroxy-2-methoxy-12-oxo-5,6,6a,7,8,9,10,12-octahydrobenzo[e]pyrido[1,2-a][1,4]diazepin-3-yl)oxy)butanoic acid (137)

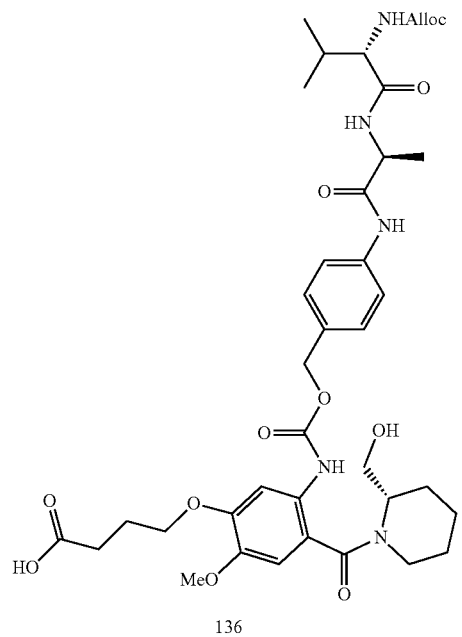

136

As suspension of 4-(5-((((4-((S)-2-((S)-2-(((allyloxy)carbonyl)amino)-3-methylbutanamido)propanamido)benzyl)oxy)carbonyeamino)-4-((S)-2-(hydroxymethyl)piperidine-1-carbonyl)-2-methoxyphenoxy)butanoic acid (136) (1.2 g, 1.56 mmol) and Dess-Martin periodinane (1.35 g, 3.18 mmol) in anhydrous dichloromethane (15 mL) was stirred at room temperature for 45 min. The reaction mixture was partitioned between dichloromethane (2×50 mL) and saturated aqueous solution of sodium metabisulfite (30 mL). The combined organic extracts were concentrated in vacua. The resulting residue was purified by column chromatography (silica), eluting with methanol/dichloromethane (from 0% to 10%), to give the title compound (760 mg, 63%) as a yellow solid.

MS (ES+): m/z=767.8 (M+H)$^+$: LCMS (Method B): $t_R$=2.98 min.

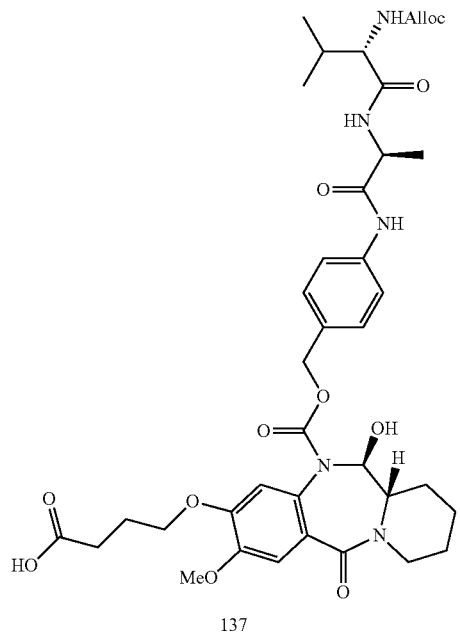

137

Example 141
4-((S)-2-((S)-2-(((Allyloxy)carbonyl)amino)-3-methylbutanamido)propanamido)benzyl (6S,6αS)-6-hydroxy-2-methoxy-3-(4-((1-methyl-5-((4-(1-methyl-5-(phenylcarbamoyl)-1H-pyrrol-3-yl)phenyl)carbamoyl)-1H-pyrrol-3-yl)amino)-4-oxobutoxy)-12-oxo-6,6a,7,8,9,10-hexahydrobenzo[e]pyrido[1,2-a][1,4]diazepine-5(12H)-carboxylate (138)
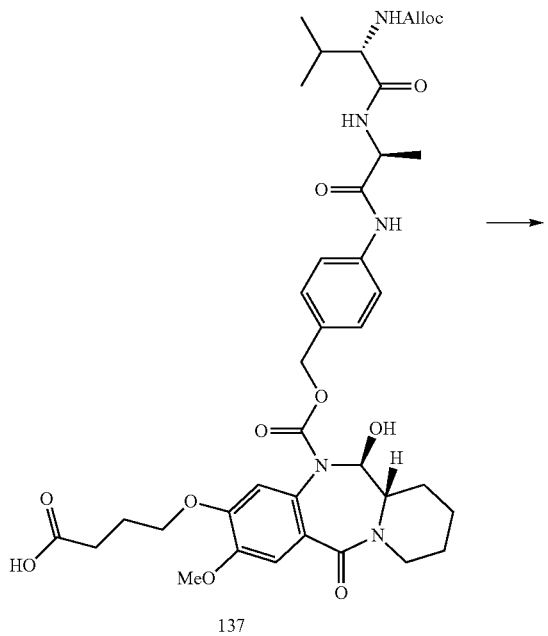
137
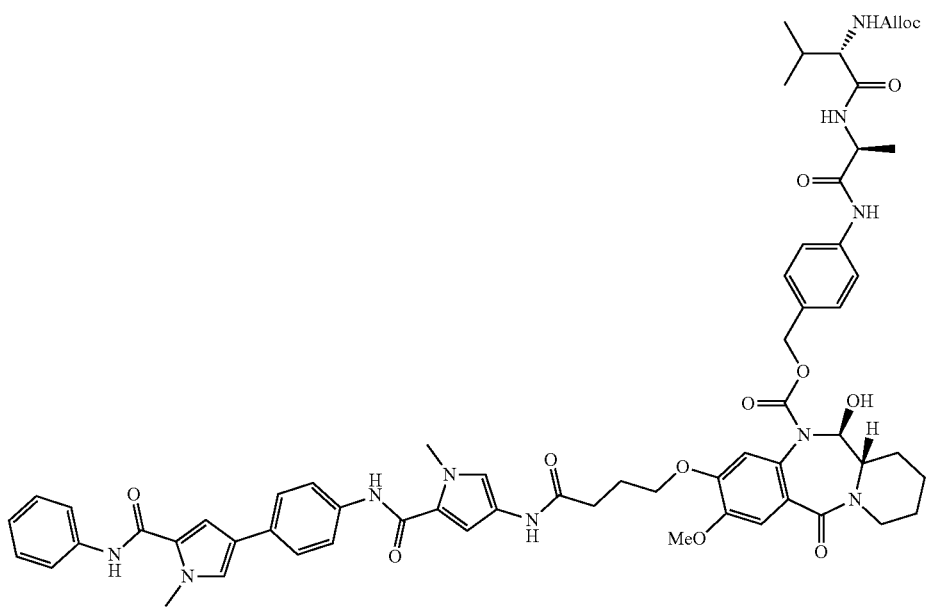
138

A solution of 4-(((6S,6αS)-5-(((4-((S)-2-((9)-2-(((allyloxy)carbonyeamino)-3-methylbutanamido)propanamido)benzyl)oxy)carbonyl)-6-hydroxy-2-methoxy-12-oxo-5,6,6a,7,8,9,10,12-octahydrobenzo[e]pyrido[1,2-a][1,4]diazepin-3-yl)oxy)butanoic acid (137) (440 mg, 0.573 mmol) in anhydrous dichloromethane (3 mL) was charged with N-[dimethylamino)-1H-1,2,3-triazolo-[4,5-b]pPyridin-1-ylmethylene]-N-methylmethanaminium hexafluorophosphate N-oxide (230 mg, 0.605 mmol) and anhydrous triethylamine (335 µL, 2.41 mmol). The reaction mixture was stirred at room temperature for 30 min. 4-Amino-1-methyl-N-(4-(1-methyl-5-(phenylcarbamoyl)-1H-pyrrol-3-yl)phenyl)-1H-pyrrole-2-carboxamide hydrochloride (128) (260, 0.578 mmol) was added and the resulting mixture was stirred at room temperature for 30 min. The reaction mixture was quenched with a saturated aqueous solution of sodium hydrogen carbonate (20 mL) and extracted with dichloromethane (2×50 mL). The combined organic extracts were washed with water containing a few drops of acetic acid (30 mL). The organic layer was then dried over sodium sulfate, filtered and concentrated in vacua. The resulting residue was then purified by column chromatography (silica), eluting with methanol/chloroform (from 0% to 5%), to give the title compound (43 mg, 6%) as a salmon solid.

MS (ES+): m/z=1163.1 (M+H)$^+$: LCMS (Method B): $t_R$=3.48 min.

Example 142

4-((S)-2-((S)-2-Amino-3-methylbutanamido)propanamido)benzyl (6S,6αS)-6-hydroxy-2-methoxy-3-(4-((1-methyl-5-((4-(1-methyl-5-(phenylcarbamoyl)-1H-pyrrol-3-yl)phenyl)carbamoyl)-1H-pyrrol-3-yl)amino)-4-oxobutoxy)-12-oxo-6,6a,7,8,9,10-hexahydrobenzo[e]pyrido[1,2-a][1,4]diazepine-5(12H)-carboxylate (139)

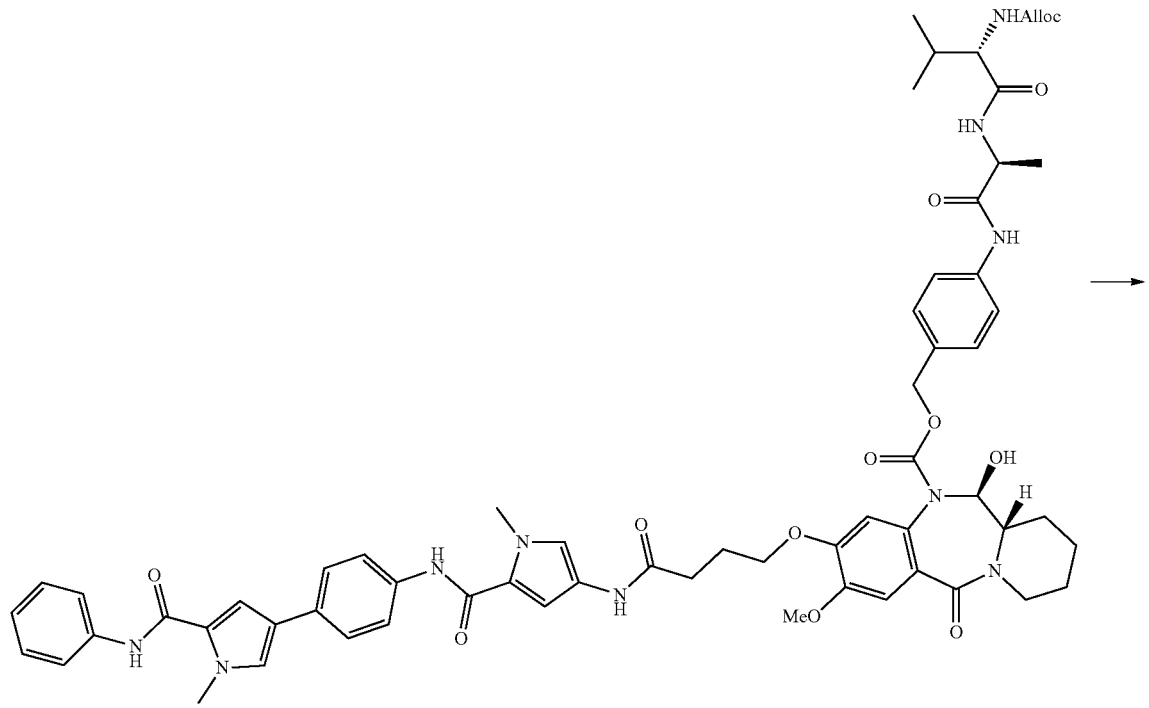

-continued

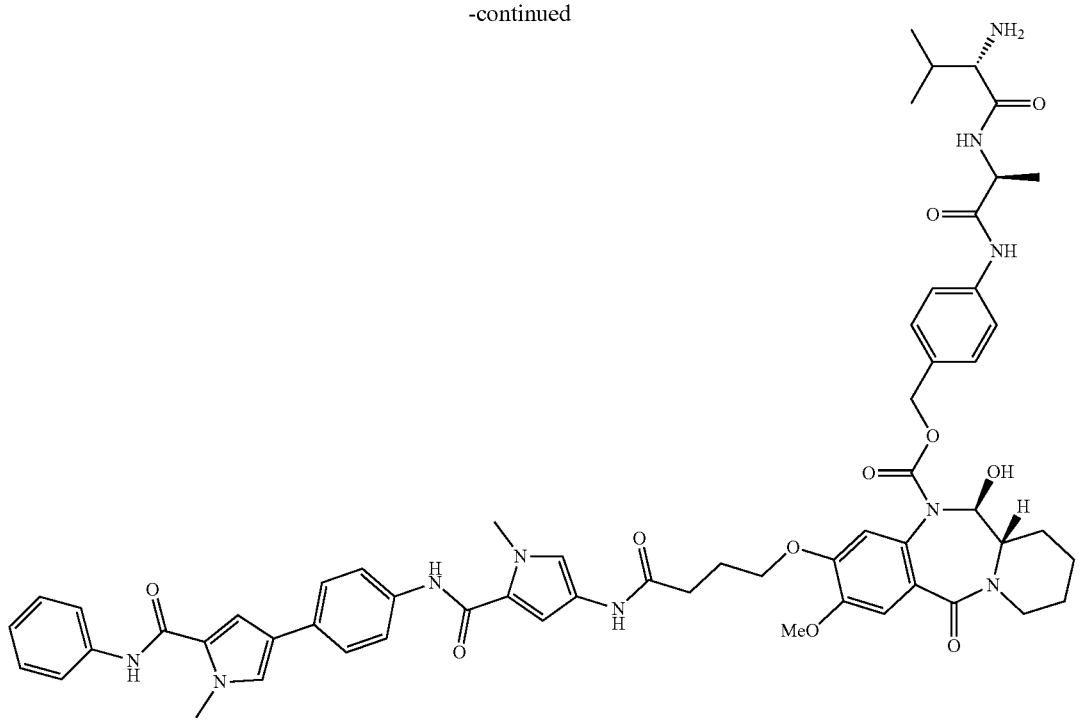

139

To a solution of 4-((S)-2-((S)-2-(((allyloxy)carbonyeamino)-3-methylbutanamido)propanamido)benzyl (6S, 6αS)-6-hydroxy-2-methoxy-3-(4-((1-methyl-5-((4-(1-methyl-5-(phenylcarbamoyl)-1H-pyrrol-3-yl)phenyl)carbamoyl)-1H-pyrrol-3-yl)amino)-4-oxobutoxy)-12-oxo-6,6a,7,8,9,10 hexahydrobenzo[e]pyrido[1,2-a][1,4]diazepine-5(12H)-carboxylate (138) (43 mg, 0.0370 mmol) in dichloromethane (1 mL) was sequentially added tetrakis(triphenylphosphine)palladium(0) (2.1 mg, 5 mol %), and pyrrolidine (3.7 μL, 0.0450 mmol). The reaction mixture was stirred at room temperature for 15 min. The reaction mixture concentrated in vacua and subjected to high vacuum for 40 min until excess pyrrolidine was removed, to give the title compound (40 mg, 99%) as a yellow gum. The product was carried through to the next step without any further purification.

MS (ES+): m/z=1079.2 (M+H)$^+$: LCMS (Method B): $t_R$=2.90 min.

Example 143
4-((2S,5S)-37-(2,5-Dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl (6S,6αS)-6-hydroxy-2-methoxy-3-(4-((1-methyl-5-((4-(1-methyl-5-(phenylcarbamoyl)-1H-pyrrol-3-yl)phenyl)carbamoyl)-1H-pyrrol-3-yl)amino)-4-oxobutoxy)-12-oxo-6,6a,7,8,9,10-hexahydrobenzo[e]pyrido[1,2-a][1,4]diazepine-5(12H)-carboxylate (140)
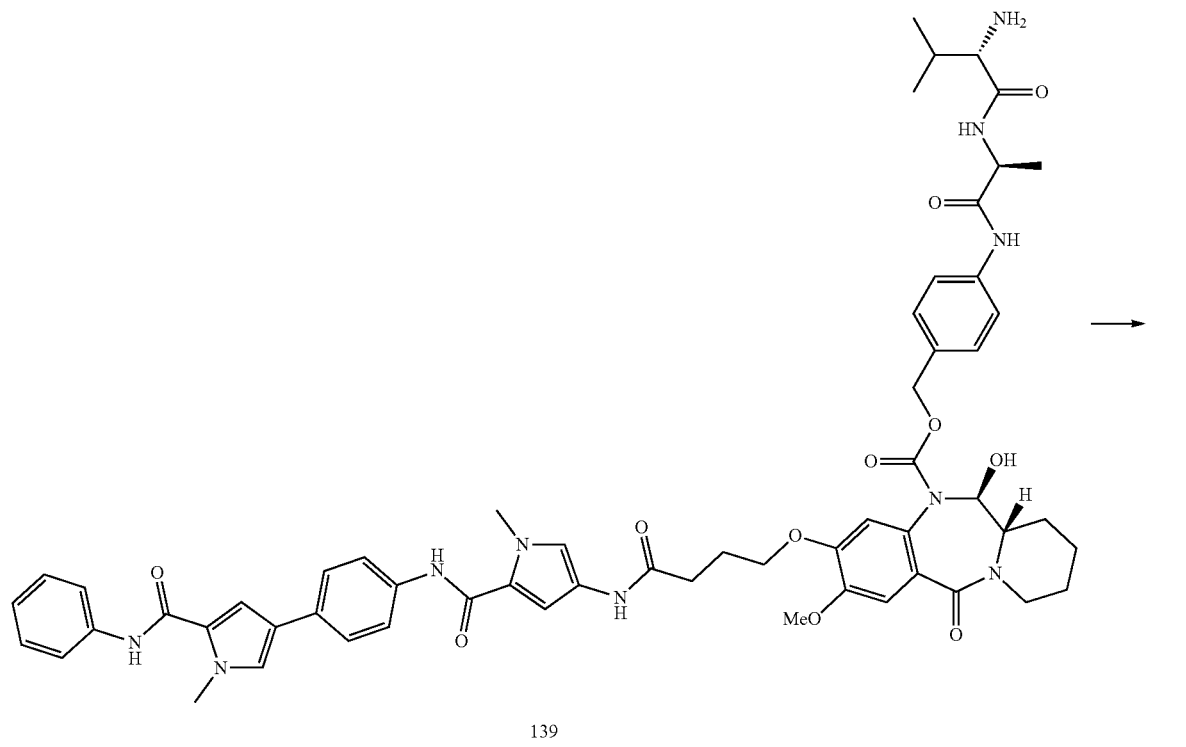
139
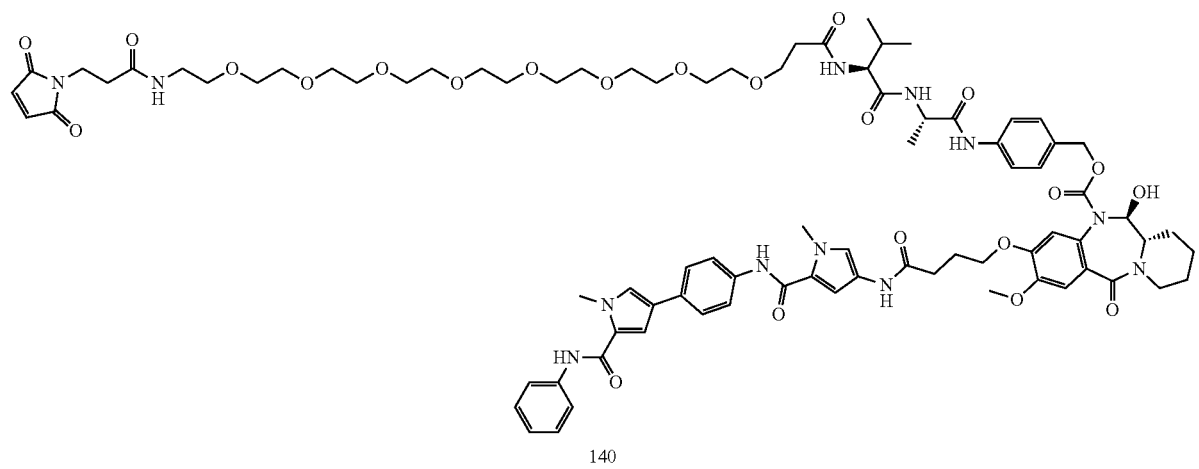
140

A solution of 4-((S)-2-((S)-2-amino-3-methylbutanamido)propanamido)benzyl (6S,6αS)-6-hydroxy-2-methoxy-3-(4-((1-methyl-5-((4-(1-methyl-5-(phenylcarbamoyl)-1H-pyrrol-3-yl)phenyl)carbamoyl)-1H-pyrrol-3-yl)amino)-4-oxobutoxy)-12-oxo-6,6a,7,8,9,10-hexahydrobenzo[e]pyrido[1,2-a][1,4]diazepine-5(12H)-carboxylate (139) (40 mg, 0.0370 mmol), 1-(2,5-dioxo-2,5-dihydro-1H-pyrrol-1-yl)-3-oxo-7,10,13,16,19,22,25,28-octaoxa-4-azahentriacontan-31-oic acid (22.0 mg, 0.0370 mmol) and N-(3-dimethylaminopropyl)-N'-ethylcarbodiimide hydrochloride (7.1 mg, 0.0370 mmol) in anhydrous DCM (1 mL) was stirred at room temperature for 30 min. The reaction mixture was directly purified by column chromatography (silica), eluting with methanol/dichloromethane (from 0% to 15%), to give the title compound (41 mg, 67%) as a brown solid.

$^1$H NMR (400 MHz, DMSO-d$_6$) δ 9.95-9.67 (m, 3H), 8.15 (d, J=6.2 Hz, 1H), 7.98 (d, J=5.1 Hz, 1H), 7.84 (d, J=8.6 Hz, 1H), 7.77-7.64 (m, 3H), 7.61-7.36 (m, 5H), 7.35-7.26 (m, 2H), 7.25-7.10 (m, 1H), 7.06-6.93 (m, 3H), 6.68 (br. s., 1H), 5.76 (br. s., 1H), 5.10 (br. s., 1H), 4.86 (d, J=5.5 Hz, 1H), 4.44-4.30 (m, 1H), 4.25-4.15 (m, 1H), 4.11 (br. s., 1H), 3.96-3.86 (m, 3H), 3.83-3.76 (m, 3H), 3.62-3.54 (m, 3H), 3.53-3.38 (m, 28H), 3.30 (br. s., 15H), 3.26-3.20 (m, 1H), 3.18-3.08 (m, 2H), 2.86 (br. s., 1H), 2.50 (br. s., 3H), 2.45-2.37 (m, 2H), 2.36-2.26 (m, 2H), 2.10-1.86 (m, 3H), 1.62 (d, J=18.4 Hz, 1H), 1.53 (br. s., 2H), 1.29 (br. s., 3H), 1.25-1.05 (m, 3H), 0.94-0.76 (m, 6H); MS (ES+): m/z=1654.6 (M+H)$^+$: LCMS (Method B): t$_R$=3.28 min; LCMS (Method A): t$_R$=6.98 min.

Example 144

N-(4-((S)-2-((S)-2-(6-(2,5-Dioxo-2,5-dihydro-1H-pyrrol-1-yl)hexanamido)-3-methylbutanamido)propanamido)phenyl)-4-(4-(4-(4-(((S)-2-methoxy-12-oxo-6a,7,8,9,10,12-hexahydrobenzo[e]pyrido[1,2-a][1,4]diazepin-3-yl)oxy)butanamido)-1-methyl-1H-1-pyrrole-2-carboxamido]phenyl)-1-methyl-1H-pyrrole-2-carboxamide (141)

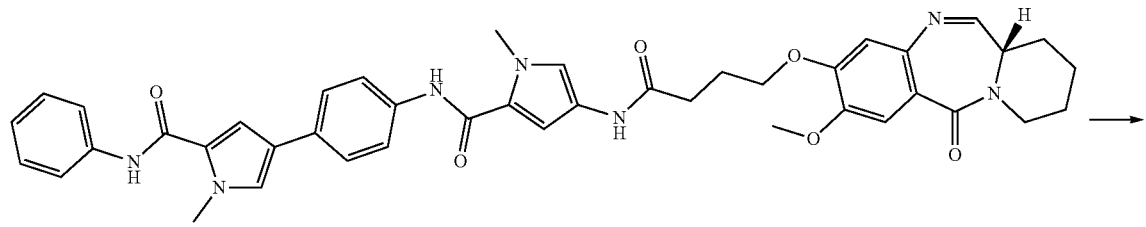

41

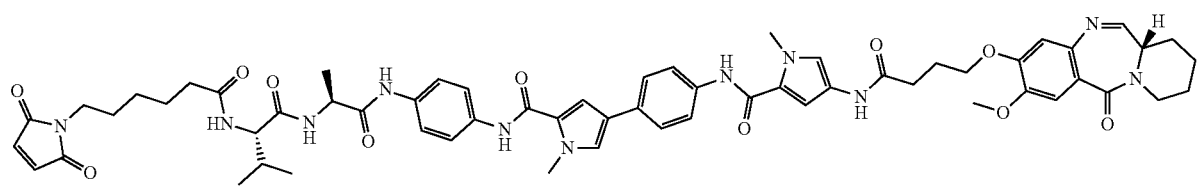

141

A mixture of (6-(2,5-dioxo-2,5-dihydro-1H-pyrrol-1-yl)hexanoyl)-L-valyl-L-alanine (160 mg, 0.420 mmol) and N-ethoxycarbonyl-2-ethoxy-1,2-dihydroquinoline (150 mg, 0.600 mmol) in dichloromethane (10 mL) was stirred at 0° C. for 30 min. (S)—N-(4-Aminophenyl)-4-(4-(4-(4-((2-methoxy-12-oxo-6a,7,8,9,10,12-hexahydrobenzo[e]pyrido[1,2-a][1,4]diazepin-3-yl)oxy)butanamido)-1-methyl-1H-pyrrole-2-carboxamido)phenyl)-1-methyl-1H-pyrrole-2-carboxamide (41) (300 mg, 0.400 mmol) in methanol (1 mL) was added to the reaction mixture at 0° C. The reaction mixture was stirred at 0° C. for 5 h and then warmed to room temperature for another 11 h. The reaction mixture was purified by neutral alumina column to afford the title compound (220 mg, 50%) as a yellow solid.

$^1$H NMR (400 MHz, DMSO-d$_6$) δ 9.92 (s, 1H), 9.86 (s, 1H), 9.81 (s, 2H), 8.15 (d, J=6.8 Hz, 1H), 8.00 (d, J=5.8 Hz, 1H), 7.83 (d, J=8.8 Hz, 1H), 7.68 (dd, J=22.8, 8.8 Hz, 4H), 7.56-7.42 (m, 5H), 7.38 (s, 1H), 7.27 (s, 1H), 7.22 (s, 1H), 7.00-6.98 (m, 3H), 6.80 (s, 1H), 4.45-4.32 (m, 1H), 4.22-4.09 (m, 2H), 4.07-3.97 (m, 2H), 3.90 (s, 3H), 3.82 (s, 6H), 3.70-3.67 (m, 1H), 3.35-3.33 (m, 1H), 3.14-3.13 (m, 1H), 2.46-2.40 (m, 2H), 2.16-2.14 (m, 2H), 2.09-2.01 (m, 3H), 1.96-1.90 (m, 1H), 1.89-1.81 (m, 1H), 1.80-1.65 (m, 3H), 1.62-1.41 (m, 6H), 1.33-1.26 (m, 4H), 1.26-1.12 (m, 6H), 0.92-0.76 (m, 6H); $^{13}$C NMR (100 MHz, DMSO-d$_6$) δ224.5, 217.8, 207.7, 204.1, 196.3, 195.7, 192.6, 192.0, 187.3, 185.2, 183.3, 175.0, 172.7, 171.5, 171.4, 169.3, 166.8, 165.1, 160.0, 150.7, 147.6, 143.0, 140.3, 137.6, 135.2, 134.9, 129.9, 126.6, 124.8, 122.5, 120.8, 120.7, 119.8, 113.4, 111.8, 109.9, 106.7, 103.9, 75.4, 58.0, 56.1, 54.1, 52.2, 49.4, 45.4, 37.4, 35.6, 32.3, 30.8, 28.2, 26.6, 25.3, 23.0, 18.6, 18.5, 18.2, 15.3, 11.6; MS (ES+): m/z=1120.5 (M+H)$^+$: MS (ES+): m/z=1120.5 (M+H)$^+$: LCMS (Method B): t$_R$=3.36 min.

Example 145

2,5-Dioxopyrrolidin-1-yl 1-(2,5-dioxo-2,5-dihydro-1H-pyrrol-1-yl)-3-oxo-7,10,13,16,19,22,25,28-octaoxa-4-azahentriacontan-31-oate (143)

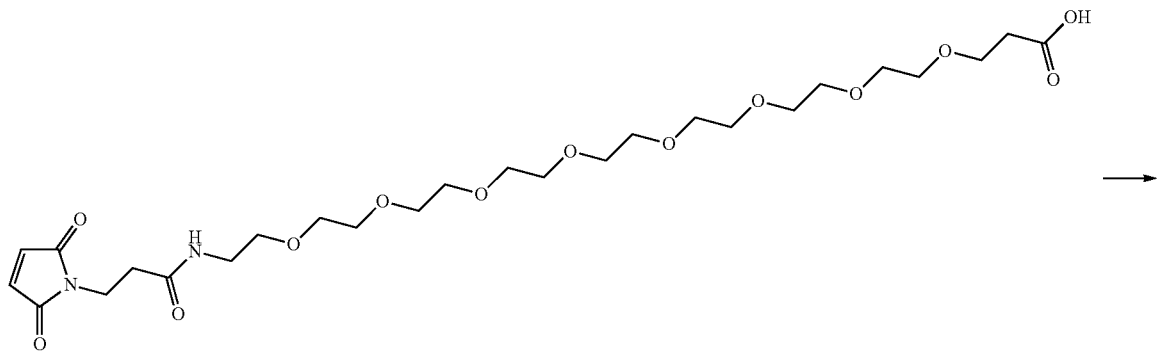

142

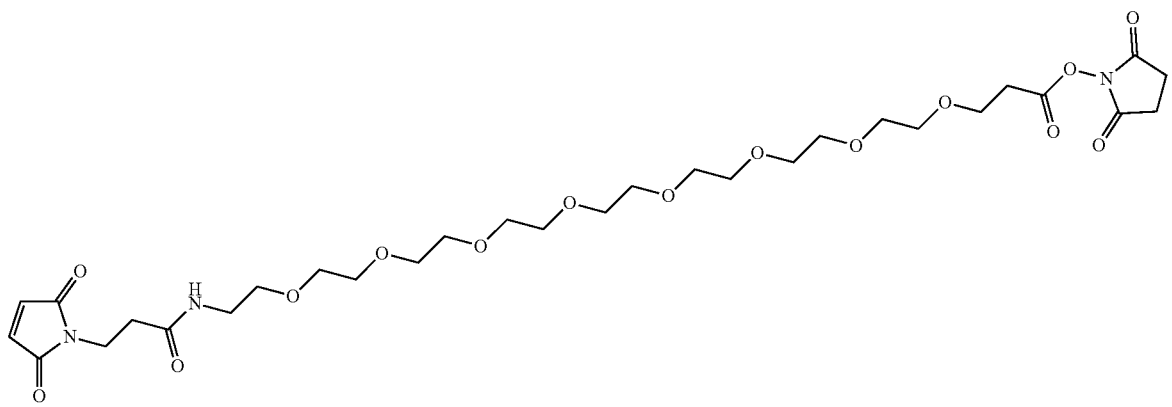

143

DCC (206 mg, 1.01 mmol) was added to a 0° C. solution of 1-(2,5-dioxo-2,5-dihydro-1H-pyrrol-1-yl)-3-oxo-7,10,13,16,19,22,25,28-octaoxa-4-azahentriacontan-31-oic acid (142) (500 mg, 0.844 mmol), 1-hydroxypyrrolidine-2,5-dione (100 mg, 0.886 mmol) in DCM/EtOAc (1/1, 20 mL). The reaction mixture was stirred at room temperature for 16 h. The reaction mixture was filtered and concentrated to dryness under reduced pressure to give the title compound (500 mg, 85%) as a yellow oil. The product was carried through to the next step without any further purification.

MS (ES+): m/z=689.3 (M+H)$^+$: LCMS (Method B): $t_R$=2.70 min.

Example 146

(9H-Fluoren-9-yl)methyl ((S)-1-(((S)-1-((4-(4-(4-(4-(4-(((S)-2-methoxy-12-oxo-6a,7,8,9,10,12-hexahydrobenzo[e]pyrido[1,2-a][1,4]diazepin-3-yl)oxy)butanamido)-1-methyl-1H-1-pyrrole-2-carboxamido)phenyl)-1-methyl-1H-pyrrole-2-carboxamido)phenyl)amino)-1-oxopropan-2-yl)amino)-3-methyl-1-oxobutan-2-yl)carbamate (144)

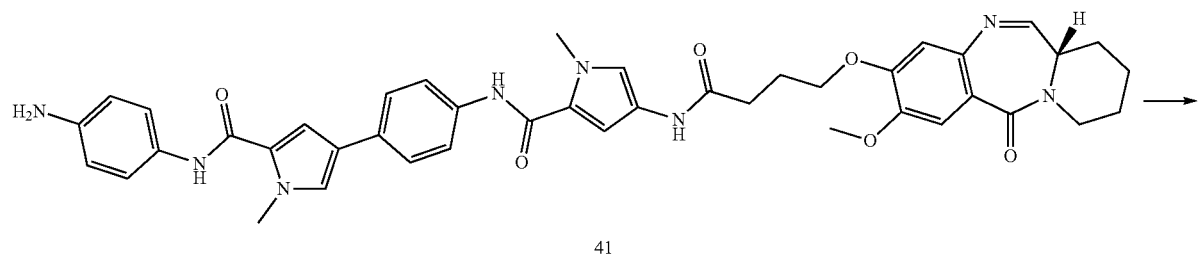

41

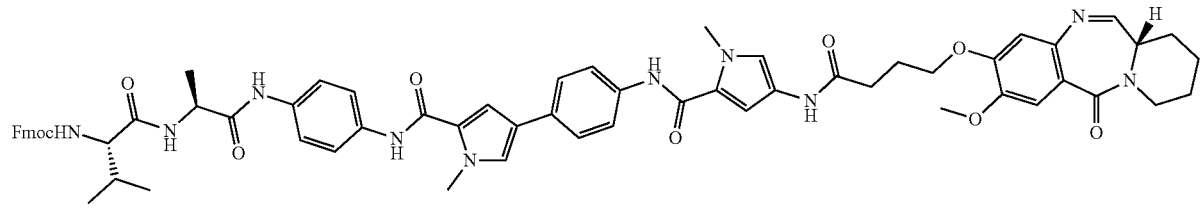

144

A mixture of (((9H-fluoren-9-yl)methoxy)carbonyl)-L-valyl-L-alanine (325 mg, 0.793 mmol) and EEDQ (326 mg, 1.32 mmol) in DMF (20 mL) was stirred at 0° C. for 1 h. (S)—N-(4-Aminophenyl)-4-(4-(4-(4-((2-methoxy-12-oxo-6a,7,8,9,10,12-hexahydrobenzo[e]pyrido[1,2-a][1,4]diazepin-3-yl)oxy)butan amido)-1-methyl-1H-pyrrole-2-carboxamido)phenyl)-1-methyl-1H-pyrrole-2-carboxamide (41) (500 mg, 0.661 mmol) was added to the reaction mixture and stirred at 0° C. for 5 h, then stirred at room temperature for 13 h. The reaction mixture was diluted with DCM/TBME (⅛, 200 mL) and stirred for 1 h before being filtered. The solid cake was dried under reduced pressure to give the title compound (500 mg, 66%) as a yellow solid. The product was carried through to the next step without any further purification.

MS (ES+): m/z=1149.2 (M+H)$^+$: LCMS (Method B): $t_R$=3.92 min.

Example 147

N-(4-((S)-2-((S)-2-Amino-3-methylbutanamido)
propanamido)phenyl)-4-(4-(4-(4-(((S)-2-methoxy-
12-oxo-6a,7,8,9,10,12-hexahydrobenzo[e]pyrido[1,
2-a][1,4]diazepin-3-yl)oxy)butanamido)-1-methyl-
1H-pyrrole-2-carboxamido)phenyl)-1-methyl-1H-1-
pyrrole-2-carboxamide (145)

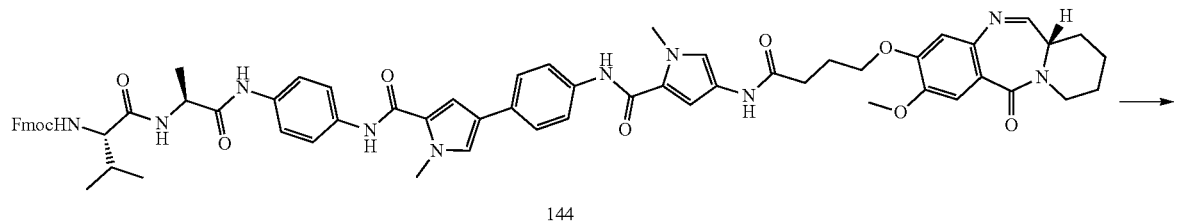

144

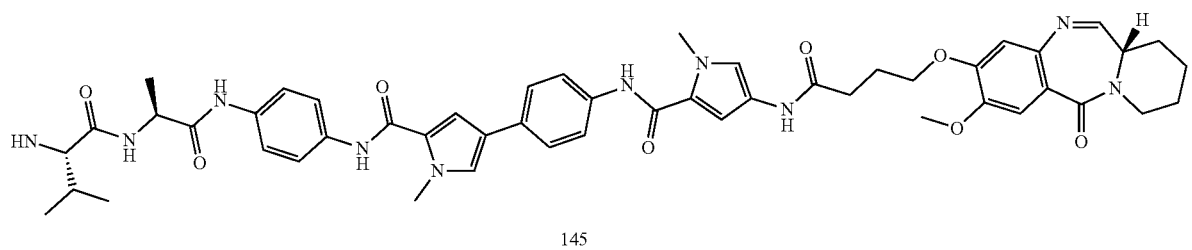

145

A mixture of (9H-fluoren-9-yl)methyl ((S)-1-(((S)-1-((4-(4-(4-(4-(((S)-2-methoxy-12-oxo-6a,7,8,9,10,12-hexahydrobenzo[e]pyrido[1,2-a][1,4]diazepin-3-yl)oxy)butanamido)-1-methyl-1H-pyrrole-2-carboxamido)phenyl)-1-methyl-1H-pyrrole-2-carboxamido)phenyeamino)-1-oxopropan-2-yl)amino)-3-methyl-1-oxobutan-2-yl) carbamate (144) (500 mg, 0.435 mmol) and piperidine (111 mg, 1.31 mmol) in DMF (10 mL) was stirred at room temperature for 16 h. The reaction mixture was diluted with DCM/TBME (⅛, 200 mL) and stirred for 1 hour before filtered. The solid cake was dried under reduced pressure to give the crude product (400 mg, 99% yield) as a yellow solid. The product was carried through to the next step without any further purification.

MS (ES+): m/z=927.2 (M+H)⁺: LCMS (Method B): $t_R$=2.81 min.

Example 148

N-(4-((2S,5S)-37-(2,5-Dioxo-2,5-dihydro-1H-pyr-
rol-1-yl)-5-isopropyl-2-methyl-4,7,35-trioxo-10,13,
16,19,22,25,28,31-octaoxa-3,6,34-triazaheptatria-
contanamido)phenyl)-4-(4-(4-(4-(((S)-2-methoxy-
12-oxo-6a,7,8,9,10,12-hexahydrobenzo[e]pyrido[1,
2-a][1,4]diazepin-3-yl)oxy)butanamido)-1-methyl-
1H-pyrrole-2-carboxamido)phenyl)-1-methyl-1H-
pyrrole-2-carboxamide (146)

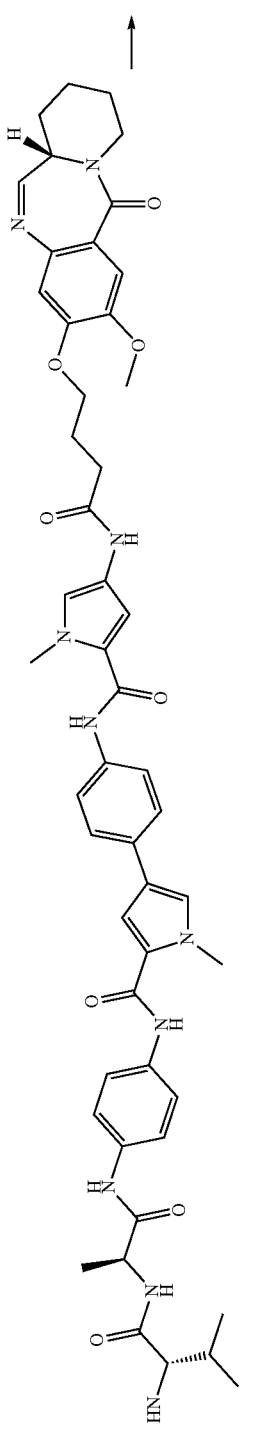
145
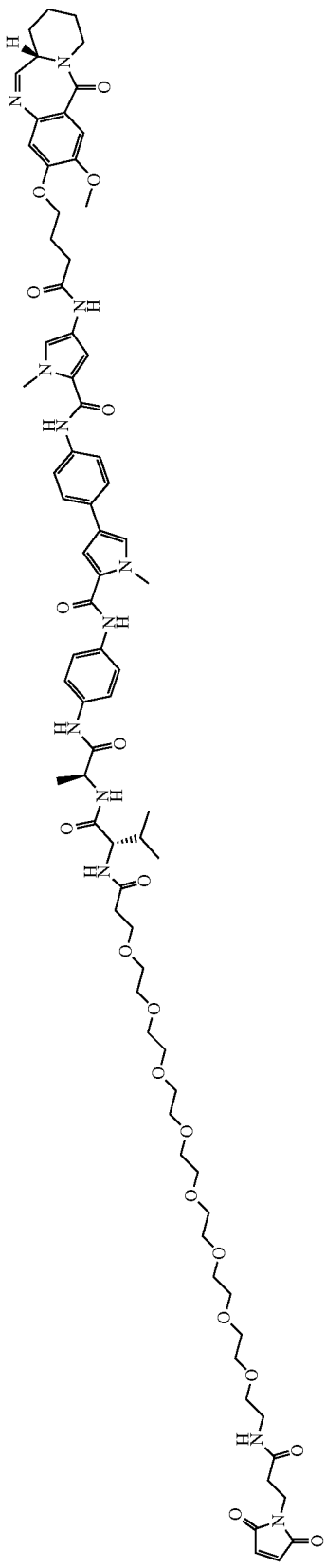
146

A mixture of N-(4-((S)-2-((S)-2-amino-3-methylbutanamido)propanamido)phenyl)-4-(4-(4-(4-(((S)-2-methoxy-12-oxo-6a,7,8,9,10,12-hexahydrobenzo[e]pyrido[1,2-a][1,4]diazepin-3-yl)oxy)butanamido)-1-methyl-1H-pyrrole-2-carboxamido)phenyl)-1-methyl-1H-pyrrole-2-carboxamide (145) (400 mg, 0.431 mmol), 2,5-dioxopyrrolidin-1-yl 1-(2,5-dioxo-2,5-dihydro-1H-pyrrol-1-yl)-3-oxo-7,10,13,16,19,22,25,28-octaoxa-4-azahentriacontan-31-oate (143) (357 mg, 0.518 mmol) and DIPEA (143 μL, 0.865 mmol) in DMF (10 mL) was stirred at room temperature for 16 h. The reaction mixture was concentrated under reduced pressure. The resulting residue was then purified by column chromatography (silica), eluting with methanol/dichloromethane (from 0% to 10%), followed by preparative TLC, to give the title compound (100 mg, 15%) as a yellow gum.

$^1$H NMR (400 MHz, DMSO-d$_6$) δ 9.95 (s, 1H), 9.88 (s, 1H), 9.81 (d, J=3.5 Hz, 2H), 8.17 (d, J=7.2 Hz, 1H), 8.05-7.97 (m, 1H), 7.90 (d, J=8.6 Hz, 1H), 7.71-(d, J=8.4 Hz, 2H), 7.66 (d, J=8.9 Hz, 2H), 7.55 (d, J=8.9 Hz, 2H), 7.49 (d, J=8.4 Hz, 2H), 7.44 (s, 1H), 7.40 (s, 1H), 7.22 (s, 1H), 7.02-6.93 (m, 2H), 4.63-4.47 (m, 1H), 4.46-4.31 (M, 1H), 4.27-4.15 (m, 1H), 4.11 (q, J=5.2 Hz, 3H), 4.06-3.97 (m, 1H), 3.90 (s, 3H), 3.86-3.80 (m, 3H), 3.74-3.64 (m, 3H), 3.64-3.55 (m, 4H), 3.52-3.46 (m, 22H), 3.19-3.10 (m, 8H), 2.67 (s, 1H), 2.46-2.38 (m, 3H), 2.32 (t, J=7.2 Hz, 2H), 2.11-1.92 (m, 4H), 1.92-1.69 (m, 2H), 1.69-1.48 (m, 3H), 1.31 (d, J=7.1 Hz, 3H), 1.23 (br. s., 6H), 0.86 (dd, J=6.7, 15.5 Hz, 6H); MS (ES+): m/z=1501.9 (M+H)$^+$: LCMS (Method B): t$_R$=3.13 min.

Example 149 tert-Butyl (5-((4-(5-((4-aminophenyl)carbamoyl)-1-methyl-1H-pyrrol-3-yl)phenyl)carbamoyl)-1-methyl-1H-pyrrol-3-yl)carbamate (147)

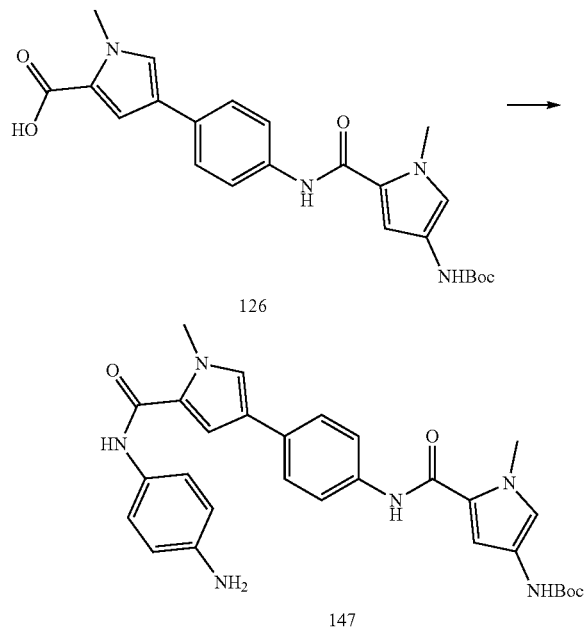

A solution of 4-(4-(4-((tert-butoxycarbonyl)amino)-1-methyl-1H-pyrrole-2-carboxamido)phenyl)-1-methyl-1H-pyrrole-2-carboxylic acid (126) (300.0 mg, 0.68 mmol) in N,N-dimethylformamide (8 mL) was charged with N,N-dimethylpyridin-4-amine (250.7 mg, 2.0 mmol) and N-(3-dimethylaminopropyl)-N'-ethylcarbodiimide hydrochloride (327.8 mg, 1.71 mmol) and it was stirred for 30 min at room temperature. To the reaction mixture, benzene-1,4-diamine (88.6 mg, 0.82 mmol) was then added and the solution was stirred for further 18 h. The reaction mixture was quenched with a saturated aqueous solution of sodium hydrogen carbonate (30 mL) and loaded with brine (80 mL). The aqueous phase was extracted with ethyl acetate (2×60 mL). The combined organic extracts were concentrated in vacua. The resulting residue was purified by column chromatography (silica), eluting with acetone/dichloromethane (from 0% to 40%), to give the title compound (355 mg, 99%) as a brown oil.

MS (ES+): m/z=529 (M+H)$^+$: LCMS (Method B): t$_R$=3.28 min.

Example 150

4-Amino-N-(4-(5-((4-aminophenyl)carbamoyl)-1-methyl-1H-pyrrol-3-yl)phenyl)-1-methyl-1H-1-pyrrole-2-carboxamide (148)

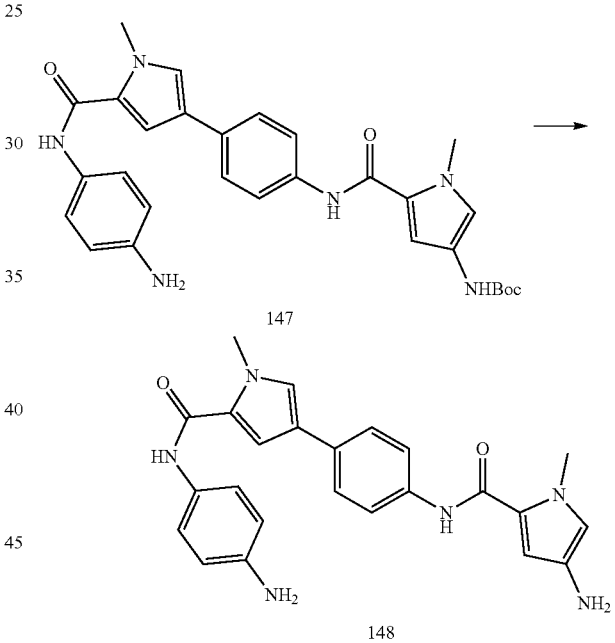

To a solution of tert-butyl (5-((4-(5-((4-aminophenyl)carbamoyl)-1-methyl-1H-pyrrol-3-yl)phenyl)carbamoyl)-1-methyl-1H-pyrrol-3-yl)carbamate (147) (100.0 mg, 0.19 mmol) in 1,4-dioxane and methanol (1:1) (2 mL) hydrochloric acid (4 M in 1,4-dioxane) (2 mL) was added drop wise. The reaction mixture was stirred for 4 h and then quenched through the addition of a 1M solution of sodium hydroxide aqueous solution (10 mL, 10 mmol). The mixture was then diluted with brine (30 mL) and the resulting aqueous phase was washed with dichloromethane (3×30 mL). The organic layer was dried over magnesium sulphate anhydrous, filtered and concentrated in vacua affording the titled compound (70 mg, 86%) as a brown oil.

$^1$H NMR (400 MHz, CD$_3$OD) δ 7.58-7.54 (m, 3H), 7.53-7.49 (m, 2H), 7.35-7.30 (m, 2H), 7.22 (s, 2H), 6.75-6.71 (m, 2H), 6.61 (s, 1H), 3.91 (s, 3H), 3.83 (s, 3H); $^{13}$C NMR (100 MHz, CD$_3$OD) δ 126.5, 124.9, 124.6, 123.1, 122.7, 121.0, 115.3, 110.0, 35.6, 35.2; MS (ES+): m/z=429 (M+H)$^+$: LCMS (Method B): $t_R$=2.35 min.

Example 151

Evidence of DNA Adduct formation by HPLC

Interaction of C8-linked PDD monomers with duplex transcription factor consensus sequence was studied with an HPLC assay utilizing a X-bridge MS C18 2.5 μM OST column (2.3×50 mm) and a gradient of 40% acetonitrile/water and 100 mM TEAB (Tetraethylammonium bromide)/water as mobile phase with a flow rate of 0.5 mL/min and UV detection at 254 nm. A 4:1 molar ratio of ligand:oligonucleotide was used, with each single-stranded oligonucleotide dissolved in 1 M ammonium acetate to form stock solutions of 1 mM. The oligonucleotides were initially annealed by heating their 1 mM solutions to 70° C. for to mins followed by gradual cooling over 8 hours and storage overnight at −20° C. Working solutions of oligonucleotides of 25 μM were then prepared by diluting the annealed stock solutions with 100 mM ammonium acetate. The ligands were dissolved in DMSO to form a stock solution of 10 mM which was stored at −20° C. for no longer than four months. Working solutions of the drug of 100 μM were prepared by diluting the stock solution with 100 mM ammonium acetate. The working solutions of the ligands were added to the working solution the oligonucleotides at RT, and the mixture incubated for different time intervals at room temperature.

Example 152

Fluorescence Resonance Energy Transfer (FRET) Assay

Oligonucleotide sequences used for the FRET assays were purchased from Eurogentec, Southampton, UK: TAMRA (6-carboxytetramethylrhodamine) and FAM (6-carboxyfluorescein) are acceptor and donor fluorophores, respectively. From 20 μM stock solutions, 400 nM solutions in FRET buffer (optimized as 50 mM potassium, 50 mM cacodylate, pH 7.4) were prepared prior to use. The oligonucleotides were annealed through heating the samples to 90° C. for to mins followed by cooling to room temperature and storing at this temperature for 5h. Dilutions from the initial 5 mM DMSO stock solution were performed using FRET buffer. Annealed DNA (50 μL) and sample solution (50 μL) were added to each well of a 96-well plate (MJ Research, Waltham, Mass.), and processed in a DNA Engine Opticon (MJ Research). Fluorescence readings were taken at intervals of 0.5° C. over the range 30-100° C., with a constant temperature maintained for 30 seconds prior to each reading. Incident radiation of 450-495 nm was used, with detection at 515-545 nm. The raw data were imported into the program Origin (Version 7.0, OringinLab Corp.), and the graphs were smoothed using a 10-point running average, and then normalized. Determination of melting temperatures was based on values at the maxima of the first derivative of the smoothed melting curves using a script. The difference between the melting temperature of each sample and that of the blank (ΔTm) was used for comparative purposes.

TABLE 1

ΔTm determined after 24 hours incubation with Transcription Factor duplex DNA sequences

| | ΔTm at 1 μM ligand concentration | | | |
|---|---|---|---|---|
| Compound | NFκB (1$^{st}$ transition) | NFκB (2$^{ND}$ transition) | AP-1 (1$^{st}$ transition) | AP-1 (2$^{ND}$ transition) |
| 13 | 12 | 23 | 11 | 19 |
| 17 | 11 | 26 | 13 | 18 |
| 20 | 9 | 12 | 8 | 13 |
| 24 | 10 | 14 | 9 | 15 |

Example 153

Cytotoxicity Analysis of C8-linked PDD monomers by MTT Assay

Cell Culture

MDA MB231 (triple negative human breast cancer) was obtained from the American Type Culture Collection. The cell-line was maintained in monolayer culture in 75 cm$^2$ flasks (TPP, Switzerland) under a humidified 5% $CO_2$ atmosphere at 37° C. The MDA MB231 cell line was maintained in high glucose DMEM (4.5 g\l; Invitrogen), foetal bovine serum (10%, Biosera UK), non-essential amino acids (1×; Invitrogen), L-glutamine (2 mM; Invitrogen) and Penicillin-Streptomycin (1% v/v, Invitrogen). The HeLa cell line was maintained in Dulbecco's Modified Eagles Media (DMEM; Invitrogen) supplemented with foetal bovine serum (10% v/v; Invitrogen), L-glutamine (2 mM; Invitrogen), non-essential amino acids (1×; Invitrogen) and Penicillin-Streptomycin (1% v/v, Invitrogen). For passaging, cells were washed with PBS (GIBCO 14040, Invitrogen, UK), incubated with trypsine (GIBCO 25300, Invitrogen, UK), and re-seeded into fresh medium. For seeding, cells were counted using a Neubauer haemocytometer (Assistant, Germany) by microscopy (Nikon, USA) on a non-adherent suspension of cells that were washed in PBS, trypsinised, centrifuged at 8° C. at 8000 rpm for 5 min and re-suspended in fresh medium.

MTT Assay

The cells were grown in normal cell culture conditions at 37° C. under a 5% $CO_2$ humidified atmosphere using appropriate medium. The cell count was adjusted to $10^5$ cells/ml and 5,000-20,000 cells were added per well depending on the cell line. The cells were incubated for 24 hours and 1 μl of the appropriate inhibitor concentrations were added to the wells in triplicates. After 72 h of continuous exposure to each compound, the cytotoxicity was determined using the 3-(4,5-Dimethylthiazol-2-yl)-2,5-diphenyltetrazolium bromide (MTT) (Lancaster Synthesis Ltd, UK) colorimetric assay.[34] Absorbance was quantified by spectrophotometry at λ=570 nm (Envision Plate Reader, PerkinElmer, USA). $IC_{50}$ values were calculated by a dose-response analysis using the GraphPad Prism® software.

TABLE 2

IC$_{50}$ values (nM) determined after 72 hours exposure for the C8-linked PDD monomers.

| | IC$_{50}$ (nanomolar) | |
| --- | --- | --- |
| Compound | MDA MB 231 (Triple negative breast cancer cell line) | HeLa (Cervical cancer cell line) |
| 13 | 64 ± 9.6 | 0.6 ± 0.4 |
| 17 | 21 ± 1.8 | 1.2 ± 0.8 |
| 20 | 0.3 ± 0.22 | 0.14 ± 0.09 |
| 24 | 0.8 ± 0.66 | 1 ± 0.12 |

Example 154

Biological and Biophysical Characterisation of Free Payloads

In Vitro Cytotoxicity

The in vitro cytotoxicity of compounds 73, 76, 81, 88 and 93 were evaluated in the JIMT-1, MCF-7, MDA-MB-453 and SK-BR-3 (all breast cancer) cell lines using the standard MTT assay for a 72 hour incubation period (Table 3).

TABLE 3

Cytotoxicity of 73, 76, 81, 88 and 93.

| Compound Number | Cytotoxicity (nM) | | | |
| --- | --- | --- | --- | --- |
| | JIMT-1 | MCF-7 | MDA-MB-453 | SK-BR-3 |
| 73 | 0.33 | 0.42 | 0.20 | 0.27 |
| 88 | 0.37 | 0.60 | 0.13 | 0.06 |
| 76 | 0.43 | 0.53 | 0.19 | 0.29 |
| 81 | 0.50 | 1.40 | 0.42 | 0.33 |
| 93 | 0.37 | 2.00 | 0.18 | 0.09 |

Compound 41 was evaluated in a broader cell-line panel (Table 4) affording low picomolar activity in a variety of cancer types, suggesting broad use for the payload class.

TABLE 4

In vitro cytotoxicity of 41 in a broad panel of cancer cell-lines (72 hour incubation).

| Cell Line | IC$_{50}$ (Nanomolar, 72 hour incubation) |
| --- | --- |
| 786-O (Renal Cell, CD70) | 0.53 |
| SK-HEP-1 (Liver) | 0.32 |
| SK-MEL-5 (Melanoma) | 0.39 |
| Calu-3 (Lung) | 0.65 |
| A549 (Lung) | 0.18 |
| AGS (Gastric) | 0.07 |
| PC3 (Prostate) | 0.36 |
| SW480 (Colorectal) | 0.29 |
| EC Cancer Stem Cell (Cancer stem cells) | 2.64 |
| AML2 (AML) | 0.016 |
| HL60 (APML) | 0.009 |
| LnCap (Prostate) | 0.47 |
| BxPC3 (Pancreas) | 0.43 |
| A375 (Skin) | 0.28 |

Example 155

DNA Cross-Linking Assay

The ability of 41 to cross-link DNA was evaluated using an assay involving a linear double-stranded TyrT fragment (FIG. 5). The PBD dimer Talirine (SGD1882) was used as a positive control, as PBD dimers have previously been shown to cross-link DNA[32]. Following denaturation conditions (treatment with formamide and heating at 65° C. for 5 min), the DNA strands were completely separated (see control C2, FIGS. 6 and 7). The presence of an interstrand cross-link holds the denatured strands in close proximity, and cross-linked adducts therefore run as double-stranded DNA on polyacrylamide gel.

Both compounds were tested at six different concentrations, and the assay was repeated twice. The cross-linking ability of 41 is shown in FIG. 6. Cross-links are not detectable at any concentration (i.e., from 10 μM to as low as 0.1 nM), whereas the PBD dimer Talirine produces cross-links at concentrations as low as 10 nM (FIG. 7). These results demonstrate that 41 is incapable of cross-linking DNA, consistent with its proposed mono-alkylation mechanism of action.

Example 156

DNA Footprinting

Figure 8A:
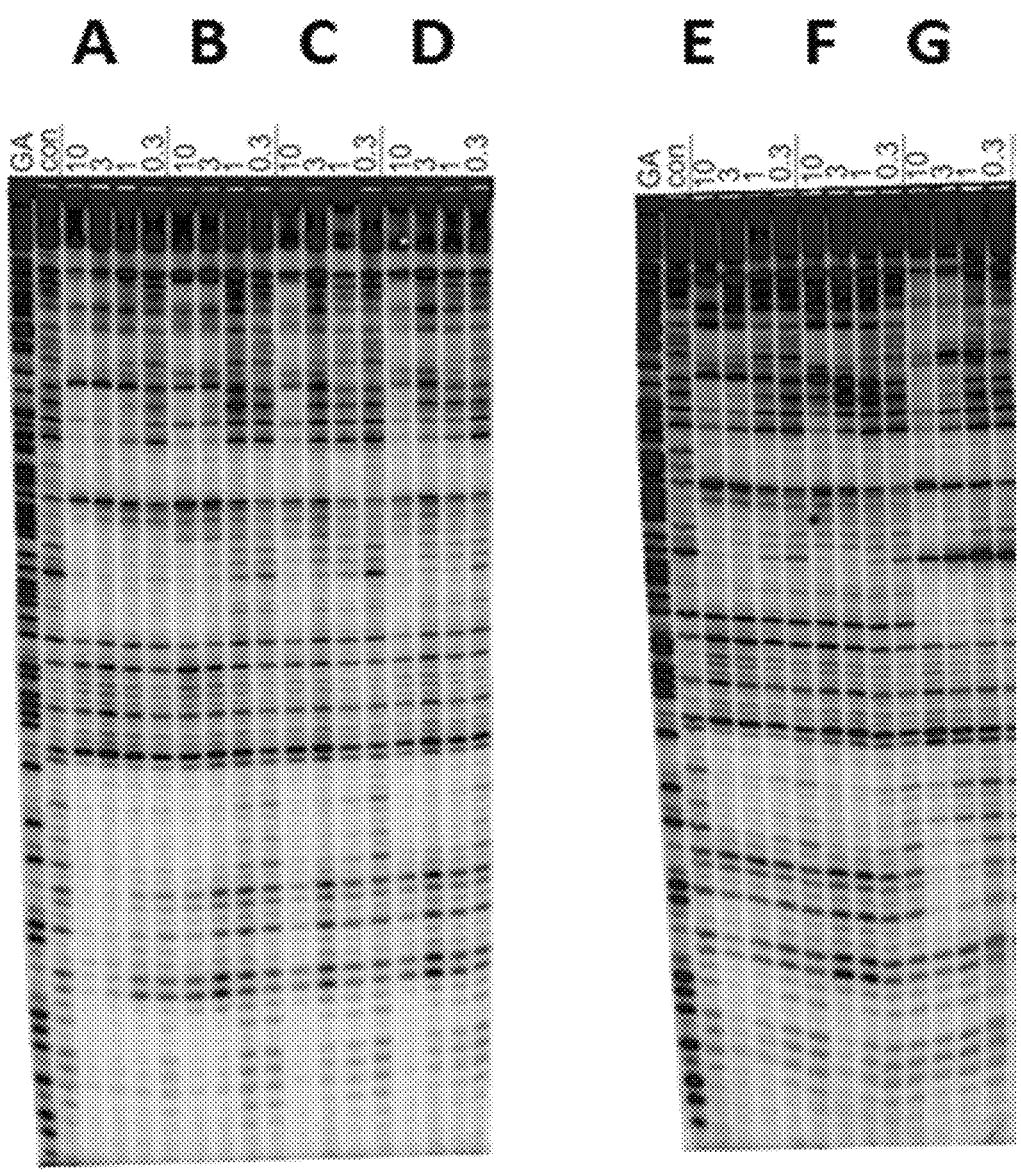
FIG. 8A shows DNA footprint illustrating the interaction of 73 (B), 76 (D), 81 (E), 88 (C) and 93 (G) with the MS1 DNA fragment. Ligand concentrations are shown at the top of the gel. Tracks labelled "GA" are markers for specific purines.

The DNA sequence selectivity profile of selected molecules was investigated using a modification of the previously established DNA footprinting assay[329]. Following an overnight incubation of the ligand-DNA complexes, the mixture was mixed with strand separation buffer containing 10 mM EDTA, 10 mM NaOH, 0.1% bromophenol blue, 80% formamide and incubated at 100° C. for 3 min. The mixture was then immediately cooled on ice and run on an 8% denaturing gel. Examination of the obtained gel (FIGS. 8A-C) shows footprints produced by the molecules on MS1 and HexA DNA sequences. FIGS. 8A and 8B shows DNA footprint illustrating the interaction of 73 (B), 76 (D), 81 (E), 88 (C) and 93 (G) with the MS1 DNA fragment and HexA DNA fragment, respectively (lanes A and F represent further controls). FIG. 8C shows a DNA footprint illustrating the interaction of the PBD dimer Talirine with the MS1 DNA fragment. Interestingly, although the MS1 and HexA DNA fragments contain multiple potential binding sites for molecules 73, 76, 81 and 88 (i.e., multiple examples of potential G-alkylating sites), only six preferred sites in the case of MS1 and five in the case of HexA were observed during this experiment. 93 was found to bind to two further sequences in MS1 not occupied by 73, 76, 81 and 88, suggesting a degree of sequence interactivity not present in other molecules in the class. Molecular modelling studies suggest that this occurs due to the ring nitrogen of the imidazole group of 93 forming sequence-interactive H-bonds with guanine bases (data not presented). These data also suggest that the molecules all act in a highly sequence selective manner with a different sequence selectivity profile to the PBD dimer Talirine (green blocks, FIG. 9). The possible adducts formed within the MS1 and HexA sequences are shown in FIGS. 9 and 10 respectively. FIG. 9 shows compounds 73, 41, 76, 81, 88 (all represented in cyan) and 93 (represented in black) all bind to a similar binding site. 93 (solid black line) also interacts with two further sites. The PBD dimer Talirine (green) illustrates a different binding pattern to 73, 76, 81, 88 and 93. Strong DNA footprints are represented by solid lines and weaker footprints are represented by hatched lines. FIG. 10 shows compounds 73, 41, 76, 81 and 88 (all represented in cyan) and 93 (represented in black) all bind to similar binding sites. Strong DNA footprints are represented by solid lines, and weaker footprints are represented by hatched lines Example 157

FRET DNA Melting

FRET DNA melting studies were undertaken on a fluorescently labelled duplex DNA sequence reacted with 41 and fragmented forms of the molecule (i.e, using intermediates 106, 107 and 148). The sequence (FIG. 10) was designed to provide additional evidence that 41 can effectively stabilise a particular DNA sequence derived through the Footprinting studies (i.e., XGXWWWW where X represents any base, G represents guanine and W indicates adenine or thymine). FIG. 11 shows fluorescently labelled DNA duplex used in the FRET melting study to study the stabilisation of DNA by 41, 106, 107 and 148. The labels were fluorescein (F) and dabcyl (Q).

Figure 12A:
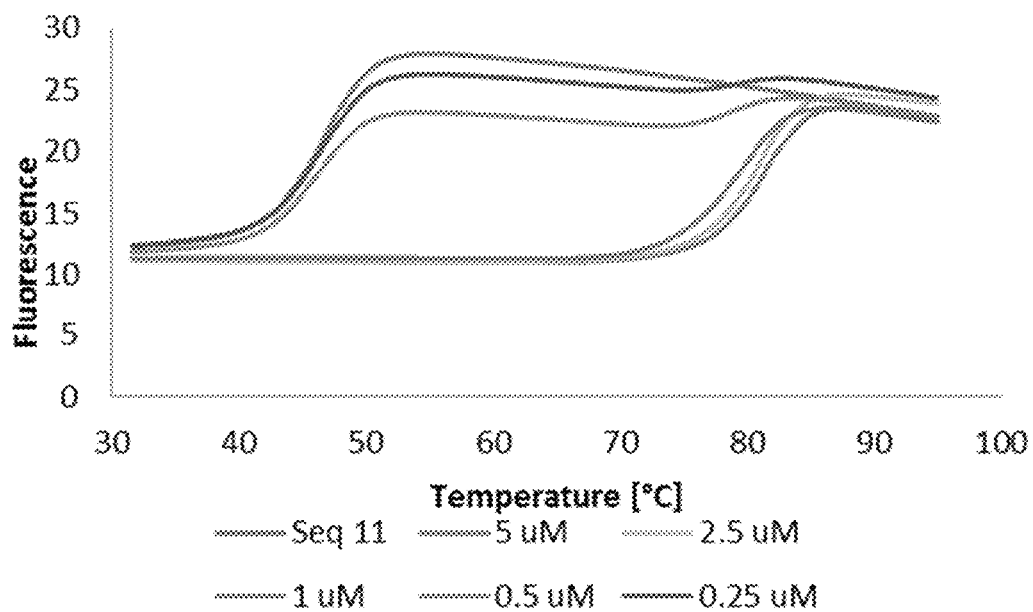
FIG. 12A shows FRET denaturation data for 5'-AAAAAAAGAAATTTAAA-3' when bound to 41.
Figure 12B:
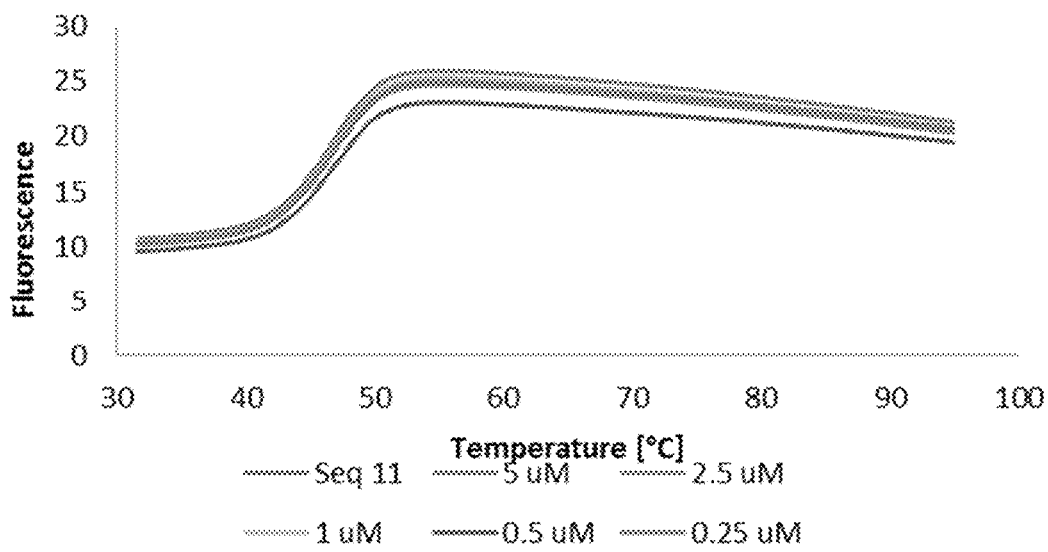
FIG. 12B shows FRET denaturation data for 5'-AAAAAAAGAAATTTAAA-3' when bound to 106, 148 and 107 (right to left).

FIGS. 12A and B show FRET Denaturation data for 5'-AAAAAAAGAAATTTAAA-3' when bound to 41 (FIG. 12A), 106, 148 and 107 (FIG. 12B, right to left). The melting temperature of the duplex increases significantly in proportion to the concentration of 41 present, providing strong supporting evidence that this compound can effectively stabilise DNA. This is in contrast to data derived for the fragments (lower panel), where little stabilisation is observed. The mono-alkylated adduct formed by 41 stabilizes the duplex form, producing very large increases in melting temperature (i.e. $T_m$ values) of >35° C. for 5'-AAAAAAAGAAAAAATTT-3' (FIG. 12A) indicating a very high binding affinity for this particular sequence. Interestingly, when fragmented into its component parts (i.e., 106, 107 and 148), the fragments exhibit little DNA stabilisation (FIG. 12B), suggesting that the enhanced DNA stabilisation and potent cytotoxicity occurs due to the unique combination of the fragments.

Example 158

Transcription Factor Plate Array Assay

Figure 13A:
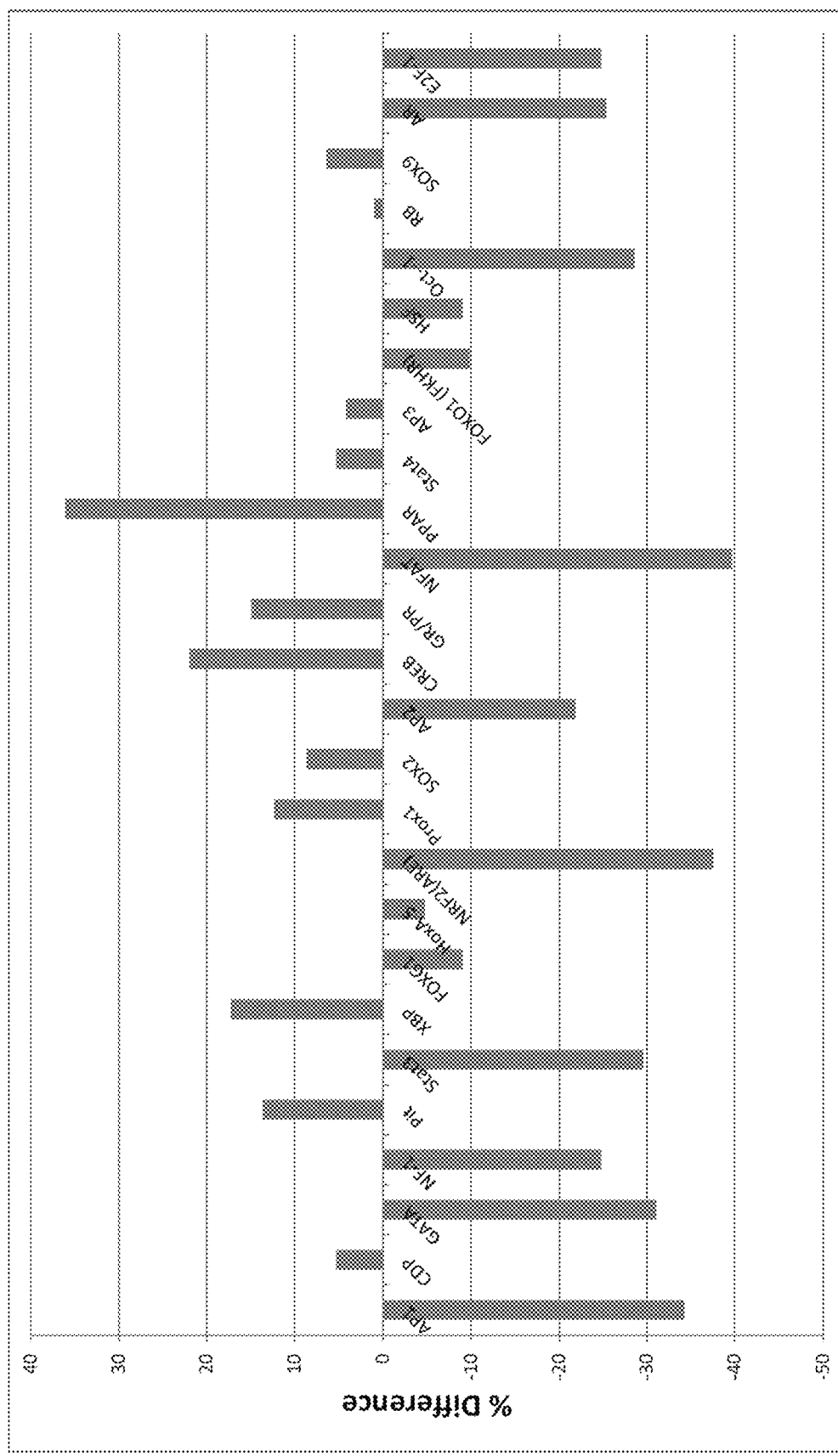
FIG. 13A shows a graph illustrating percentage difference in TF activation in cells treated with compound 4 iversus cells not treated with 41.
Figure 13B:
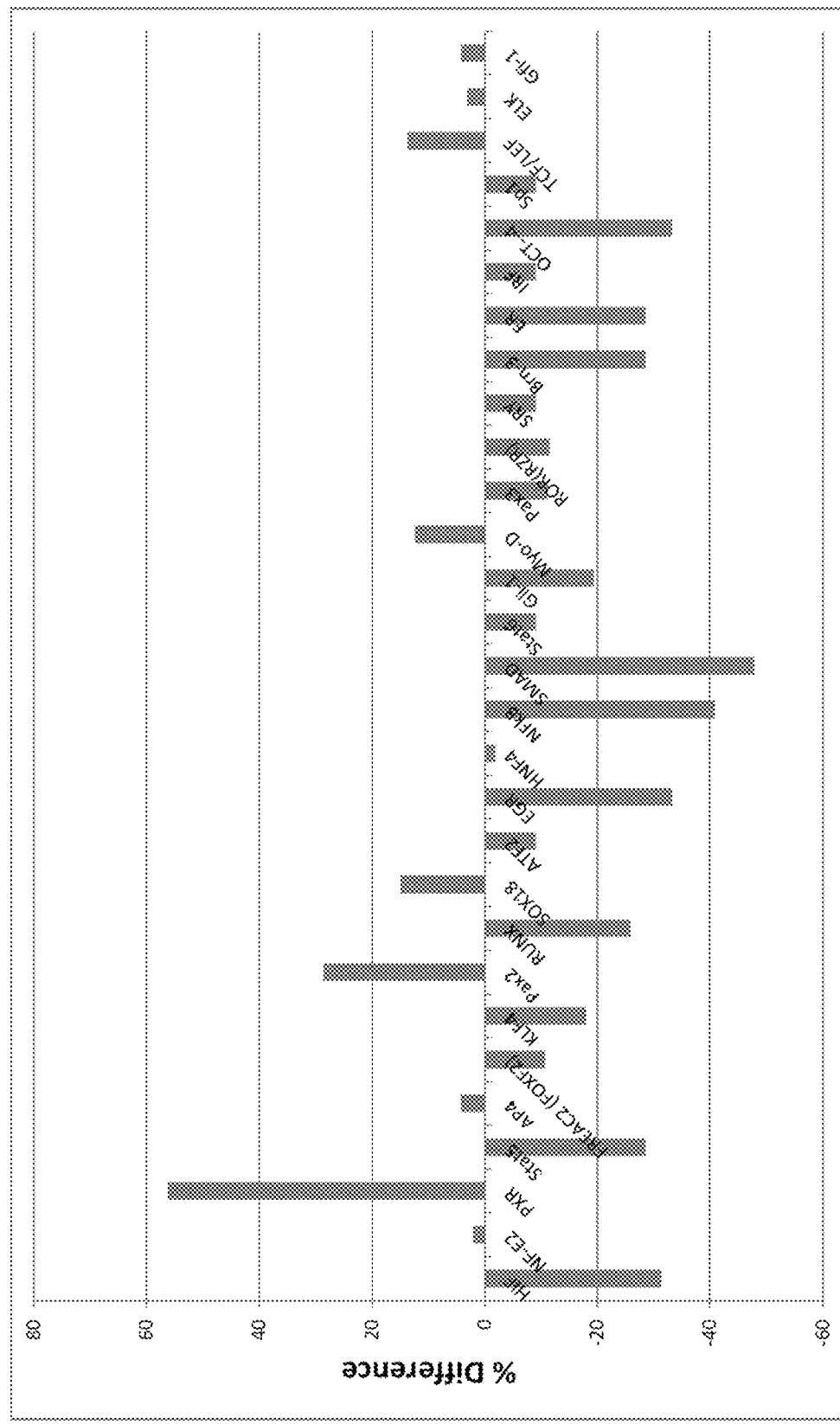
FIG. 13B shows the percentage difference in TF activation in cells not treated with 41.
Figure 14:
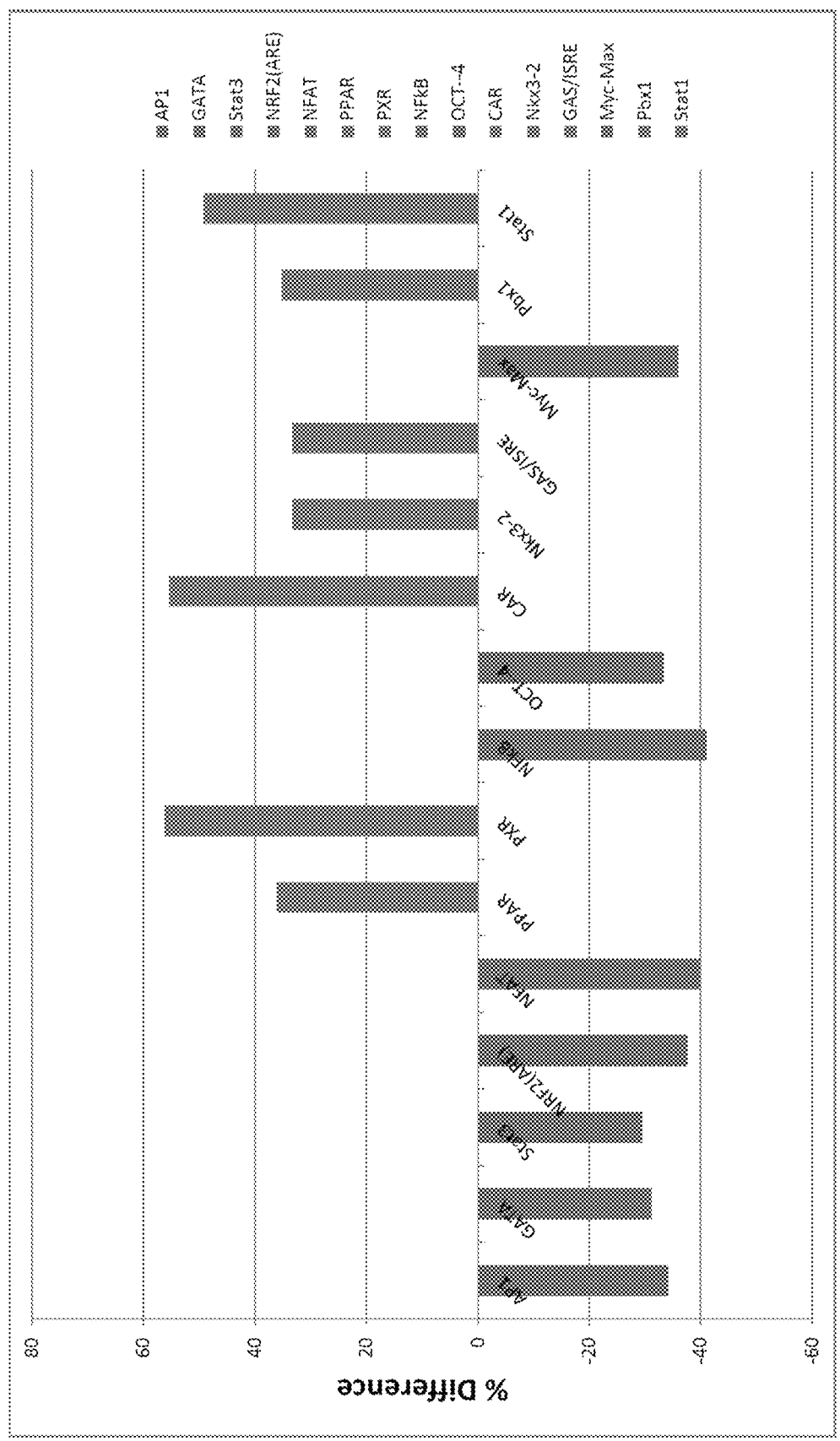
FIG. 14 shows a graph illustrating a summary of the major transcription factors up- and down-regulated by 41.

A transcription factor plate array assay experiment was undertaken to establish which transcription factors are down-regulated through the alkylation of DNA by 41. The study showed that the major transcription factors down-regulated were NFAT, NF-κB, OCT-4 and GATA. FIG. 13 shows a graph illustrating percentage difference in TF activation in treated cells and FIG. 13B shows the percentage difference in TF activation in cells not treated with 41. FIG. 14 shows a graph illustrating a summary of the major transcription factors up- and down-regulated by 41. The consensus sequences of each of these transcription factors corresponds to the DNA footprinting pattern observed for 41.

41 has been found to bind to XGXWWWW where X is any base, G represents guanine and W is A or T. In the case of the transcription factor GATA (consensus site WGATAR, where R is A or G), an obvious binding site matching to the footprint is evident. Similarly, in the case of NF-κB (consensus site GGGRRNNYYCC where N is any base, and Y is C or T), a binding site (bold and underlined) can be identified, and the consensus sequence of NFAT (GGGAA) also directly corresponds to the DNA footprint.

Summary of Examples 154 to 158

Taken together, the biophysical data presented above provide strong evidence that 73, 41, 76, 81, 88 and 93 effectively stabilise DNA with a high degree of sequence-specificity. Furthermore, when fragmented into its component parts, the individual fragments of 41 exhibit a low degree of DNA stabilisation when reacted with DNA, but provide a large degree of stabilisation when joined, highlighting the uniqueness of the parent structure to recognize specific DNA sequences. Together, these data suggest that the population of DNA adduct types derived may account for the cytotoxicity of this family of compounds in cells. Furthermore, DNA Footprinting studies indicate a degree of sequence selectivity for the class, with the DNA-binding site generally corresponding to XGXWWWW where X represents any base and W indicates adenine or thymine. 41 was shown to down-regulate a number of key transcription factors (e.g., NF-κB and GATA), and analysis suggests that their binding sites correspond to the main DNA Footprint observed for this class of molecules. Overall, these data suggest that the potent cytotoxicity observed for the PDD class of payloads is directly related to their DNA-binding affinity and sequence selectivity which can result in the inhibition and down-regulation of key transcription factors. The fact that these compounds mono-alkylate rather than cross-link DNA as occurs with the PBD dimers, suggests that they may produce less overall systemic toxicity[3], and may provide a higher Therapeutic Index in animal models or human clinical trials.

Example 159 yH2aX Assay

Figure 15A:
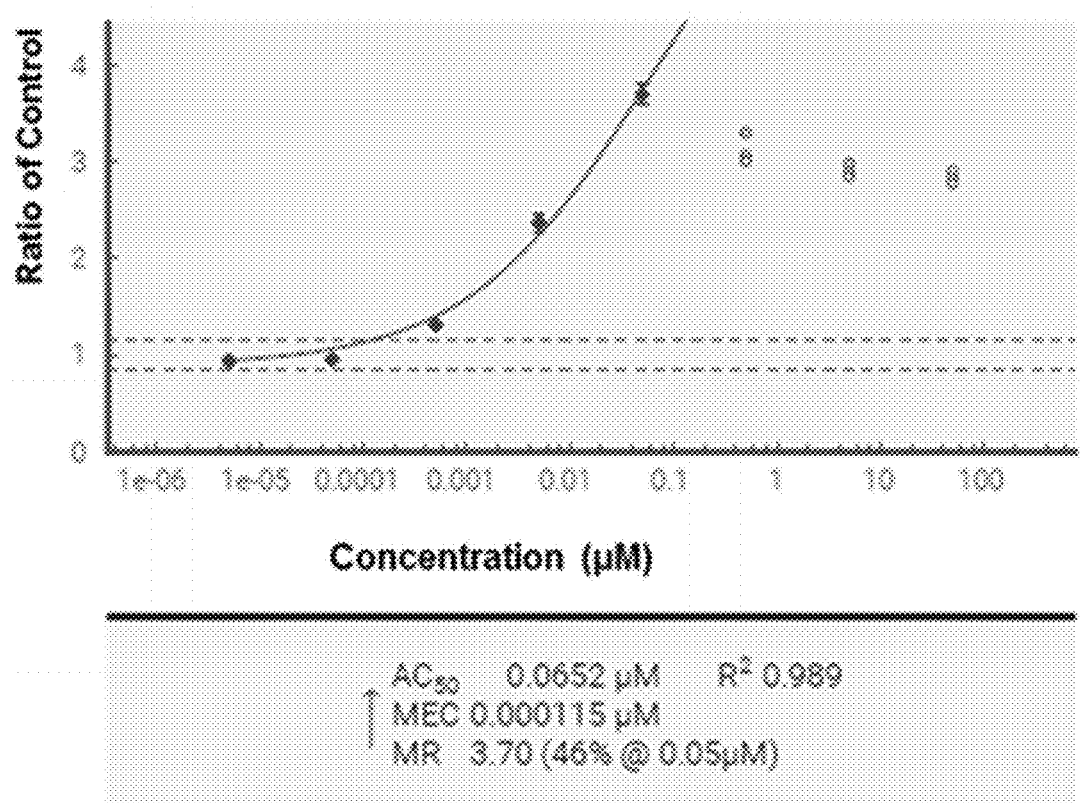
FIG. 15A shows a graph illustrating cell cycle arrest by 41.
Figure 15B:
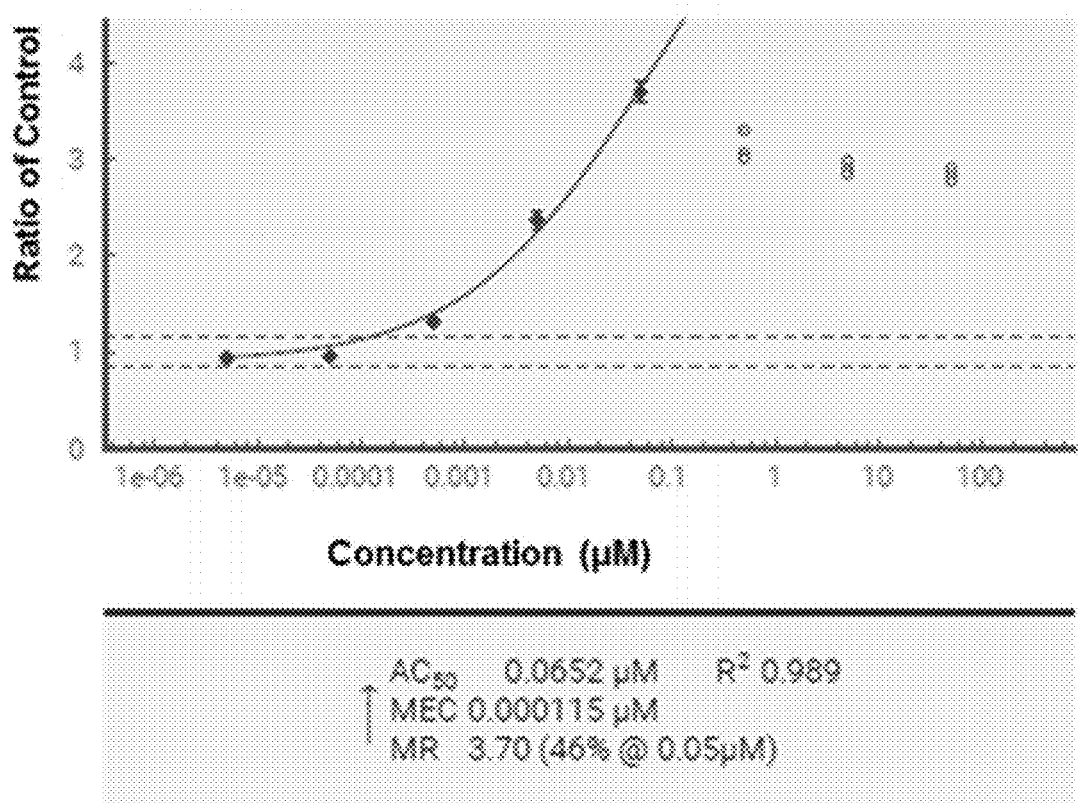
FIG. 15B shows a graph illustrating cell cycle arrest by Talirine.

The yH2aX assay was used to evaluate the level of DNA damage caused by 41 and Talirine. FIG. 13 shows a graph illustrating percentage difference in TF activation in treated cells versus cells not treated with 41. FIG. 14 shows a graph illustrating a summary of the major transcription factors up- and down-regulated by 41. FIGS. 15A and B show graphs illustrating cell cycle arrest by 41 (FIG. 15A) and Talirine (FIG. 15B), where MEC represents Minimum Effective Concentration that significantly crosses the vehicle control threshold, AC50 represents the concentration at which 50% maximum effect is observed for each cell health parameter, and MR is the maximum response.

The results show an equal amount of DNA damage (FIG. 13) at similar concentrations, despite the fact the PBD dimer cross-links DNA, but 41, and analogues, only mono-alkylate DNA. This degree of DNA damage may provide a rationale for the potent cytotoxicity observed for 73, 41, 76, 81, 88 and 93.

Example 160

Cell Cycle

Figure 16:
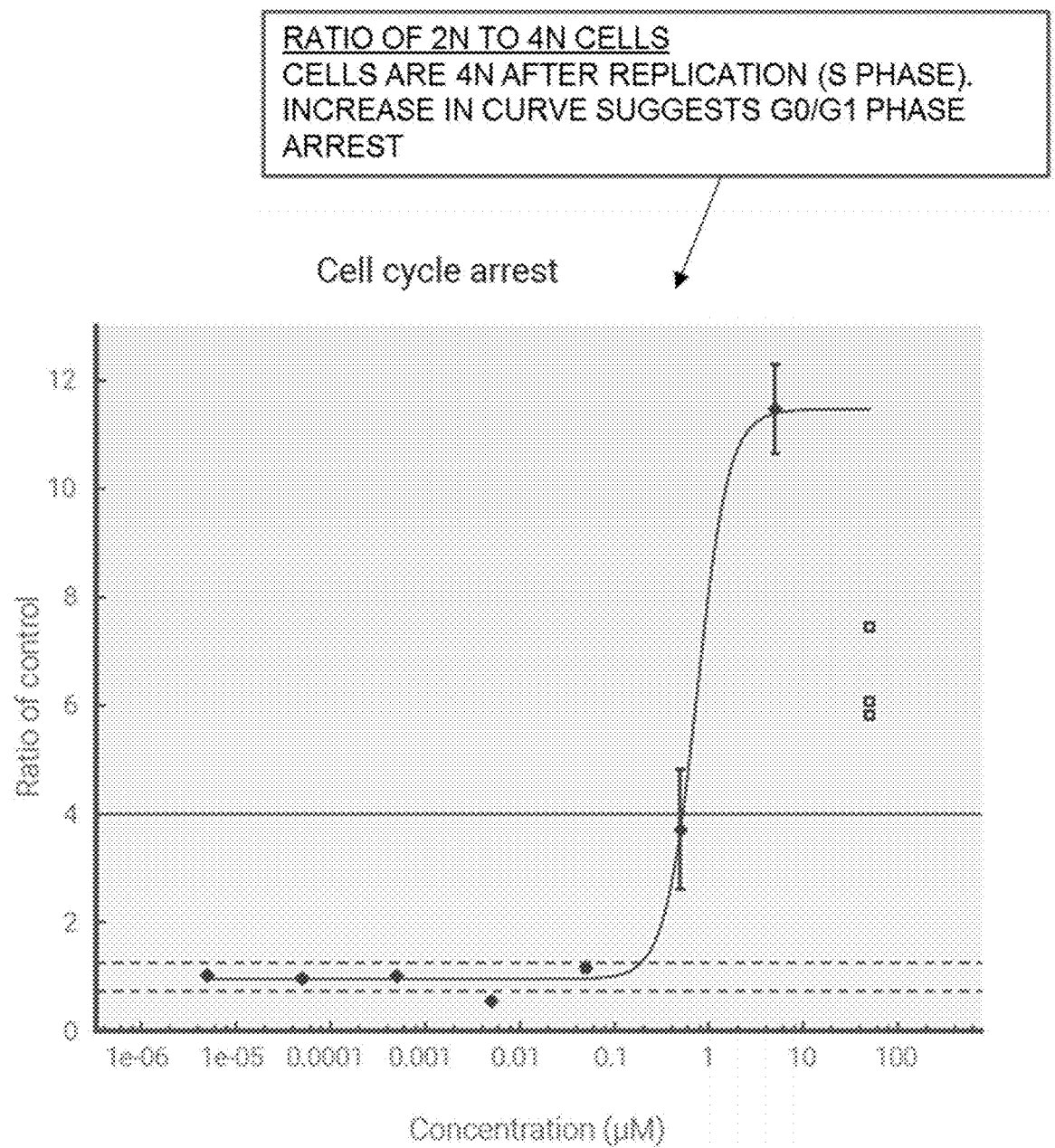
FIG. 16 shows a graph outlining cell cycle arrest induced by 41.

FIG. 16 shows a graph outlining cell cycle arrest induced by 41. Studies on the arrest of cell cycle indicate that 41 arrests at the G0/G1-S phase, a distinctly different mechanism of action to other DNA-interactive agents (e.g., PBD dimers[33] and the IGN mono-alkylator[34] which arrest cell cycle at the G2-M phase).

Examples 161

Conjugation of Compound 141 to IgG1 Antibody (Forming ADC1)

Figure 17:
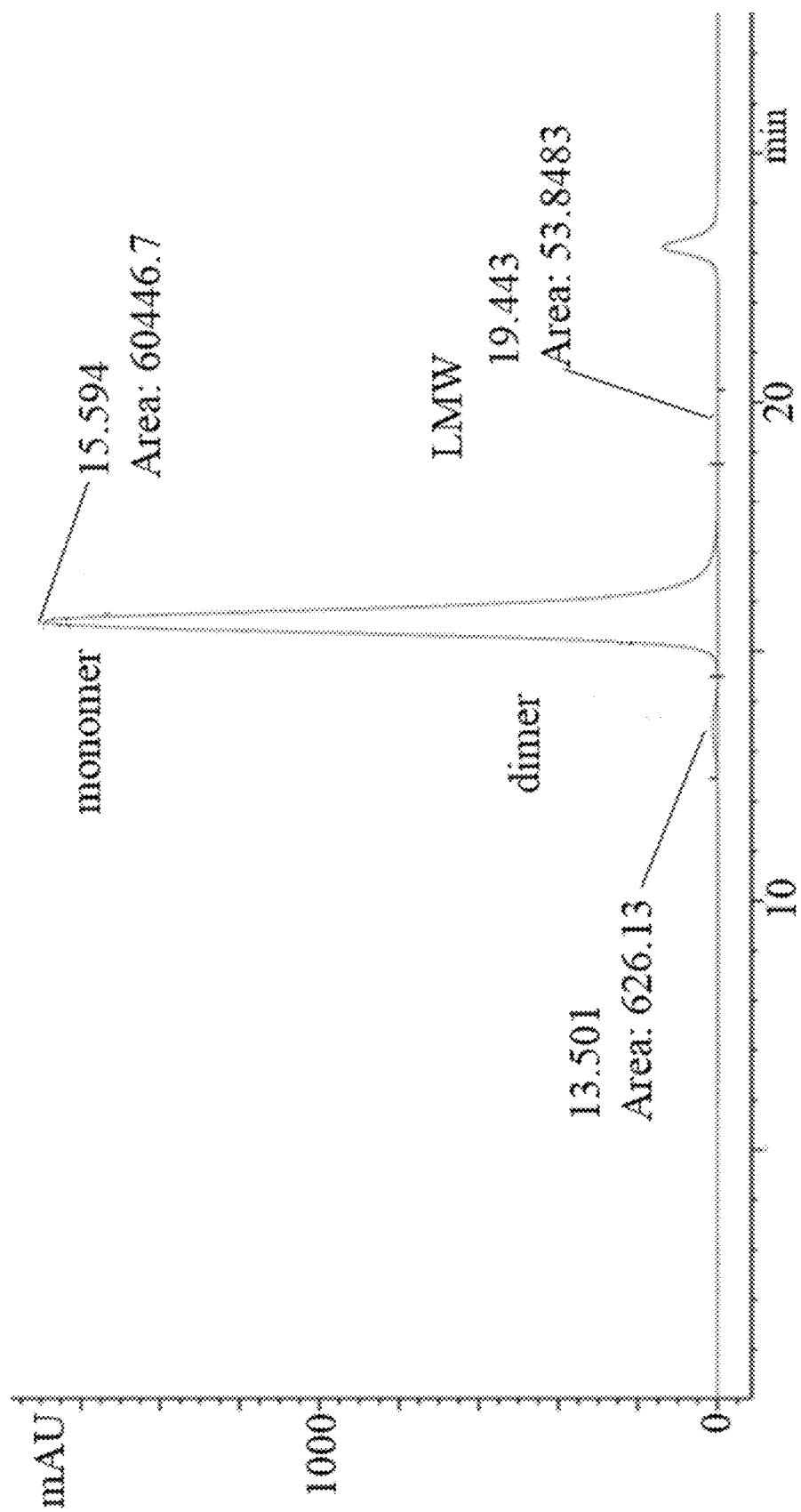
FIG. 17 shows an SEC profile of Antibody X.
Figure 18:
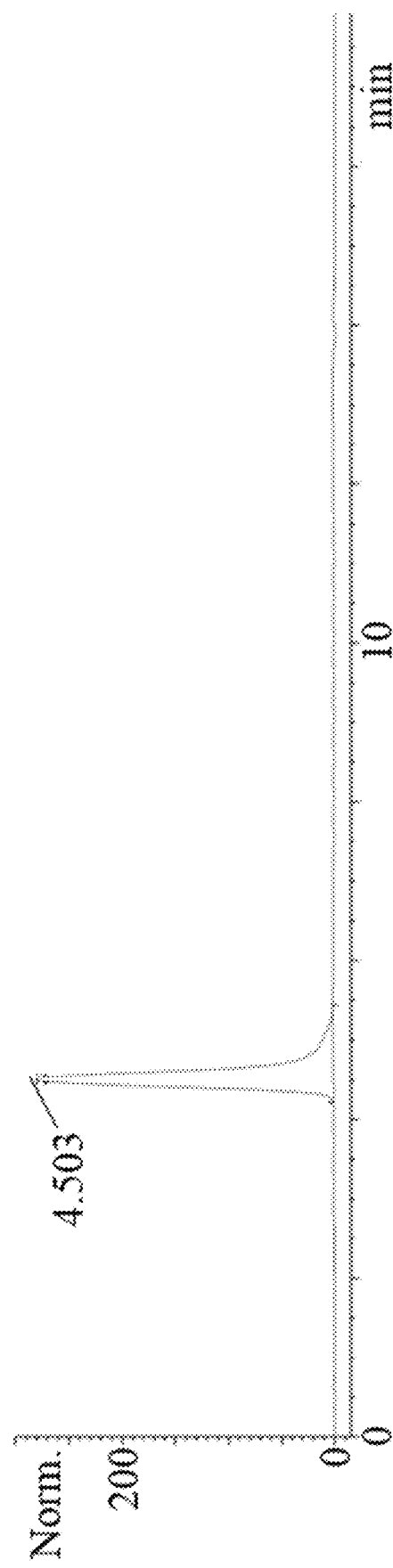
FIG. 18 shows an HIC profile of Antibody X.
Figure 19:
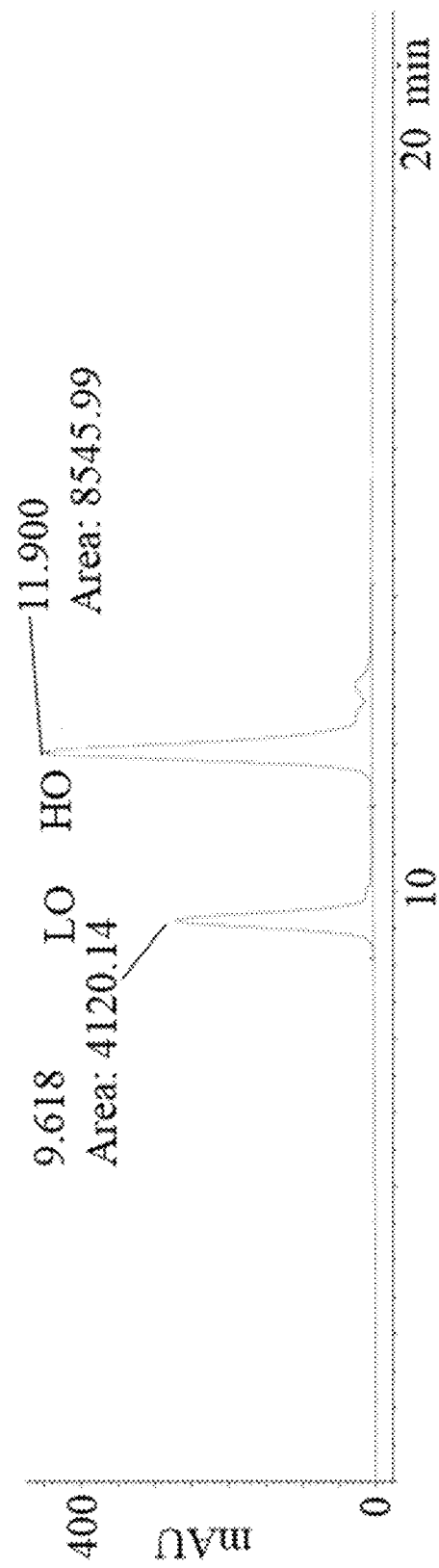
FIG. 19 shows a PLRP trace of Antibody X. Heavy (Ho) and light (Lo) chain peaks as indicated.

141 was conjugated to an IgG1 antibody targeted to Antigen X in a stochastic manner. FIG. 17 shows an SEC profile of Antibody X. 98.9% monomer, 1.0% dimer, and 0.1% LMW as indicated. The peak at about 23 minutes originates from the formulation of the antibody. FIG. 18 shows an HIC profile of Antibody X. FIG. 19 shows a PLRP trace of Antibody X. Heavy (Ho) and light (Lo) chain peaks as indicated.

The antibody was of good quality with 98.9% monomer content (FIG. 17) and a single peak with a small shoulder on HIC (FIG. 18). PLRP showed the expected pattern for reduced Light and Heavy chain. The minor peaks eluting after the main Lo and Ho are likely the result of intrachain disulphide reduction (FIG. 19).

Figure 20:
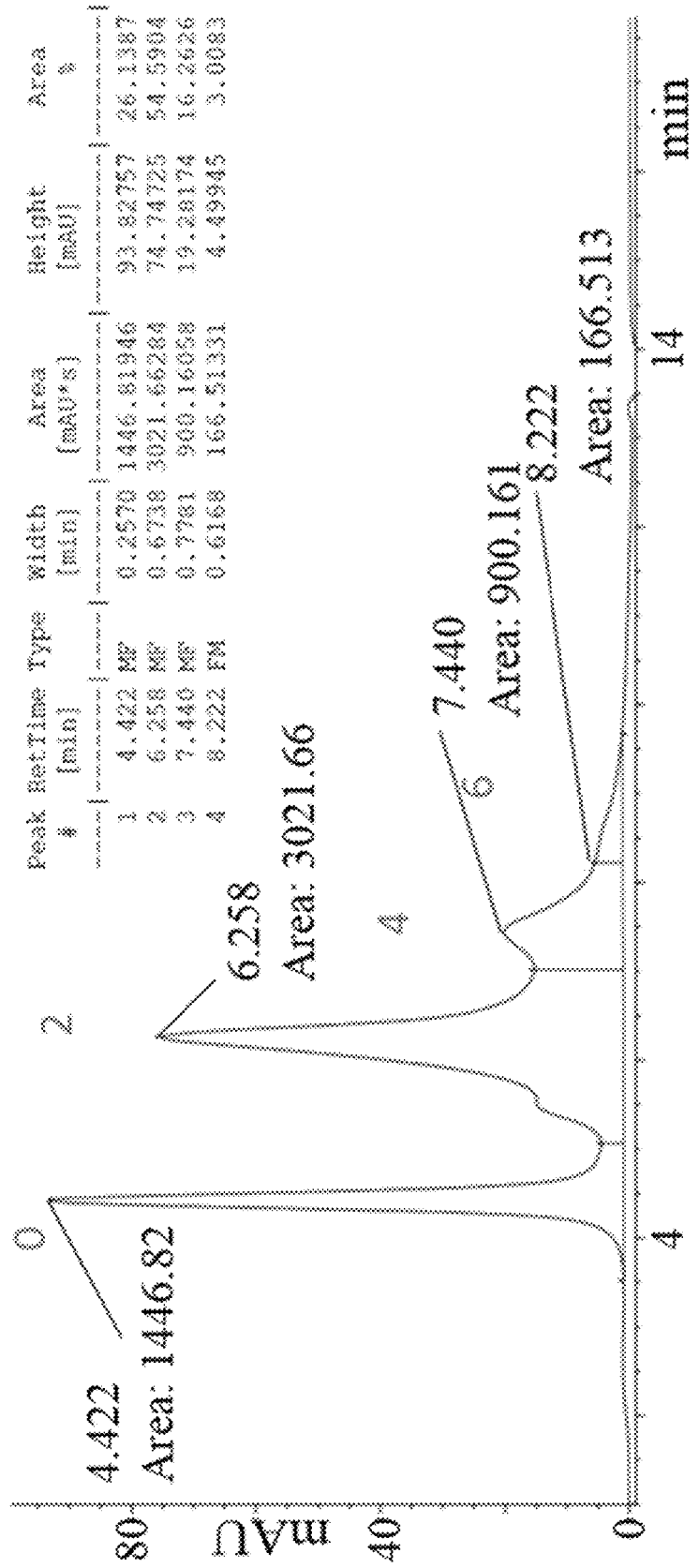
FIG. 20 shows an HIC profile of IgG1-141. Average DAR calculated as 1.9 with the DAR species assignments as indicated.
Figure 21:
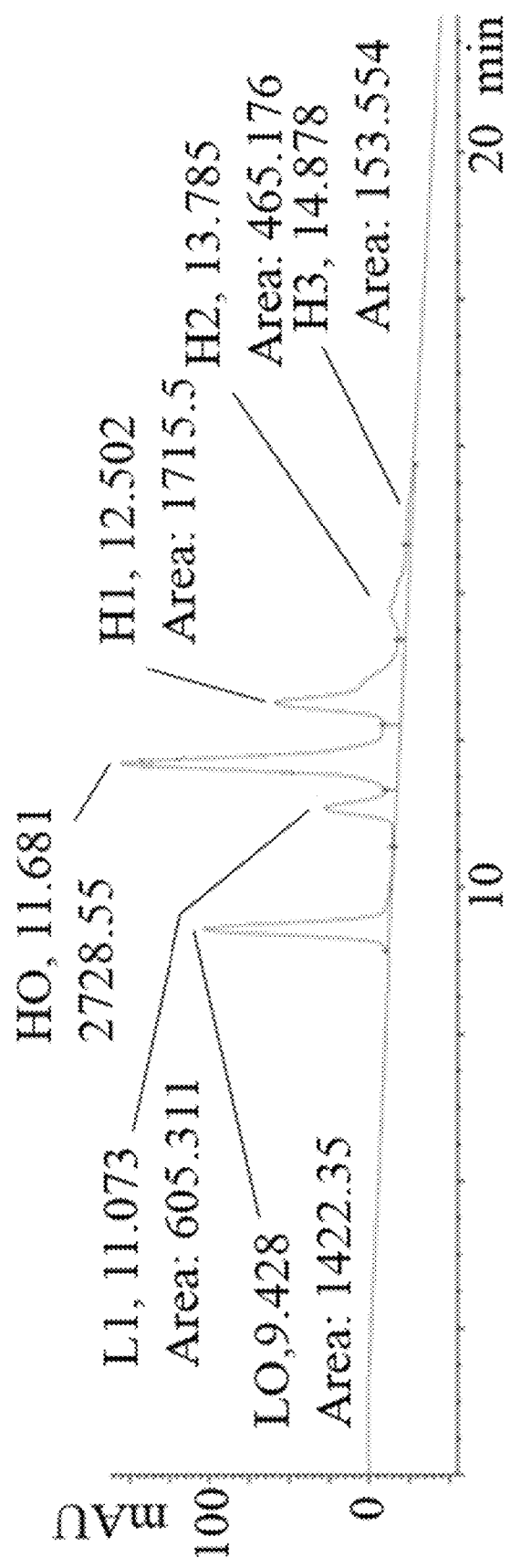
FIG. 21 shows a PLRP trace of IgG1-141. Average DAR calculated as 1.8 with the light/heavy chain species assigned as indicated.
Figure 22:
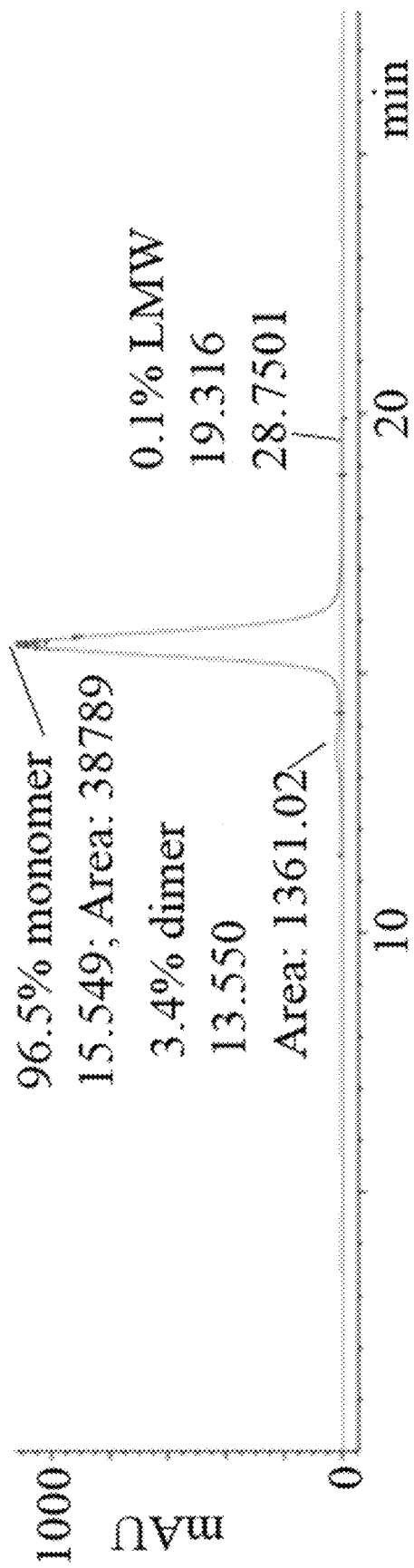
FIG. 22 shows an SEC profile of IgG1-141; 96.5% monomer, 3.4% dimer, 0.1% HMW as indicated.
Figure 23:
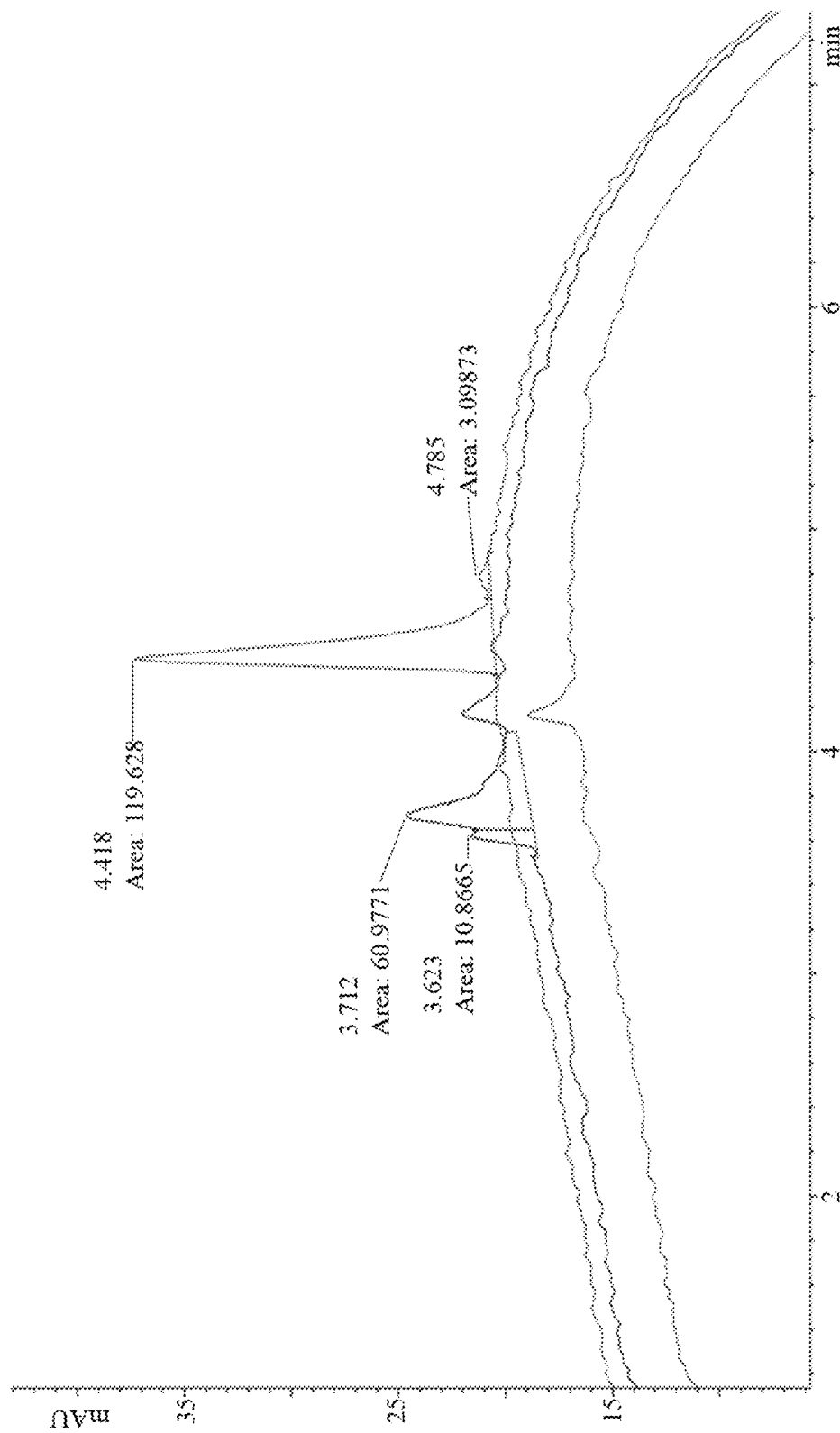
FIG. 23 shows the free toxin linker traces of the IgG1-141 sample. No free toxin linker could be detected in the ADC trace. Red: 100 pmol NAC-141. Blue: IgG1-141 after protein precipitation; the identified peaks show residual proteinaceous material. Green: PBS.

DAR (Drug Antibody Ratio) assignment was possible through PLRP analysis (FIG. 21; average DAR calculated as 1.8 with the light/heavy chain species assigned as indicated) and is in good agreement with the value calculated by HIC using the integration highlighted in FIG. 20 (average DAR calculated as 1.9 with the DAR species assignments as indicated). The conjugation process caused no significant aggregation compared to the starting antibody. Dimer level was increased by 2.4%, but LMW remained the same. FIG. 22 shows an SEC profile of IgG1-141; 96.5% monomer, 3.4% dimer, 0.1% HMW as indicated No free toxin linker could be detected in the ADC sample (see FIG. 23).

Example 162

Conjugation of 82 to Trastuzumab (Forming ADC2)

Figure 24A:
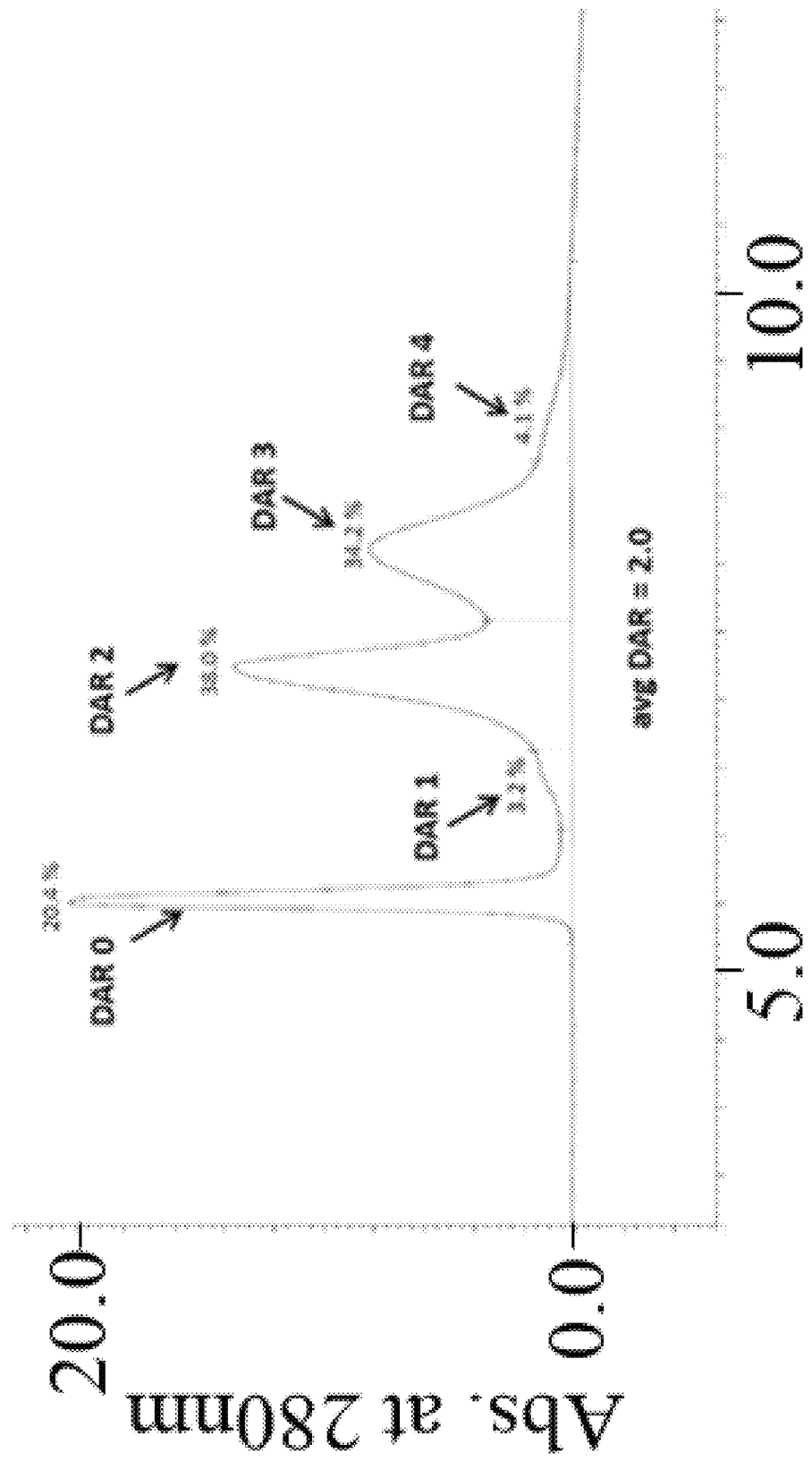
FIG. 24A shows an example of HIC analysis used to assign DAR to the trastuzumab-based ADC.
Figure 24B:
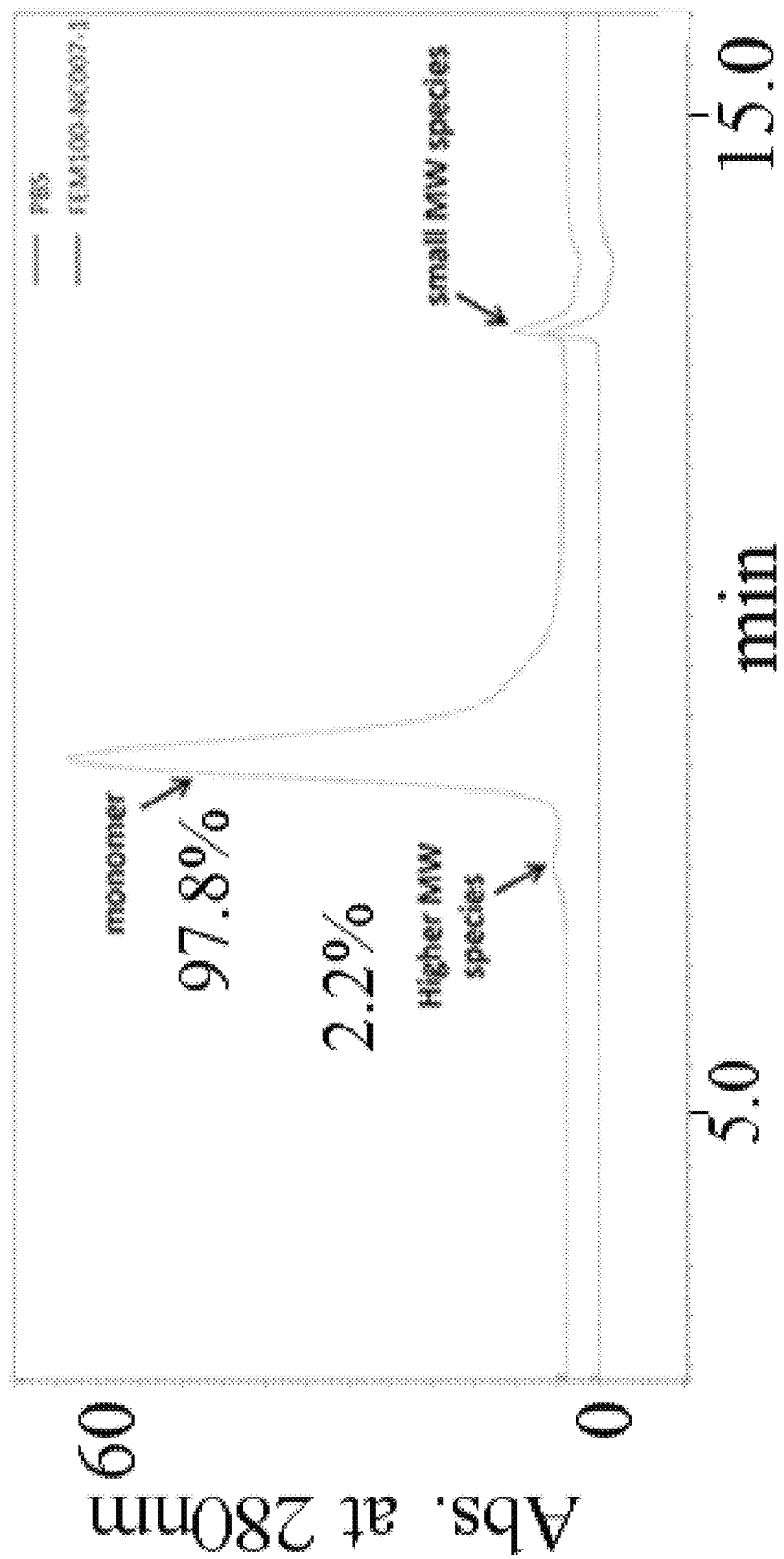
FIG. 24B shows an example of SEC analysis used to assign DAR to the trastuzumab-based ADC.

141 was successfully conjugated to Trastuzumab (stochastic conjugation, DAR 1.9) and an isotype control antibody. DAR assignment was possible through HIC (FIG. 24A) and SEC analysis (FIG. 24B). Little hydrophobicity was observed.

Example 163

Site-Specific Conjugation (Forming ADC3)

Figure 25:
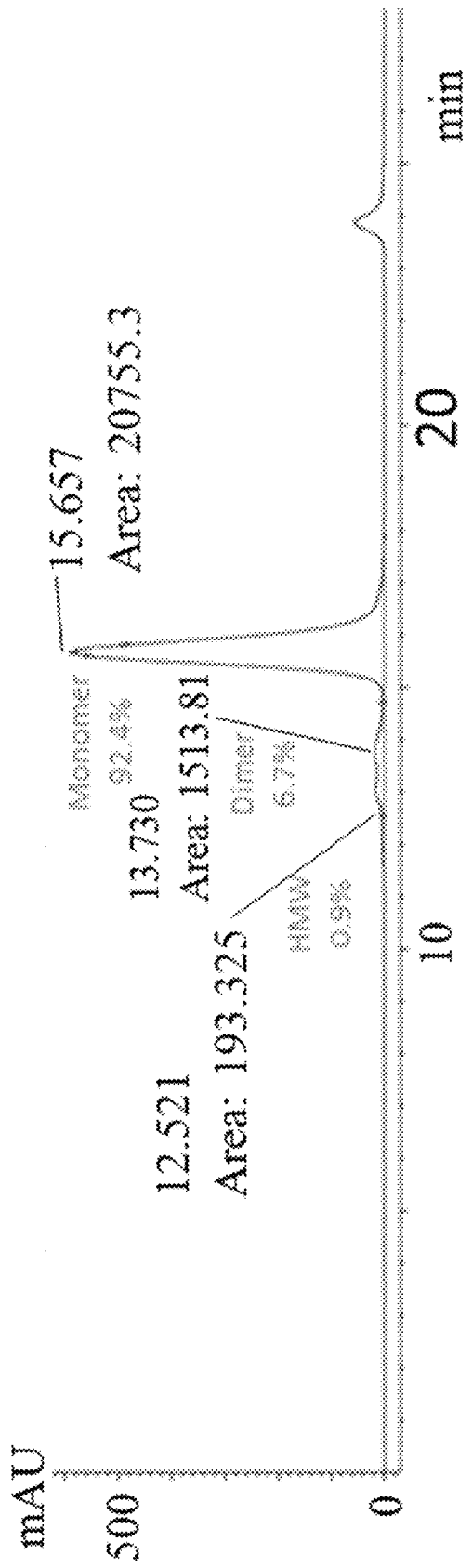
FIG. 25 shows an SEC profile of the THIOMAB. 92.4% monomer, 6.7% dimer, and 0.9% HMW as indicated. The peak at about 23 minutes originates from the formulation of the antibody.
Figure 26:
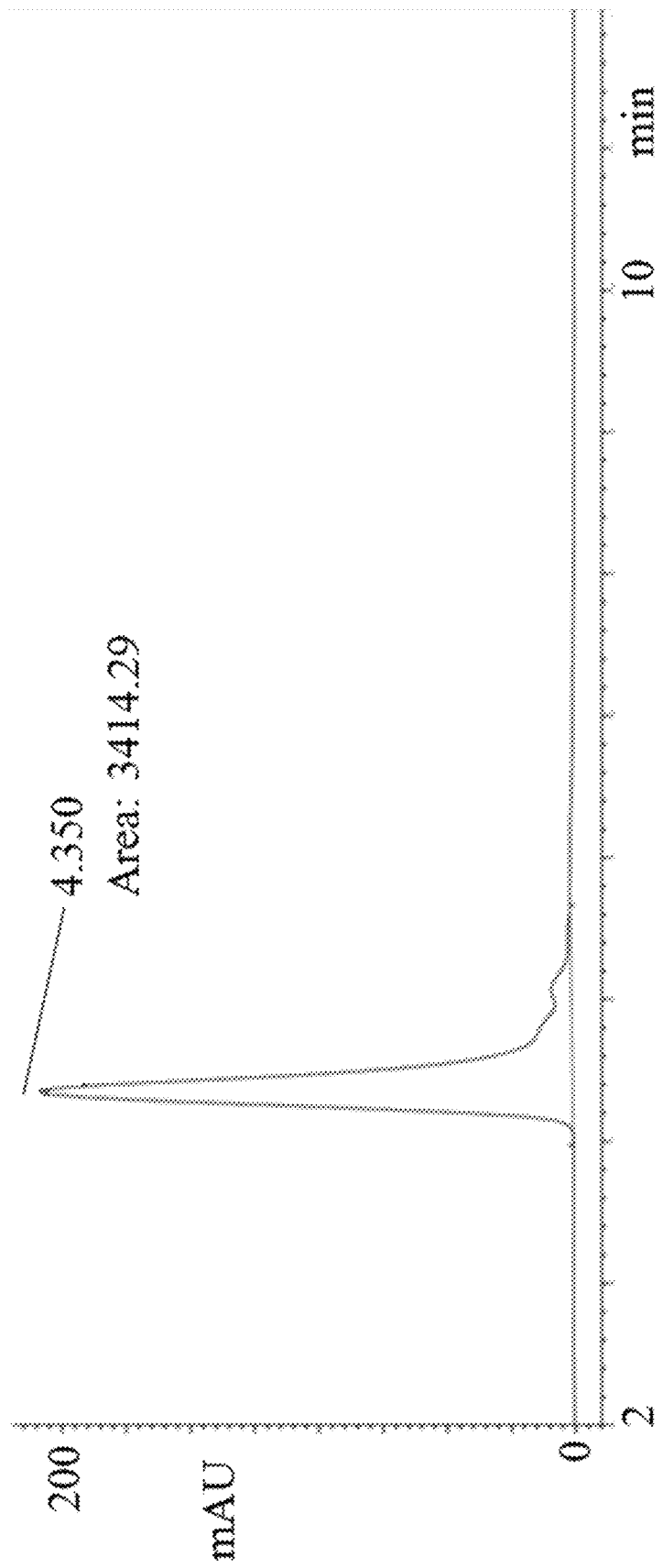
FIG. 26 shows an HIC profile of the THIOMAB®-based Trastuzumab.
Figure 27:
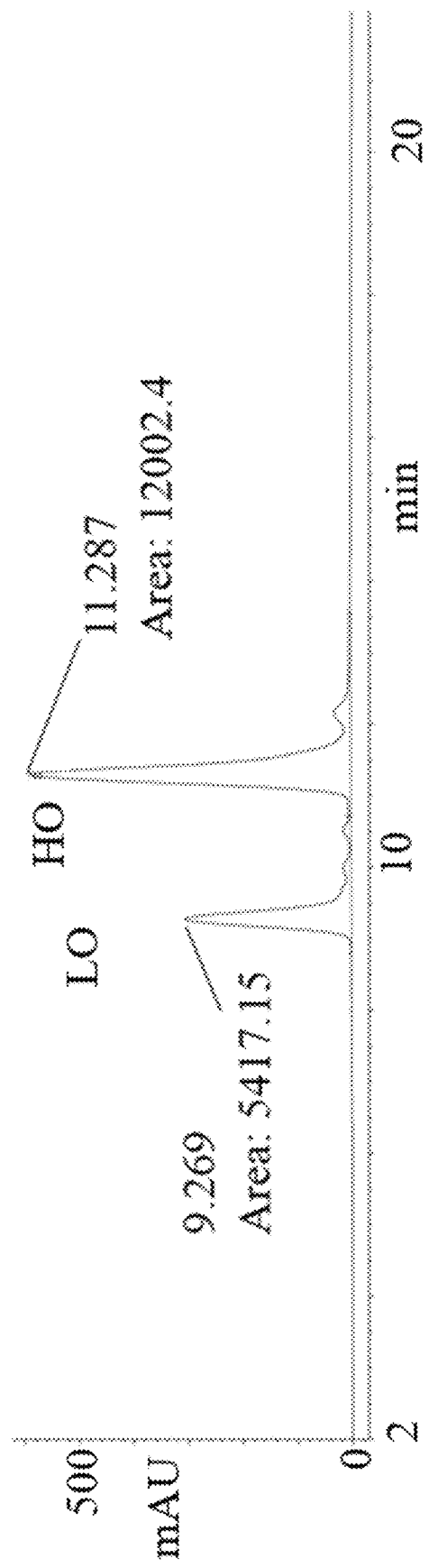
FIG. 27 shows the reducing-PLRP trace of the THIOMAB. Heavy (Ho) and light (Lo) chain peaks as indicated.

141 was conjugated to a THIOMAB®-based version of Trastuzumab (DAR 2). The THIOMAB antibody had a relatively low monomer content of 92.4% with 6.7% dimer (see FIG. 25). This was not unexpected and has been seen before with this antibody due to the formation of inter molecular disulfide bonds with the mutated cysteines. The HIC and PLRP profiles for the THIOMAB are shown in FIGS. 26 and 27 respectively.

Figure 28:
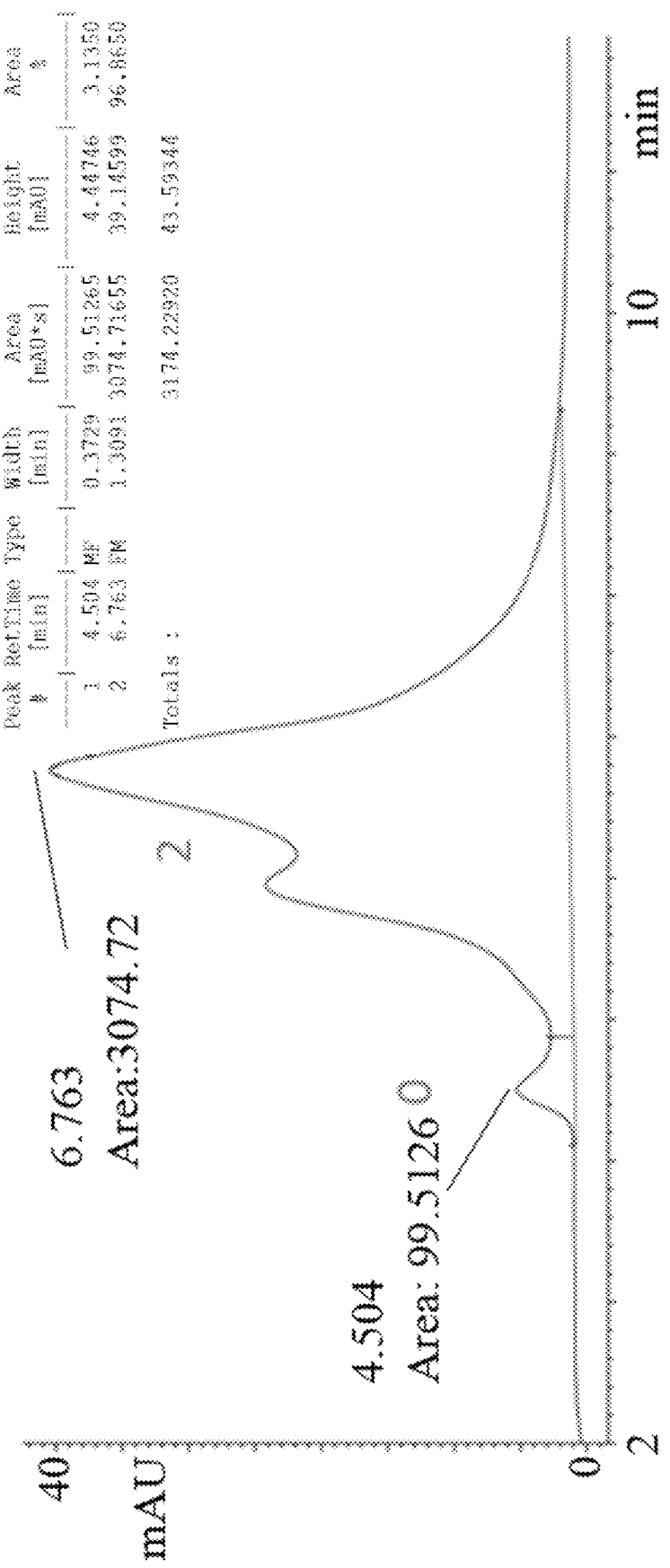
FIG. 28 shows the HIC profile of THIOMAB-141. Average DAR calculated as 1.9 with the DAR species assignments as indicated.
Figure 29:
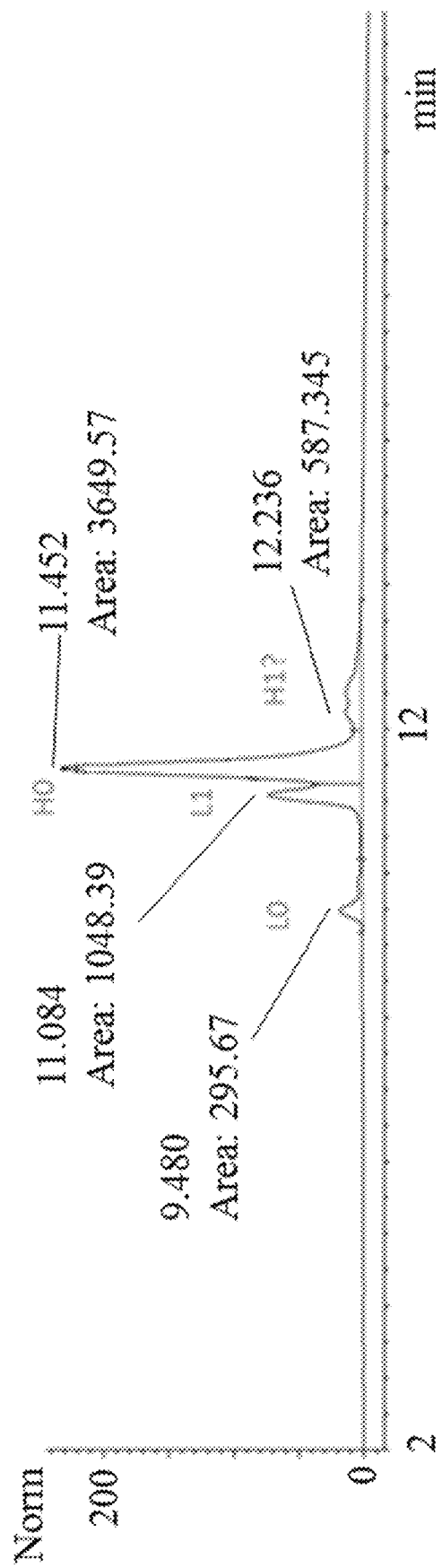
FIG. 29 shows the PLRP trace of THIOMAB-141. Average DAR calculated as 1.8 with the light/heavy chain species assigned as indicated.
Figure 30:
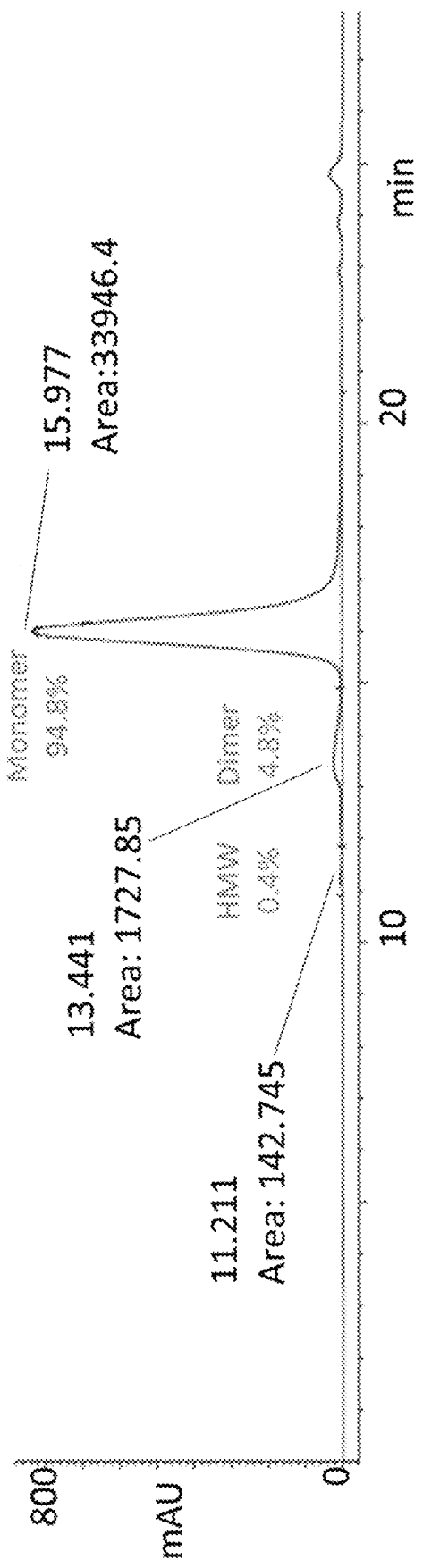
FIG. 30 shows the SEC profile of THIOMAB-141; 94.8% monomer, 4.8% dimer, 0.4% HMW as indicated.

The THIOMAB-141 conjugate resolves reasonably well by hydrophobic interaction chromatography. An identification of DAR species is possible by using the relative absorbance at 280 and 330 nm to identify species with different drug loading or isomers of the same drug loading. The DAR 2 species appears in two overlapping peaks (same DAR confirmed by spectral comparison), and are almost fully resolved from the DAR 0. There is probably some $DAR_1$ species as there is an inflection at the position this is expected; DAR 1 species clearly observed during development when underconjugation was achieved. The PLRP profile shows a high degree of site specific conjugation and a small amount of non-specific conjugation to the heavy chain because of incomplete re-oxidation of all S—S bonds; typical of all THOMAB processes. The monomer level is higher than the starting antibody due to reduction of inter molecular S—S bonds. FIG. 28 shows the HIC profile of THIOMAB-141. Average DAR calculated as 1.9 with the DAR species assignments as indicated. FIG. 29 shows the PLRP trace of THIOMAB-141. Average DAR calculated as 1.8 with the light/heavy chain species assigned as indicated. The peak labelled as "H1?" might contain L2 species. The conjugation process caused a sizable amount of dimerization and the formation of a small amount of high molecular weight aggregates (HMW). FIG. 30 shows the SEC profile of THIOMAB-141; 94.8% monomer, 4.8% dimer, 0.4% HMW as indicated.

Example 164

In Vitro Cytotoxicity of ADCs

The resulting ADCs were evaluated in vitro against relevant antigen positive cell-lines. In the case of the ADC targeted to Antigen X (ADC1), potent cytotoxicity was observed.

TABLE 5

Summary of in vitro cytotoxicity data derived for IgG1-based ADC targeted to Antigen X using 41 as the payload.

| | | IC50 (nM) | |
|---|---|---|---|
| | | Antigen Positive Cell-Line 1 | Antigen Positive Cell-Line 2 |
| IgG1-based ADC (Average DAR = 2) | 5 day incubation | 0.67 | 0.47 |

In the case of the trastuzumab-based ADC (ADC2), the ADC possessed potent activity in the antigen-positive cell-line (i.e., SK-BR-3) and no cell-killing was observed in both the JIMT-1 and MCF-7 cell-lines indicating the targeted effect of the ADC. Furthermore, potency of the free payload was enhanced through attachment to the antibody.

TABLE 6

Summary of in vitro cytotoxicity data derived for trastuzumab-based ADC using 41 as the payload.

| | IC50 (nM) (72 hour incubation | | |
|---|---|---|---|
| | SK-BR-3 (HER2+++) | ZR75-1 (HER2++) (Trastuzumab resistant) | MCF-7 (HER2−) |
| Trastuzumab-THIOMAB ®based ADC (average DAR = 2) | 0.009 | 28.8 | 82.3 |
| IgG1 control ADC (average DAR = 2) | 18 | 122.2 | 157 |
| Free Payload | 0.086 | 0.63 | 0.289 |

Finally, the THIOMAB®-based ADC (ADC3) possessed potent activity in the antigen-positive cell-line (i.e., SK-BR-3) and limited cell-killing was observed in both the ZR75-1 and MCF-7 cell-lines indicating the targeted effect of the ADC. Furthermore, potency of the free payload was enhanced through attachment to the antibody.

Example 165

In Vivo Tolerability of ADCs

Figure 31:
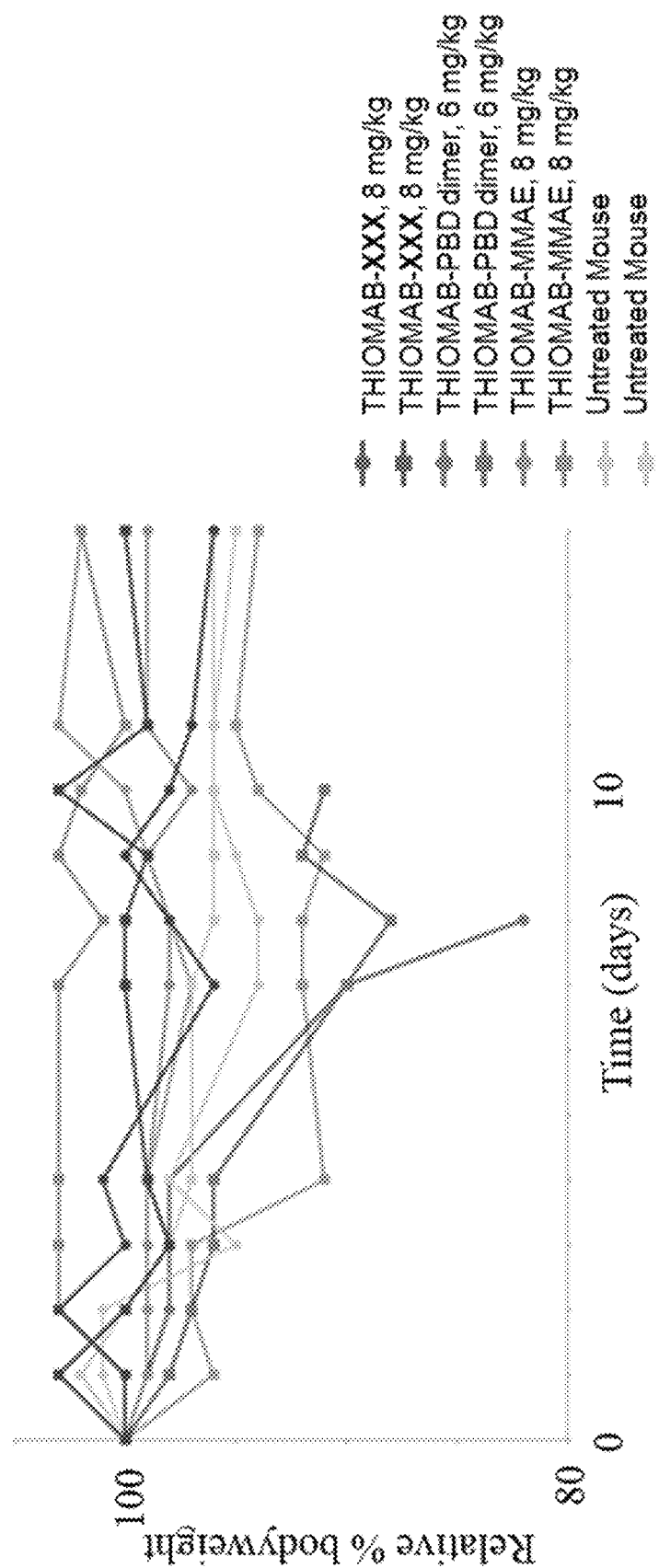
FIG. 31 shows a graph illustrating dose tolerability of 141, PBD dimer (Talirine) and MMAE-based ADCs.

The maximum tolerated dose for ADC 3 was established as 9 mg/kg. The PBD dimer-based THIOMAB® ADC was found to have an MTD of ~4 mg/kg, suggesting enhanced tolerability of the mono-alkylating payload. The THIOMAB®-141-based ADC possesses similar tolerability to the non-alkylating MMAE-based ADC. In this instance, loss of 15% of body weight was considered a toxic dose. FIG. 31 shows a graph illustrating dose tolerability of 141, PBD dimer (Talirine) and MMAE-based ADCs. The MTDs of the ADCs conjugated in a stochastic manner (i.e., ADCs 1 and 2) were found to be ~6 mg/kg.

Example 166

In Vivo Efficacy

Figure 32:
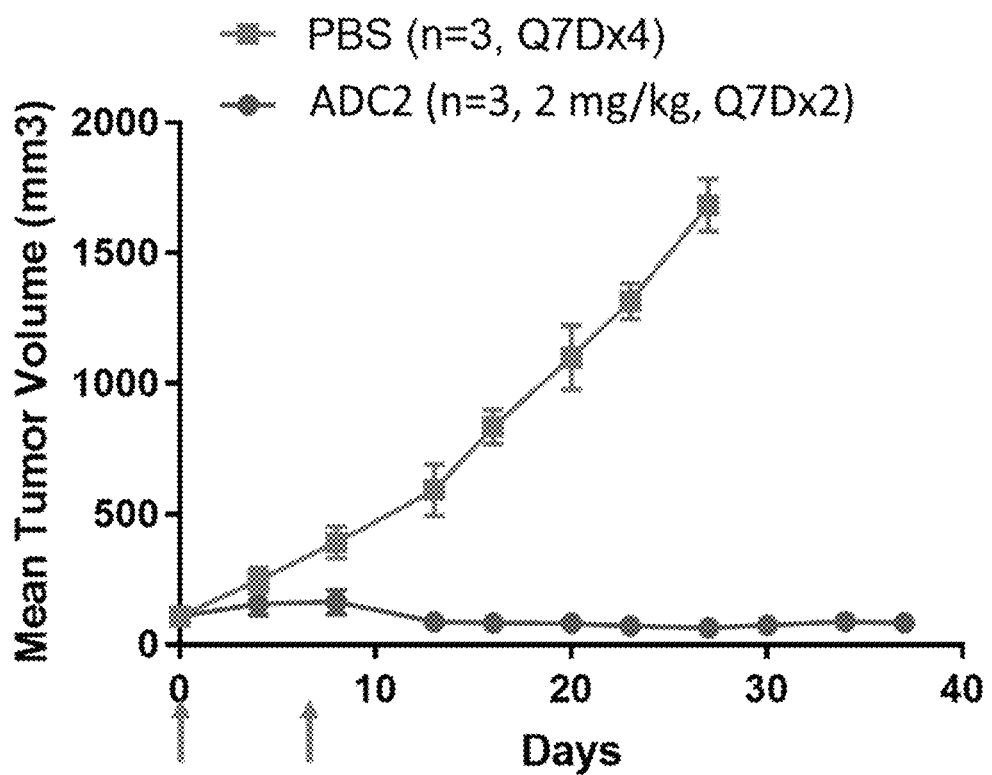
FIG. 32 shows a graph illustrating mean tumour volume versus time after two doses of ADC 2 (Day 0 and Day 7).
Figure 33:
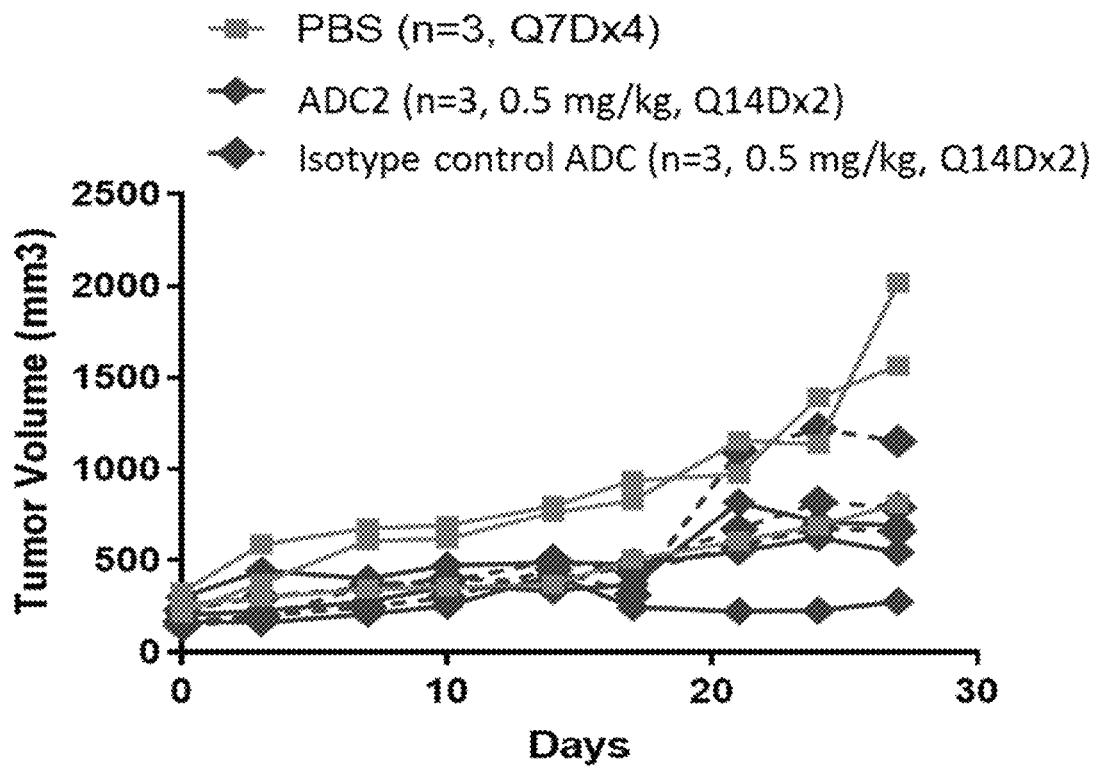
FIG. 33 shows a graph illustrating mean tumour volume of a PDX model versus time after two doses of ADC 2 (Day 0 and Day 14).
Figure 34A:
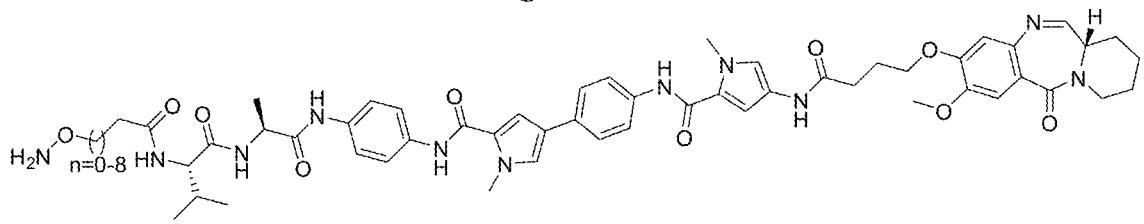
FIG. 34A shows an example of a compound of the disclosure attached to linker group containing an exemplary terminal alkoxyamine groups
Figure 34B:
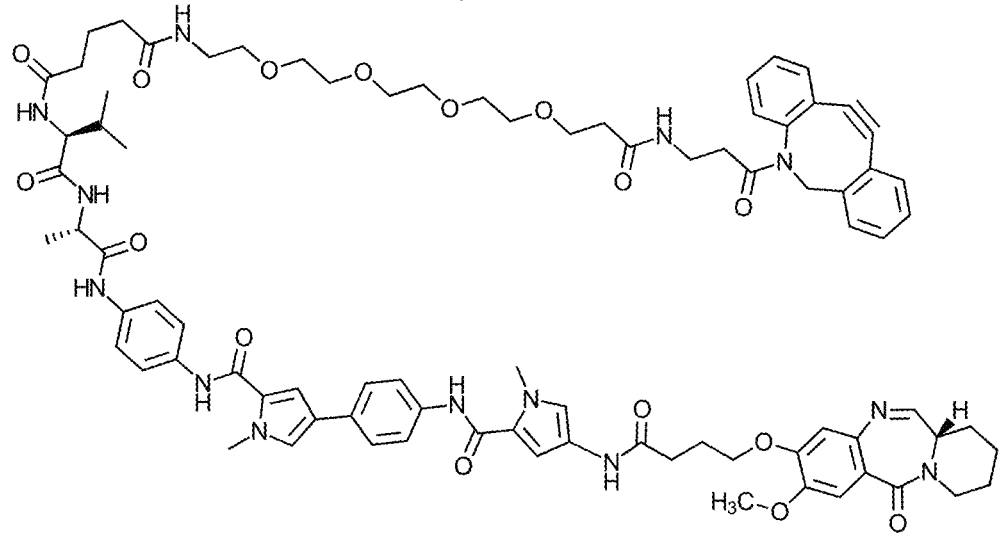
FIG. 34B shows an example of a compound of the disclosure attached to linker group containing an exemplary terminal diarylcyclooctyne group, DBCO.

FIG. 32 shows a graph illustrating mean tumour volume versus time after two doses of ADC 2 (Day 0 and Day 7). ADC2 was found to be highly efficacious in a cancer-derived xenograft model (in mice) expressing Target X, where complete tumour remission was observed out to a period of 38 days after two doses of the ADC. FIG. 33 shows a graph illustrating mean tumour volume of a PDX model versus time after two doses of ADC 2 (Day 0 and Day 14). Similarly, in the case of a PDX model expressing the same target, cytostasis was observed at 0.5 mg/kg after two doses.

Example 167

Materials and Methods for Examples 154 to 166

DNA Ffragments and Footprinting

The preparation of the TyrT DNA fragment (FIG. 5) has been previously described[35]. Briefly, the sequence which had been cloned into the BamHI site of pUC18 was obtained by cutting with HindIII and EcoRI. Radiolabelled DNA fragments were prepared by filling in the 3'-end of the HindIII site with [$\alpha$-$^{32}$P]dATP using Klenow DNA polymerase (exo-).

The radiolabelled DNA fragment was separated from the remainder of the plasmid DNA on a 6% non-denaturing polyacrylamide gel. The gel (20 cm long, 0.3 mm thick) was run at 400 V in 1×TBE running buffer for about 1-2h, until the bromophenol blue had run most of the way down the gel. The glass plates were separated and the position of the labelled DNA fragment was established by short (i min) exposure to an X-ray film. The relevant band was then cut from the gel and the radiolabelled DNA eluted by adding 300 µL, 10 mM Tris-HCl, pH 7.5 containing 0.1 mM EDTA and gently agitating overnight at room temperature. The eluted DNA was finally precipitated with ethanol and resuspended in a suitable volume of 10 mM Tris-HCl, pH 7.5 containing 0.1 mM EDTA buffer so as to give at least 10 counts per second/µL on a hand-held Geiger counter. With fresh plasmid and $\alpha$-$^{32}$P-dATP this process typically generated about 150 µL of radiolabelled fragment DNA. The absolute concentration of the DNA is not important, and it is typically lower than 10 nM.

Footprinting reactions were performed as previously described[36] using the DNA fragments HexA and HexB, which together contain all 64 symmetrical hexanucleotide sequences[6], and MS1 that contains all possible 134 tetranucleotide sequences[38]. The DNA fragments were obtained by cutting the parent plasmids with HindIII and SacI (for HexA and MS1) or EcoRI and PstI (for HexB), and were labelled at the 3'-end of the HindIII or EcoRI sites with [$\alpha$-$^{32}$P]dATP using reverse transcriptase or exo-Klenow fragment. After gel purification, the radiolabelled DNA was dissolved in 10 mM Tris-HCl pH 7.5 containing 0.1 mM EDTA, at a concentration of about 10 c.p.s per µL as determined on a hand held Geiger counter. 1.5 µL of radiolabelled DNA was mixed with 1.5 µL ligand that had been freshly diluted in 10 mM Tris-HCl pH 7.5, containing 10 mM NaCl. The complexes were left to equilibrate for at least 12 hours before digesting with 2 µL DNase I (final concentration about 0.01 units/mL). The reactions were stopped after 1 minute by adding 4 µL of formamide containing 10 mM EDTA and bromophenol blue (0.1% w/v). The samples were then heated at 100° C. for 3 minutes before loading onto 8% denaturing polyacrylamide gels containing 8 M urea. Gels were fixed in 10% acetic acid, transferred to 3MM paper, dried and exposed to a phosphor screen overnight, before analysing with a Typhoon phosphorimager Compounds 73, 41, 76, 81, 88 and 93 were synthesised as described above and the PBD dimer Talirine was obtained from a commercial source. Stock solution was prepared by dissolving the ligands in DMSO to give a concentration of 10 mM. From this stock solution, working solutions of the desired concentration were prepared by diluting with 10 mM Tris-HCl, pH 7.5 containing 10 mM NaCl.

Cross-Linking Assay

Radiolabelled DNA (1.5 µL) was mixed with 1.5 µL ligand solution of various concentrations (10 µM-10 nM) and incubated overnight at 37° C.

After overnight incubation, the samples were mixed with 7 µL loading solution (80% formamide containing 10 mM EDTA, 10 mM NaOH, 0.1% bromophenol blue) and incubated at 65° C. for 5 min. Control 1 (C1) for native double-stranded DNA consisted of 1.5 µL labelled DNA, 1.5 µL 10 mM Tris-HCl, pH 7.5 containing 0.1 mM EDTA and 7 µL 1× loading dye. Control 2 (C2) for denatured native single-stranded DNA was composed of 1.5 µL labelled DNA, 1.5 µL 10 mM Tris-HCl, pH 7.5 containing 0.1 mM EDTA which was incubated at 65° C. for 5 min. Control 3 (C3) for native double-stranded DNA consisted of 1.5 µL labelled DNA, 1.5 µL 10 mM Tris-HCl, pH 7.5 containing 0.1 mM EDTA and 7 µL SSB. Control 4 (C4) for denatured native single-stranded DNA was composed of 1.5 µLlabelled DNA, 1.5 µL 10 mM Tris-HCl, pH 7.5 containing 0.1 mM EDTA and 7 µL SSB which was incubated at 65° C. for 5 min. Separation was performed on a 7.5% denaturing polyacrylamide gel (20 cm long, 0.3 mm thick) at 500V for about 4 h until the dye reached the bottom of the gel. The gel plates were then separated, the gels fixed by immersing in 10% (v/v) acetic acid, followed by transfer to Whatmann 3MM paper and drying under vacuum at 80° C. The dried gel was then exposed to a phosphorimager screen overnight before scanning using a Typhon FLA 7000 instrument.

FRET Studies Methodology

Oligonucleotides were obtained from ATDbio (Southampton, UK) in lyophilised form. They were labelled with a fluorophore molecule (F=fluorescein) at the 5'-end and a quencher molecule (Q=dabcyl) at the 3'-end of the complementary strand. Each oligonucleotide was dissolved in distilled $H_2O$ to form stock solutions of 100 µM. Working solutions of 5 µM were prepared by diluting the stock solution with distilled $H_2O$.

The following buffers were used: 250 mM phosphate buffer pH 7.4 (consisting of sodium dihydrogen phosphate and sodium phosphate diluted in distilled $H_2O$) and 5 M sodium chloride buffer. All buffers and distilled $H_2O$ were filtered through a 0.2 μM filter prior to use.

For the FRET experiments stock solutions of 41, 106, 107 and 148 were prepared by dissolving the compounds in DMSO to give a concentration of 10 mM. From this stock solution, working solutions of the desired concentration were prepared by diluting the stock solution with distilled $H_2O$.

The reaction mixture was comprised of 4 μL of 250 mM phosphate buffer (final concentration of 50 mM), 4 μL flourophor and 4 μL quencher molecule of the appropriate oligonucleotide for a final concentration of 0.2 μM, 4 μL 5 M sodium chloride (final concentration of 1 M NaCl), and 4 μL of distilled $H_2O$. This mixture was heated in an Eppendorf tube at 90° C. for 1 min and slowly cooled down to room temperature. This process was carried out to anneal the single strands to double-stranded DNA. Following this, 4 μL of the ligand was added in the desired concentration and the mixture incubated overnight either at room temperature or 4° C. A control sample of DNA only was prepared by mixing 4 μL 250 mM phosphate buffer (final concentration of 50 mM) with 4 μL fluorophore-labelled and 4 μL quencher-labelled oligonucleotides (of the appropriate sequence) to give a final concentration of 0.2 μM, 4 μL 5 M sodium chloride (final concentration of 1 M NaCl) and 4 μL distilled $H_2O$. This mixture was analysed without prior annealing.

Fluorescence melting profiles were measured using a Roche LightCycler using a total reaction volume of 20 μL. Initially, the samples were denatured by heating to 95° C. at a rate of 1° C. $min^{-1}$. The samples were then maintained at 95° C. for 5 min before annealing by cooling to 25° C. at 1° C. $min^{-1}$. The samples were then held at 25° C. for a further 5 min and finally melted by heating to 95° C. at 1° C. $min^{-1}$. Annealing steps and melting steps were all recorded and changes in fluorescence were measured at 520 nm.

Tin values were obtained from the first derivates of the melting profiles using the Roche LightCycler software.

MTT Cytotoxicity (Example 154)

Tumor cell lines were maintained in RPMI1640 medium supplemented with 10% heat-inactivated fetal bovine serum, 2 mM L-glutamine and imM sodium pyruvate. 1800 cells per well were seeded in a volume of 180 μl in a 96-well flat bottom polystyrene plate. The cells were allowed to adhere overnight at 37° C. in a $CO_2$ incubator. Ligands were initially formulated in DMSO, and stocks stored at −80° C. They were then further formulated at lox concentration in RPMI1640 medium. 20 μl of diluted samples were added into each treatment well. On each plate, blank wells with no cells, and untreated wells containing cells, were included. Plates were then cultured at 37° C. in a $CO_2$ incubator for 72 hrs. Cytotoxicity was evaluated using a tetrazolium salt-based assay, the MTT assay. After 72 hours, the supernatant was removed from each well and 200 μl of a sterile filtered 500 μg/ml MTT solution in water added to each well. The plates were then incubated at 37° C. in a $CO_2$ incubator for 4 hrs. The supernatant was then removed and the formazan crystals formed solubilized by adding 150 μl of DMSO to each well. The plate was then read on a plate reader at 540 nm, and percentage cell survival calculated as follows: ((mean absorbance treated wells at concentration x− mean absorbance blank wells)÷ (mean absorbance untreated wells at concentration x− mean absorbance blank wells))×100. Data were plotted as concentration in nM vs. % cell survival in Microsoft Excel, and $IC_{50}$ values (concentration where cell survival is reduced by a half) were determined from the graph.

yH2ax Assay and Cell Cycle Arrest

HepG2 cells were plated on 96-well tissue culture treated black walled clear bottomed polystyrene plates, 100 μL per well. The cells were dosed with test compound at a range of concentrations. At the end of the incubation period, the cells were loaded with the relevant dye/antibody for each cell health marker. The plates were then scanned using an automated fluorescent cellular imager, ArrayScan® (Thermo Scientific Cellomics).

Cytotoxicity and DNA damage were assessed using a multi-parametric approach using High Content Screening (HCS). Decreased cell count is a direct indication of toxicity, but many molecules cause sub-lethal toxicities that do not cause changes in cell viability over the incubation period. This assay scores compounds across direct and indirect measures of toxicity. An increase in DNA damage (p-H2AX) indicates a rise in the number of double strand breaks (DSBs). DSBs cause the phosphorylation of the histone H2AX at Ser139. DSBs are an indication of genotoxicity and can lead to apoptosis (programmed cell death). Cell cycle arrest was determined as the ratio of G0/G1(2N) to G2/M(4N), where an increase is linked to G0/G1 arrest and a decreases is linked to G2/M arrest.

Transcription Factor Plate Array Assay

The transcription factor plate array assay kit was obtained from Signosis Inc (USA). Briefly, 2×106 HeLa cells were treated with 100 nM 41 and incubated for 6 hours before extracting the nuclear protein and carrying out the TF plate array assay. The assay was carried out following the manufacturer's protocol. In the case of each transcription factor, the RLU value obtained for the cells treated with 41 was deducted from the respective values obtained for the untreated cells to obtain the differences in TF activation/inhibition.

Conjugation of Payload to Antibody

All ADC conjugations were completed using a similar methodology, an example of which is provided below. 21.5 mg IgGi antibody (8.0 mg/ml in PBS) were charged with EDTA to a final concentration of 2 mM. Reduction was attained by adding 1.27 molar equivalents TCEP (10 mM in water) and incubating for 2 hours at 20° C. After 1.5 hours, a reduction in-process test conjugation with Mal-vcMMAE was performed, and analyzed by HIC to test for the reduction level. As the target reduction level had not been reached, another 0.1 molar equivalents TCEP were added and the reduction time extended by 1 hour. After 0.5 hours, a second in-process test was run. After confirmation of the desired reduction level, 20% (v/v) Propylene glycol was added to the reduced antibody followed by 6.4 molar equivalents 141 (10 mM stock in DMSO). The solution was incubated for 1 hour at rt. The reaction was quenched by adding 6.4 molar equivalents N-Acetylcysteine (10 mM in water). The ADC was buffer exchanged via G25 into PBS and washed by dead-end filtration (Vivaspin-20, 30 kDa MWCO, 0.0006 $m^2$) for 10 DVs. Samples were taken for analysis by HIC, SEC, PLRP, free toxin linker, Endosafe, and the concentration was determined using a SEC calibration curve. Aliquotting was carried out under laminar flow, and the product was stored at −80° C. Only disposable, sterile and pyrogen/DNA/RNA-free plasticware was used.

In Vivo Efficacy Studies

In vivo efficacy and tolerability studies were performed using adaptations of the same basic protocol. An example of this is provided below:

Antitumour activity of the selected ADCs was assessed in tumour xenograft models (both cancer-derived and patient-derived) obtained by inoculation of the relevant cell-line (e.g., SK-BR-3 in the case of ADC1) in nude mice (CD-1 or appropriate depending on the cell-line).

Maximum tolerated dose (MTD) of the relevant ADC was established on 3-5 CD1 mice (or equivalent) at four concentrations (e.g., 2.5 mg/kg, 5 mg/kg, 7.5 mg/kg and 10 mg/kg) through IV administration once per week for a period of four weeks. Once the MTD was determined, an efficacy study was initiated at doses under the maximum tolerated dose. Briefly, tumours were implanted onto the flank of the mice using a 23-gauge needle, and were randomly assigned to groups (e.g., control or ADC). After implantation, tumours were measured 3 times per week using digital calipers. The length and width of the tumour was measured and volume calculated using the following formula: volume=(length×width$^2$)/2. The bodyweight of all mice on the study was measured and recorded 3 times per week. Mice were observed daily and any signs of distress or changes to general condition (e.g., starred fur, lack of movement, difficulty breathing). Specific criteria were set for early termination, and this only occurred if tumour volume exceeded 1500 mm$^3$, weight loss of 15% occurred or animals became compromised (e.g., inability to eat/drink).

Mice were housed in IVC cages (5 mice per cage) with individual mice identified by ear punch. Cages, bedding and water were sanitized before use. Animals were provided with Corn-o-cobs enrichment bedding to provide environment enrichment and nesting material. All animals had free access to a standard certified commercial diet and water. The animal holding room was maintained as follows—room temperature at 20-24° C., humidity at 30-70% and a 12 h light/dark cycle used. Cages were changed once a week with food and water replaced when necessary. All procedures were carried out under the guidelines of the Animal (Scientific Procedures) Act 1986.

All publications mentioned in the above specification are herein incorporated by reference. Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

REFERENCES

1. Antonow, D., and Thurston, D. E. (2011) *Chem Rev* 111, 2815-2864.
2. Cipolla, L., Araujo, A. C., Airoldi, C., and Bini, D. (2009) *Anticancer Agents Med Chem* 9, 1-31.
3. Gerratana, B. (2012) *Med Res Rev* 32, 254-293.
4. Hartley, J. A. (2011) *Expert Opin Investig Drugs* 20, 733-744.
5. Kamal, A., Reddy, K. L., Devaiah, V., Shankaraiah, N., and Reddy, D. R. (2006) *Mini Rev Med Chem* 6, 53-69.
6. Hurley, L. H., Reck, T., Thurston, D. E., Langley, D. R., Holden, K. G., Hertzberg, R. P., Hoover, J. R., Gallagher, G., Jr., Faucette, L. F., Mong, S. M., (1988) *Chem Res Toxicol* 1, 258-268.
7. Wells, G., Martin, C. R., Howard, P. W., Sands, Z. A., Laughton, C. A., Tiberghien, A., Woo, C. K., Masterson, L. A., Stephenson, M. J., Hartley, J. A., Jenkins, T. C., Shnyder, S. D., Loadman, P. M., Waring, M. J., and Thurston, D. E. (2006) *J Med Chem* 49, 5442-5461.
8. Brucoli, F., Hawkins, R. M., James, C. H., Jackson, P. J., Wells, G., Jenkins, T. C., Ellis, T., Kotecha, M., Hochhauser, D., Hartley, J. A., Howard, P. W., and Thurston, D. E. (2013) *J Med Chem* 56, 6339-6351.
9. Kotecha, M., Kluza, J., Wells, G., O'Hare, C. C., Forni, C., Mantovani, R., Howard, P. W., Morris, P., Thurston, D. E., Hartley, J. A., and Hochhauser, D. (2008) *Mol Cancer Ther* 7, 1319-1328.
10. Puvvada, M. S., Hartley, J. A., Jenkins, T. C., and Thurston, D. E. (1993) *Nucleic Acids Res* 21, 3671-3675.
11. Clingen, P. H., De Silva, I. U., McHugh, P. J., Ghadessy, F. J., Tilby, M. J., Thurston, D. E., and Hartley, J. A. (2005) *Nucleic Acids Res* 33, 3283-3291.
12. Puvvada, M. S., Forrow, S. A., Hartley, J. A., Stephenson, P., Gibson, I., Jenkins, T. C., and Thurston, D. E. (1997) *Biochemistry* 36, 2478-2484.
13. Barkley, M. D., Cheatham, S., Thurston, D. E., and Hurley, L. H. (1986) *Biochemistry* 25, 3021-3031.
14. Seifert, J., Pezeshki, S., Kamal, A., and Weisz, K. (2012) *Organic & Biomolecular Chemistry* 10, 6850-6860.
15. Smellie, M., Bose, D. S., Thompson, A. S., Jenkins, T. C., Hartley, J. A., and Thurston, D. E. (2003) *Biochemistry* 42, 8232-8239.
16. Kopka, M. L., Goodsell, D. S., Baikalov, I., Grzeskowiak, K., Cascio, D., and Dickerson, R. E. (1994) *Biochemistry* 33, 13593-13610.
17. Kizu, R., Draves, P. H., and Hurley, L. H. (1993) *Biochemistry* 32, 8712-8722.
18. Leimgruber, W., Stefanovic, V., Schenker, F., Karr, A., and Berger, J. (1965) *J Am Chem Soc* 87, 5791-5793.
19. Arima, K., Kosaka, M., Tamura, G., Imanaka, H., and Sakai, H. (1972) *J Antibiot* (Tokyo) 25, 437-444.
20. Sato, S., Iwata, F., Yamada, S., Kawahara, H., and Katayama, M. (2011) *Bioorg Med Chem Lett* 21, 7099-7101.
21. Thurston D.E. and Bose D.S., *Chem Rev* (1994); 94:433-465.
22. Damayanthi, Y., et al.; *Journal of Organic Chemistry* (1999), 64, 290-292;
23. Kumar, et al., *Heterocyclic Communications* (2002) 8, 19-26.
24. Kumar, R, Lown, J. W.; *Oncology Research*, (2003) 13, 221-233.
25. Baraldi, P. G. et al., *Journal of Medicinal Chemistry* (1999) 42, 5131-5141.
26. Wells, G., et al., *Proc. Am. Assoc. Canc. Res.* (2003) 44, 452.
27. Thurston, D. E.; Howard, P. W. WO 2004/043963.
28. Bose, D. S., Thompson, A. S., Ching, J. S., Hartley, J. A., Berardini, M.D., Jenkins, T. C., Neidele, S., Hurley, L. H., and Thurston, D. E. (1992) *J. Am. Chem. Soc.* 114, 4939.
29. Wu, J., Clingen, P. H., Spanswick, V. J., Mellinas-Gomez, M., Meyer, T., Puzanov, I., Jodrell, D., Hochhauser, D., and Hartley, J. A. (2013) *Clin Cancer Res* 19, 721-730.
30. Jenkins, T. C., Hurley, L. H., Neidle, S., and Thurston, D. E. (1994) *J Med Chem* 37, 4529-4537.
31. Hochhauser, D., Meyer, T., Spanswick, V. J., Wu, J., Clingen, P. H., Loadman, P., Cobb, M., Gumbrell, L., Begent, R. H.,Hartley, J. A., Jodrell, D., (2009) *Clin Cancer Res* 15, 2140-2147.
32. A. J. Hampshire, D. A. Rusling, V. J. Broughton-Head, K. R. Fox, *Methods* 2007, 42, 128-140.
33. M. J. Flynn, F. Zammarchi, P. C. Tyrer, A. U. Akarca, N. Janghra, C. E. Britten, C. E. Havenith, J. N. Levy, A.

Tiberghien, L. A. Masterson, C. Barry, F. D'Hooge, T. Marafioti, P. W. Parren, D. G. Williams, P. W. Howard, P. H. van Berkel, J. A. Hartley, *Mol Cancer Ther* 2016, 15, 2709-2721.

34. M. L. Miller, N. E. Fishkin, W. Li, K. R. Whiteman, Y. Kovtun, E. E. Reid, K. E. Archer, E. K. Maloney, C. A. Audette, M. F. Mayo, A. Wilhelm, H. A. Modafferi, R. Singh, J. Pinkas, V. Goldmacher, J. M. Lambert, R. V. Chari, *Mol Cancer Ther* 2016, 15, 1870-1878.

35. H. R. Drew, A. A. Travers, *Cell* 1984, 37, 491-502.

36. A. J. Hampshire, D. A. Rusling, V. J. Broughton-Head, K. R. Fox, *Methods* 2007, 42, 128-140.E 37. A. J. Hampshire, K. R. Fox, *Anal. Biochem.* 2008, 374, 298-303.

38. M. Lavesa, K. R. Fox, *Anal. Biochem.* 2001, 293, 246-250.

Example 168

A tetrahydroisoquinolinebenzodiazepine (QBD) derivative consists of a four-ring system (6-7-6-6), but alkylates DNA in an identical manner to the PBD[3]. It can be synthesised in the following manner, and then coupled to the DNA-interactive side-chain using standard amide-coupling conditions.

General Synthetic Scheme for QBD (R represents side-chain):

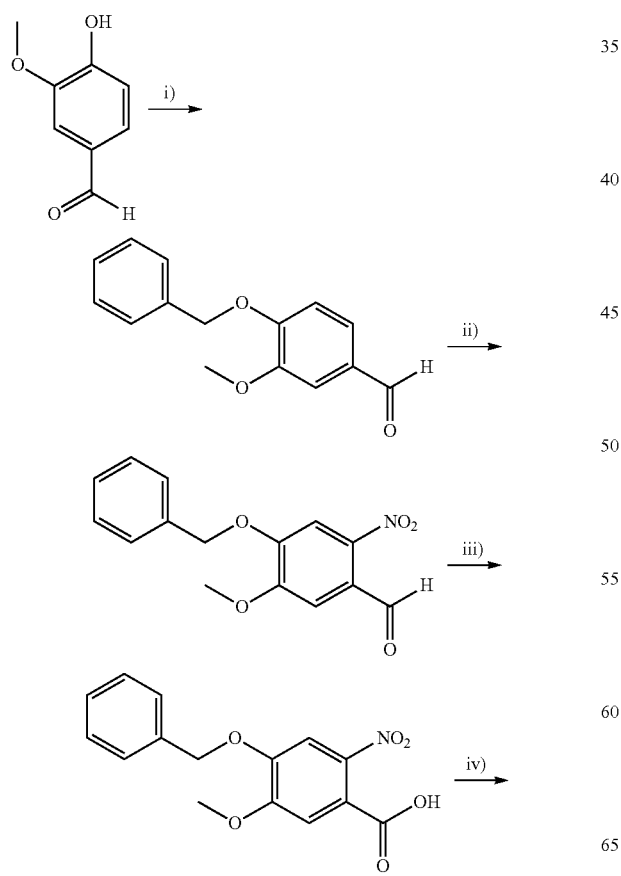

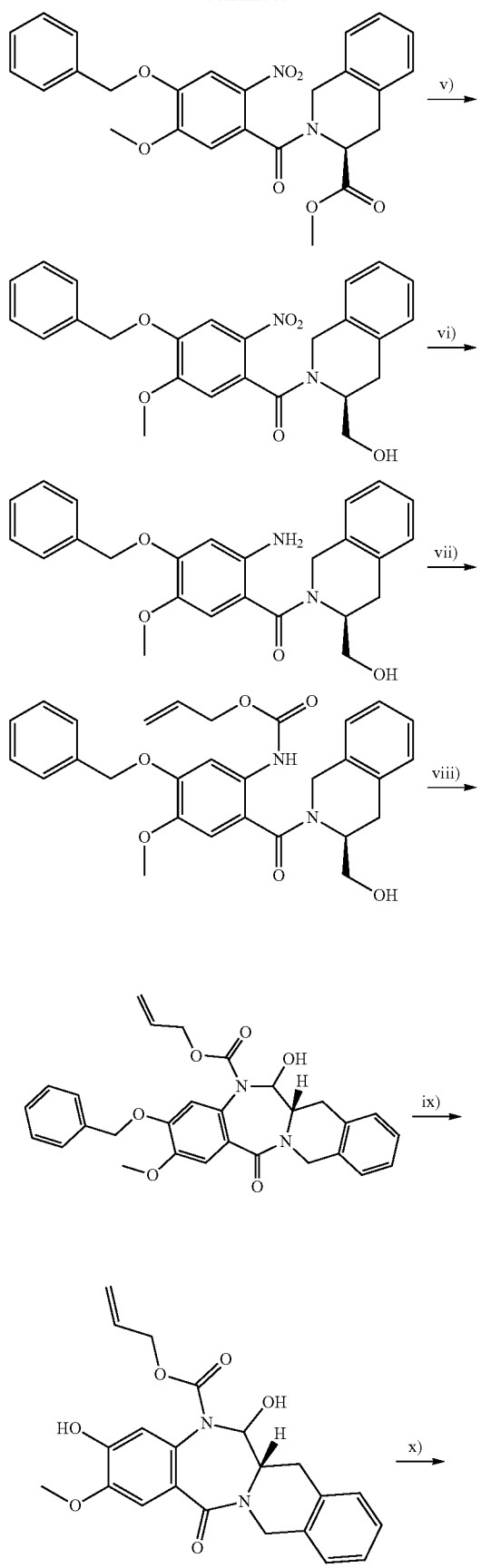

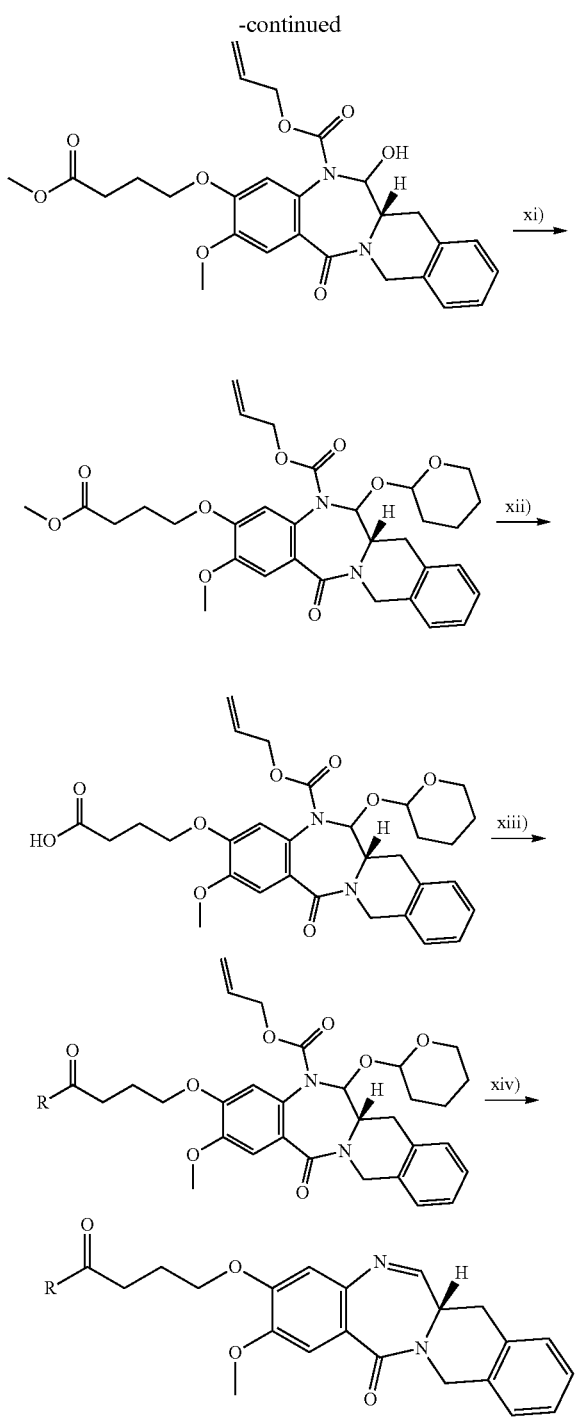

i) BnBr, K₂CO₃, acetone, r.t;
ii) KNO₃, TFA, 0° C.;
iii) KMnO₄, actone, H₂O, reflux;
iv) (COCl)₂, DMF cat., Et₃N, methyl (S)-1,2,3,4-tetrahydroisoquinoline-3-carboxylate, CH₂Cl₂, r.t.;
v) LiBH₄, THF, 0° C.;
vi) FeCl₆•6H₂O, NH₂NH₂•H₂O, activated charcoal, MeOH, reflux;
vii) Allylchloroformate, pyridine, CH₂Cl₂, -10° C.-r.t.;
viii) TEMPO, BAIB, CH₂Cl, r.t.;
ix) BCl₃ (1M in CH₂Cl₂), CH₂Cl₂, -78° C.;
x) metyl 4-bromobutanoate, K₂CO₃, DMF, r.t.;
xi) DHP, p-TSA, EtOAC, r.t.;
xii) NaOH, 1,4-dioxane, r.t.;
xiii) R, EDCI•DMA, r.t.; xiv) Pd(PPh₃)₄,pyrrolidine, CH₂Cl₂, r.t.

General Remarks

Unless otherwise stated, all reagents were purchased from standard commercial suppliers and used as purchased. Solvents were purchased from Sigma-Aldrich (UK) and Fisher Scientific (UK). Anhydrous reactions were carried out in pre-oven-dried glassware under an inert atmosphere of nitrogen or argon. Anhydrous solvents were used as purchased without further drying. Thin Layer Chromatography (TLC) was performed on silica gel aluminium plates (Merck 60, $F_{254}$), and flash column chromatography was carried out either manually, using silica gel (Merck 9385, 230-400 mesh ASTM, 40-63 μM) (whilst monitoring by thin layer chromatography: UV (254 nm) and an aqueous alkaline solution of potassium permanganate as stain), or using a Grace Reveleris® X2 automated Flash Chromatography System. All NMR spectra were obtained at room temperature using a Bruker DPX400 spectrometer, for which chemical shifts are expressed in ppm relative to the solvent and coupling constants are expressed in Hz. Microwave reactions were carried out on an Anton Paar Monowave 300 microwave synthesis reactor. Yields refer to isolated material (homogeneous by TLC or NMR) unless otherwise stated and names are assigned according to IUPAC nomenclature. All Liquid Chromatography Mass Spectroscopy (LCMS) analysis was performed on a Waters Alliance 2695 with water (A) and acetonitrile (B) comprising the mobile phases. Formic acid (0.1%) was added to both acetonitrile and water to ensure acidic conditions throughout the analysis. Function type: Diode array (535 scans). Column type: Monolithic C18 50×4.60 mm. Mass spectrometry data were collected using a Waters Micromass ZQ instrument coupled to a Waters 2695 HPLC with a Waters 2996 PDA, Waters Micrornass ZQ parameters used were: Capillary (kV), 3.38; Cone (V), 35; Extractor (V), 3,0; Source temperature (° C.), 100; De-solvation Temperature (° C.), 200; Cone flow rate (L/h), 50; De-solvation flow rate (L/h), 250. LCMS gradient conditions are described as follows.

Method A (10 min): from 95% A/5% B to 50% B over 3 min. Then from 50% B to 80% B over 2 min. Then from 80% B to 95% B over 1.5 min and held constant for 1.5 min. This was then reduced to 5% B over 0.2 min and maintained to 5% B for 1.8 min. The flow rate was 0.5 mL/min, 200 μL was split via a zero dead volume T piece which passed into the mass spectrometer. The wavelength range of the UV detector was 220-400 nm.

Method B (5 min): from 95% A 5B to 90% B over 3 min. Then from 90% B to 95% B over 0.5 min and held constant for 1 min. This was then reduced to 5% B over 0.5 min. The flow rate was 1.0 mL/min, 100 μL was split via a zero dead volume T piece which passed into the mass spectrometer. The wavelength range of the UV detector was 220-500 nm.

Method C (5 min): from 95% A/5% B, which was increased to 90% B over 3 min and to 95% B over a further 0.5 min. The gradient was then held at 95% B for 1 min and then returned to 5% B over 0.5 min. The total duration of the run was 5 minutes and the solvent flow rate was 1 mL/min, 100 μL was split via a zero dead volume T piece which passed into the mass spectrometer. The wavelength range of the UV detector was 220-500 nm.

Example 169

Methyl (S)-2-(4-(benzyloxy)-5-methoxy-2-nitrobenzoyl)-1,2,3,4-tetrahydroisoquinoline-3-carboxylate (150)

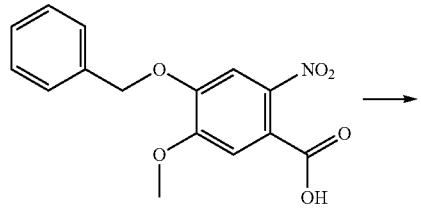

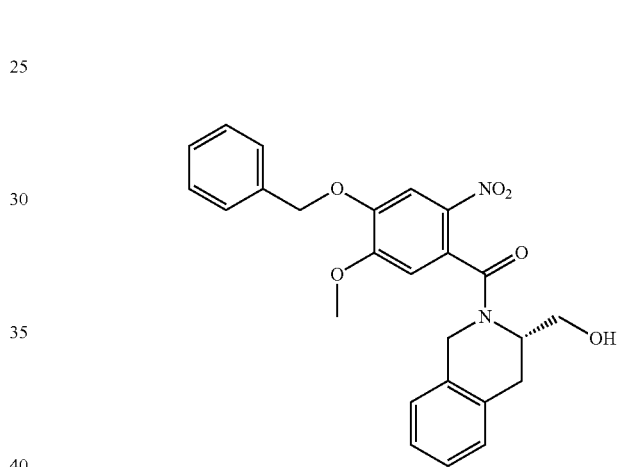

A mixture of 4-(benzyloxy)-5-methoxy-2-nitrobenzoic acid (149) (2.0 g, 6.6 mmol), oxalyl chloride (1.70 mL, 19.8 mmol) and anhydrous N,N-dimethylformamide (2 drops) in anhydrous dichloromethane (40 mL) was stirred at room temperature for 3 h. Anhydrous toluene (8 mL) was added to the reaction mixture which was then concentrated in vacua. A solution of the resulting residue in anhydrous dichloromethane (10 mL) was added dropwise to a solution of methyl (S)-1,2,3,4-tetrahydroisoquinoline-3-carboxylate (1.65 g, 7.26 mmol) and triethylamine (2.0 mL, 14.5 mmol) in anhydrous dichloromethane (30 mL), at −10° C. The reaction mixture was stirred at room temperature for 2 h and then washed with hydrochloric acid (1 M, 20 mL) and brine (20 mL), dried over sodium sulfate, filtered and concentrated. The resulting residue was purified by column chromatography (silica), eluting with acetone/dichloromethane (from 0% to 30%), to give the title compound (2.5 g, 79%) as a yellow oil.

$^1$H NMR (400 MHz, CDCl$_3$) δ 7.49-7.42 (m, 6H), 7.24-7.19 (m, 5H), 5.25 (s, 2H), 4.64-4.60 (m, 1H), 4.38-4.26 (m, 2H), 3.93 (s, 3H), 3.58 (s, 3H), 3.33-3.23 (m, 2H); $^{13}$C NMR (100 MHz, CDCl$_3$) δ 170.8, 170.3, 154.6, 148.4, 135.3, 133.5, 130.5, 130.1, 128.9, 128.8, 128.6, 128.4, 127.7, 127.4, 126.7, 109.3, 109.1, 71.4, 56.8, 52.6, 31.8, 31.0, 30.5; MS (ES+): m/z=477 (M+H)$^+$: LCMS (Method B): t$_R$=4.10 min.

Example 170

(S)-(4-(Benzyloxy)-5-methoxy-2-nitrophenyl)(3-(hydroxymethyl)-3,4-dihydroisoquinolin-2(1H)-yl)methanone (151)

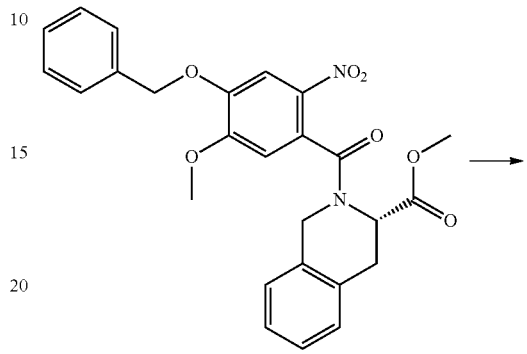

A solution of methyl (S)-2-(4-(benzyloxy)-5-methoxy-2-nitrobenzoyl)-1,2,3,4-tetrahydroisoquinoline-3-carboxylate (150) (2.4 g, 5.0 mmol) in anhydrous tetrahydrofuran (48 mL) was charged with a solution of lithium borohydride (2 M in tetrahydrofuran, 3.8 mL, 8.7 mmol) at 0° C. The reaction mixture was stirred at room temperature for 3 hours. Water (150 mL) was added dropwise at 0° C. and the reaction mixture was then extracted with ethyl acetate (2×100 mL). The combined organic extracts were then concentrated in vacua. The resulting residue was purified by column chromatography (silica), eluting with acetone/dichloromethane (from 0% to 30%), to give the title compound (2.2 g, 97%) as creamy oil.

$^1$H NMR (400 MHz, CDCl$_3$) δ 7.42-7.39 (m, 4H), 7.36-7.34 (m, 5H), 7.30 (s, 1H), 7.29 (s, 1H), 5.17 (s, 2H), 4.62 (s, 1H), 4.36-4.25 (m, 1H), 4.23-4.16 (m, 2H), 3.87 (s, 3H), 3.70-3.63 (m, 1H), 3.58-3.50 (m, 1H), 3.05-2.97 (m, 2H); $^{13}$C NMR (100 MHz, CDCl$_3$) δ 168.2, 150.2, 148.3, 133.7, 128.9, 128.9, 128.8, 128.6, 127.7, 127.6, 127.5, 127.0, 126.5, 114.4, 110.6, 108.9, 103.9, 91.6, 71.4, 65.4, 54.4, 33.3; MS (ES+): m/z=449 (M+H)$^+$: LCMS (Method B): t$_R$=3.78 min.

Example 171

(S)-(2-Amino-4-(benzyloxy)-5-methoxyphenyl)(3-(hydroxymethyl)-3,4-dihydroisoquinolin-2(1H)-yl)methanone (152)

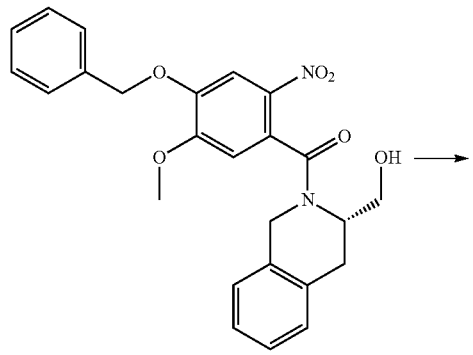

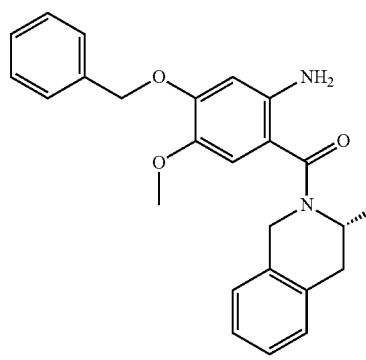

A solution of (S)-(4-(benzyloxy)-5-methoxy-2-nitrophenyl)(3-(hydroxymethyl)-3,4-dihydroisoquinolin-2(1H)-yl)methanone (151) (2.20 g, 4.90 mmol) in tetrahydrofuran (50 mL) and methanol (50 mL) was charged with iron (III) chloride hexahydrate (0.80 g, 2.90 mmol), activated charcoal (2.60 g, 221 mmol) and hydrazine (2.90 mL, 58.9 mmol). The reaction mixture was then stirred at reflux (85° C.) for 16 h. The mixture was subsequently allowed to cool to room temperature and filtered through a plug of celite. The filter cake was washed with ethyl acetate and methanol and then concentrated in vacua to give the title compound (1.7 g, 83%) as brown solid.

$^1$H NMR (400 MHz, MeOD) δ 7.48 (s, 1H), 7.46 (s, 1H), 7.41-7.33 (m, 4H), 7.20-7.18 (m, 3H), 6.84 (s, 1H), 6.56 (s, 1H), 5.11 (s, 2H), 4.61 (s, 1H), 4.54-4.40 (m, 1H), 3.77 (s, 3H), 3.62-3.54 (m, 2H), 3.19 (dd, J=16.2, 5.9 Hz, 2H), 2.92-2.80 (m, 2H); $^{13}$C NMR (100 MHz, MeOD) δ 169.1, 149.8, 141.0, 135.5, 130.7, 129.0, 128.7, 128.6, 128.5, 128.4, 128.2, 127.4, 127.0, 126.7, 110.1, 109.1, 71.0, 68.7, 64.8, 56.4, 50.3, 27.9; MS (ES+): m/z=419 (M+H)$^+$; LCMS (Method B): $t_R$=3.50 min.

Example 172

Allyl (S)-(5-(benzyloxy)-2-(3-(hydroxymethyl)-1,2,3,4-tetrahydroisoquinoline-2-carbonyl)-4-methoxyphenyl)carbamate (153)

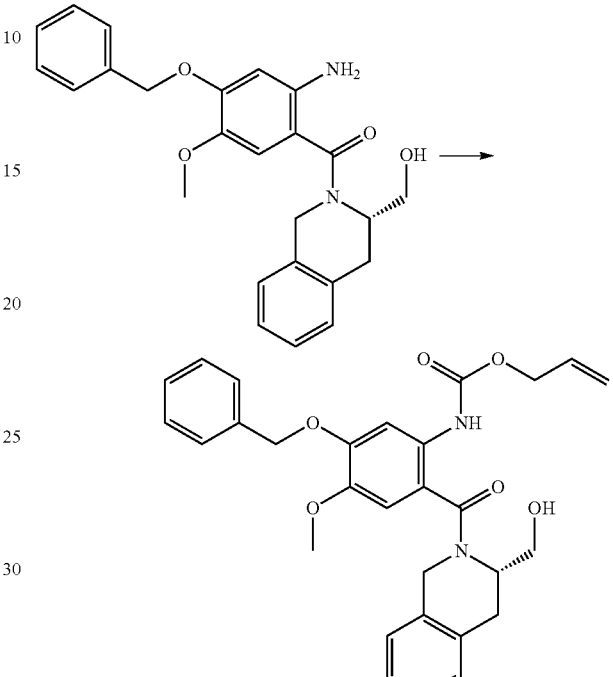

A solution of (S)-(2-amino-4-(benzyloxy)-5-methoxyphenyl)(3-(hydroxymethyl)-3,4-dihydroisoquinolin-2(1H)-yl)methanone (152) (1.50 g, 3.6 mmol) and anhydrous pyridine (696 µL, 8.97 mmol) in anhydrous dichloromethane (50 mL) at −10° C. was slowly charged with a solution of allylchloroformate (343 µL, 3.23 mmol) in anhydrous dichloromethane (30 mL). The reaction mixture was stirred at room temperature for 30 min and then sequentially washed with a saturated aqueous solution of copper (II) sulfate (50 mL), water (50 mL) and a saturated aqueous solution of sodium hydrogen carbonate (50 mL). The organic layer was dried over sodium sulfate, filtered and concentrated in vacua. The resulting residue was purified by column chromatography (silica), eluting with acetone/dichloromethane (from 0% to 20%), to give the title compound (1.47 g, 81%) as an off-white solid.

$^1$H NMR (400 MHz, MeOD) δ 8.14 (s, 1H), 7.81 (s, 1H), 7.51 (s, 1H), 7.49 (s, 1H), 7.42-7.32 (m, 4H), 7.23-7.17 (m, 3H), 6.82 (s, 1H), 5.97-5.87 (m, 1H), 5.33 (dq, J=17.2, 1.5 Hz, 1H), 5.22 (dq, J=10.6, 1.3 Hz, 1H), 5.19 (s, 2H), 4.68-4.64 (m, 1H), 4.61 (dd, J=5.5, 1.3 Hz, 2H), 4.44 (br. s, 2H), 3.82 (s, 3H), 3.70-3.64 (m, 1H), 3.21-3.15 (m, 1H), 2.74 (br. s, 1H); $^{13}$C NMR (100 MHz, CDCl$_3$) δ 169.4, 152.9, 148.7, 144.1, 140.1, 135.3, 131.4, 130.5, 129.1, 128.1, 127.5, 127.0, 126.7, 125.9, 125.5, 117.9, 116.8, 109.6, 105.7, 69.7, 67.4, 66.0, 64.7, 55.3, 53.8, 26.8; MS (ES+): m/z=503 (M+H)$^+$; LCMS (Method B): $t_R$=3.95 min.

Example 173

Allyl (6aS)-3-(benzyloxy)-6-hydroxy-2-methoxy-14-oxo-6,6a,7,12-tetrahydrobenzo[5,6][1,4]diazepino[1,2-b]isoquinoline-5 (14H)-carboxylate (154)

Example 174

Allyl (6aS)-3,6-dihydroxy-2-methoxy-14-oxo-6,6a,7,12-tetrahydrobenzo[5,6][1,4]diazepino[1,2-b]isoquinoline-5(14H)-carboxylate (155)

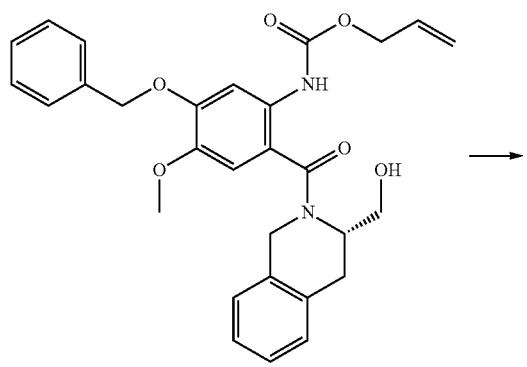

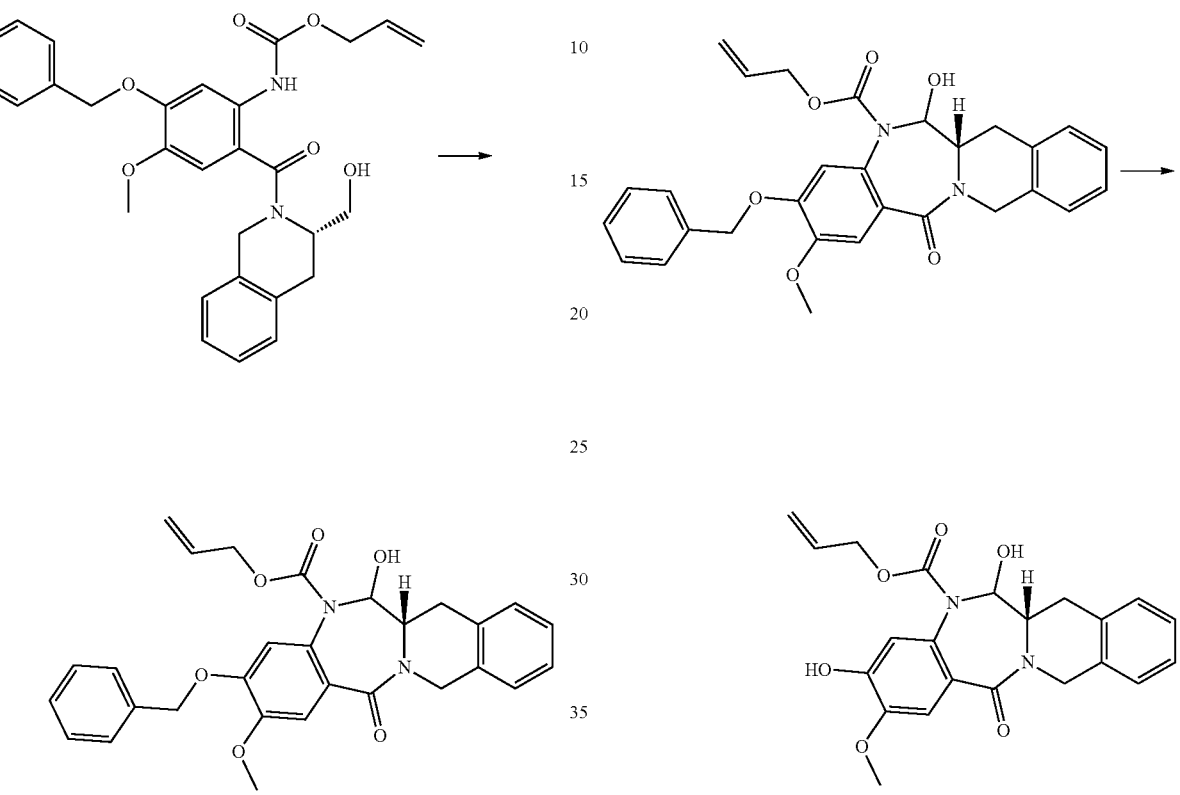

A solution of allyl (S)-(5-(benzyloxy)-2-(3-(hydroxymethyl)-1,2,3,4-tetrahydroisoquinoline-2-carbonyl)-4-methoxyphenyecarbamate (153) (1.4 g, 2.78 mmol) in dichloromethane (80 mL) was charged with 2,2,6,6-tetramethyl-1-piperidinyloxy (44 mg, 0.28 mmol) and (diacetoxyiodo)benzene (1.0 g, 3.33 mmol). The reaction mixture was stirred at room temperature for 16 h and was then sequentially washed with a saturated aqueous solution of sodium metabisulfite (40 mL), a saturated aqueous solution of sodium hydrogen carbonate (40 mL), water (30 mL) and brine (30 mL). The organic layer was then dried over sodium sulfate, filtered and concentrated. The resulting residue was purified by column chromatography (silica), eluting with acetone/dichloromethane (from 0% to 20%), to give the title compound (1.2 g, 86%) as an off-white solid.

$^1$H NMR (400 MHz, CDCl$_3$) δ 7.44-7.31 (m, 6H), 7.28-7.26 (m, 5H), 6.72 (s, 1H), 5.70-5.61 (m, 1H), 5.31 (d, J=9.8 Hz, 1H), 5.20-5.17 (m, 1H), 5.11-5.07 (m, 3H), 4.83 (d, J=15.6 Hz, 1H), 4.58 (d, J=15.6 Hz, 1H), 4.48-4.34 (m, 2H), 3,94 (s, 3H), 3.74-3.69 (m, 1H), 3.17-3.05 (m, 2H); $^{13}$C NMR (100 MHz, CDCl$_3$) δ 169.0, 149.0, 136.2, 134.3, 133.7, 131.8, 126.7, 128.2, 127.9, 127.8, 127.3, 126.7, 118.1, 114.0, 111.2, 84.8, 71.0, 66.7, 56.2, 53.5, 50.8, 44.3, 30.2; MS (ES+): m/z=501 (M+H)$^+$: LCMS (Method B): t$_R$=3.80 min.

A solution of allyl (6aS)-3-(benzyloxy)-6-hydroxy-2-methoxy-14-oxo-6,6a,7,12-tetrahydrobenzo[5,6][1,4]diazepino[1,2-b]isoquinoline-5(14H)-carboxylate (154) (1.10 g, 2.20 mmol) in anhydrous dichloromethane (20 mL) was charged with a solution of boron trichloride (1 M in hexane, 4.4 mL, 4.4 mmol) at −78° C. The resulting mixture was stirred for 5 h at −78° C. and then quenched via dropwise addition of water (5 mL). An aqueous acetic acid solution (50 mL) was added to adjust to pH=3, and the resulting mixture was then extracted with ethyl acetate (2×60 mL). The combined organic extracts were then concentrated in vacua. The resulting residue was purified by column chromatography (silica), eluting with acetone/dichloromethane (from 0% to 30%), to give the title compound (860 mg, 95%) as a pale yellow solid.

$^1$H NMR (400 MHz, CDCl$_3$) δ 7.29-7.26 (m, 6H), 6.76 (s, 1H), 6.02 (s, 1H), 5.84-5.75 (m, 1H), 5.34-5.31 (m, 1H), 5.17-5.13 (m, 2H), 4.83 (d, J=15.6 Hz, 1H), 4.64-4.56 (m, 2H), 4.46-4.43 (m, 1H), 3.95 (s, 3H), 3.75-3.70 (m, 1H), 3.19-3.06 (m, 2H); $^{13}$C NMR (100 MHz, CDCl$_3$) δ 169.0, 159.4, 148.0, 146.0, 134.3, 133.7, 131.8, 127.9, 127.8, 127.3, 126.7, 118.1, 115.3, 110.6, 84.8, 66.8, 56.3, 44.3, 31.0, 30.2; MS (ES+): m/z=411 (M+H)$^+$: LCMS (Method B): t$_R$=3.15 min.

Example 175

Allyl (6aS)-6-hydroxy-2-methoxy-3-(4-methoxy-4-oxobutoxy)-14-oxo-6,6a,7,12-tetrahydrobenzo[5,6][1,4]diazepino[1,2-b]isoquinoline-5(14H)-carboxylate (156)

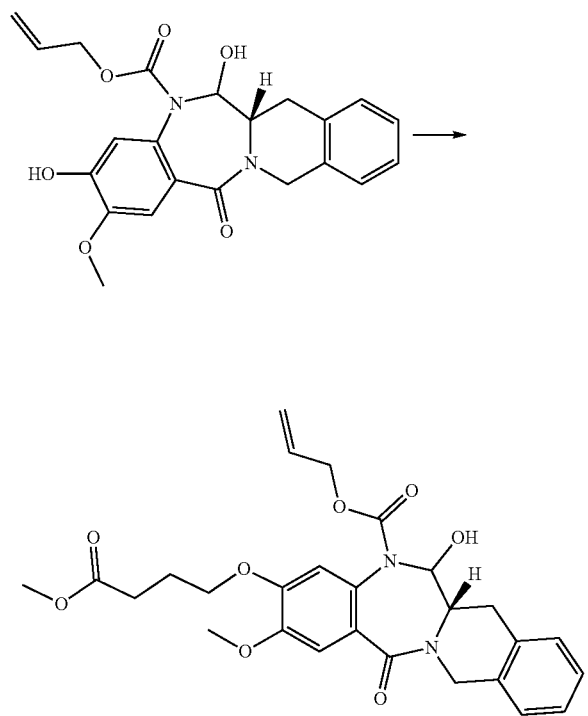

A solution of allyl (6aS)-3,6-dihydroxy-2-methoxy-14-oxo-6,6a,7,12-tetrahydrobenzo[5,6][1,4]diazepino[1,2-b]isoquinoline-5(14H)-carboxylate (155) (300 mg, 0.73 mmol) in N,N-dimethylformamide (3 mL) was charged with methyl 4-bromobutanoate (166 µL, 1.31 mmol) and potassium carbonate (151 mg, 1.10 mmol) and stirred at room temperature under an inert atmosphere of argon for 20 h. The reaction mixture was diluted with water (30 mL) and extracted with ethyl acetate (3×20 mL). The combined organic extracts were then washed with brine (20 mL), dried over magnesium sulfate, filtered and concentrated in vacua to give the title compound (368 mg, 99%) as a yellow oil, which was carried through to the subsequent step without further purification.

$^1$H NMR (400 MHz, CDCl$_3$) δ 7.30 (s, 5H), 6.75 (br. s, 1H), 5.86-5.74 (m, 1H), 5.38 (d, J=9.8 Hz, 1H), 5.13 (d, J=11.3 Hz, 2H) 4.83 (d, J=15.6 Hz, 1H), 4.43 (br. s, 1H), 4.08 (q, J=5.9 Hz, 2H), 3.94-3.91 (m, 3H), 3.71 (s, 3H), 3.50 (t, J=6.4 Hz, 2H) 3.07-3.20 (m, 2H), 2.56-2.59 (m, 2H), 2.25-2.17 (m, 4H); $^{13}$C NMR (100 MHz, CDCl$_3$) δ 173.3, 172.9, 169.0, 148.7, 134.3, 133.8, 131.9, 127.7, 127.7, 127.1, 126.6, 124.9, 117.7, 113.6, 111.1, 84.7, 67.9, 66.5, 56.0, 55.8, 51.6, 51.6, 44.2, 32.6, 30.3, 27.7, 24.2; MS (ES+): m/z=511 (M+H)$^+$, MS (ES): m/z=509 (M−1)$^−$; LCMS (Method B): t$_R$=3.63 min, LCMS (Method A): t$_R$=6.97 min.

Example 176

Allyl (6as)-2-methoxy-3-(4-methoxy-4-oxobutoxy)-14-oxo-6-((tetrahydro-2H-pyran-2-yl)oxy)-6,6a,7,12-tetrahydrobenzo[5,6][1,4]diazepino[1,2-b]isoquinoline-5(14H)-carboxylate (157)

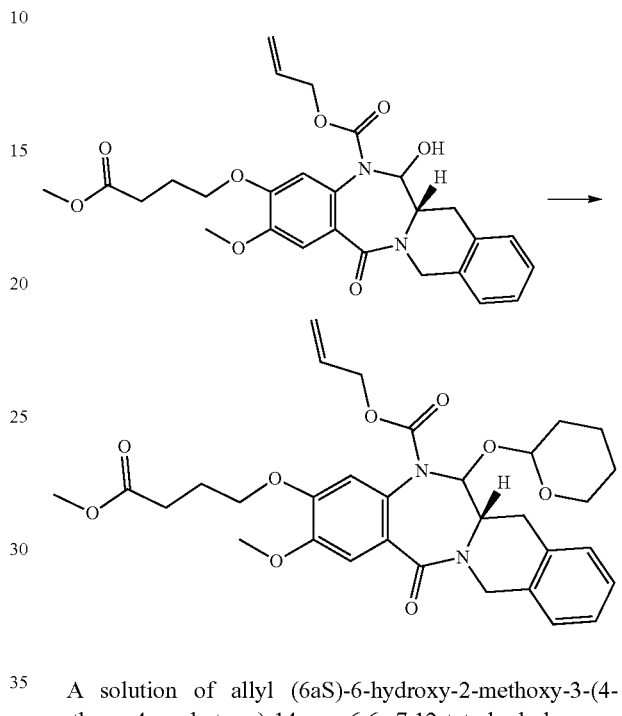

A solution of allyl (6aS)-6-hydroxy-2-methoxy-3-(4-methoxy-4-oxobutoxy)-14-oxo-6,6a,7,12-tetrahydrobenzo[5,6][1,4]diazepino[1,2-b]isoquinoline-5(14H)-carboxylate (156) (367 mg, 0.72 mmol) in ethyl acetate (2 mL) was charged with p-toluenesulfonic acid monohydrate (3.7 mg, 1% w/w) and 3,4-dihydro-2H-pyran (657 µL, 7.20 mmol).

The resulting mixture was stirred at room temperature for 20 h, then diluted with ethyl acetate (15 mL) and subsequently washed with a saturated aqueous solution of sodium hydrogen carbonate (10 mL), water (15 mL) and brine (15 mL), dried over magnesium sulfate, filtered and concentrated in vacuo. Column chromatography (silica gel), eluting ethyl acetate/petroleum ether (50%, isocratic) afforded the title compound (390 mg, 91%) as a light-yellow gel.

$^1$H NMR (400 MHz, CDCl$_3$) δ 7.73-7.70 (m, 1H), 7.56-7.52 (m, 1H), 7.30-7.28 (m, 1H), 7.23 (d, J=8.2 Hz, 1H), 6.86 (s, 1H), 6.60 (s, 1H), 5.81-5.63 (m, 1H), 5.46 (d, J=9.4 Hz, 1H), 5.11-5.03 (m, 2H), 4.79 (d, J=15.6 Hz, 1H), 4.74-4.48 (m, 2H), 4.48-4.31 (m, 1H), 4.28-4.18 (m, 2H), 4.06 (q, J=6.0 Hz, 2H), 3.91 (s, 3H), 3.69 (s, 3H), 3.63-3.51, (m, 2H), 3.25-3.17 (m, 1H), 3.12-3.05 (m, 1H), 2.62-2.47 (m, 2H), 2.26-2.10 (m, 2H), 1.90-1.65 (m, 3H), 1.58 (d, J=10.9 Hz, 3H); $^{13}$C NMR (100 MHz, CDCl$_3$) δ 173.4, 169.2, 167.7, 149.2, 134.7, 132.4, 130.8, 128.8, 126.5, 117.2, 117.1, 114.5, 113.9, 111.2, 110.8, 99.9, 90.2, 67.7, 68.1, 66.3, 63.6, 56.1, 51.6, 44.2, 31.1, 30.4, 28.9, 25.2, 23.7, 23.0, 20.1, 10.9; MS (ES+): m/z=595 (M+H)$^+$: LCMS (Method B): t$_R$=4.35 min, LCMS (Method A): t$_R$=8.27 min.

Example 177

4-(((6aS)-5-((Allyloxy)carbonyl)-2-methoxy-14-oxo-6-((tetrahydro-2H-pyran-2-yl)oxy)-5,6,6a,7,12,14-hexahydrobenzo[5,6][1,4]diazepino[1,2-b]isoquinolin-3-yl)oxy)butanoic acid (158)

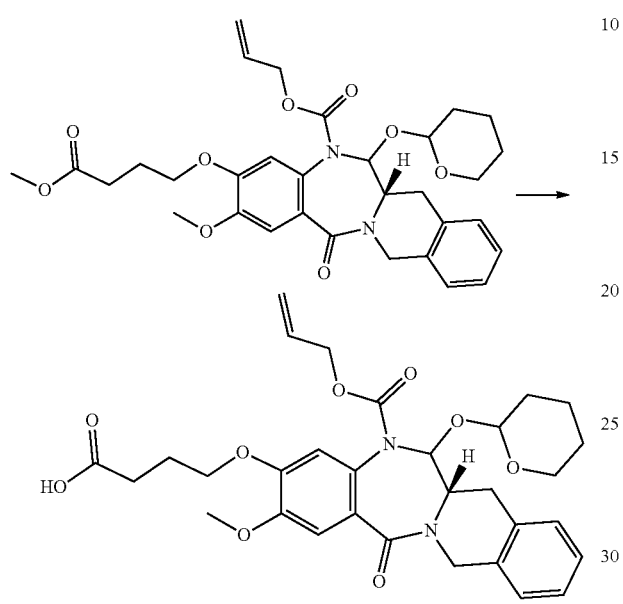

A solution of allyl (6aS)-2-methoxy-3-(4-methoxy-4-oxobutoxy)-14-oxo-6-((tetrahydro-2H-pyran-2-yl)oxy)-6,6a,7,12-tetrahydrobenzo[5,6][1,4]diazepino[1,2-b]isoquinoline-5(14H)-carboxylate (157) (332 mg, 0.55 mmol) in 1,4-dioxane (1 mL) was charged with an aqueous solution of sodium hydroxide (1 M, 1.20 mL, 1.2 mmol) and stirred at room temperature for 15 h. The reaction mixture was then concentrated in vacuo, whereupon water (10 mL) was added and the suspension was acidified to pH=1 with an aqueous solution of citric acid (1 M). The aqueous layer was then extracted with ethyl acetate (3×15 mL) and the combined organic extracts were then washed with brine (15 mL) and concentrated in vacua to give the title compound (278 mg, 87%) as a white solid.

$^1$H NMR (400 MHz, CDCl$_3$) δ 7.78-7.69 (m, 1H), 7.60-7.53 (m, 1H), 7.32-7.30 (m, 1H), 7.30 (br. s, 1H), 6.89 (s, 1H), 6.61 (br. s, 1H), 5.82-5.62 (m, 1H), 5.47 (d, J=9.8 Hz, 1H), 5.13-5.03 (m, 2H), 4.82 (d, J=16.0 Hz, 1H), 4.73-4.55 (m, 2H), 4.30-4.20 (m, 2H), 4.18-4.06 (m, 2H), 3.99 (dd, J=10.7, 5.3 Hz, 1H), 3.93 (s, 3H), 3.80-3.68 (m, 1H), 3.60 (br. s, 1H), 3.21 (d, J=3.1 Hz, 1H), 3.15-3.08 (m, 1H), 2.61 (q, J=7.3 Hz, 2H), 2.18 (quin, J=6.6 Hz, 2H), 1.89-1.67 (m, 3H), 1.65-1.53 (m, 3H); $^{13}$C NMR (100 MHz, CDCl$_3$) δ 177.8, 169.4, 169.4, 167.8, 149.2, 149.0, 134.6, 132.4, 130.9, 128.8, 127.7, 127.5, 126.8, 126.5, 117.2, 68.1, 67.6, 66.3, 63.3, 56.1, 44.2, 38.7, 31.1, 30.3, 28.9, 25.3, 23.7, 23.0, 20.0, 14.0, 10.9; MS (ES+): m/z=581 (M+H)$^+$, MS (ES): m/z=579 (M−1)$^-$; LCMS (Method B): t$_R$=3.93 min, LCMS (Method A): t$_R$=7.53 min.

Example 178

An indolinobenzodiazepine (IBD) is a synthetic analogue of a PBD and consists of a four-ring system (6-7-5-6 ring system)[4]. It alkylates DNA in an identical manner to the PBD. It can be synthesised using the following methodology, and then coupled to a DNA-reactive side-chain using standard amide-coupling conditions.

General Synthetic Scheme for IBD (R represents side-chain):

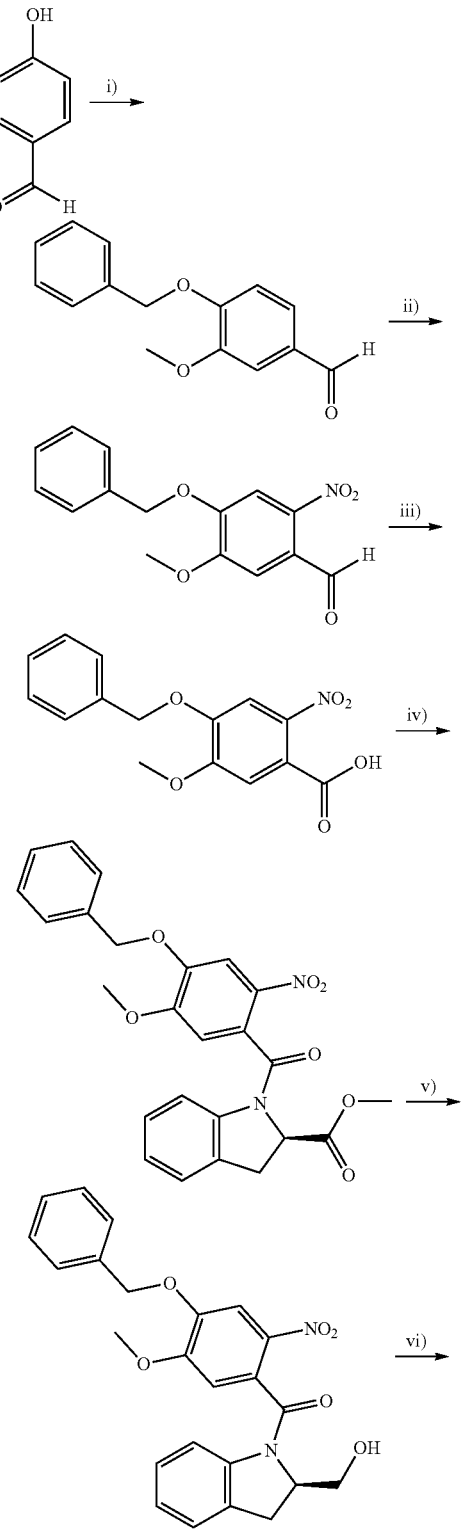

309
-continued

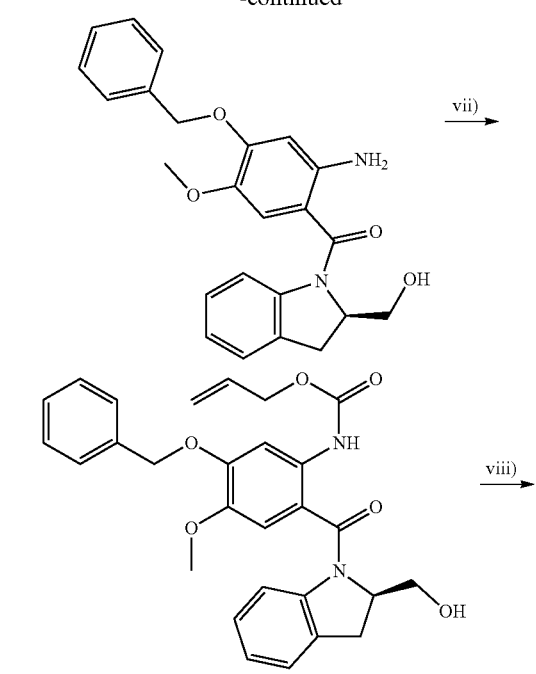

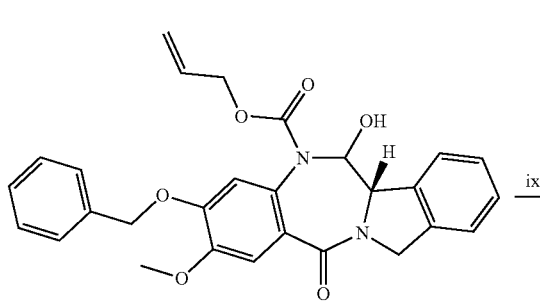

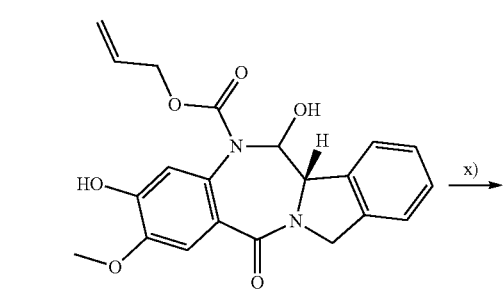

310
-continued

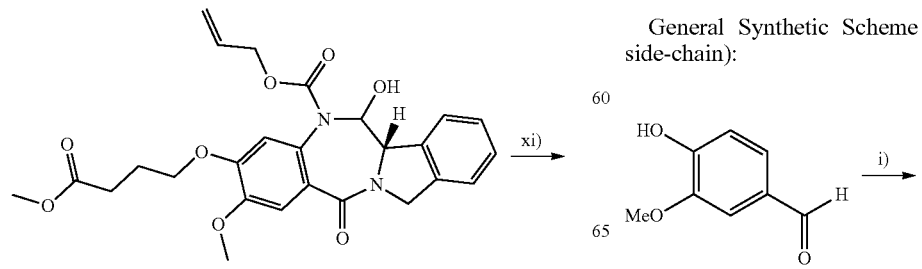

i) BnBr, K₂CO₃, acetone, r.t;
ii) KNO₃, TFA, 0° C.;
iii) KMnO₄, actone, H₂O, reflux;
iv) (COCl)₂, DMF cat., Et₃N, methyl (S)-1,2,3,4-tetrahydroisoquinoline-3-carboxylate, CH₂Cl₂, r.t.;
v) LiBH₄, THF, 0° C.;
vi) FeCl₃•6H₂O, NH₂NH₂•H₂O, activated charcoal, MeOH, reflux;
vii) Allylchloroformate, pyridine CH₂Cl₂, -10° C.-r.t.;
viii) TEMPO, BAIB, CH₂Cl, r.t.;
ix) BCl₃ (1M in CH₂Cl₂), CH₂Cl₂, -78° C;
x) metyl 4-bromobutanoate, K₂CO₃, DMF, r.t.;
xi) DHP, p-TSA, EtOAc, r.t.;
xii) NaOH, 1,4-dioxane, r.t.;
xiii) R, EDCI•HCl, DMA, r.t.;
xiv) Pd(PPh₃)₄, pyrrolidine, CH₂Cl₂, r.t.

Example 179

General Synthetic Scheme for an IGN (R represents side-chain):

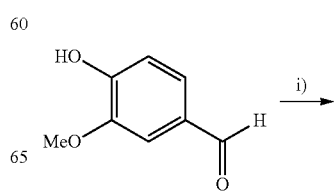

311
-continued
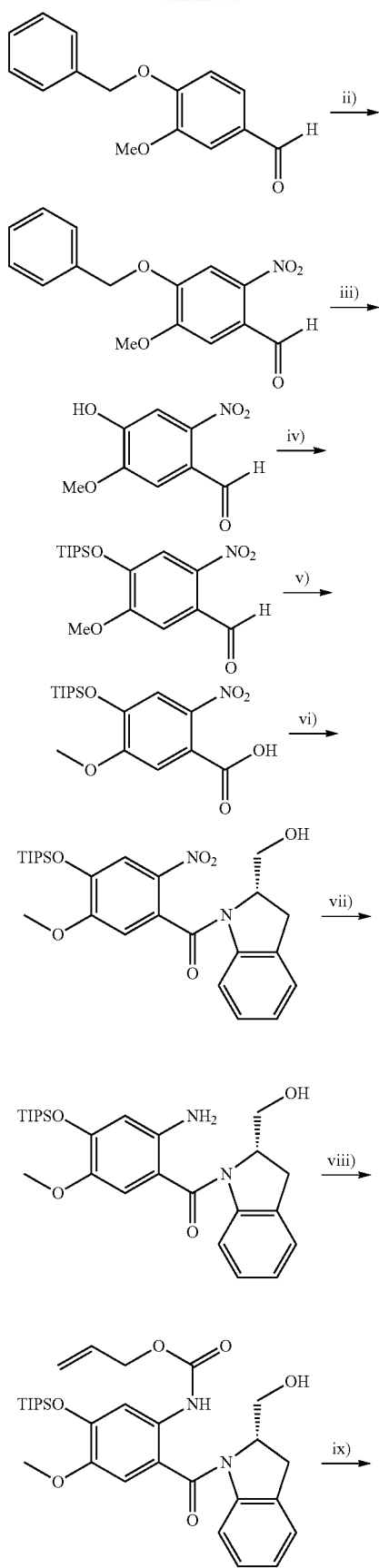
312
-continued
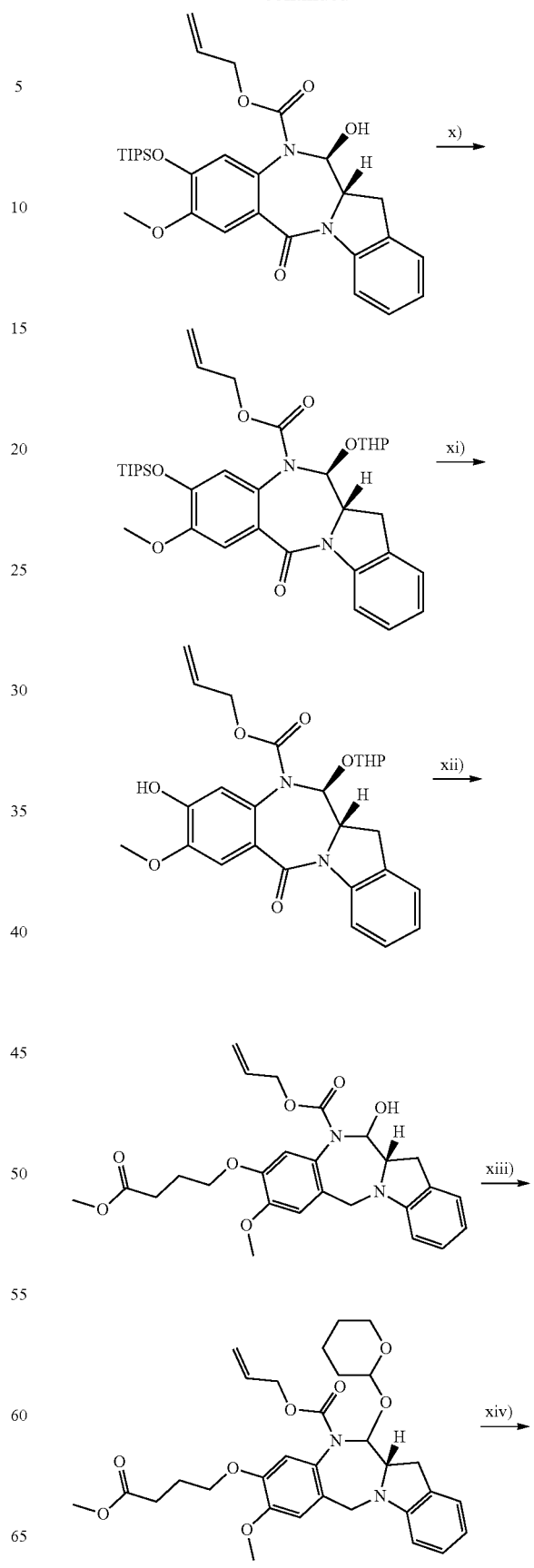

313

-continued

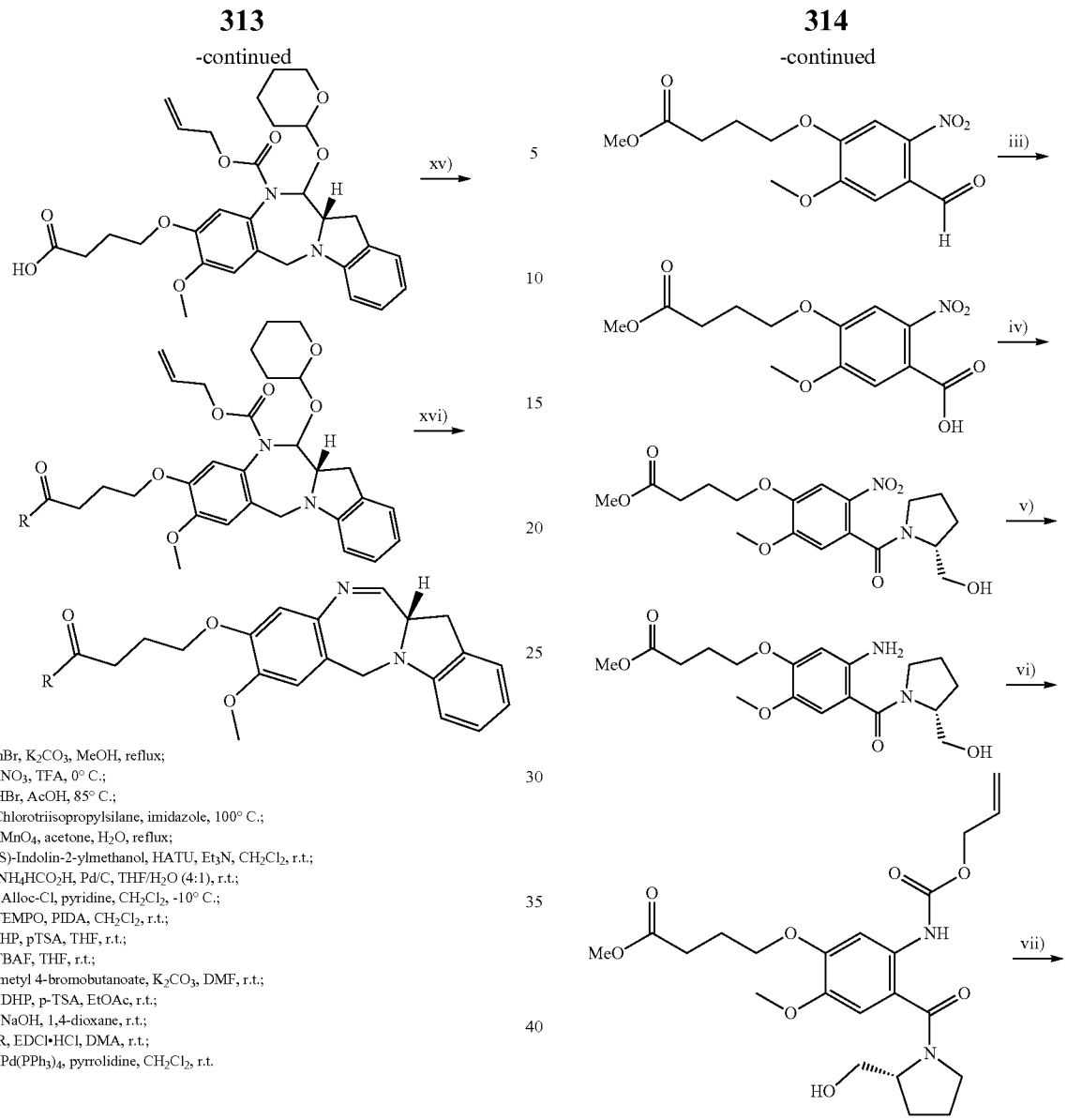

i) BnBr, K$_2$CO$_3$, MeOH, reflux;
ii) KNO$_3$, TFA, 0° C.;
iii) HBr, AcOH, 85° C.;
iv) Chlorotriisopropylsilane, imidazole, 100° C.;
v) KMnO$_4$, acetone, H$_2$O, reflux;
vi) (S)-Indolin-2-ylmethanol, HATU, Et$_3$N, CH$_2$Cl$_2$, r.t.;
vii) NH$_4$HCO$_2$H, Pd/C, THF/H$_2$O (4:1), r.t.;
viii) Alloc-Cl, pyridine, CH$_2$Cl$_2$, -10° C.;
ix) TEMPO, PIDA, CH$_2$Cl$_2$, r.t.;
x) DHP, pTSA, THF, r.t.;
xi) TBAF, THF, r.t.;
xii) metyl 4-bromobutanoate, K$_2$CO$_3$, DMF, r.t.;
xiii) DHP, p-TSA, EtOAc, r.t.;
xiv) NaOH, 1,4-dioxane, r.t.;
xv) R, EDCl·HCl, DMA, r.t.;
xvi) Pd(PPh$_3$)$_4$, pyrrolidine, CH$_2$Cl$_2$, r.t.

Example 180

General Synthetic Scheme of a PBD (R represents side-chain):

314

-continued

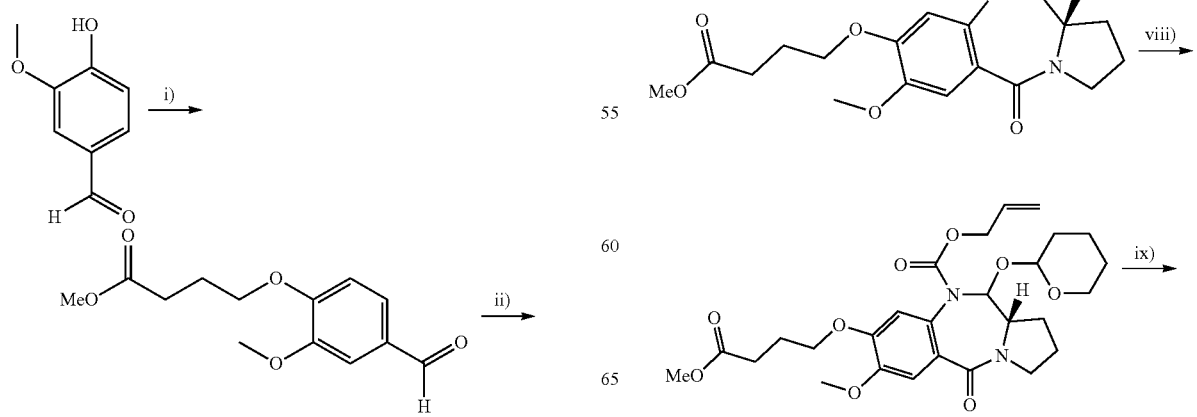

315

-continued

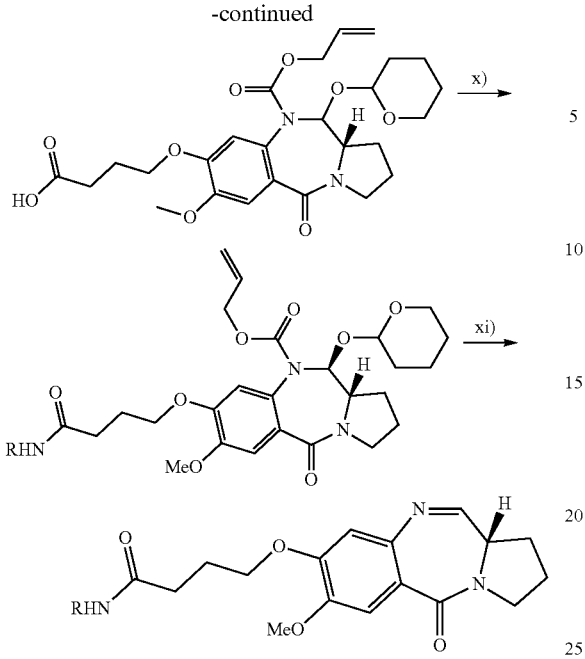

i) K₂CO₃, DMF, methyl-4-bromobutyrate, r.t.;
ii) KNO₃, TFA, 0-5° C.;
iii) KMnO₄, acetone, H₂O, reflux;
iv) Oxalyl chloride, (S)-piperidin-2-ylmethanol, DMF cat., Et₃N, CH₂Cl₂, 0° C.-r.t.;
v) H₂, Pd/C, EtOH/EtOAc;
vi) Allychloroformate, pyridine, CH₂Cl₂, -10° C.-r.t.;
vii) TEMPO, BAIB, CH₂Cl₂, r.t.;
viii) pTSA, DHP, EtOAc, r.t.;
ix) NaOH, dioxane, H₂O, r.t.;
x) RNH₂, EDCl, DMAP, DMF, r.t.;
xi) PPh₃,Pd(PPh₃)₄, pyrrolidine, CH₂Cl₂, r.t.

Example 181

General Synthetic Scheme of a C2-exo PBD (R represents side-chain):

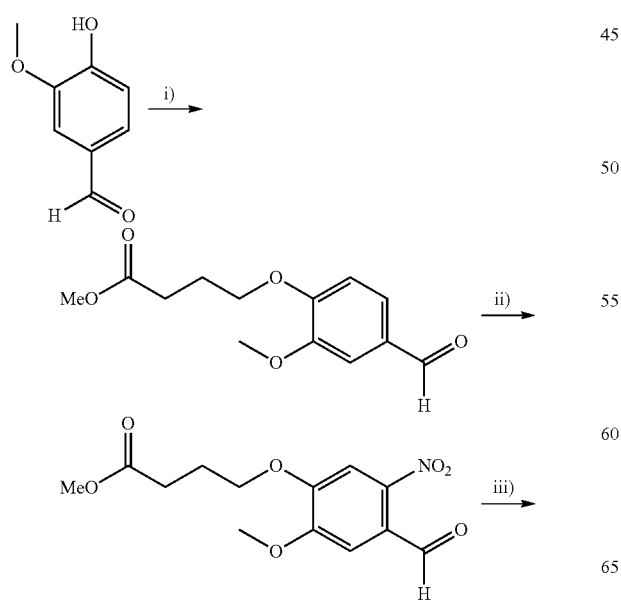

316

-continued

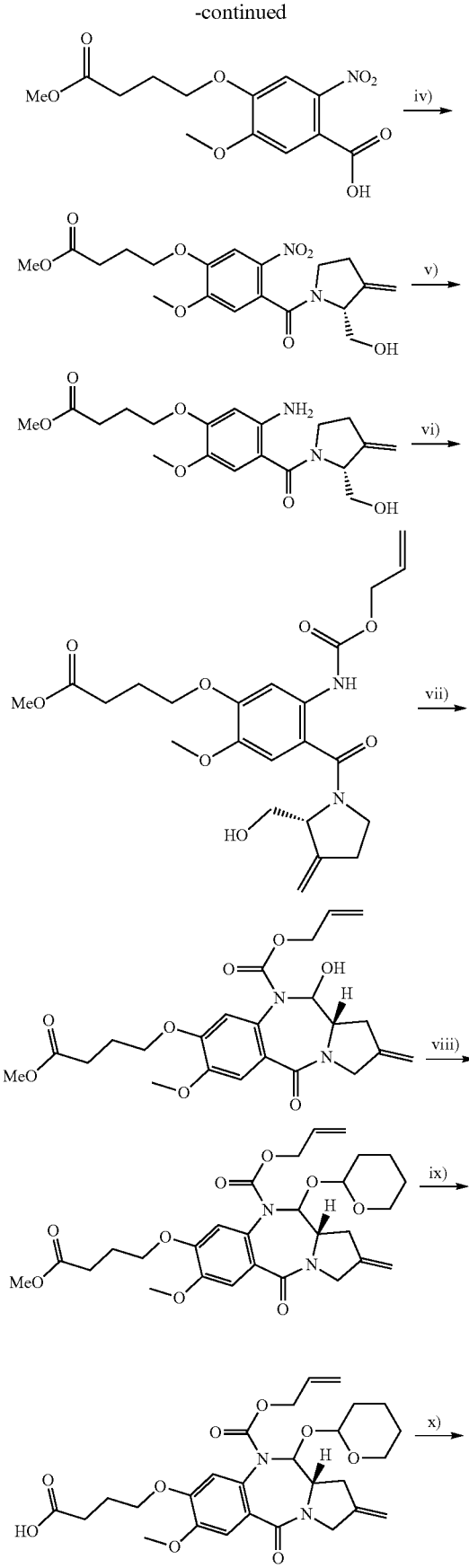

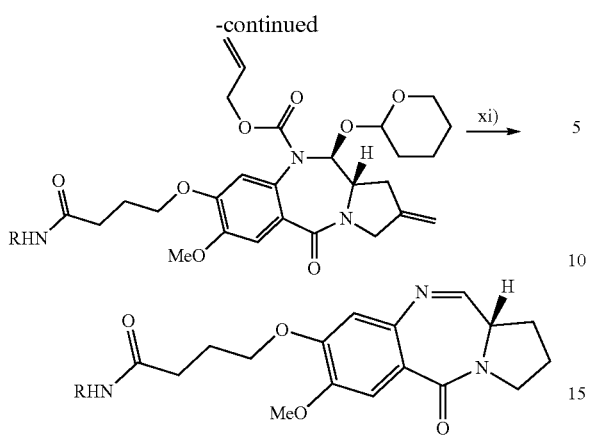

i) K₂CO₃, DMF, methyl-4-bromobutyrate, r.t.;
ii) KNO₃, TFA, 0-5° C.;
iii) KMnO₄, acetone, H₂O, reflux;
iv) Oxalyl chloride, (S)-piperidin-2-ylmethanol, DMF cat., Et₃N, CH₂Cl₂, 0° C.-r.t.;
v) H₂, Pd/C, EtOH/EtOAc;
vi) Allychloroformate, pyridine, CH₂Cl₂, -10° C.-r.t.;
vii) TEMPO, BAIB, CH₂Cl, r.t.;
viii) pTSA, DHP, EtOAc, r.t.;
ix) NaOH, dioxane, H₂O, r.t.;
x) RNH₂, EDCl, DMAP, DMF, r.t.;
xi) PPh₃, Pd(PPh₃)₄, pyrrolidine, CH₂Cl₂, r.t.

REFERENCES

[1] a G. Wells, P. W. Howard, C. Martin, Z. A. Sands, C. A. Laughton, A. Tiberghien, C. K. Woo, L. A. Masterson, A. I. John, T. C. Jenkins, S. D. Shnyder, P. M. Loadman, D. E. Thurston, *Clinical Cancer Research* 2005, 11, 9015s-9015s; b G. Wells, C. R. Martin, P. W. Howard, Z. A. Sands, C. A. Laughton, A. Tiberghien, C. K. Woo, L. A. Masterson, M. J. Stephenson, J. A. Hartley, T. C. Jenkins, S. D. Shnyder, P. M. Loadman, M. J. Waring, D. E. Thurston, *Journal of medicinal chemistry* 2006, 49, 5442-5461; c F. Brucoli, R. M. Hawkins, C. H. James, P. J. Jackson, G. Wells, T. C. Jenkins, T. Ellis, M. Kotecha, D. Hochhauser, J. A. Hartley, P. W. Howard, D. E. Thurston, *Journal of medicinal chemistry* 2013, 56, 6339-6351; d F. Brucoli, R. M. Hawkins, C. H. James, G. Wells, T. C. Jenkins, T. Ellis, J. A. Hartley, P. W. Howard, D. E. Thurston, *Bioorganic & Medicinal Chemistry Letters* 2011, 21, 3780-3783; e F. Brucoli, R. M. Hawkins, G. Wells, T. C. Jenkins, T. Ellis, M. Kotecha, D. Hochhauser, J. A. Hartley, P. W. Howard, D. E. Thurston, *Ejc Supplements* 2010, 8, 168-168; f K. M. Rahman, P. J. Jackson, C. H. James, B. P. Basu, J. A. Hartley, M. de la Fuente, A. Schatzlein, M. Robson, R. B. Pedley, C. Pepper, K. R. Fox, P. W. Howard, D. E. Thurston, *Journal of medicinal chemistry* 2013.

[2] Z. V. Zhilina, A. J. Ziemba, J. O. Trent, M. W. Reed, V. Gorn, Q. Zhou, W. Duan, L. Hurley, S. W. Ebbinghaus, *Bioconjugate Chemistry* 2004, 15, 1182-1192.

[3] S. W. Smith, V. Jammalamadaka, D. Borkin, J. Zhu, S. J. Degrado, J. Lu, J. Huang, Y.-P. Jiang, N. Jain, J. R. Junutula, *ACS Medicinal Chemistry Letters* 2018, 9, 56-60.

[4] M. L. Miller, N. E. Fishkin, W. Li, K. R. Whiteman, Y. Kovtun, E. E. Reid, K. E. Archer, E. K. Maloney, C. A. Audette, M. F. Mayo, A. Wilhelm, H. A. Modafferi, R. Singh, J. Pinkas, V. Goldmacher, J. M. Lambert, R. V. Chari, *Mol Cancer Ther* 2016, 15, 1870-1878.

---

What is claimed:

1. A compound of formula (Ia):

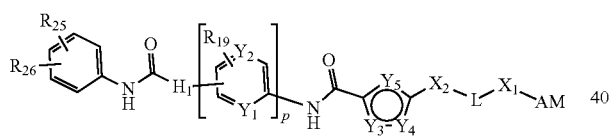

or a pharmaceutically acceptable salt thereof,
wherein:
p is 0 or 1;
when p is 0:
  $H_1$ is $C_9$ heteroaryl, optionally substituted with 1 or 2 substituents independently selected from the group consisting of $C_{1-6}$ alkyl, $(CH_2)_j$—$CO_2R_{11}$, $(CH_2)_j$—$NR_{11}R_{12}$, C(=O)—NH—$R_{24}$, C(=O)—NH—$(CH_2)_k$—$NR_{11}R_{12}$, C(=O)—NH—$(CH_2)_k$—C(=NH)$NR_{11}R_{12}$, OH, $OC_{1-6}$ alkyl, and O—$(CH_2)_k$—$NR_{11}R_{12}$;
when p is 1:
  $H_1$ is $C_5$ heteroaryl, optionally substituted with 1 or 2 substituents independently selected from the group consisting of $C_{1-6}$ alkyl, $(CH_2)_j$—$CO_2R_{11}$, $(CH_2)_j$—$NR_{11}R_{12}$, C(=O)—NH—$R_{24}$, C(=O)—NH—$(CH_2)_k$—$NR_{11}R_{12}$, C(=O)—NH—$(CH_2)_k$—C(=NH)$NR_{11}R_{12}$, OH, $OC_{1-6}$ alkyl, and O—$(CH_2)_k$—$NR_{11}R_{12}$;
each $R_{24}$ is phenyl, optionally substituted with 1, 2, or 3 substituents independently selected from the group consisting of $C_{1-6}$ alkyl, $(CH_2)_j$—$CO_2R_{11}$, $(CH_2)$,—$NR_{11}R_{12}$, C(=O)—NH—$(CH_2)_k$—$NR_{11}R_{12}$, C(=O)—NH—$(CH_2)_k$—C(=NH)$NR_{11}R_{12}$, OH, $OC_{1-6}$ alkyl, and O—$(CH_2)_k$—$NR_{11}R_{12}$;
$R_{25}$ is H, $C_{1-6}$ alkyl, $(CH_2)_j$—$CO_2R_{11}$, $(CH_2)_j$—$NR_{11}R_{12}$, C(=O)—NH—$(CH_2)_k$—$NR_{11}R_{12}$, C(=O)—NH—$(CH_2)_k$—C(=NH)$NR_{11}R_{12}$, OH, $OC_{1-6}$ alkyl, or O—$(CH_2)_k$—$NR_{11}R_{12}$;
$R_{26}$ is H, $C_{1-6}$ alkyl, $(CH_2)_j$—$CO_2R_{11}$, $(CH_2)$,—$NR_{11}R_{12}$, C(=O)—NH—$(CH_2)_k$—$NR_{11}R_{12}$, C(=O)—NH—$(CH_2)_k$—C(=NH)$NR_{11}R_{12}$, OH, $OC_{1-6}$ alkyl, or O—$(CH_2)_k$—$NR_{11}R_{12}$;
each $R_{11}$ is independently H or $C_{1-6}$ alkyl;
each $R_{12}$ is independently H or $C_{1-6}$ alkyl;
$R_{19}$ is H or $(CH_2)_t$—$NR_{20}R_{21}$;
$R_{20}$ is H or $C_{1-6}$ alkyl;
$R_{21}$ is H or $C_{1-6}$ alkyl;
each j is independently 0, 1, 2, 3, 4, 5, or 6;
each k is independently 1, 2, 3, 4, 5, or 6;
t is 0, 1, 2, 3, 4, 5, or 6;
L is selected from the group consisting of:
  (i) an amino acid;
  (ii) a peptide chain having 2, 3, 4, 5, or 6 amino acids, wherein the peptide chain is optionally interrupted by one or more atoms or groups independently selected from the group consisting of NH, O, S, phenylene, and $C_{5-9}$ heteroarylene;
  (iii) —$C_{1-12}$ alkylene-, wherein the $C_{1-12}$ alkylene optionally contains one or more C—C double bonds or C—C triple bonds, and further wherein the $C_{1-12}$ alkylene is optionally interrupted by one or more atoms or groups independently selected from the group consisting of NH, O, S, phenylene, and $C_{5-9}$ heteroarylene;
  (iv) —$(OCH_2)_{1-12}$—, wherein the —$(OCH_2)_{1-12}$— is optionally interrupted by one or more atoms or groups independently selected from the group consisting of NH, O, S, phenylene, and $C_{5-9}$ heteroarylene; and (v) —(OCH$_2$CH$_2$)$_{1-6}$—, wherein the —(OCH$_2$CH$_2$)$_{1-6}$ is optionally interrupted by one or more atoms or groups independently selected from the group consisting of NH, O, S, phenylene, and C$_{5-9}$ heteroarylene;

X$_1$ is —CR$_{13}$R$_{14}$—, —CR$_{13}$R$_{14}$O—, —(C═O)—, —(C═O)NR$_{13}$—, —C(═O)O—, —NR$_{13}$(C═O)—, —O—, —O(C═O)—, or —S—;

X$_2$ is —CR$_{15}$R$_{16}$—, —CR$_{15}$R$_{16}$O—, —(C═O)—, —(C═O)NR$_{15}$—, —(C═O)O—, —NR$_{15}$—, —NR$_{15}$(C═O)—, —O—, —O(C═O)—, or —S—; or

X$_2$ is absent;

Y$_1$ is N or CH;

Y$_2$ is N or CH;

(i) Y$_3$ is NR$_{17}$, O, or S; and
Y$_4$ is CH; or (ii) Y$_3$ is CH; and
Y$_4$ is NR$_{17}$, O, or S;

Y$_5$ is CH, COH, N, or S;

R$_{13}$ is H or C$_{1-6}$ alkyl;
R$_{14}$ is H or C$_{1-6}$ alkyl;
R$_{15}$ is H or C$_{1-6}$ alkyl;
R$_{16}$ is H or C$_{1-6}$ alkyl;
R$_{17}$ is H or C$_{1-6}$ alkyl; and AM is formula (XXVII):

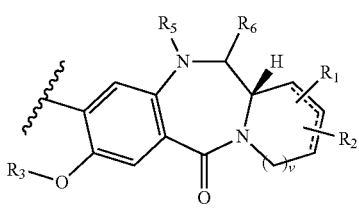

(XXVII)

wherein:
the dotted line represents either single bonds or one single bond and one double bond;
v is 0 or 1;
when v is 0 and the dotted line represents single bonds, either:
(a) R$_1$ is H, halogen, C$_{1-6}$ alkyl, OH, or OC$_{1-6}$ alkyl; and
R$_2$ is H, halogen, C$_{1-6}$ alkyl, OH, or OC$_{1-6}$ alkyl; or
(b) R$_1$ is absent; and
R$_2$ is ═C(RD$_5$)(RD$_6$), wherein R$_2$ is attached to C-2; or
(c) R$_1$ and R$_2$ are attached to adjacent carbons and together with the carbons to which they are attached, form an aromatic 6-membered ring, substituted with RD$_1$, RD$_2$, RD$_3$, and RD$_4$;
when v is 0 and the dotted line represents one single bond and one double bond, wherein the double bond is between C1 and C2 or between C2 and C3:
R$_1$ is absent; and
R$_2$ is C$_{1-6}$ alkyl, phenyl, or C$_{5-9}$ heteroaryl, wherein the C$_{1-6}$ alkyl, phenyl, and C$_{5-9}$ heteroaryl are optionally substituted with RD$_1$, RD$_2$, RD$_3$, RD$_4$, and RD$_7$;
when v is 1, the dotted line represents single bonds:
R$_1$ and R$_2$ are attached to adjacent carbons and together with the carbons to which they are attached, form an aromatic 6-membered ring, substituted with RD$_1$, RD$_2$, RD$_3$, and RD$_4$;

R$_3$ is H, C$_{1-12}$ alkyl, or CH$_2$-phenyl;

(i) R$_5$ is H; and
R$_6$ is OH or OC$_{1-6}$ alkyl; or (ii) R$_5$ is SO$_3$H; and
R$_6$ is H; or (iii) R$_5$ and R$_6$ together form a double bond;

RD$_1$ is H, halogen, C$_{1-6}$ alkyl, OH, or OC$_{1-6}$ alkyl;
RD$_2$ is H, halogen, C$_{1-6}$ alkyl, OH, or OC$_{1-6}$ alkyl;
RD$_3$ is H, halogen, C$_{1-6}$ alkyl, OH, or OC$_{1-6}$ alkyl;
RD$_4$ is H, halogen, C$_{1-6}$ alkyl, OH, or OC$_{1-6}$ alkyl;
RD$_5$ is H or C$_{1-6}$ alkyl;
RD$_6$ is H or C$_{1-6}$ alkyl; and
RD$_7$ is H, halogen, C$_{1-6}$ alkyl, OH, or OC$_{1-6}$ alkyl;

with the proviso that at least one of Y$_1$ and Y$_2$ is CH.

2. The compound of claim 1, or a pharmaceutically acceptable salt thereof, wherein L is —C$_{1-12}$ alkylene-, wherein the C$_{1-12}$ alkylene optionally contains one or more C—C double bonds or C—C triple bonds, and further wherein the C$_{1-12}$ alkylene is optionally interrupted by one or more atoms or groups independently selected from the group consisting of NH, O, S, phenylene, and C$_{5-9}$ heteroarylene.

3. The compound of claim 1, or a pharmaceutically acceptable salt thereof, wherein:
Y$_3$ is NR$_{17}$; and
Y$_4$ is CH.

4. The compound of claim 1, or a pharmaceutically acceptable salt thereof, wherein one, two, three, or all of RD$_1$, RD$_2$, RD$_3$, and RD$_4$ are independently H.

5. The compound of claim 1, or a pharmaceutically acceptable salt thereof, wherein the compound is of formula (XXIV):

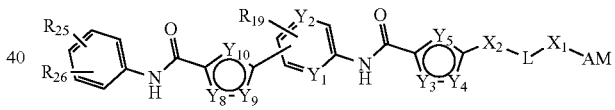

(XXIV)

wherein:
(i) Y$_8$ is NH, O, or S, wherein the NH is optionally substituted with a substituent selected from the group consisting of C$_{1-6}$ alkyl, (CH$_2$)$_j$—CO$_2$R$_{11}$, (CH$_2$)$_j$—NR$_{11}$R$_{12}$, C(═O)—NH-phenyl-R$_{18}$, C(═O)—NH—(CH$_2$)$_k$—NR$_{11}$R$_{12}$, C(═O)—NH—(CH$_2$)$_k$—C(═NH)NR$_{11}$R$_{12}$, OH, OC$_{1-6}$ alkyl, and O—(CH$_2$)$_k$—NR$_{11}$R$_{12}$; and Y$_9$ is CH, wherein the CH is optionally substituted with a substituent selected from the group consisting of C$_{1-6}$ alkyl, (CH$_2$)$_j$—CO$_2$R$_{11}$, (CH$_2$)$_j$—NR$_{11}$R$_{12}$, C(═O)—NH-phenyl-R$_{18}$, C(═O)—NH—(CH$_2$)$_k$—NR$_{11}$R$_{12}$, C(═O)—NH—(CH$_2$)$_k$—C(═NH)NR$_{11}$R$_{12}$, OH, OC$_{1-6}$ alkyl, and O—(CH$_2$)$_k$—NR$_{11}$R$_{12}$;

R$_{18}$ is CO$_2$R$_{11}$ or NR$_{11}$R$_{12}$; or (ii) Y$_8$ is CH, wherein the CH is optionally substituted with a substituent selected from the group consisting of C$_{1-6}$ alkyl, (CH$_2$)$_j$—CO$_2$R$_{11}$, (CH$_2$)$_j$—NR$_{11}$R$_{12}$, C(═O)—NH-phenyl-R$_{18}$, C(═O)—NH—(CH$_2$)$_k$—NR$_{11}$R$_{12}$, C(═O)—NH—(CH$_2$)$_k$—C(═NH)NR$_{11}$R$_{12}$, OH, OC$_{1-6}$ alkyl, and O—(CH$_2$)$_k$—NR$_{11}$R$_{12}$; and Y$_9$ is NH, O, or S, wherein the NH is optionally substituted with a substituent selected from the group consisting of $C_{1-6}$ alkyl, $(CH_2)_j$—$CO_2R_{11}$, $(CH_2)_j$—$NR_{11}R_{12}$, $C(=O)$—NH-phenyl-$R_{18}$, $C(=O)$—NH—$(CH_2)_k$—$NR_{11}R_{12}$, $C(=O)$—NH—$(CH_2)_k$—$C(=NH)NR_{11}R_{12}$, OH, $OC_{1-6}$ alkyl, and O—$(CH_2)_k$—$NR_{11}R_{12}$;

$R_{18}$ is $CO_2R_{11}$ or $NR_{11}R_{12}$;

$Y_{10}$ is CH or N, wherein the CH is optionally substituted with a substituent selected from the group consisting of $C_{1-6}$ alkyl, $(CH_2)_j$—$CO_2R_{11}$, $(CH_2)_j$—$NR_{11}R_{12}$, $C(=O)$—NH-phenyl-$R_{18}$, $C(=O)$—NH—$(CH_2)_k$—$NR_{11}R_{12}$, $C(=O)$—NH—$(CH_2)_k$—$C(=NH)NR_{11}R_{12}$, OH, $OC_{1-6}$ alkyl, and O—$(CH_2)_k$—$NR_{11}R_{12}$; and each $R_{18}$ is independently $CO_2R_{11}$ or $NR_{11}R_{12}$.

6. The compound of claim 5, or a pharmaceutically acceptable salt thereof, wherein:
   $Y_8$ is NH; and
   $Y_9$ is CH.

7. The compound of claim 5, wherein the compound is of formula (XXIVa) or formula (XXIVb):

(XXIVa)

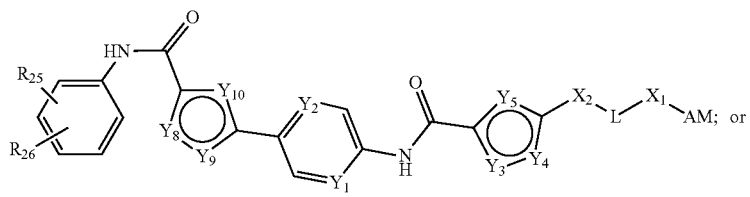

or (XXIVb)

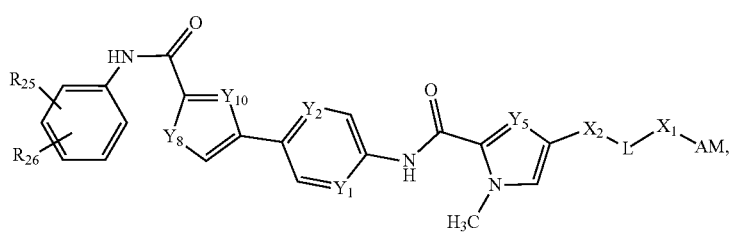

or a pharmaceutically acceptable salt thereof.

8. The compound of claim 1, wherein the compound is of formula (XXV) or formula (XXVI):

(XXV)

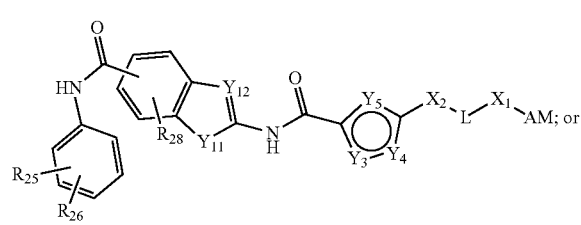

(XXVI)

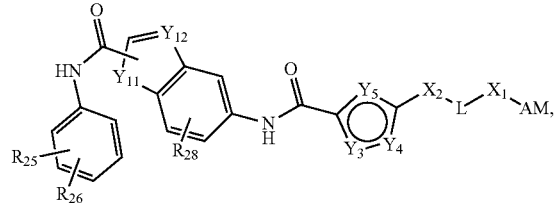

or a pharmaceutically acceptable salt thereof,
wherein:
$Y_{11}$ is $NR_{27}$, O, or S;
$Y_{12}$ is CH or N;
$R_{27}$ is H, $C_{1-6}$ alkyl, $(CH_2)_j$—$CO_2R_{11}$, $(CH_2)_j$—$NR_{11}R_{12}$, $C(=O)$—NH—$(CH_2)_k$—$NR_{11}R_{12}$, $C(=O)$—NH—$(CH_2)_k$—$C(=NH)NR_{11}R_{12}$, OH, $OC_{1-6}$ alkyl, or O—$(CH_2)_k$—$NR_{11}R_{12}$; and $R_{28}$ is H, $C_{1-6}$ alkyl, $(CH_2)_j$—$CO_2R_{11}$, $(CH_2)_j$—$NR_{11}R_{12}$, $C(=O)$—NH—$(CH_2)_k$—$NR_{11}R_{12}$, $C(=O)$—NH—$(CH_2)_k$—$C(=NH)NR_{11}R_{12}$, OH, $OC_{1-6}$ alkyl, or O—$(CH_2)_k$—$NR_{11}R_{12}$;

with the proviso that the heteroaryl containing $Y_{11}$ and $Y_{12}$ is not indolyl.

9. The compound of claim 8, or a pharmaceutically acceptable salt thereof, wherein:
   (i) $R_{25}$ is H; or
   (ii) $R_{26}$ is H; or
   (iii) $R_{25}$ is H; and
   $R_{26}$ is H.

10. The compound of claim 8, or a pharmaceutically acceptable salt thereof, wherein:
    (i) $R_{25}$ is $CH_3$, $CO_2CH_3$, or $NH_2$; and
    $R_{26}$ is H; or
    (ii) $R_{25}$ is H; and
    $R_{26}$ is $CH_3$, $CO_2CH_3$, or $NH_2$.

11. The compound of claim 8, or a pharmaceutically acceptable salt thereof, wherein $R_{27}$ is H or $CH_3$.

12. The compound of claim 8, or a pharmaceutically acceptable salt thereof, wherein $Y_{11}$ is S.

13. The compound of claim 8, wherein the compound is of formula (XXVa) or formula (XXVb):

(XXVa)

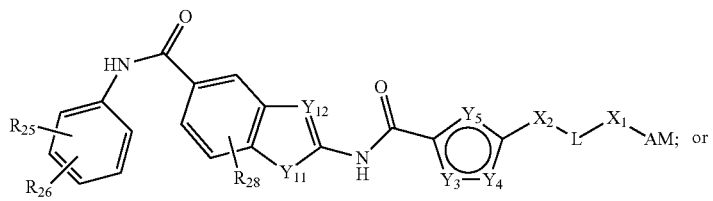

(XXVb)

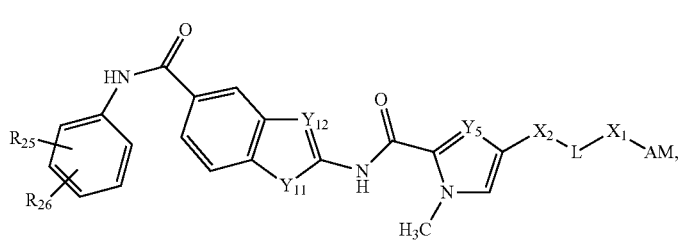

or a pharmaceutically acceptable salt thereof.

14. The compound of claim 8, wherein the compound is of formula (XXVIa) or formula (XXVIb):

(XXVIa)

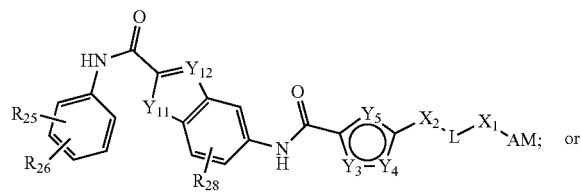

(XXVIb)

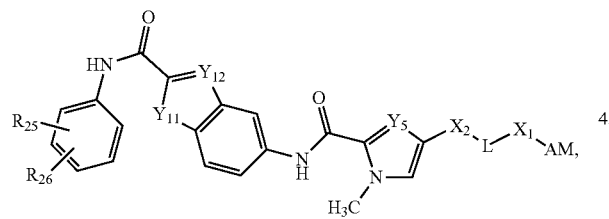

or a pharmaceutically acceptable salt thereof.

15. The compound of claim 1, wherein AM is formula (XXVIIIa), formula (XXVIIIb), or formula (XXVIIIc):

(XXVIIIa)

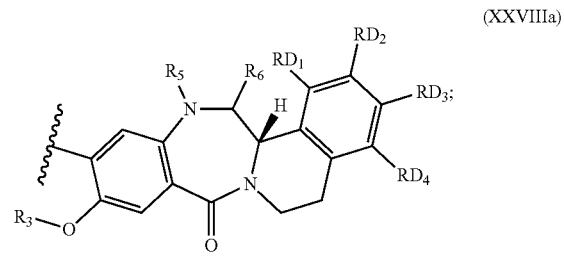

-continued (XXVIIIb)

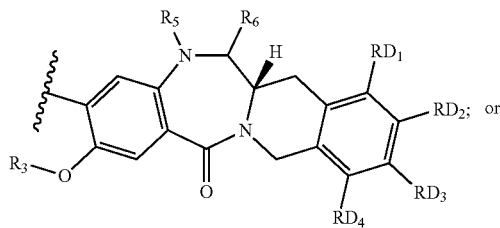

(XXVIIIc)

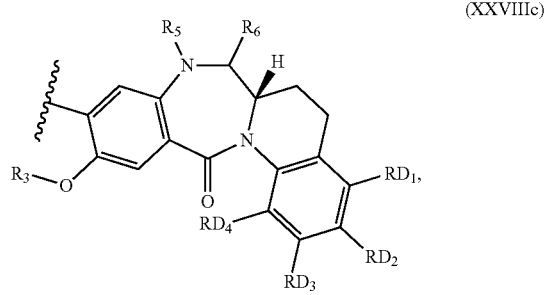

or a pharmaceutically acceptable salt thereof.

16. The compound of claim 1, wherein AM is formula (XXIXa) or formula (XXIXb):

(XXIXa)

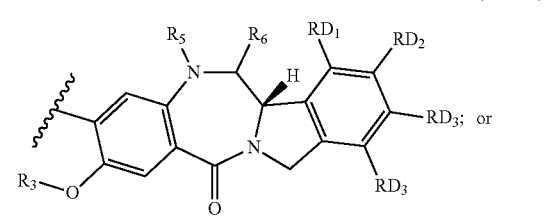

-continued

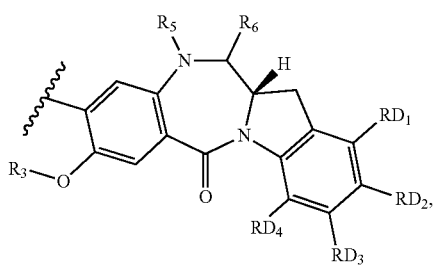

(XXIXb)

or a pharmaceutically acceptable salt thereof.

17. The compound of claim 16, or a pharmaceutically acceptable salt thereof, wherein one, two, three, or all of $RD_1$, $RD_2$, $RD_3$, and $RD_4$ are independently H.

18. The compound of claim 1, wherein AM is formula (XXXa), formula (XXXb), or formula (XXXc):

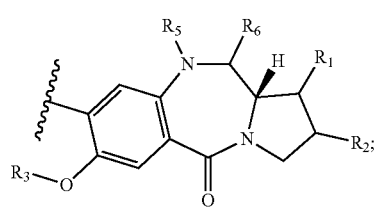

(XXXa)

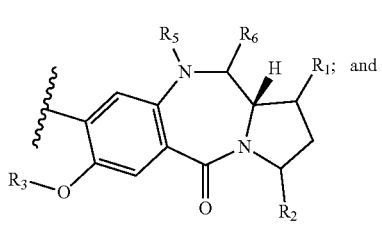

(XXXb)

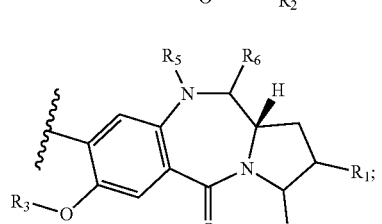

(XXXc)

or a pharmaceutically acceptable salt thereof.

19. The compound of claim 1, wherein AM is formula (XXXI):

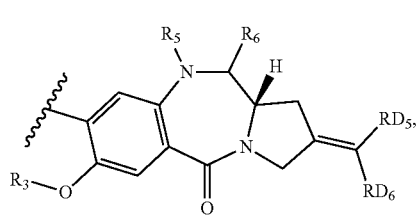

(XXXI)

or a pharmaceutically acceptable salt thereof.

20. The compound of claim 1, wherein AM is formula (XXXII):

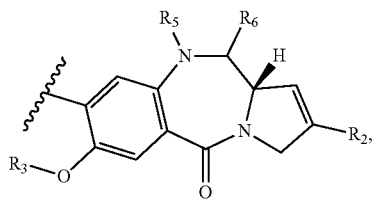

(XXXII)

or a pharmaceutically acceptable salt thereof.

21. The compound of claim 20, or a pharmaceutically acceptable salt thereof, wherein one, two, three, four, or all of $RD_1$, $RD_2$, $RD_3$, $RD_4$, and $RD_7$ are independently H.

22. The compound of claim 20, wherein AM is formula (XXXIIa) or formula (XXXIIb):

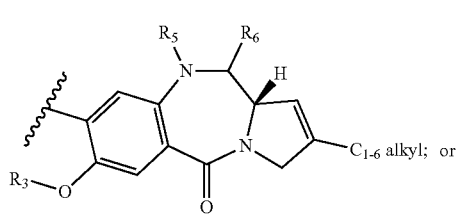

(XXXIIa)

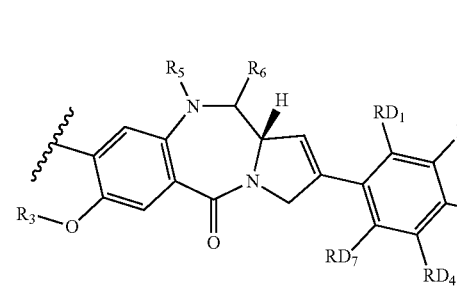

(XXXIIb)

or a pharmaceutically acceptable salt thereof.

23. The compound of claim 1, wherein AM is formula (XXXIII):

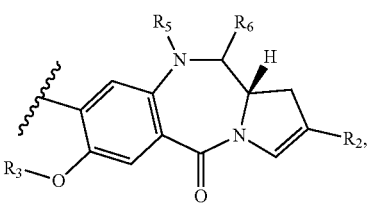

(XXXIII)

or a pharmaceutically acceptable salt thereof.

24. The compound of claim 23, or a pharmaceutically acceptable salt thereof, wherein one, two, three, four, or all of $RD_1$, $RD_2$, $RD_3$, $RD_4$, and $RD_7$ are independently H.

25. The compound of claim 23, wherein AM is formula (XXXIIIa) or formula (XXXIIIb):

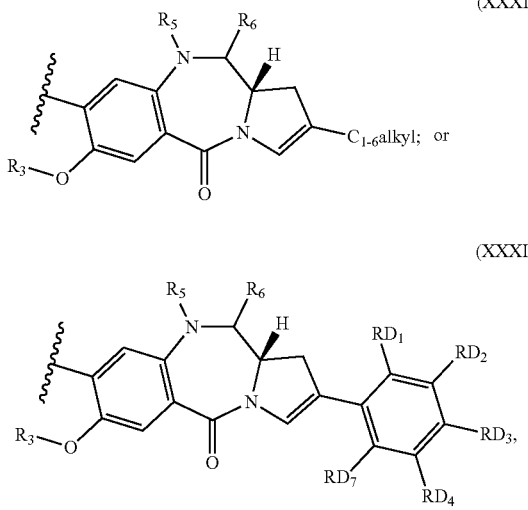

or a pharmaceutically acceptable salt thereof,
wherein:
one, two, three, four, or all of $RD_1$, $RD_2$, $RD_3$, $RD_4$, and $RD_7$ are independently H.

26. The compound of claim 1, or a pharmaceutically acceptable salt thereof, wherein the compound is further linked to a targeting agent to provide a targeting conjugate.

27. The compound of claim 26, or a pharmaceutically acceptable salt thereof, wherein the targeting agent is an antibody.

28. A pharmaceutical composition comprising a pharmaceutically acceptable excipient, carrier, or diluent and a compound of claim 1, or a pharmaceutically acceptable salt thereof.

29. A method for inhibiting cancer cell proliferation in a patient in need thereof, comprising administering to the patient a therapeutically effective amount of a compound of claim 1, or a pharmaceutically acceptable salt thereof, or a pharmaceutical composition of claim 26.

30. The method of claim 29, wherein the patient suffers from a cancer selected from the group consisting of leukemia, melanoma, breast cancer, cervical cancer, colorectal cancer, gastric cancer, liver cancer, lung cancer, pancreatic cancer, prostate cancer, rectal cancer, renal cancer, skin cancer, and stomach cancer.

* * * * *

SEQUENCE LISTING

<160> NUMBER OF SEQ ID NOS: 5

<210> SEQ ID NO 1
<211> LENGTH: 160
<212> TYPE: DNA
<213> ORGANISM: Escherichia coli

<400> SEQUENCE: 1
aaggccaatg gaaattaggc aatgcctact tttaatgcgt tggtcaagaa aaaagagaag      60
gattgtgaaa tgtcgccgcg cagtaaacta tactacgcgg ggcgaagggc tattccctcg     120
tccggtcatt tttcgtaatg gggcaccacc cccaagggct                            160

<210> SEQ ID NO 2
<211> LENGTH: 166
<212> TYPE: DNA
<213> ORGANISM: artificial sequence
<220> FEATURE:
<223> OTHER INFORMATION: probe

<400> SEQUENCE: 2
ggatccatat gcggcaatac acatggcaga tttccaactg cactagtcgt agcgcgatca      60
aggttaagct cccgttctat cctggtatag caattagggc gtgaagagtt atgtaaagta    120
cgtccggtgg ggtctgtttt gtcatctcag cctcgaatgc ggatcc                   166

<210> SEQ ID NO 3
<211> LENGTH: 140
<212> TYPE: DNA

```
<213> ORGANISM: Staphylococcus pneumoniae

<400> SEQUENCE: 3
ggatcccggg atatcgatat atggcgccaa atttagctat agatctagaa ttccggaccg      60
cggtttaaac gttaaccggt acctaggcct gcagctgcgc atgctagcgc ttaagtacta     120
gtgcacgtgg ccatggatcc                                                 140

<210> SEQ ID NO 4
<211> LENGTH: 17
<212> TYPE: DNA
<213> ORGANISM: artificial sequence
<220> FEATURE:
<223> OTHER INFORMATION: probe

<400> SEQUENCE: 4
aaaaaaagaa atttaaa                                                     17

<210> SEQ ID NO 5
<211> LENGTH: 17
<212> TYPE: DNA
<213> ORGANISM: artificial sequence
<220> FEATURE:
<223> OTHER INFORMATION: probe

<400> SEQUENCE: 5
tttttttctt ttttaaa                                                     17
```